United States Patent
Takashima et al.

(10) Patent No.: US 8,940,412 B2
(45) Date of Patent: Jan. 27, 2015

(54) MATERIAL FOR ORGANIC ELECTROLUMINESCENT ELEMENT, AND ORGANIC ELECTROLUMINESCENT ELEMENT

(75) Inventors: Yoriyuki Takashima, Chiba (JP); Toshihiro Iwakuma, Chiba (JP); Toshinari Ogiwara, Chiba (JP); Chishio Hosokawa, Chiba (JP); Mitsunori Ito, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 609 days.

(21) Appl. No.: 13/142,357

(22) PCT Filed: Dec. 22, 2009

(86) PCT No.: PCT/JP2009/071337
§ 371 (c)(1), (2), (4) Date: Aug. 31, 2011

(87) PCT Pub. No.: WO2010/074087
PCT Pub. Date: Jul. 1, 2010

(65) Prior Publication Data
US 2011/0315965 A1    Dec. 29, 2011

(30) Foreign Application Priority Data
Dec. 26, 2008  (JP) ............................. 2008-334961
Sep. 7, 2009   (WO) ................. PCT/JP2009/065613

(51) Int. Cl.
*H01L 51/50*    (2006.01)
*C07D 307/91*   (2006.01)
(Continued)

(52) U.S. Cl.
CPC .............. *C07D 307/91* (2013.01); *C09K 11/06* (2013.01); *H01L 51/0052* (2013.01);
(Continued)

(58) Field of Classification Search
None
See application file for complete search history.

(56) References Cited

U.S. PATENT DOCUMENTS

2004/0170863 A1*   9/2004   Kim et al. ...................... 428/690
2006/0154105 A1*   7/2006   Yamamoto et al. ........... 428/690
(Continued)

FOREIGN PATENT DOCUMENTS

EP   2 100 941 A2   9/2009
EP   2 100 941 A3   9/2009
(Continued)

OTHER PUBLICATIONS

Thompson et al., Synthesis and Characterization of Phosphorescent Cyclometalated Iridium Complexes, 2001, Inorganic Chemistry, vol. 40, pp. 1704-1711.*
(Continued)

*Primary Examiner* — Gregory Clark
(74) *Attorney, Agent, or Firm* — Oblon, Spivak, McClelland, Maier & Neustadt, L.L.P.

(57) ABSTRACT

An organic electroluminescence device and a material for producing the organic electroluminescence device. The organic electroluminescence device includes an organic thin film layer between a cathode and an anode, the organic thin film layer including one or more layers, in which the organic thin film layer includes one or more light emitting layers and at least one of the light emitting layers includes a phosphorescent material and a host material. The host material has an essential structure in which a naphthalene ring is bonded to a fluorene skeleton, dibenzofuran skeleton, or dibenzothiophene skeleton. The organic electroluminescence device is a phosphorescent device having high efficiency and long lifetime.

12 Claims, 1 Drawing Sheet

(51) Int. Cl.
*C09K 11/06* (2006.01)
*H01L 51/00* (2006.01)
*H05B 33/14* (2006.01)
*H05B 33/20* (2006.01)

(52) U.S. Cl.
CPC ........ *H01L 51/0054* (2013.01); *H01L 51/0055* (2013.01); *H05B 33/14* (2013.01); *H05B 33/20* (2013.01); *C09K 2211/1029* (2013.01); *C09K 2211/1059* (2013.01); *C09K 2211/185* (2013.01); *H01L 51/0059* (2013.01); *H01L 51/006* (2013.01); *H01L 51/0071* (2013.01); *H01L 51/0079* (2013.01); *H01L 51/0085* (2013.01); *H01L 51/0087* (2013.01); *H01L 51/5016* (2013.01); *Y10S 428/917* (2013.01)
USPC ........... 428/690; 428/917; 313/504; 313/505; 313/506; 257/40; 257/E51.05; 257/E51.026; 257/E51.032; 585/27; 548/304.1; 548/418; 548/440; 544/179; 544/183; 544/233; 544/245; 544/342

(56) References Cited

U.S. PATENT DOCUMENTS

| | | |
|---|---|---|
| 2008/0100207 A1 | 5/2008 | Park et al. |
| 2009/0091252 A1 | 4/2009 | Kosuge et al. |
| 2009/0153039 A1 | 6/2009 | Kim et al. |
| 2009/0200919 A1 | 8/2009 | Kamatani et al. |
| 2009/0230852 A1 | 9/2009 | Lee et al. |

FOREIGN PATENT DOCUMENTS

| | | | | |
|---|---|---|---|---|
| JP | 2004-42485 A | | 2/2004 | |
| JP | 2004-043349 | * | 2/2004 | ............. C09K 11/06 |
| JP | 2004 43349 | | 2/2004 | |
| JP | 2007 302650 | | 11/2007 | |
| JP | 2008-308449 | * | 12/2008 | ............... H01I 51/50 |
| JP | 2009 84256 | | 4/2009 | |
| JP | 2009 149638 | | 7/2009 | |
| JP | 2009 249378 | | 10/2009 | |
| WO | WO 2007/046658 A1 | | 4/2007 | |
| WO | WO 2008/015949 A1 | | 2/2008 | |
| WO | 2008 143416 | | 11/2008 | |
| WO | WO 2012/005724 A1 | | 1/2012 | |

OTHER PUBLICATIONS

International Search Report issued Mar. 23, 2010 in PCT/JP09/071337 filed Dec. 22, 2009.
Extended European Search Report issued on Jun. 4, 2012, in patent Application No. 09834888.1.
Office Action issued Nov. 5, 2013 in Japanese Patent Application No. 2010-544086.
Extended European Search Report issued Feb. 27, 2014 in Patent Application No. 13198972.5.

* cited by examiner

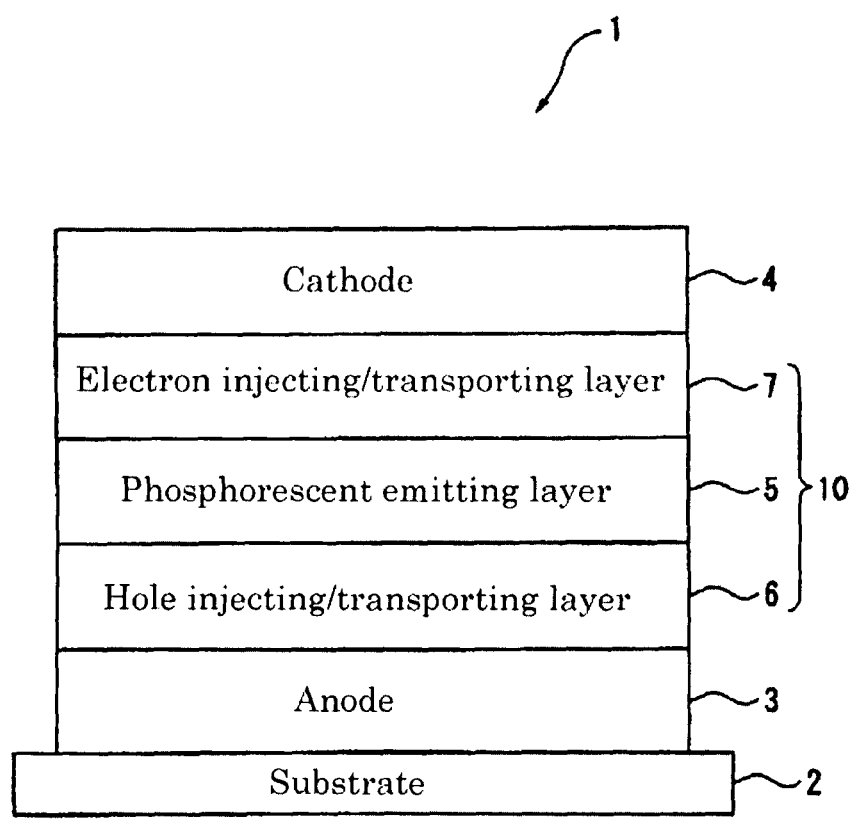

MATERIAL FOR ORGANIC ELECTROLUMINESCENT ELEMENT, AND ORGANIC ELECTROLUMINESCENT ELEMENT

This application is a National Stage of PCT/JP09/071337 Dec. 22, 2009 and claims the benefit of JP2008-334961 filed Dec. 26, 2008 and PCT/JP09/065613 filed Sep. 7, 2009.

TECHNICAL FIELD

The present invention relates to an organic electroluminescence device (hereinafter referred to as "organic EL device") and a material for organic electroluminescence device. In particular, it relates to an organic electroluminescence device having a green-emitting layer and a material for use in the production of such an organic electroluminescence device.

BACKGROUND ART

An organic EL device, which has an organic thin film layer including a light emitting layer between an anode and a cathode and which emits light from an exciton energy resulted from the recombination of holes and electrons injected into the light emitting layer, has been known.

Sine the organic EL device is a spontaneous emitting device, it has been expected to be applicable, using its advantages, to a light emitting device with high current efficiency, high image quality, low power consumption and wide design freedom for thinner products. The organic EL device has been still required to be further improved in its properties, for example, in the current efficiency.

In this regard, to enhance the internal quantum efficiency, a light emitting material (phosphorescent material) which emits light from triplet exciton has been developed, and a phosphorescent organic EL device are reported in recent years.

By forming a light emitting layer (phosphorescent layer) using the above phosphorescent material, an internal quantum efficiency of 75% or more, theoretically about 100% is obtained, to realize an organic EL device having high efficiency and low power consumption. Further, a doping method in which a light emitting material is doped as a dopant into a host material for forming a light emitting layer is known.

In a doped light emitting layer, excitons can be efficiently generated from charges injected into a host material. The exciton energy of generated excitons is transferred to a dopant, and this allows the dopant to emit light in high efficiency.

To intermolecularly transfer the energy from a host material to a phosphorescent dopant, the excited triplet energy Eg(T) of the host material has to be larger than the excited triplet energy Eg(S) of the phosphorescent dopant.

CBP (4,4'-bis(N-carbazolyl)biphenyl) is a well known material which has an effectively large excited triplet energy (Patent Document 1).

If CBP is used as a host material, the energy can be transferred to a phosphorescent dopant which emits light with a specific wavelength (for example, green and red), and an organic EL device having high efficiency can be obtained.

When CBP is used as a host material, the current efficiency is drastically enhanced by phosphorescent emission on one hand, but the lifetime is very short to make the device unsuitable for practical use on the other hand.

This may be because that CBP has a molecular structure less resistant to oxidation and therefore its molecule is largely degraded by holes.

Patent Document 2 discloses a technique in which a condensed ring derivative having a nitrogen-containing ring such as carbazole is used as a host material for a red-emitting phosphorescent layer. This technique enables the improvement of current efficiency and lifetime, but is not satisfactory for practical application in some cases.

A wide variety of fluorescent host materials (fluorescent hosts) for a fluorescent dopant is known, and various host materials which can form, in combination with a fluorescent dopant, a fluorescent layer excellent in current efficiency and lifetime are proposed.

The excited singlet energy Eg(S) of a fluorescent host is larger than that of a fluorescent dopant, but its excited triplet energy Eg(T) is not necessarily large. Therefore, the fluorescent host cannot be simply used as a host material (phosphorescent host) for a phosphorescent layer.

For example, an anthracene derivative is well known as a fluorescent host. However, the excited triplet energy Eg(T) of anthracene derivative is as relatively small as about 1.9 eV. Therefore, the energy transfer to a phosphorescent dopant having an emission wavelength in a visible light region of 500 to 720 nm can not be secured. Further, the anthracene derivative cannot confine the excited triplet energy within a light emitting layer.

Therefore, the anthracene derivative is unsuitable as a phosphorescent host.

Further, perylene derivatives, pyrene derivatives and naphthacene derivatives are not preferred as a phosphorescent host for the same reason.

Patent Document 3 proposes to use an aromatic hydrocarbon compound as a phosphorescent host, which has a central benzene skeleton having two aromatic substituents at its meta positions.

However, the aromatic hydrocarbon compound described in Patent Document 3 has a highly symmetric, rigid molecular structure composed of five aromatic rings which are arranged bilaterally symmetrically with respect to the central benzene skeleton. Therefore, the light emitting layer would be likely to crystallize.

Patent Documents 4 to 6 disclose organic EL devices each employing an aromatic hydrocarbon compound, and Patent Documents 7 to 9 disclose organic EL devices each employing a fluorene compound. However, these documents are completely silent about the effectiveness of these compounds as a phosphorescent host.

Patent Documents 10 to 15 describe devices which employ a phosphorescent host material comprising a fluorene compound, Patent Documents 11, 13 and 15 disclose divalent fluorene compounds characterized by benzene rings directly bonded to both ends of the fluorene ring, and Patent Document 12 discloses a compound having a fluorene structure having an aryl group at its 9-position. However, the current efficiency and the device lifetime are not satisfactory even if these compounds are used as a phosphorescent host material.

Patent Documents 8 and 16 disclose hydrocarbon compounds having a condensed polycyclic aromatic ring and a fluorene ring which are directly bonded to each other. However, these documents are completely silent about the effectiveness of an organic EL device employing these compounds in combination with a phosphorescent material. In addition, a perylene ring and a pyrene ring, which are not suitable for use in a light emitting layer of phosphorescent device because of their low triplet energy level, are exemplified in these documents as the condensed polycyclic aromatic ring. Namely, these documents fail to teach materials which are effective for a phosphorescent device.

Patent Document 17 discloses a host material for phosphorescent device which essentially includes two or more fluorene rings and a naphthalene ring. Patent Document 18 discloses a material in which a divalent fluorene is bonded to a substituted phenanthrene ring and a benzene ring or other condensed polycyclic aromatic rings.

PRIOR ART DOCUMENTS

Patent Documents

Patent document 1: US 2002/182441
Patent document 2: WO 2005/112519
Patent document 3: JP 2003-142267A
Patent document 4: WO 2007/046658
Patent document 5: JP 2005-197262A
Patent document 6: JP 2004-75567A
Patent document 7: JP 2007-314512A
Patent document 8: JP 2004-043349A
Patent document 9: JP 2007-314506A
Patent document 10: JP 2004-083481A
Patent document 11: JP 2006-124373A
Patent document 12: JP 2007-016237A
Patent document 13: JP 2007-302650A
Patent document 14: JP 2007-332127A
Patent document 15: JP 2008-222589A
Patent document 16: JP 2004-042485A
Patent document 17: JP 2009-108014A
Patent document 18: US 2008/100207

DISCLOSURE OF THE INVENTION

Problems to be Solved by the Invention

As described above, a host material which can efficiently transfer the energy to a phosphorescent material and which have a practically long lifetime is not known, and the practical application of device employing a phosphorescent material have not been advanced.

An object of the present invention is to provide a phosphorescent organic EL device having high efficiency and long lifetime and a material for use in the production of the organic electroluminescence device.

Means for Solving the Problems

As a result of extensive research for achieving the above object, the inventors have found that the driving voltage can be reduced, the driving lifetime can be improved, and the lifetime of device can be drastically improved, as compared with known compounds mentioned above, by a compound in which two or more condensed polycyclic aromatic rings are serially bonded to a fluorene skeleton, a dibenzofuran skeleton or a dibenzothiophene skeleton or a compound in which a group containing different condensed polycyclic aromatic rings is bonded to a fluorene skeleton, a dibenzofuran skeleton or a dibenzothiophene skeleton at a position capable of extending the conjugated system.

Thus, the present invention provides the following materials for organic electroluminescence device and organic electroluminescence devices.

1. A material for organic electroluminescence device represented by the following formula (A-1):

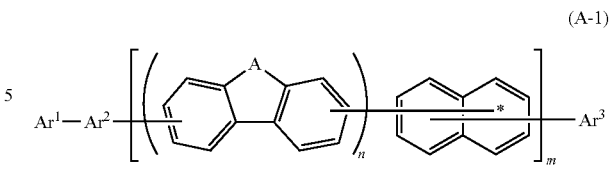

wherein $Ar^1$ and $Ar^3$ each independently represent a hydrogen atom, a heavy hydrogen atom, a residue of a substituted or unsubstituted benzene ring, or a residue of a substituted or unsubstituted condensed aromatic hydrocarbon ring selected from a substituted or unsubstituted naphthalene ring, a substituted or unsubstituted chrysene ring, a substituted or unsubstituted phenanthrene ring, a substituted or unsubstituted benzophenanthrene ring, a substituted or unsubstituted dibenzophenanthrene ring, a substituted or unsubstituted triphenylene ring, a substituted or unsubstituted benzo[a]triphenylene ring, a substituted or unsubstituted benzochrysene ring, a substituted or unsubstituted fluoranthene ring, a substituted or unsubstituted benzo[b]fluoranthene ring, and a substituted or unsubstituted picene ring;

$Ar^2$ represents a residue of a substituted or unsubstituted benzene ring, a residue of substituted or unsubstituted naphthalene ring, or a residue of substituted or unsubstituted phenanthrene ring;

A represents O, S, or $CR^1R^2$, wherein $R^1$ and $R^2$ each independently represent a substituted or unsubstituted alkyl group having 1 to 20 carbon atoms, a substituted or unsubstituted cycloalkyl group having 3 to 20 ring carbon atoms, a substituted or unsubstituted aralkyl group having 7 to 24 carbon atoms, or a substituted or unsubstituted silyl group having 3 to 20 carbon atoms;

n represents an integer of 1 to 3 and m represents an integer of 1 or 2; and when n is 2 or more, the following formula (A-1-a);

in $(\ )_n$ may be the same or different.

2. The material for organic electroluminescence device of 1, which is represented by the following formula (A-2);

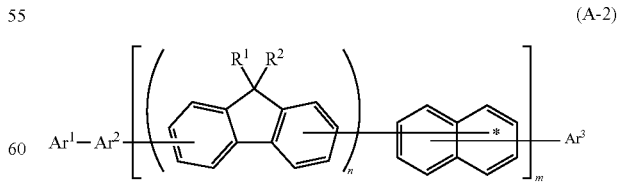

wherein $Ar^1$, $Ar^2$, $Ar^3$, $R^1$, $R^2$, n, and m are the same as defined above.

3. The material for organic electroluminescence device of 1, which is represented by the following formula (A-3);

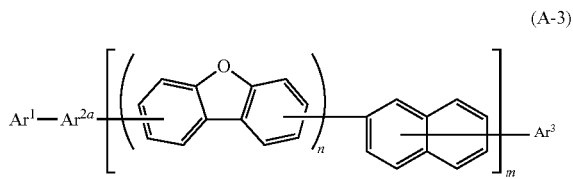

(A-3)

wherein Ar¹, Ar³, n, and m are the same as defined above, $Ar^{2a}$ represents a residue of a substituted or unsubstituted benzene ring or a residue of a substituted or unsubstituted phenanthrene ring, and Ar³ is bonded to 6-position or 7-position of the naphthalene ring residue which is bonded to the dibenzofuran ring residue.

4. The material for organic electroluminescence device of 1, which is represented by the following formula (A-4):

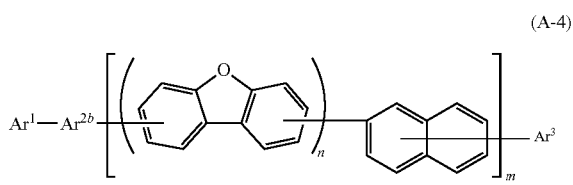

(A-4)

wherein Ar¹, Ar³, n, and m are the same as defined above; $Ar^{2b}$ represents a residue of a substituted or unsubstituted naphthalene ring; when $Ar^{2b}$ is bonded to the dibenzofuran ring residue at 2-position of $Ar^{2b}$, one of Ar¹ and Ar³ is bonded to 6-position or 7-position of the naphthalene ring residue to which it is bonded; when $Ar^{2b}$ is bonded to the dibenzofuran ring residue at a position other than 2-position of $Ar^{2b}$, Ar³ is bonded to 6-position or 7-position of the naphthalene ring residue; and Ar¹ and Ar³ are not hydrogen at the same time.

5. The material for organic electroluminescence device of 1, which is represented by the following formula (A-5);

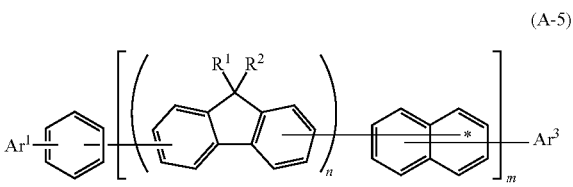

(A-5)

wherein Ar¹, Ar³, R¹, R², n, and m are the same as defined above.

6. The material for organic electroluminescence device of 1 to 4, wherein when any one of Ar¹, Ar², $Ar^{2a}$, $Ar^{2b}$, Ar³, R¹, and R² in formulae (A-1) to (A-5) has one or more substituents, the substituent is an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom or an aryl group having 6 to 22 ring carbon atoms.

7. A material for organic electroluminescence device represented by the following formula (B-1);

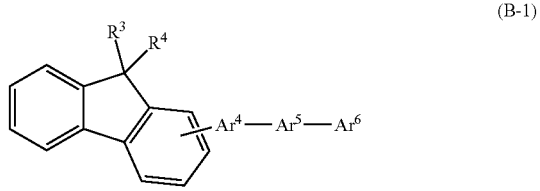

(B-1)

wherein R³ and R⁴ each independently represent a hydrogen atom inclusive of a heavy hydrogen atom, an alkyl group having 1 to 10 carbon atoms or an aryl group having 6 to 12 ring carbon atoms; Ar⁴ is a residue of a condensed polycyclic aromatic hydrocarbon ring having 10 to 22 ring carbon atoms; Ar⁵ is a benzene ring or a residue of a condensed polycyclic aromatic hydrocarbon ring having 10 to 22 ring carbon atoms;

Ar⁶ is a hydrogen atom inclusive of a heavy hydrogen atom, a benzene ring or a residue of a condensed polycyclic aromatic hydrocarbon ring having 10 to 22 ring carbon atoms; and R³, R⁴, Ar⁴, Ar⁵ and Ar⁶ each may be independently substituted;

provided that each of Ar⁴, Ar⁵ and Ar⁶ does not have an anthracene, pyrene, perylene, triphenylene, naphthacene and pentacene skeleton; and the material does not include the following compounds (1) to (6):

(1) a compound wherein Ar⁴ is any of a naphthalene ring, a phenanthrene ring, a chrysene ring, a benzoanthracene ring and a fluoranthene ring and Ar⁵ is a fluorene ring;

(2) a compound wherein Ar⁴ is a naphthalene ring, Ar⁵ is a benzene ring, and Ar⁶ is a benzene ring or a hydrogen atom;

(3) (i) a compound wherein Ar⁴ is a naphthalene-2,6-diyl group, Ar⁵ is a β-naphthyl group, and Ar⁶ is a hydrogen atom, and (ii) a compound wherein Ar⁴ is a naphthalene-2,6-diyl group, Ar⁵ is a naphthalene-2,6-diyl group, and Ar⁶ is a β-naphthyl group;

(4) a compound wherein Ar⁴ is a fluorene ring and Ar⁵ is a benzene ring, a fluorene ring or a fluoranthene ring, and a compound wherein Ar⁴ is a fluorene ring and Ar⁶ is a hydrogen atom or a β-naphthyl group;

(5) a compound wherein Ar⁴ is a phenanthrene ring or a fluoranthene ring, Ar⁵ is a benzene ring, and Ar⁶ is a hydrogen atom; and (6) a compound wherein Ar⁴ is a benzene ring, a biphenyl ring, a naphthalene ring, a binaphthalene ring or a fluorene ring and Ar⁵ is a fluoranthene ring.

8. The material for organic electroluminescence device of 7, wherein Ar⁴ is a naphthalene ring, Ar⁵ is a benzene ring, and Ar⁶ is a residue of a condensed polycyclic aromatic hydrocarbon ring having 10 to 22 ring carbon atoms.

9. The material for organic electroluminescence device of 7, wherein Ar⁴ is a naphthalene ring, Ar⁵ is a naphthalene ring, and Ar⁶ is a residue of a condensed polycyclic aromatic hydrocarbon ring having 11 to 22 ring carbon atoms, provided that the material does not include a compound wherein Ar⁴ is a naphthalene-2,6-diyl group, Ar⁵ is a naphthalene-2,6-diyl group, and Ar⁶ is a β-naphthyl group.

10. The material for organic electroluminescence device of 7, wherein Ar⁴ is a naphthalene ring, Ar⁵ is a residue of a condensed polycyclic aromatic hydrocarbon ring having 11 to 22 ring carbon atoms, and Ar⁶ is a hydrogen atom inclusive of a heavy hydrogen atom, provided that the material does not include the following compounds (1) to (3):

(1) a compound wherein Ar⁴ is a naphthalene-2,6-diyl group, Ar⁵ is a β-naphthyl group, and Ar⁶ is a hydrogen atom;
(2) a compound wherein Ar⁴ is a naphthalene-1,4-diyl group or a naphthalene-1,5-diyl group, Ar⁵ is a fluoranthene ring, and Ar⁶ is a hydrogen atom; and (3) a compound wherein Ar⁴ is a naphthalene-1,4-diyl group, a naphthalene-2,6-diyl group, or a naphthalene-2,8-diyl group, Ar⁵ is a fluorene ring, and Ar⁶ is a hydrogen atom.

11. The material for organic electroluminescence device of 7, which does not include the following compounds:

2-251

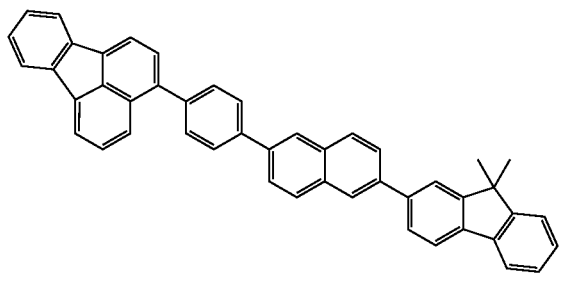

2-252

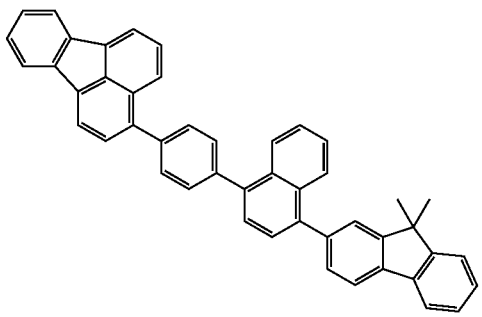

2-253

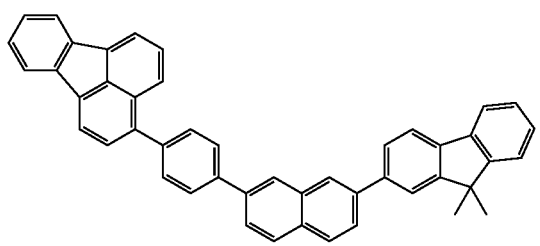

2-254

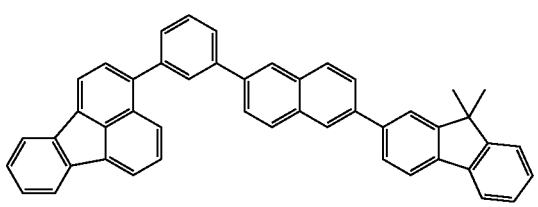

2-255

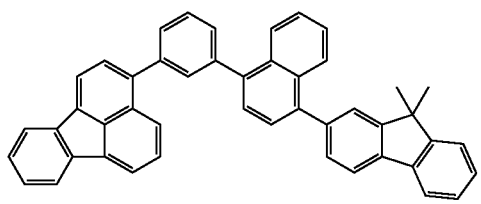

2-256

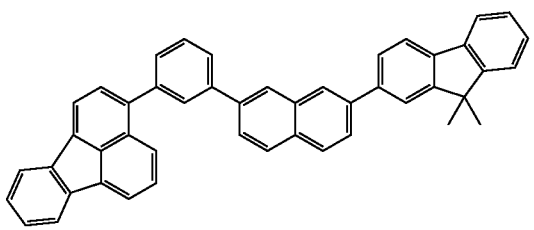

2-257

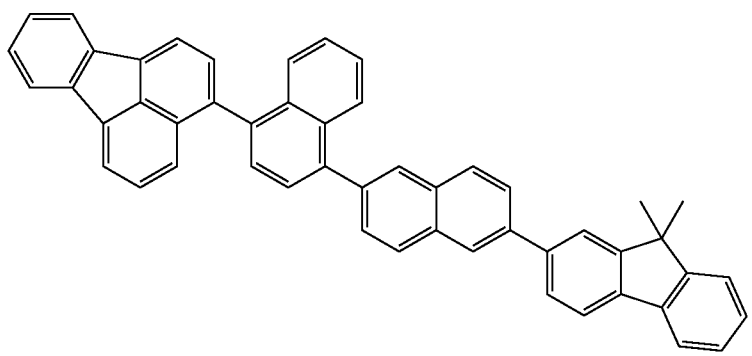

2-258
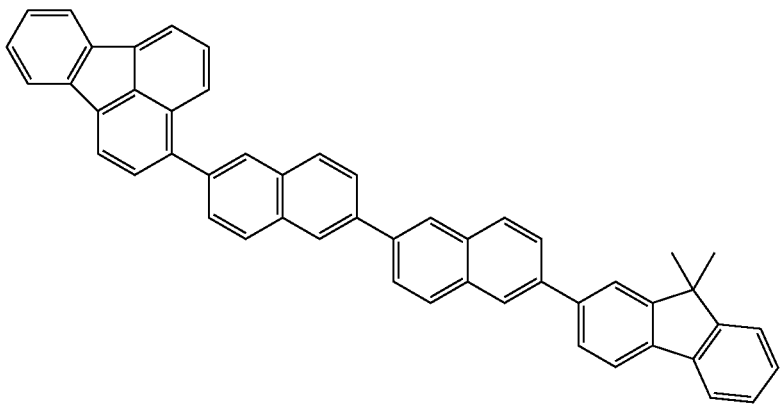
2-259
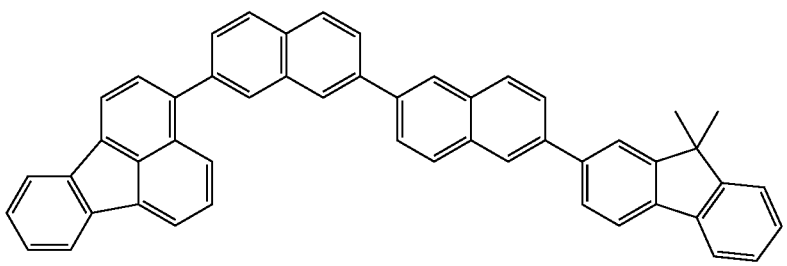
2-260
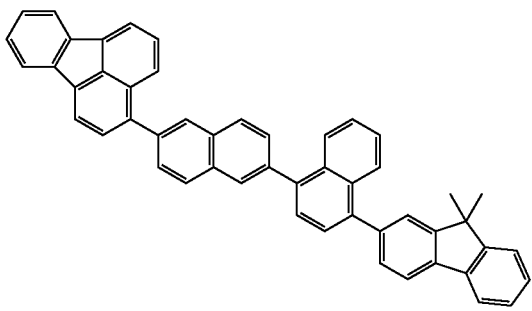
2-261
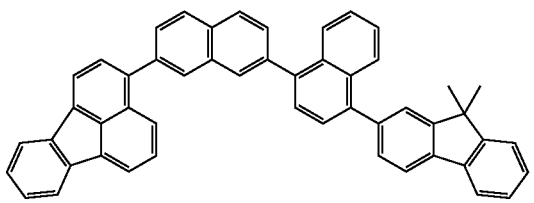
2-262
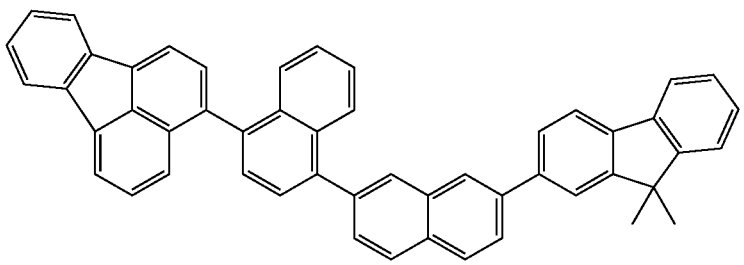
2-263
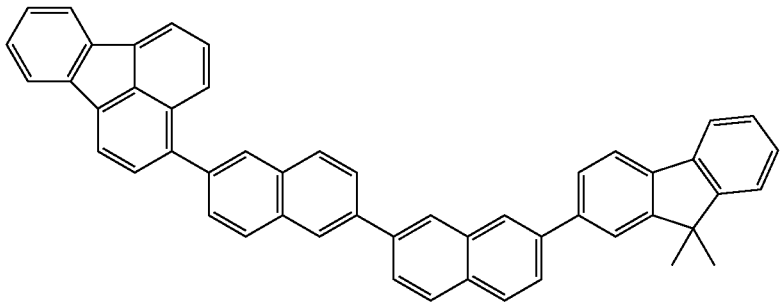

-continued
2-264
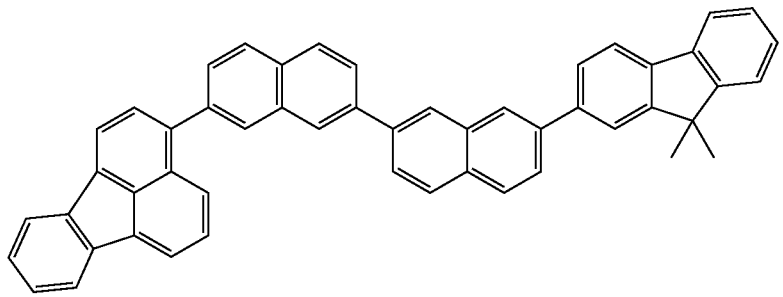
2-311
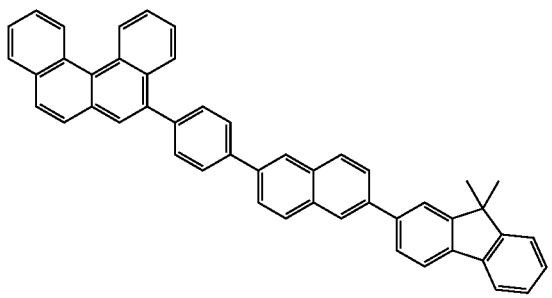
2-312
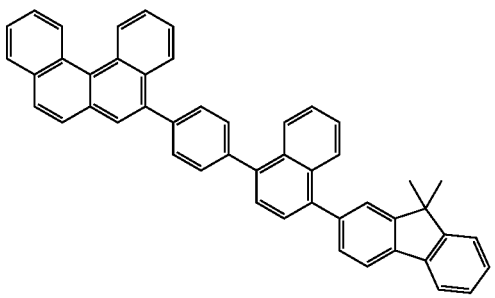
2-313
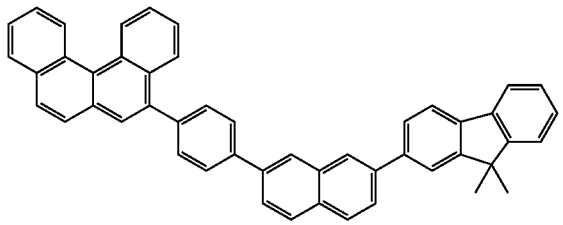
2-314
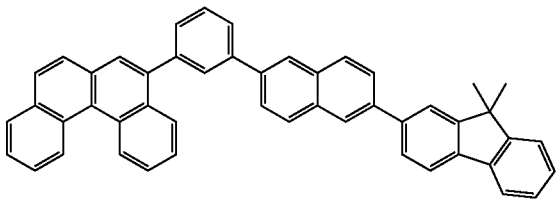
2-315
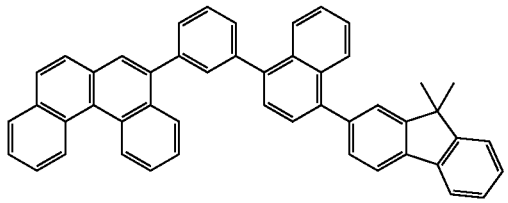
2-316
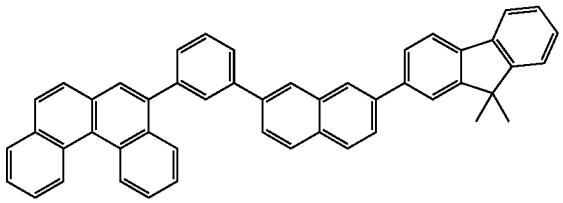
2-317
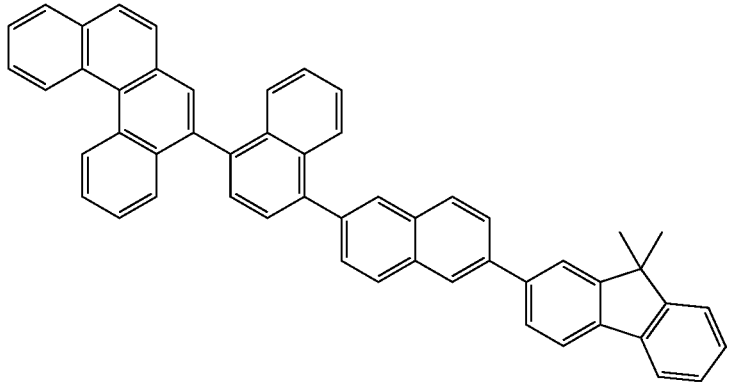

-continued
2-318
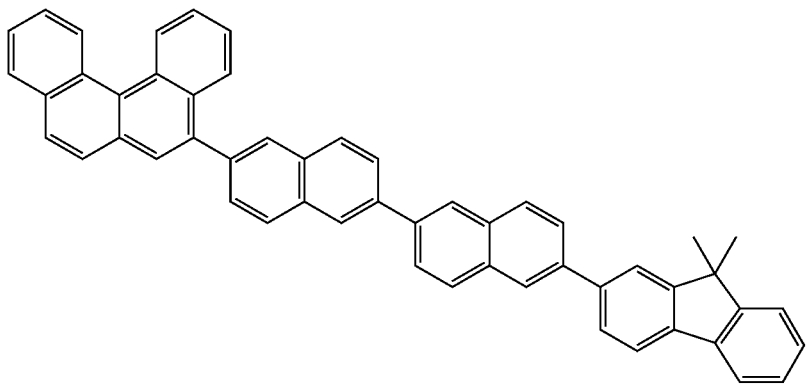
2-319
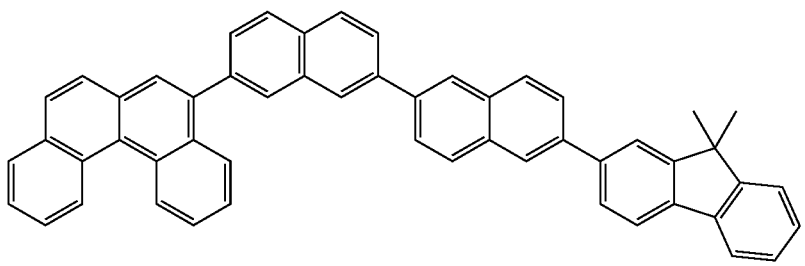
2-320     2-321
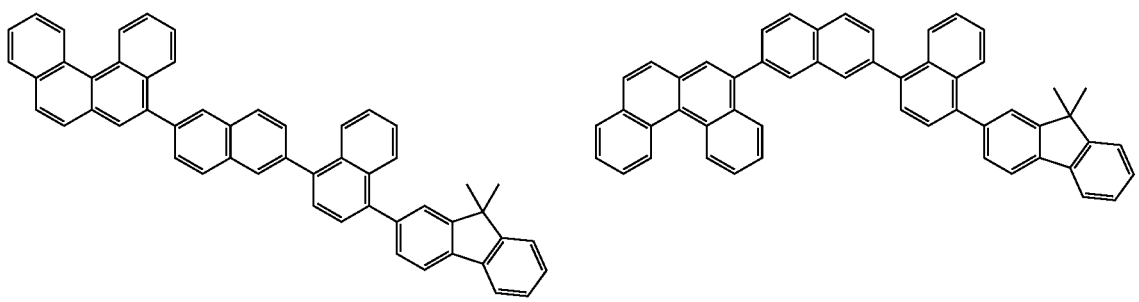
3-322
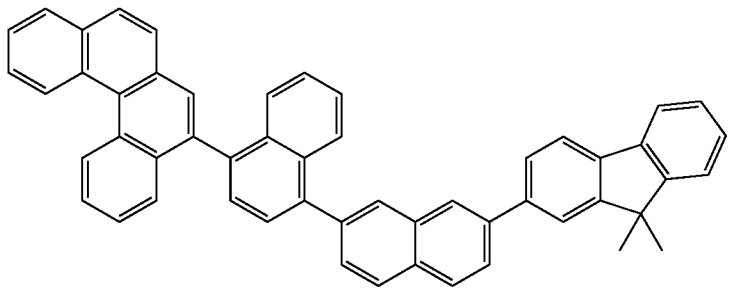
3-323
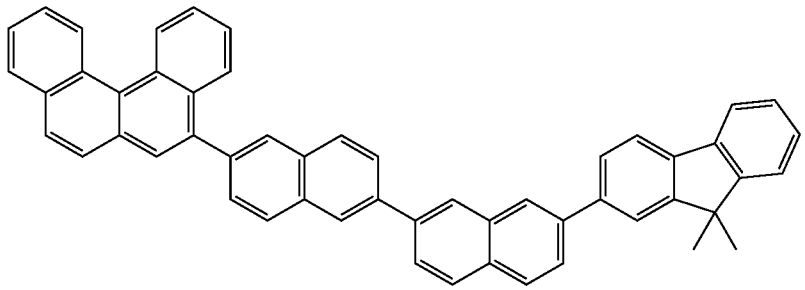

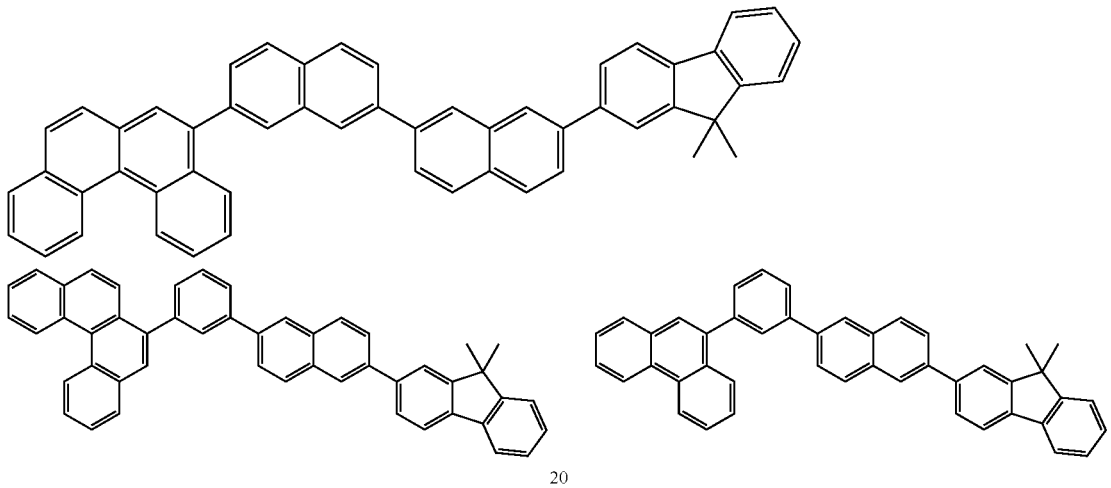

12. The material for organic electroluminescence device of 7, which is represented by the following formula (B-2):

(B-2)

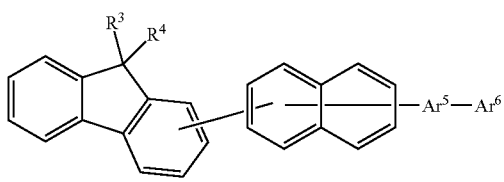

wherein $R^3$, $R^4$, $Ar^5$ and $Ar^6$ are the same as defined above.

13. The material for organic electroluminescence device of 7, which is represented by the following formula (B-3):

(B-3)

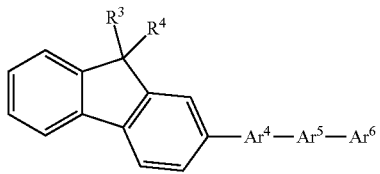

wherein $R^3$, $R^4$, $Ar^4$, $Ar^5$ and $Ar^6$ are the same as defined above.

14. The material for organic electroluminescence device of 7, which is represented by the following formula (B-4);

(B-4)

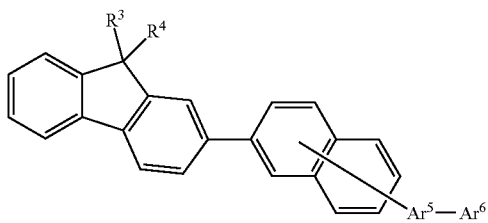

wherein $R^3$, $R^4$, $Ar^5$ and $Ar^6$ are the same as defined above.

15. The material for organic electroluminescence device of 7, wherein the condensed polycyclic aromatic hydrocarbon rings having 10 to 22 ring carbon atoms for $Ar^4$ to $Ar^6$ of formula (B-1) are independently selected from a naphthalene ring, a chrysene ring, a phenanthrene ring, a benzophenanthrene ring, a dibenzophenanthrene ring, a benzo[a]triphenylene ring, a benzochrysene ring, a fluoranthene ring, a benzo[b]fluoranthene ring, and a picene ring; and $Ar^6$ represents a hydrogen atom inclusive of a heavy hydrogen atom or the residue of the condensed polycyclic aromatic hydrocarbon ring having 10 to 22 ring carbon atoms.

16. The material for organic electroluminescence device of 14, wherein the condensed polycyclic aromatic hydrocarbon rings for $Ar^5$ and $Ar^6$ of formula (B-4) are independently selected from a naphthalene ring, a chrysene ring, a phenanthrene ring, a benzophenanthrene ring, a dibenzophenanthrene ring, a benzo[a]triphenylene ring, a benzochrysene ring, a fluoranthene ring, a benzo[b]fluoranthene ring, and a picene ring; and $Ar^6$ represents a hydrogen atom inclusive of a heavy hydrogen atom or the residue of the condensed polycyclic aromatic hydrocarbon ring having 10 to 22 ring carbon atoms.

17. The material for organic electroluminescence device of 13, wherein $R^3$ and $R^4$ in formula (B-4) each independently represent an alkyl group having 1 to 10 carbon atoms or a phenyl group.

18. The material for organic electroluminescence device of any one of 7 to 17, wherein when any one of $R^3$, $R^4$, $Ar^4$, $Ar^5$ and $Ar^6$ in formulae (B-1) to (B-4) has one or more substituents, the substituent is an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom or an aryl group having 6 to 22 ring carbon atoms.

19. A material for organic electroluminescence device represented by the following formula (C-1):

(C-1)

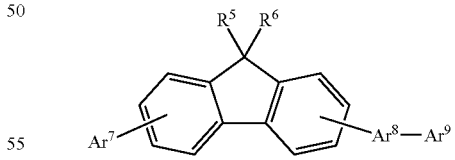

wherein $Ar^7$ to $Ar^9$ each independently represent a benzene ring or a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring and a picene ring; and $Ar^9$ may be a hydrogen atom inclusive of a heavy hydrogen atom;

$R^5$ and $R^6$ each independently represent a hydrogen atom inclusive of a heavy hydrogen atom, an alkyl group having 1 to 10 carbon atoms or an aryl group having 6 to 12 ring carbon atoms;

$R^5$, $R^6$, $Ar^7$, $Ar^8$ and $Ar^9$ each may independently have a substituent;

provided that the material dose not include the following compounds (1) to (4):
(1) a compound wherein $Ar^7$ is a benzene ring and $Ar^8$ is a benzene ring or a fluorene ring;
(2) a compound wherein $Ar^9$ is a hydrogen atom and $Ar^7$ and $Ar^8$ are residues of the same condensed aromatic hydrocarbon ring;
(3) a compound wherein $Ar^7$ and $Ar^8$-$Ar^9$ have the same structure; and
(4) a compound wherein $Ar^7$ is a β-naphthyl group or a naphthalene-2,6-diyl group, $Ar^8$ is a naphthalene-2,6-diyl group, and $Ar^9$ is a β-naphthyl group.

20. The material for organic electroluminescence device of 19, wherein $Ar^7$ is a naphthalene ring; $Ar^8$ is a benzene ring; and $Ar^9$ is a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring, and a picene ring.

21. The material for organic electroluminescence device of 19, wherein $Ar^7$ is a naphthalene ring; $Ar^8$ is a naphthalene ring; and $Ar^9$ is a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring, and a picene ring, provided that the material does not include a compound wherein $Ar^7$ is a β-naphthyl group, $Ar^8$ is a naphthalene-2,6-diyl group, and $Ar^9$ is a β-naphthyl group.

22. The material for organic electroluminescence device of 19, wherein $Ar^7$ and $Ar^8$ each independently represent a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring, and a picene ring; and $Ar^9$ is a hydrogen atom inclusive of a heavy hydrogen atom.

23. The material for organic electroluminescence device of 19, which is represented by the following formula (C-2):

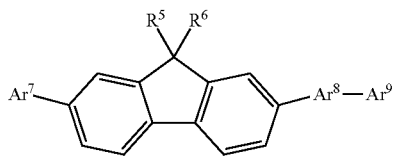

(C-2)

wherein $Ar^7$, $Ar^8$, $Ar^9$, $R^5$ and $R^6$ are the same as defined above.

24. The materials for organic electroluminescence device of any one of 19 to 23, wherein when any one of $R^5$, $R^6$, $Ar^7$, $Ar^8$ and $Ar^9$ in formulae (C-1) and (C-2) has one or more substituents, the substituent is an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom, or an aryl group having 6 to 22 ring carbon atoms.

25. The material for organic electroluminescence device of 23, which is represented by any of the following formulae (C-3) to (C-6):

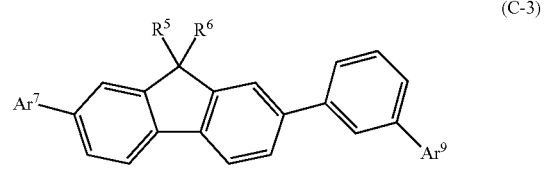

(C-3)

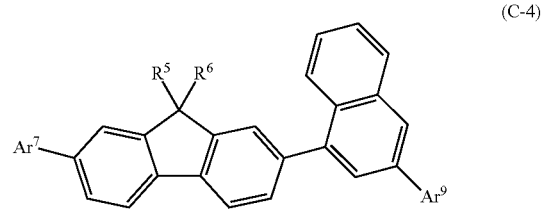

(C-4)

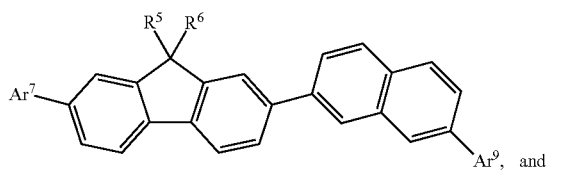

(C-5), and

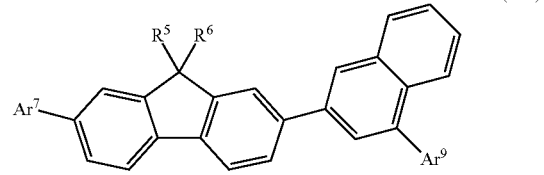

(C-6)

wherein $Ar^7$, $Ar^9$, $R^5$ and $R^6$ are the same as defined above.

26. The material for organic electroluminescence device of 25, wherein when any one of $R^5$, $R^6$, $Ar^7$ and $Ar^9$ in formulae (C-3) to (C-6) has one or more substituents, the substituent is an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom or an aryl group having 6 to 22 ring carbon atoms.

27. A material for organic electroluminescence device represented by any of the following formulae:

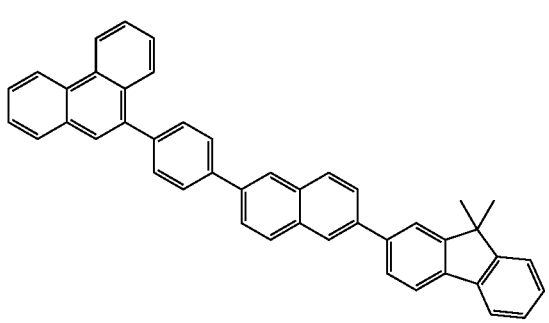

2-46

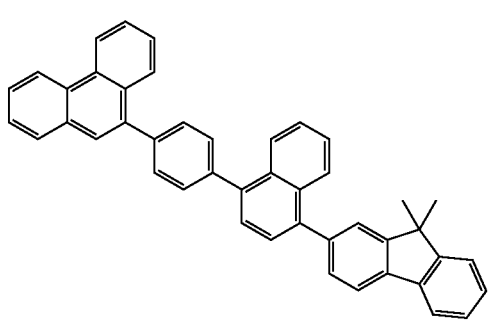

2-47

-continued
2-48
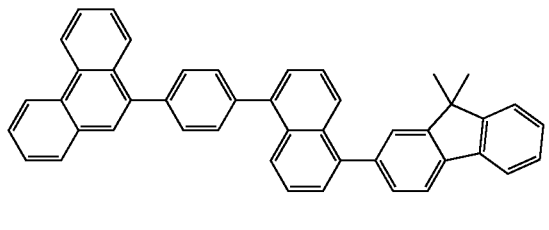
2-49
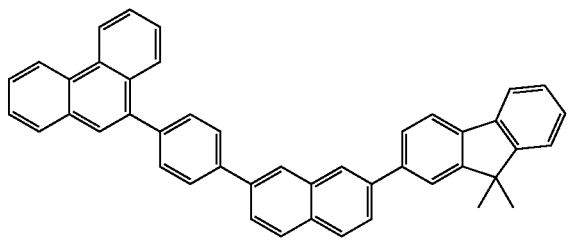
2-50
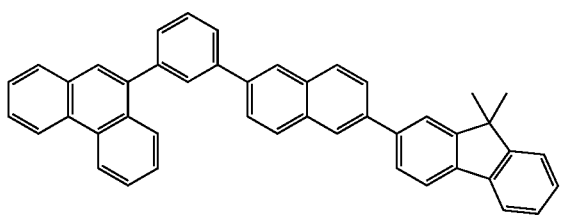
2-51
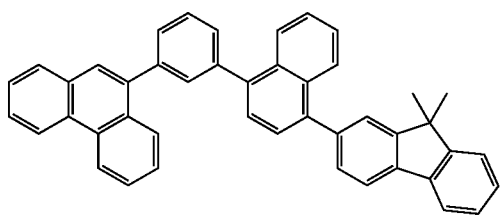
2-52
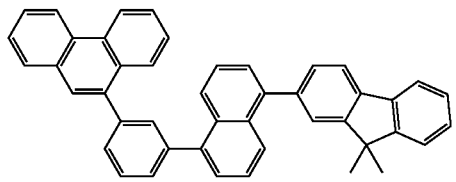
2-53
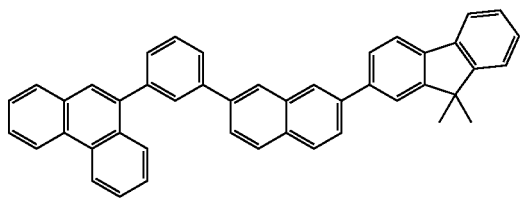
2-54
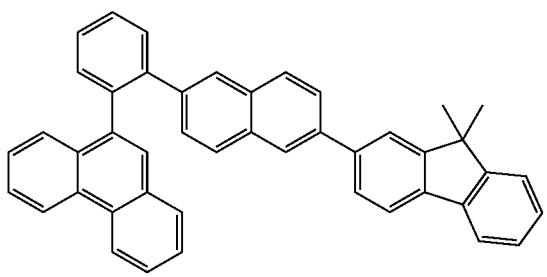
2-55
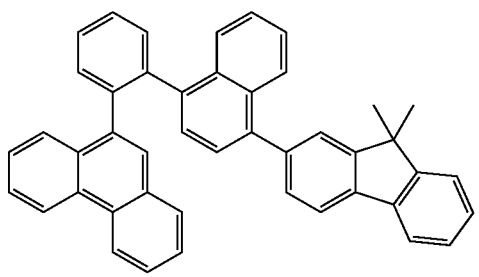
2-56
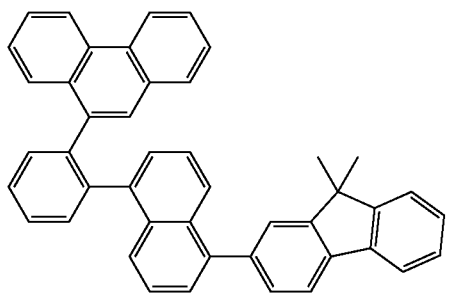
2-57
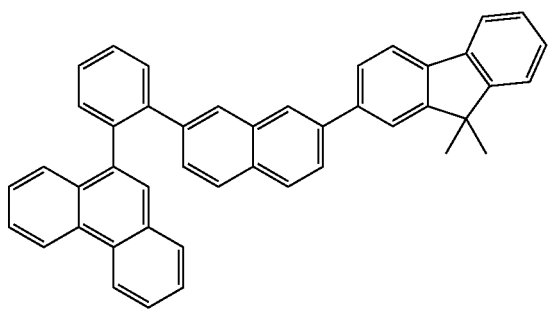

-continued
2-58
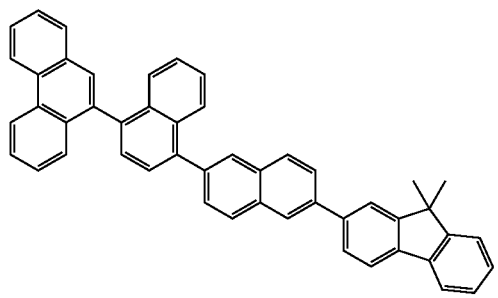
2-59
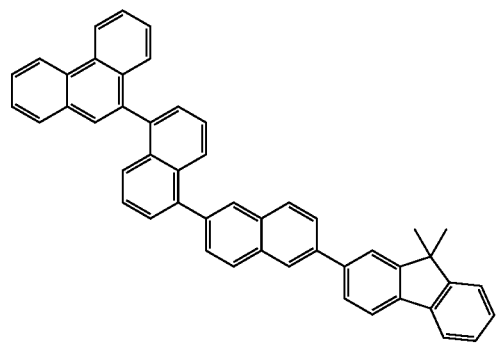
2-60
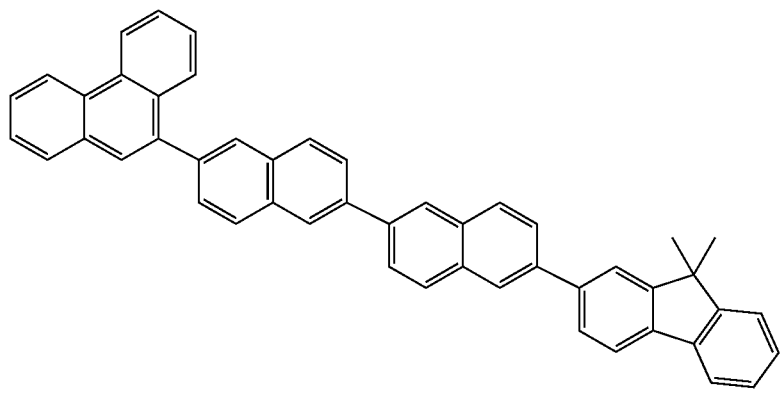
2-61
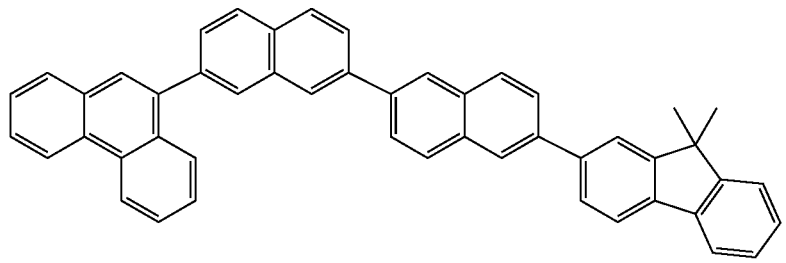
2-62
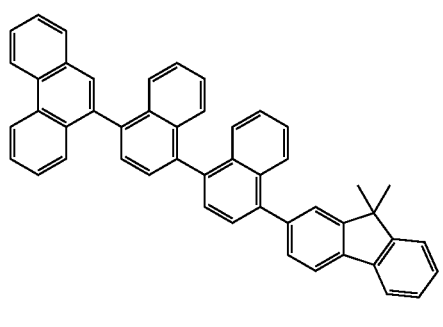
2-63
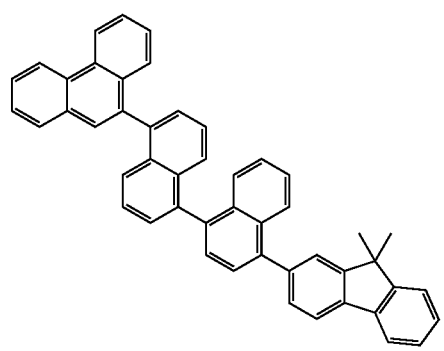

2-64
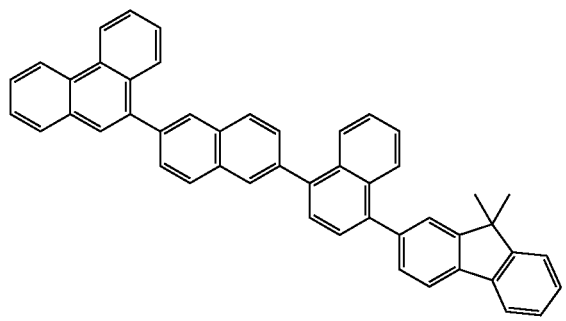
2-65
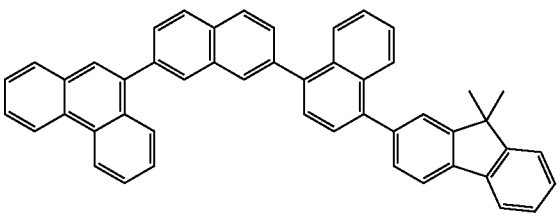
2-66
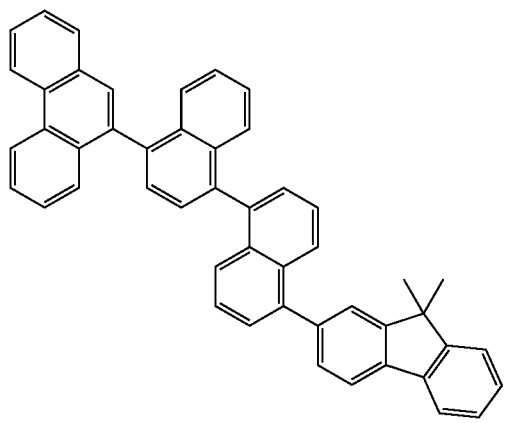
2-67
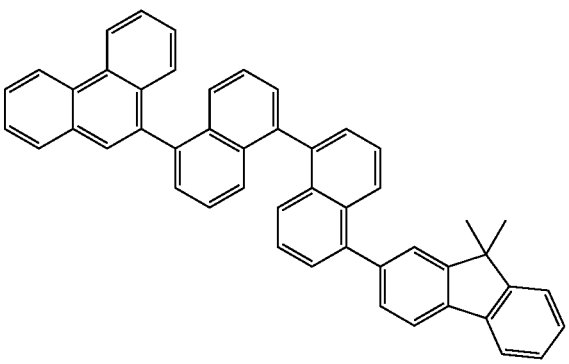
2-68
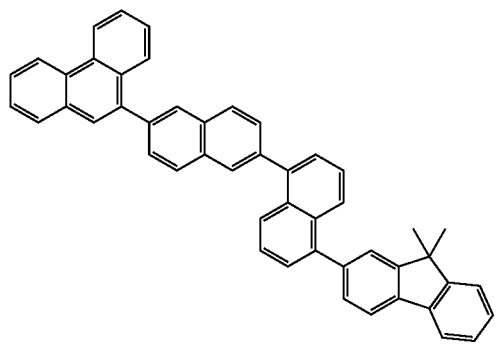
2-69
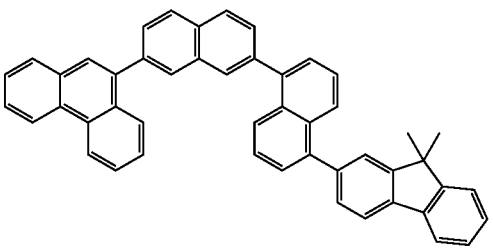
2-70
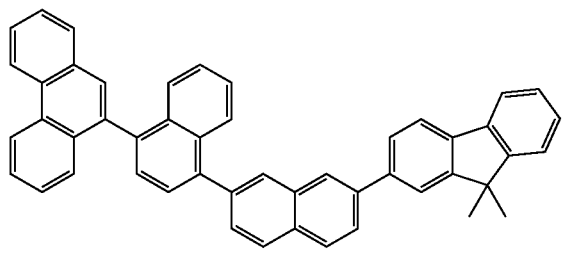
2-71
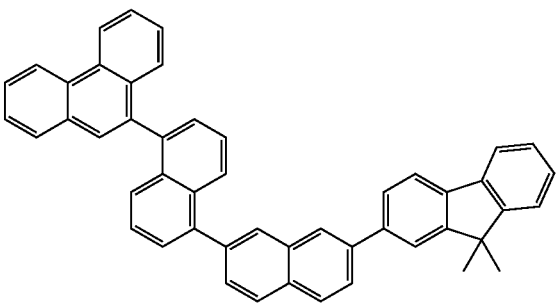

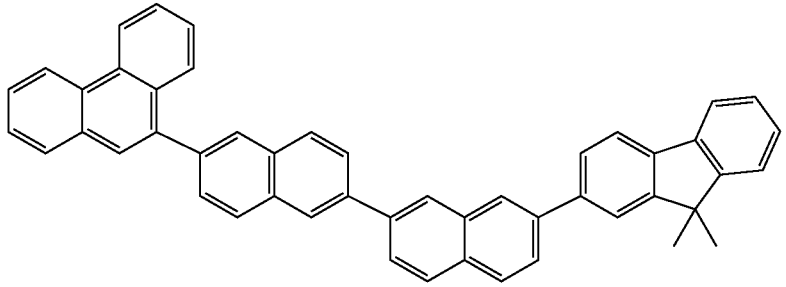
2-72
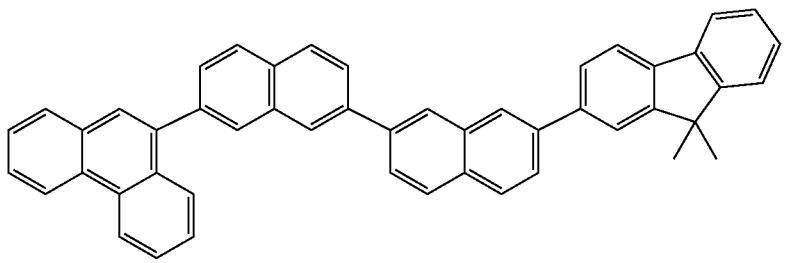
2-73
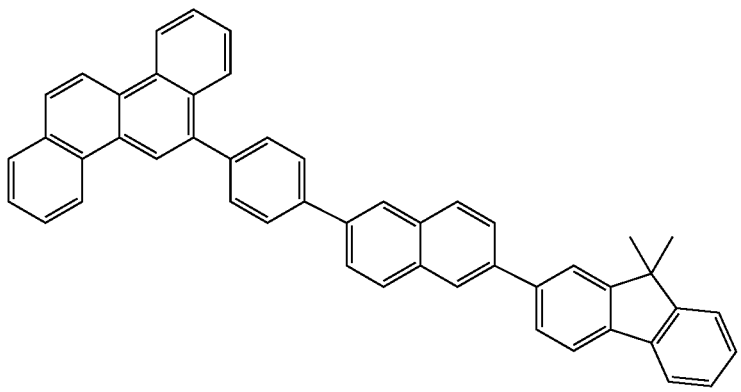
2-231
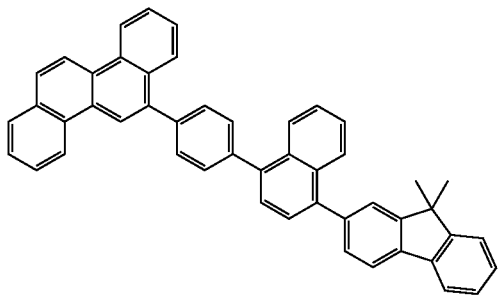
2-232
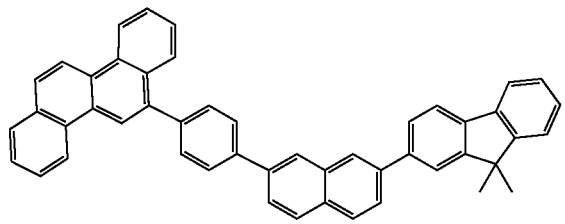
2-233
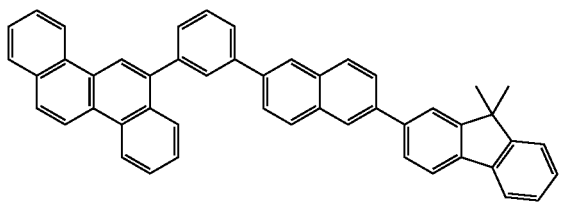
2-234
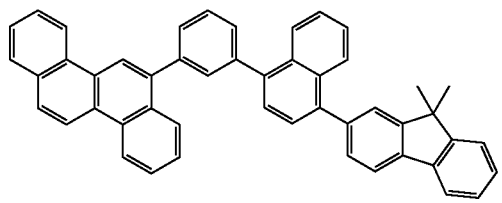
2-235

-continued
2-236
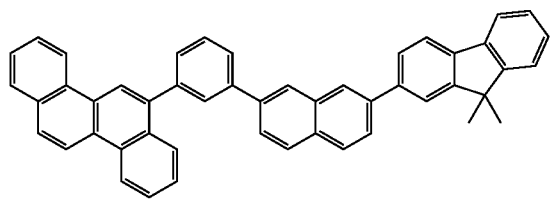
2-237
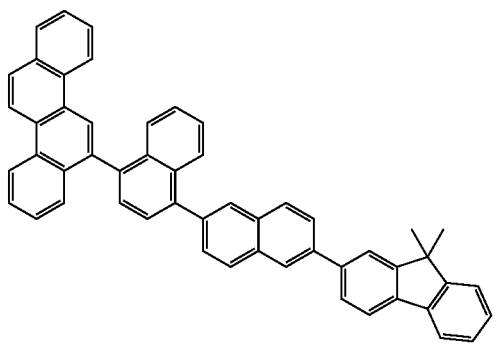
2-238
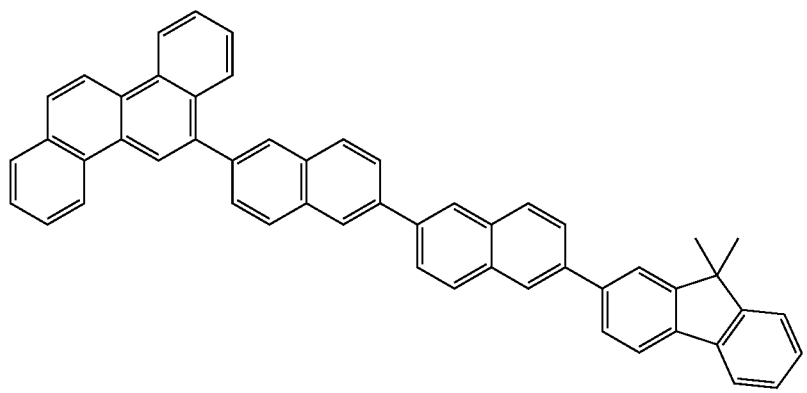
2-239
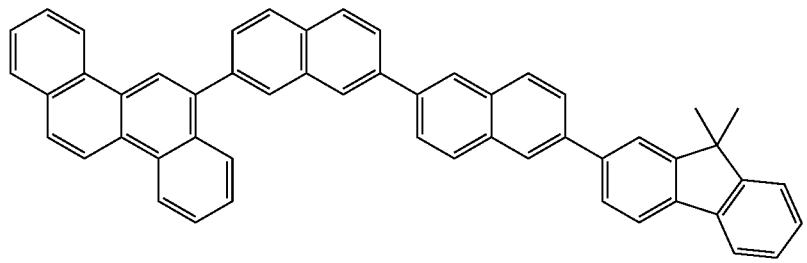
2-240
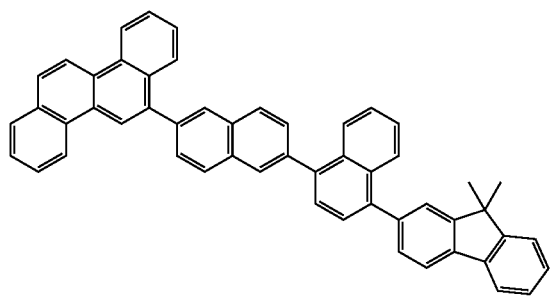
2-241
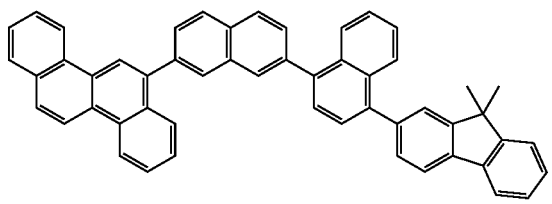

-continued
2-242
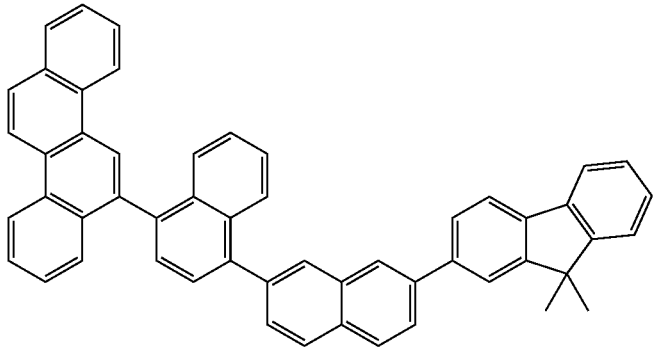
2-243
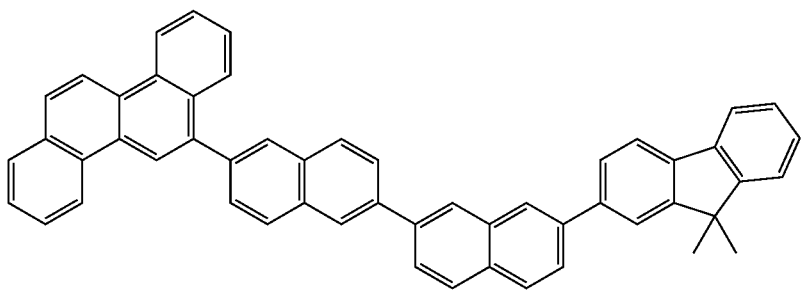
2-244
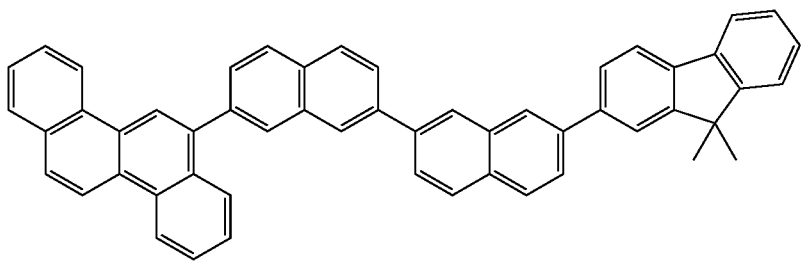
2-251
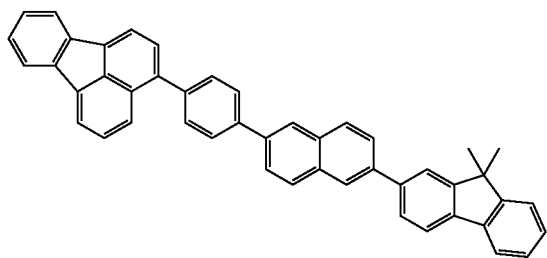
2-252
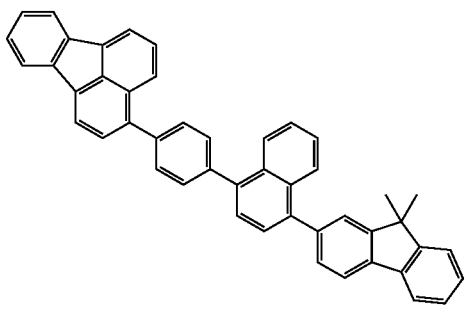
2-253
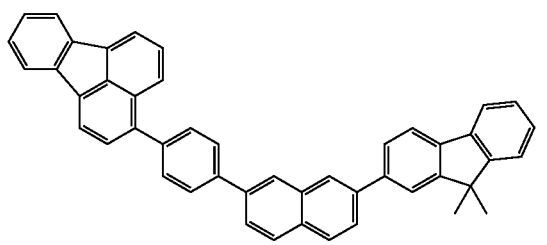
2-254
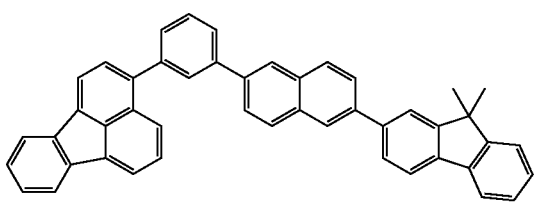

-continued
2-255
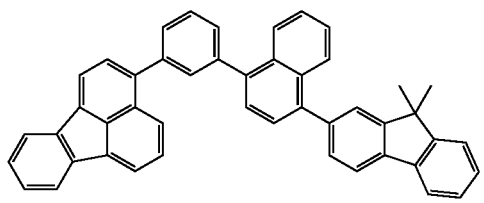
2-256
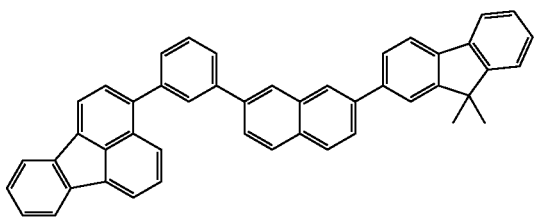
2-257
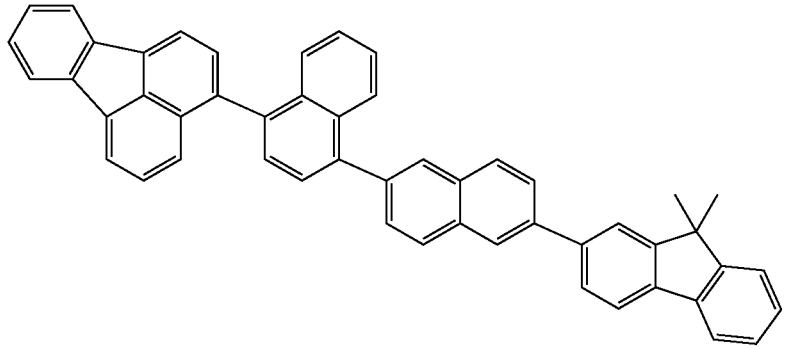
2-258
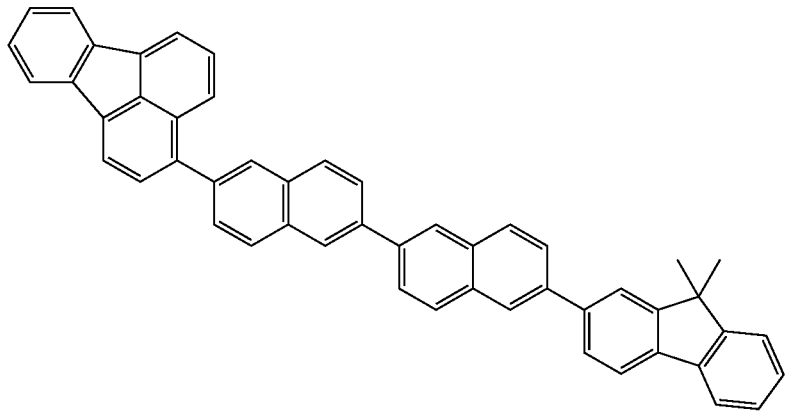
2-259
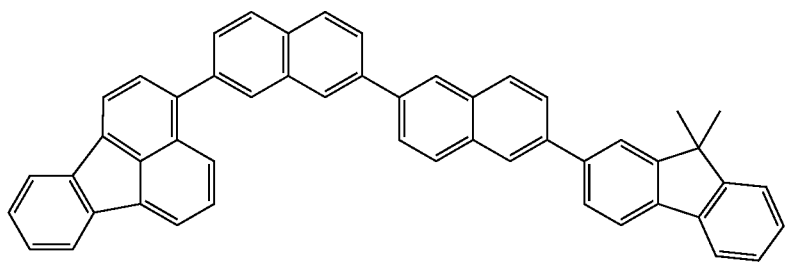
2-260
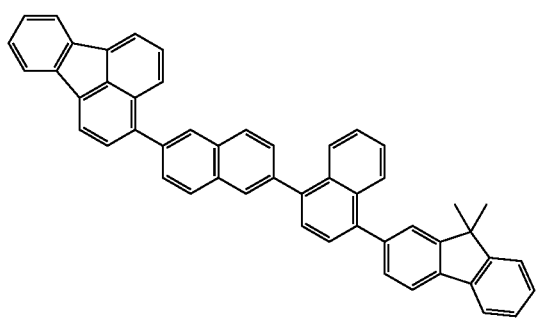
2-261
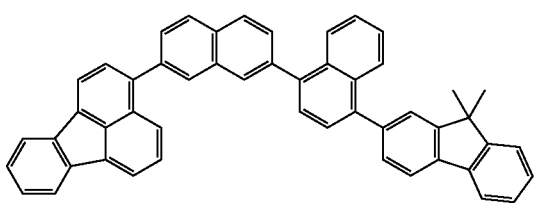

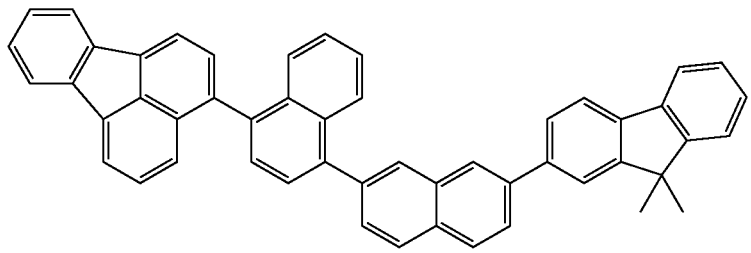

-continued
2-275
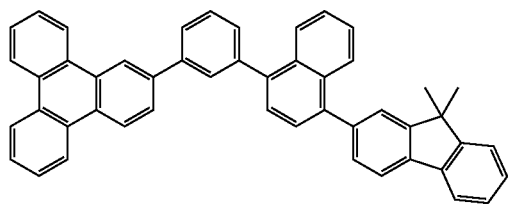
2-276
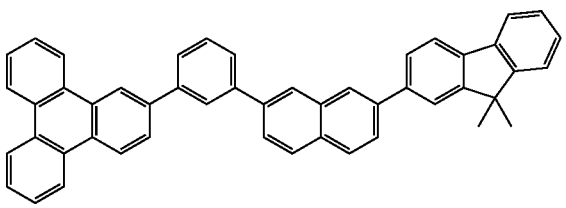
2-277
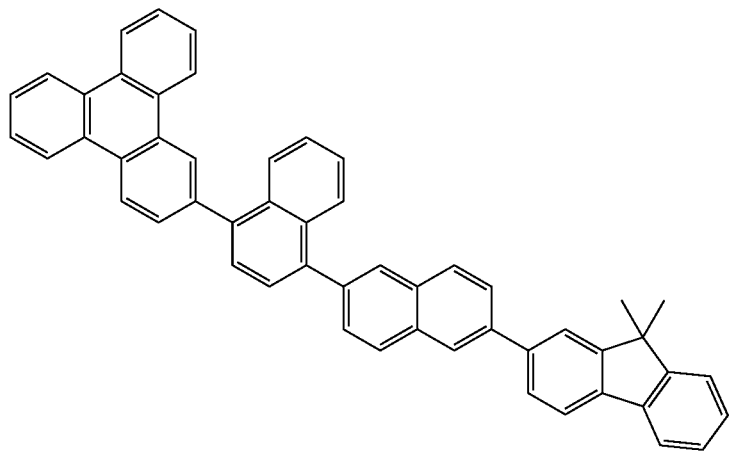
2-278
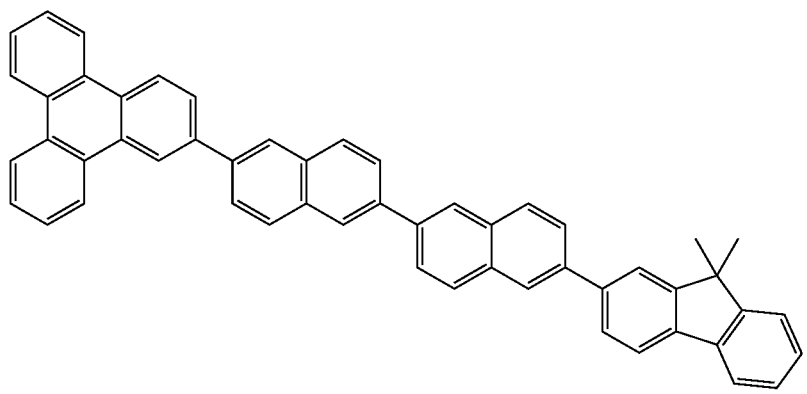
2-279
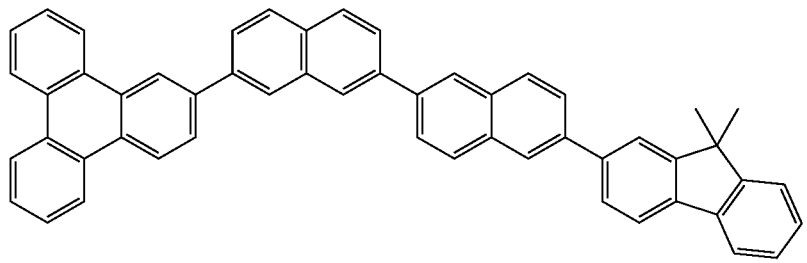

2-280
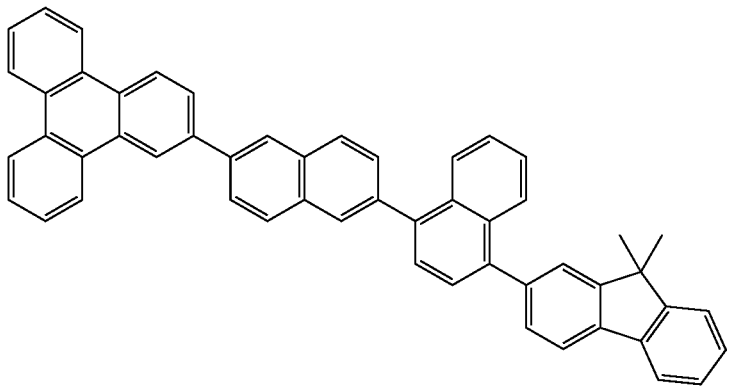
2-281
2-282
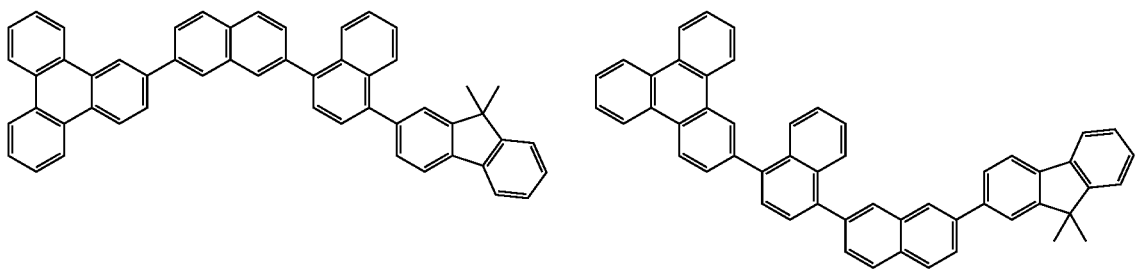
2-283
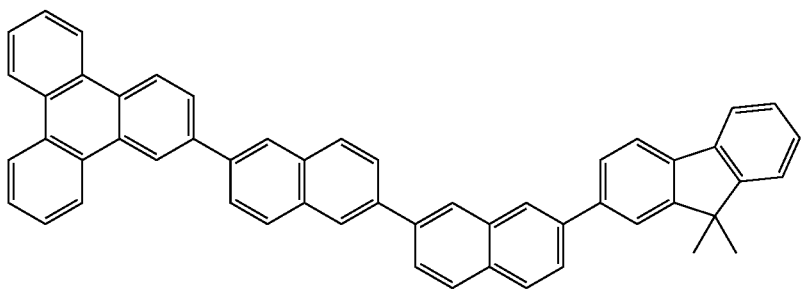
2-284
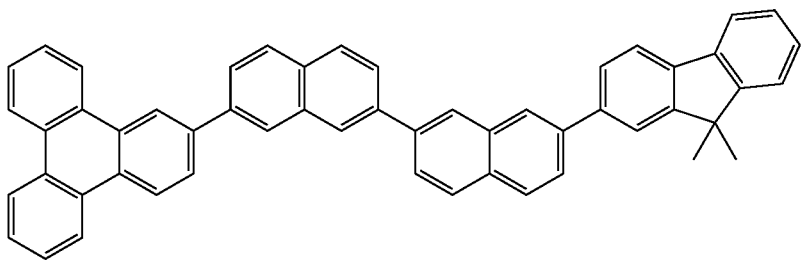
2-291
2-292
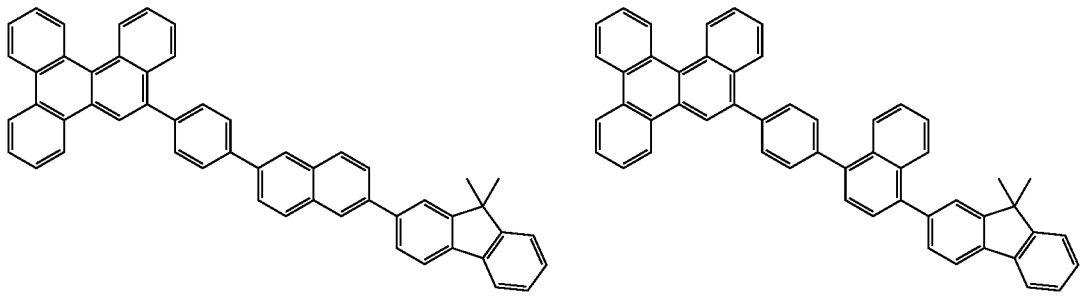

-continued
2-293
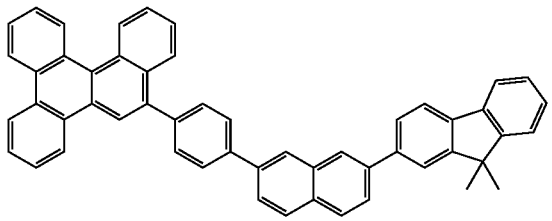
2-294
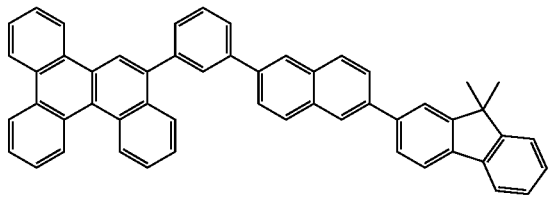
2-295
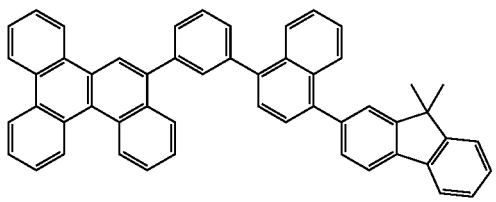
2-296
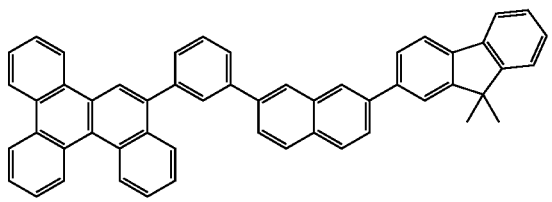
2-297
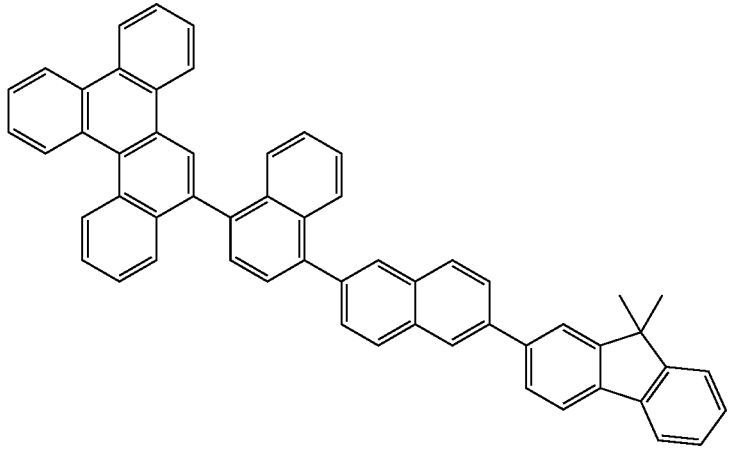
2-298
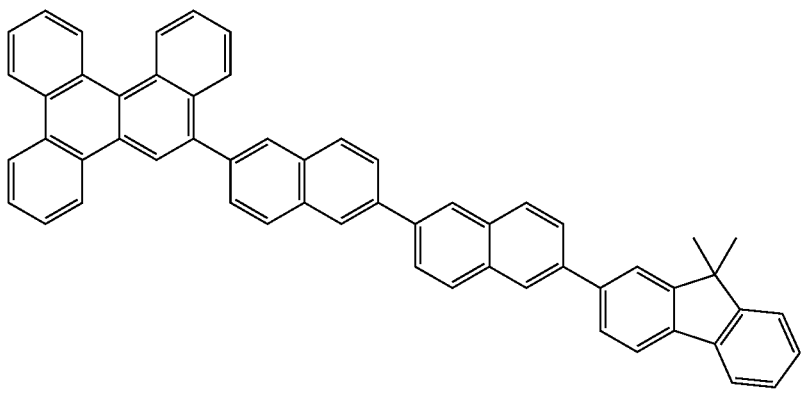
2-299
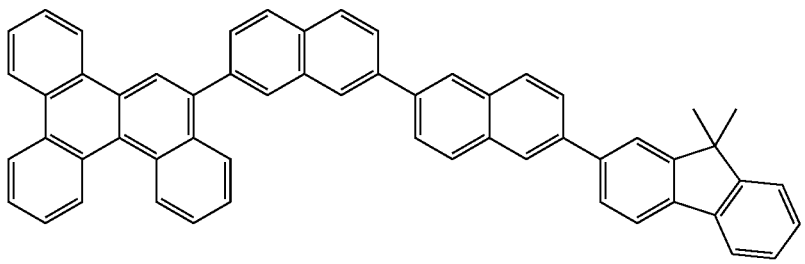

-continued
2-300
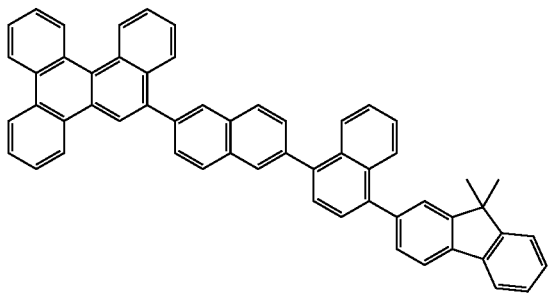
2-301
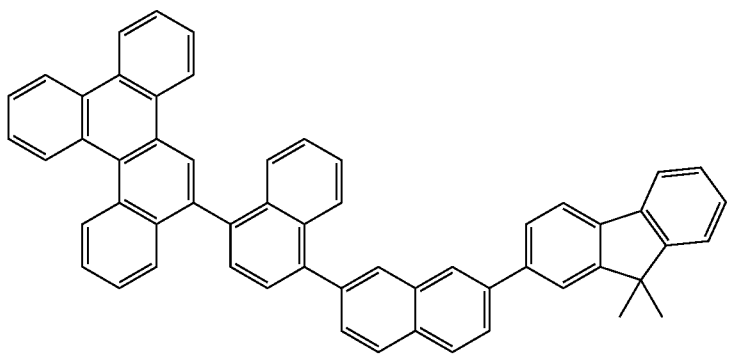
2-302
2-303
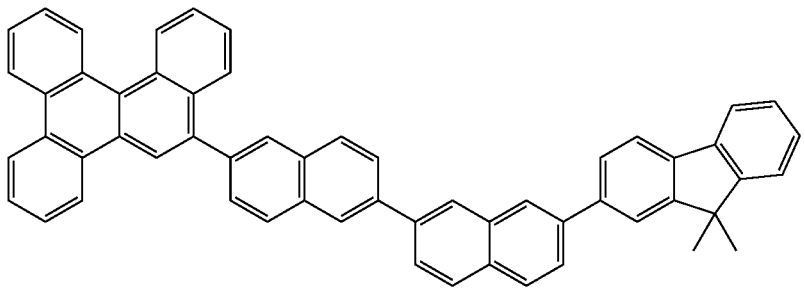
2-304
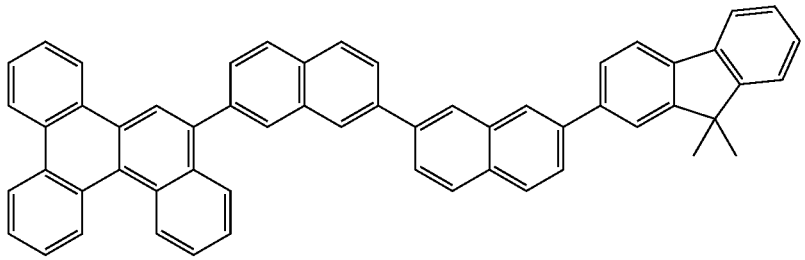
2-311
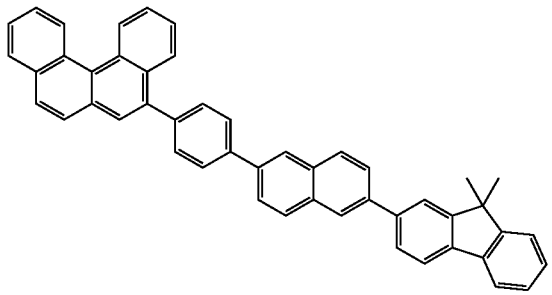
2-312
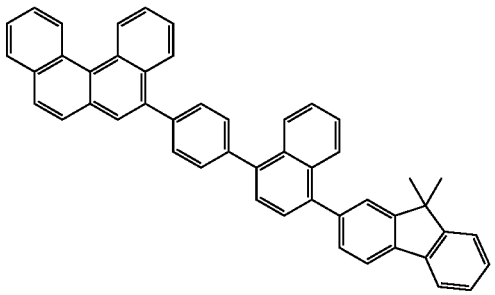

-continued
2-313
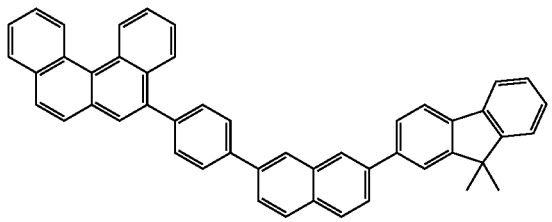
2-314
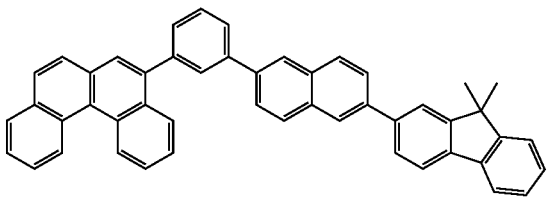
2-315
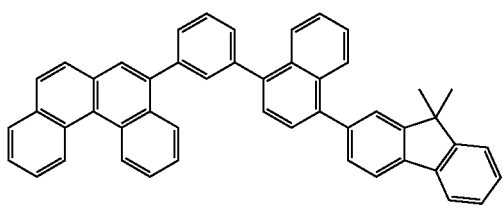
2-316
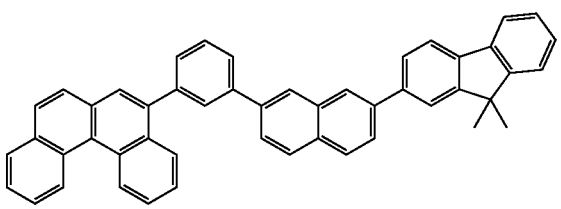
2-317
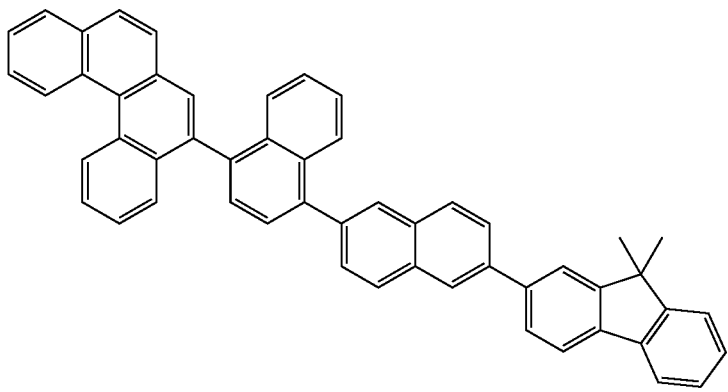
2-318
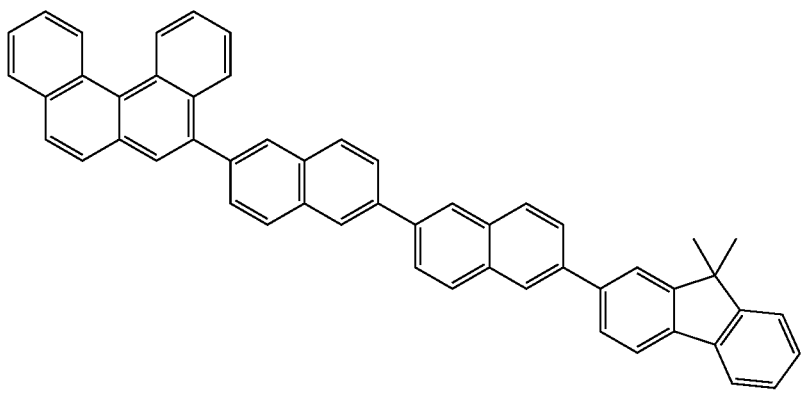
2-319
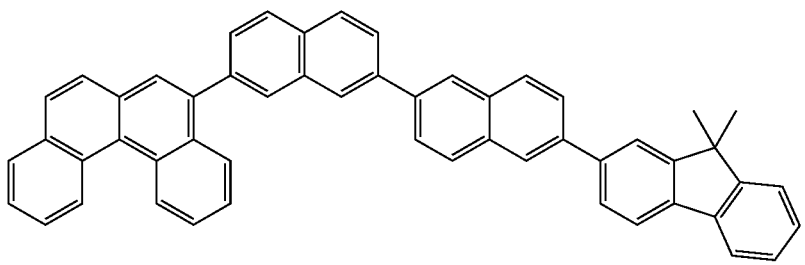

-continued
2-320
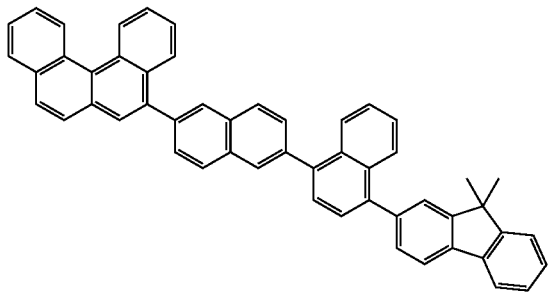
2-321
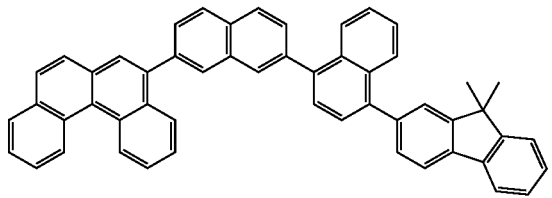
2-322
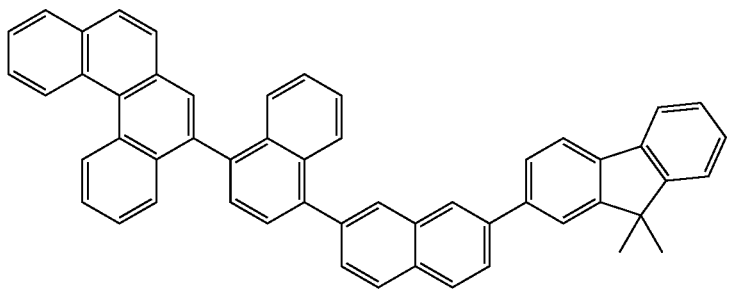
2-323
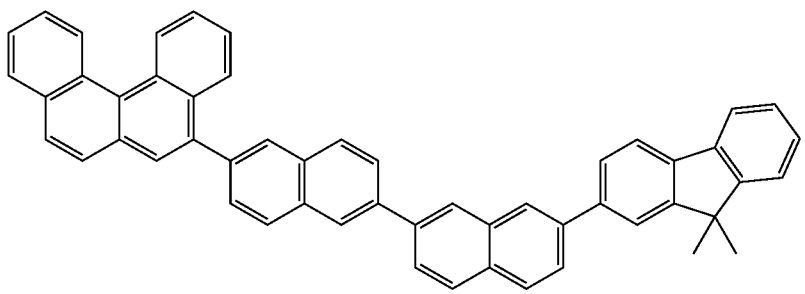
2-324
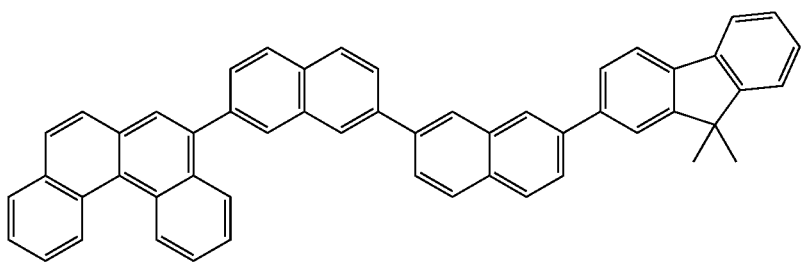
2-331
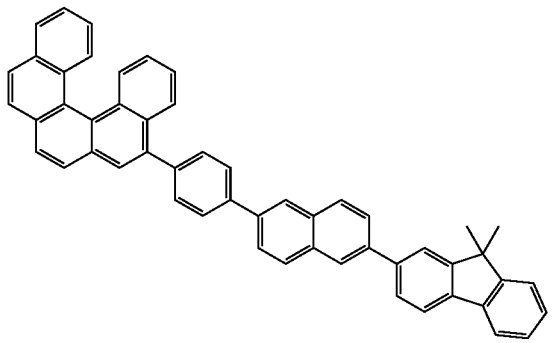
2-332
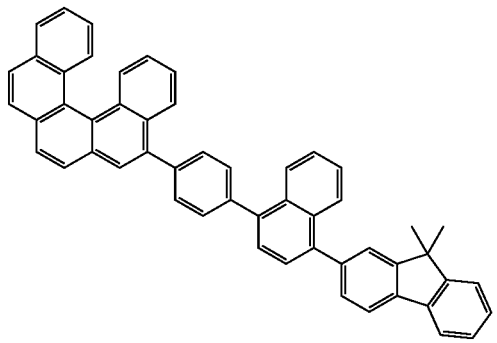

2-333
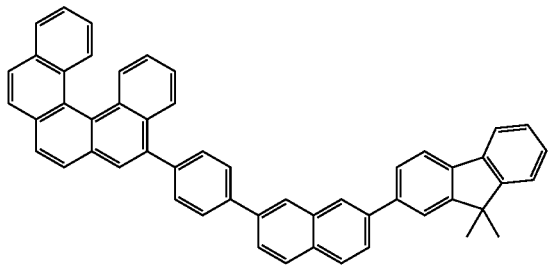
2-334
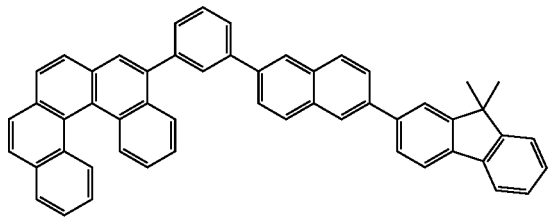
2-335
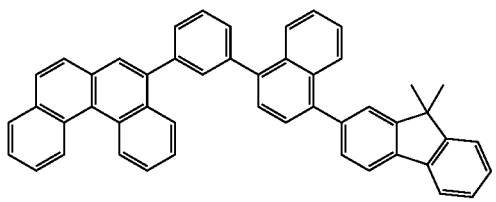
2-336
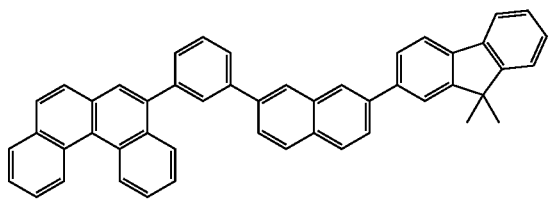
2-337
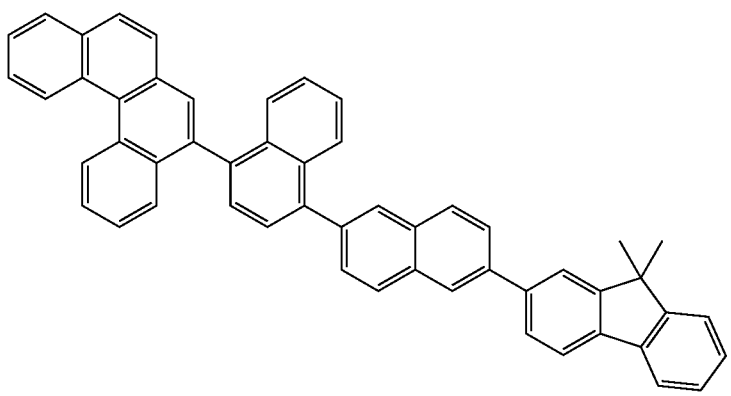
2-338
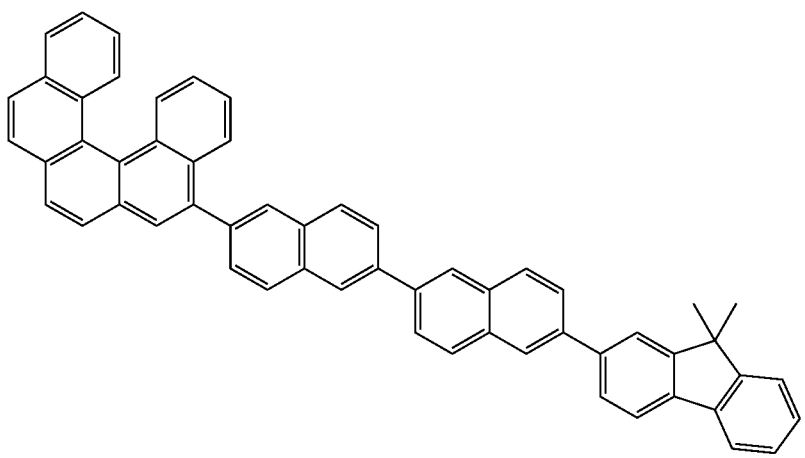

-continued
2-339
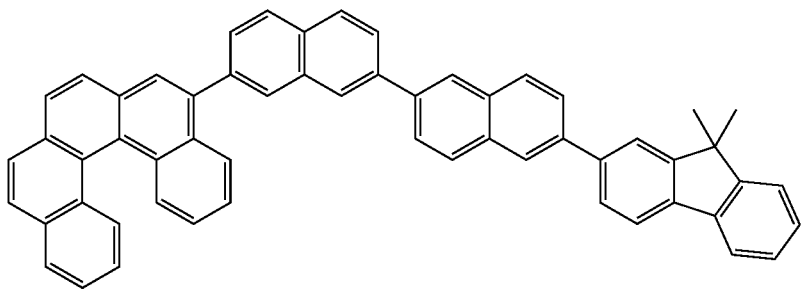
2-340
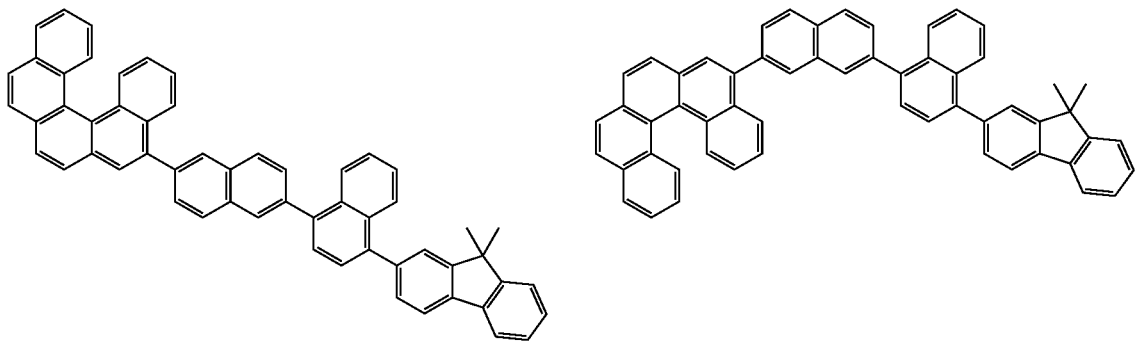
2-341
2-342
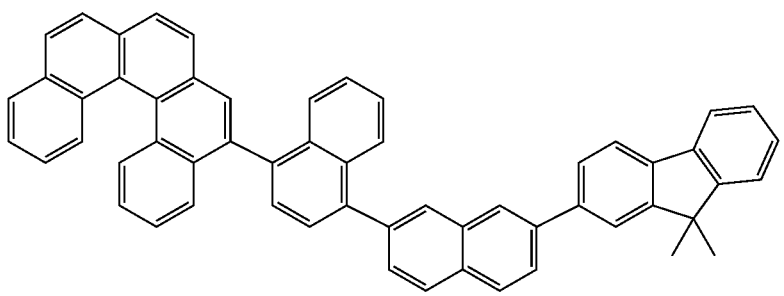
2-343
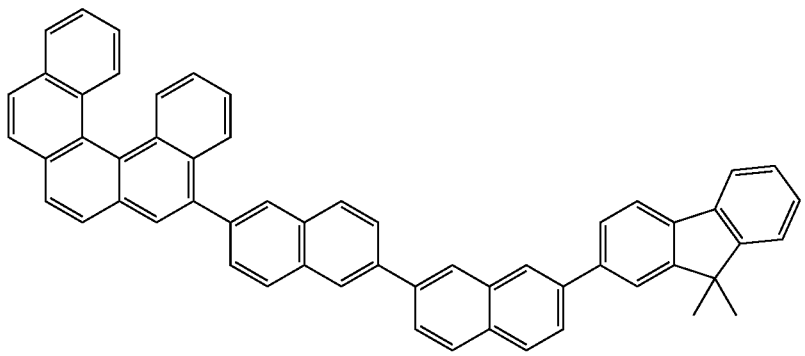
2-344
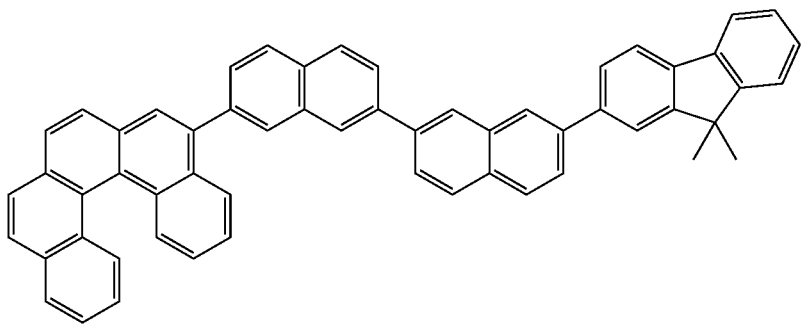

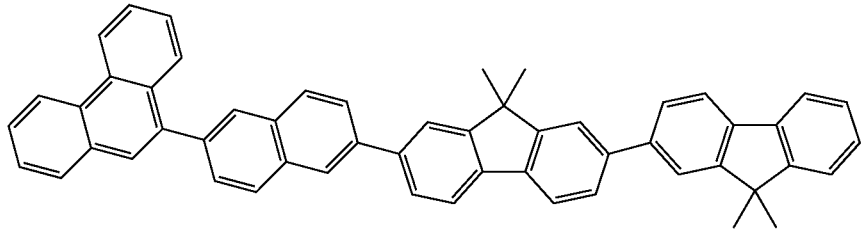

-continued
2-386
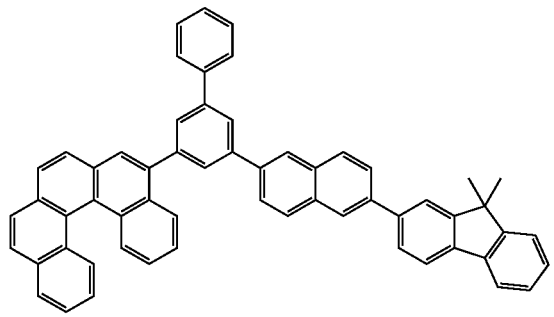
2-389
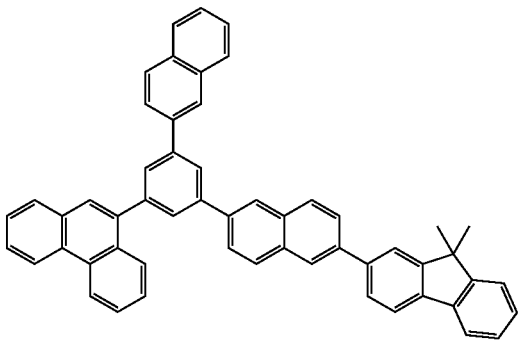
2-392
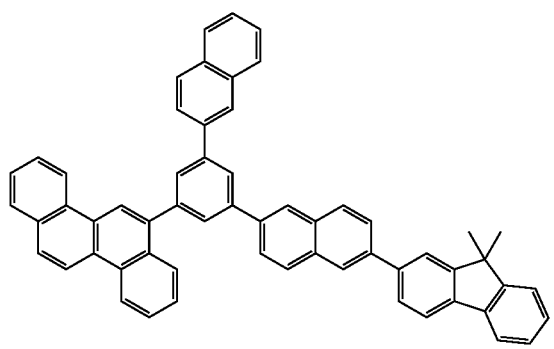
2-394
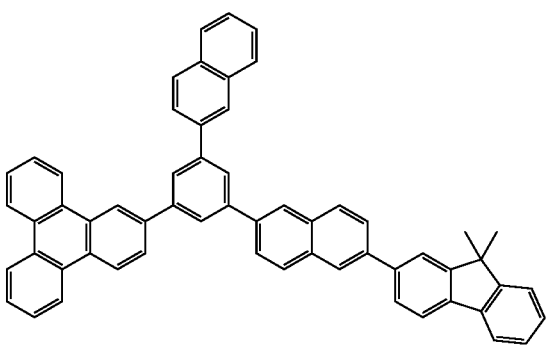
2-396
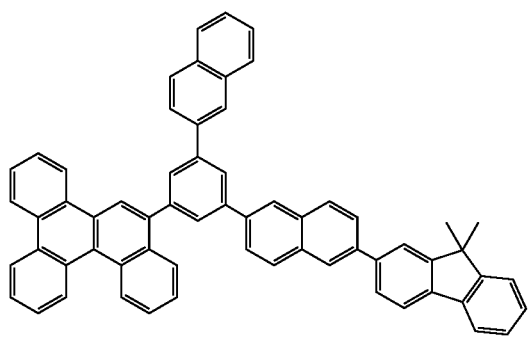
2-398
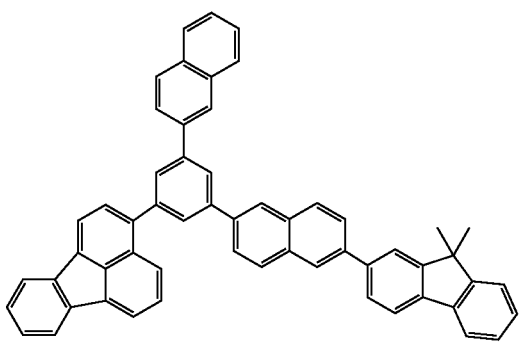
2-400
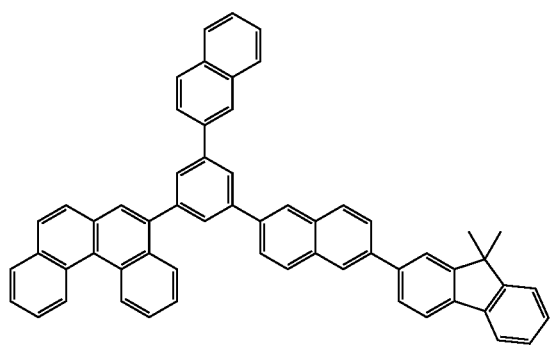
2-402
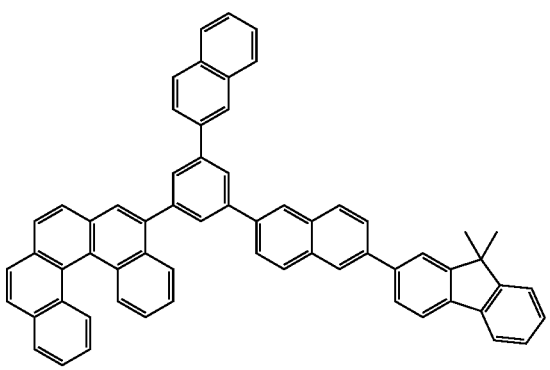

-continued
2-1
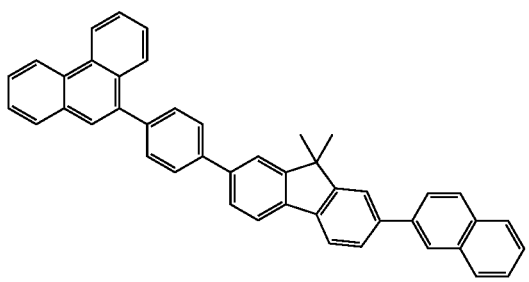
2-2
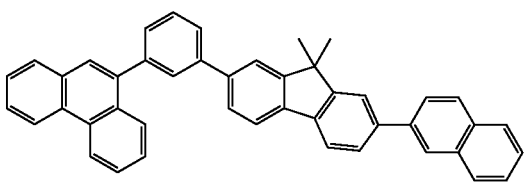
2-3
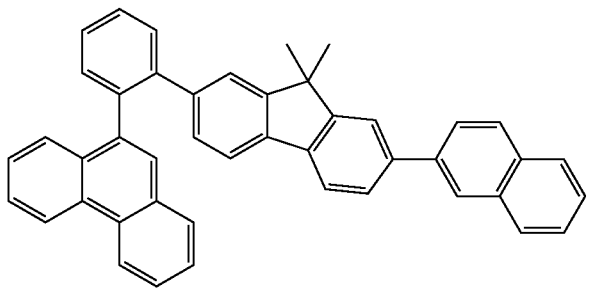
2-4
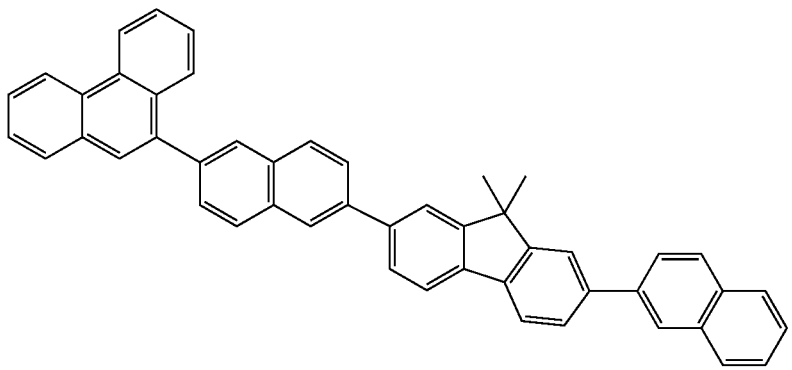
2-5
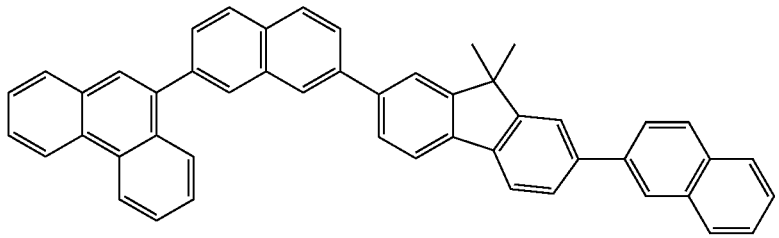
2-6
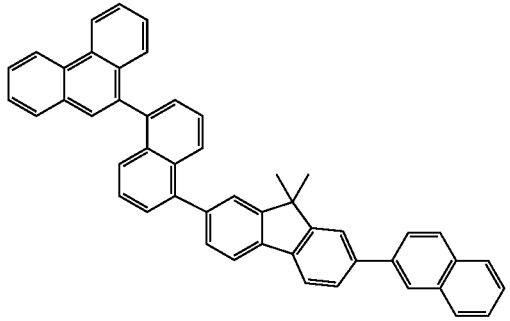
2-7
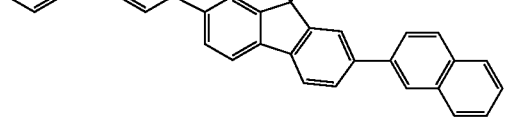

-continued
2-8
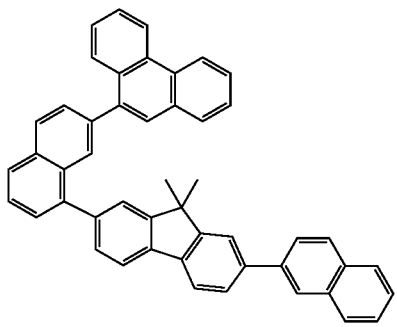
2-9
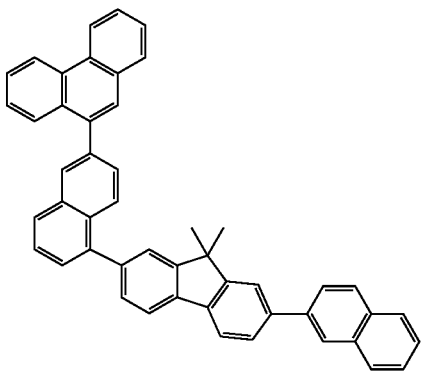
2-10
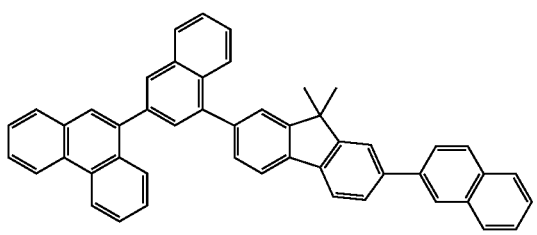
2-11
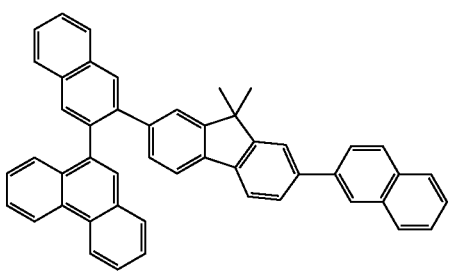
2-12
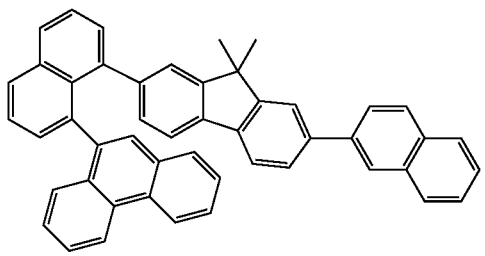
2-13
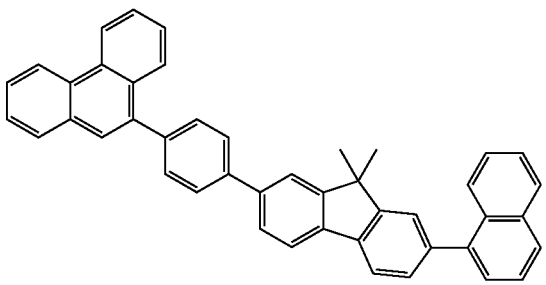
2-14
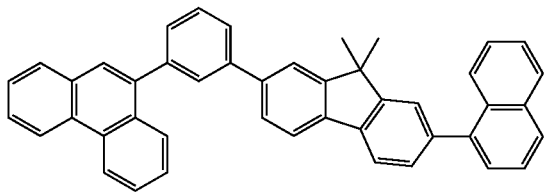
2-15
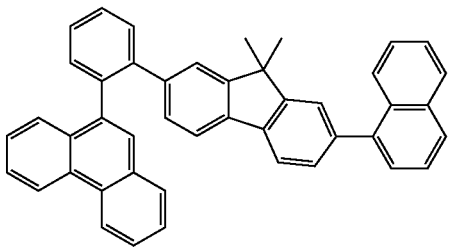
2-16
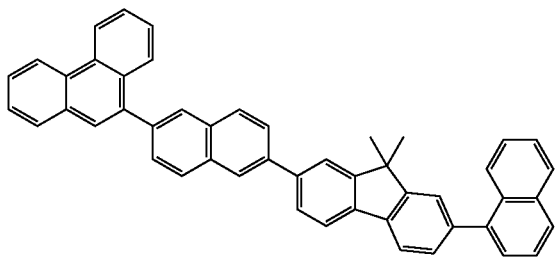
2-17
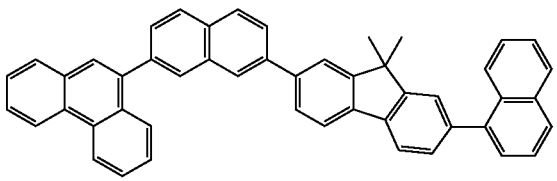

-continued
2-18
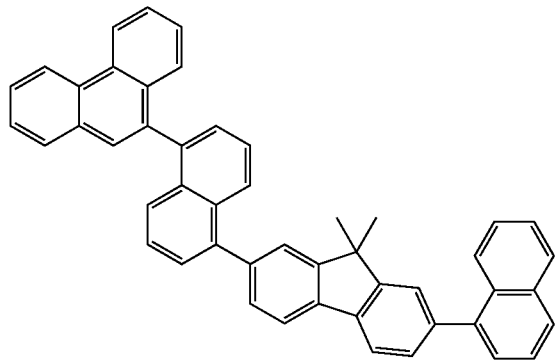
2-19
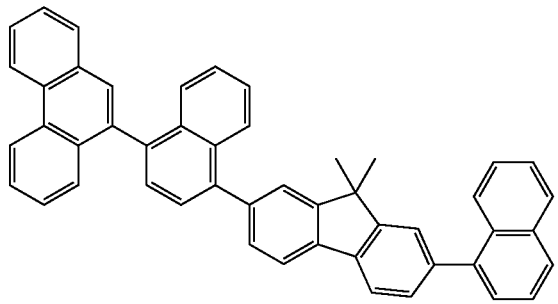
2-20
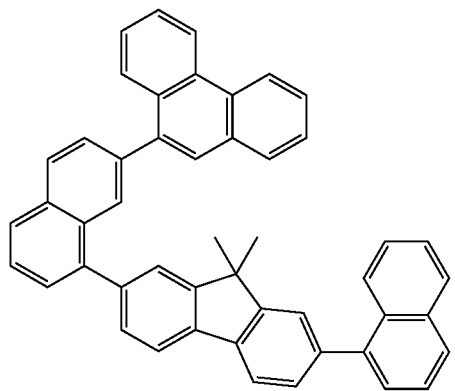
2-21
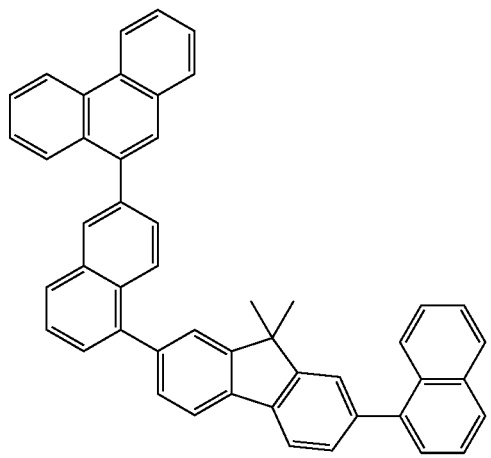
2-22
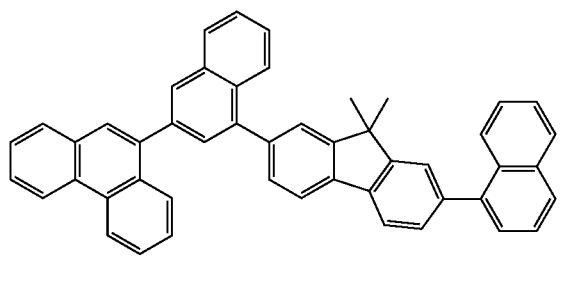
2-23
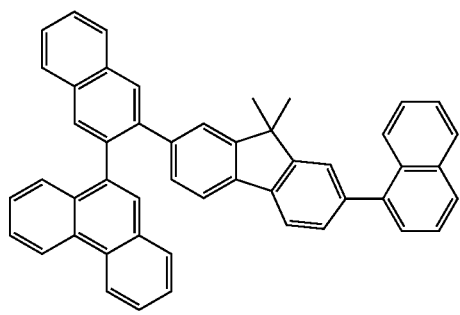
2-24
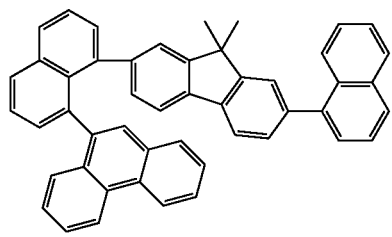
2-25
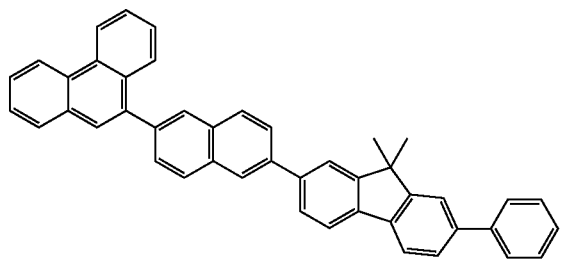

2-26
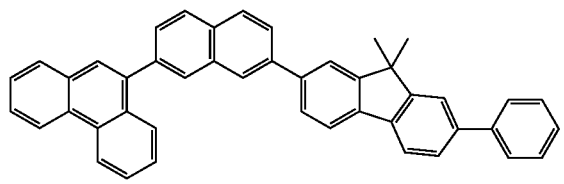
2-27
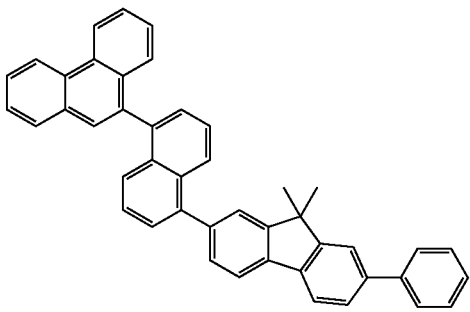
2-28
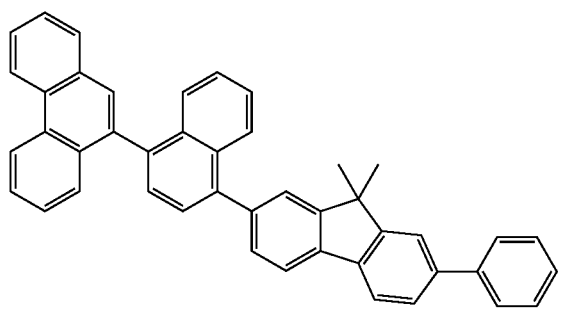
2-29
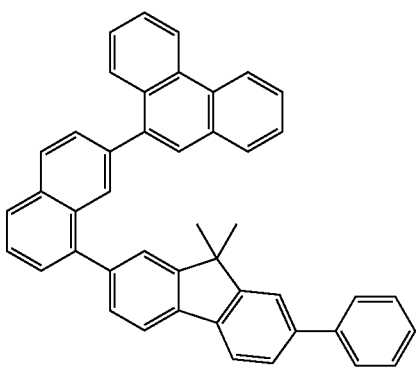
2-30
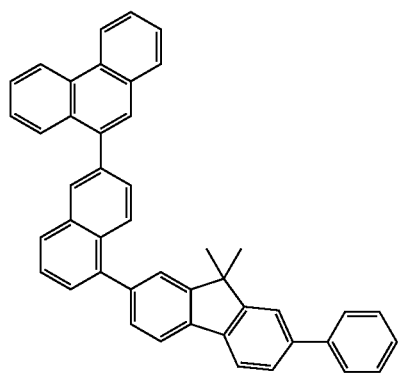
2-31
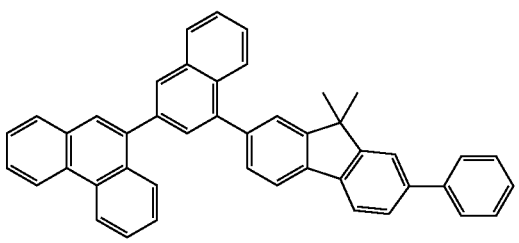
2-32
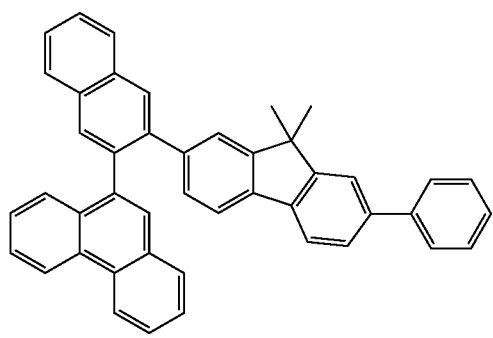
2-33
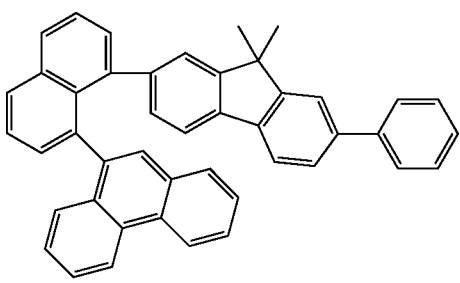

-continued
2-34
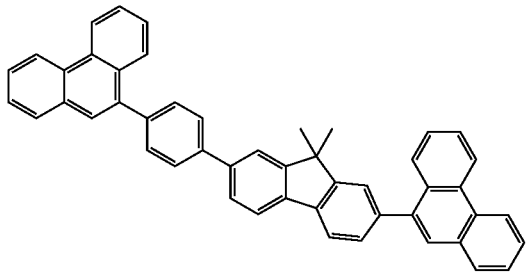
2-35
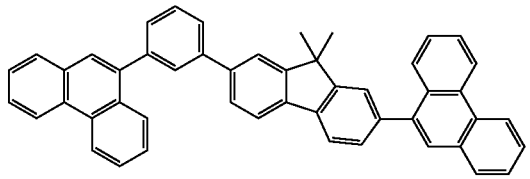
2-36
2-37
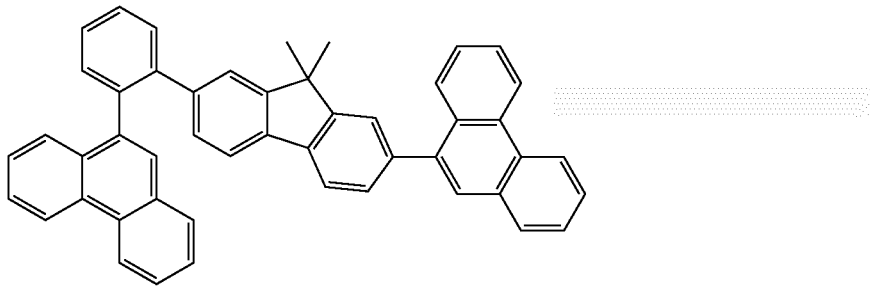
2-38
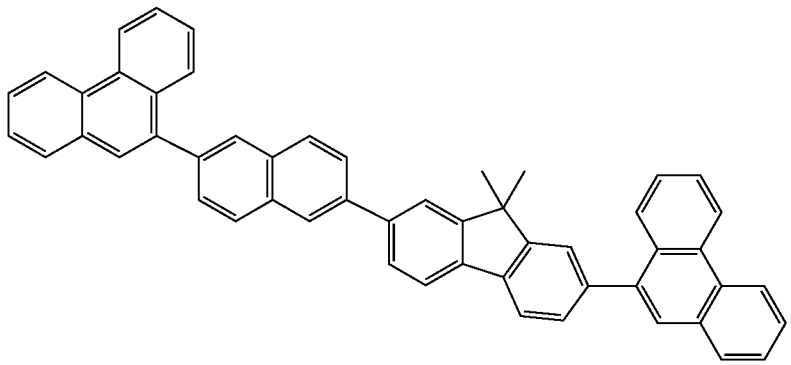
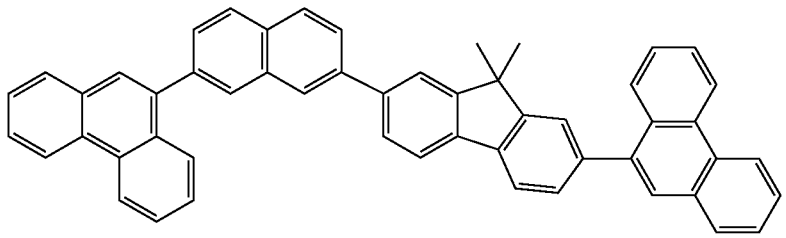
2-39
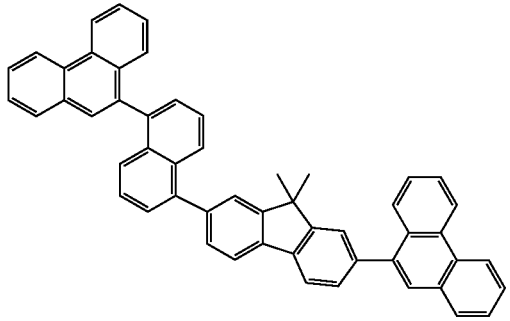
2-40
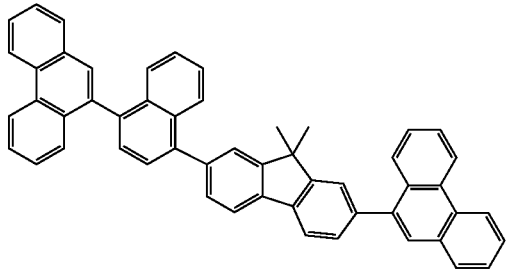

-continued
2-41
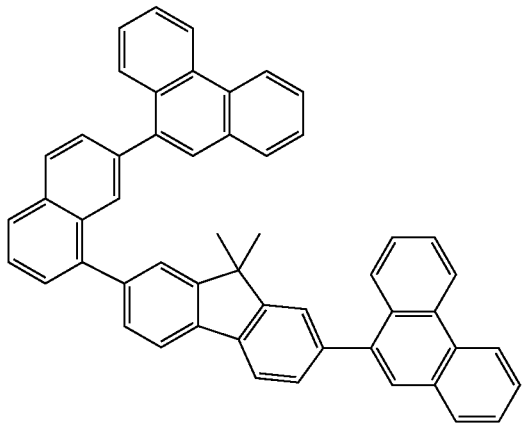
2-42
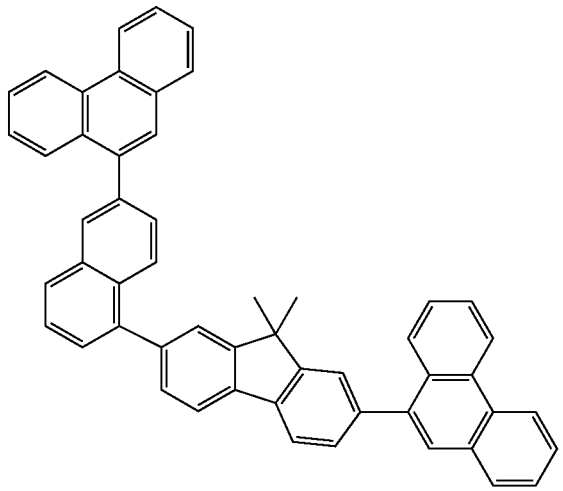
2-43
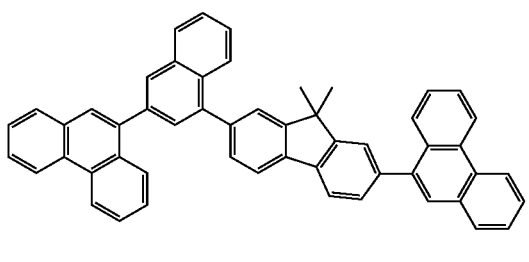
2-44
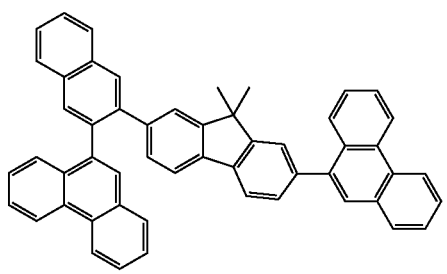
2-45
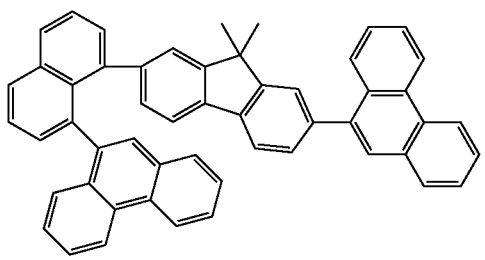
2-74
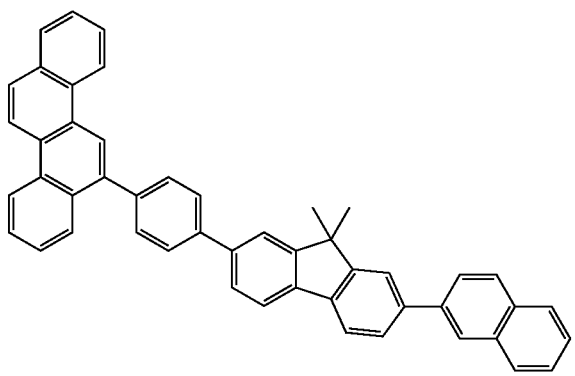
2-75
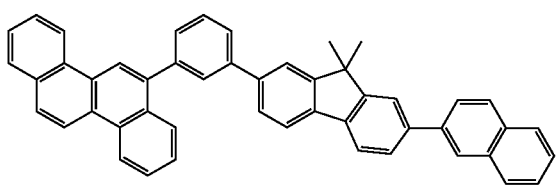
2-76
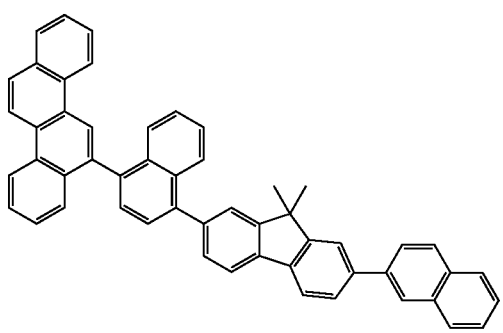

2-77
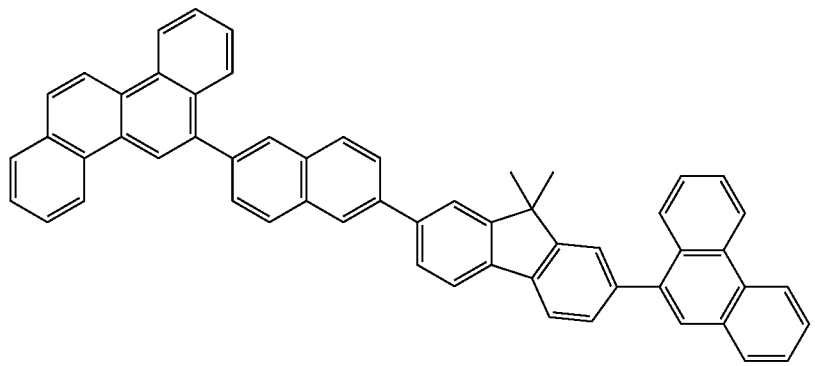
2-78
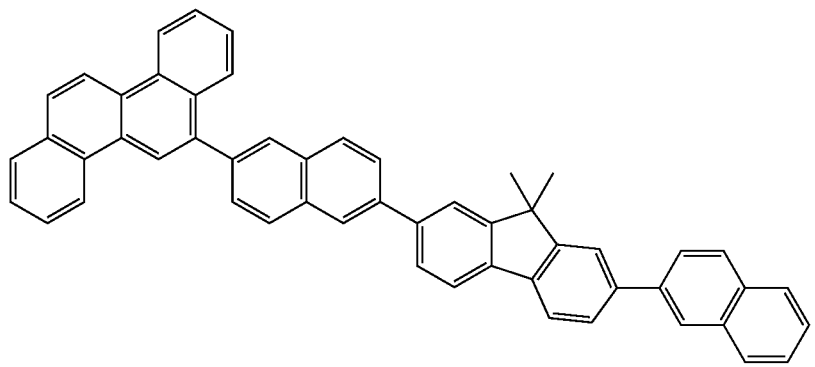
2-79
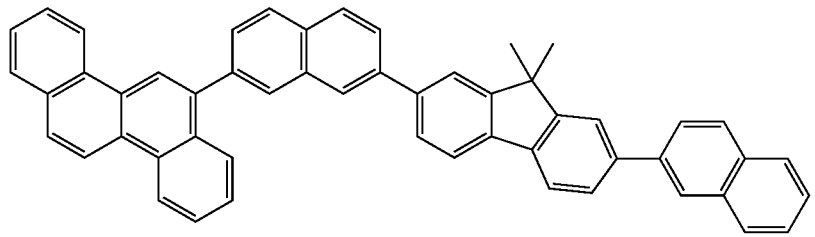
2-80
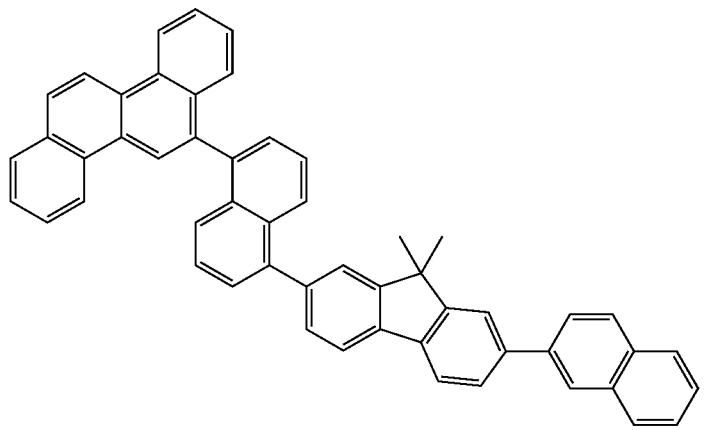
2-81
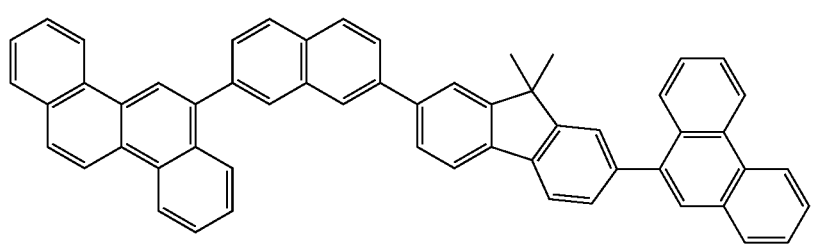

2-82
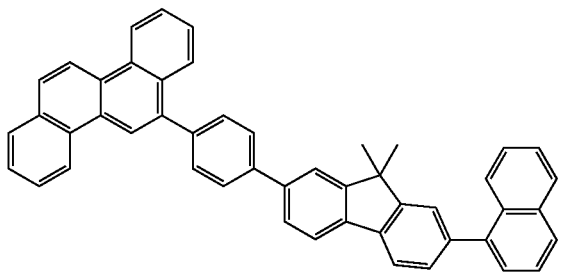
2-83
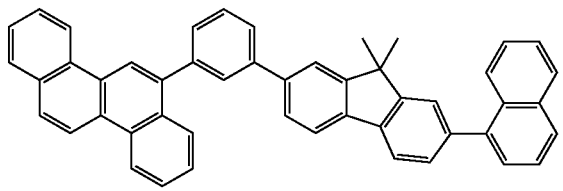
2-84
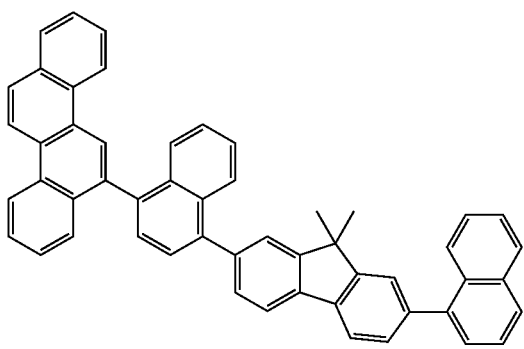
2-85
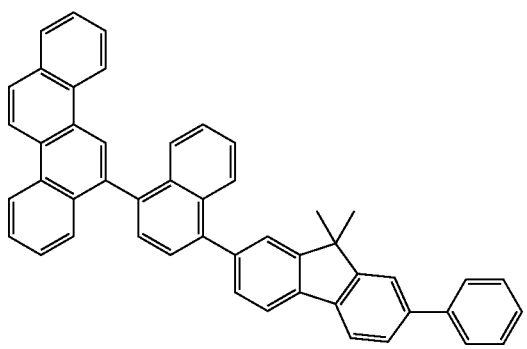
2-86
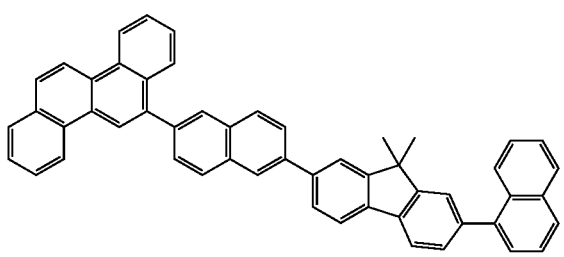
2-87
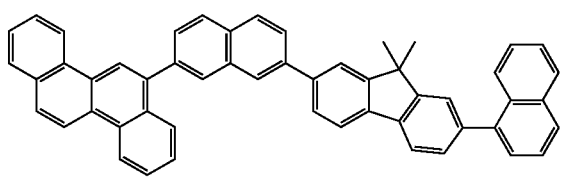
2-88
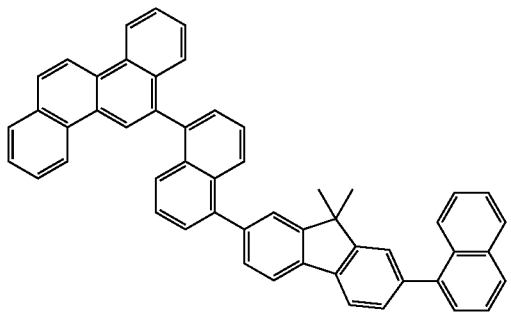
2-89
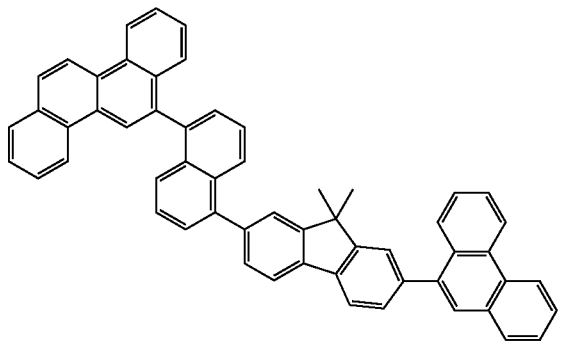
2-90
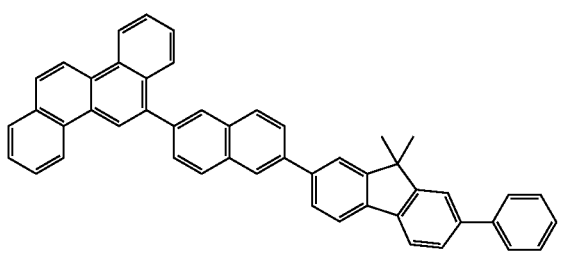
2-91
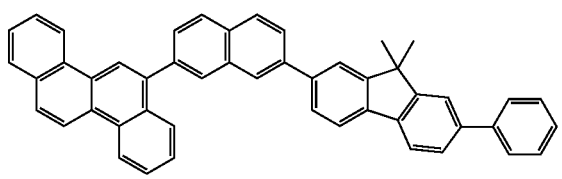

-continued
2-92
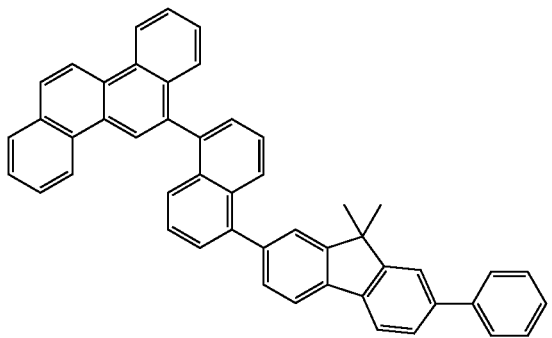
2-93
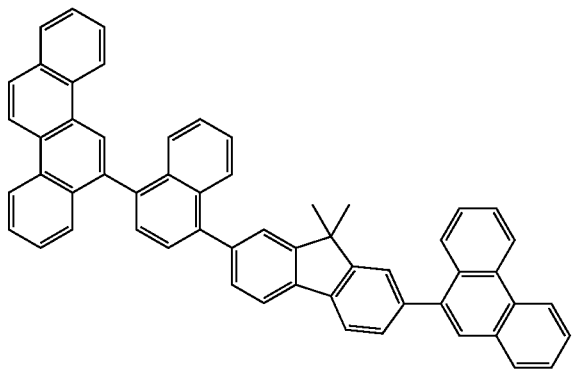
2-94
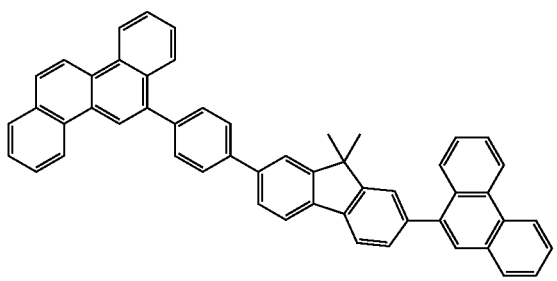
2-95
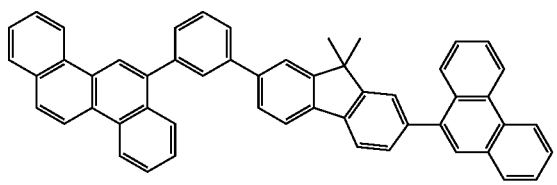
2-96
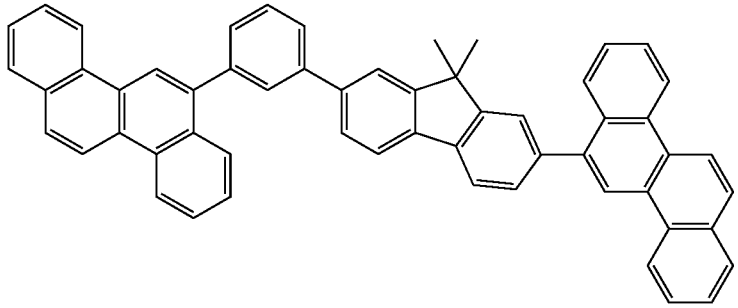
2-97
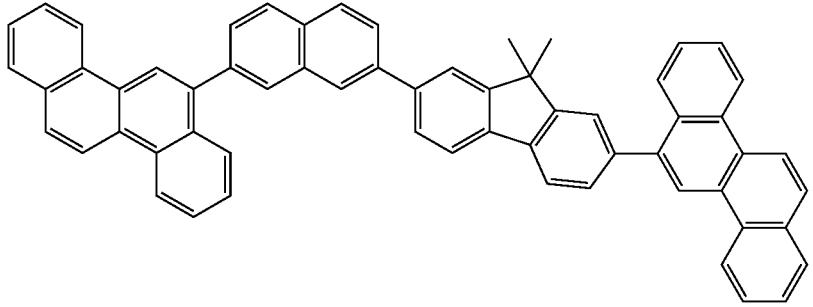
2-98
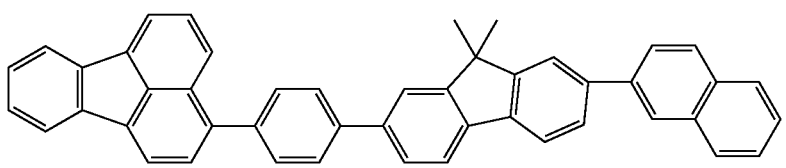

-continued
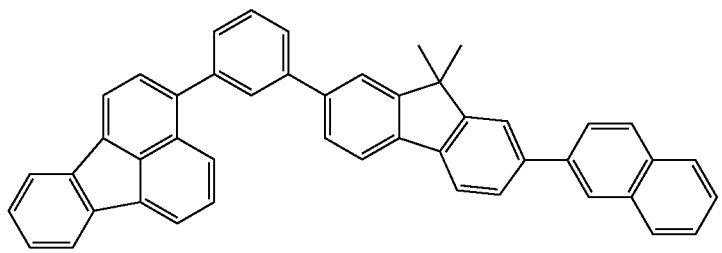
2-99
2-100
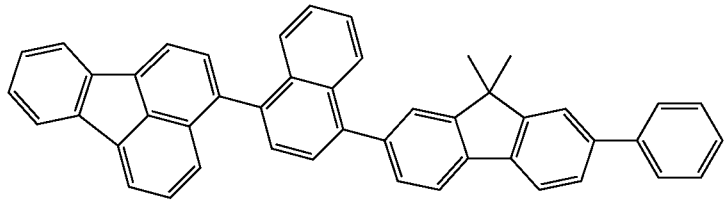
2-101
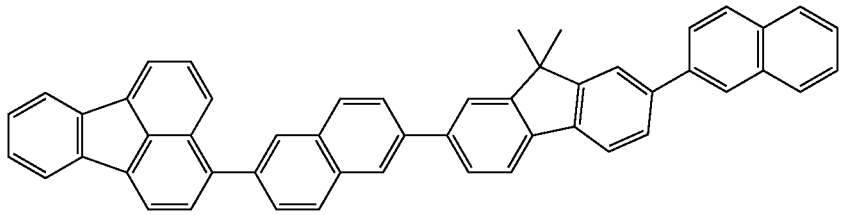
2-102
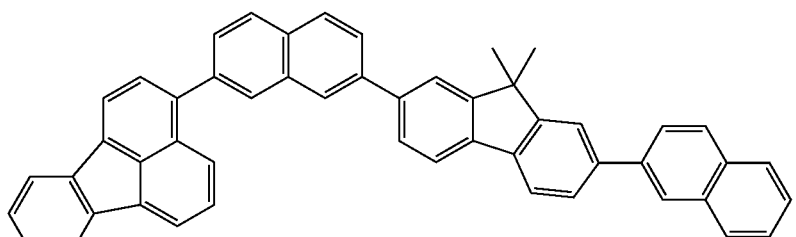
2-103
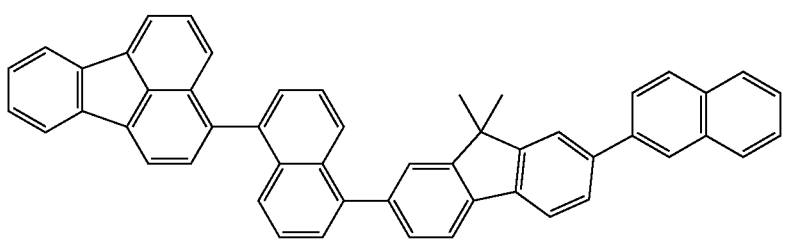
2-104
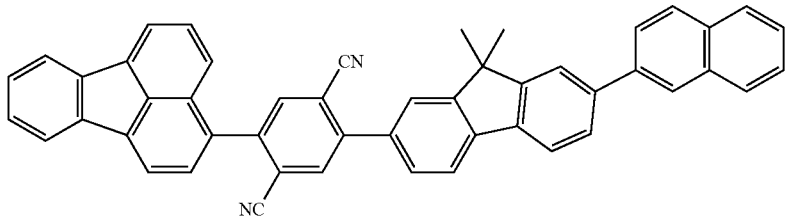
2-105

-continued
2-106
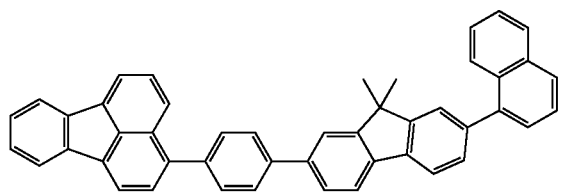
2-107
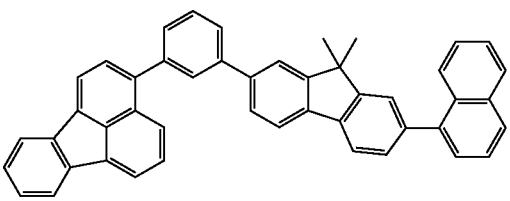
2-108
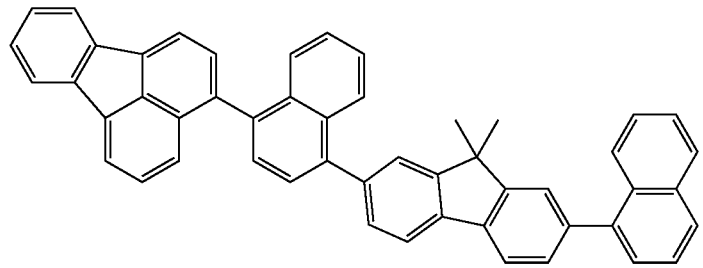
2-109
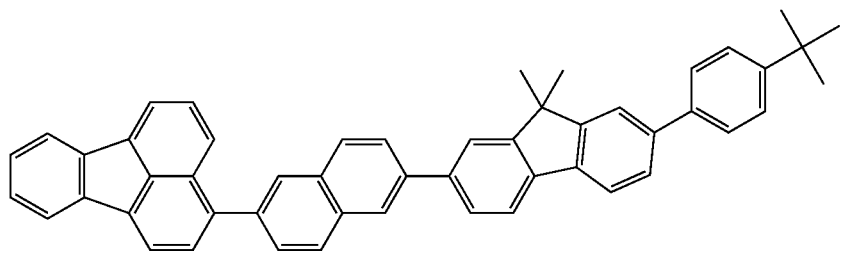
2-110
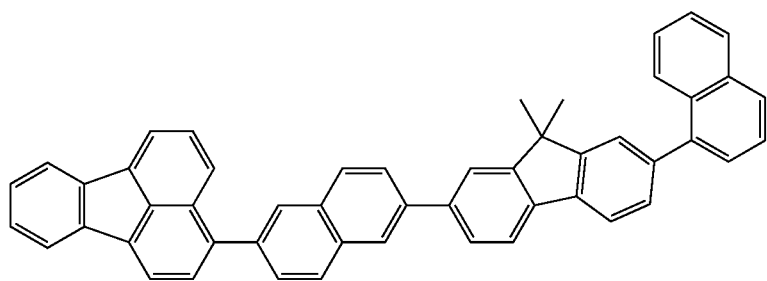
2-111
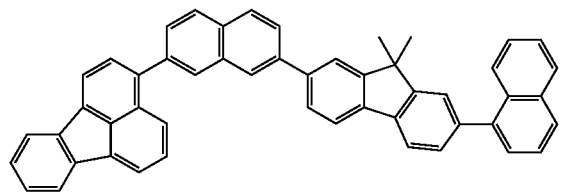
2-112
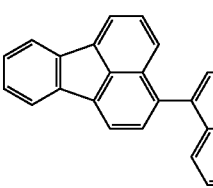
2-113
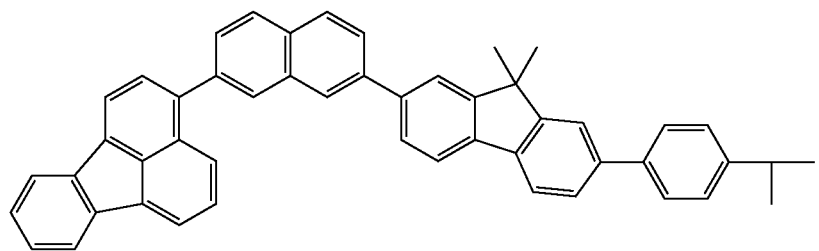

-continued
2-114
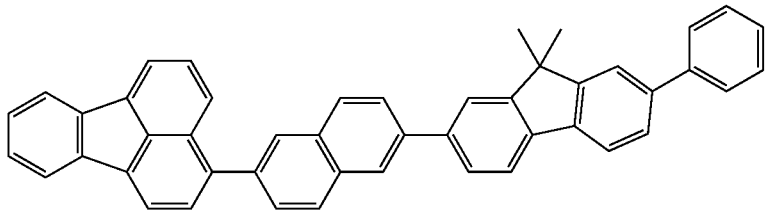
2-115
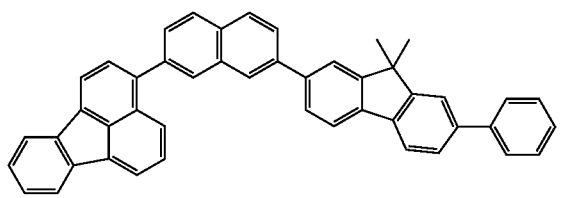
2-116
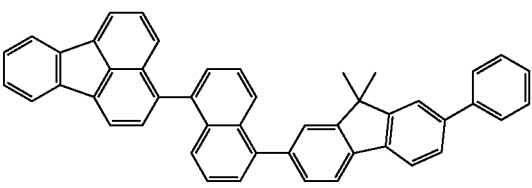
2-117
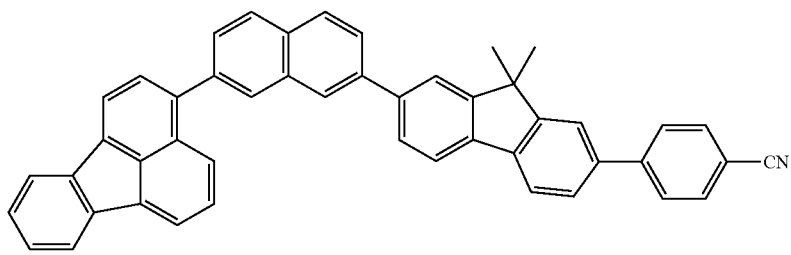
2-118
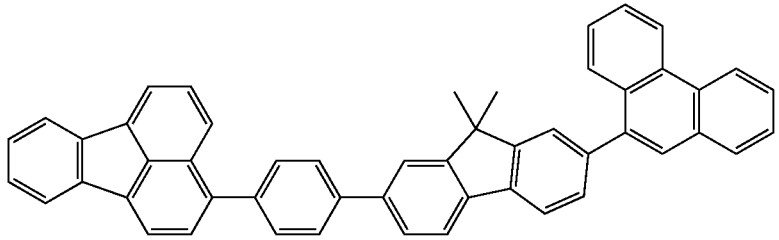
2-119
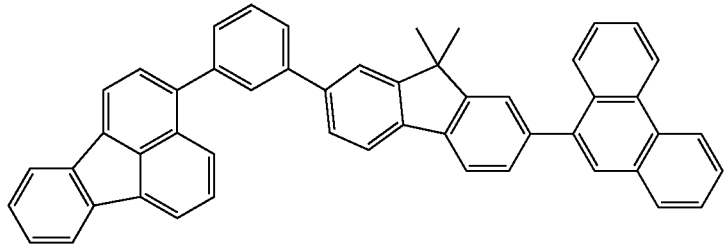
2-120
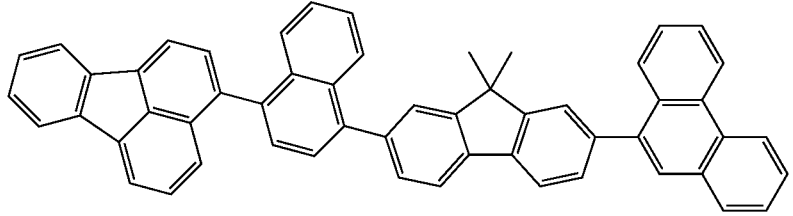

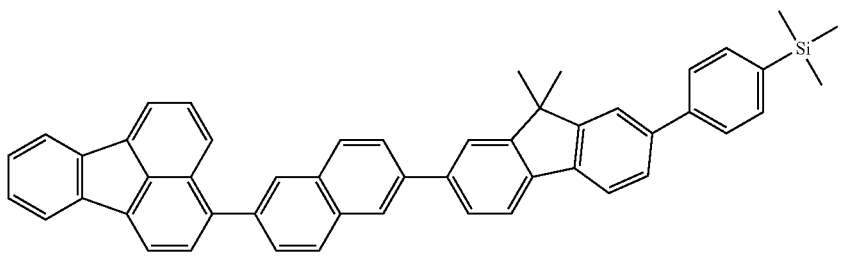
2-121
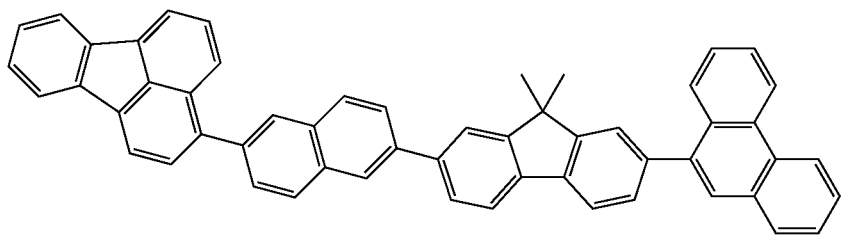
2-122
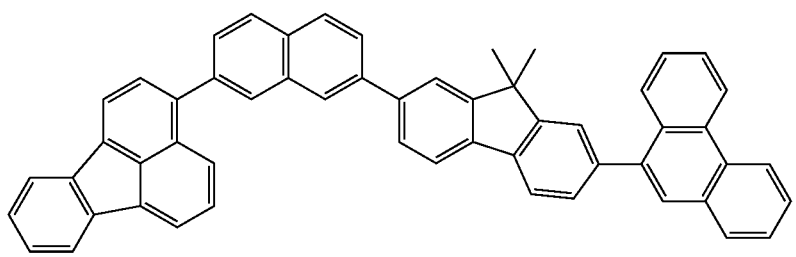
2-123
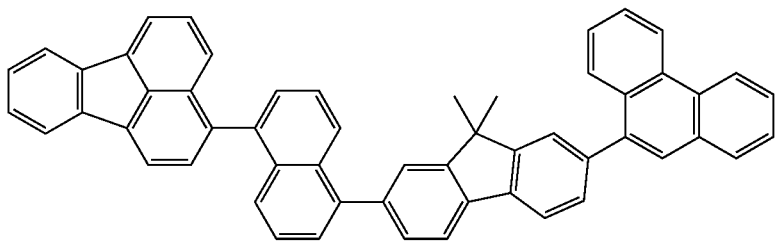
2-124
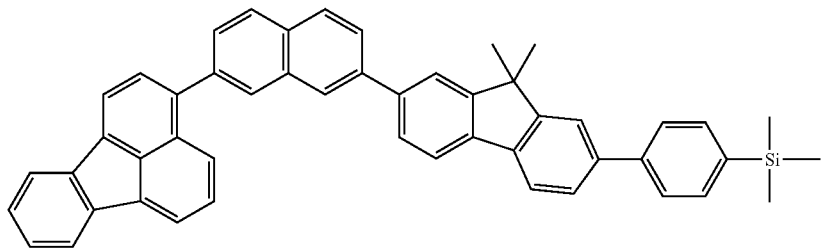
2-125
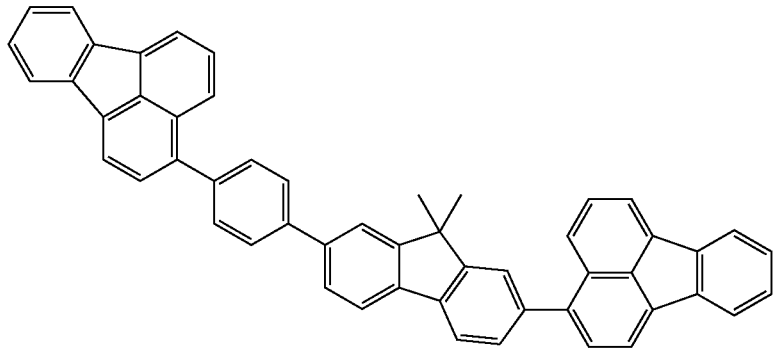
2-126

2-127
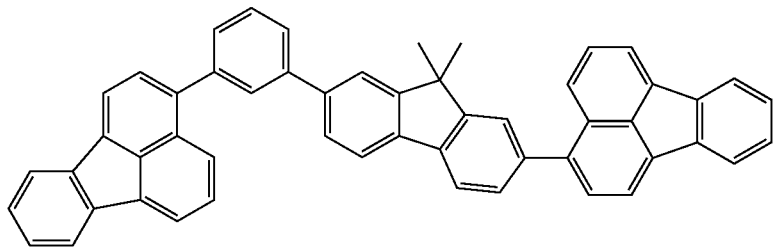
2-128
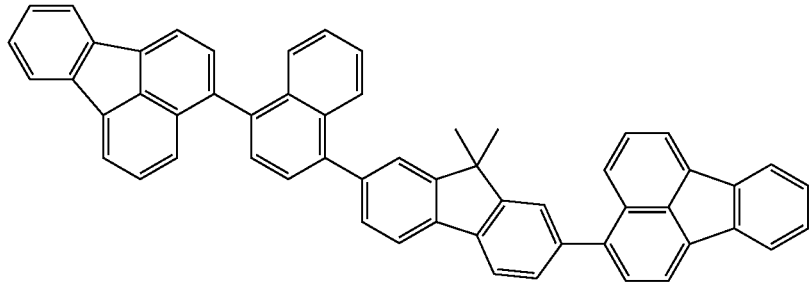
2-129
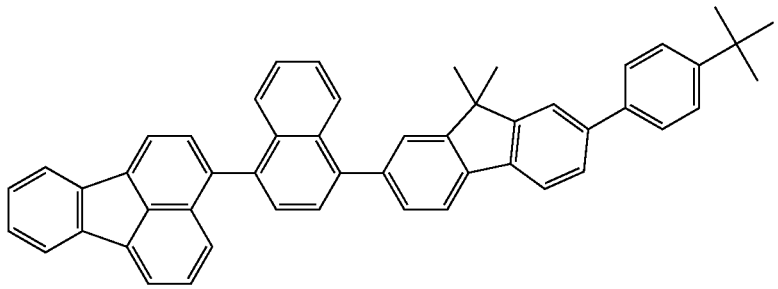
2-130
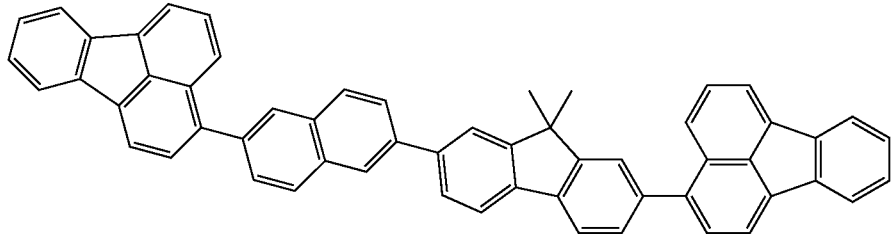
2-131
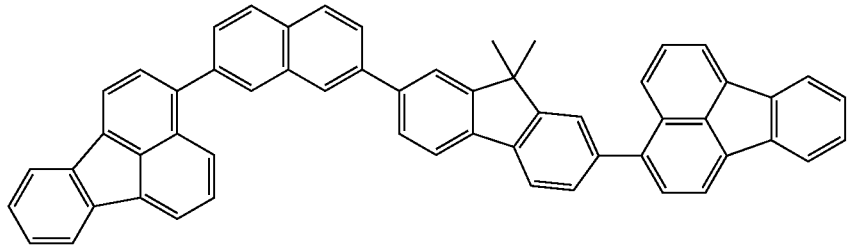
2-132
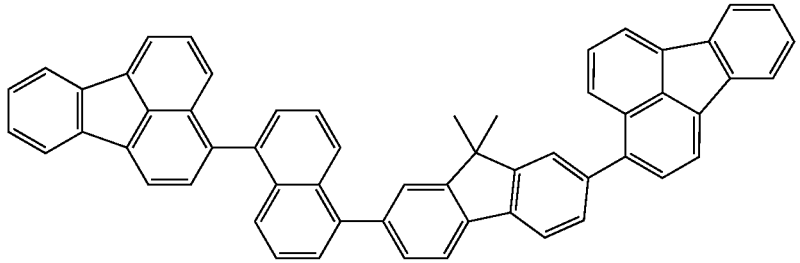

-continued
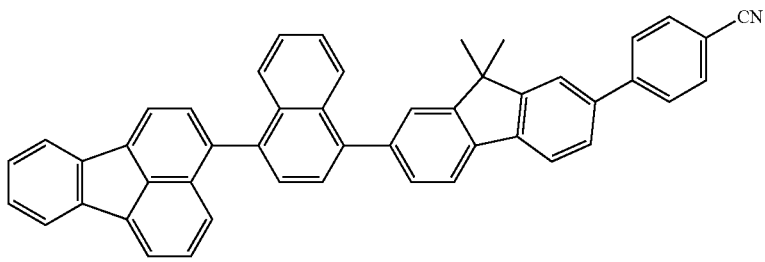
2-133
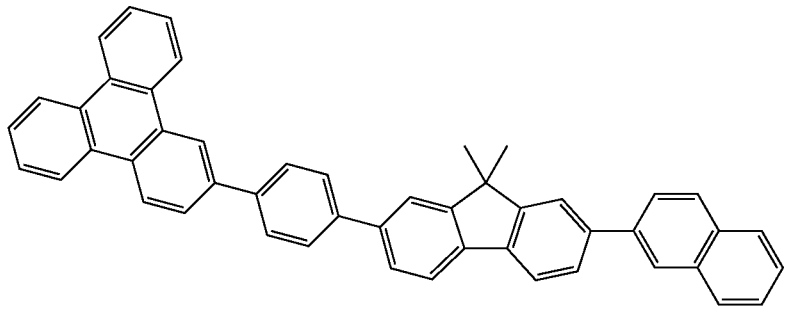
2-134
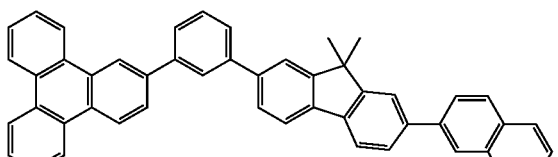
2-135
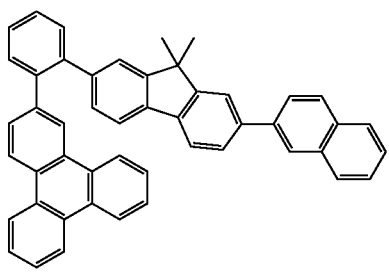
2-136
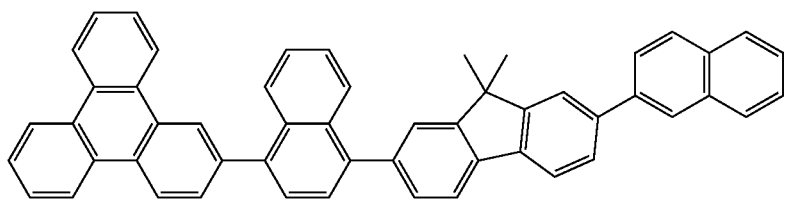
2-137
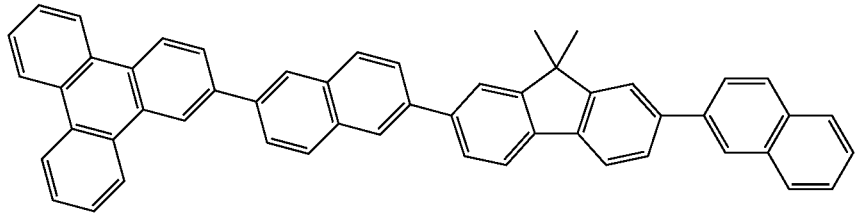
2-138
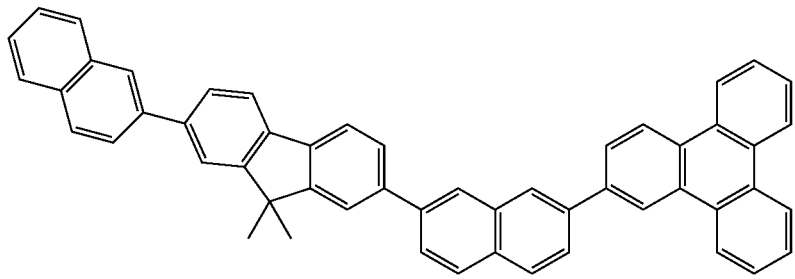
2-139

2-140
2-141
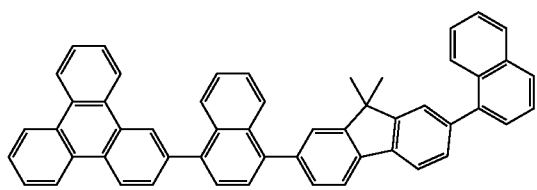
2-142
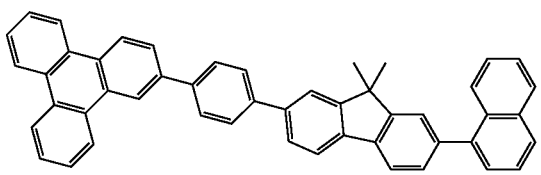
2-143
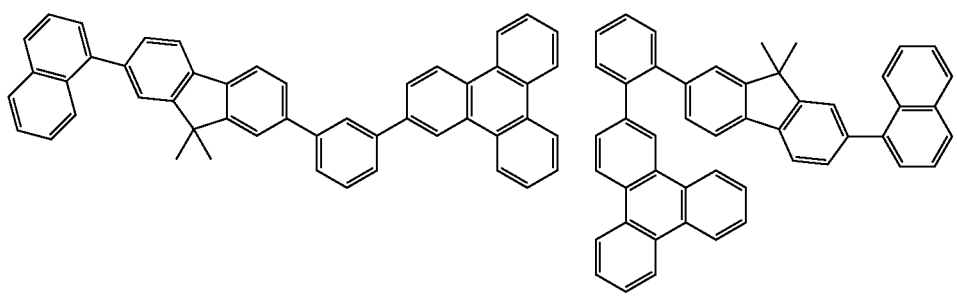
2-144
2-145
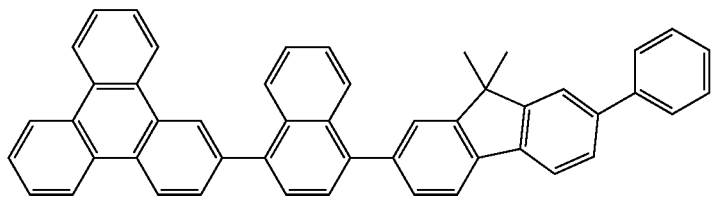
2-146
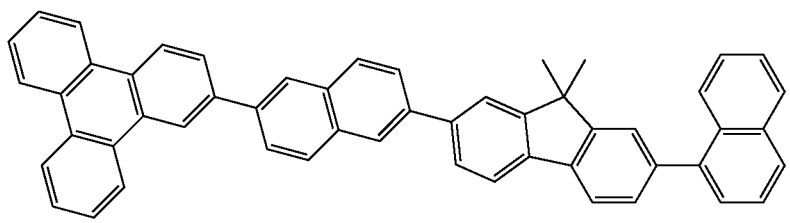
2-147
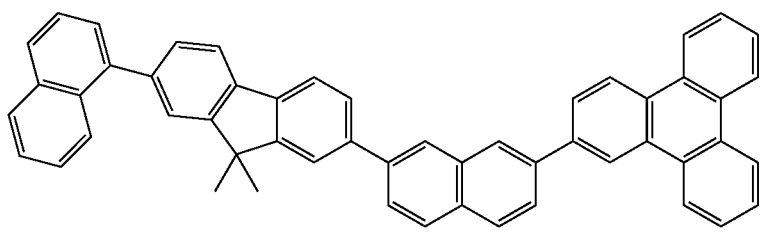

-continued
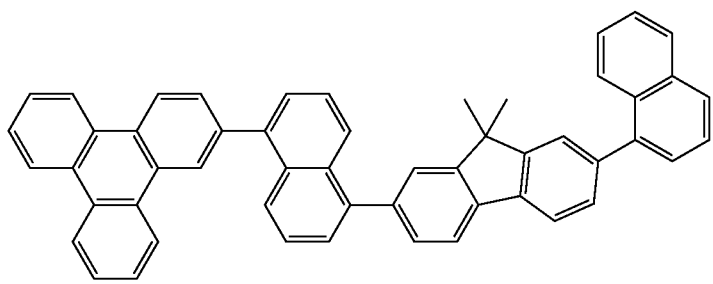
2-148
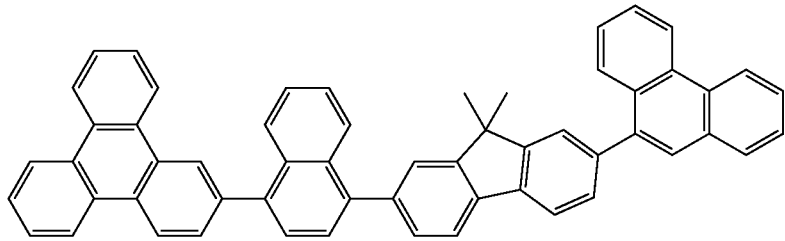
2-149
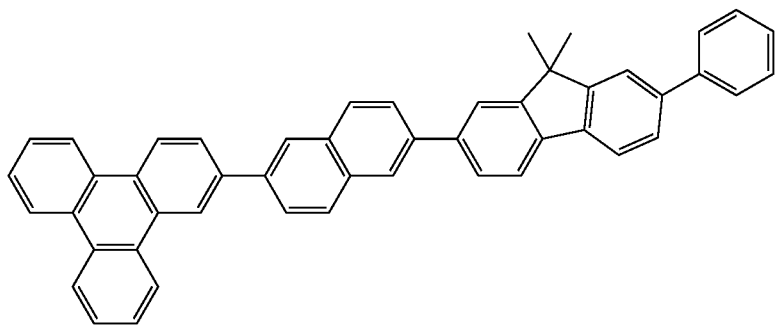
2-150
2-151 2-152
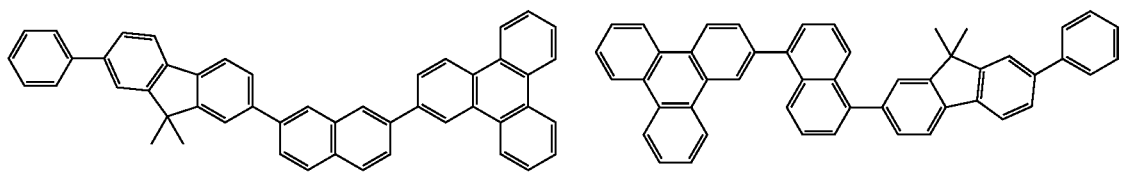
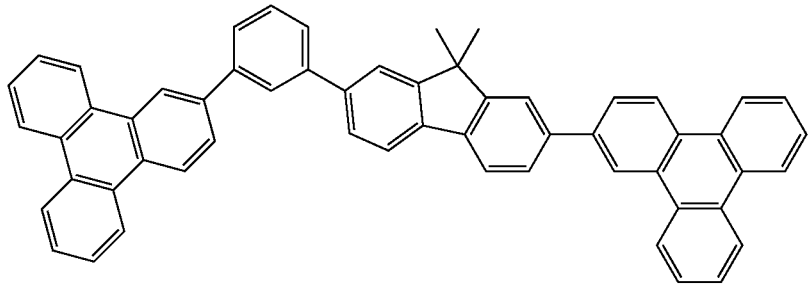
2-153
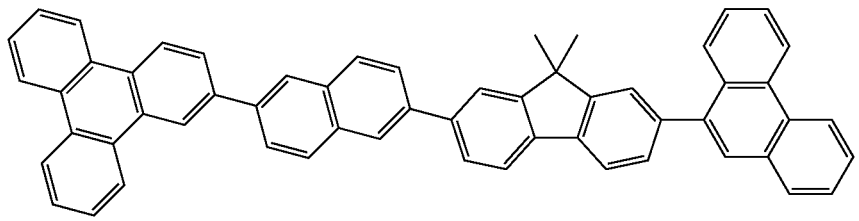
2-154

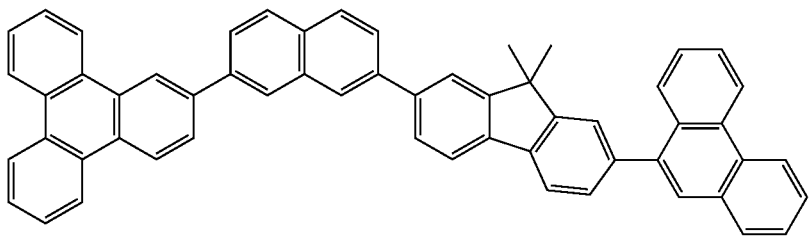
2-155
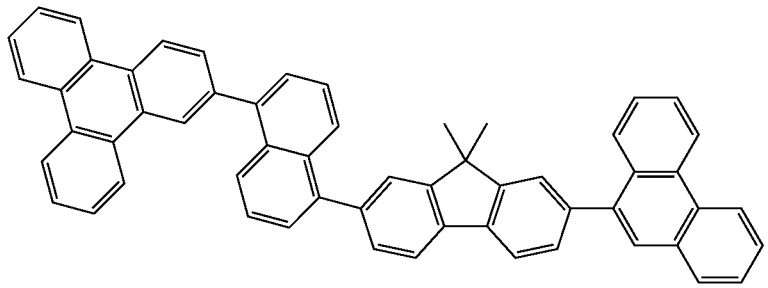
2-156
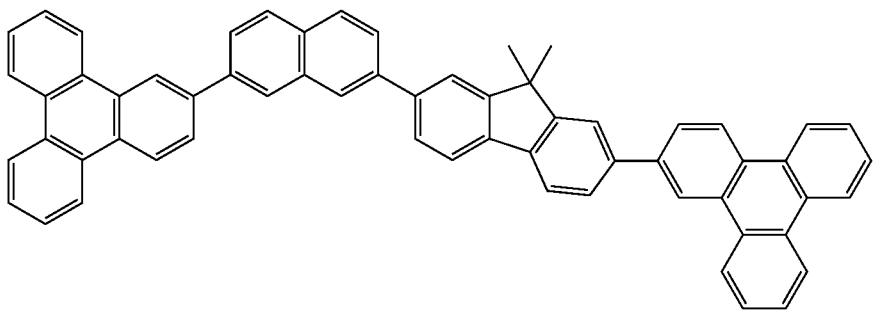
2-157
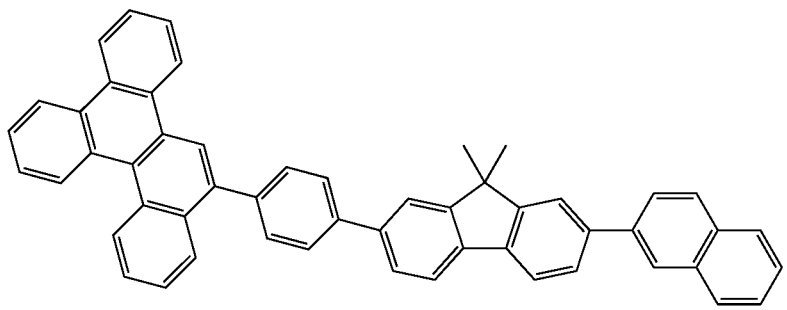
2-158
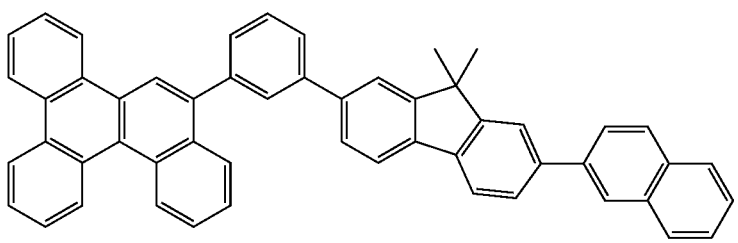
2-159

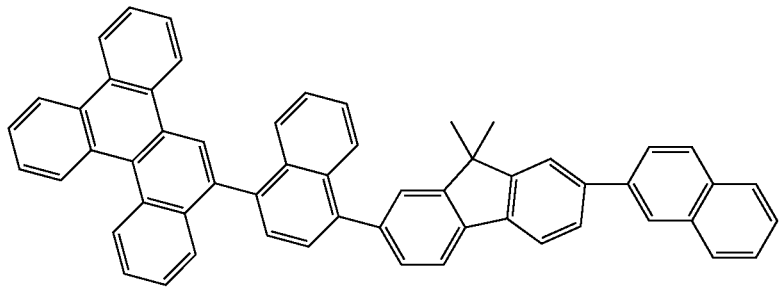
2-160
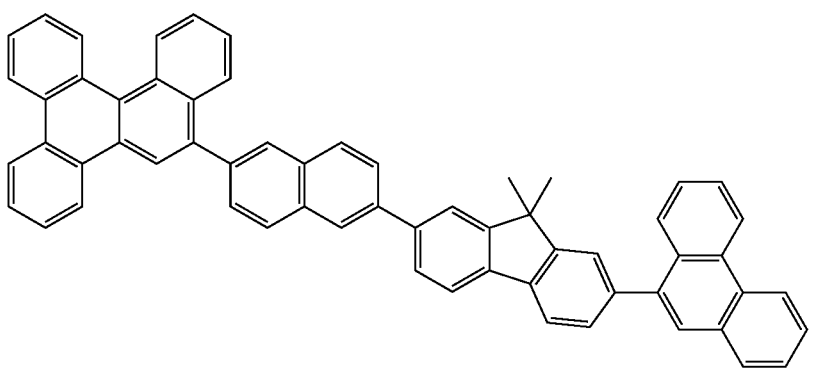
2-161
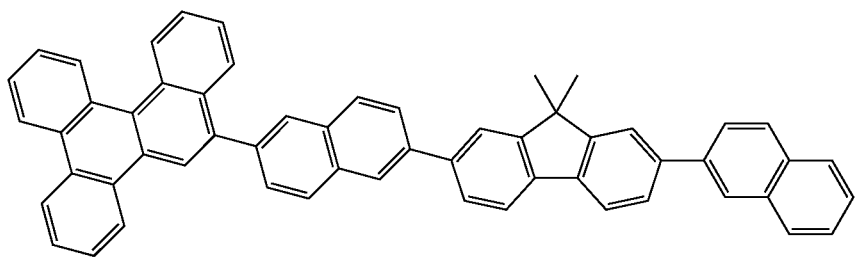
2-162
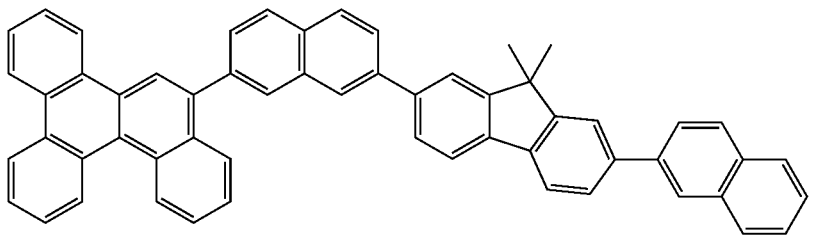
2-163
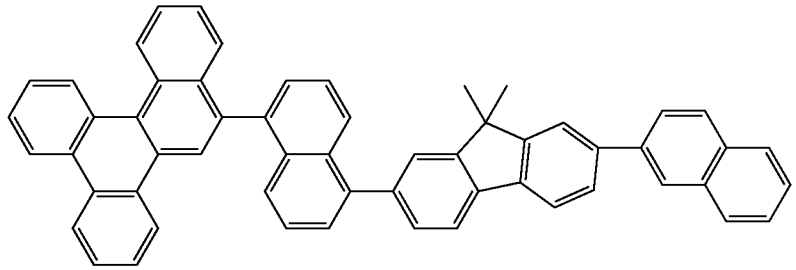
2-164

-continued
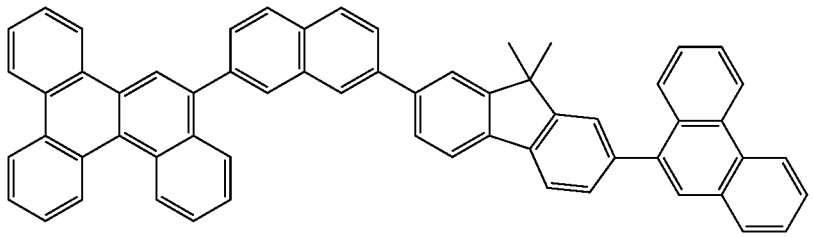

2-174
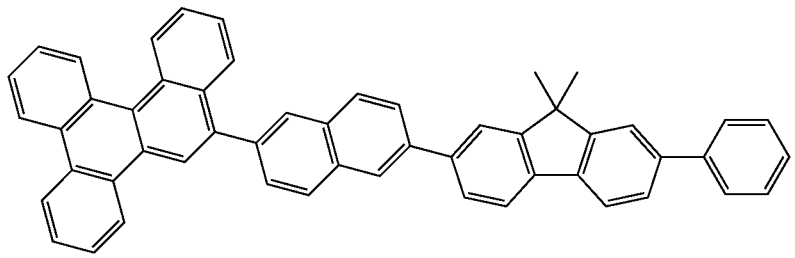
2-175
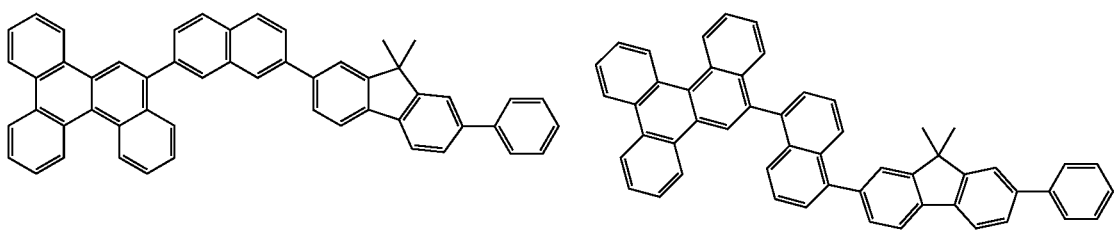
2-176
2-177
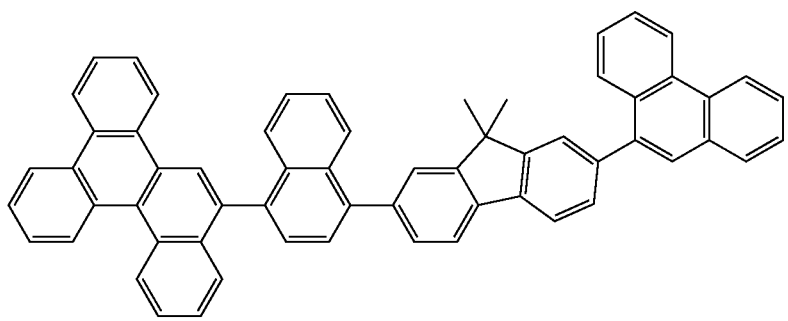
2-178
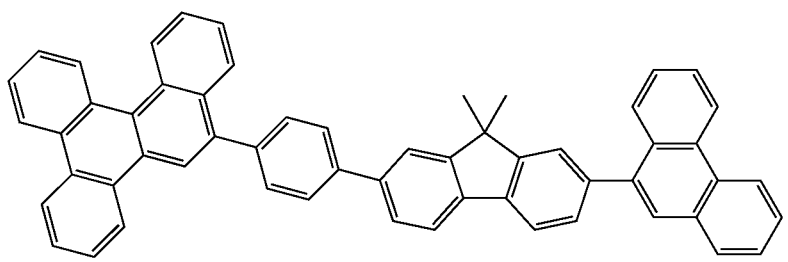
2-179
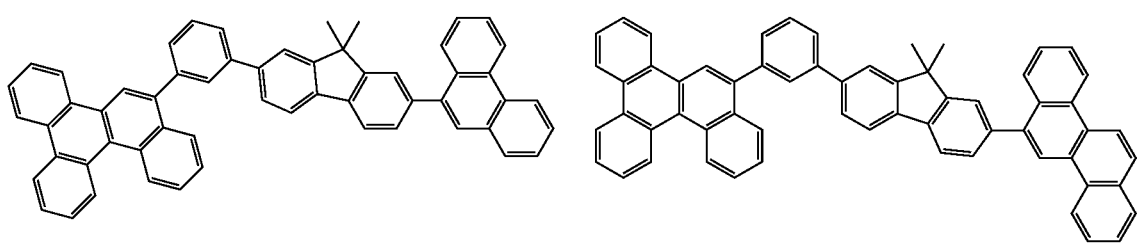
2-180

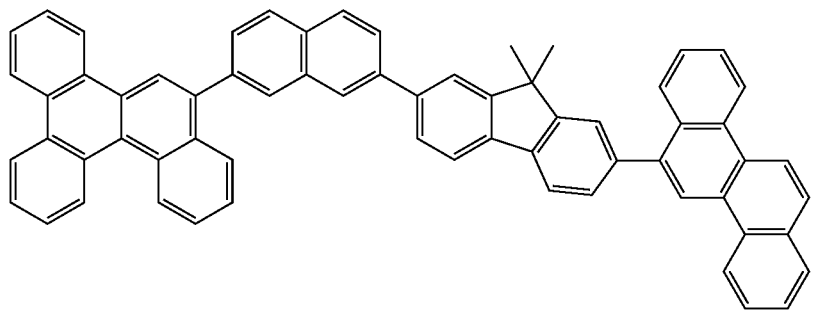
2-181
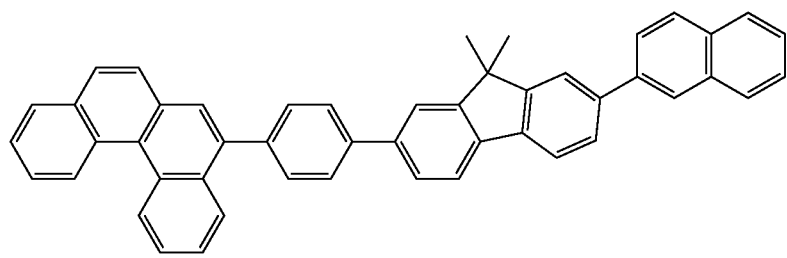
2-183
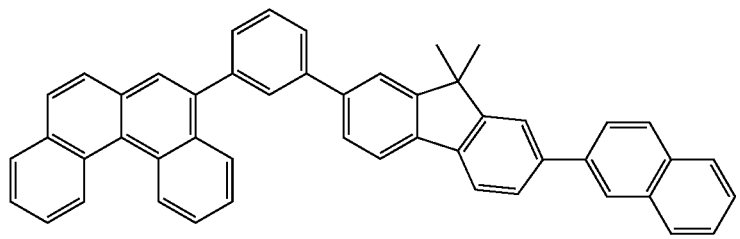
2-184
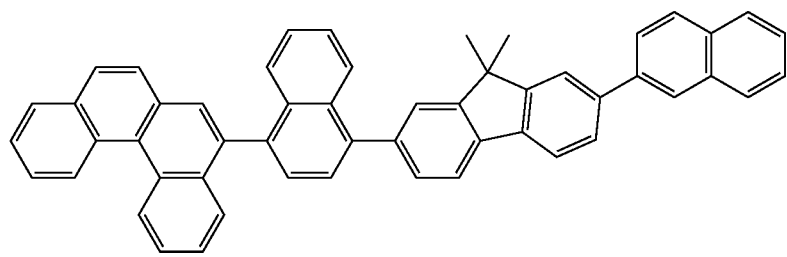
2-185
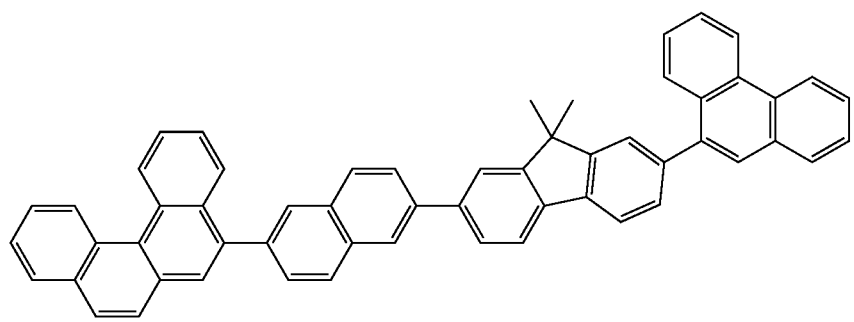
2-186

-continued
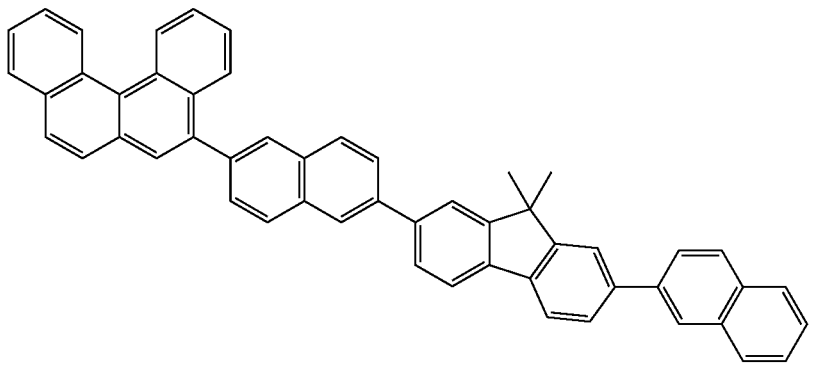
2-187
2-188
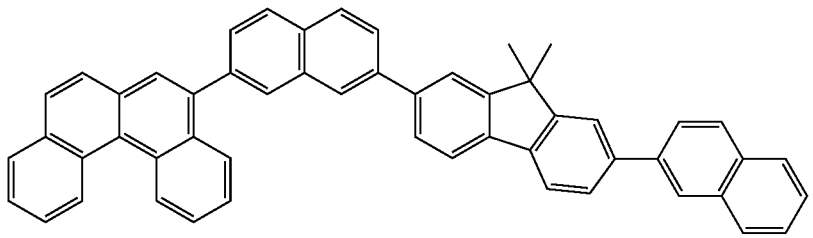
2-189
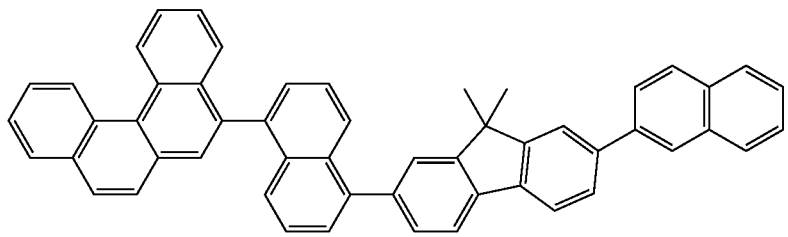
2-190
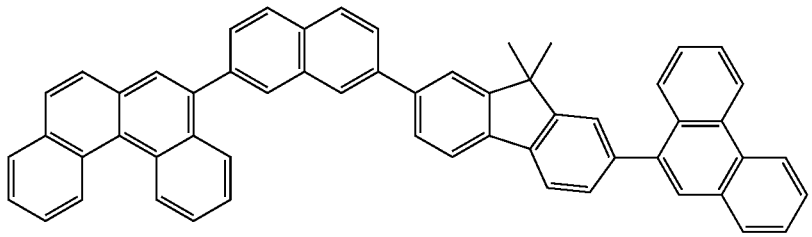
2-191  2-192
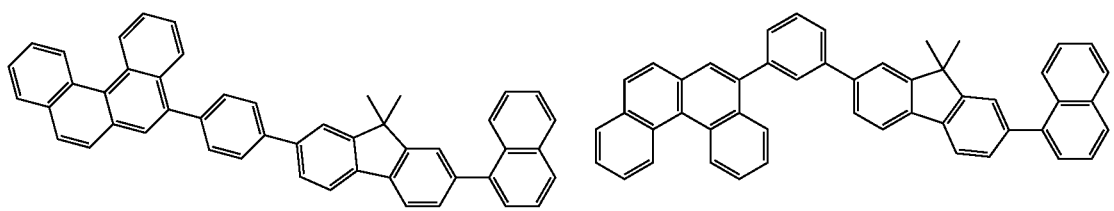
2-193  2-194
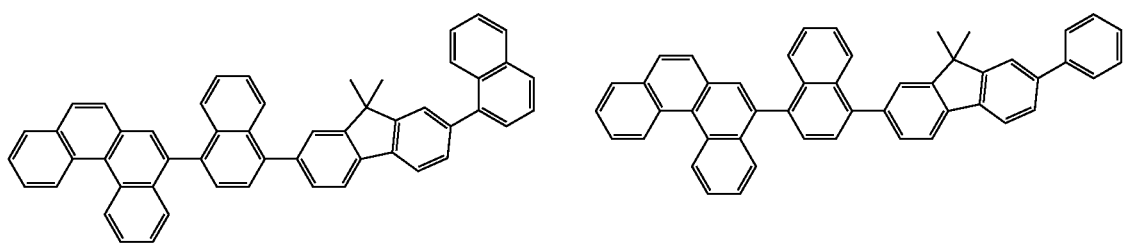

-continued
2-195
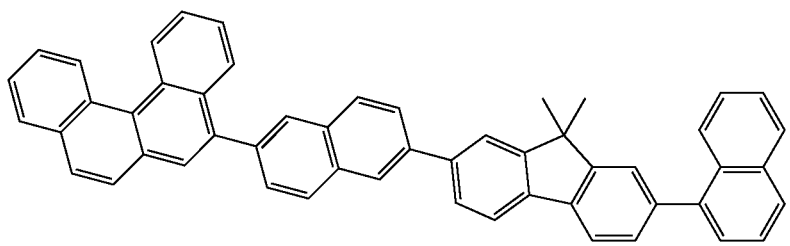
2-196
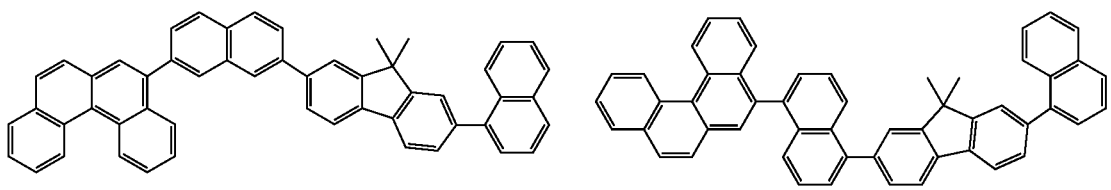
2-197
2-198
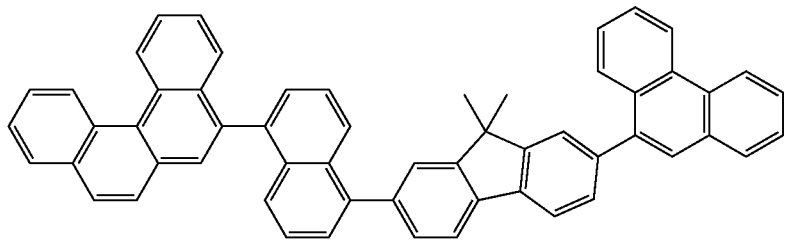
2-199
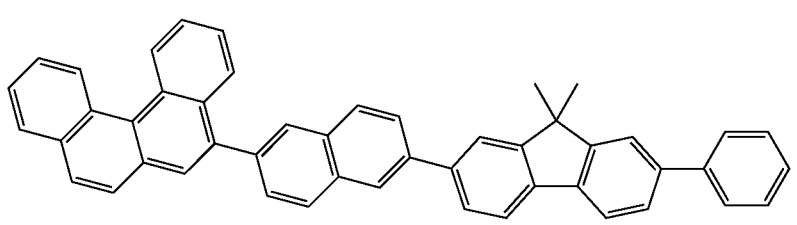
2-200

2-201
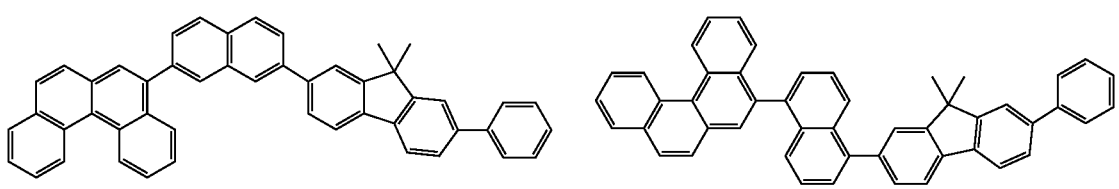
2-202
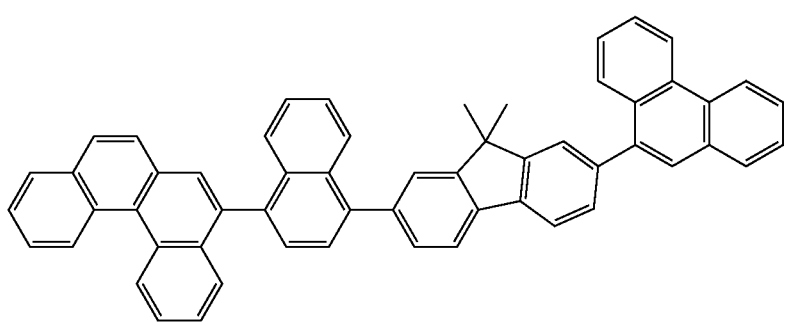

-continued
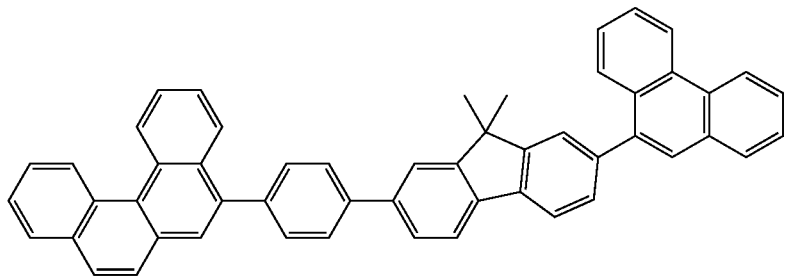
2-203
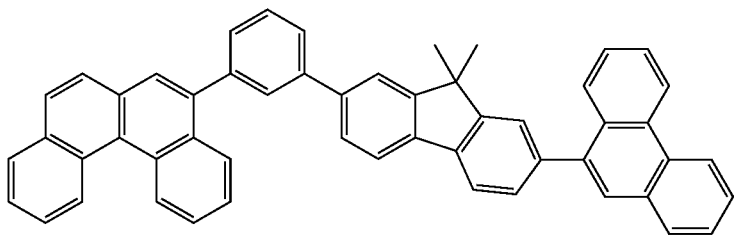
2-204
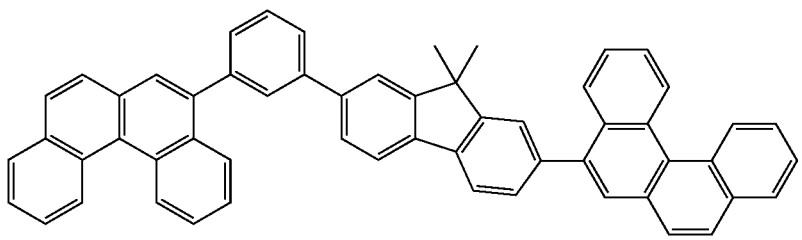
2-205
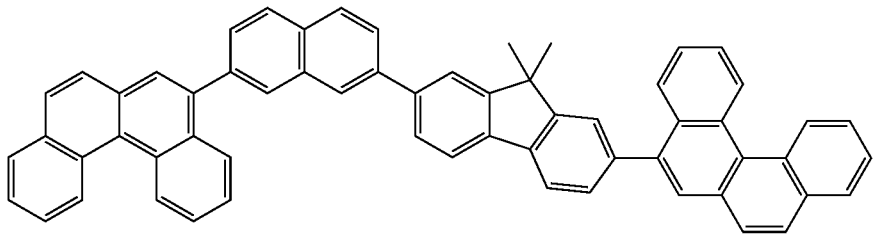
2-206
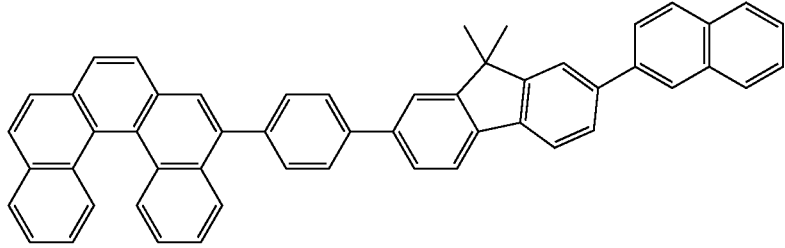
2-207
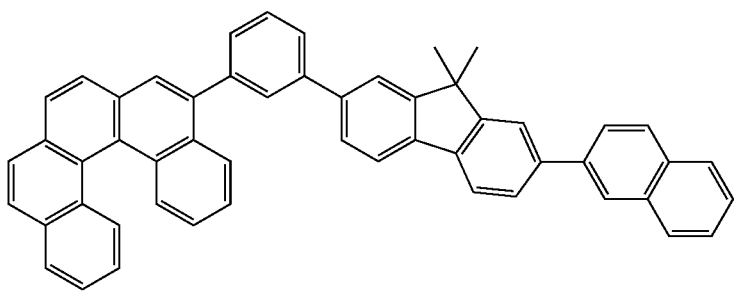
2-208

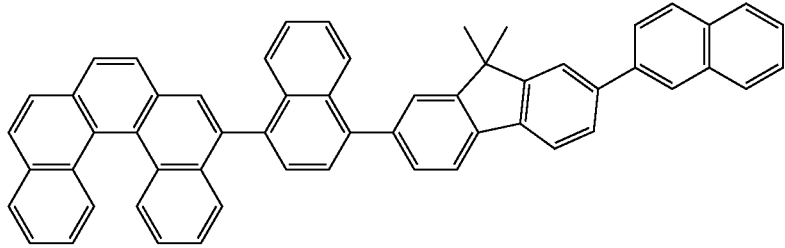
2-209
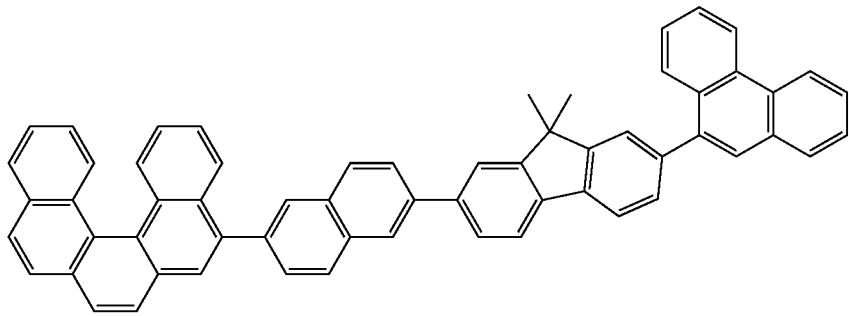
2-210
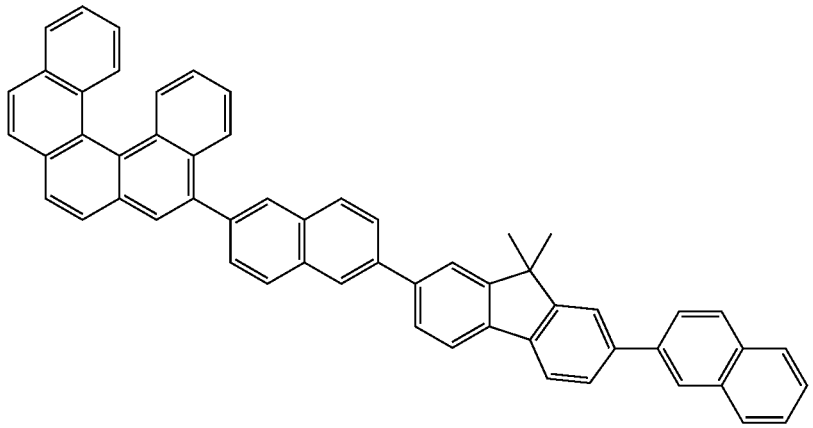
2-211
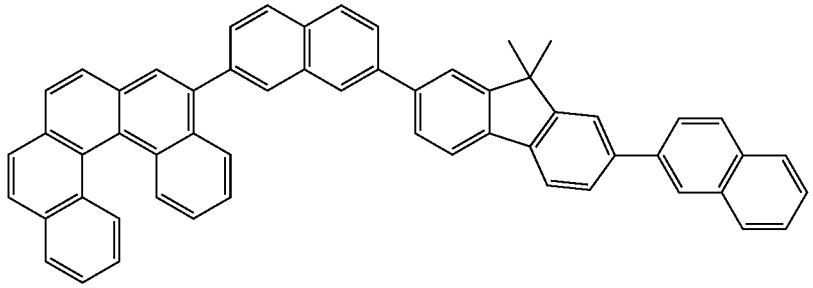
2-212
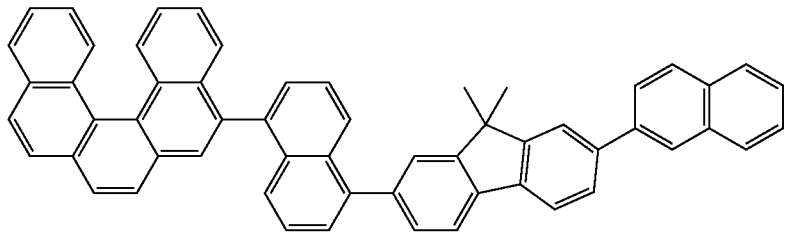
2-213

-continued
2-214
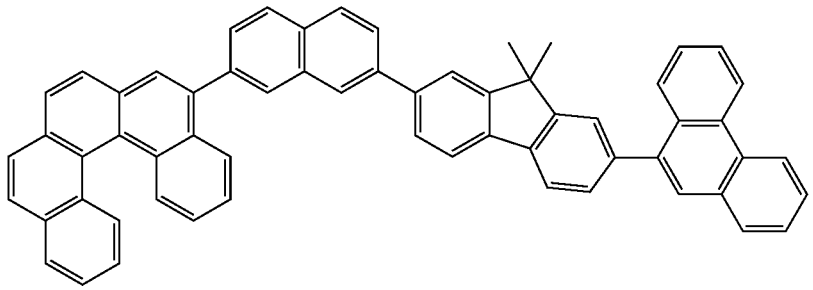
2-215
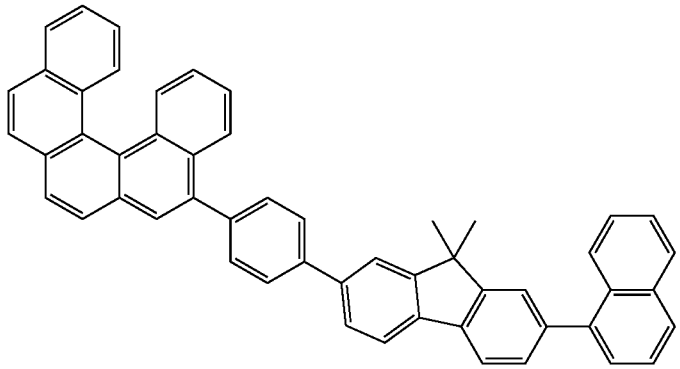
2-216 2-217
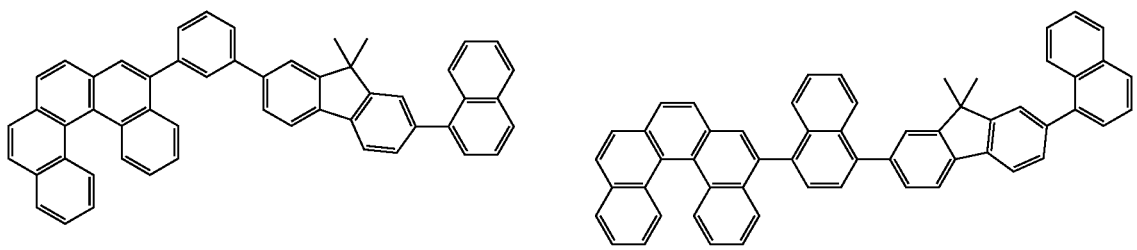
2-218 2-219
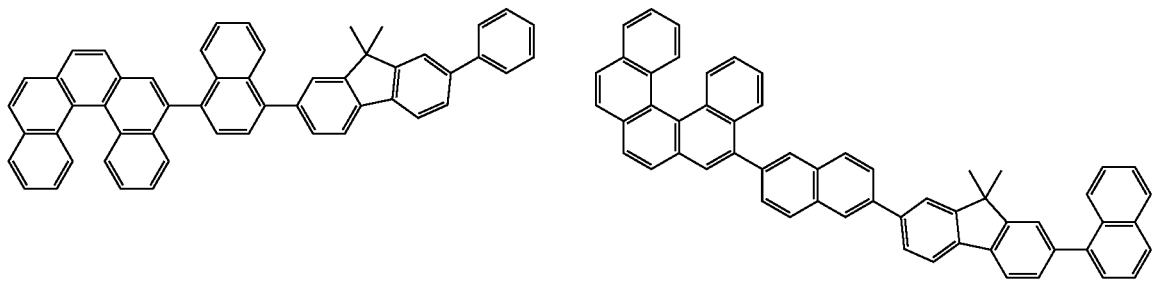
2-220 2-221
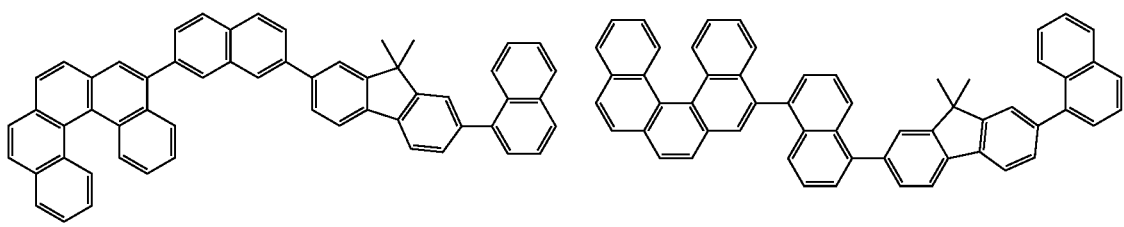

-continued
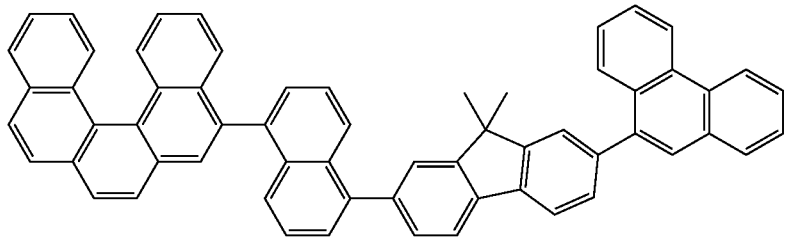
2-222
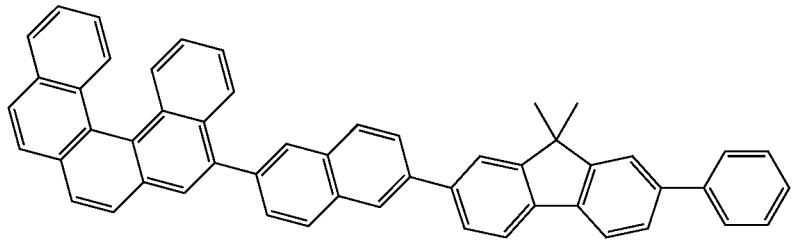
2-223
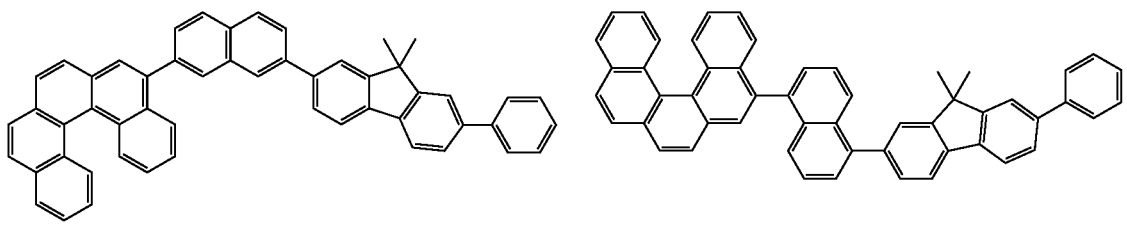
2-224  2-225
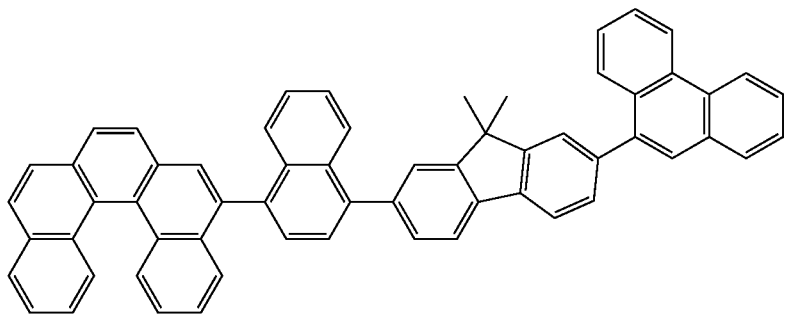
2-226
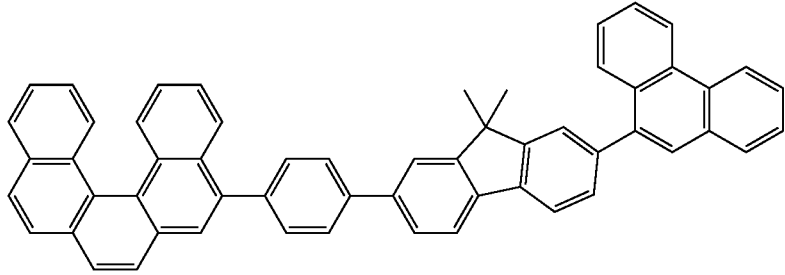
2-227
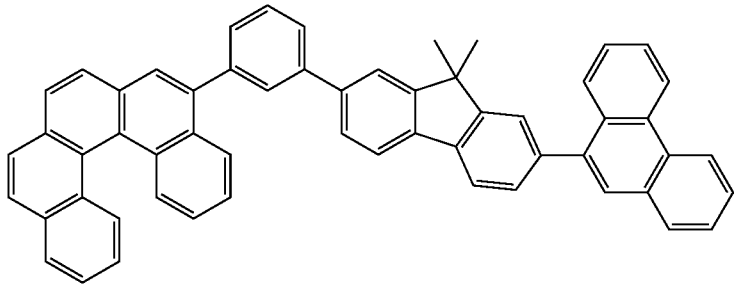
2-228

-continued
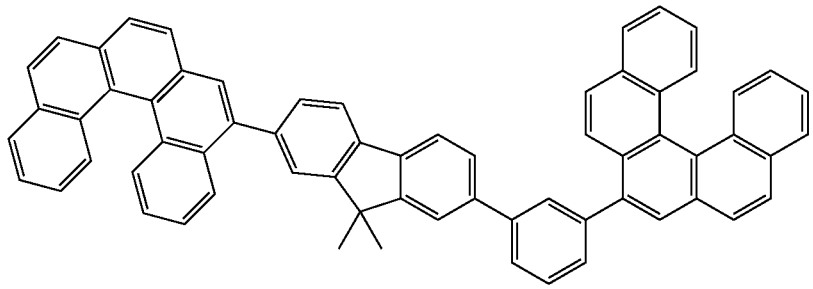
2-229
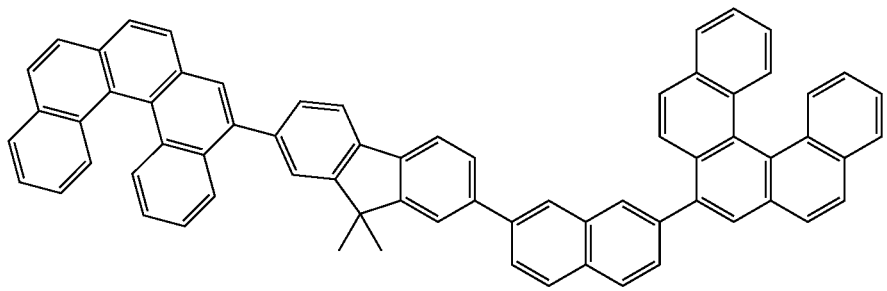
2-230
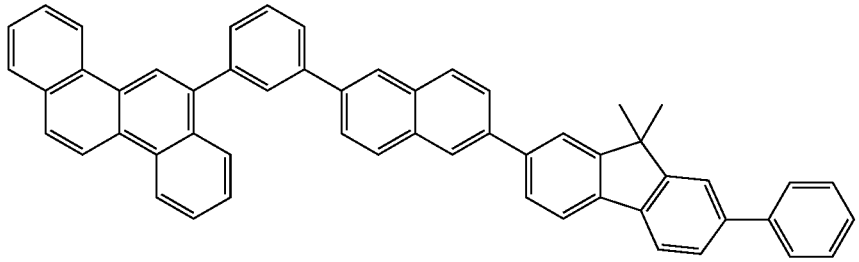
2-247
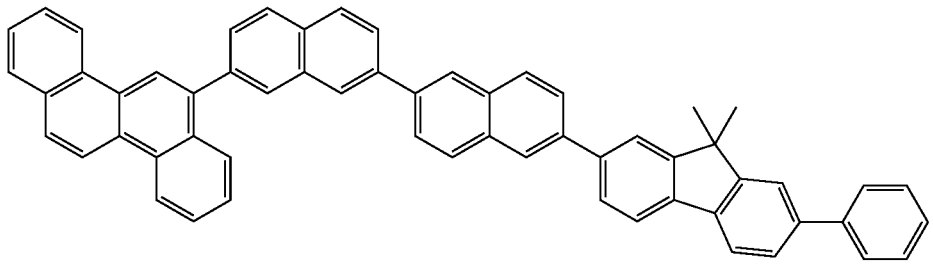
2-248
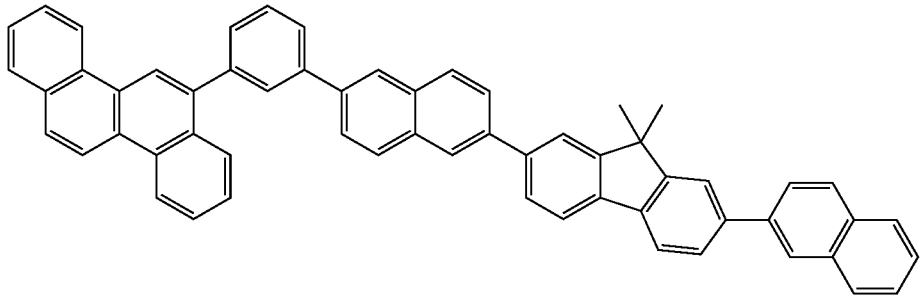
2-249

-continued
2-250
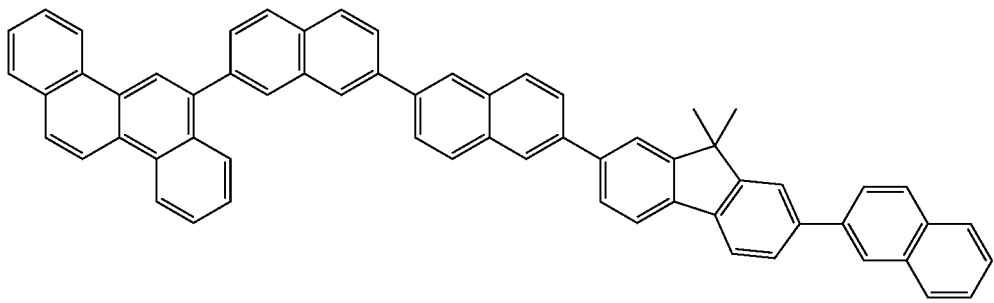
2-267
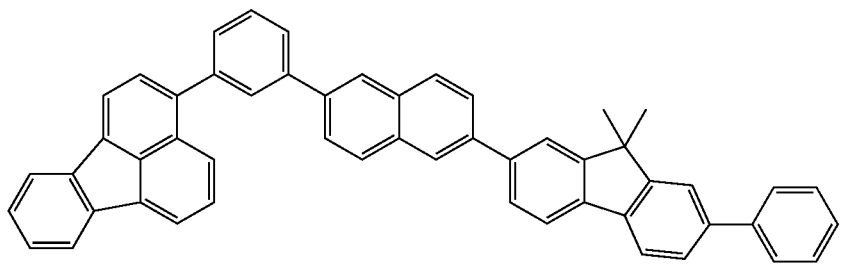
2-268
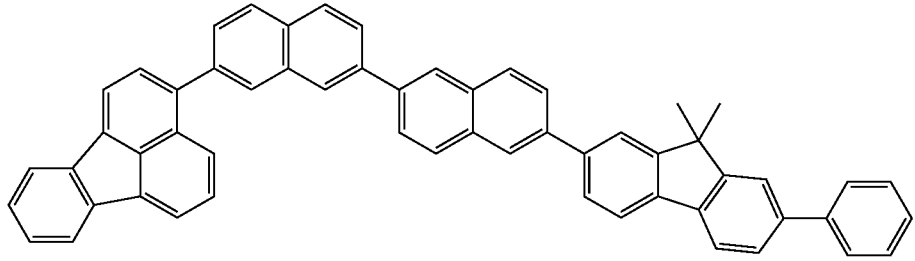
2-269
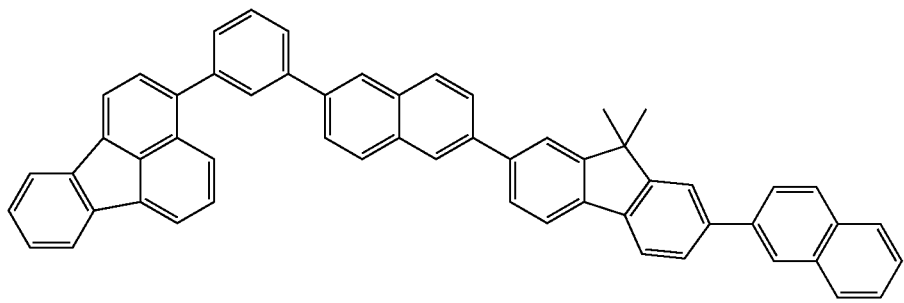
2-270
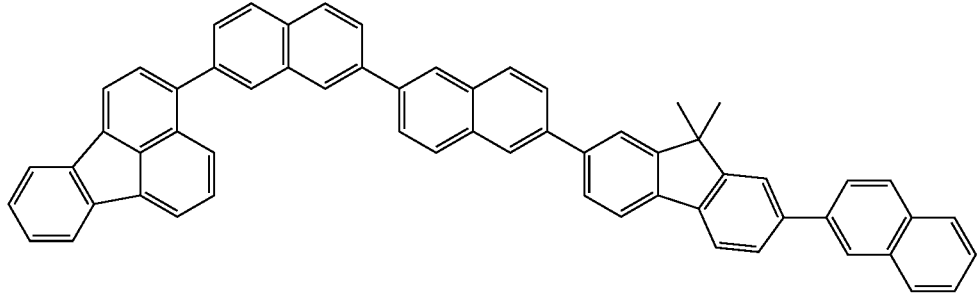

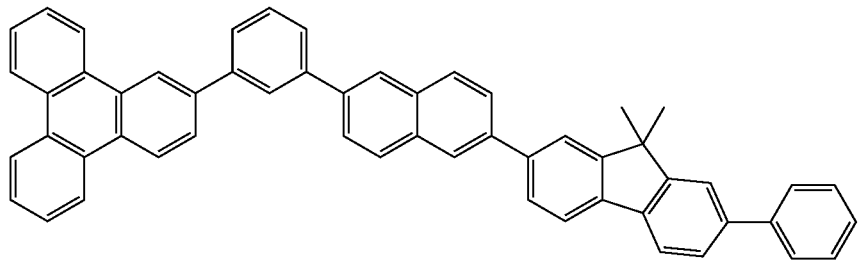
2-287
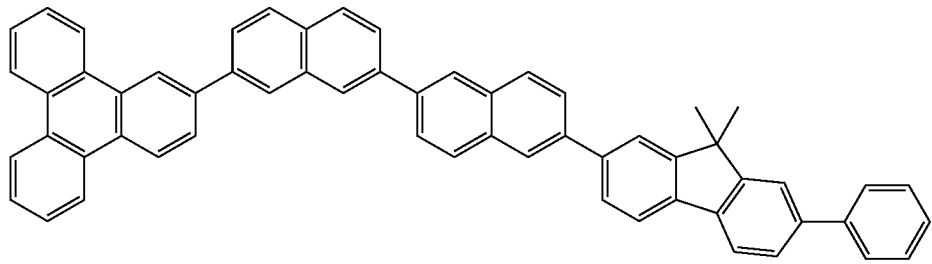
2-288
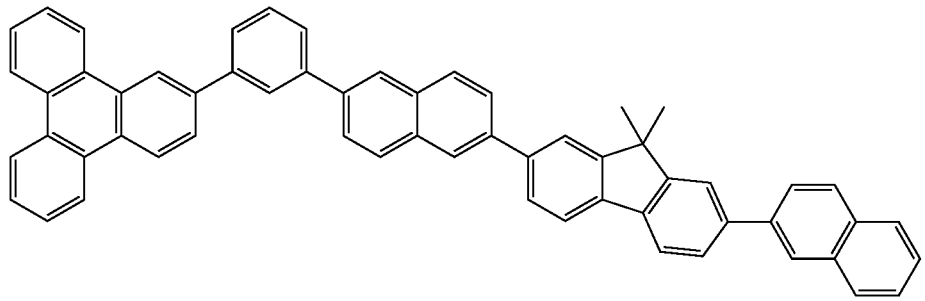
2-289
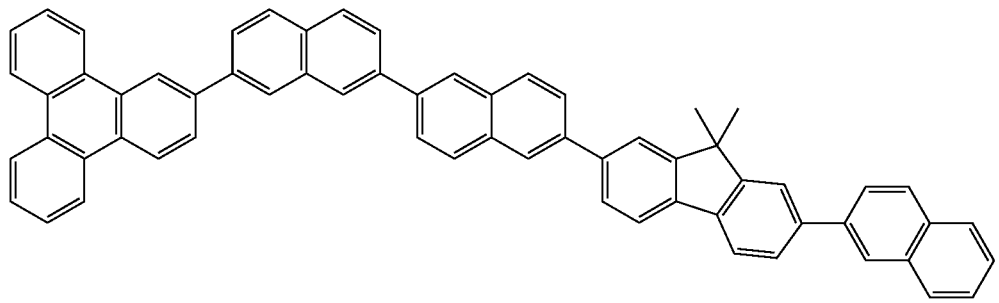
2-290
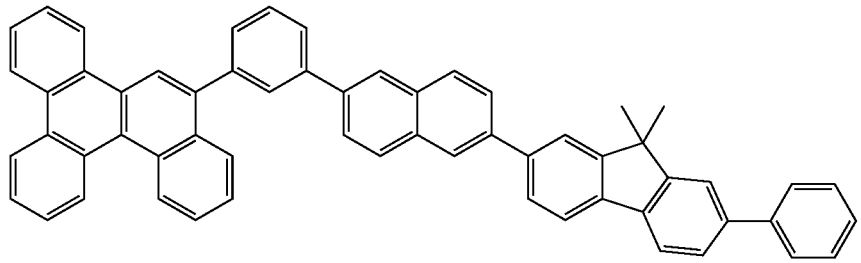
2-307

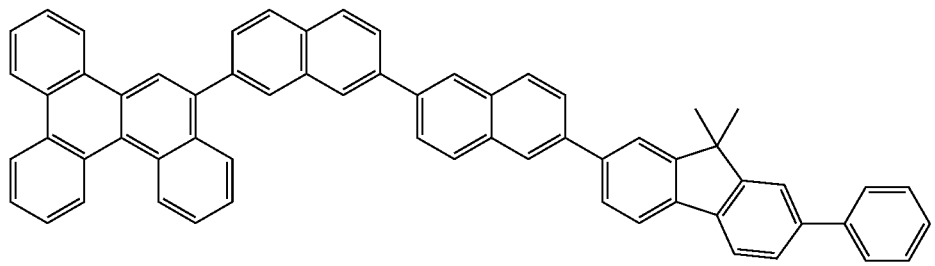
2-308
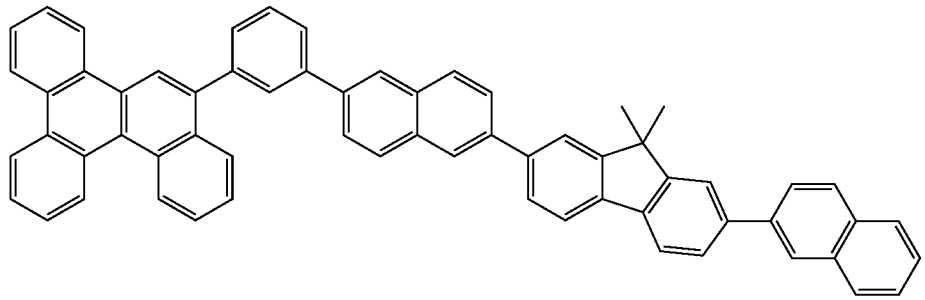
2-309
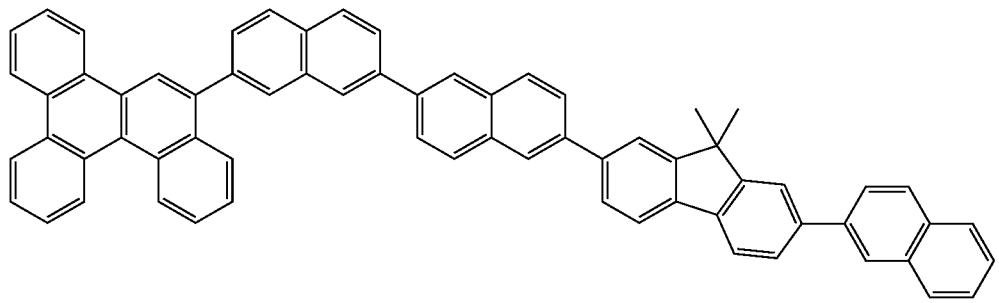
2-310
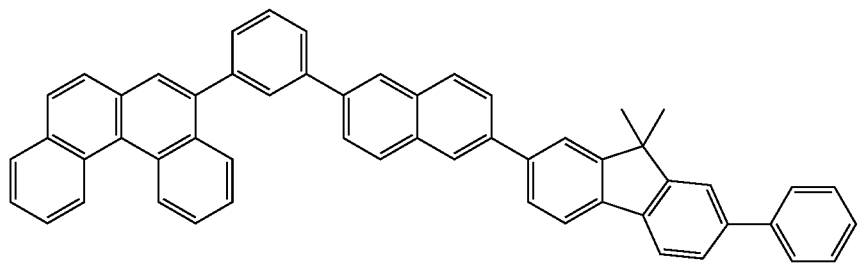
2-327
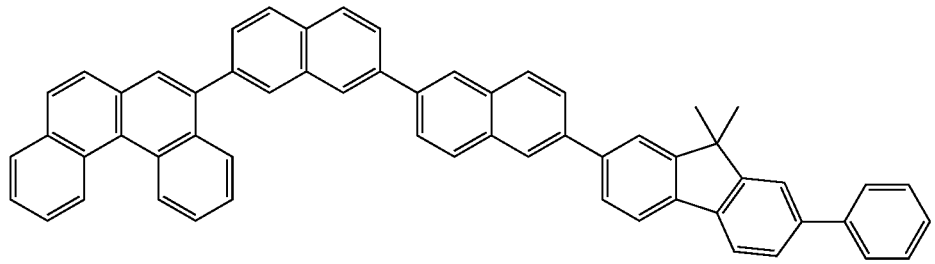
2-328

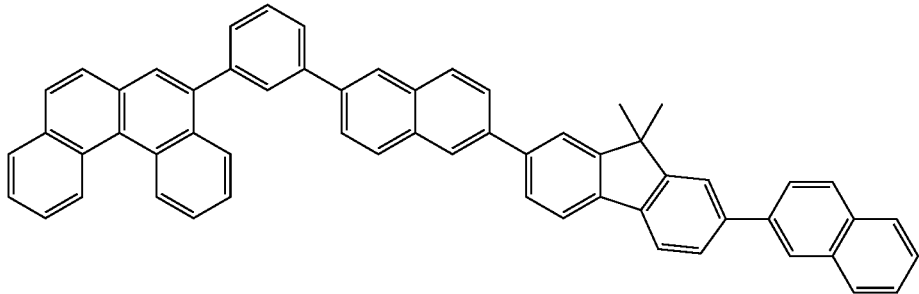
2-329
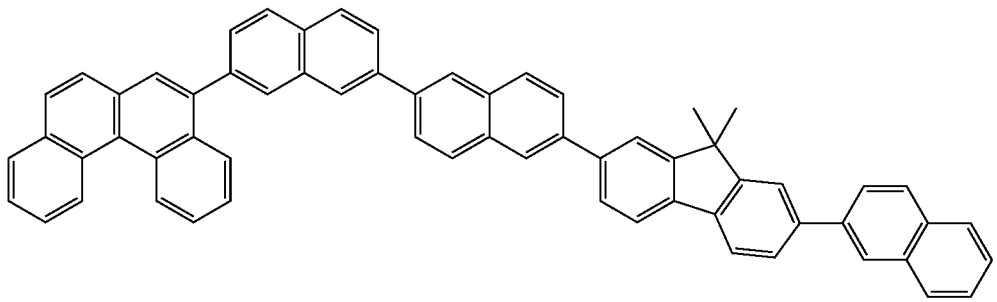
2-330
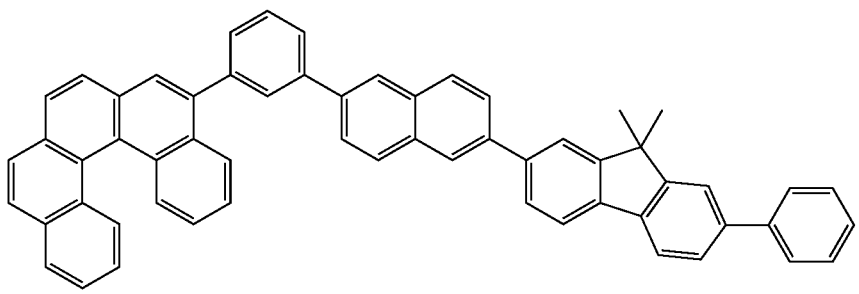
2-347
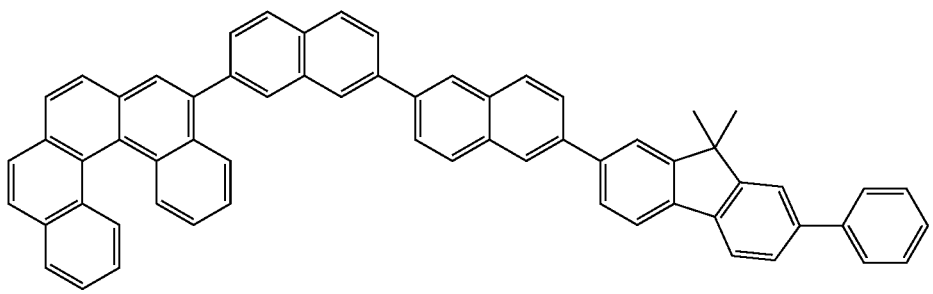
2-348
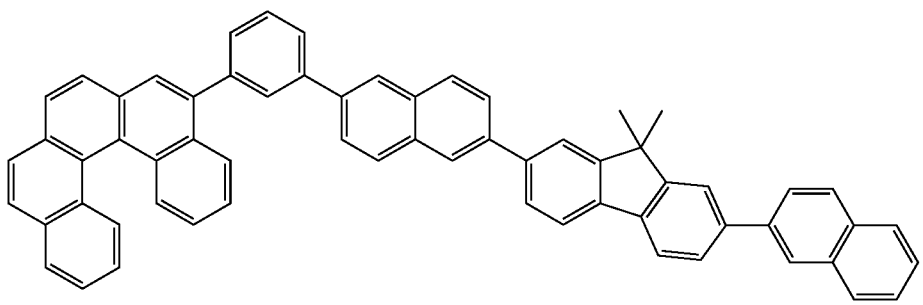
2-349

-continued
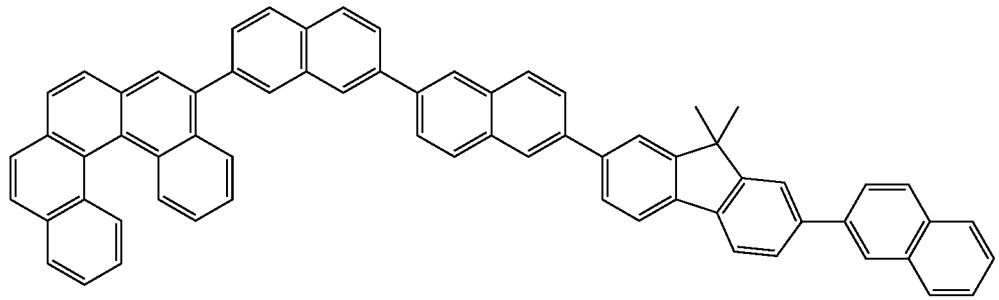
2-350
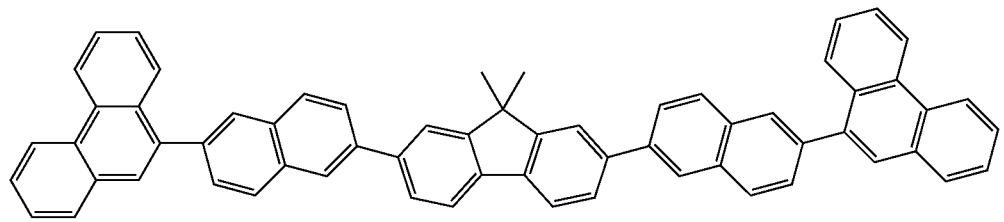
2-351
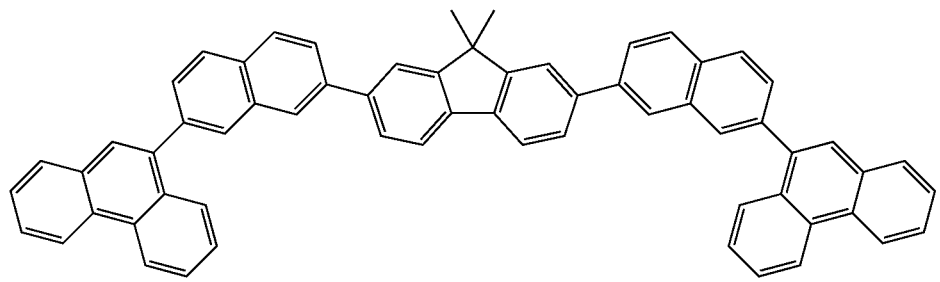
2-352
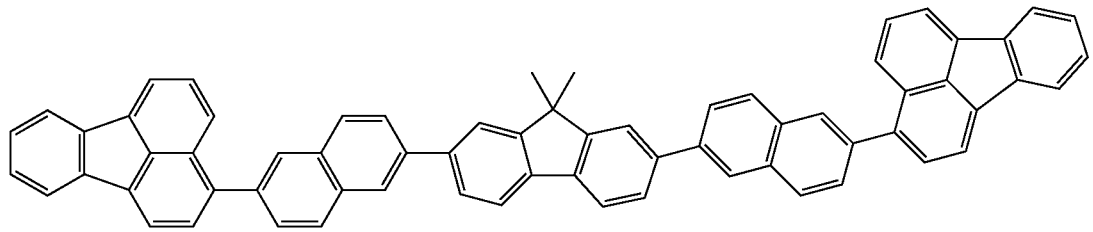
2-353
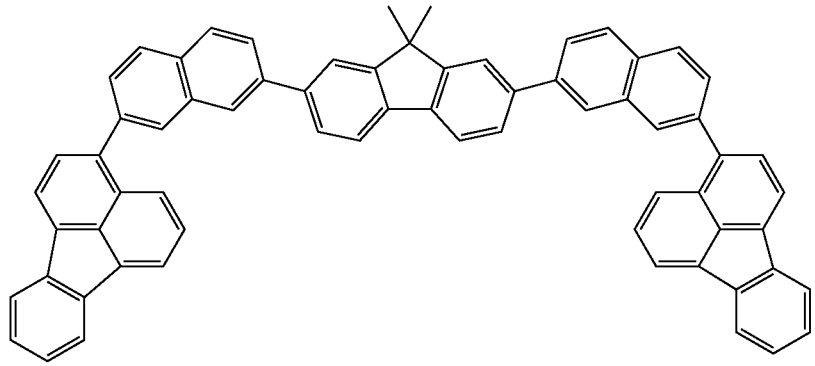
2-354

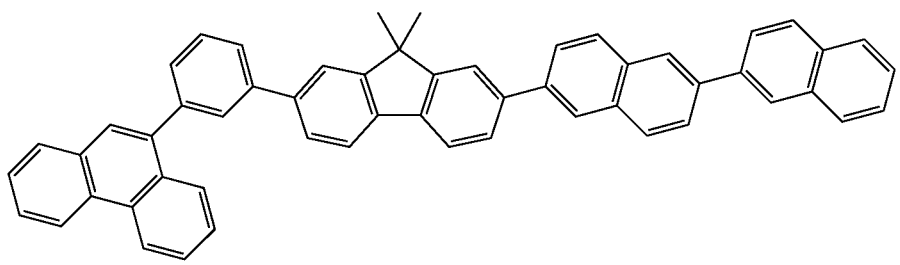

-continued
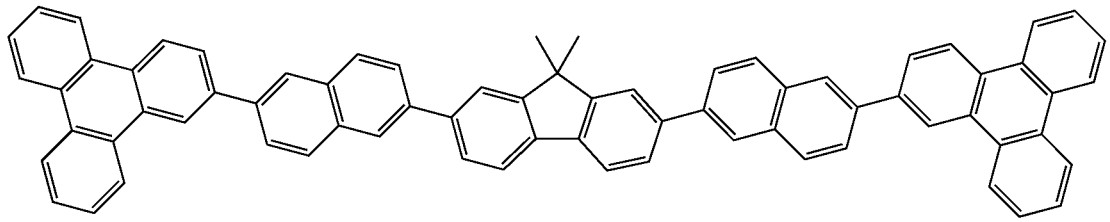
2-366
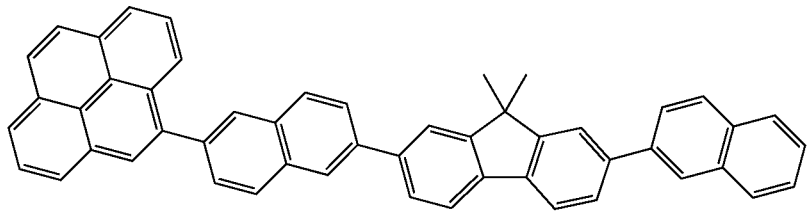
2-367
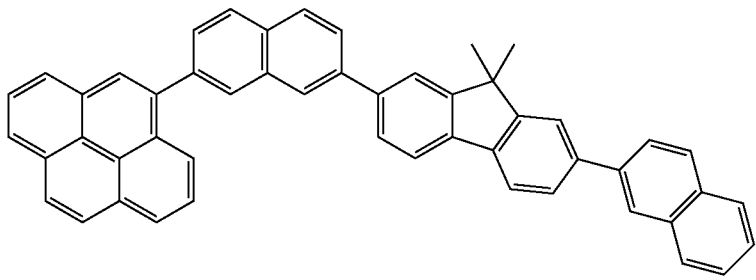
2-368
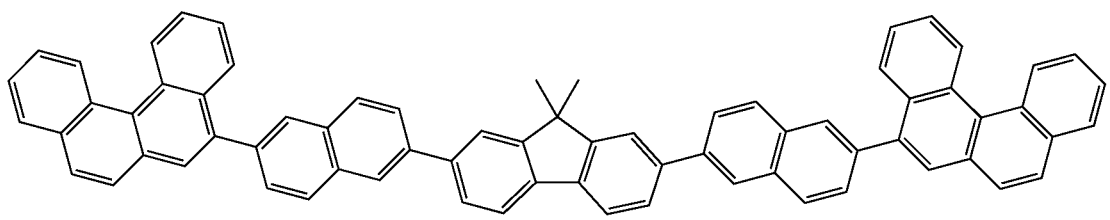
2-369
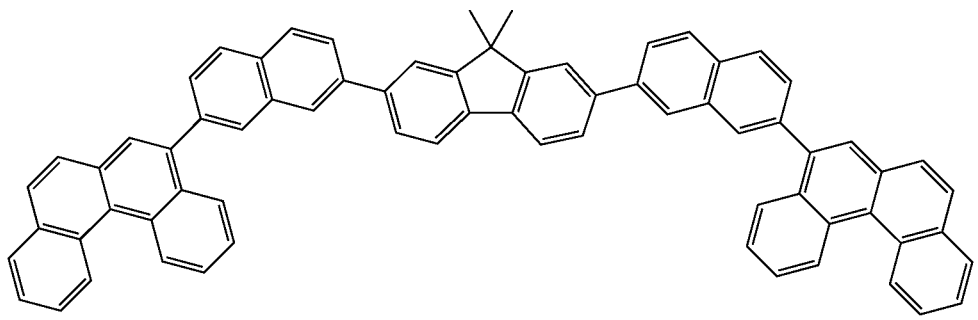
2-370
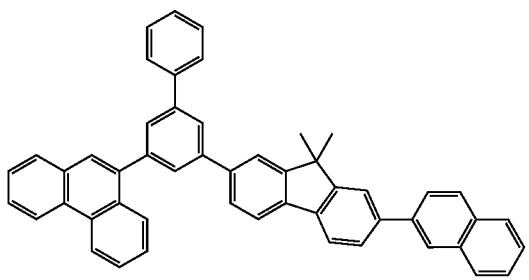
2-371
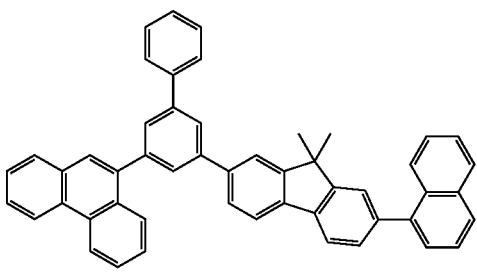
2-372

-continued
2-374
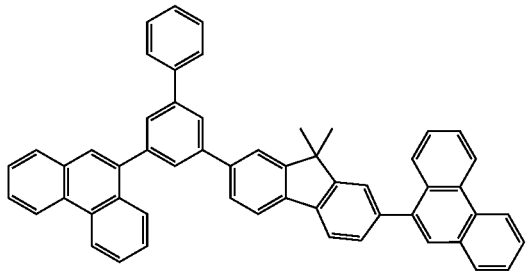
2-375
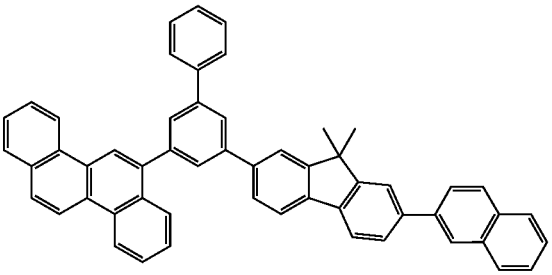
2-377
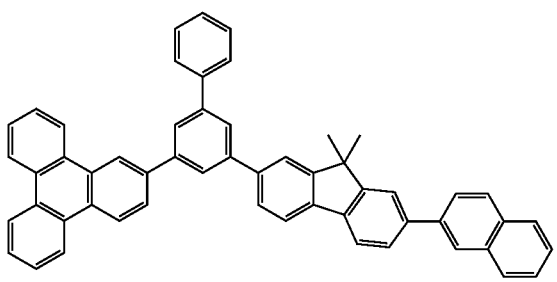
2-379
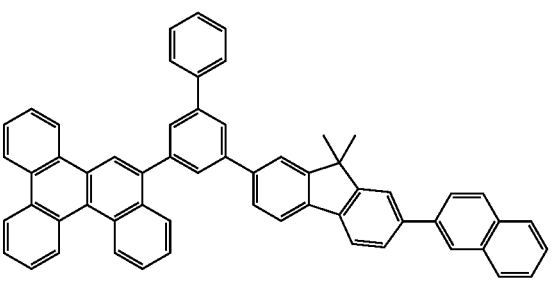
2-381
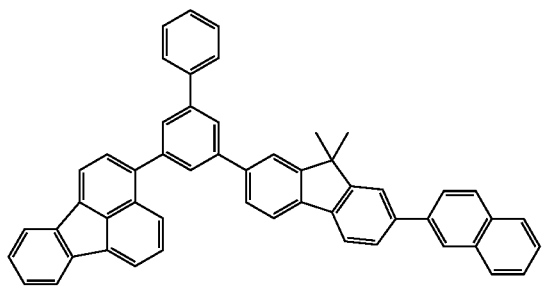
2-383
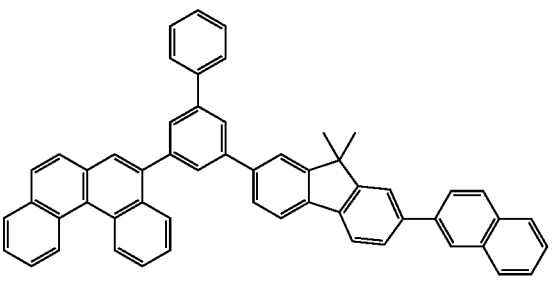
2-385
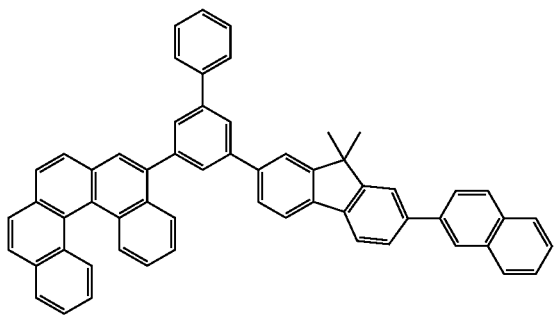
2-387
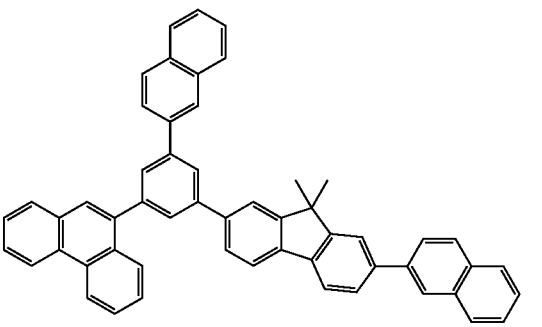
2-388
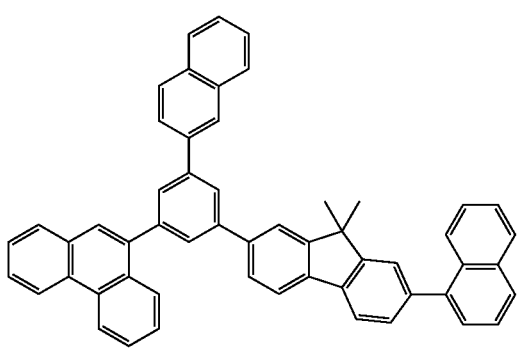
2-390
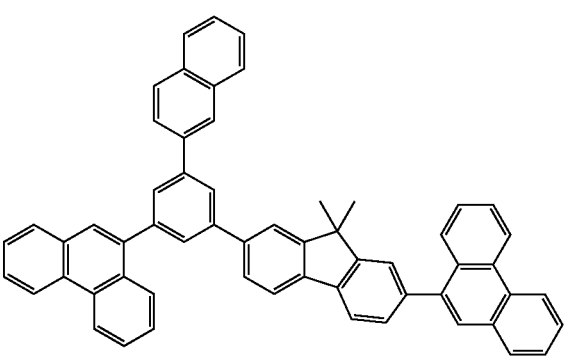

-continued

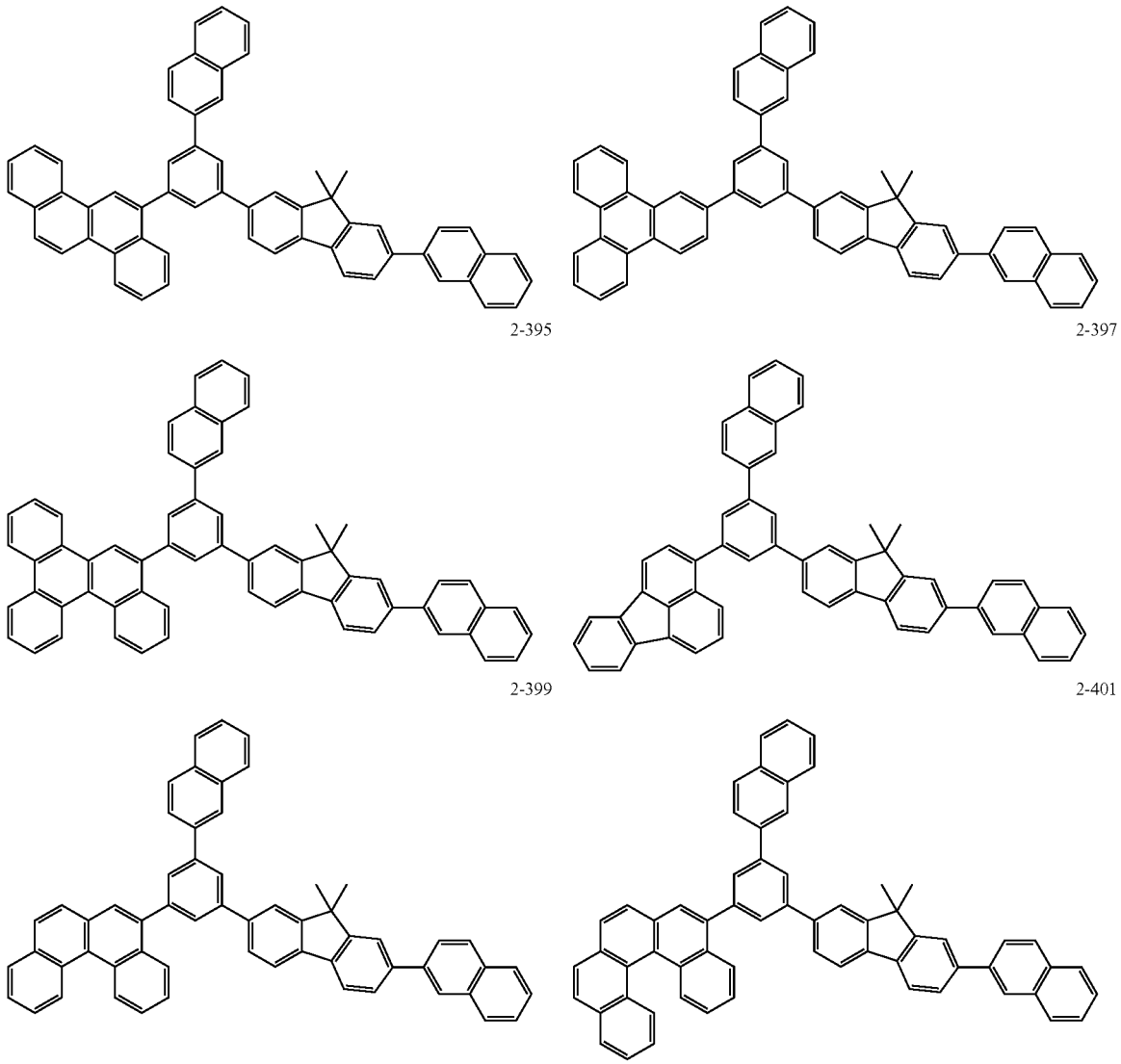

28. An organic electroluminescence device comprising an organic thin film layer between a cathode and an anode, the organic thin film layer comprising one or more layers, wherein the organic thin film layer comprises one or more light emitting layers; and at least one of the light emitting layers comprises a phosphorescent material and a host material represented by the following formula (A-1):

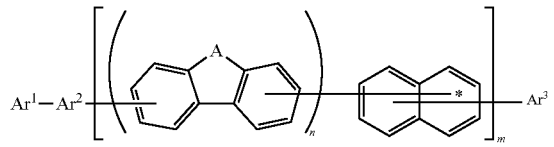

(A-1)

wherein $Ar^1$ and $Ar^3$ each independently represent a hydrogen atom inclusive of a heavy hydrogen atom, a residue of a substituted or unsubstituted benzene ring, or a residue of a substituted or unsubstituted condensed aromatic hydrocarbon ring selected from a substituted or unsubstituted naphthalene ring, a substituted or unsubstituted chrysene ring, a substituted or unsubstituted phenanthrene ring, a substituted or unsubstituted benzophenanthrene ring, a substituted or unsubstituted dibenzophenanthrene ring, a substituted or unsubstituted triphenylene ring, a substituted or unsubstituted benzo[a]triphenylene ring, a substituted or unsubstituted benzochrysene ring, a substituted or unsubstituted fluoranthene ring, a substituted or unsubstituted benzo[b]fluoranthene ring, and a substituted or unsubstituted picene ring;

$Ar^2$ represents a residue of a substituted or unsubstituted benzene ring, a residue of substituted or unsubstituted naphthalene ring, or a residue of substituted or unsubstituted phenanthrene ring;

A represents O, S, or $CR^1R^2$, wherein $R^1$ and $R^2$ each independently represent an alkyl group having 1 to 20 carbon atoms, a substituted or unsubstituted cycloalkyl group having 3 to 20 ring carbon atoms, an aralkyl group having 7 to 24 carbon atoms, or a silyl group having 3 to 20 carbon atoms;

n represents an integer of 1 to 3 and m represents an integer of 1 or 2; and when n is 2 or more, the following formula (A-1-a):

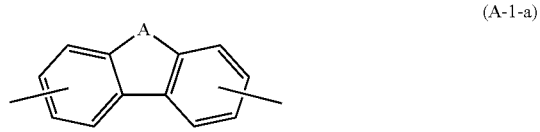

(A-1-a)

in ( )$_n$ may be the same or different.

29. The organic electroluminescence device of 28, wherein formula (A-1) is represented by the following formula (A-2):

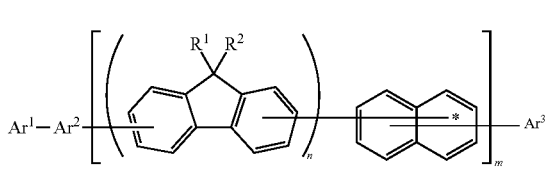

(A-2)

wherein $Ar^1$, $Ar^2$, $Ar^3$, $R^1$, $R^2$, n, and m are the same as defined above.

30. The organic electroluminescence device of 28, wherein formula (A-1) is represented by the following formula (A-3):

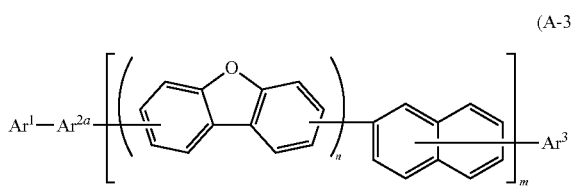

(A-3)

wherein $Ar^1$, $Ar^3$, n, and m are the same as defined above, $Ar^{2a}$ represents a residue of a substituted or unsubstituted benzene ring or a residue of a substituted or unsubstituted phenanthrene ring, and $Ar^3$ is bonded to 6-position or 7-position of the naphthalene ring residue which is bonded to the dibenzofuran ring residue.

31. The organic electroluminescence device of 28, wherein formula (A-1) is represented by the following formula (A-4):

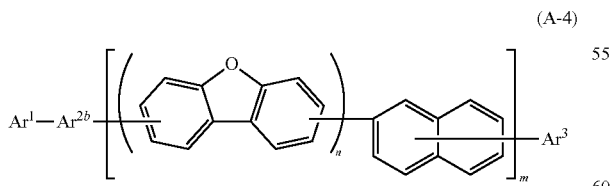

(A-4)

wherein $Ar^1$, $Ar^3$, n, and m are the same as defined above; $Ar^{2b}$ represents a residue of a substituted or unsubstituted naphthalene ring; when $Ar^{2b}$ is bonded to the dibenzofuran ring residue at 2-position of $Ar^{2b}$, one of $Ar^1$ and $Ar^3$ is bonded to 6-position or 7-position of the naphthalene ring residue to which it is bonded; when $Ar^{2b}$ is bonded to the dibenzofuran ring residue at a position other than 2-position of $Ar^{2b}$, $Ar^3$ is bonded to 6-position or 7-position of the naphthalene ring residue; and $Ar^1$ and $Ar^3$ are not hydrogen at the same time.

32. An organic electroluminescence device which comprises an organic thin film layer between a cathode and an anode, the organic thin film layer comprising one or more layers; the organic thin film layer comprises one or more light emitting layers; at least one of the layers of the organic thin film layer comprises a phosphorescent material and any one of the materials for organic electroluminescence device 1 to 23 and 25 to 27.

33. The organic electroluminescence device of 32, wherein at least one of the light emitting layers comprises the material for organic electroluminescence device and the phosphorescent material.

34. The organic electroluminescence device of 32, wherein the phosphorescent material comprises a metal complex, and the metal complex comprises a metal atom selected from Ir, Pt, Os, Au, Cu, Re and Ru and a ligand.

35. The organic electroluminescence device of 34, wherein the ligand is orthometalated by the metal atom which forms the complex.

36. The organic electroluminescence device of 32, wherein an exited triplet energy of the material for organic electroluminescence device is 2.0 eV or more and 2.8 eV or less.

37. The organic electroluminescence device of 32, wherein a wavelength of a maximum emission of at least one of the phosphorescent materials is 520 nm or more and 720 nm or less.

38. The organic electroluminescence device of 32, wherein the organic thin film layer comprises an electron transporting layer which is disposed between the cathode and the light emitting layer, and the electron transporting layer comprises the material for organic electroluminescence device.

39. The organic electroluminescence device of 32, wherein the organic thin film layer comprises an electron transporting layer or an electron injecting layer which is disposed between the cathode and the light emitting layer, and the electron transporting layer or the electron injecting layer comprises an aromatic ring compound having a nitrogen-containing six- or five-membered ring or a condensed aromatic ring compound comprising a nitrogen-containing six- or five-membered ring.

40. The organic electroluminescence device of 32, wherein the organic thin film layer comprises an electron transporting layer or an electron injecting layer which is disposed between the cathode and the light emitting layer, and the electron transporting layer or the electron injecting layer comprises the material for organic electroluminescence device.

41. The organic electroluminescence device of 32, wherein a reduction-causing dopant is added to an interfacial area between the cathode and the organic thin film layer.

Effect of the Invention

According to the present invention, a phosphorescent organic EL device having high efficiency and long lifetime can be provided by using the materials for organic electroluminescence device represented by formulae (A-1) to (A-5), (B-1) to (B-4), and (C-1) to (C-6) as a host material, particularly as a phosphorescent host.

BRIEF DESCRIPTION OF THE DRAWINGS

FIG. 1 is a schematic illustration showing an embodiment of architecture of the organic electroluminescence device according to the present invention.

REFERENCE NUMERALS

1 Organic EL device
2 Substrate
3 Anode
4 Cathode
5 Phosphorescent emitting layer
6 Hole injecting/transporting layer
7 Electron injecting/transporting layer
10 Organic thin film layer

MODE FOR CARRYING OUT THE INVENTION

The embodiments of the invention will be described below.
Architecture of Organic EL Device First, the architecture of the organic EL device will be described.

Representative architecture of the organic electroluminescence device includes, but not limited to,
(1) anode/light emitting layer/cathode,
(2) anode/hole injecting layer/light emitting layer/cathode,
(3) anode/light emitting layer/electron injecting/transporting layer/cathode,
(4) anode/hole injecting layer/light emitting layer/electron injecting/transporting layer/cathode,
(5) anode/organic semiconductor layer/light emitting layer/cathode,
(6) anode/organic semiconductor layer/electron blocking layer/light emitting layer/cathode,
(7) anode/organic semiconductor layer/light emitting layer/adhesion improving layer/cathode,
(8) anode/hole injecting/transporting layer/light emitting layer/electron injecting/transporting layer/cathode,
(9) anode/insulating layer/light emitting layer/insulating layer/cathode,
(10) anode/inorganic semiconductor layer/insulating layer/light emitting layer/insulating layer/cathode,
(11) anode/organic semiconductor layer/insulating layer/light emitting layer/insulating layer/cathode,
(12) anode/insulating layer/hole injecting/transporting layer/light emitting layer/insulating layer/cathode, and
(13) anode/insulating layer/hole injecting/transporting layer/light emitting layer/electron injecting/transporting layer/cathode,
with the device architecture (8) being preferably used.

An example of the architecture of the organic electroluminescence device according to the present invention is schematically shown in FIG. 1.

The organic EL device 1 comprises a transparent substrate 2, an anode 3, a cathode 4, and an organic thin film layer 10 disposed between the anode 3 and the cathode 4.

The organic thin film layer 10 includes a phosphorescent emitting layer 5 comprising a phosphorescent host (host material) and a phosphorescent dopant (phosphorescent material). A hole injecting/transporting layer 6 may be disposed between the phosphorescent emitting layer 5 and the anode 3, and an electron injecting/transporting layer 7 may be disposed between the phosphorescent emitting layer 5 and the cathode 4.

An electron blocking layer may be formed on the side of the phosphorescent emitting layer 5 facing the anode 3, and a hole blocking layer may be formed on the side of the phosphorescent emitting layer 5 facing the cathode 4.

With such layers, electrons and holes are confined in the phosphorescent emitting layer 5, to facilitate the formation of excitons in the phosphorescent emitting layer 5.

In the present invention, the host is referred to as a fluorescent host when combinedly used with a fluorescent dopant and as a phosphorescent host when combinedly used with a phosphorescent dopant. Therefore, the fluorescent host and the phosphorescent host are not distinguished from each other merely on the basis of the difference in their molecular structures.

Namely, the term "fluorescent host" means a material for constituting a fluorescent emitting layer containing a fluorescent dopant and does not mean a material usable only as a host of a fluorescent material.

Similarly, the term "phosphorescent host" means a material for constituting a phosphorescent emitting layer containing a phosphorescent dopant and does not mean a material usable only as a host of a phosphorescent material.

In the present invention, the term "hole injecting/transporting layer" means at least one of a hole injecting layer and a hole transporting layer, and the term "electron injecting/transporting layer" means at least one of an electron injecting layer and an electron transporting layer.
Light-Transmissive Substrate The organic electroluminescence device of the invention is formed on a light-transmissive substrate. The light-transmissive substrate serves as a support for the organic electroluminescence device and preferably a flat substrate having a transmittance of 50% or more to 400 to 700 nm visible light.

Examples of the substrate include a plate of glass and a plate of polymer.

The plate of glass may include a plate made of soda-lime glass, barium-strontium-containing glass, lead glass, aluminosilicate glass, borosilicate glass, barium borosilicate glass, or quartz.

The plate of polymer may include a plate made of polycarbonate, acrylic resin, polyethylene terephthalate, polyether sulfide, or polysulfone.
Anode and Cathode The anode of the organic electroluminescence device injects holes to the hole injecting layer, the hole transporting layer or the light emitting layer, and an anode having a work function of 4.5 eV or more is effective.

Examples of material for anode include indium tin oxide alloy (ITO), tin oxide (NESA), indium zinc oxide alloy, gold, silver, platinum, and copper.

The anode is formed by making the electrode material into a thin film by a method, such as a vapor deposition method or a sputtering method.

When getting the light emitted from the light emitting layer through the anode as employed in the embodiments of the present invention, the transmittance of anode to visible light is preferably 10% or more. The sheet resistance of anode is preferably several hundreds $\Omega/\square$ or less. The film thickness of anode depends upon the kind of material and generally 10 nm to 1 μm, preferably 10 to 200 nm.

The cathode is formed preferably from a material having a small work function in view of injecting electrons to the electron injecting layer, the electron transporting layer or the light emitting layer.

Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy.

Like the anode, the cathode is formed by making the material into a thin film by a method, such as the vapor deposition method and the sputtering method. The emitted light may be taken from the side of cathode.

Light Emitting Layer

The light emitting layer of organic electroluminescence device combines the following functions:
(1) Injection function: allowing holes to be injected from the anode or hole injecting layer, and allowing electrons to be injected from the cathode or electron injecting layer, by the action of electric field;
(2) Transporting function: transporting the injected charges (holes and electrons) by the force of electric field; and
(iii) Emission function: providing a zone for recombination of electrons and holes to cause the emission.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method.

The light emitting layer is preferably a molecular deposit film.

The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences. The light emitting layer can be also formed by making a solution of a binder, such as a resin, and its material in a solvent into a thin film by a spin coating method, as disclosed in JP 57-51781A.

The thickness of the light emitting layer is preferably 5 to 50 nm, more preferably 7 to 50 nm, and most preferably 10 to 50 nm. If being less than 5 nm, the light emitting layer is difficult to form and the control of color is difficult. If exceeding 50 nm, the driving voltage may increase.

The organic EL device of the invention comprises an organic thin film layer between a cathode and an anode, which comprises one or more layers. The organic thin film layer comprises one or more light emitting layers and at least one layer of the organic thin film layer contains at least one kind of a phosphorescent material and at least one kind of the materials A to C for organic electroluminescence device of the invention which are mentioned below. Preferably, at least one light emitting layer contains the material for organic electroluminescence device of the invention and at least one kind of a phosphorescent material.

Material A for Organic Electroluminescence Device

The material A for organic electroluminescence device is represented by the following formula (A-1) and preferably by the following formulae (A-2) to (A-5):

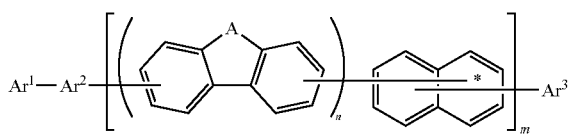

(A-1)

wherein $Ar^1$ and $Ar^3$ each independently represent a hydrogen atom inclusive of a heavy hydrogen atom, a residue of a substituted or unsubstituted benzene ring, or a residue of a substituted or unsubstituted condensed aromatic hydrocarbon ring selected from a substituted or unsubstituted naphthalene ring, a substituted or unsubstituted chrysene ring, a substituted or unsubstituted phenanthrene ring, a substituted or unsubstituted benzophenanthrene ring, a substituted or unsubstituted dibenzophenanthrene ring, a substituted or unsubstituted triphenylene ring, a substituted or unsubstituted benzo[a]triphenylene ring, a substituted or unsubstituted benzochrysene ring, a substituted or unsubstituted fluoranthene ring, a substituted or unsubstituted benzo[b]fluoranthene ring, and a substituted or unsubstituted picene ring;

$Ar^2$ represents a residue of a substituted or unsubstituted benzene ring, a residue of substituted or unsubstituted naphthalene ring, or a residue of substituted or unsubstituted phenanthrene ring;

A represents O, S, or $CR^1R^2$, wherein $R^1$ and $R^2$ each independently represent a substituted or unsubstituted alkyl group having 1 to 20 carbon atoms, a substituted or unsubstituted cycloalkyl group having 3 to 20 ring carbon atoms, a substituted or unsubstituted aralkyl group having 7 to 24 carbon atoms, or a substituted or unsubstituted silyl group having 3 to 20 carbon atoms;

n represents an integer of 1 to 3 and m represents an integer of 1 or 2; and when n is 2 or more, the following formula (A-1-a) in $(\ )_n$ may be the same or different.

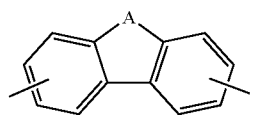

(A-1-a)

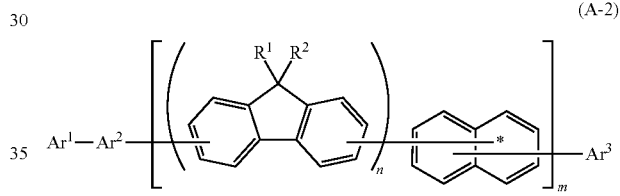

(A-2)

wherein $Ar^1$, $Ar^2$, $Ar^3$, $R^1$, $R^2$, n, and m are the same as defined above.

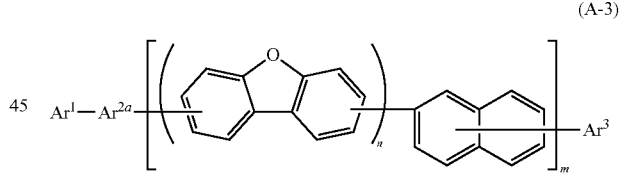

(A-3)

wherein $Ar^1$, $Ar^3$, n, and m are the same as defined above, $Ar^{2a}$ represents a residue of a substituted or unsubstituted benzene ring or a substituted or unsubstituted phenanthrene ring, and $Ar^3$ is bonded to 6-position or 7-position of the naphthalene ring residue bonded to the dibenzofuran ring residue.

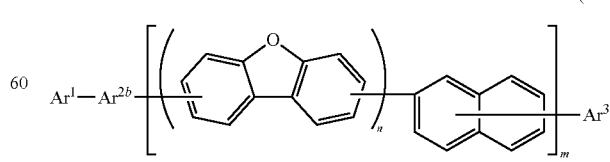

(A-4)

wherein $Ar^1$, $Ar^3$, n, and m are the same as defined above; $Ar^{2b}$ represents a residue of a substituted or unsubstituted naphthalene ring; when $Ar^{2b}$ is bonded to the dibenzofuran ring residue at 2-position of $Ar^{2b}$, one of $Ar^1$ and $Ar^3$ is bonded to 6-position or 7-position of the naphthalene ring residue to which it is bonded; and when $Ar^{2b}$ is bonded to the dibenzofuran ring residue at a position other than 2-position of $Ar^{2b}$, $Ar^3$ is bonded to 6-position or 7-position of the naphthalene ring residue.

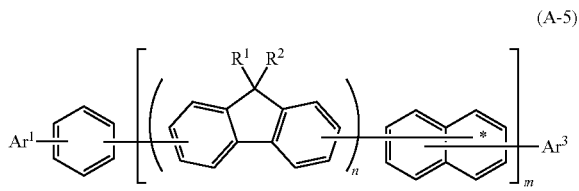

(A-5)

wherein $Ar^1$, $Ar^3$, $R^1$, $R^2$, n, and m are the same as defined above.

When any one of $Ar^1$, $Ar^2$, $Ar^{2a}$, $Ar^{2b}$, $Ar^3$, $R^1$, and $R^2$ in formulae (A-1) to (A-5) has one or more substituents, the substituent is preferably an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom or an aryl group having 6 to 22 ring carbon atoms.

Material B for Organic Electroluminescence Device

The material B for organic electroluminescence device of the present invention is represented by the following formula (B-1) and preferably by the following formulae (B-2) to (B-4):

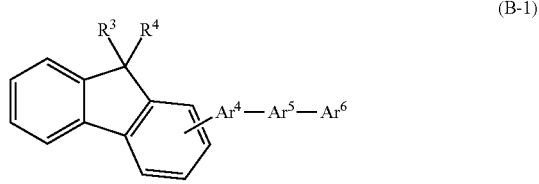

(B-1)

wherein $R^3$ and $R^4$ each independently represent a hydrogen atom inclusive of a heavy hydrogen atom, an alkyl group having 1 to 10 carbon atoms or an aryl group having 6 to 12 ring carbon atoms; $Ar^4$ is a residue of a condensed polycyclic aromatic hydrocarbon ring having 10 to 22 ring carbon atoms; $Ar^5$ is a benzene ring or a residue of a condensed polycyclic aromatic hydrocarbon ring having 10 to 22 ring carbon atoms; $Ar^6$ is a hydrogen atom inclusive of a heavy hydrogen atom, a benzene ring or a residue of a condensed polycyclic aromatic hydrocarbon ring having 10 to 22 ring carbon atoms; and $R^3$, $R^4$, $Ar^4$, $Ar^5$ and $Ar^6$ each may be independently substituted;
provided that each of $Ar^4$, $Ar^5$ and $Ar^6$ does not have an anthracene, pyrene, perylene, triphenylene, naphthacene and pentacene skeleton; and the material does not include the following compounds (1) to (6):
(1) a compound wherein $Ar^4$ is any of a naphthalene ring, a phenanthrene ring, a chrysene ring, a benzoanthracene ring and a fluoranthene ring and $Ar^5$ is a fluorene ring;
(2) a compound wherein $Ar^4$ is a naphthalene ring, $Ar^5$ is a benzene ring, and $Ar^6$ is a benzene ring or a hydrogen atom;
(3) (i) a compound wherein $Ar^4$ is a naphthalene-2,6-diyl group, $Ar^5$ is a β-naphthyl group, and $Ar^6$ is a hydrogen atom, and (ii) a compound wherein $Ar^4$ is a naphthalene-2,6-diyl group, $Ar^5$ is a naphthalene-2,6-diyl group, and $Ar^6$ is a β-naphthyl group;
(4) a compound wherein $Ar^4$ is a fluorene ring and $Ar^5$ is a benzene ring, a fluorene ring or a fluoranthene ring, and a compound wherein $Ar^4$ is a fluorene ring and $Ar^6$ is a hydrogen atom or a β-naphthyl group;
(5) a compound wherein $Ar^4$ is a phenanthrene ring or a fluoranthene ring, $Ar^5$ is a benzene ring, and $Ar^6$ is a hydrogen atom; and
(6) a compound wherein $Ar^4$ is a benzene ring, a biphenyl ring, a naphthalene ring, a binaphthalene ring or a fluorene ring and $Ar^5$ is a fluoranthene ring.

A material wherein $Ar^4$ is a naphthalene ring, $Ar^5$ is a benzene ring, and $Ar^6$ is a residue of a condensed polycyclic aromatic hydrocarbon ring having 10 to 22 ring carbon atoms is preferred. $Ar^6$ is preferably a phenanthryl group, a benzophenanthryl group, a dibenzophenanthryl group, a chrysenyl group, a fluoranthenyl group, a triphenylene group, or a benzotriphenylene group.

A compound wherein $Ar^4$ is a naphthalene ring, $Ar^5$ is a naphthalene ring, and $Ar^6$ is a residue of a condensed polycyclic aromatic hydrocarbon ring having 10 to 22 ring carbon atoms is also preferred, with the proviso that a compound wherein $Ar^4$ is a naphthalene-2,6-diyl group, $Ar^5$ is a naphthalene-2,6-diyl group, and $Ar^6$ is a β-naphthyl group is excluded. $Ar^6$ is preferably a phenanthryl group, a benzophenanthryl group, a dibenzophenanthryl group, a chrysenyl group, a fluoranthenyl group, a triphenylene group, or a benzotriphenylene group.

A compound wherein $Ar^4$ is a naphthalene ring, $Ar^5$ is a residue of a condensed polycyclic aromatic hydrocarbon ring having 11 to 22 ring carbon atoms, and $Ar^6$ is a hydrogen atom inclusive of a heavy hydrogen atom is also preferred, with the proviso that (1) a compound wherein $Ar^4$ is a naphthalene-2,6-diyl group, $Ar^5$ is a β-naphthyl group, and $Ar^6$ is a hydrogen atom, (2) a compound wherein $Ar^4$ is a naphthalene-1,4-diyl group or a naphthalene-1,5-diyl group, $Ar^5$ is a fluoranthene ring, and $Ar^6$ is a hydrogen atom, and (3) a compound wherein $Ar^4$ is a naphthalene-1,4-diyl group, a naphthalene-2,6-diyl group, or a naphthalene-2,8-diyl group, $Ar^5$ is a fluorene ring, and $Ar^6$ is a hydrogen atom are excluded. $Ar^5$ is preferably a phenanthrene ring, a benzophenanthrene ring, a dibenzophenanthrene ring, a chrysene ring, a fluoranthene ring, a triphenylene ring, or a benzotriphenylene ring.

In addition, a compound wherein $Ar^4$ is a fluoranthene ring, a phenanthrene ring or a chrysene ring, $Ar^5$ is a condensed polycyclic aromatic hydrocarbon ring having 10 to 22 ring carbon atoms, and $Ar^6$ is a hydrogen atom inclusive of a heavy hydrogen atom is preferred. $Ar^5$ is preferably a naphthalene ring, a phenanthrene ring, a benzophenanthrene ring, a dibenzophenanthrene ring, a chrysene ring, a fluoranthene ring, a triphenylene ring, or a benzotriphenylene ring.

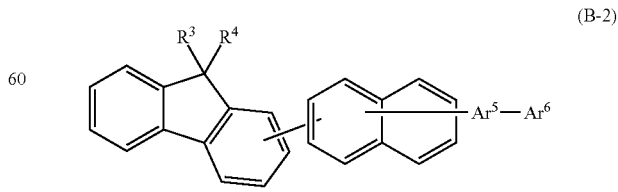

(B-2)

wherein $R^3$, $R^4$, $Ar^5$ and $Ar^6$ are the same as defined above.

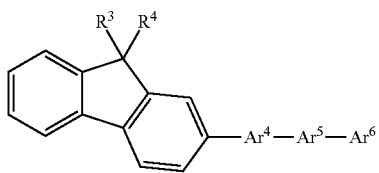

(B-3)

wherein R³, R⁴, Ar⁴, Ar⁵ and Ar⁶ are the same as defined above.

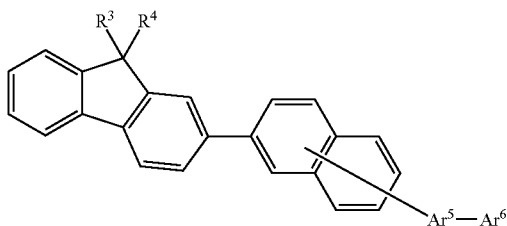

(B-4)

wherein R³, R⁴, Ar⁵ and Ar⁶ are the same as defined above.

The condensed polycyclic aromatic hydrocarbon rings having 10 to 22 ring carbon atoms for Ar⁴ to Ar⁶ of formula (B-1) are independently and preferably selected from a naphthalene ring, a chrysene ring, a phenanthrene ring, a benzophenanthrene ring, a dibenzophenanthrene ring, a benzo[a]triphenylene ring, a benzochrysene ring, a fluoranthene ring, a benzo[b]fluoranthene ring, and a picene ring. Ar⁶ is preferably a hydrogen atom inclusive of a heavy hydrogen atom or a residue of the condensed polycyclic aromatic hydrocarbon ring having 10 to 22 ring carbon atoms.

The condensed polycyclic aromatic hydrocarbon rings for Ar⁵ and Ar⁶ of formula (B-4) are independently and preferably selected from a naphthalene ring, a chrysene ring, a phenanthrene ring, a benzophenanthrene ring, a dibenzophenanthrene ring, a benzo[a]triphenylene ring, a benzochrysene ring, a fluoranthene ring, a benzo[b]fluoranthene ring, and a picene ring. Ar⁶ is preferably a hydrogen atom inclusive of a heavy hydrogen atom or a residue of the condensed polycyclic aromatic hydrocarbon ring having 10 to 22 ring carbon atoms.

R³ and R⁴ in formula (B-4) each independently and preferably represent an alkyl group having 1 to 10 carbon atoms or a phenyl group.

Material C for Organic Electroluminescence Device

The material C for organic electroluminescence device is represented by the following formula (C-1), preferably by the following formulae (C-2) to (C-6), and formulae (C-1) to (C-6) do not include a compound which is bilaterally symmetric:

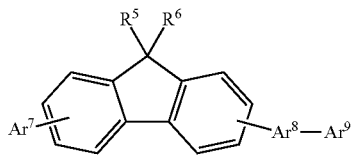

(C-1)

wherein Ar⁷ to Ar⁹ each independently represent a benzene ring or a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring and a picene ring; and Ar⁹ may be a hydrogen atom inclusive of a heavy hydrogen atom;

R⁵ and R⁶ each independently represent a hydrogen atom inclusive of a heavy hydrogen atom, an alkyl group having 1 to 10 carbon atoms or an aryl group having 6 to 12 ring carbon atoms;

R⁵, R⁶, Ar⁷, Ar⁸ and Ar⁹ each may independently have a substituent;

provided that the material dose not include the following compounds (1) to (4):

(1) a compound wherein Ar⁷ is a benzene ring and Ar⁸ is a benzene ring or a fluorene ring;

(2) a compound wherein Ar⁹ is a hydrogen atom and Ar⁷ and Ar⁸ are residues of the same condensed aromatic hydrocarbon ring;

(3) a compound wherein Ar⁷ and Ar⁸-Ar⁹ have the same structure; and (4) a compound wherein Ar⁷ is a β-naphthyl group or a naphthalene-2,6-diyl group, Ar⁸ is a naphthalene-2,6-diyl group, and Ar⁹ is a β-naphthyl group.

A compound wherein Ar⁷ is a naphthalene ring; Ar⁸ is a benzene ring; and Ar⁹ is a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring, and a picene ring is preferred. A compound wherein Ar⁹ is a chrysene ring, a phenanthrene ring, a benzophenanthrene ring, a dibenzophenanthrene ring, a triphenylene ring, a benzo[a]triphenylene ring, a benzochrysene ring, or a fluoranthene ring is particularly preferred.

A compound wherein Ar⁷ is a naphthalene ring; Ar⁸ is a naphthalene ring; and Ar⁹ is a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring, and a picene ring is also preferred. However, a compound wherein Ar⁷ is a β-naphthyl group, Ar⁸ is a naphthalene-2,6-diyl group, and Ar⁹ is a β-naphthyl group is excluded. Ar⁹ is particularly preferably a phenanthrene ring.

A compound wherein Ar⁷ and Ar⁸ each independently represent a residue of a condensed aromatic hydrocarbon ring selected from a naphthalene ring, a chrysene ring, a phenanthrene ring, a benzophenanthrene ring, a dibenzophenanthrene ring, a triphenylene ring, a benzo[a]triphenylene ring, a benzochrysene ring, a fluoranthene ring, a benzo[b]fluoranthene ring, and a picene ring; and Ar⁹ is a hydrogen atom is also preferred. A compound wherein Ar⁷ and Ar⁸ each independently represent a benzophenanthrene ring, a benzo[a]triphenylene ring or a fluoranthene ring is particularly preferred.

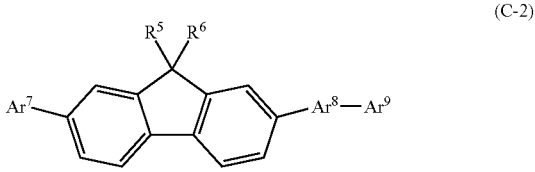

(C-2)

wherein Ar⁷, Ar⁸, Ar⁹, R⁵ and R⁶ are the same as defined above.

When any one of $R^5$, $R^6$, $Ar^7$, $Ar^8$ and $Ar^9$ in formulae (C-1) and (C-2) has one or more substituents, the substituent is preferably an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom, or an aryl group having 6 to 22 ring carbon atoms.

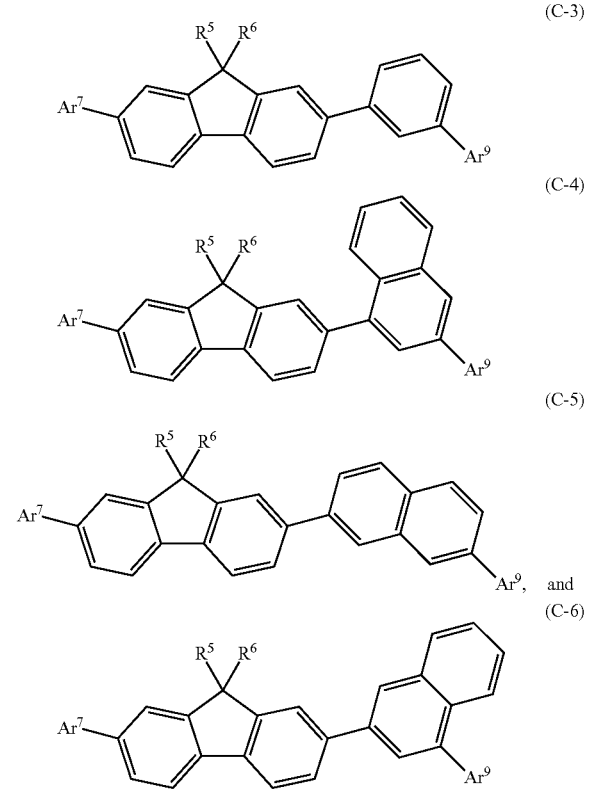

wherein $Ar^7$, $Ar^9$, $R^5$ and $R^6$ are the same as defined above.

When any one of $R^5$, $R^6$, $Ar^7$ and $Ar^9$ in formulae (C-1) to (C-6) has one or more substituents, the substituent is preferably an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom or an aryl group having 6 to 22 ring carbon atoms.

Since the materials A to C for electroluminescence device have a large triplet energy gap (excited triplet energy), the energy is transferred from the material to a phosphorescent dopant, to cause the phosphorescent emission.

An anthracene derivative well known as a fluorescent host is unsuitable as a host of a red-emitting phosphorescent dopant. In contrast, the host of the invention allows a green-emitting phosphorescent dopant to effectively emit light because of its large triplet energy gap.

CBP, a well-known phosphorescent host, is usable as a host of a phosphorescent dopant which emits light having a wavelength shorter than that of green light. However, the host material of the invention is usable as a host of a phosphorescent dopant which emits green light or light having a longer wavelength.

In the present invention, the stability of molecule is enhanced to prolong the lifetime of device, because the skeleton of the host material has a partial structure composed of a polycondensed ring containing no nitrogen atom.

When the number of ring atoms of the skeleton is excessively small, the stability of the compound is not sufficient. When the number of condensed rings in the polycondensed rings which constitutes the host material is excessively large, the HOMO to LUMO gap is narrow and therefore the triplet energy gap is narrow for the wavelength of desired emission. In this regard, since the host material comprising the material for organic electroluminescence device of the invention has a moderate number of ring atoms, the compound is suitably used as a phosphorescent host for a phosphorescent emitting layer, which allows the emission of desired wavelength and is highly stable.

Conventionally, a host material applicable to a wide range of phosphorescent dopants which emit light of a wide range of wavelengths from green to red has been selected. Therefore, a compound, such as CBP, having a wide triplet energy gap has been used as the host material.

Although the triplet energy gap Eg(T) of BCP is wide, BCP involves a problem of short lifetime.

Although not applicable as a host of a phosphorescent dopant having a wide gap corresponding to blue light, the compound of the invention works as a host of a red- or green-emitting phosphorescent dopant. If the triplet energy gap is excessively wide as in CBP, the energy is not effectively transferred to a green-emitting phosphorescent dopant because of an excessively large difference in the energy gaps. In contrast, when the host of the invention is used, the energy is effectively transferred from the exciton of host to a green-emitting phosphorescent dopant because their energy gaps are matched, giving a phosphorescent emitting layer with extremely high efficiency.

Thus, according to the present invention, a phosphorescent emitting layer with high efficiency and long lifetime is obtained.

The triplet energy gap Eg(T) of the material for an organic electroluminescence device is determined, for example, from the phosphorescent emission spectrum. In the present invention, it is determined, for example, as described below.

A sample for phosphorescent measurement is prepared by dissolving a test material in EPA solvent (diethyl ether:isopentane:ethanol=5:5:2 by volume) at 10 μmol/L.

The sample for phosphorescent measurement is charged into a quartz cell, cooled to 77 K, and irradiated with exciting light, and the wavelength of emitted phosphorescent light is measured.

A line tangent to the rising portion at the short-wavelength side of the obtained phosphorescent emission spectrum is drawn, and the wavelength at the intersection of the tangent line and the base line is converted to a value of energy unit, employing the converted value as the triplet energy gap Eg(T).

The phosphorescent measurement is carried out, for example, by using a commercially available apparatus, such as F-4500 (manufactured by Hitachi, Ltd.).

The triplet energy gap may be determined in different manner without departing from the spirit and scope of the present invention.

When any one of $Ar^1$ to $Ar^9$ and $R^1$ to $R^6$ of formulae (A-1) to (A-5), (B-1) to (B-4) and (C-1) to (C-6) has one or more substituents, the substituent is preferably an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom, or an aryl group having 6 to 22 ring carbon atoms. The fluorene ring of formulae (A-1) to (A-5), (B-1) to (B-4) and (C-1) to (C-6) may be substituted by an alkyl group having 1 to 20 carbon atoms, a haloalkyl group having 1 to 20 carbon atoms, a cycloalkyl group having 5 to 18 ring carbon atoms, a silyl group having 3 to 20 carbon atoms, a cyano group, a halogen atom, or an aryl group having 6 to 22 ring carbon atoms.

Since these substituents do not include nitrogen atom, the stability of the host material is further enhanced and the lifetime of device is prolonged.

If each of $Ar^1$ to $Ar^6$ and $R^1$ to $R^6$ is substituted by an aryl group, the number of the aryl substituents in each of $Ar^1$ to $Ar^9$ and $R^1$ to $R^6$ is preferably 2 or less and more preferably 1 or less.

Examples of the alkyl group having 1 to 20 carbon atoms include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group.

Examples of the haloalkyl group having 1 to 20 carbon atoms include chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodot-butyl group, and 1,2,3-triiodopropyl group.

Examples of the cycloalkyl group having 5 to 18 ring carbon atoms include cyclopentyl group, cyclohexyl group, cyclooctyl group, and 3,5-tetramethylcyclohexyl group.

The silyl group having 3 to 20 carbon atoms is preferably an alkylsilyl group, an arylsilyl group, or an aralkyl silyl group. Examples thereof include trimethylsilyl group, triethylsilyl group, tributylsilyl group, trioctylsilyl group, triisobutylsilyl group, dimethylethylsilyl group, dimethylisopropylsilyl group, dimethylpropylsilyl group, dimethylbutylsilyl group, dimethyl-t-butylsilyl group, diethylisopropylsilyl group, phenyldimethylsilyl group, diphenylmethylsilyl group, diphenylt-butylsilyl group, and triphenylsilyl group.

Examples of the halogen atom include fluorine atom, chlorine atom, bromine atom, and iodine atom.

Examples of the aryl group having 6 to 22 ring carbon atoms include phenyl group, biphenyl group, terphenyl group, naphthyl group, fluoranthenyl group, 9,10-dialkylfluorenyl group, 9,10-diarylfluorenyl group, triphenylenyl group, phenanthrenyl group, and dibenzofuranyl group, with an aryl group having 6 to 18 ring carbon atoms, such as phenyl group, biphenyl group, terphenyl group, naphthyl group, 9,10-dimethylfluorenyl group, triphenylenyl group, phenanthrenyl group, and dibenzofuranyl, being preferred, and an aryl group having 6 to 14 ring carbon atoms, such as phenyl group, biphenyl group, naphthyl group, phenanthrenyl group, and dibenzofuranyl group, being more preferred.

The excited triplet energy of the material for organic electroluminescence device of the invention is preferably 2.0 eV or more and 2.8 eV or less.

If being 2.0 eV or more, the energy can be transferred to a phosphorescent emitting material which emits light of 520 nm or longer and 720 nm or shorter. If being 2.8 eV or less, the problem of failing to efficient emission due the energy gap excessively large for a red-emitting phosphorescent dopant is avoided.

The excited triplet energy of the material for organic electroluminescence device is more preferably 2.1 eV or more and 2.7 eV or less.

Examples of the material for organic electroluminescence device represented by formulae (A-1) to (A-5) are shown below.

2-1

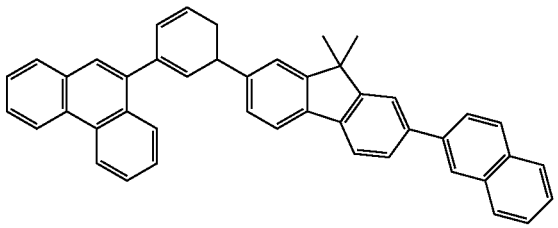

2-2


2-3

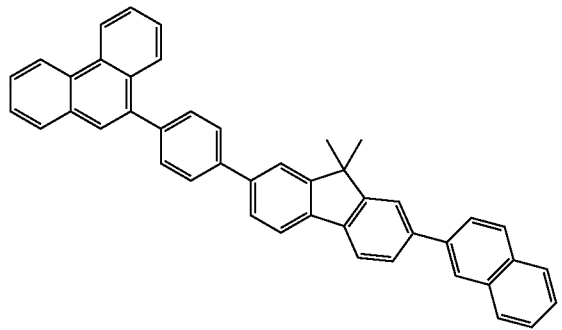

2-4

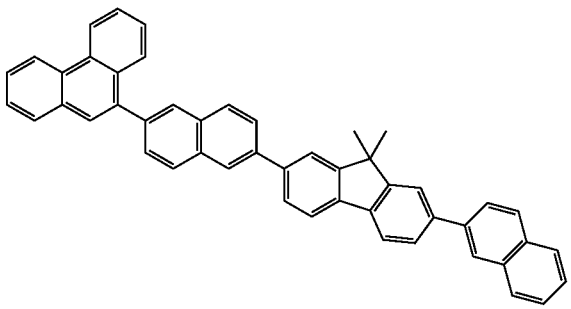

2-5
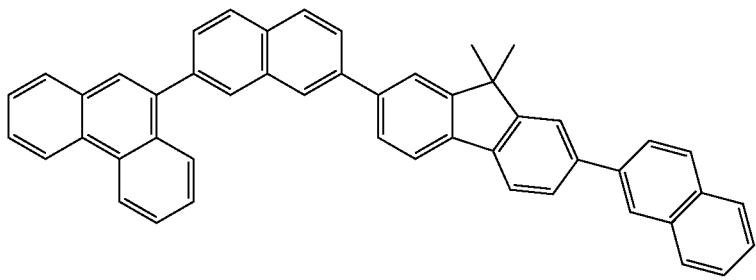
2-6
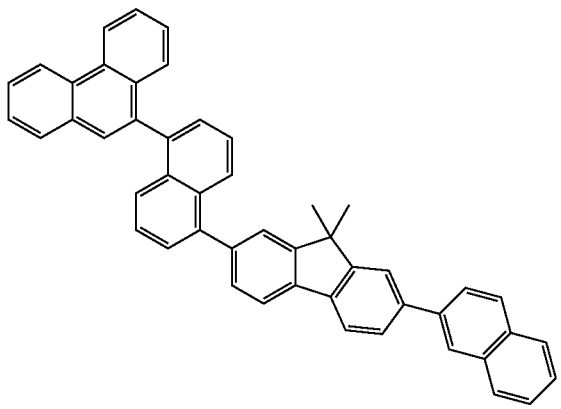
2-7
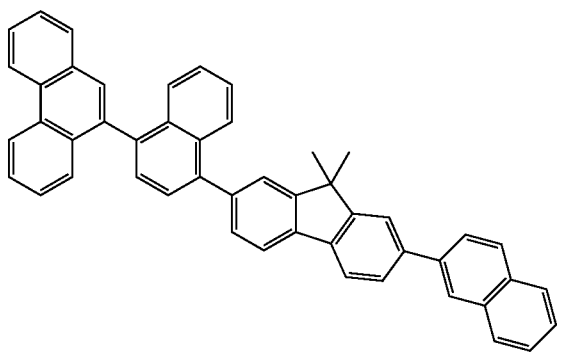
2-8
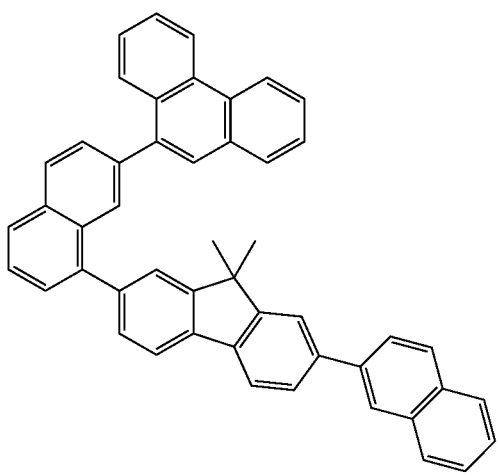
2-9
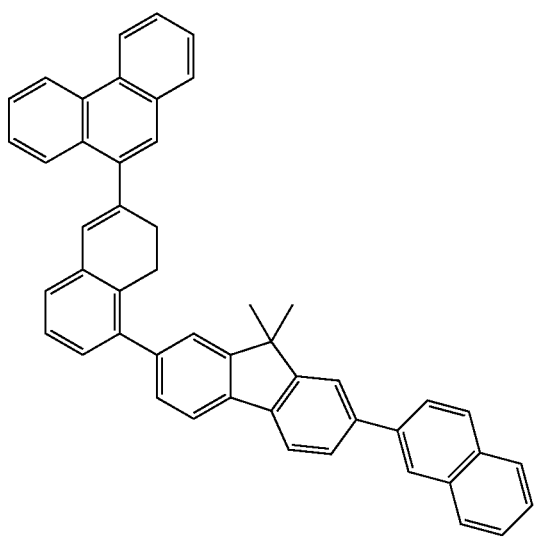
2-10
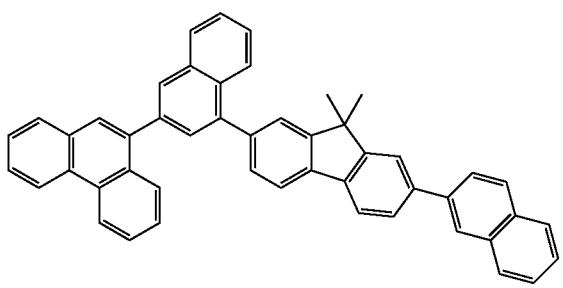
2-11
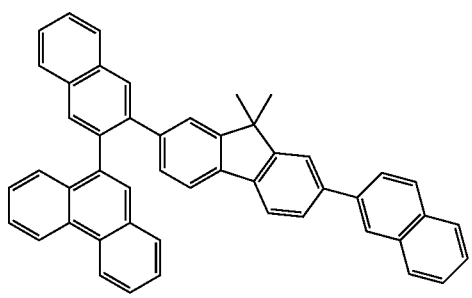

2-12
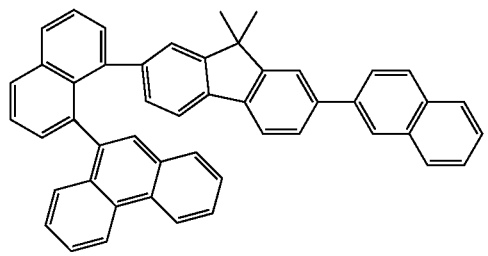
2-13
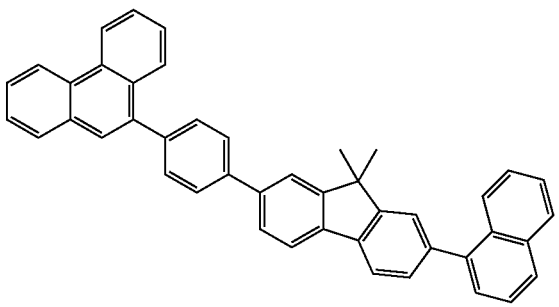
2-14
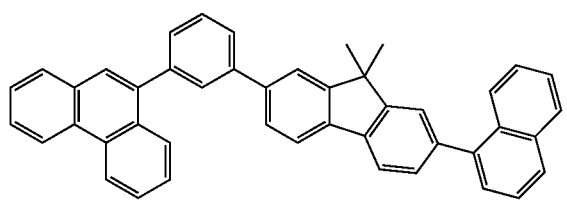
2-15
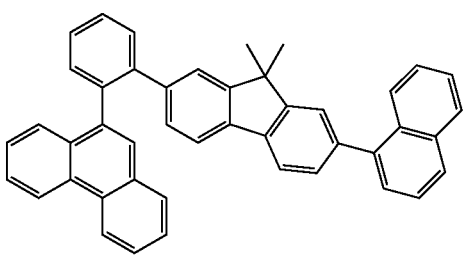
2-16
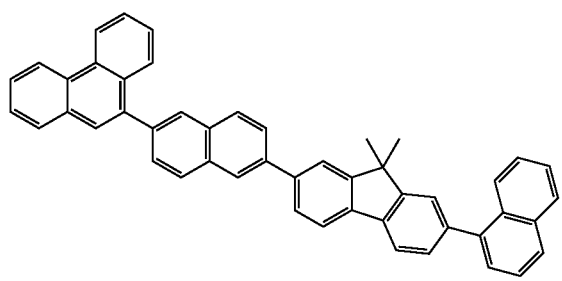
2-17
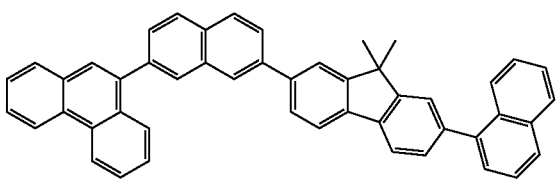
2-18
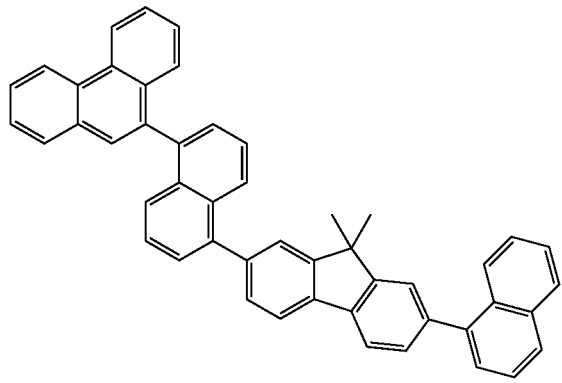
2-19
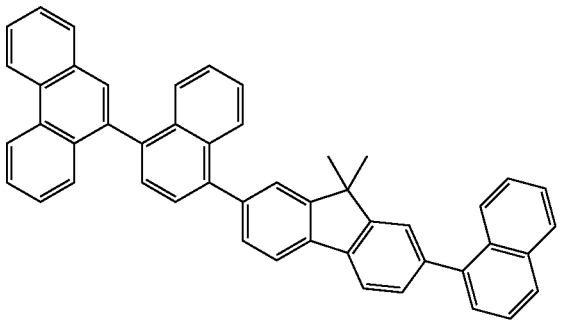

-continued
2-20
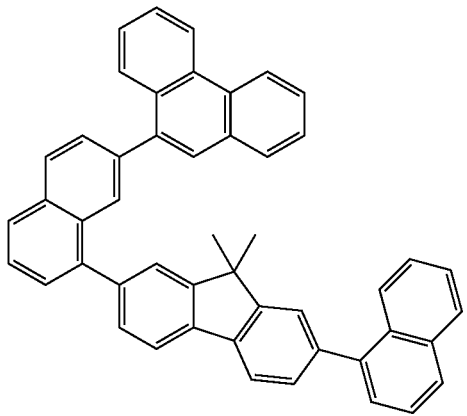
2-21
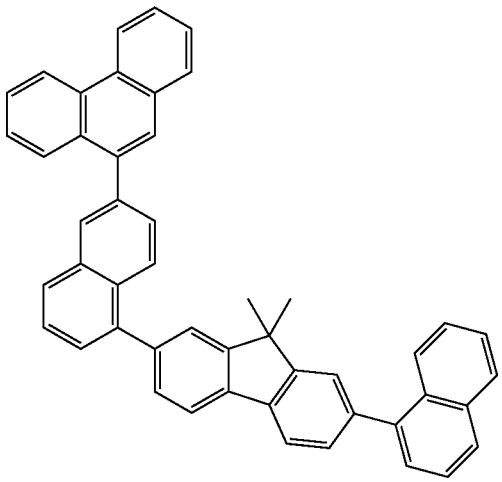
2-22
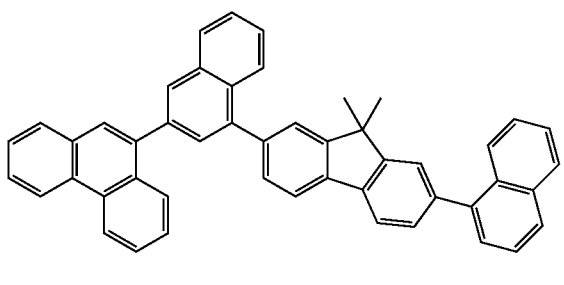
2-23
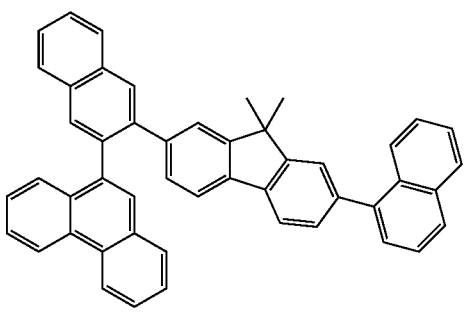
2-24
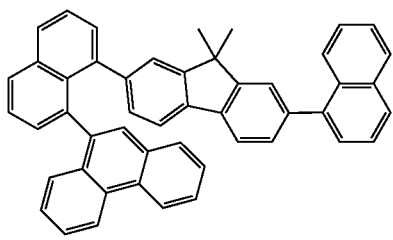
2-25
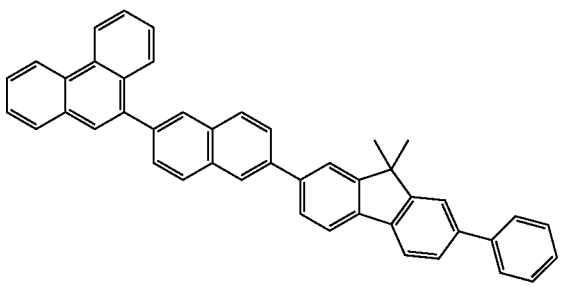
2-26
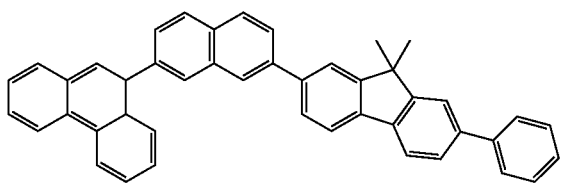
2-27
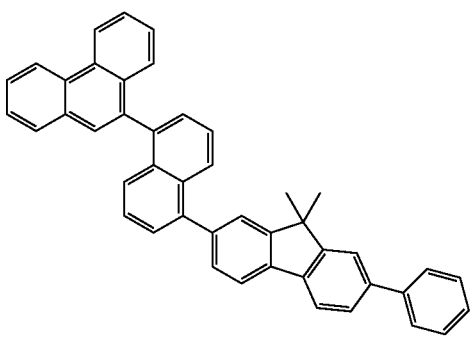

-continued
2-28
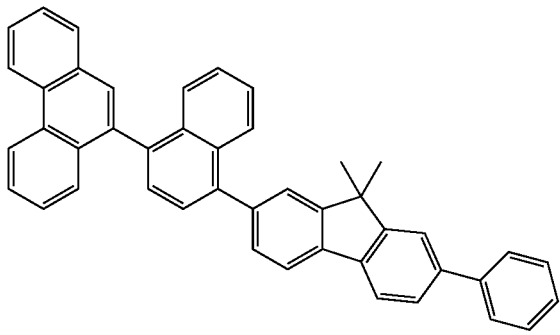
2-29
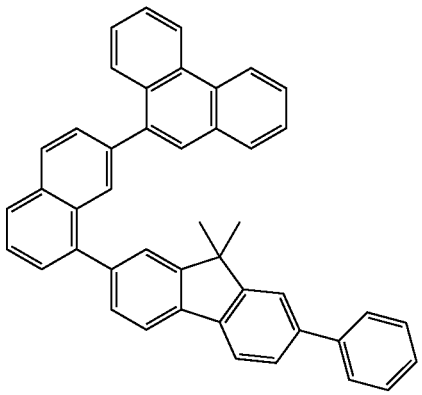
2-30
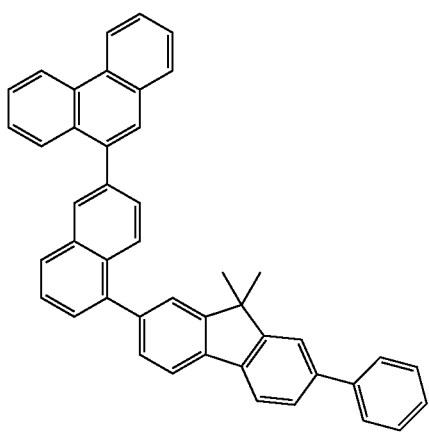
2-31
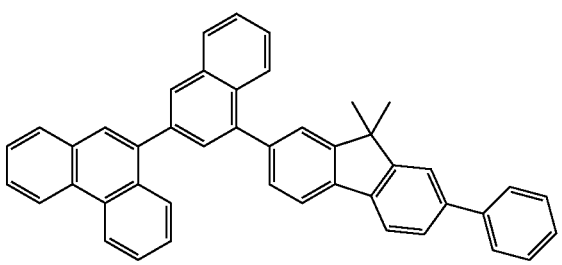
2-32
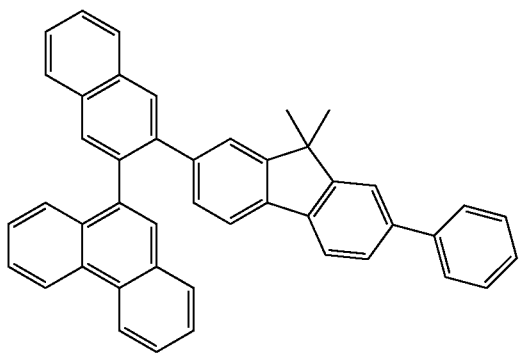
2-33
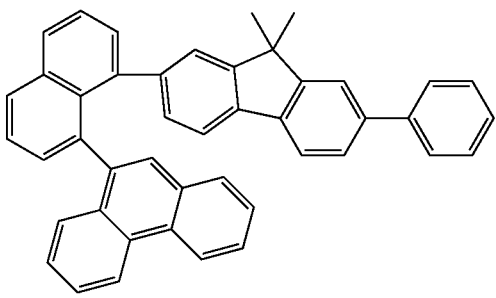
2-37
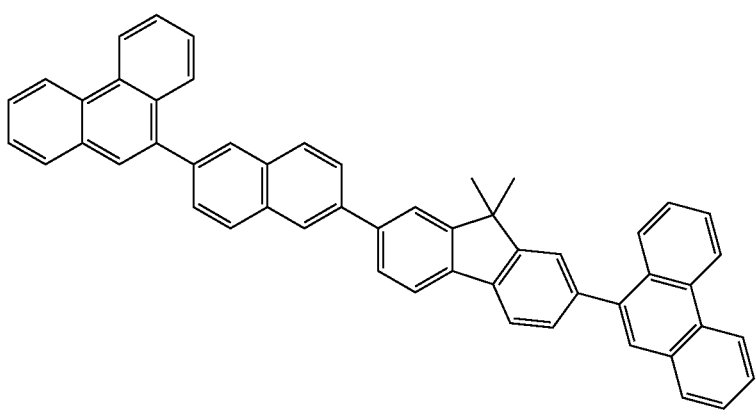

-continued
2-38
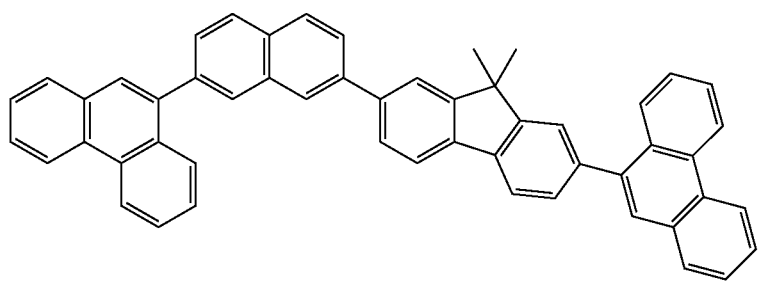
2-39
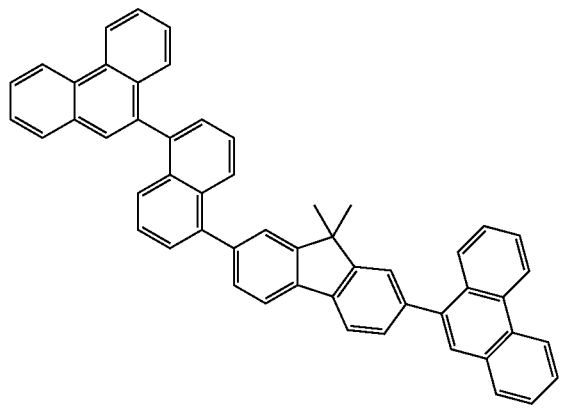
2-40
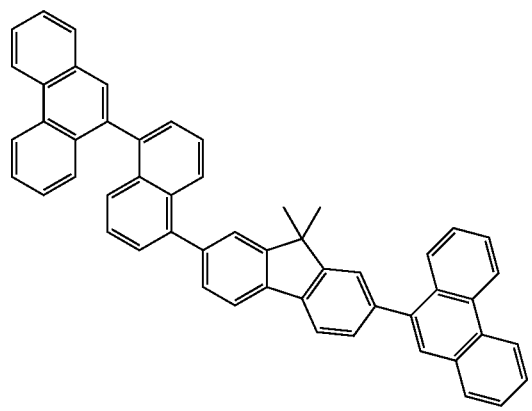
2-41
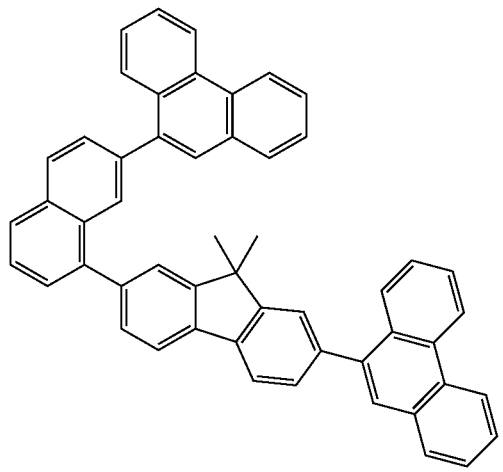
2-42
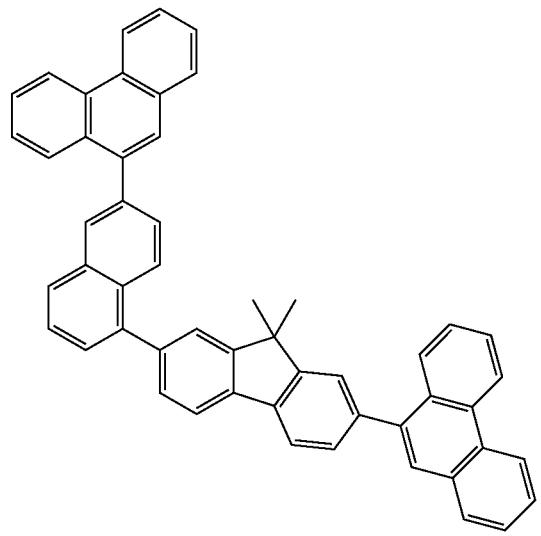
2-43
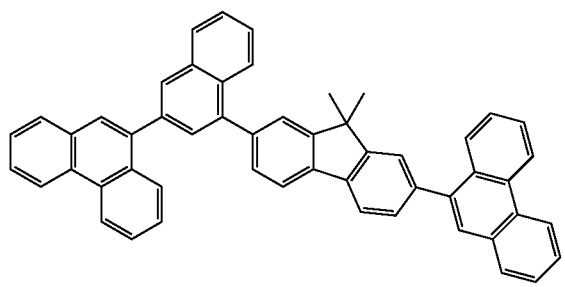
2-44
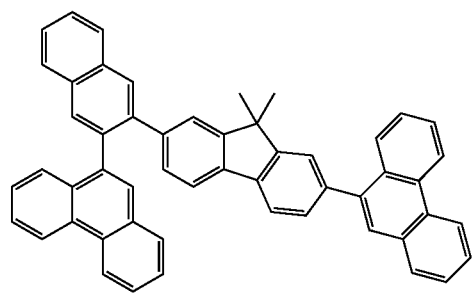

-continued
2-45
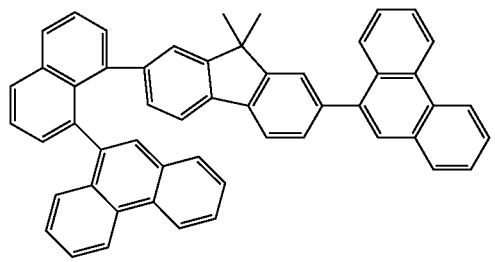
2-74
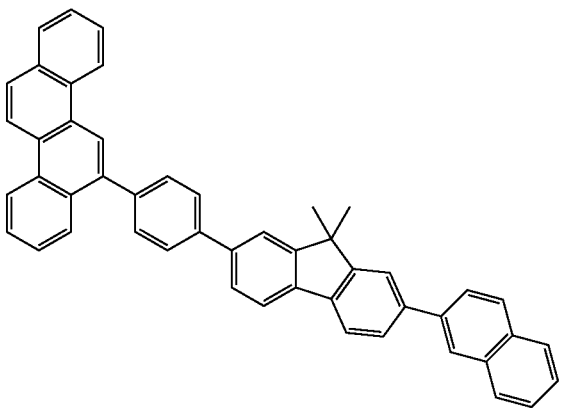
2-75
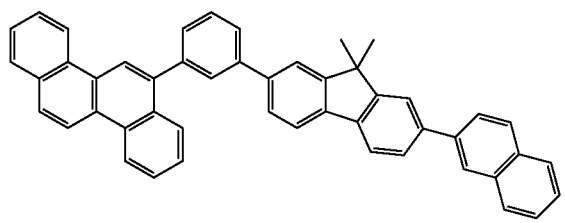
2-76
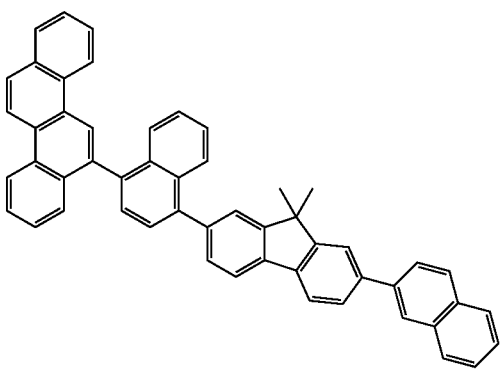
2-77
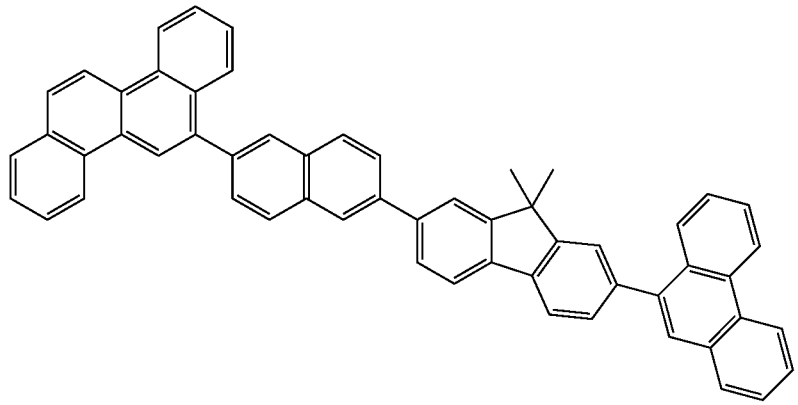
2-78
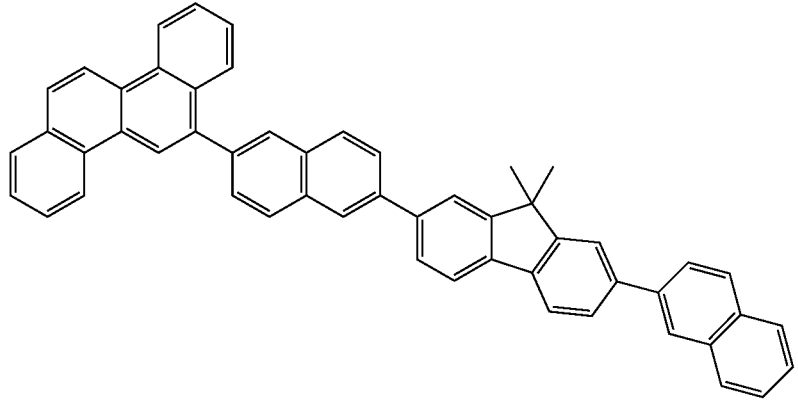

-continued
2-79
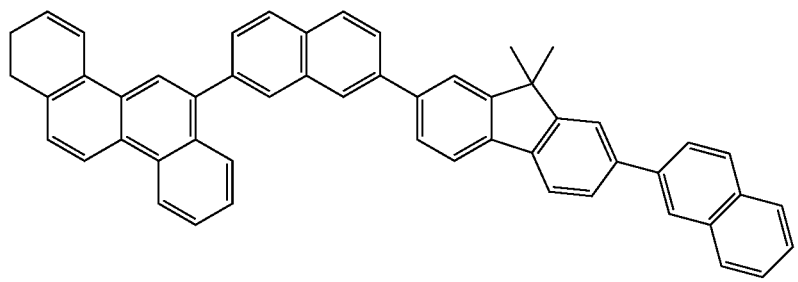
2-80
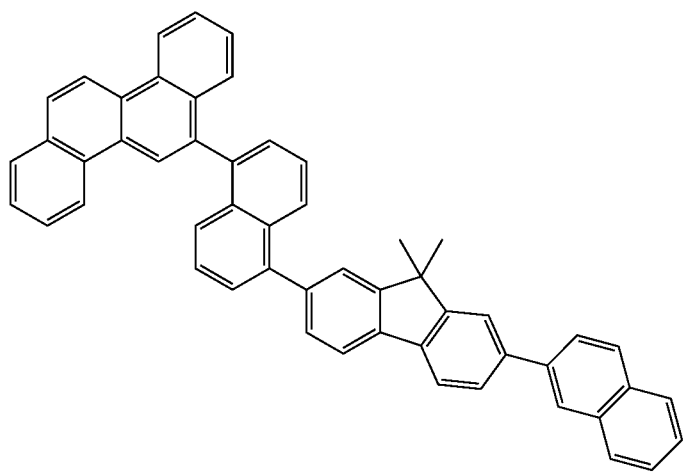
2-81
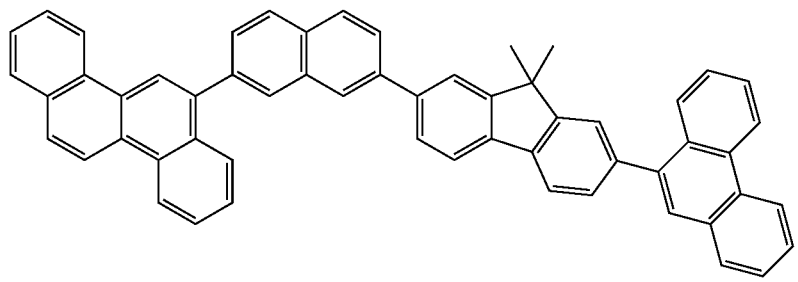
2-82
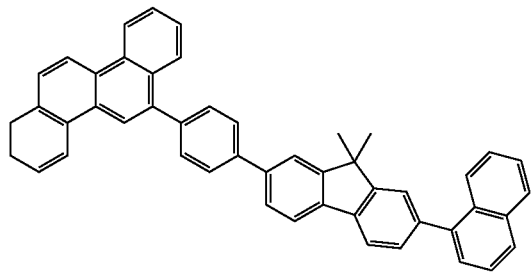
2-83
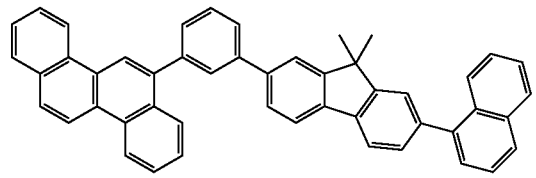

2-84
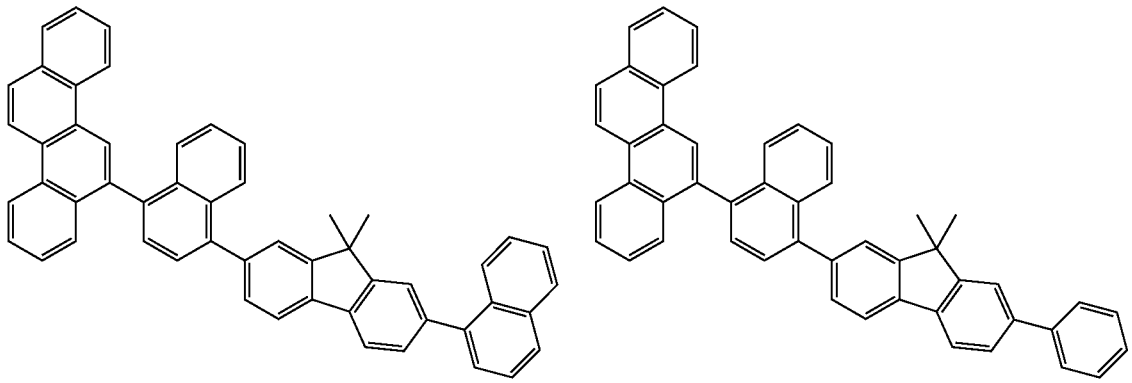
2-85
2-86
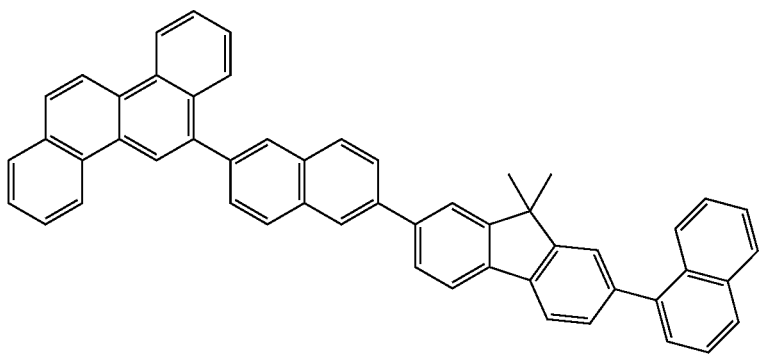
2-87
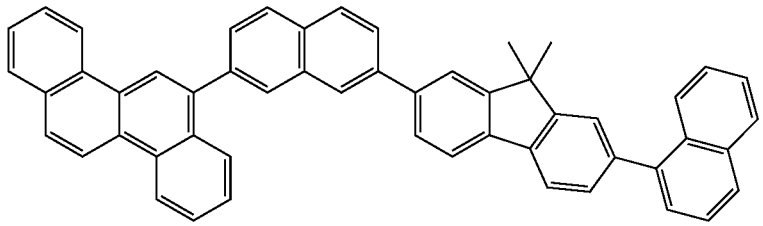
2-88
2-89
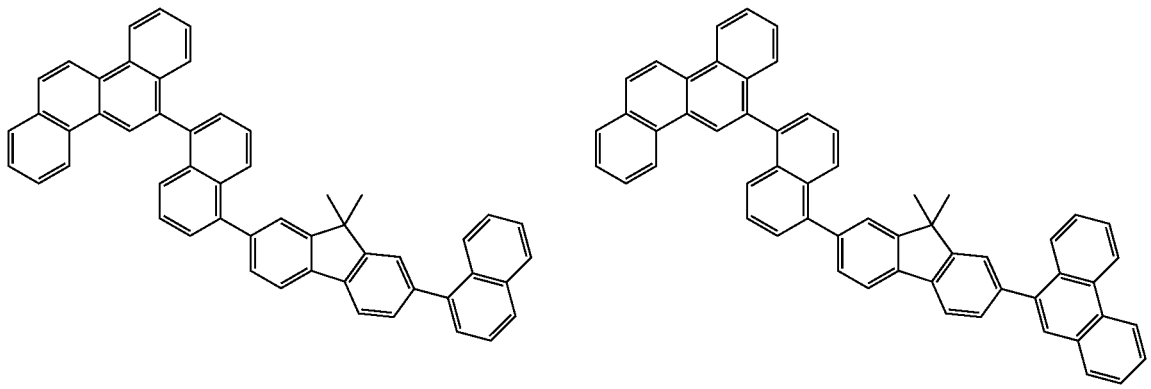

-continued
2-90
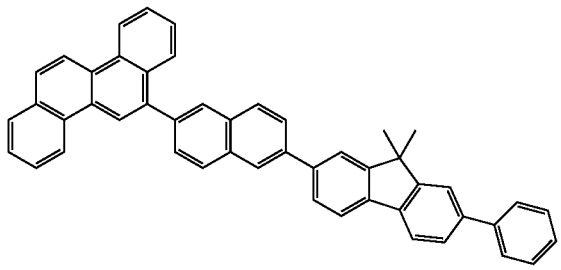
2-91
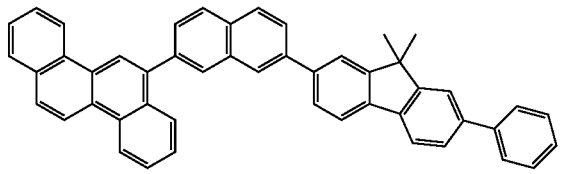
2-92
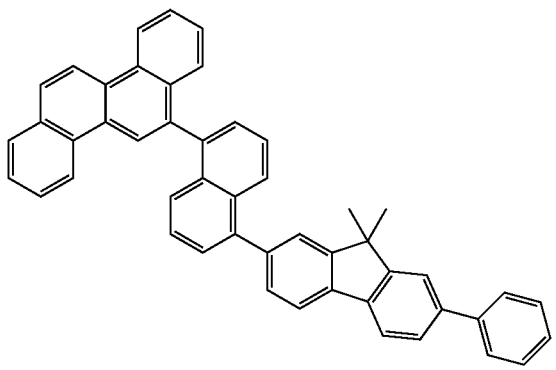
2-93
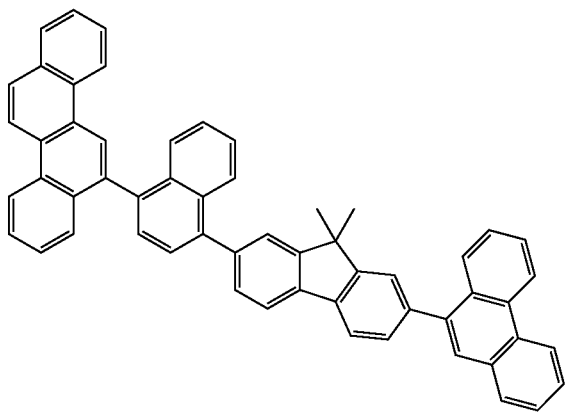
2-97
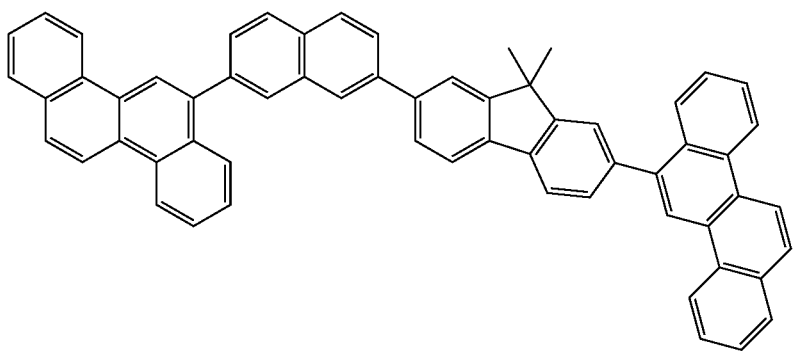
2-98
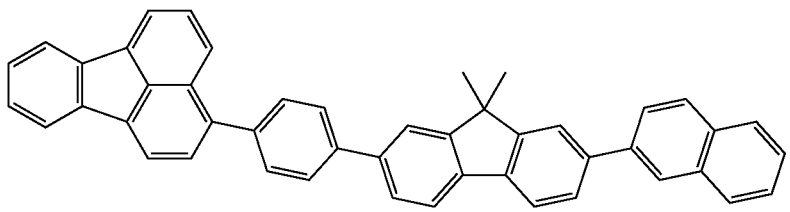
2-99
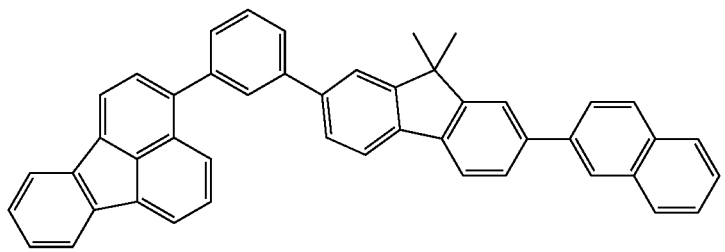

-continued
2-100
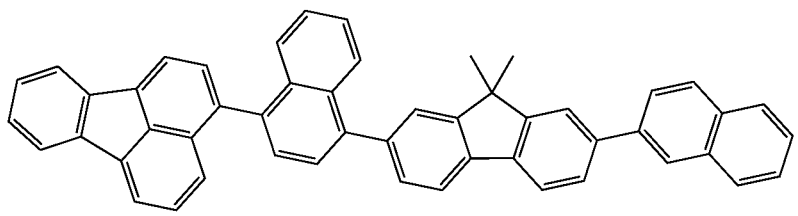
2-101
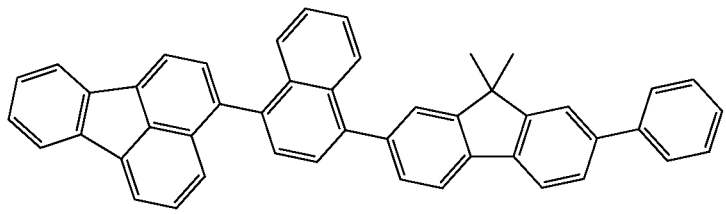
2-102
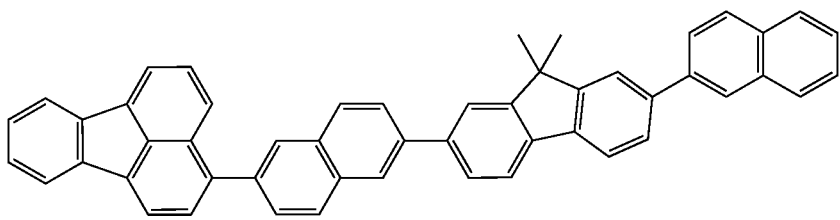
2-103
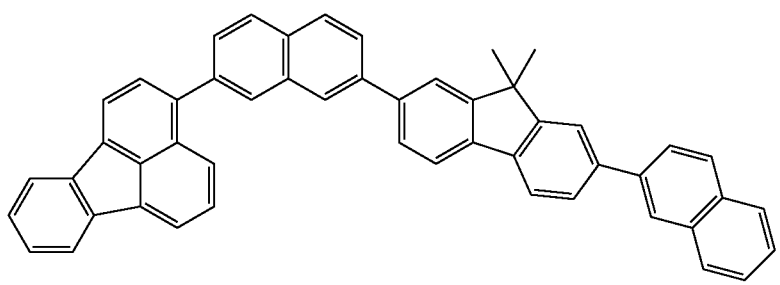
2-104
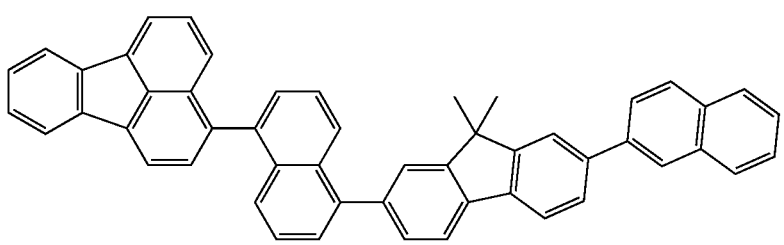
2-105
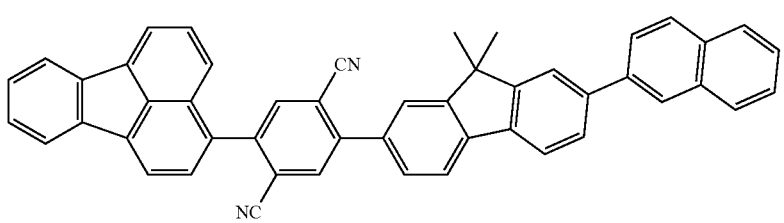
2-106
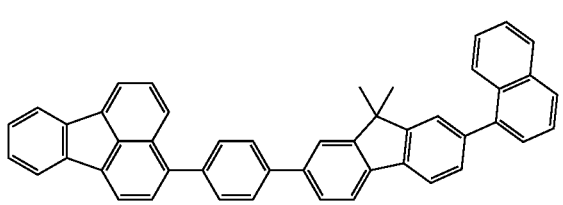
2-107
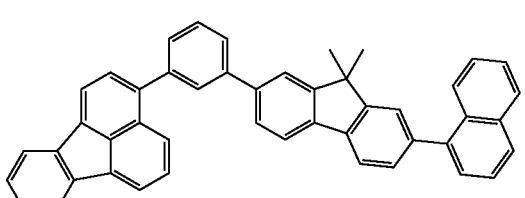

-continued
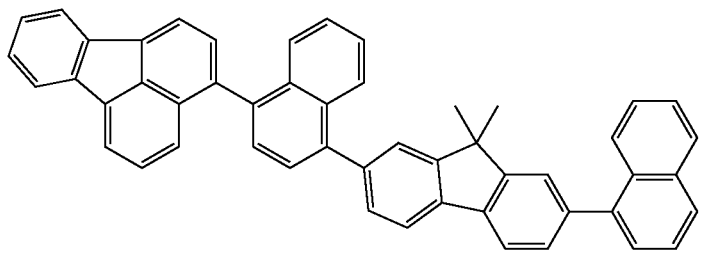
2-108
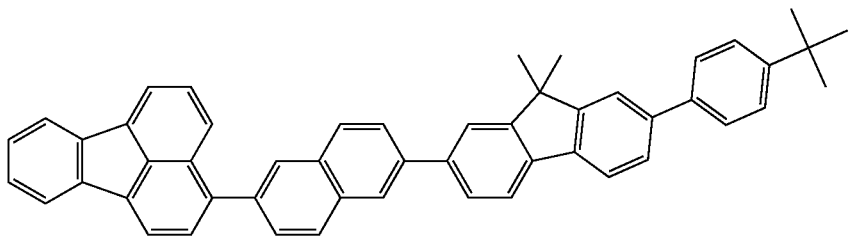
2-109
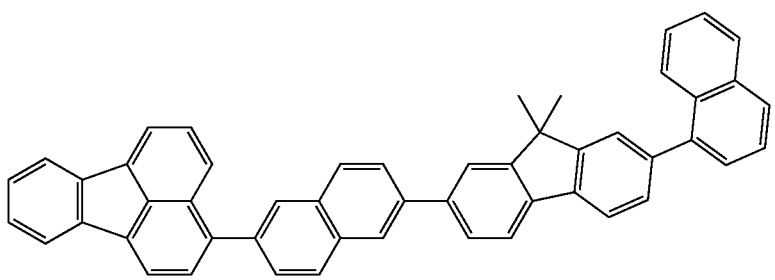
2-110
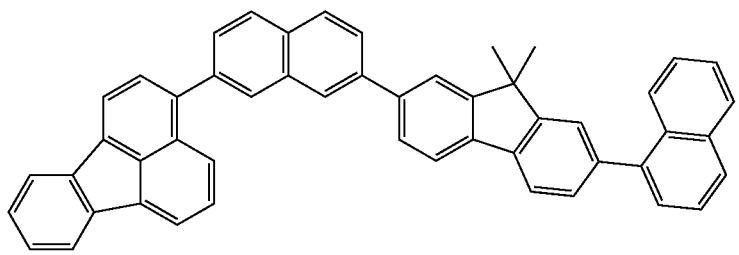
2-111
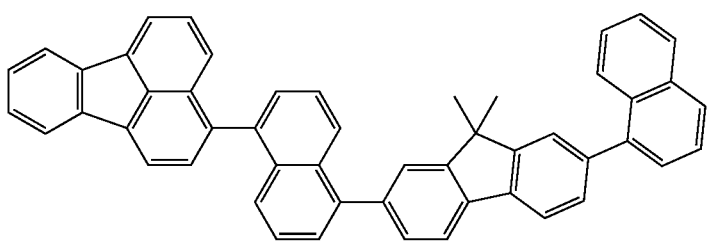
2-112
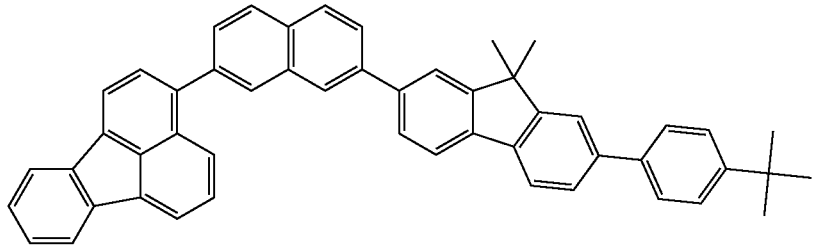
2-113

-continued
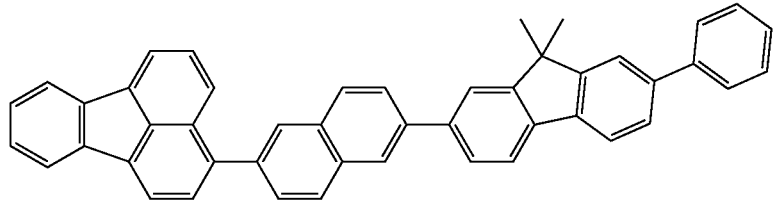
2-114
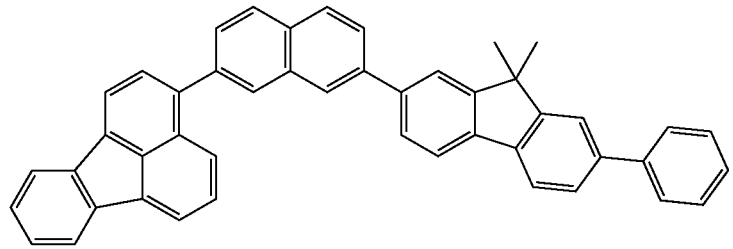
2-115
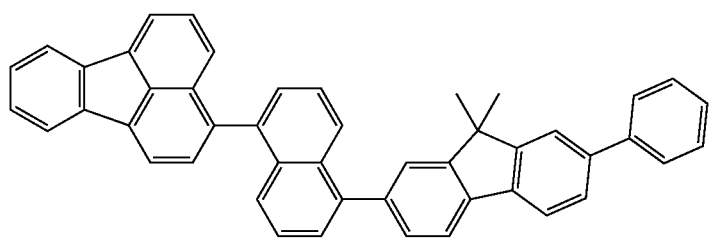
2-116
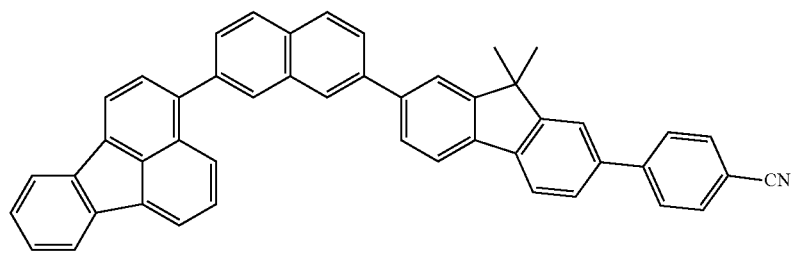
2-117
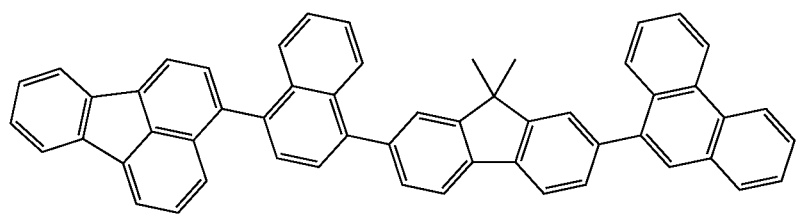
2-120
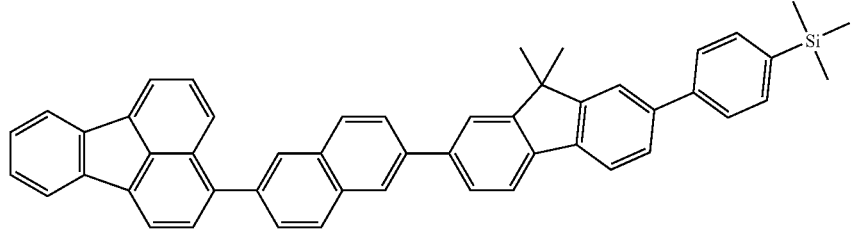
2-121
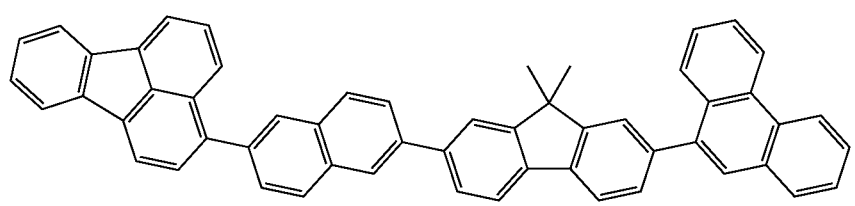
2-122

-continued
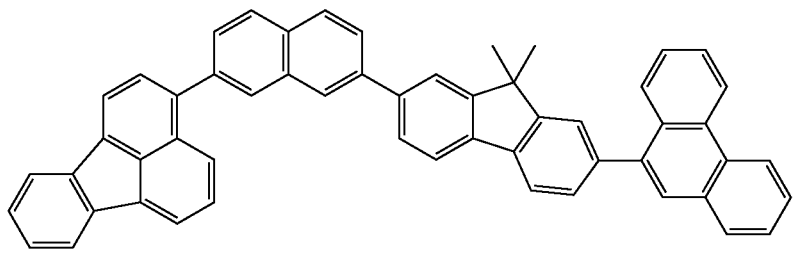
2-123
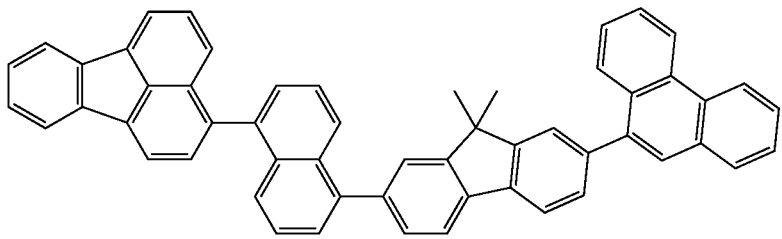
2-124
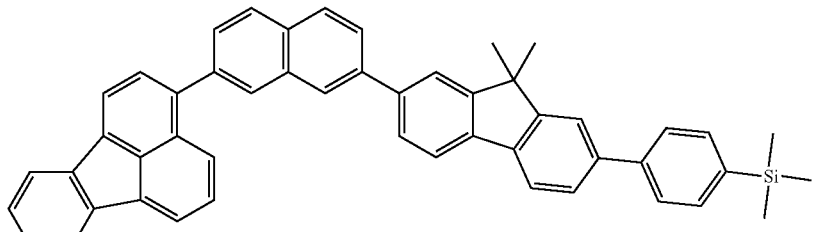
2-125
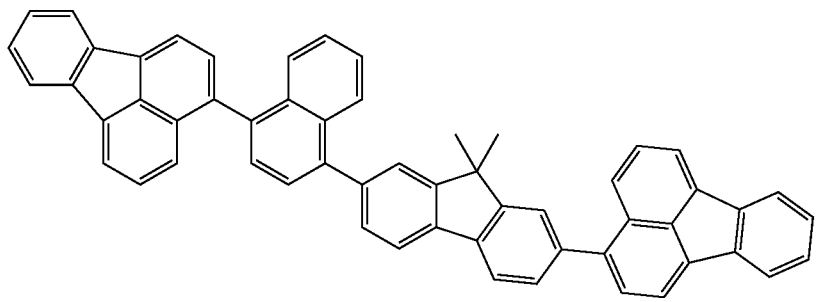
2-128
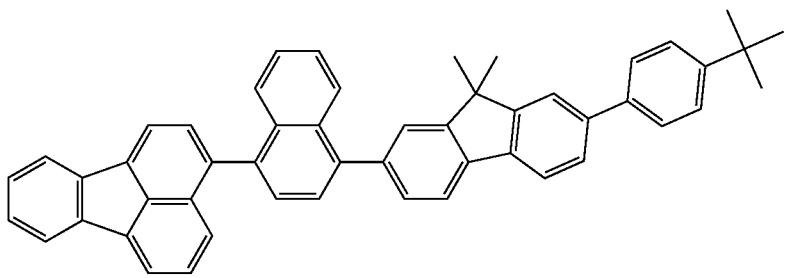
2-129
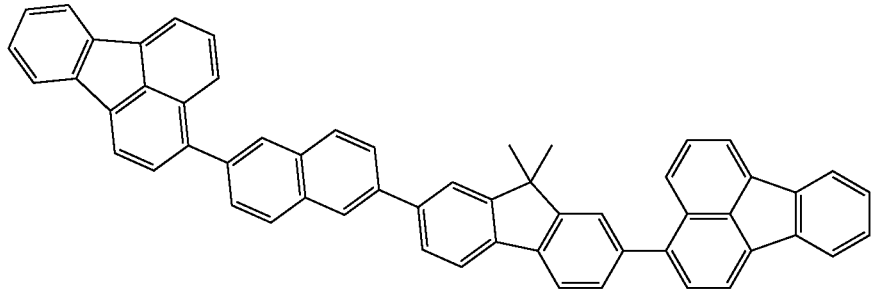
2-130

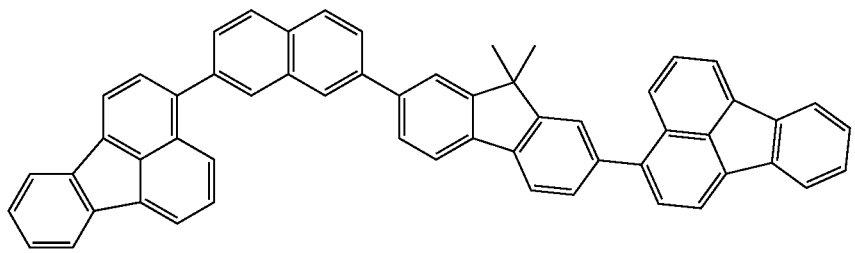
2-131
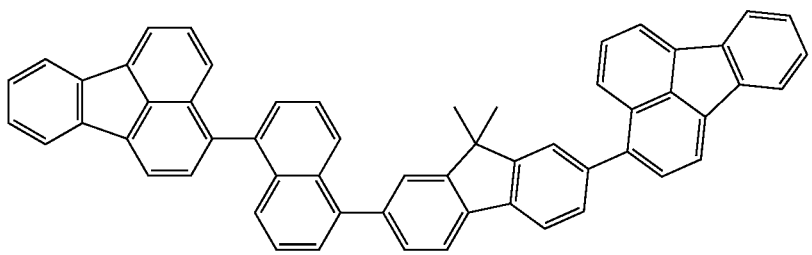
2-132
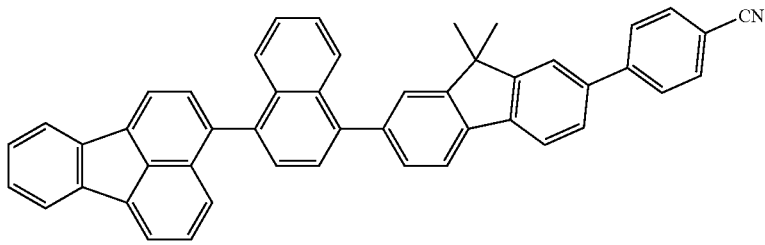
2-133
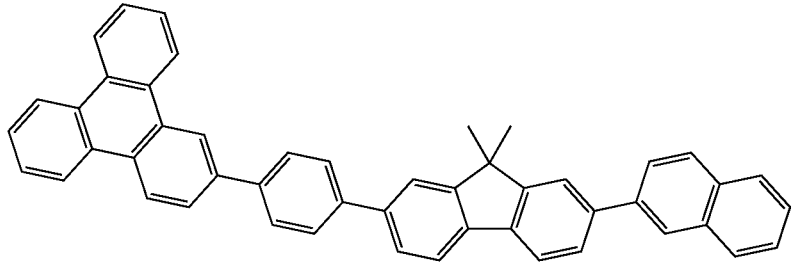
2-134
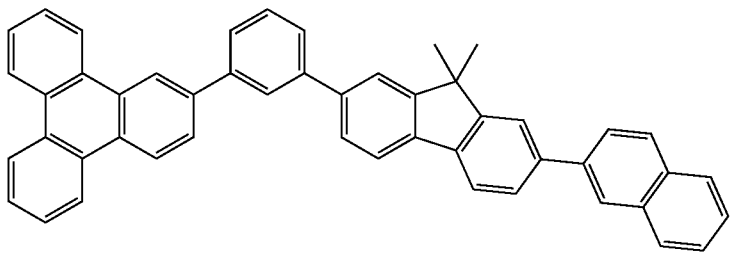
2-135

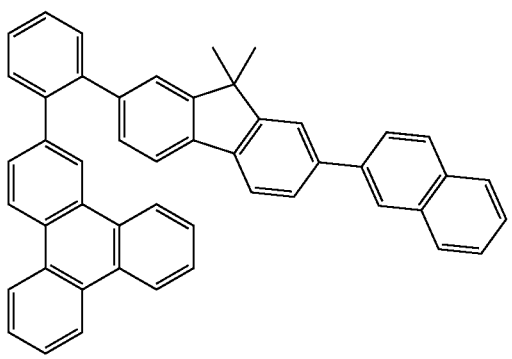
2-136
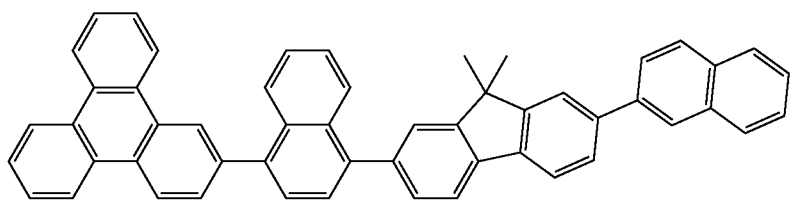
2-137
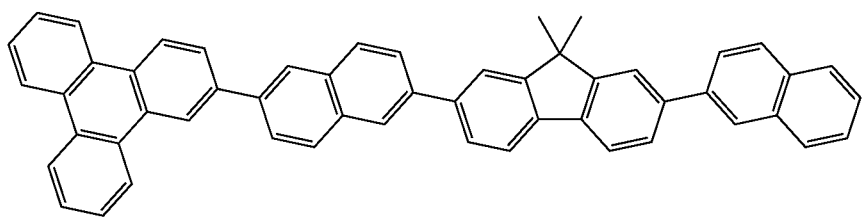
2-138
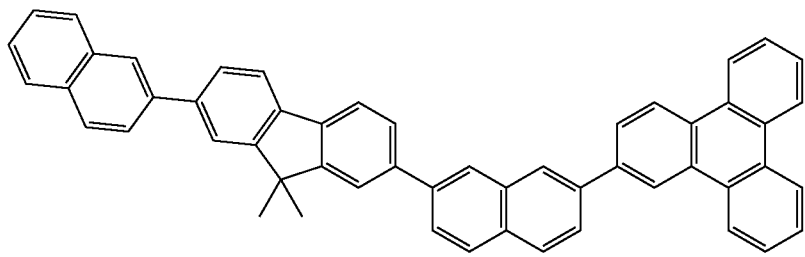
2-139
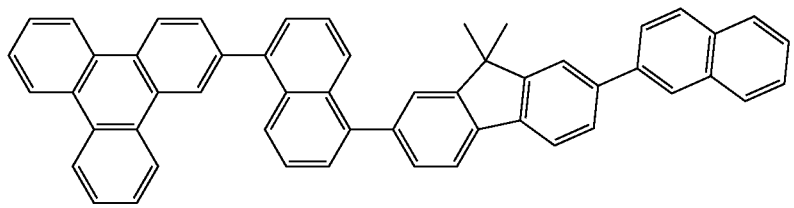
2-140
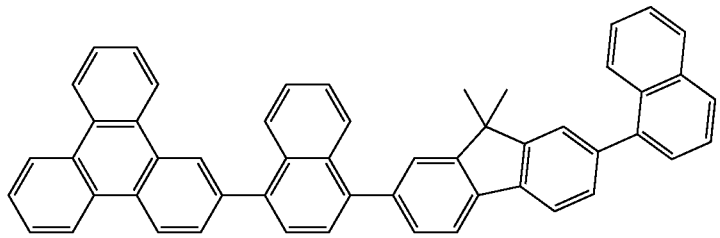
2-141

-continued
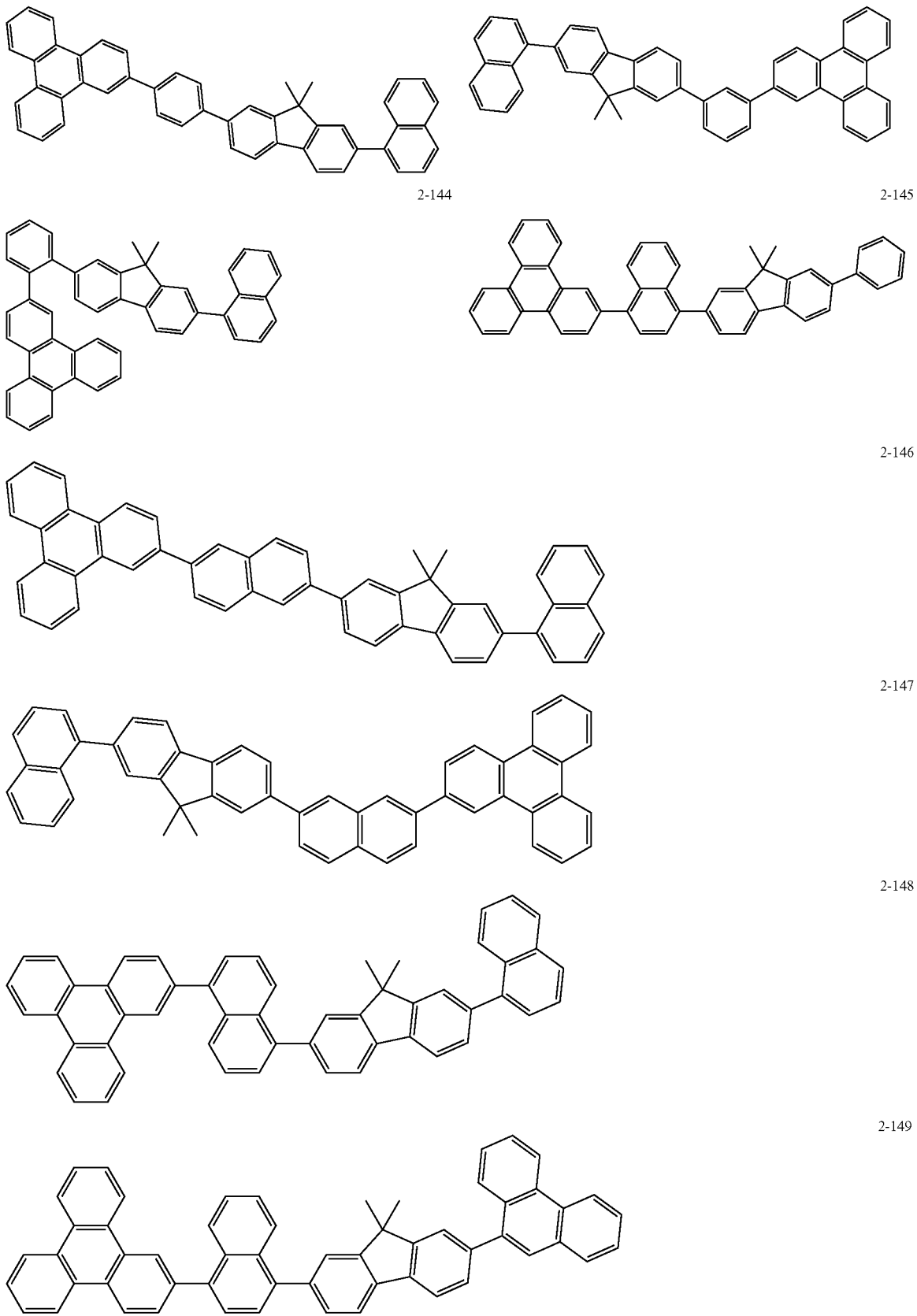

-continued
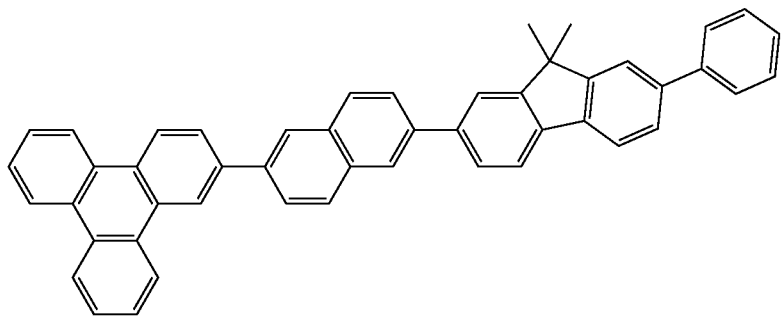
2-150
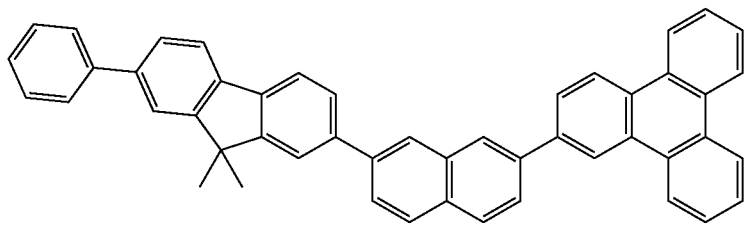
2-151
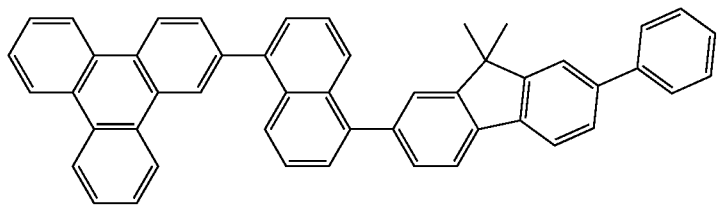
2-152
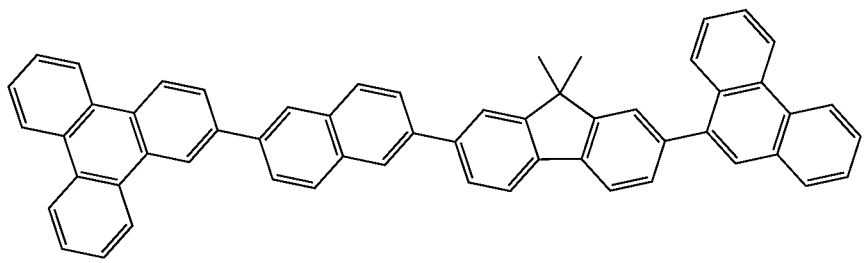
2-154
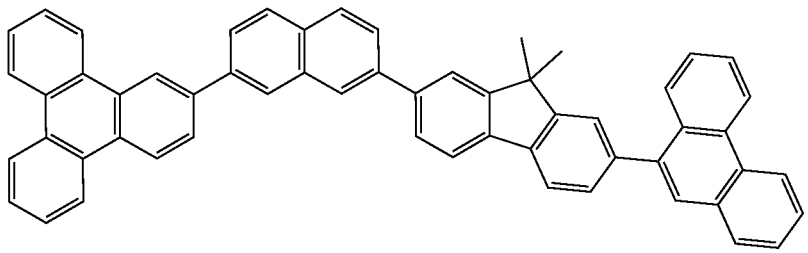
2-155
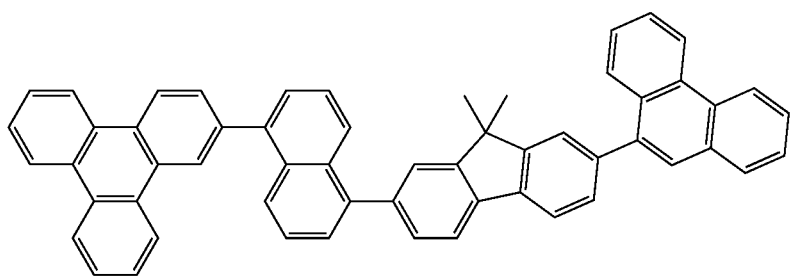
2-156

-continued
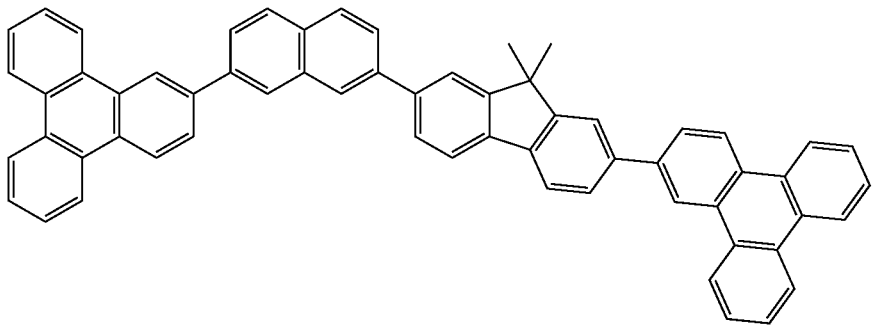
2-157
2-158
2-159
2-160
2-161

-continued
2-162
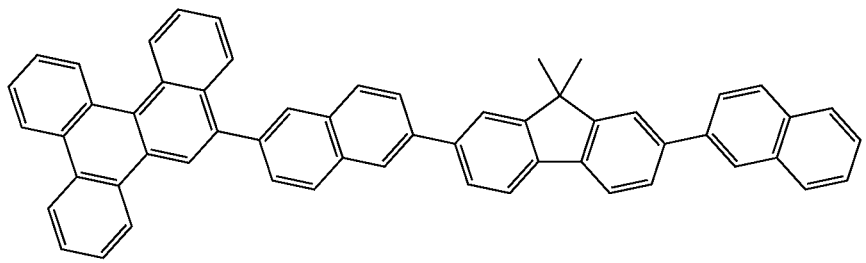
2-163
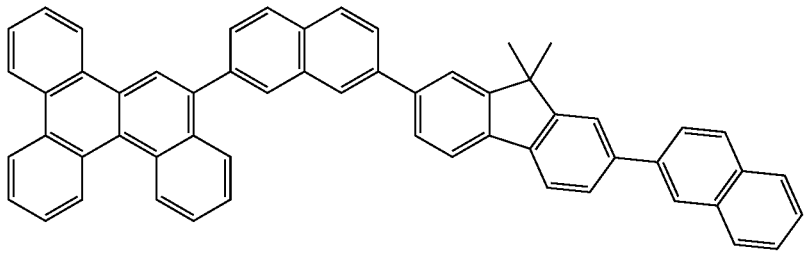
2-164
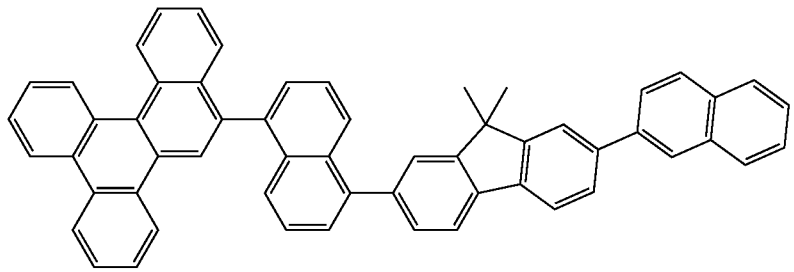
2-165
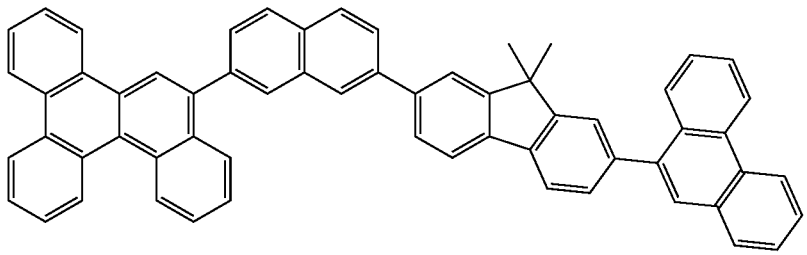
2-166
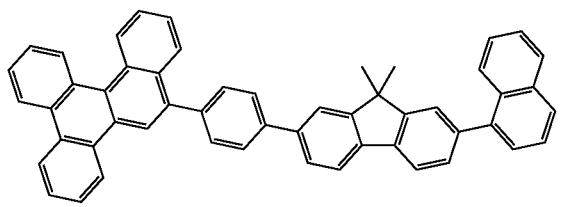
2-167
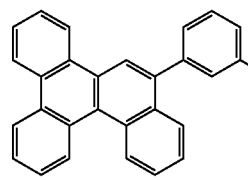
2-168
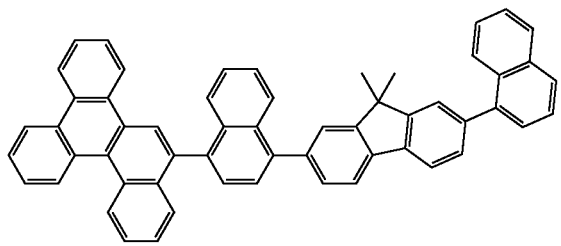
2-169
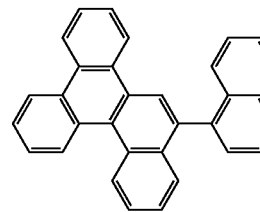

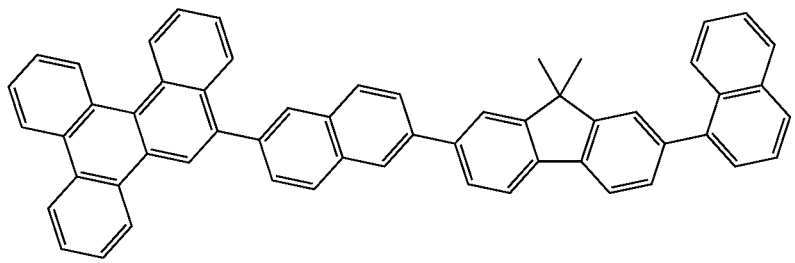
2-170
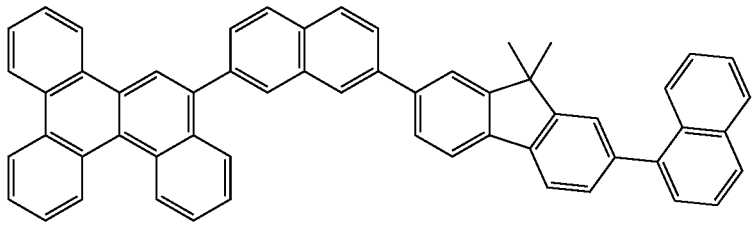
2-171
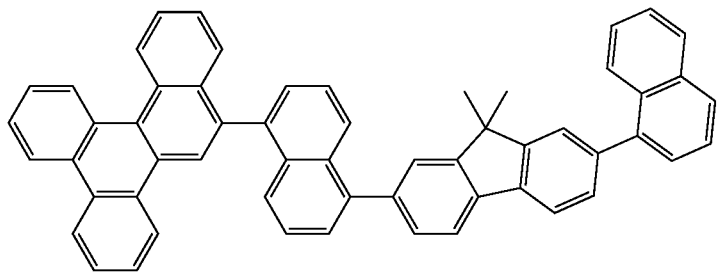
2-172
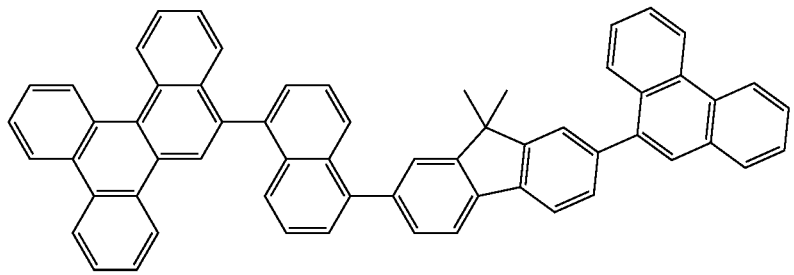
2-173
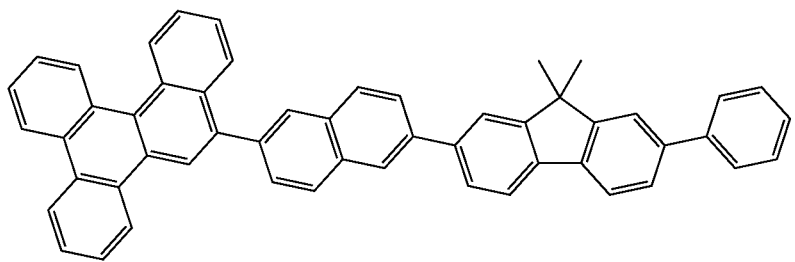
2-174
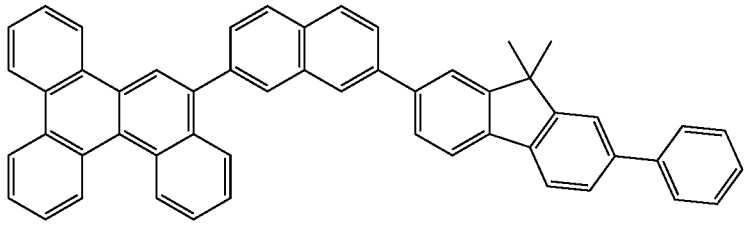
2-175

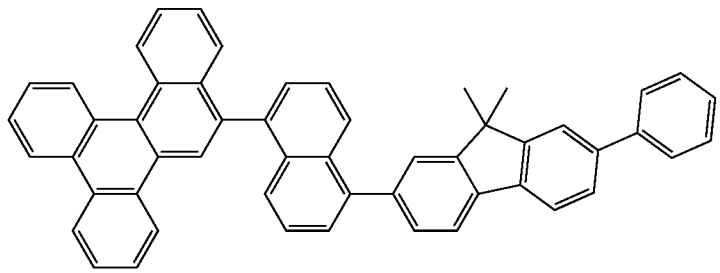
2-176
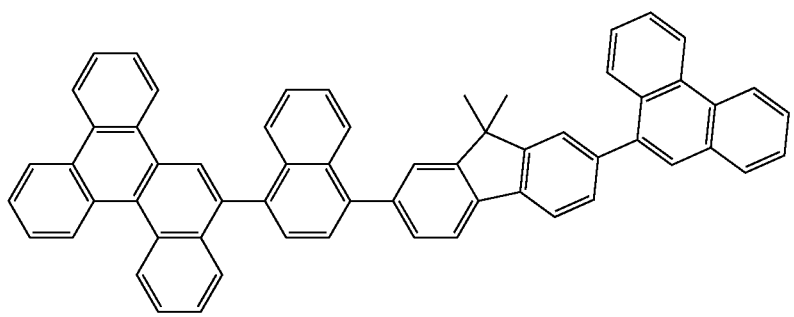
2-177
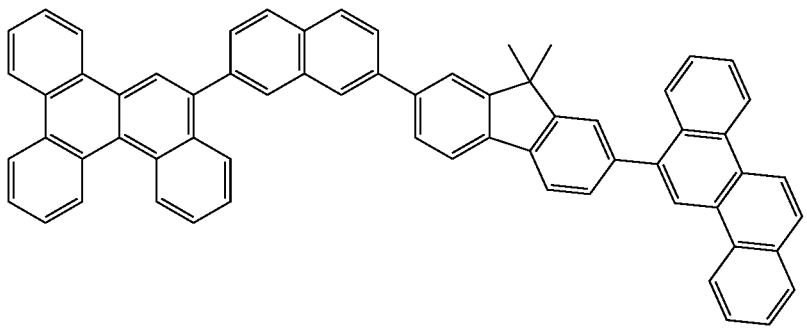
2-181
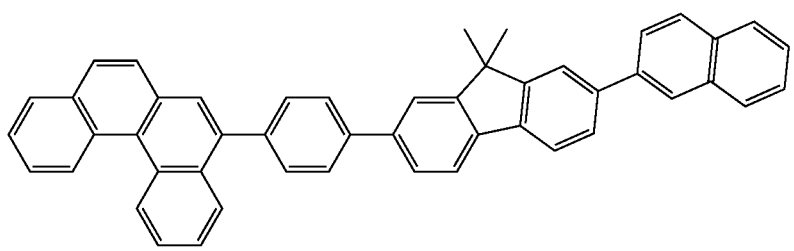
2-183
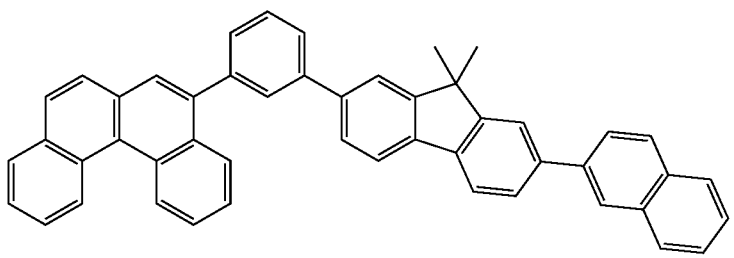
2-184

-continued
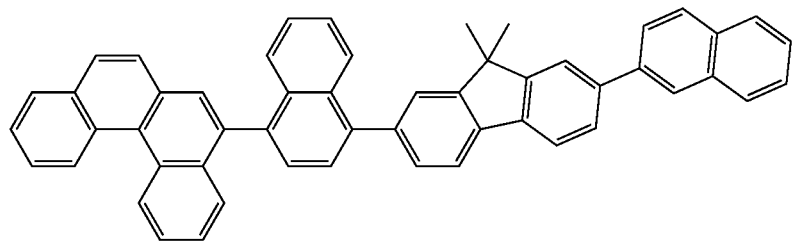
2-185
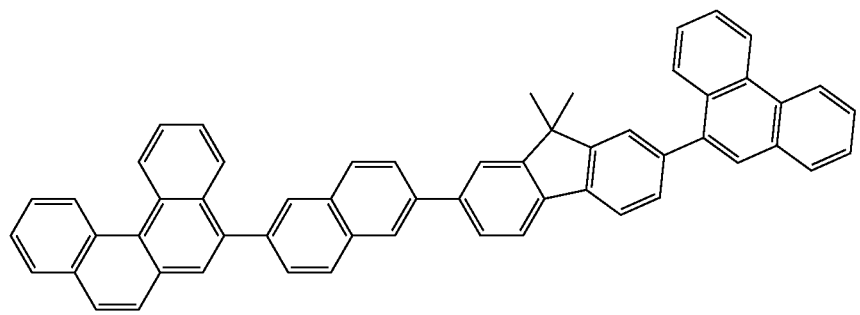
2-186
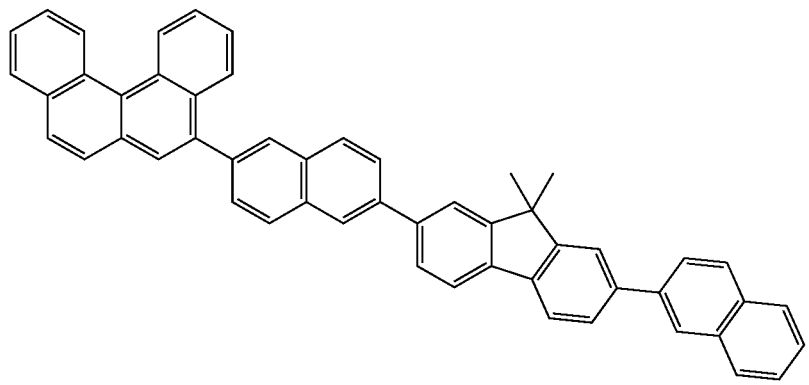
2-187
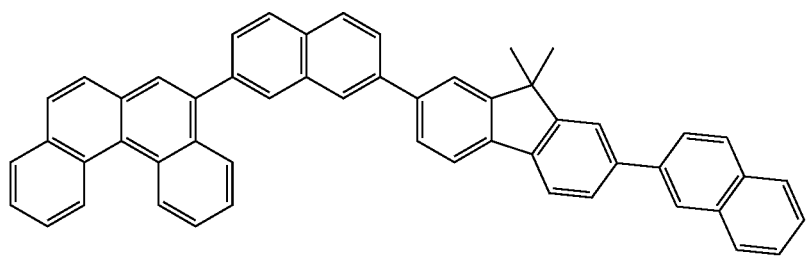
2-188
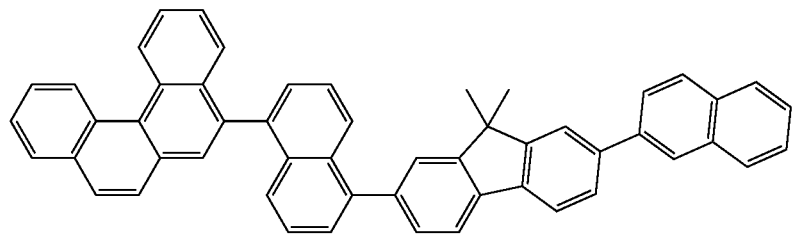
2-189

-continued
2-190
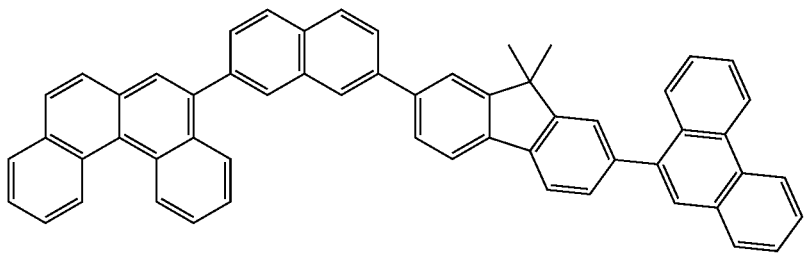
2-191
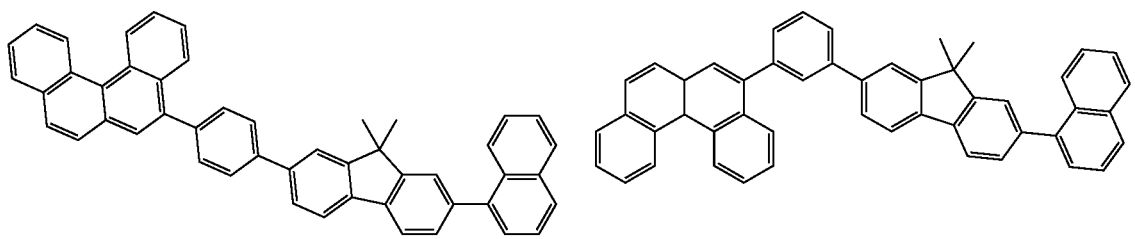
2-192
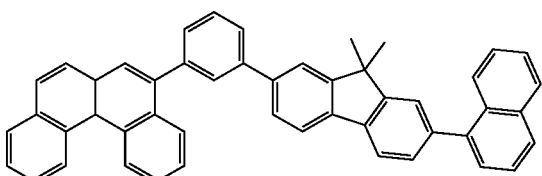
2-193
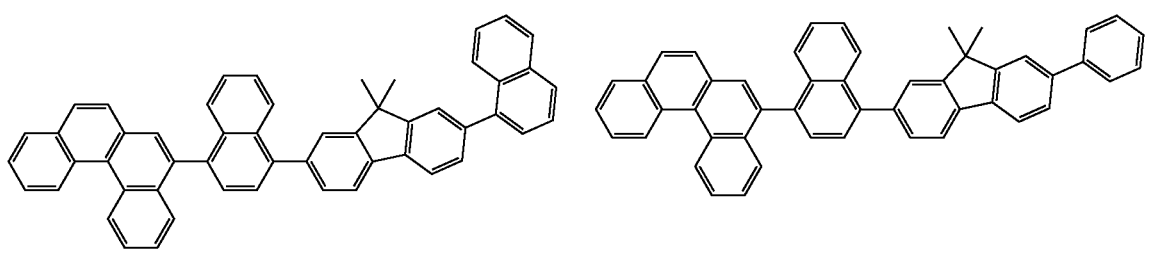
2-194
2-195
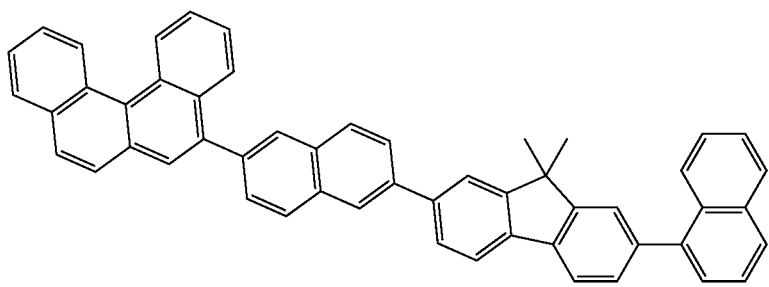
2-196
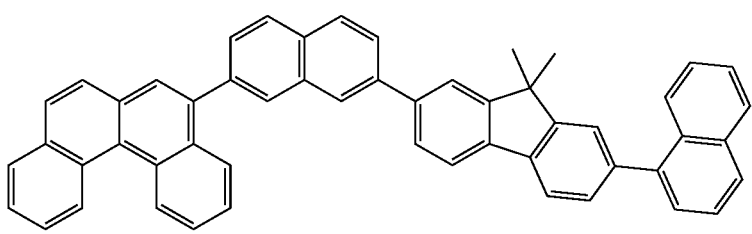
2-197
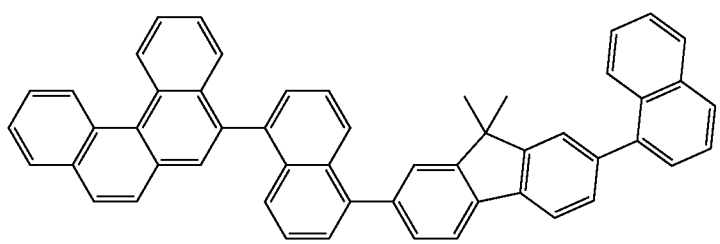

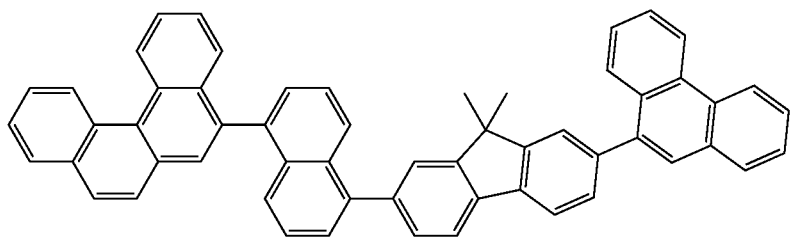
2-198
2-199
2-200
2-201
2-202
2-206

-continued
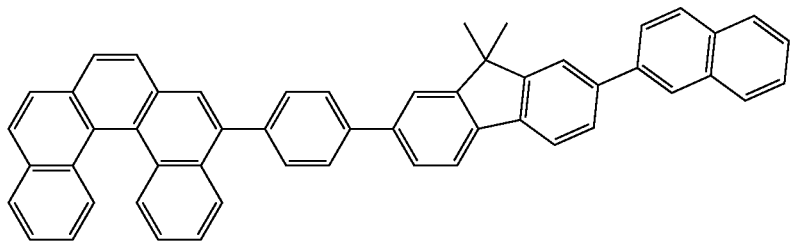
2-207
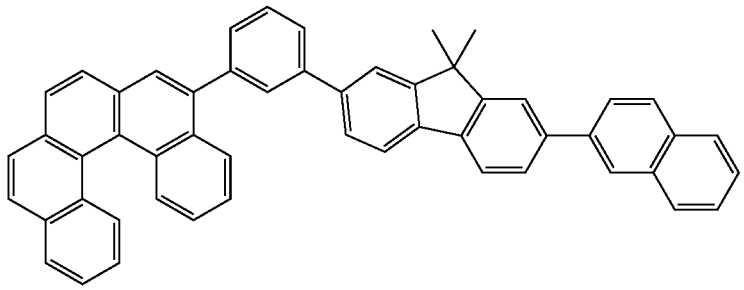
2-208
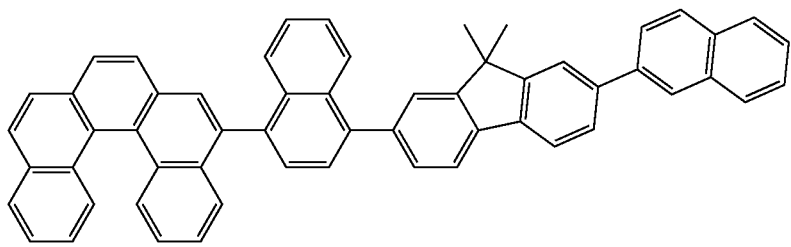
2-209
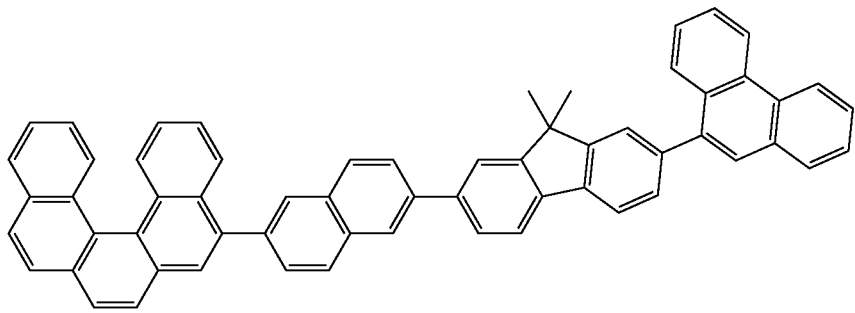
2-210
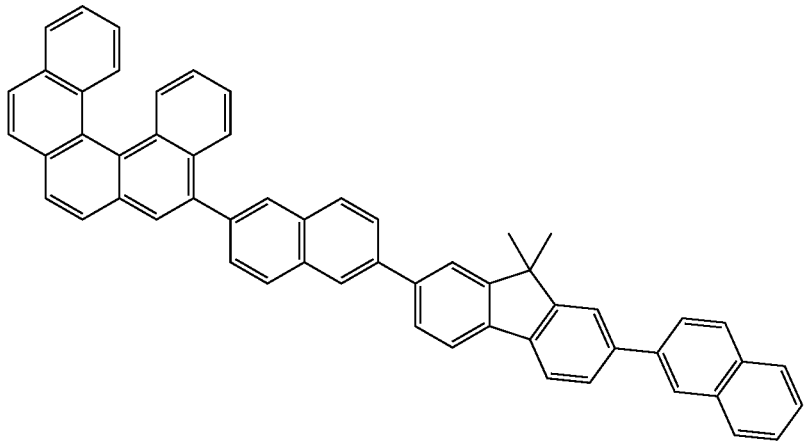
2-211

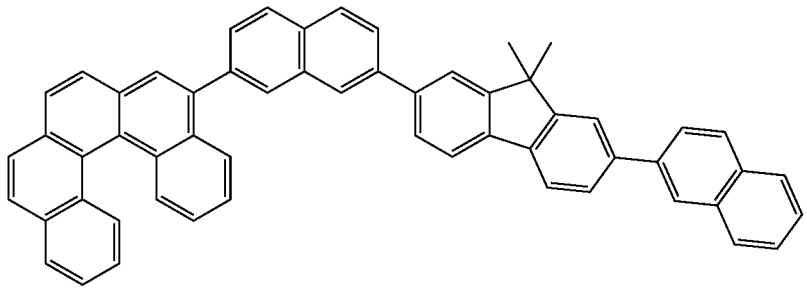

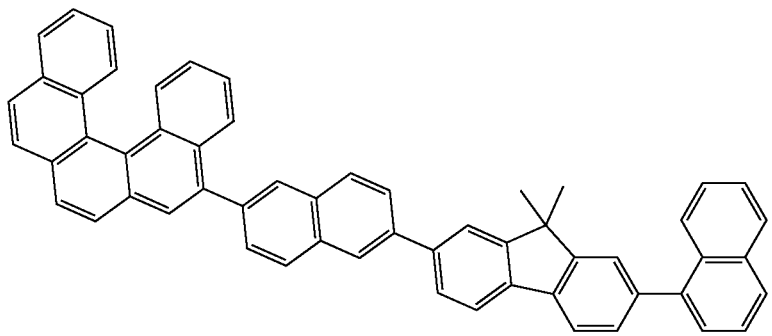
2-219
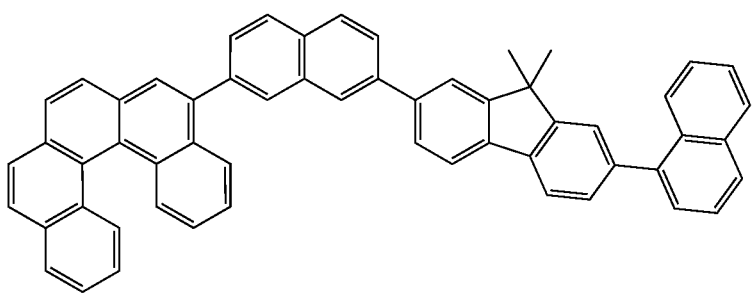
2-220
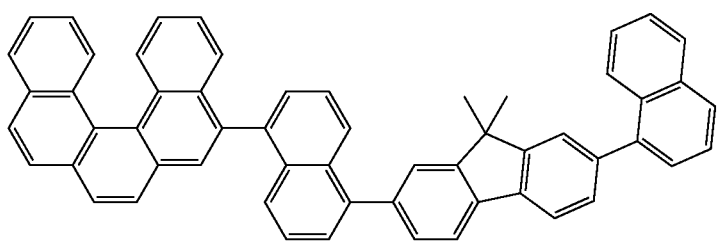
2-221
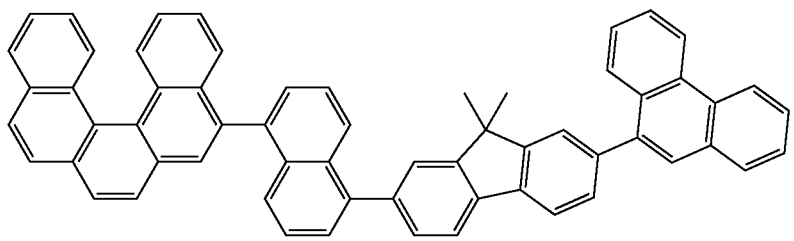
2-222
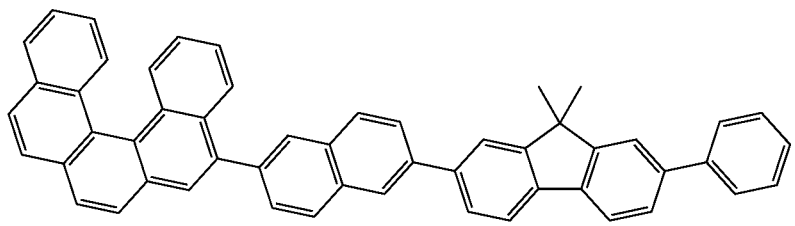
2-223
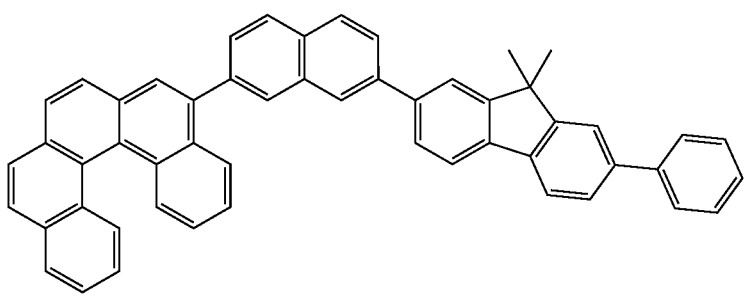
2-224

-continued
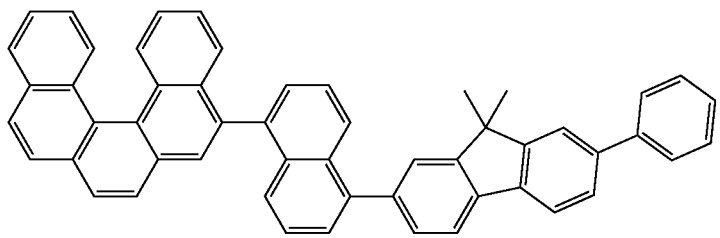
2-225
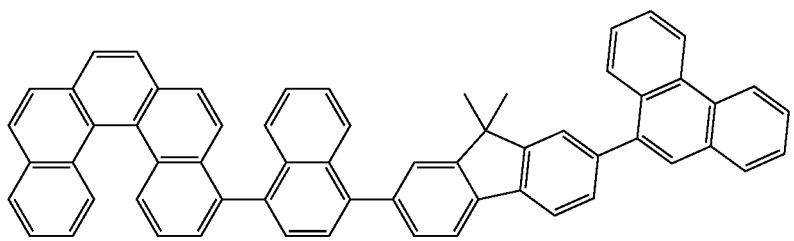
2-226
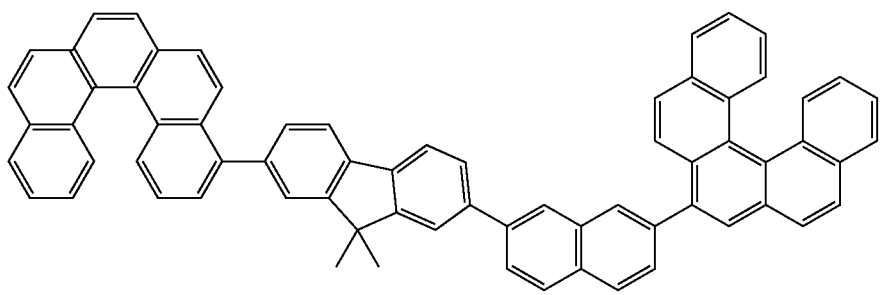
2-230
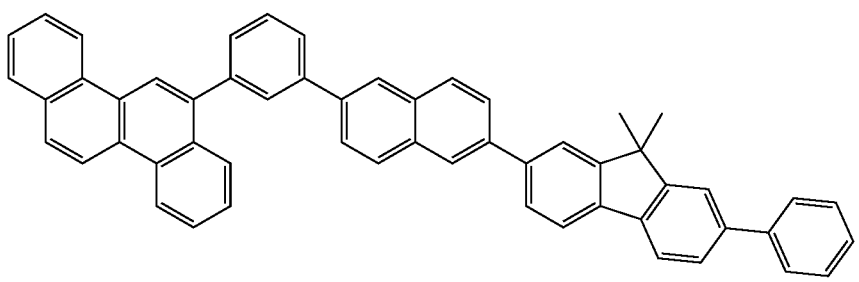
2-247
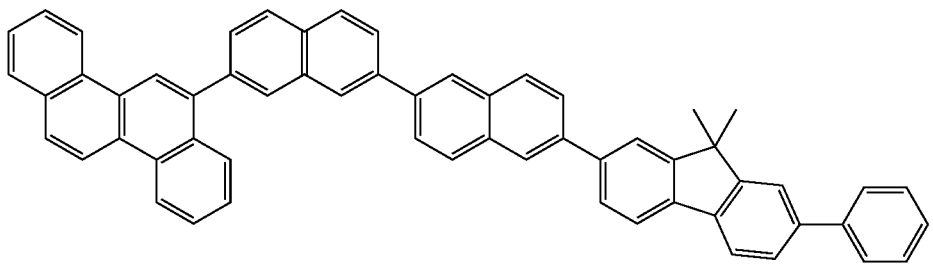
2-248
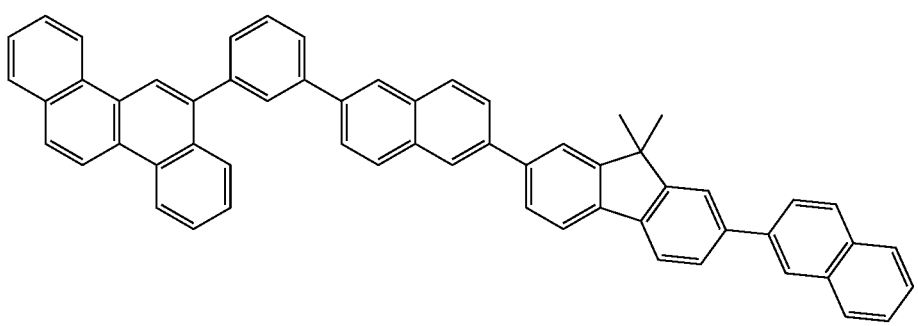
2-249

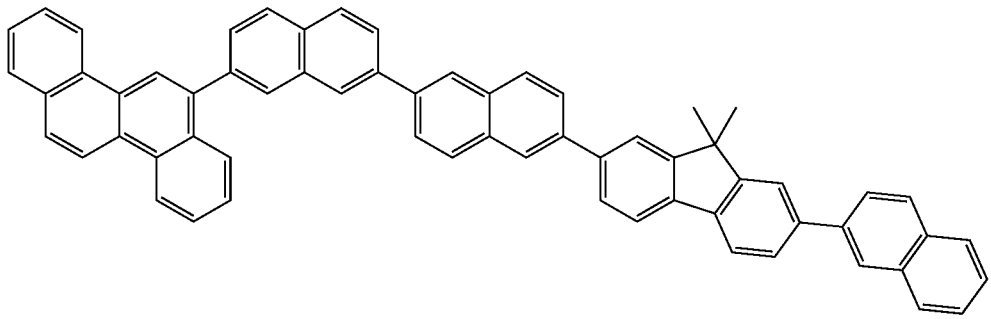
2-250
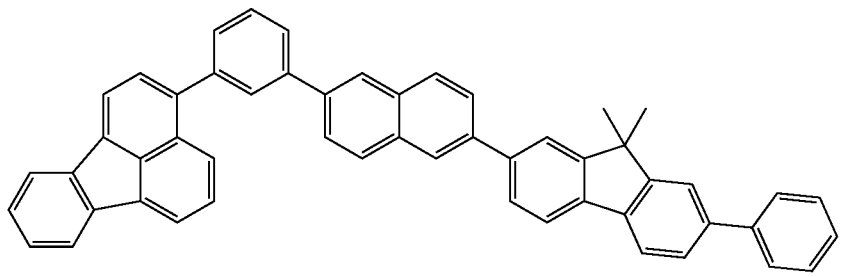
2-267
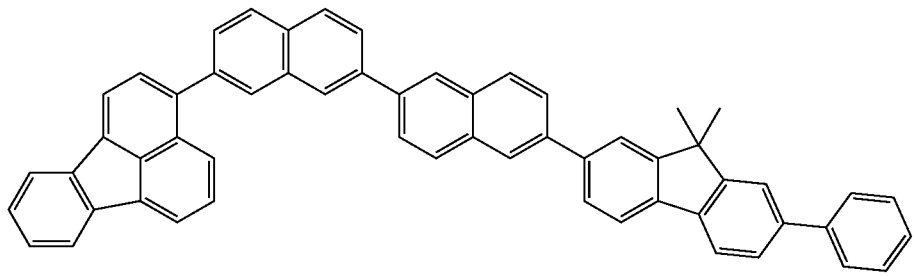
2-268
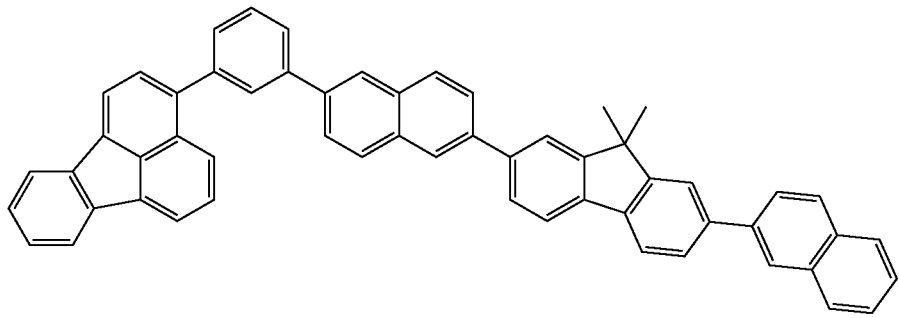
2-269
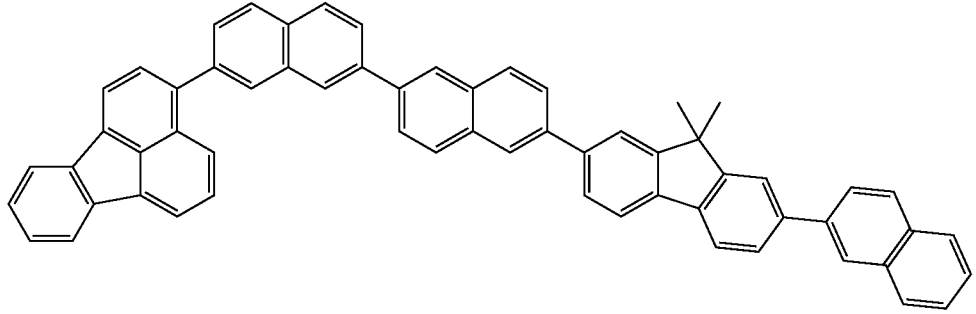
2-270

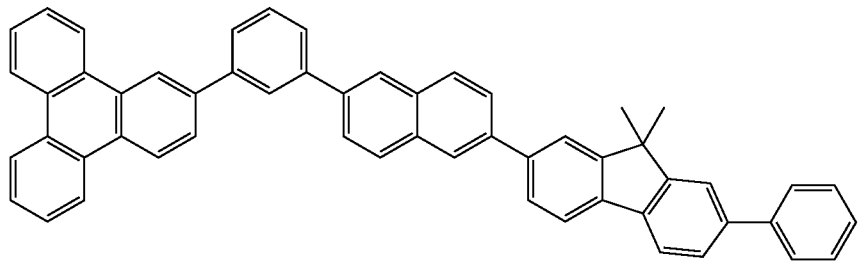
2-287
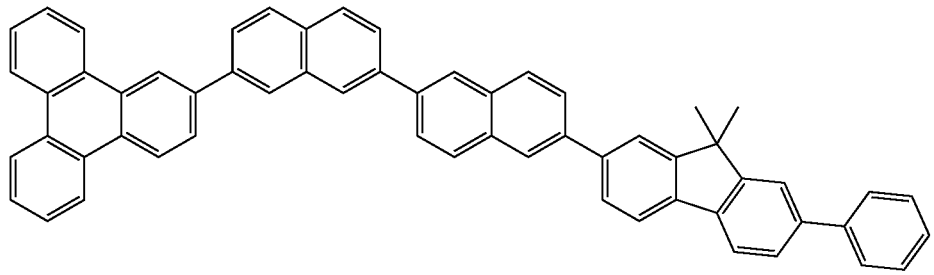
2-288
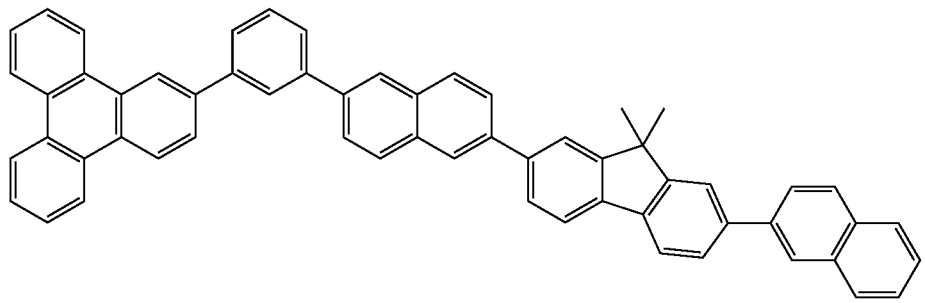
2-289
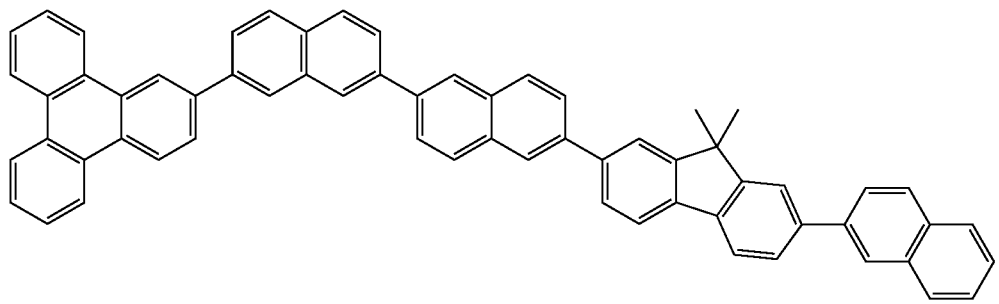
2-290
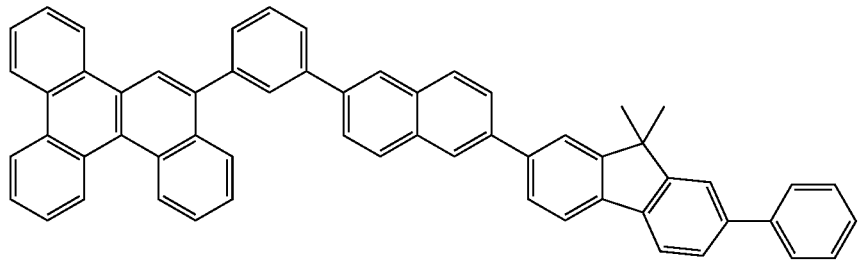
2-307

-continued
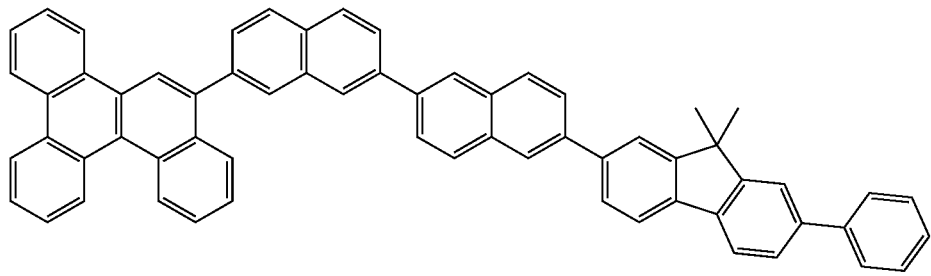
2-308
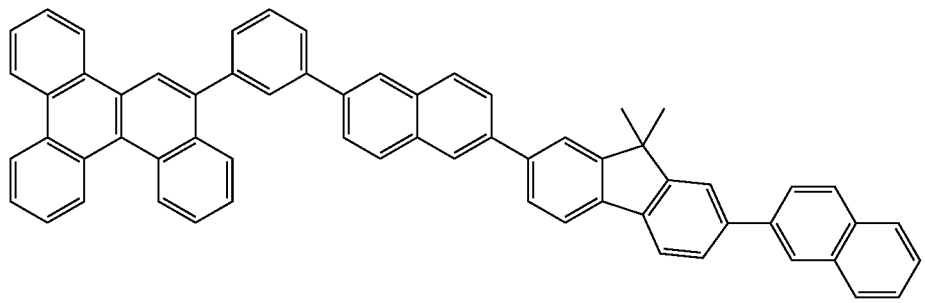
2-309
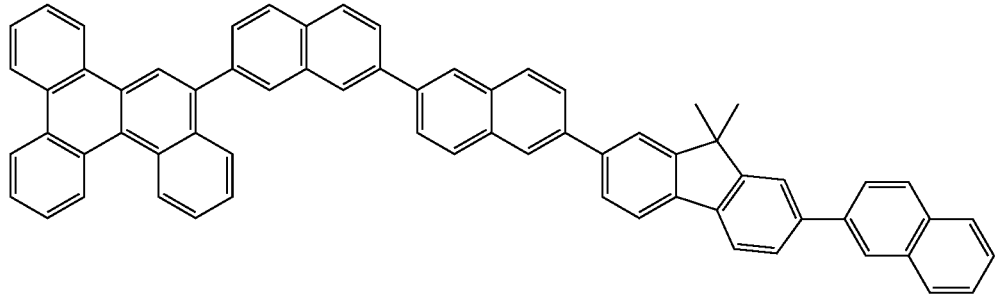
2-310
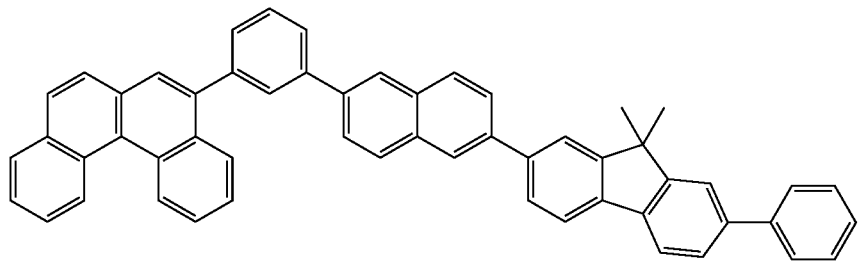
2-327
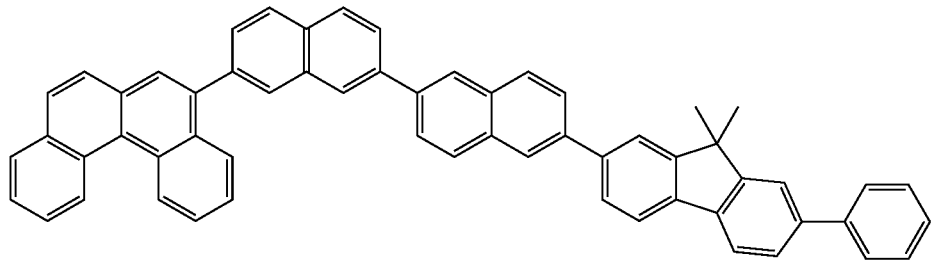
2-328

-continued 2-329

2-330

2-347

2-348

2-349

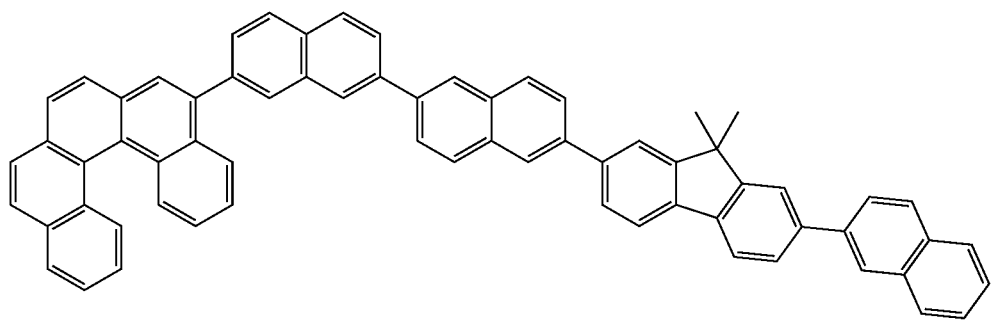
2-350
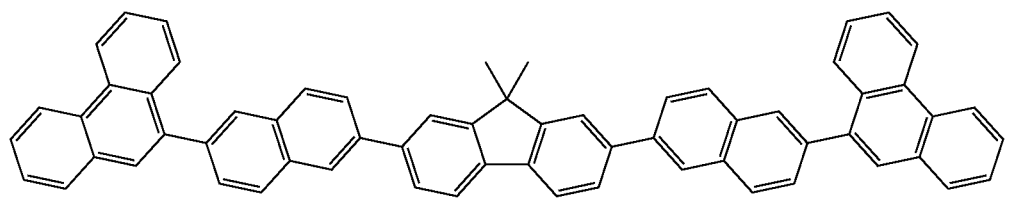
2-351
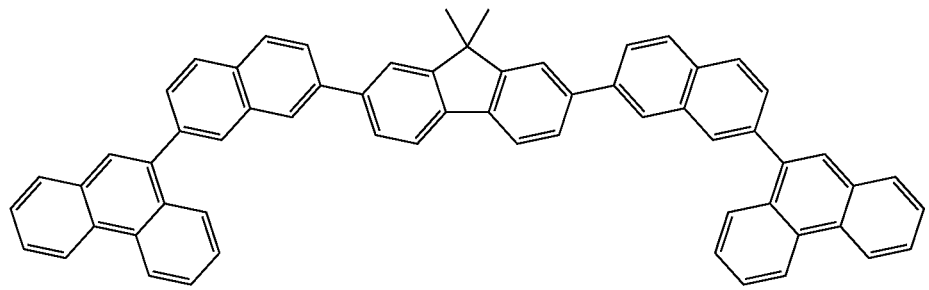
2-352
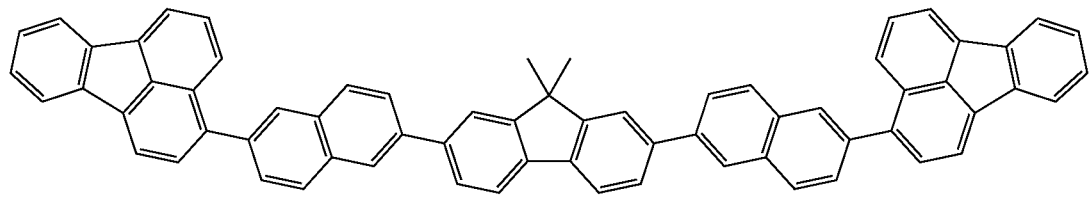
2-353
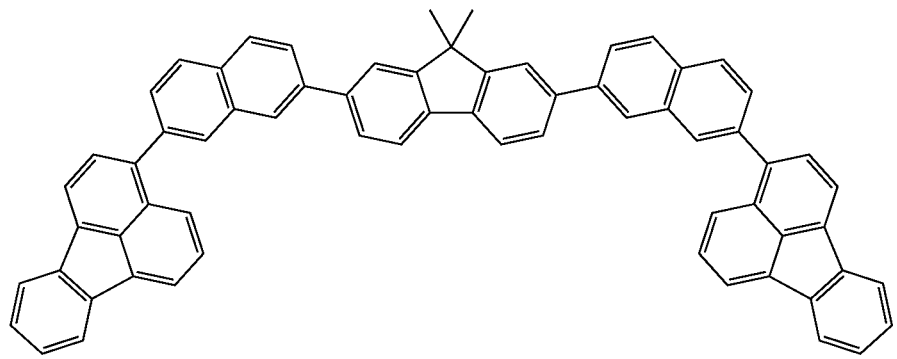
2-354

-continued
2-359
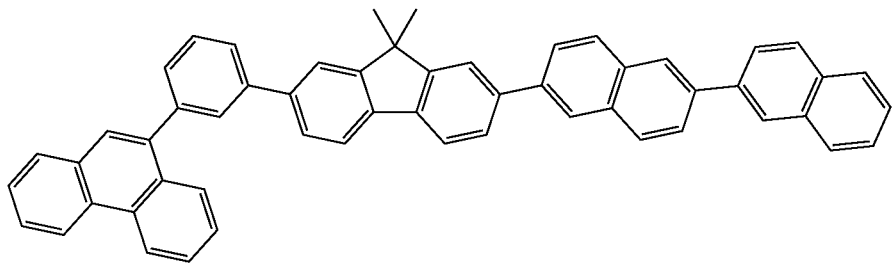
2-361
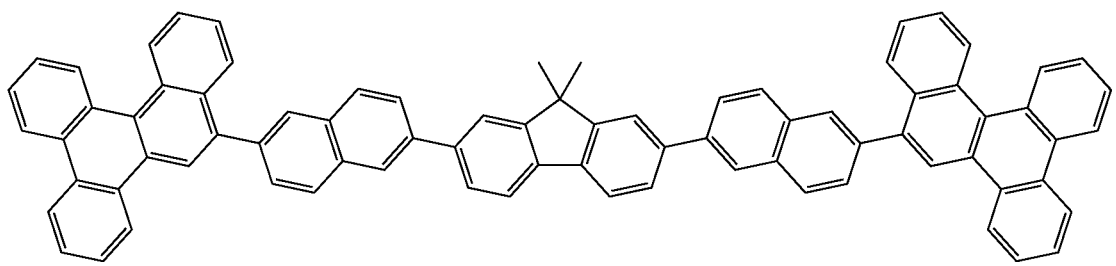
2-362
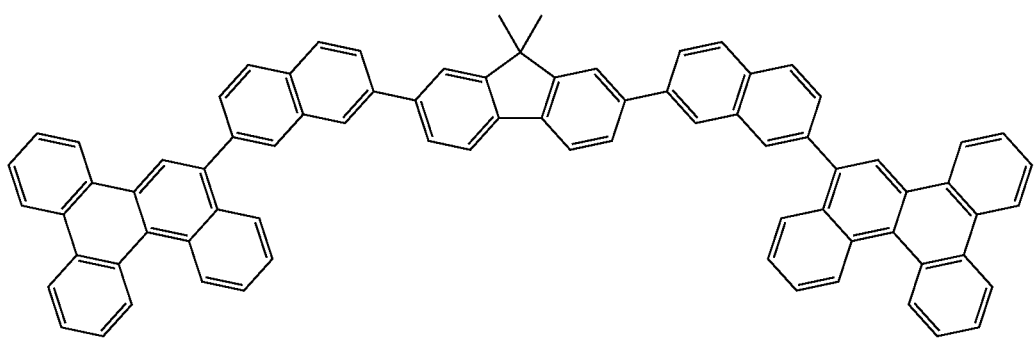
2-365
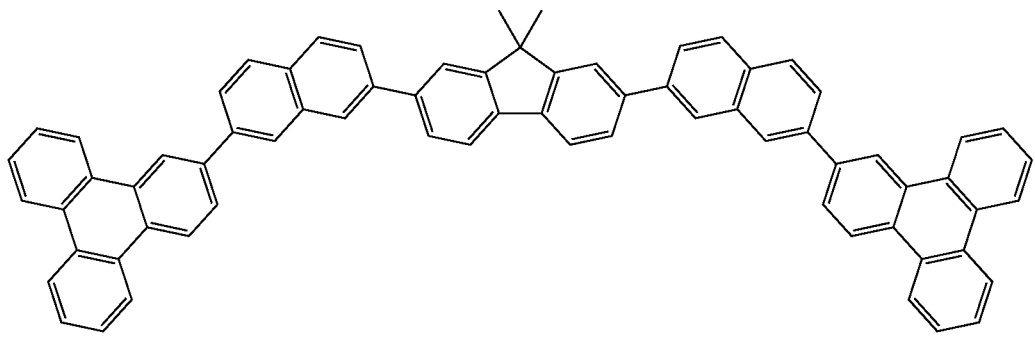
2-366
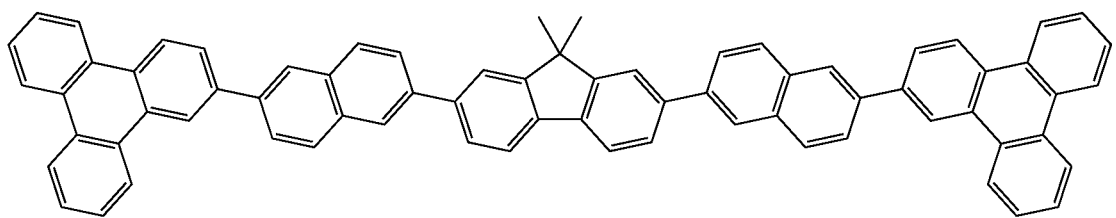

-continued
2-367
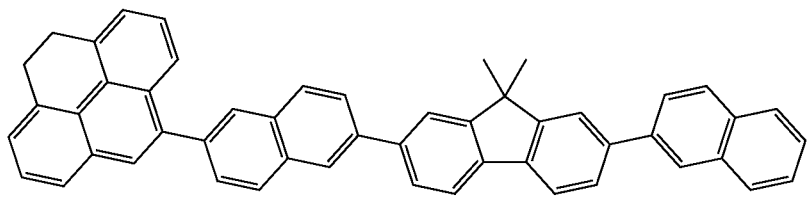
2-368
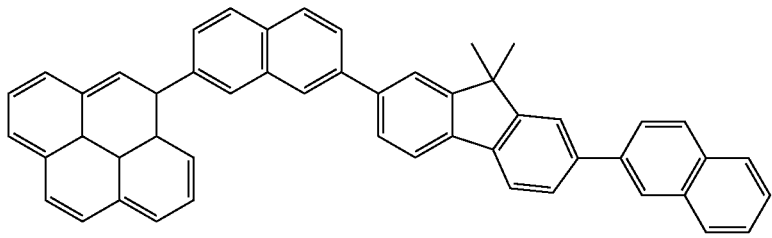
2-369
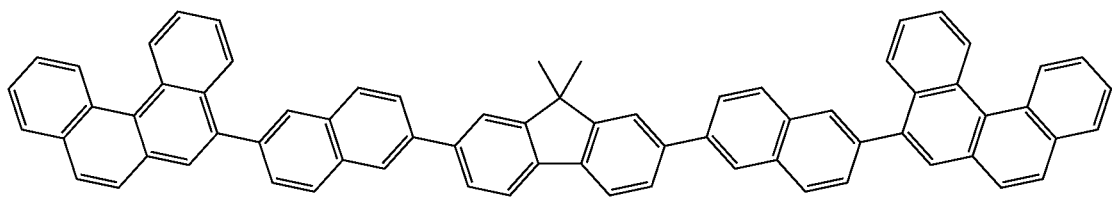
2-370
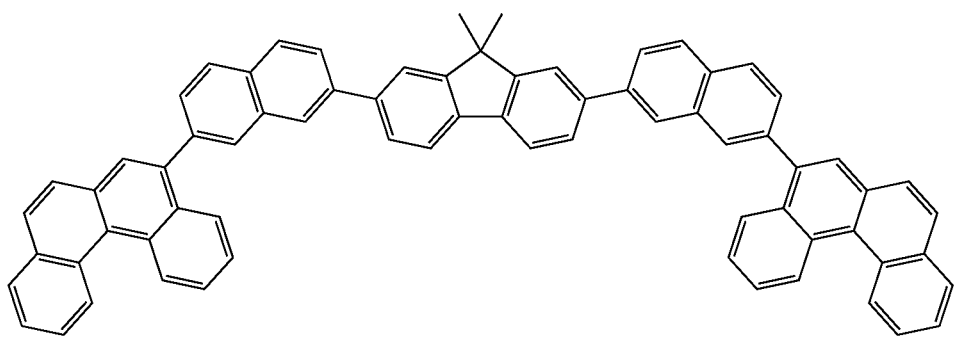
2-371
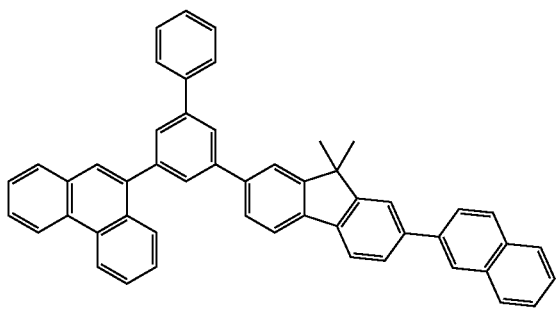
2-372
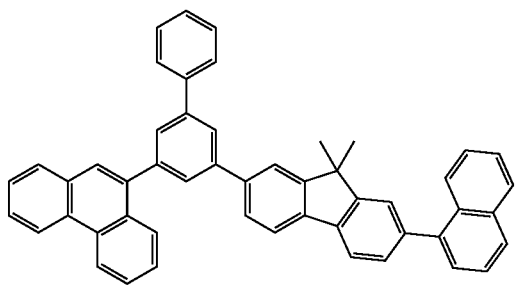

-continued
2-375
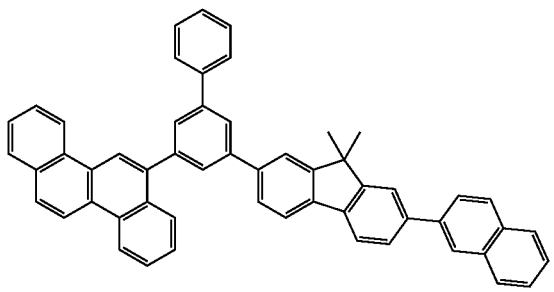
2-377
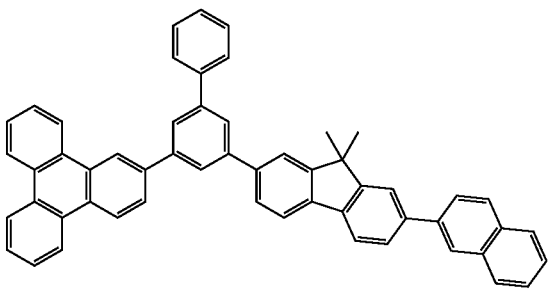
2-379
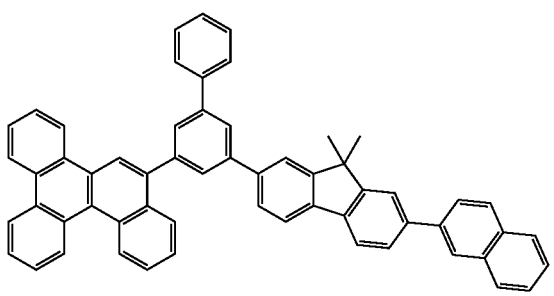
2-381
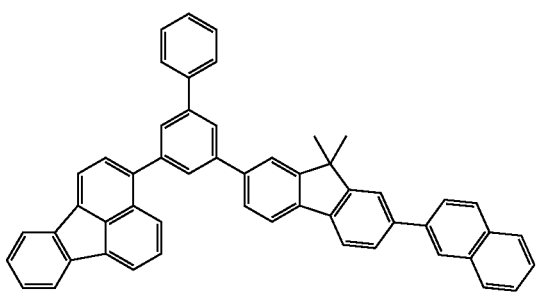
2-383
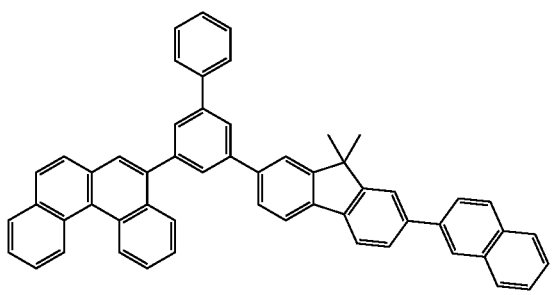
2-385
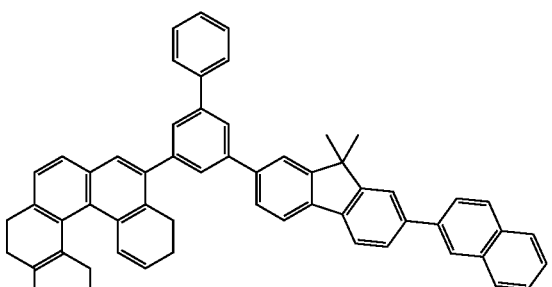
2-387
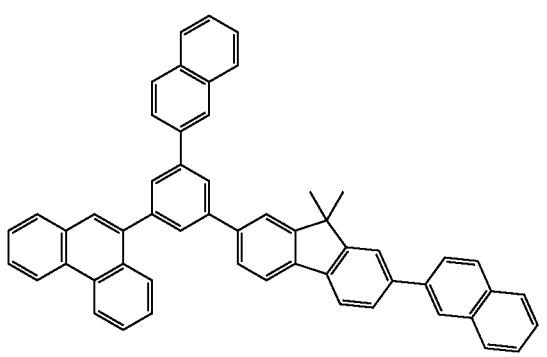
2-388
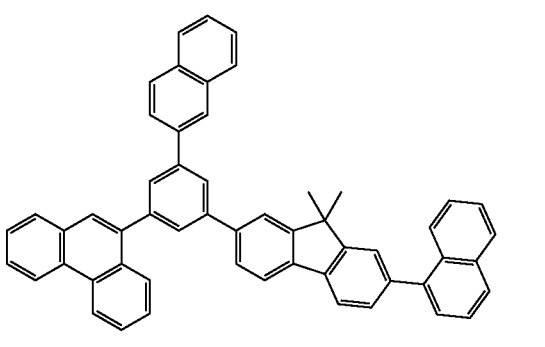

-continued
2-391
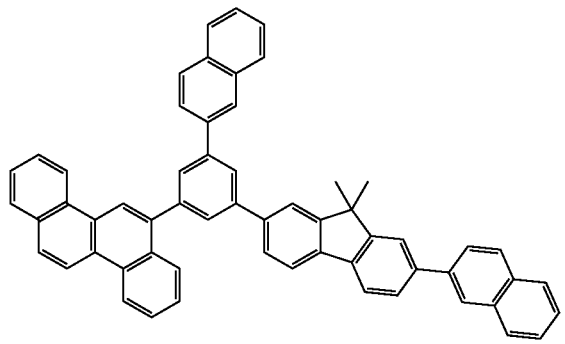
2-393
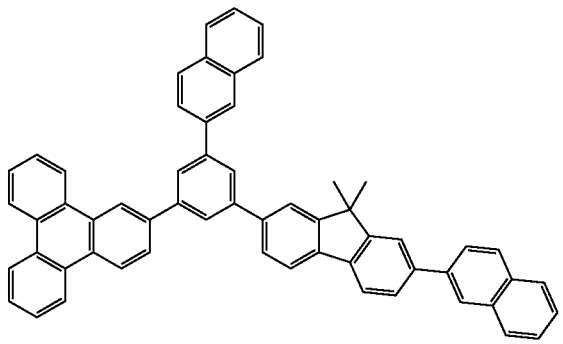
2-395
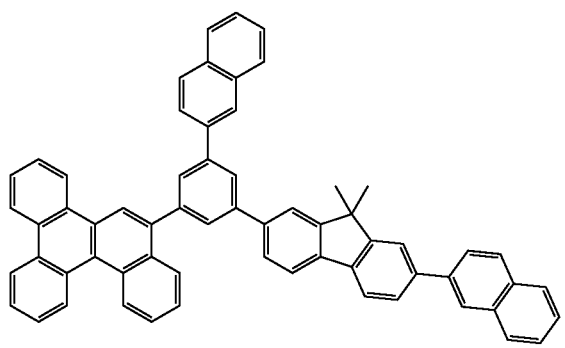
2-397
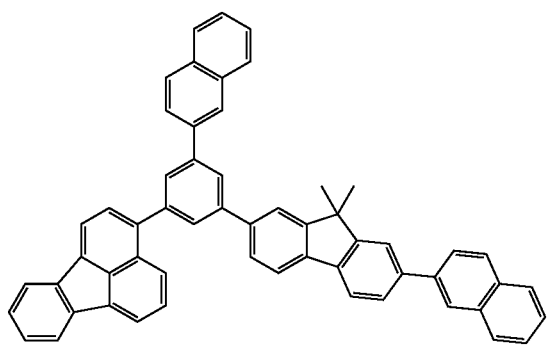
2-399
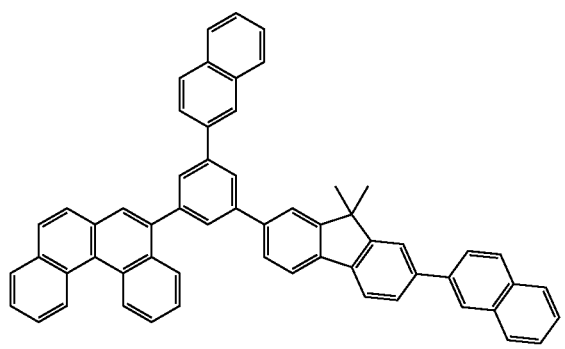
2-401
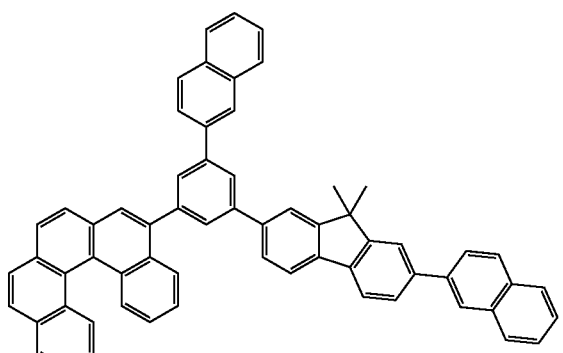
3-1
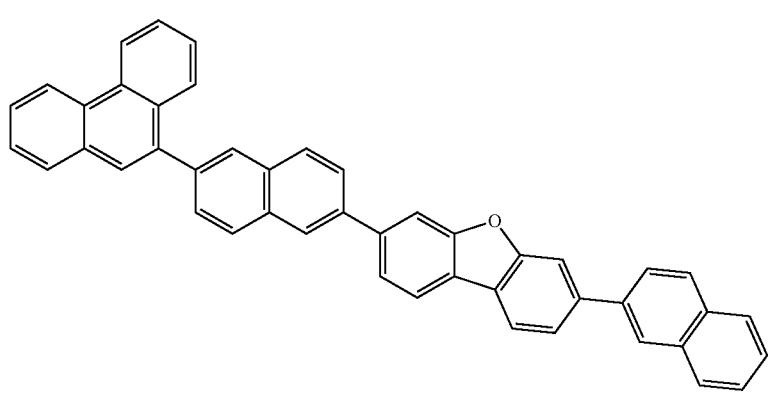

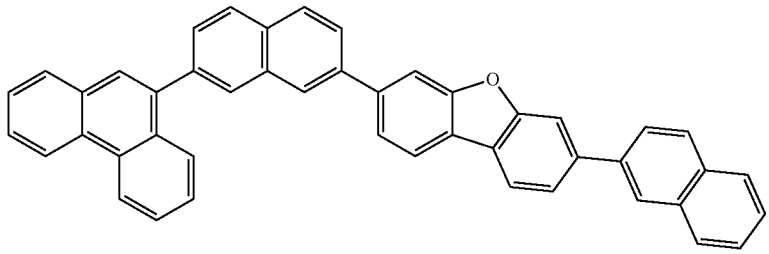
3-2
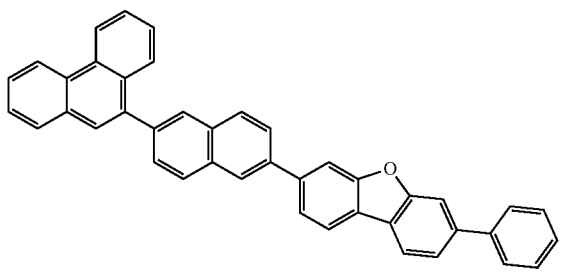
3-3
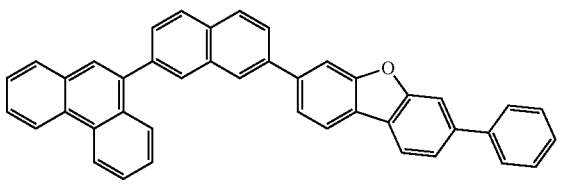
3-4
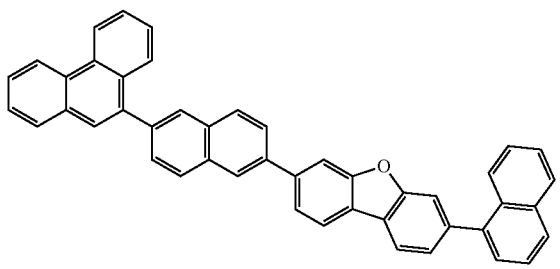
3-5
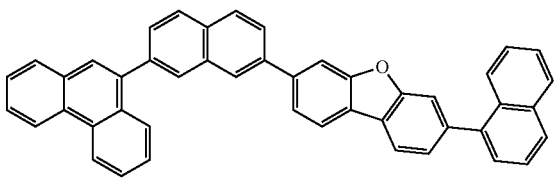
3-6
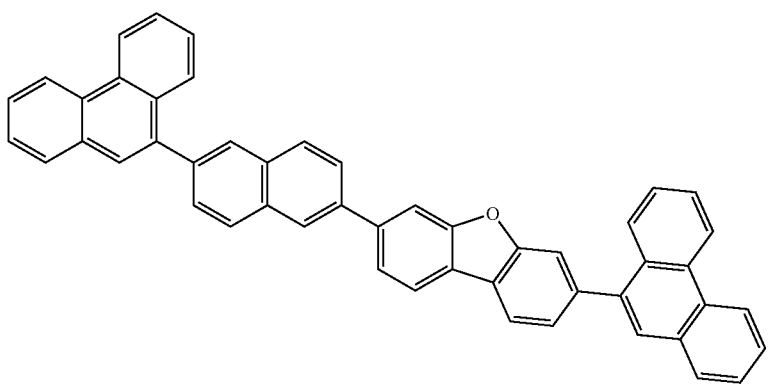
3-7
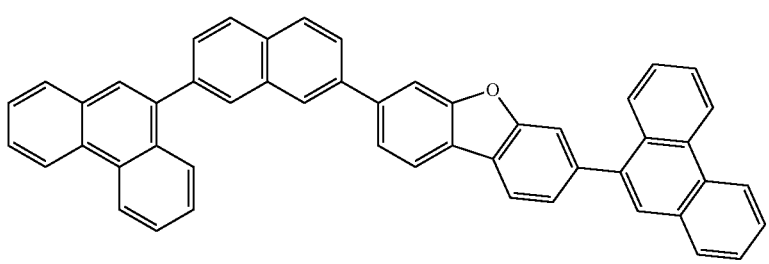
3-8

3-9
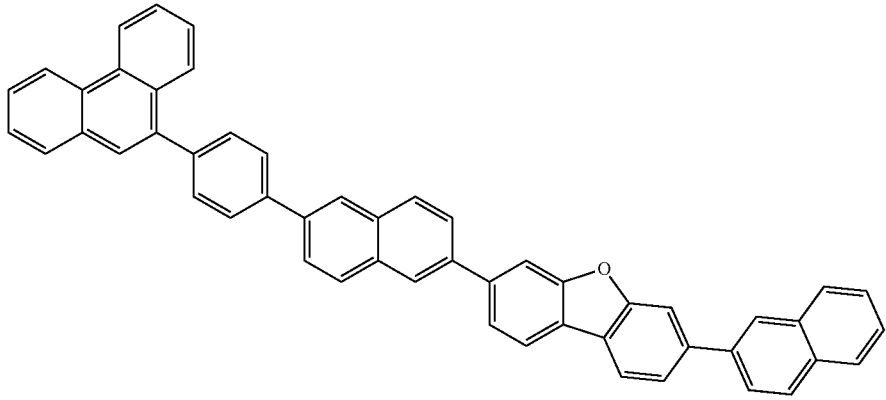
3-10
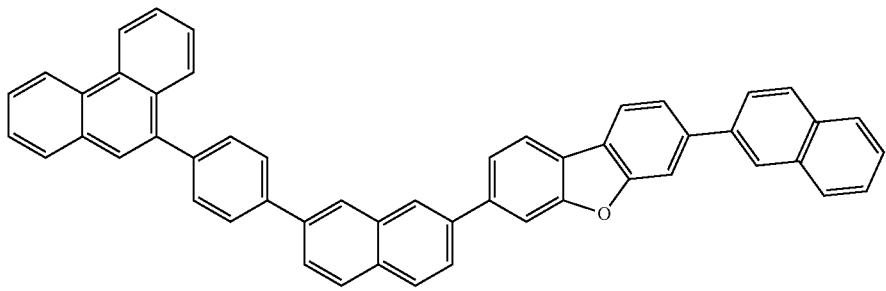
3-11
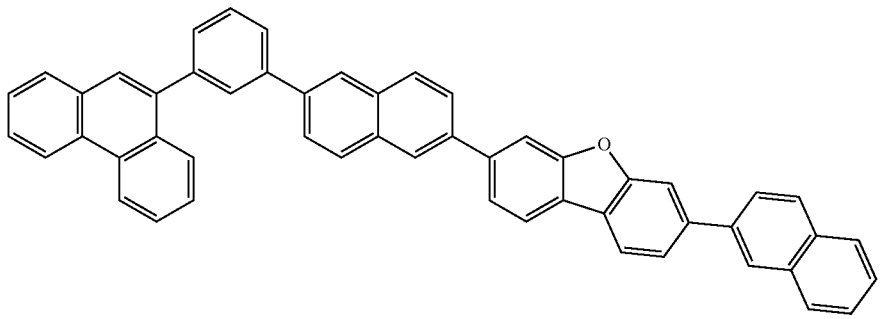
3-12
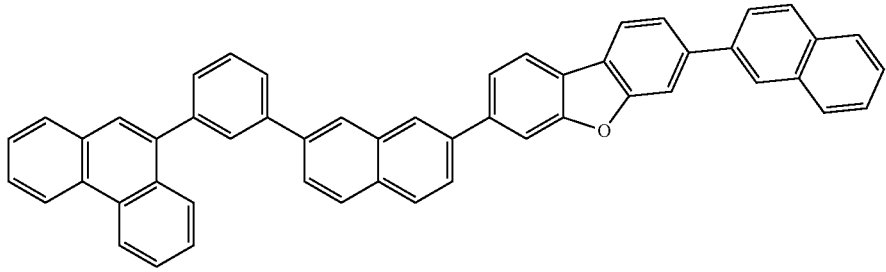
3-13
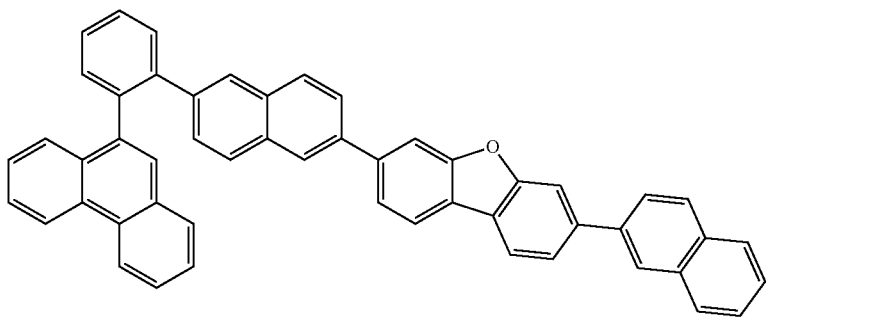

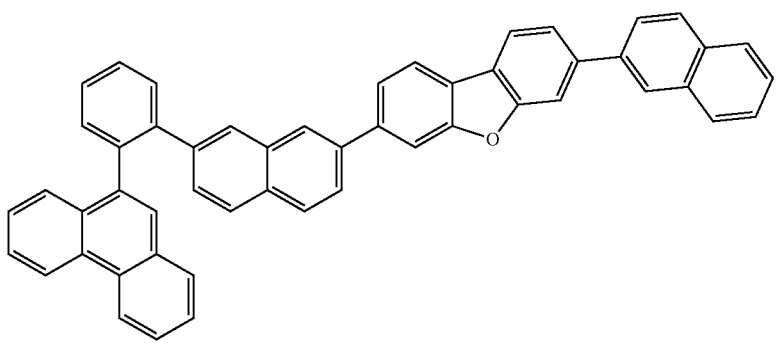
3-14
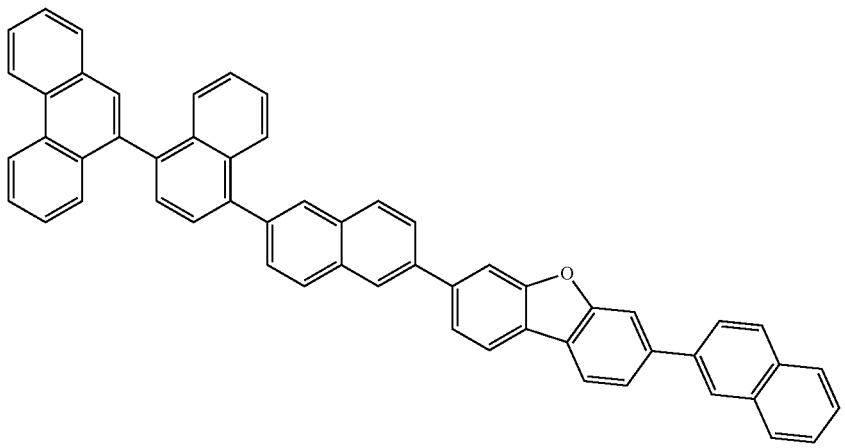
3-15
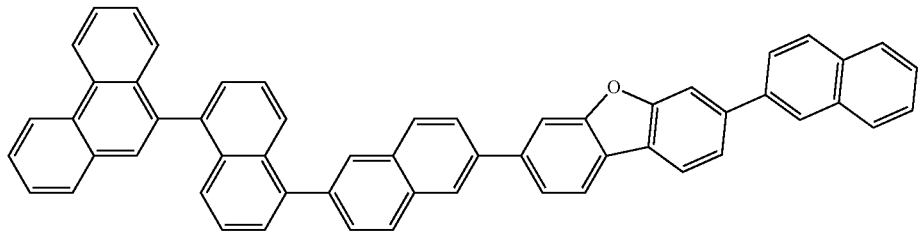
3-16
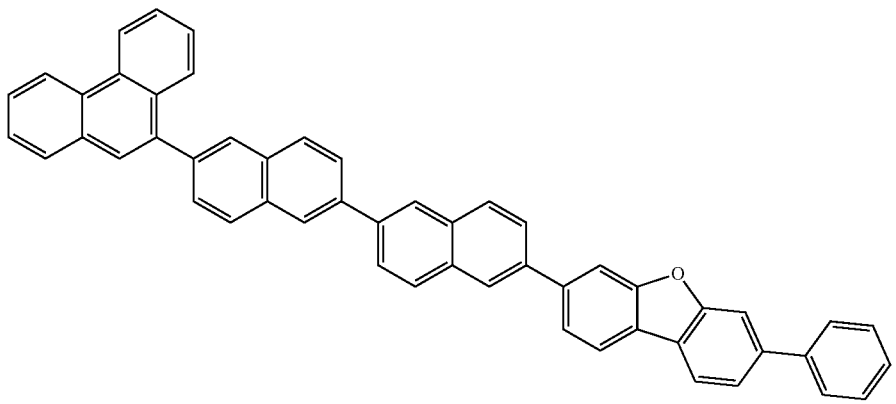
3-17

-continued
3-18
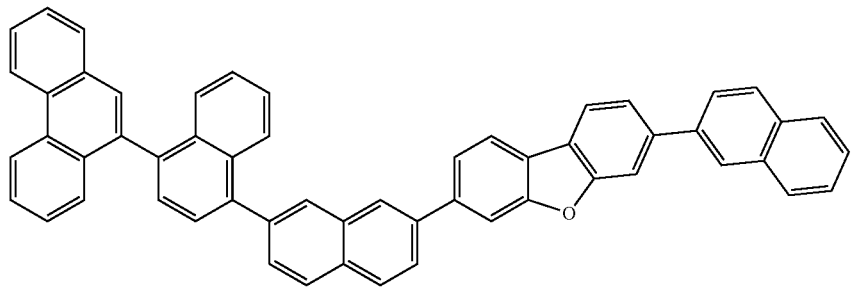
3-19
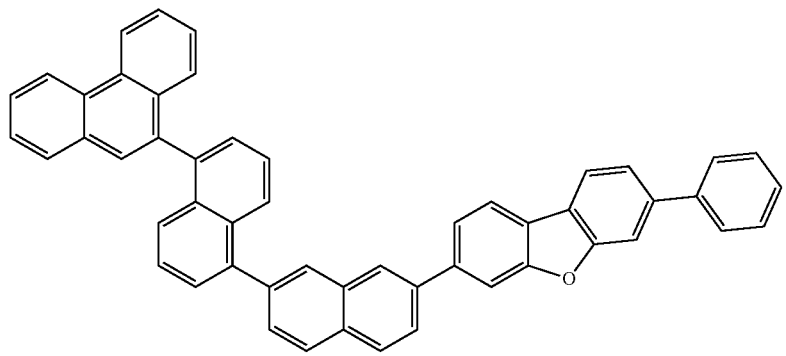
3-20
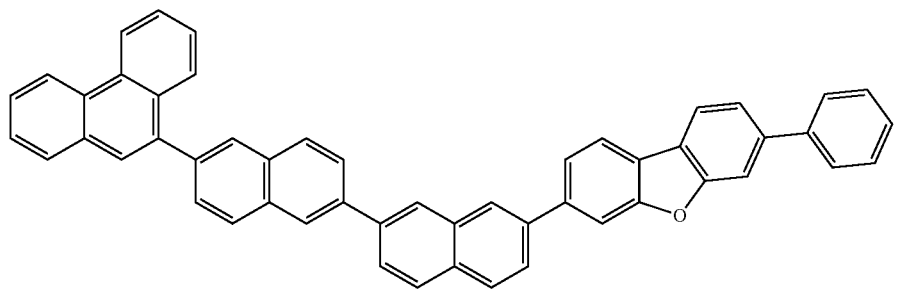
3-21
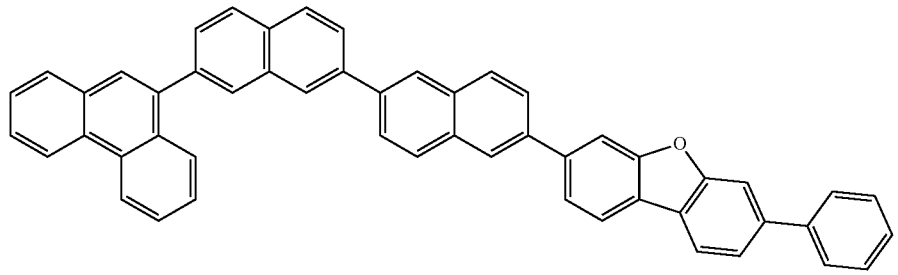
3-22
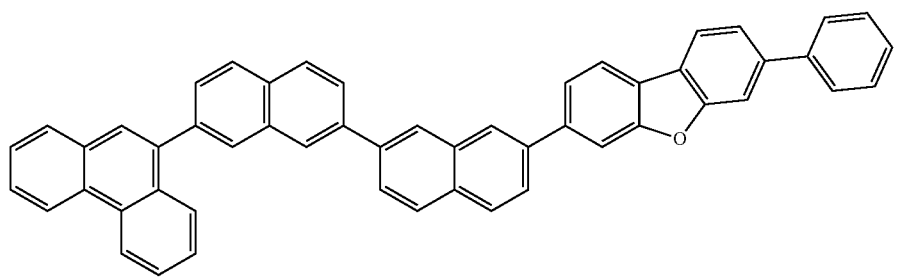

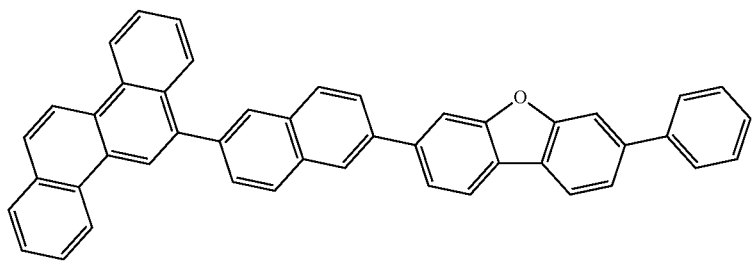
3-23
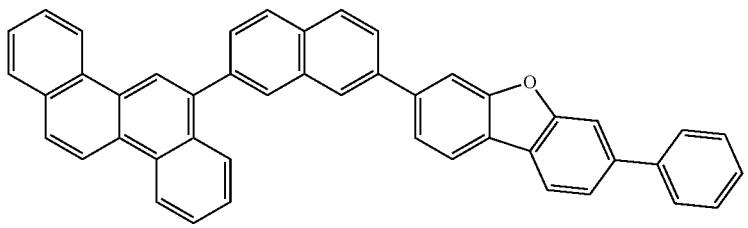
3-24
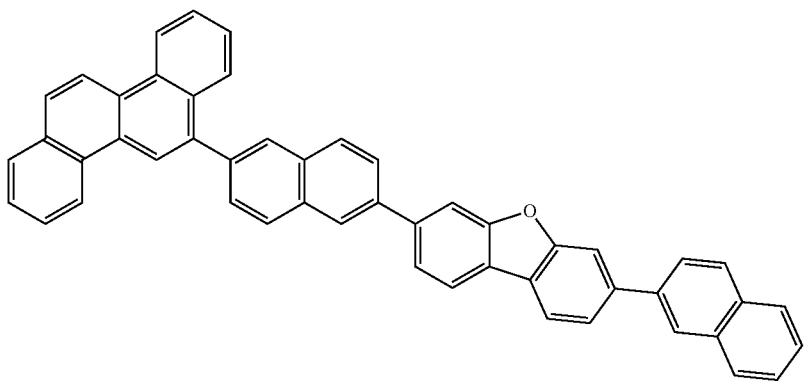
3-25
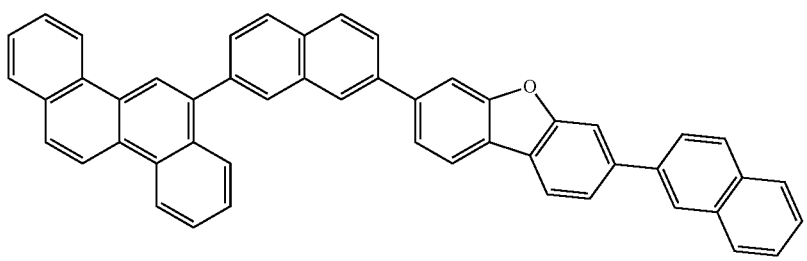
3-26
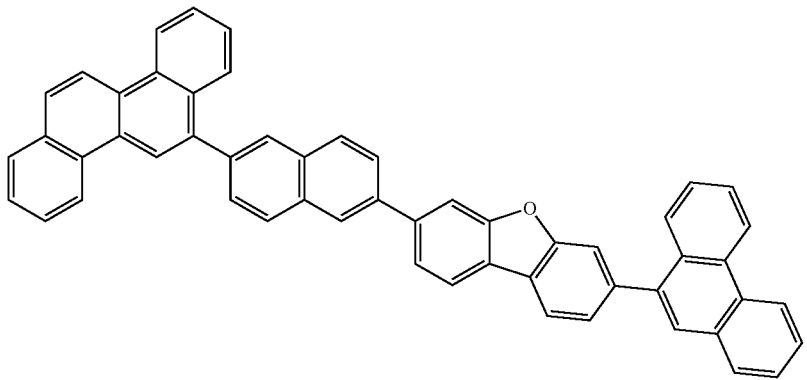
3-27

-continued
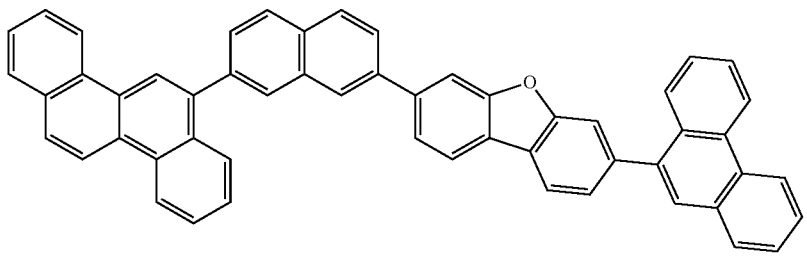
3-28
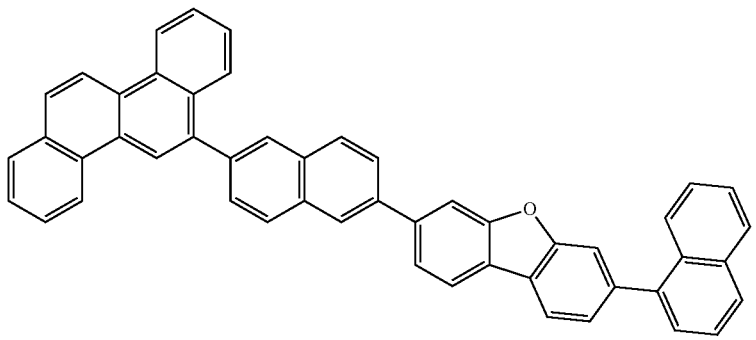
3-29
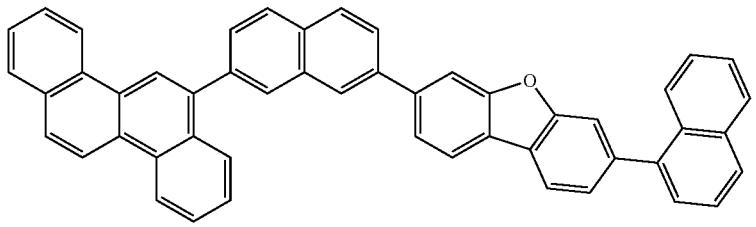
3-30
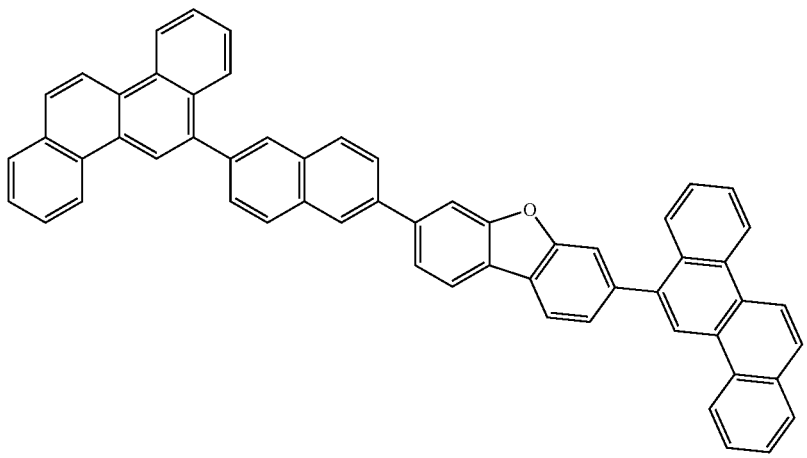
3-31
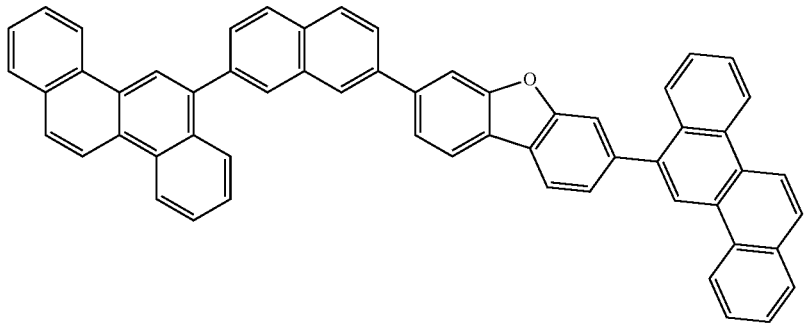
3-32

-continued
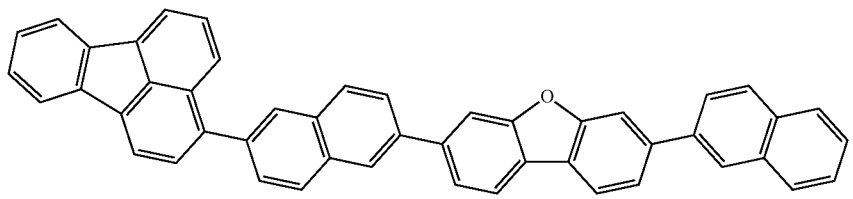
3-33
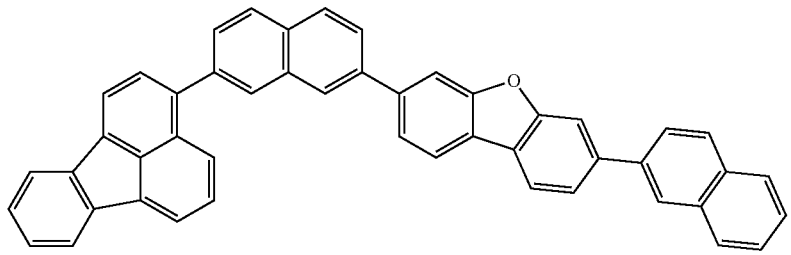
3-34
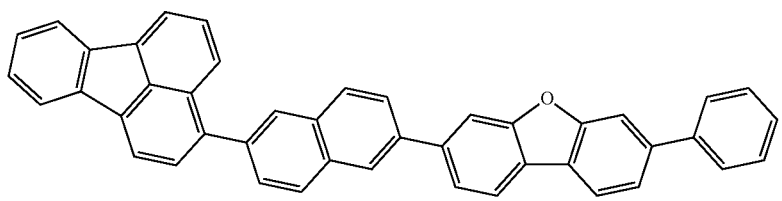
3-35
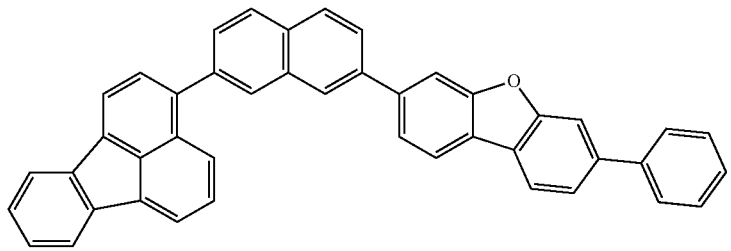
3-36
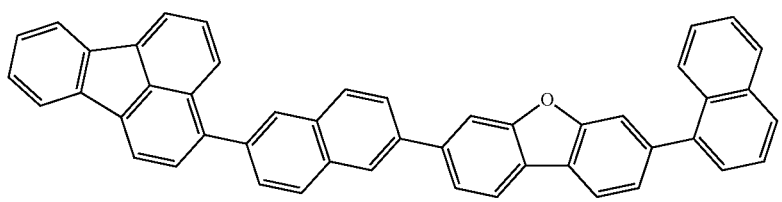
3-37
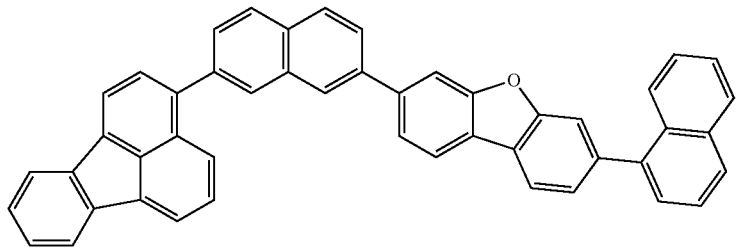
3-38
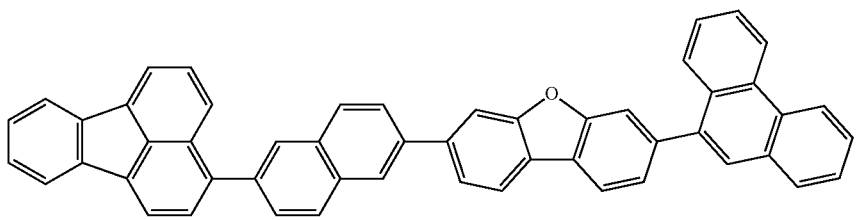
3-39

-continued
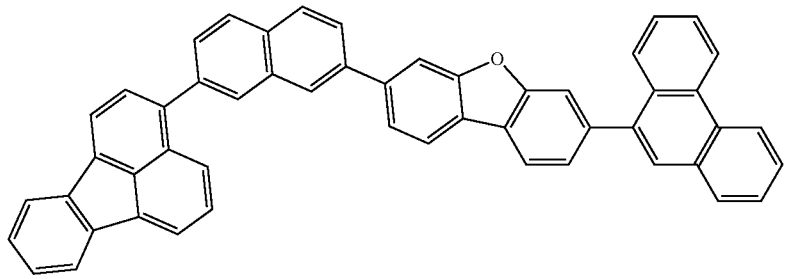
3-40
3-41
3-42
3-43
3-44
3-45

-continued 3-46

3-47

3-48

3-49

3-50

3-51

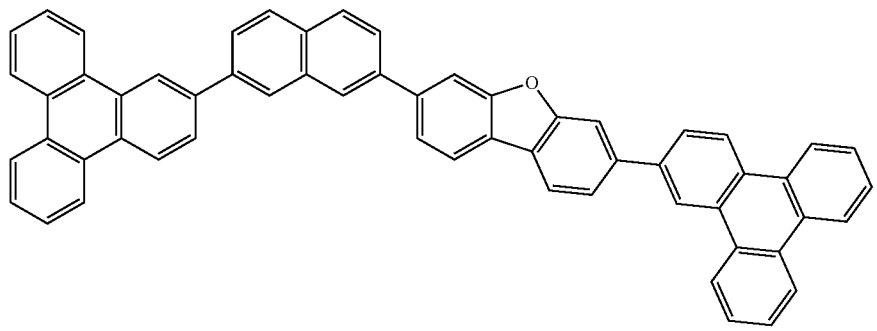
3-52
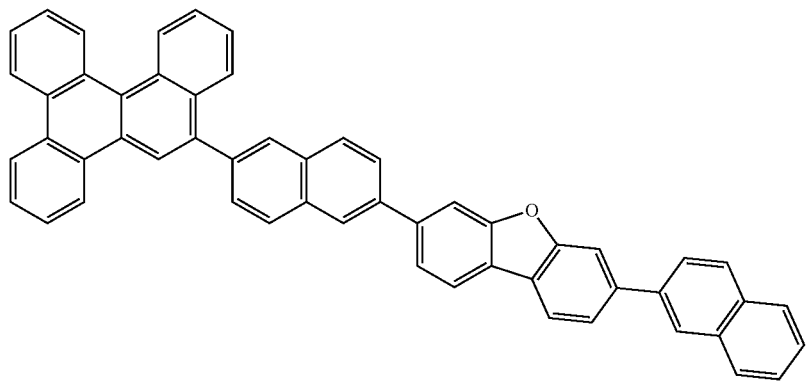
3-53
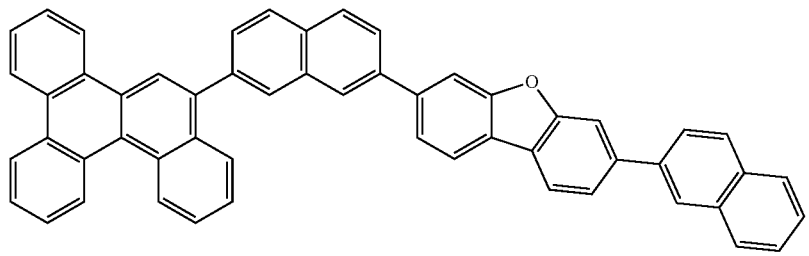
3-54
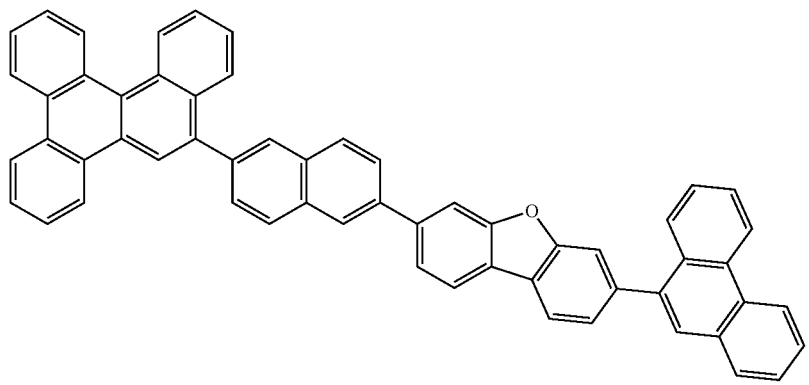
3-55
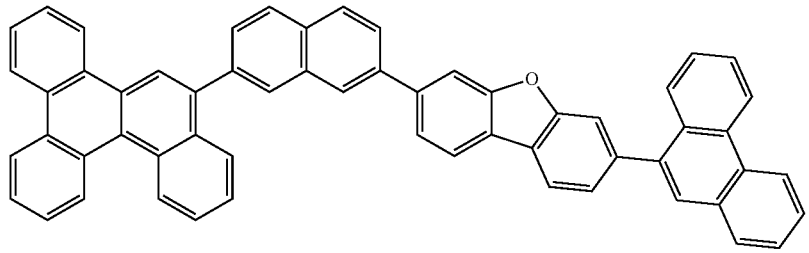
3-56

-continued
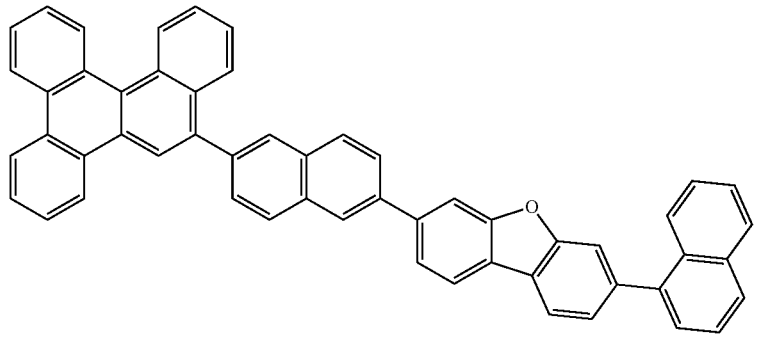
3-57
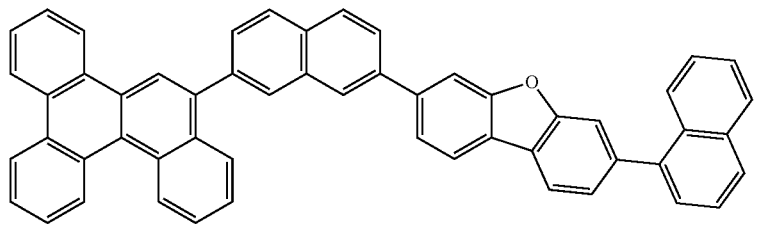
3-58
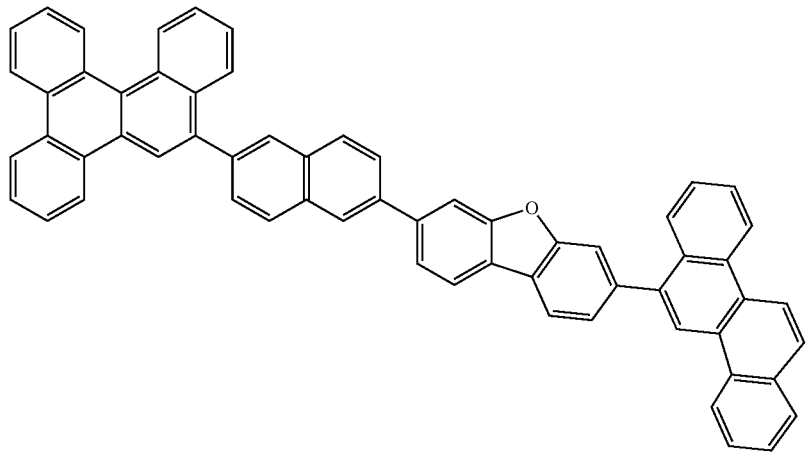
3-59
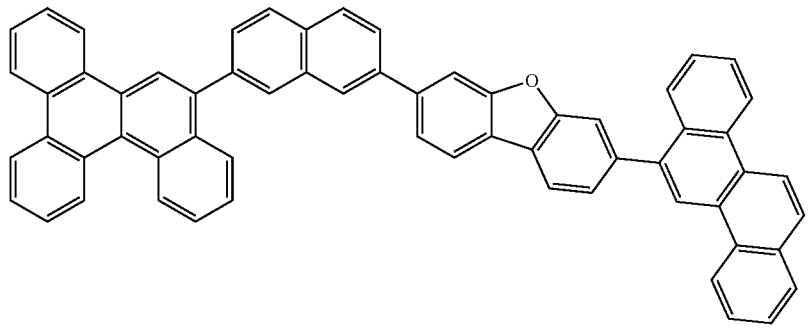
3-60
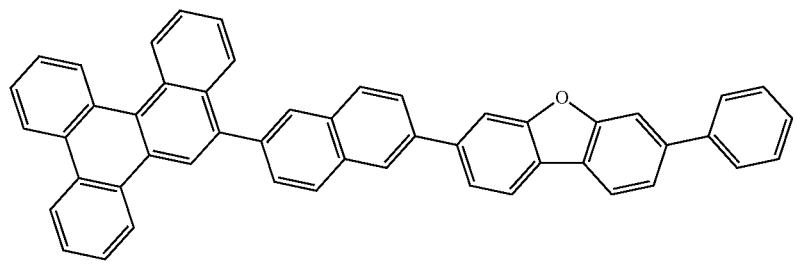
3-61

-continued
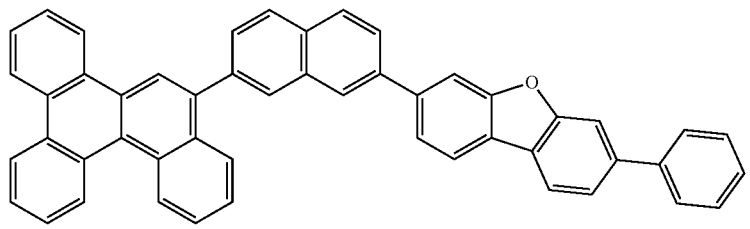
3-62
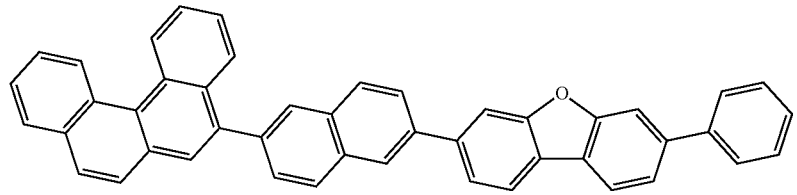
3-63
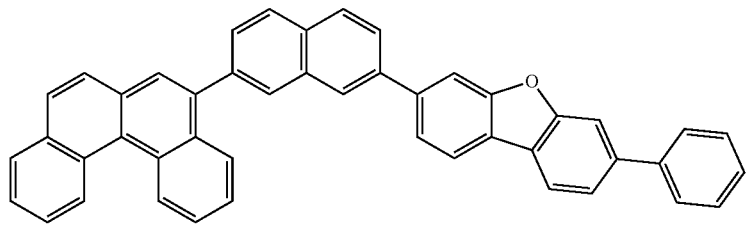
3-64
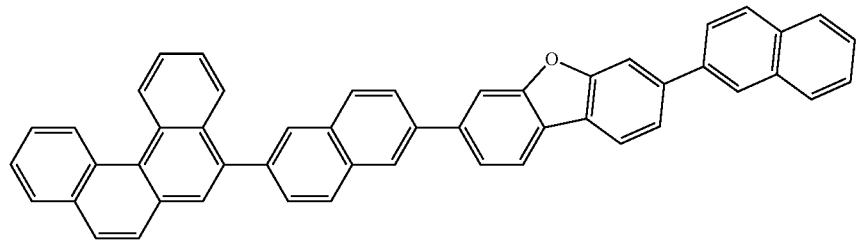
3-65
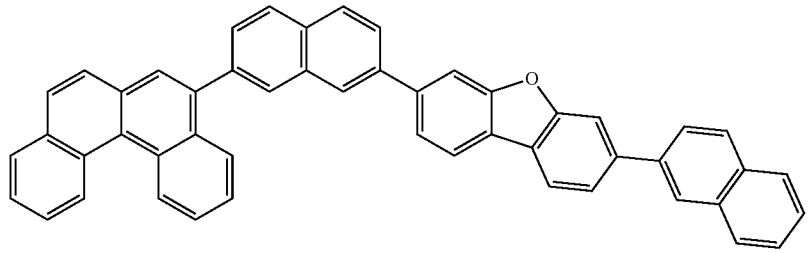
3-66
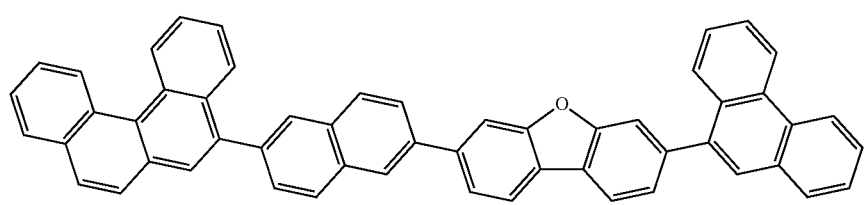
3-67
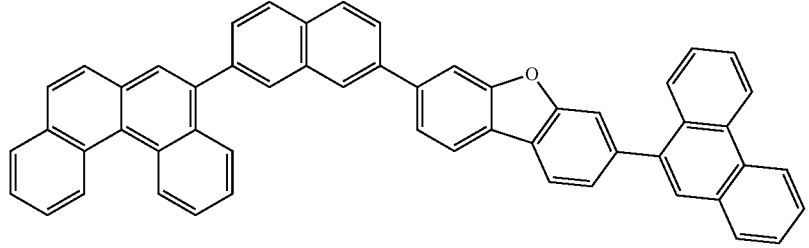
3-68

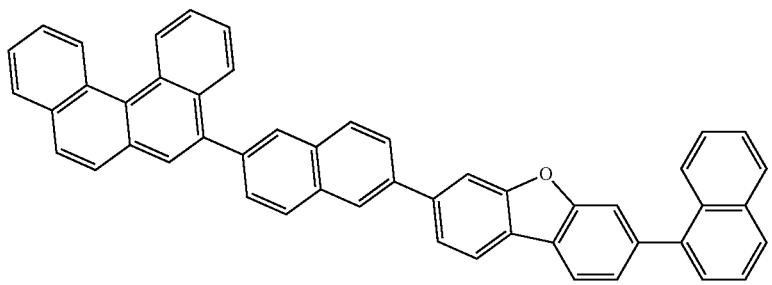
3-69
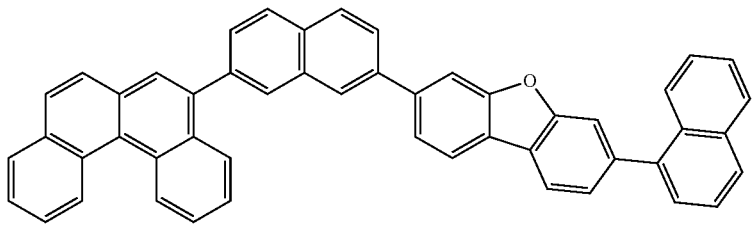
3-70
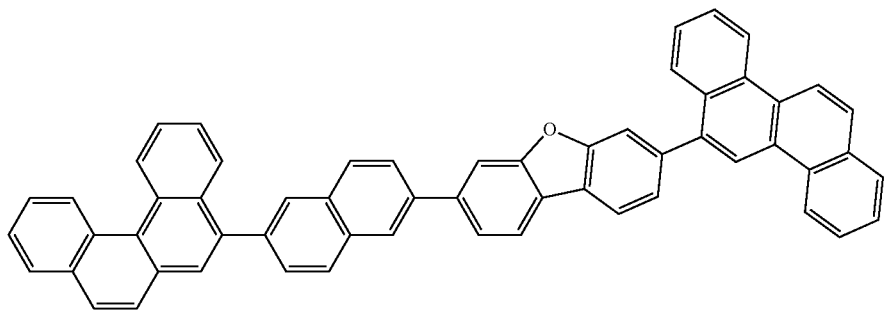
3-71
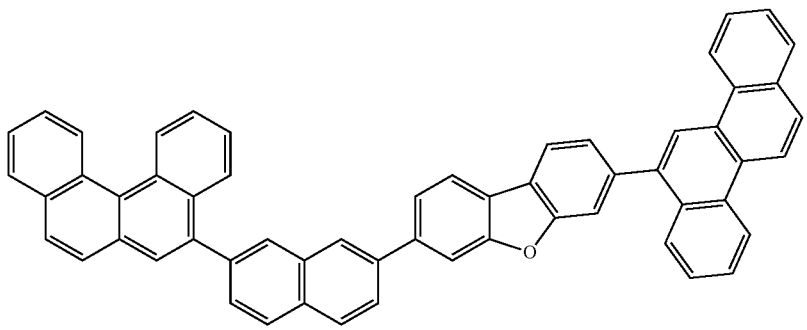
3-72
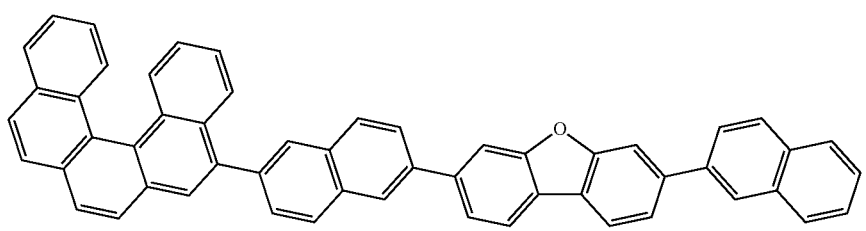
3-73

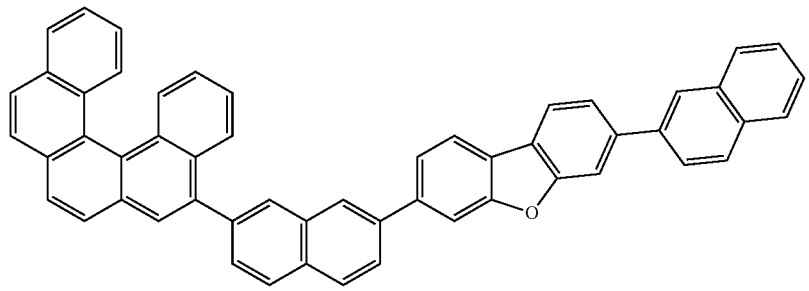
3-74
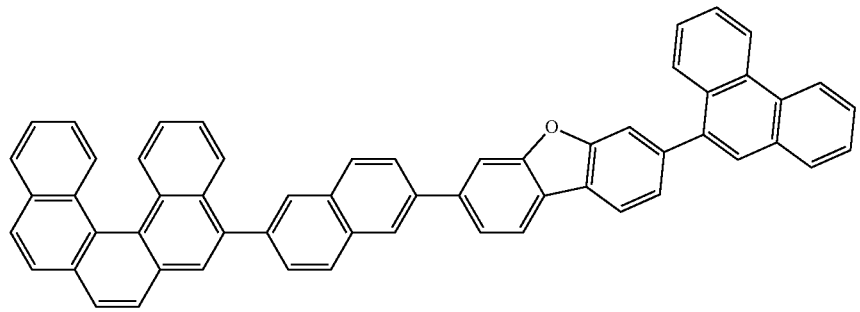
3-75
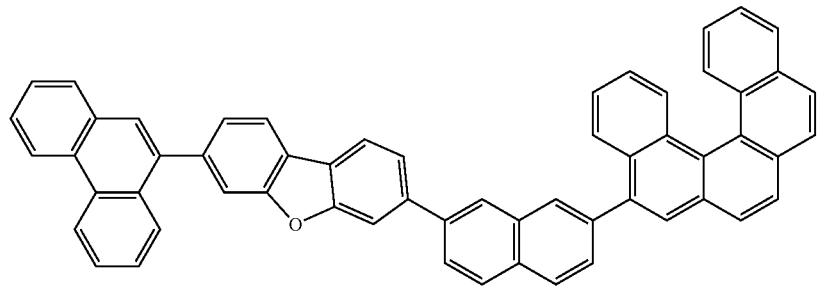
3-76
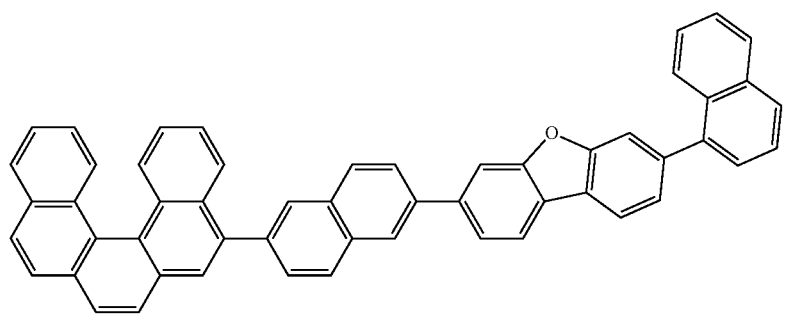
3-77
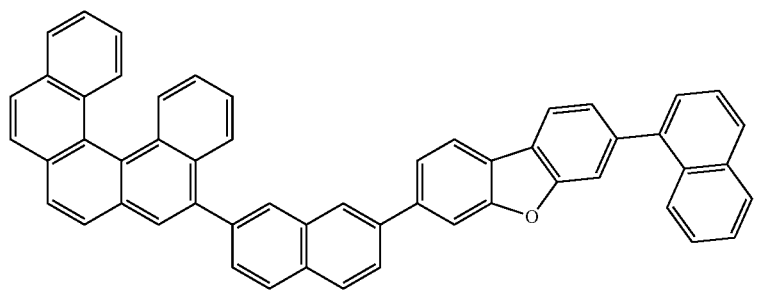
3-78

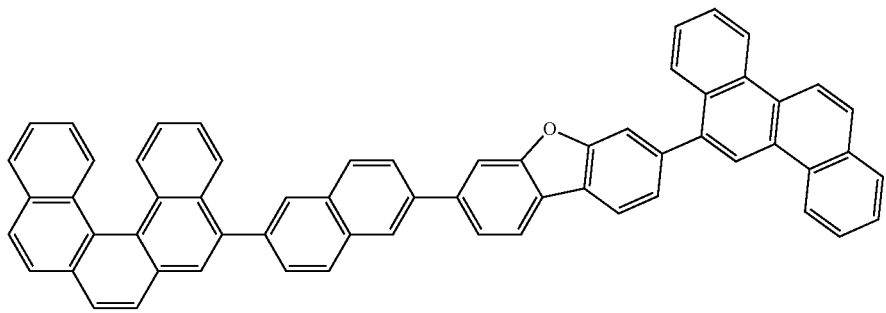

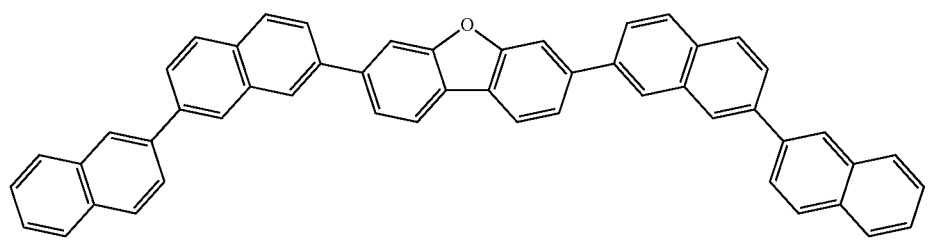
3-84
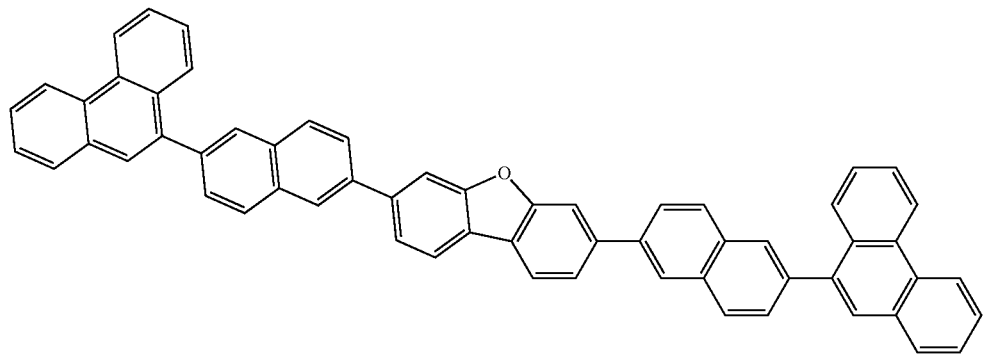
3-85
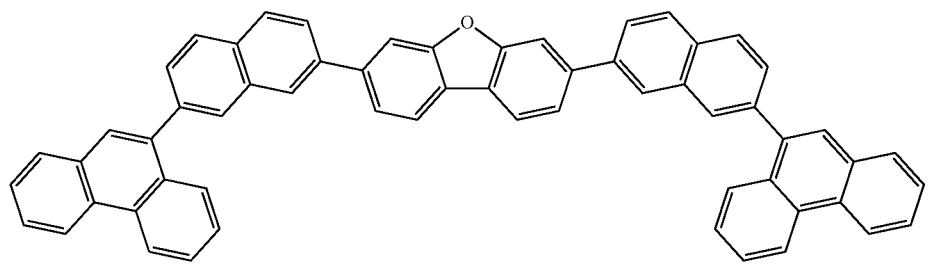
3-86
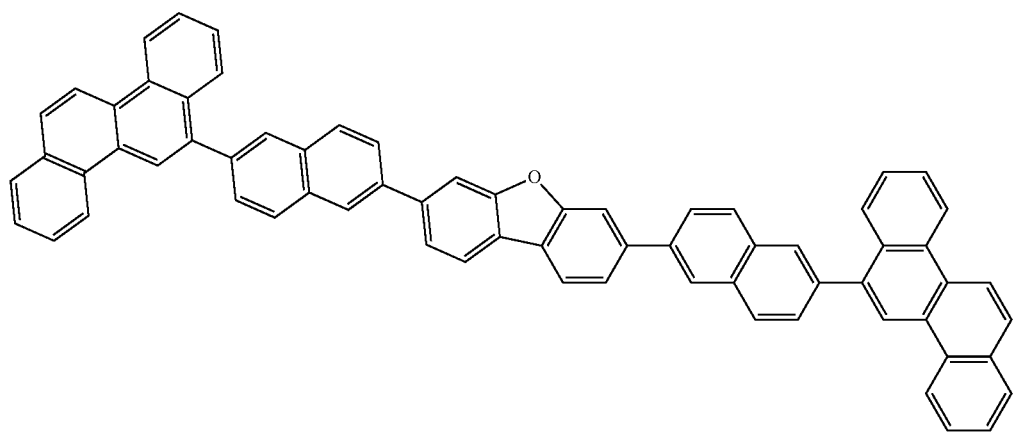
3-87
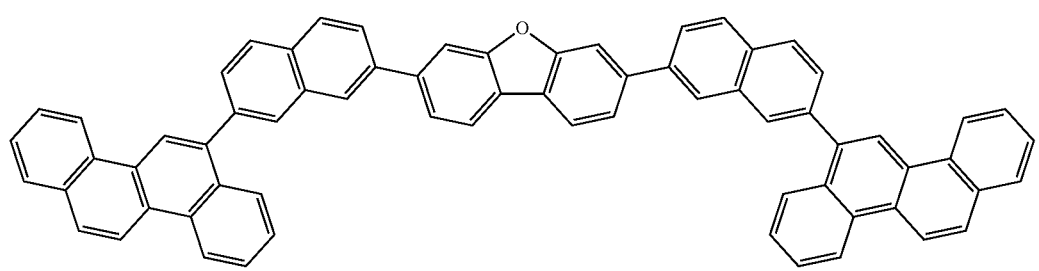
3-88

3-89
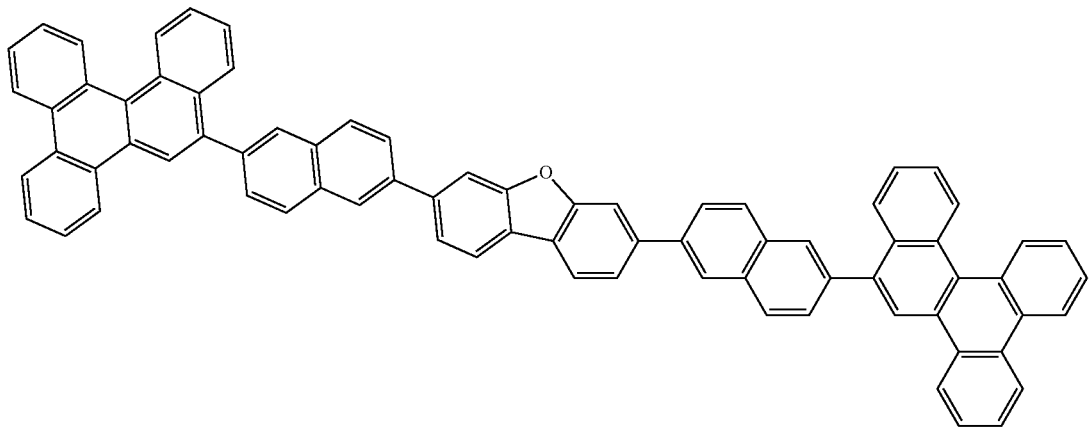
3-90
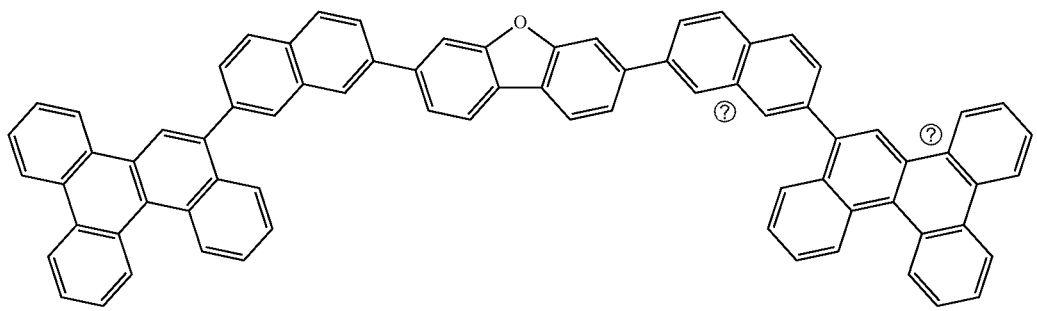
3-91
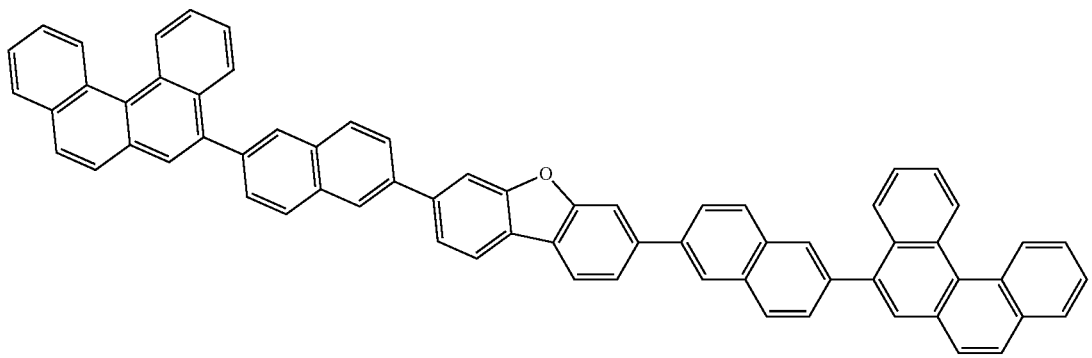
3-92
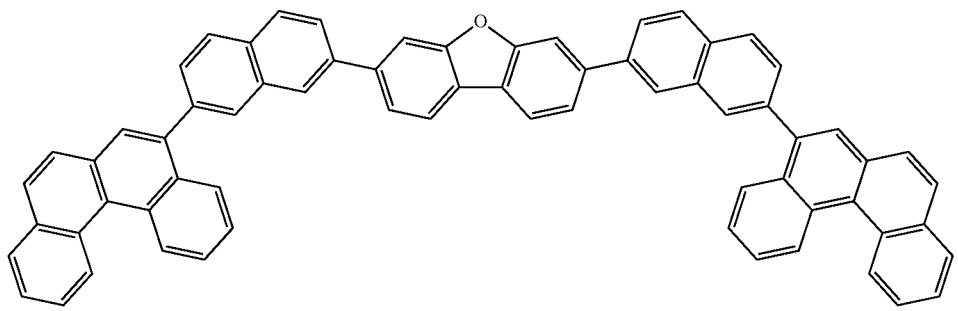

-continued
3-93
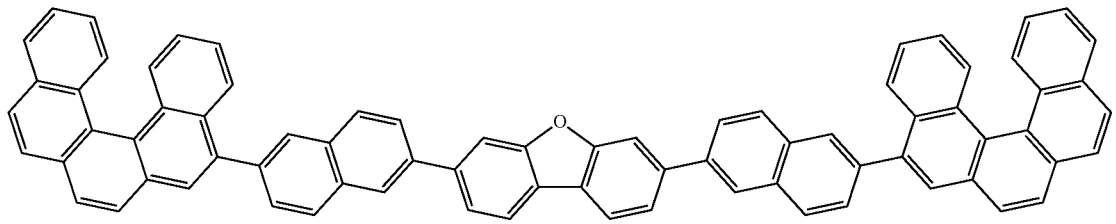
3-94
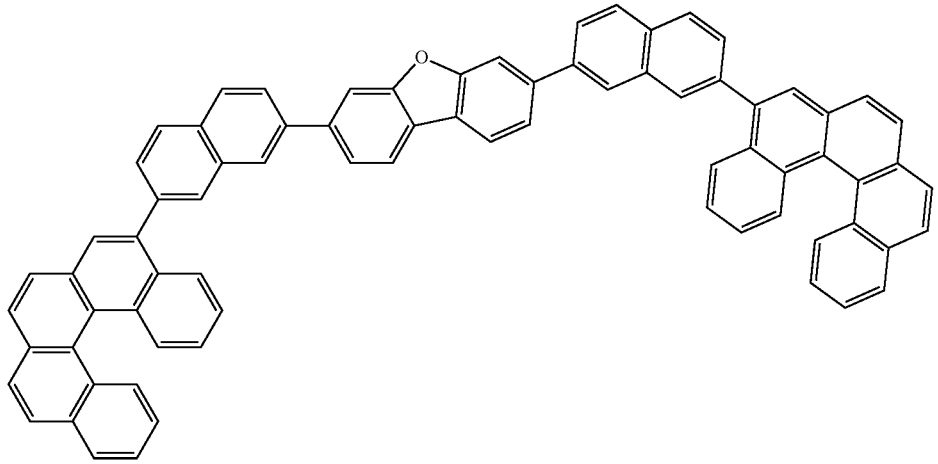
3-95
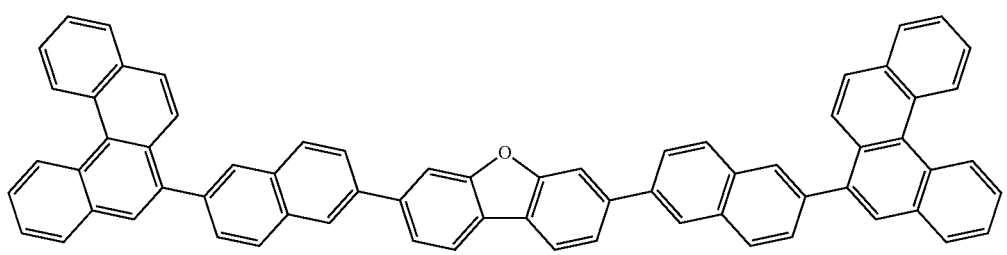
3-96
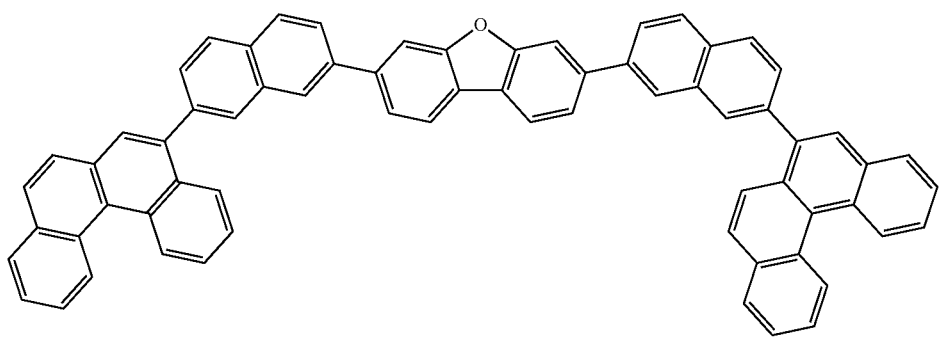
3-97 3-98
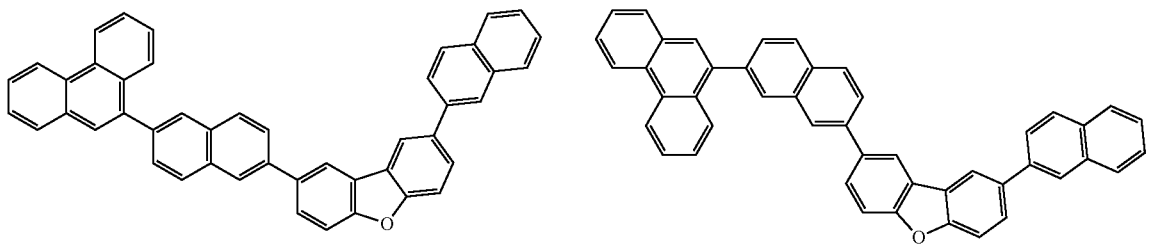

-continued
3-99
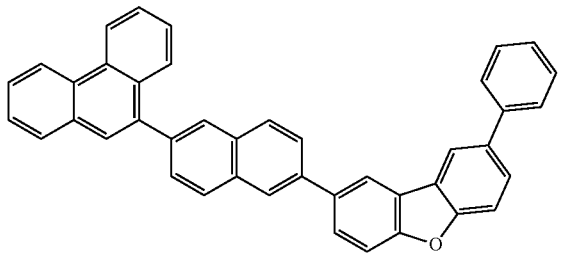
3-100
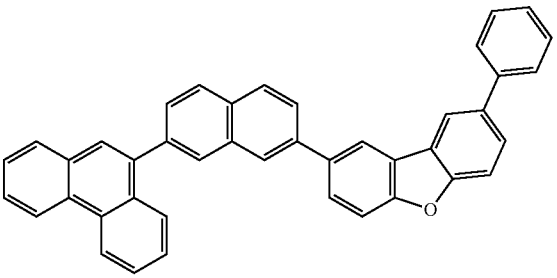
3-101
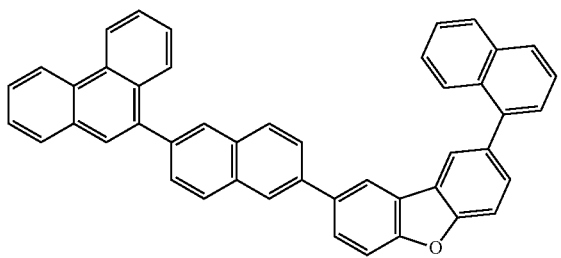
3-102
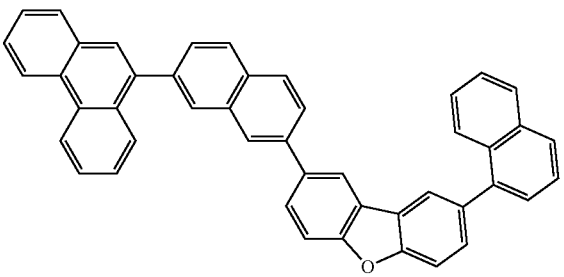
3-103
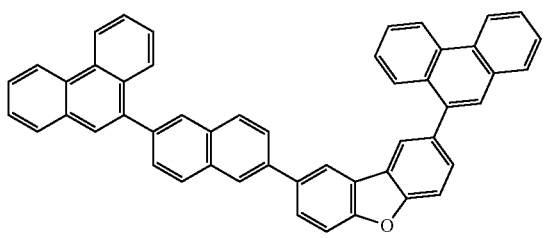
3-104
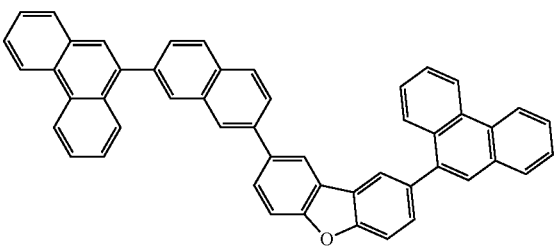
3-109
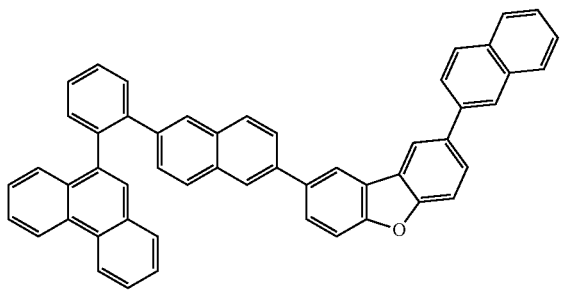
3-110
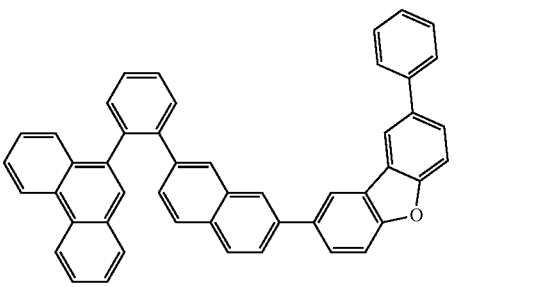
3-111
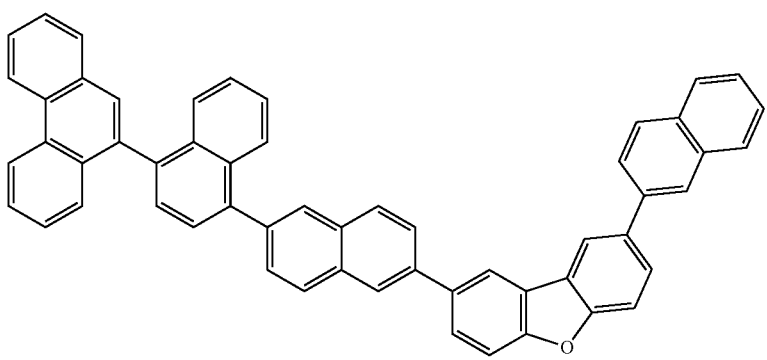

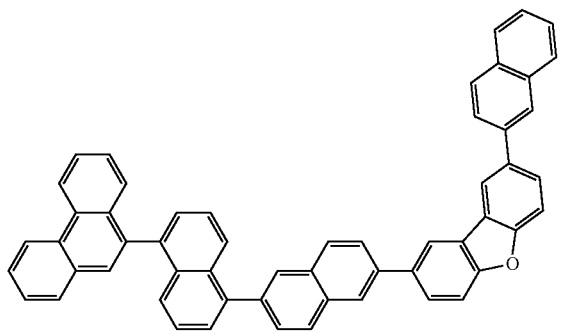

-continued
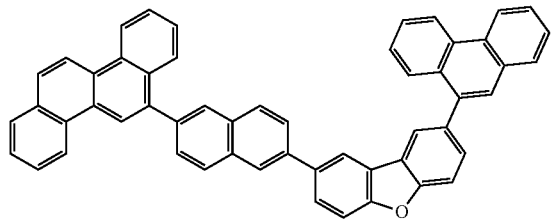

-continued
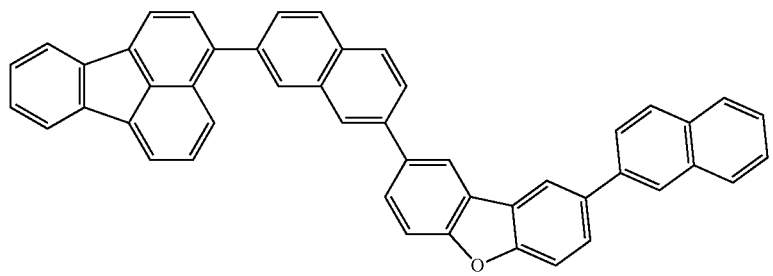
3-130
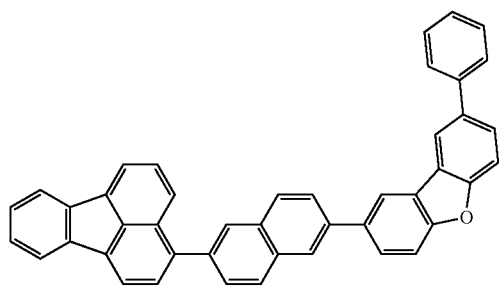
3-131
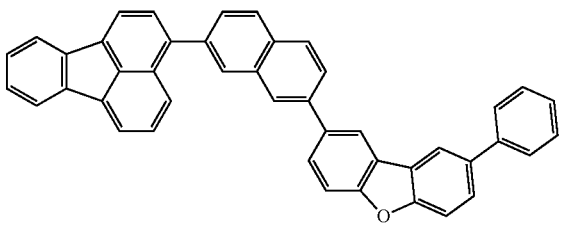
3-132
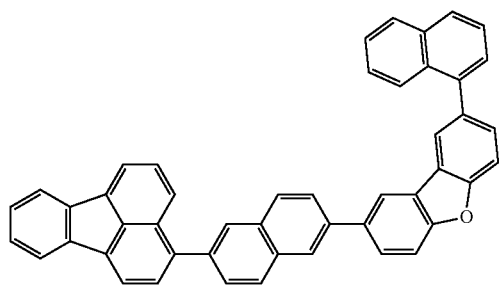
3-133
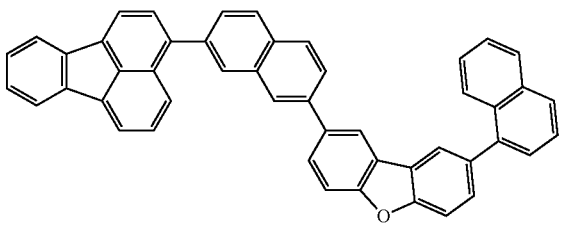
3-134
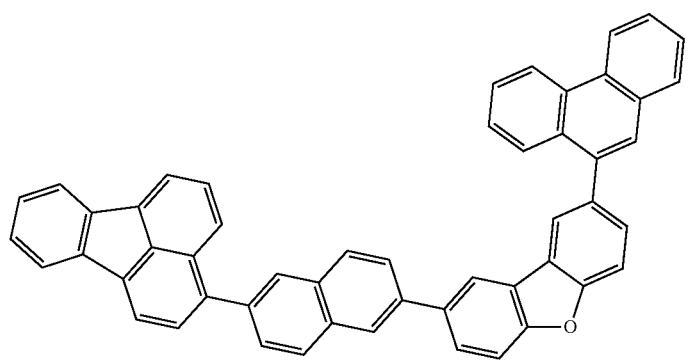
3-135
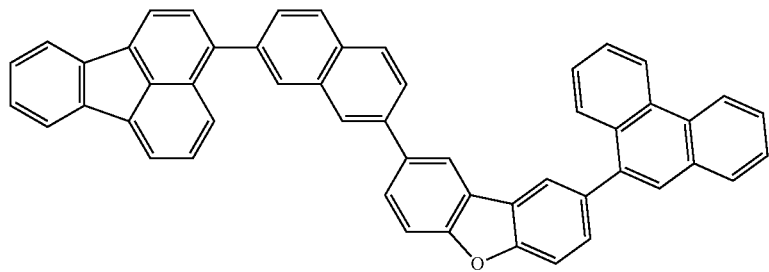
3-136

-continued
3-137
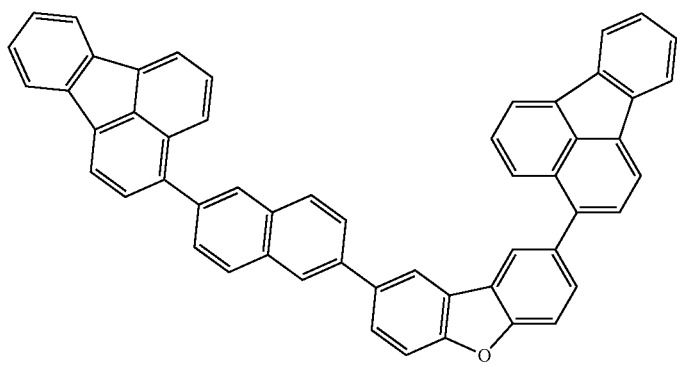
3-138
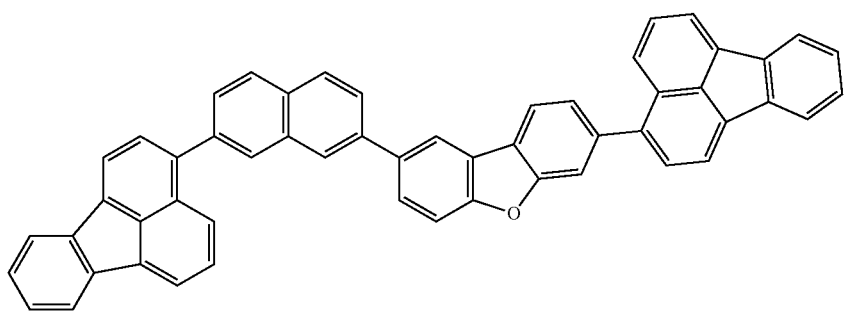
3-139     3-140
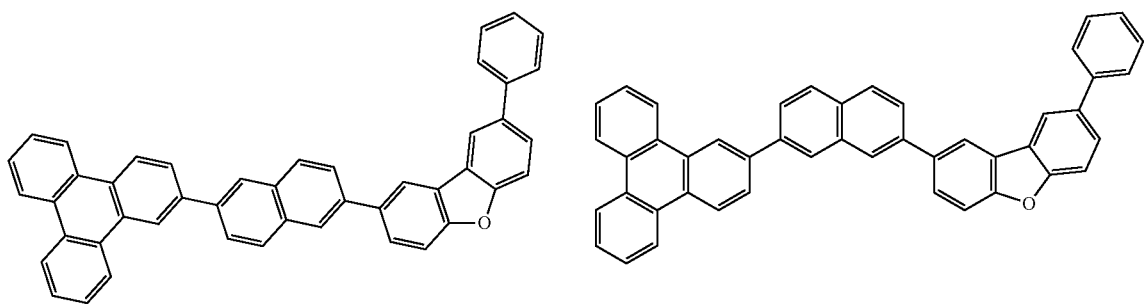
3-145
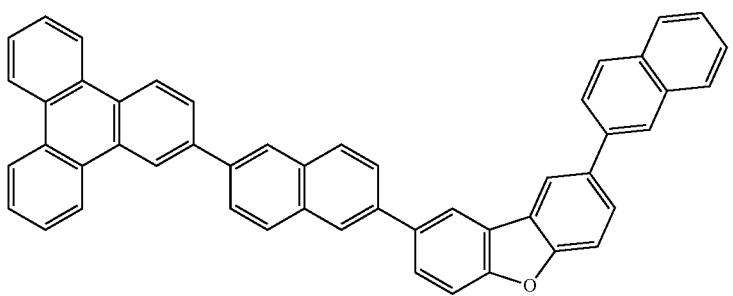

3-146
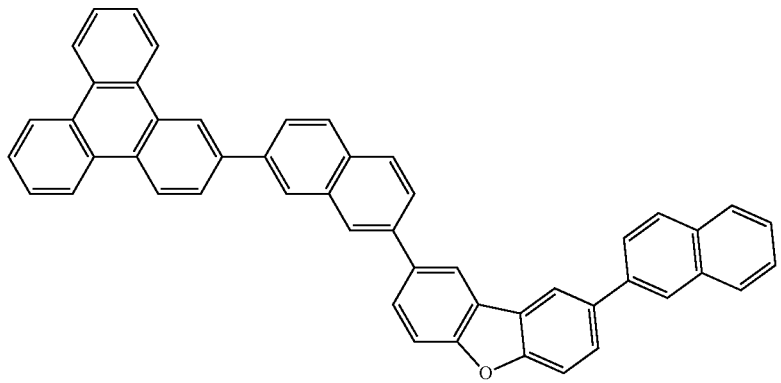
3-147
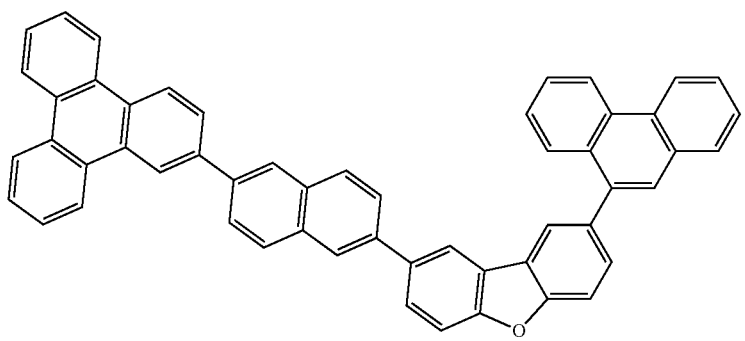
3-148
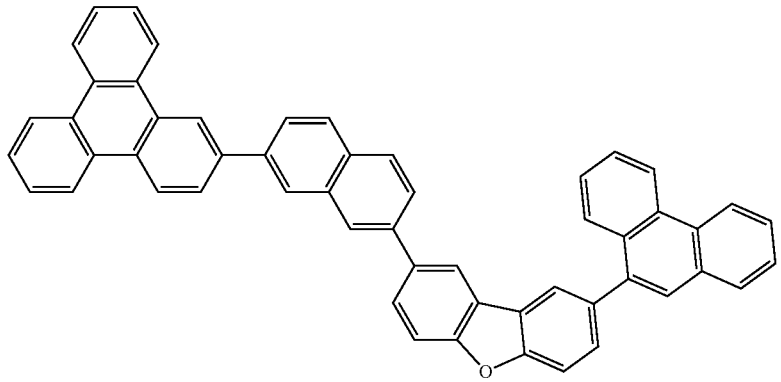
3-149 3-150
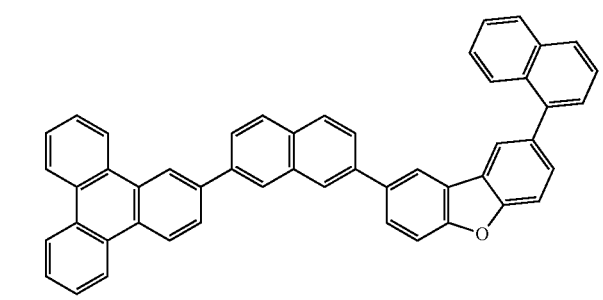

-continued
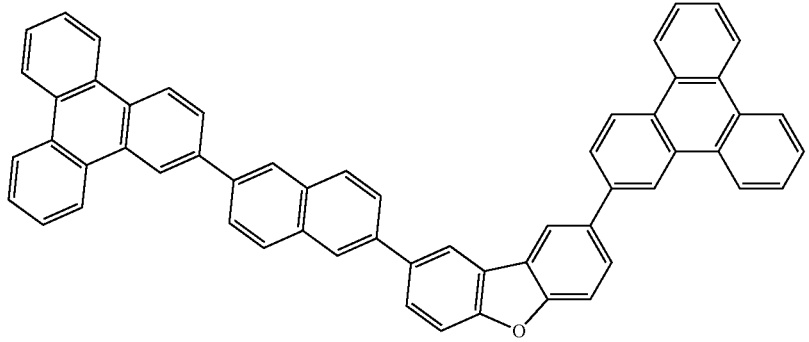
3-151
3-152
3-153
3-154

-continued
3-155
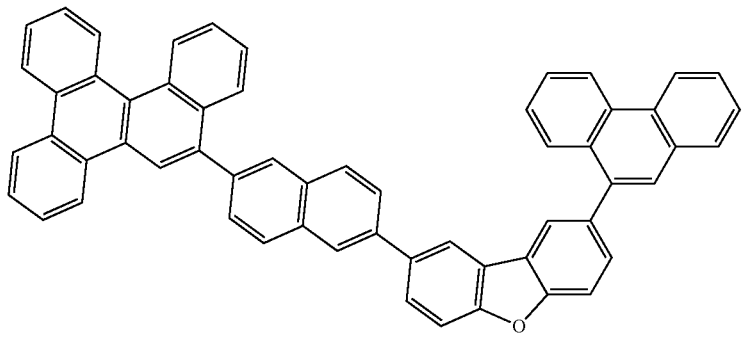
3-156
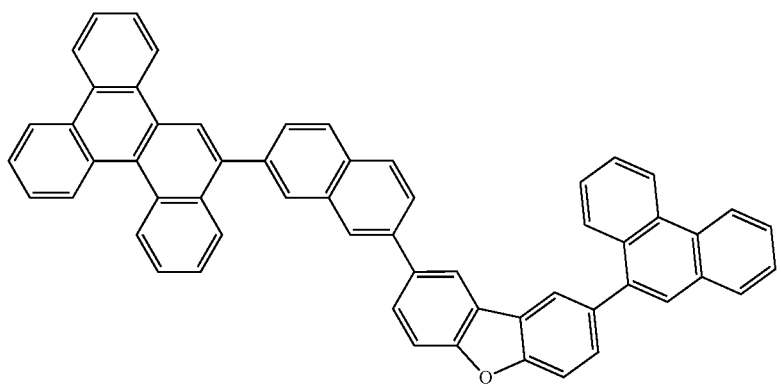
3-157 3-158
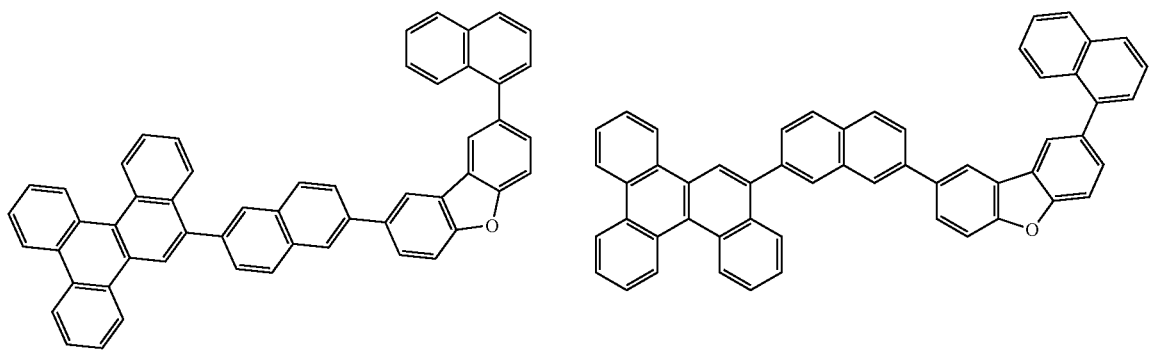
3-159
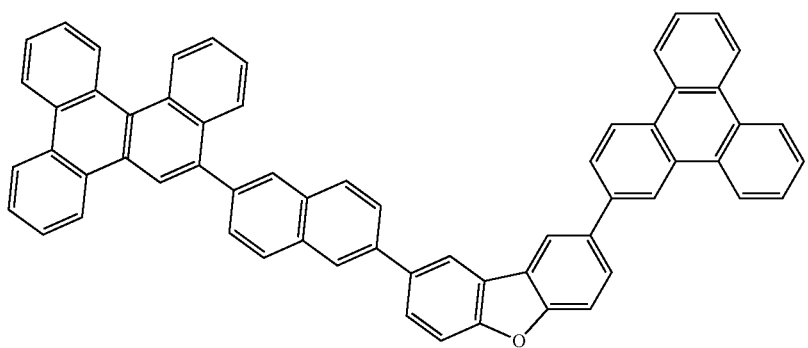

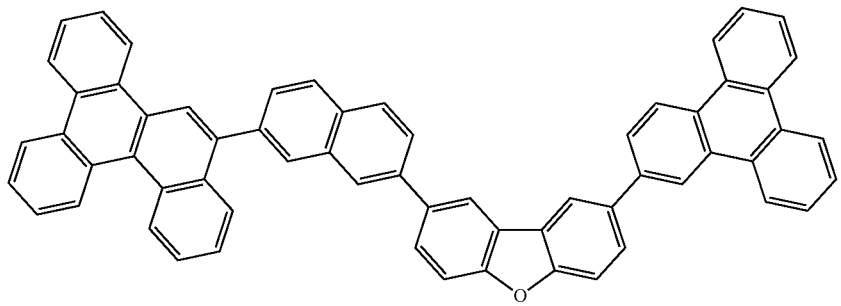

-continued
3-167
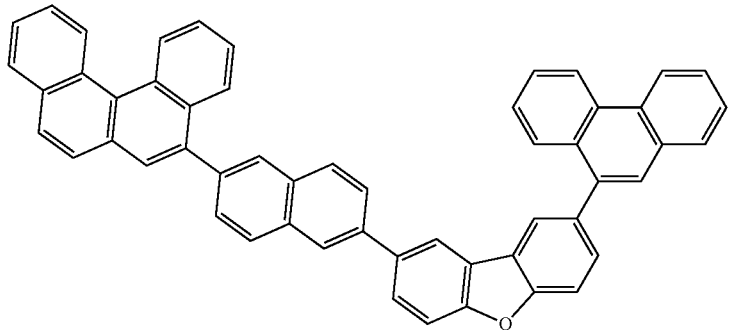
3-168
3-169 3-170
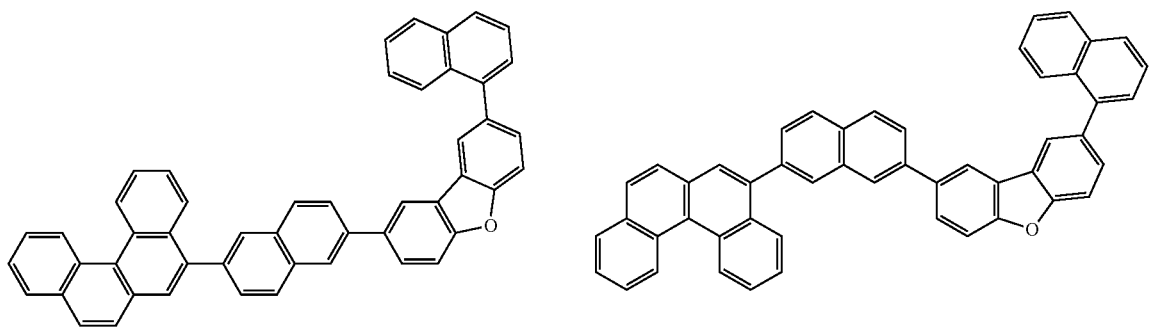
3-171
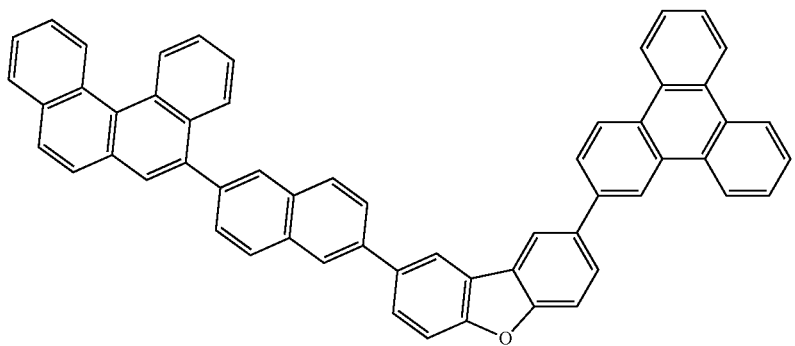

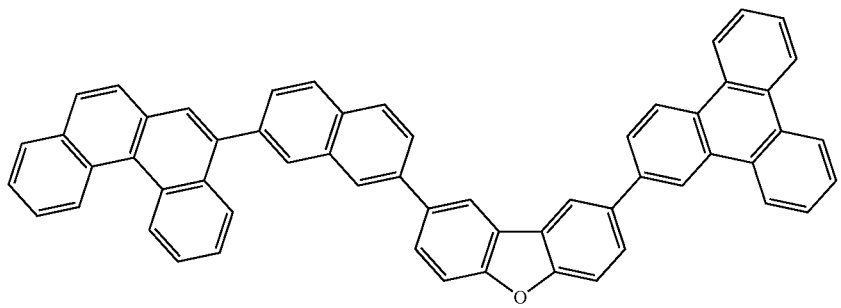
3-172
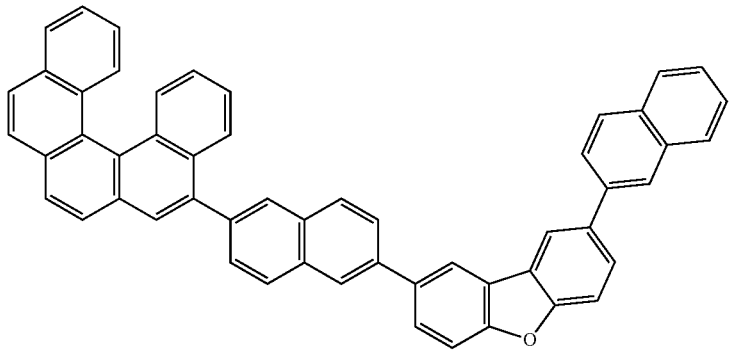
3-173
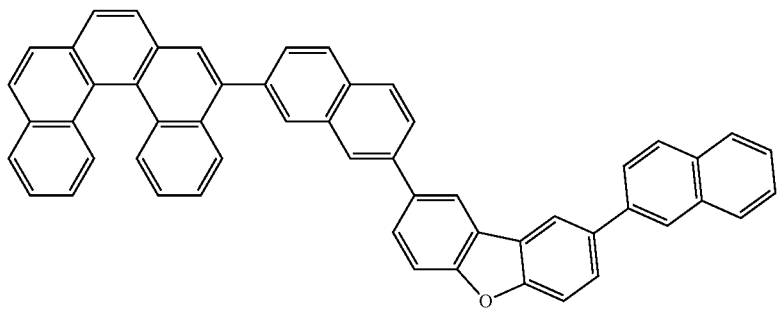
3-174
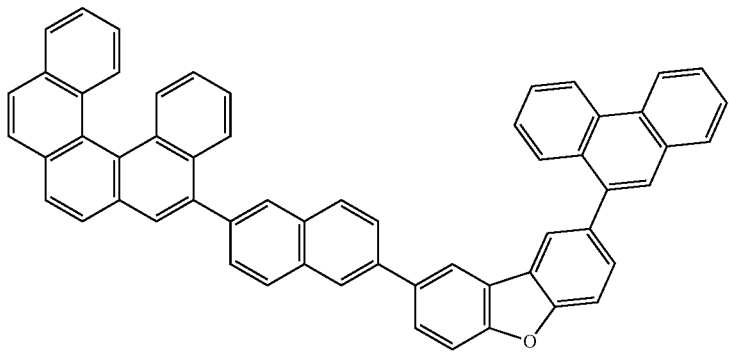
3-175
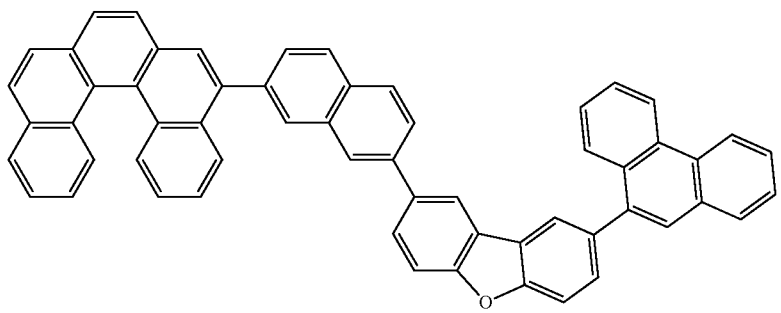
3-176

-continued
3-177
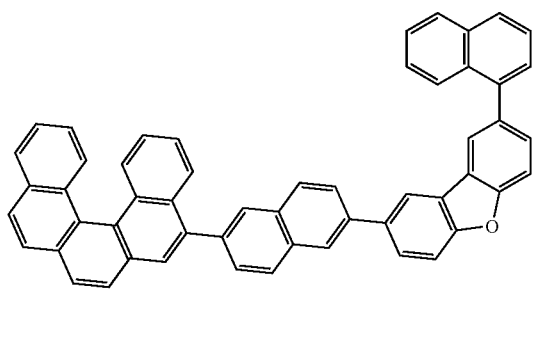
3-178
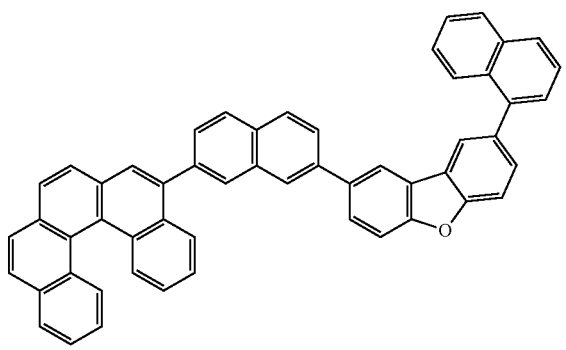
3-179
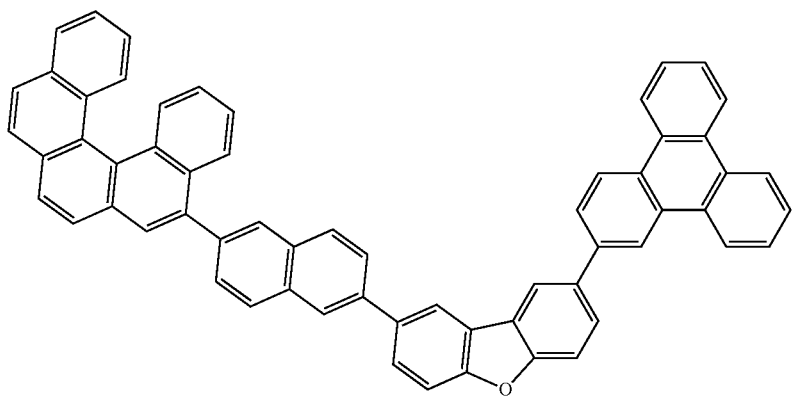
3-180
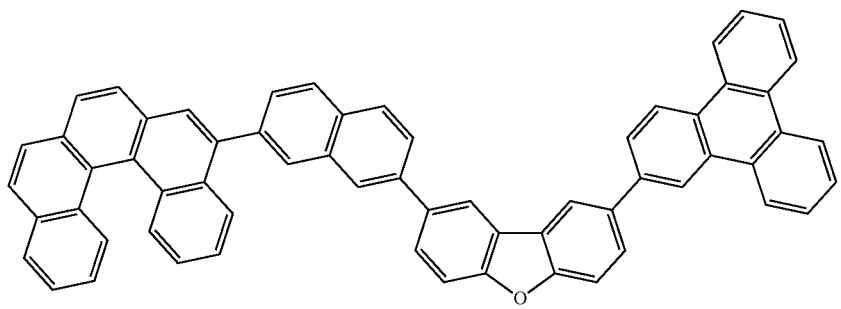
3-181
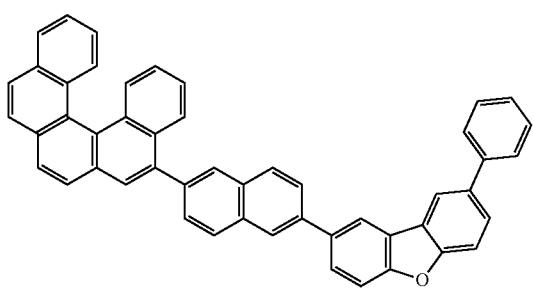
3-182
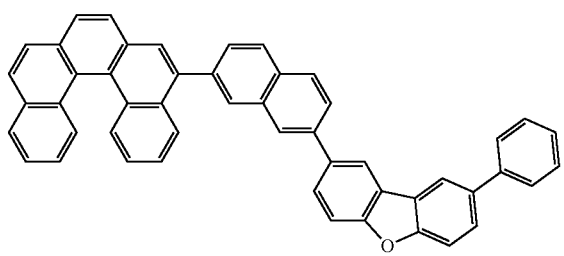

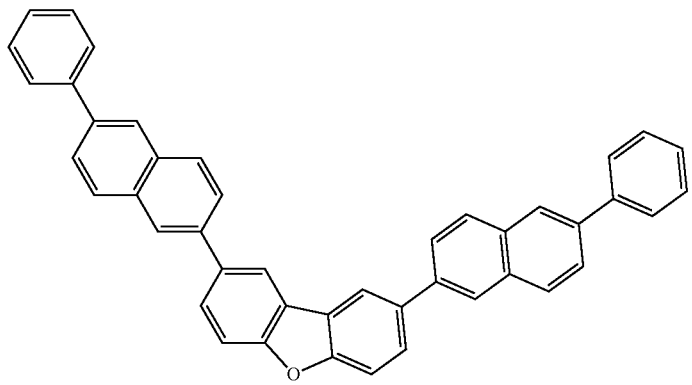
3-183
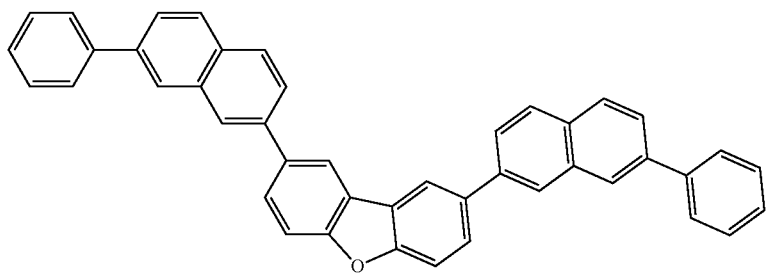
3-184
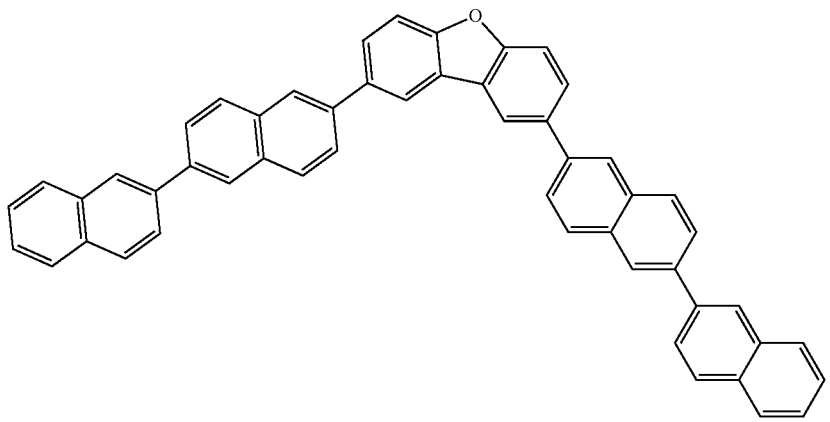
3-185
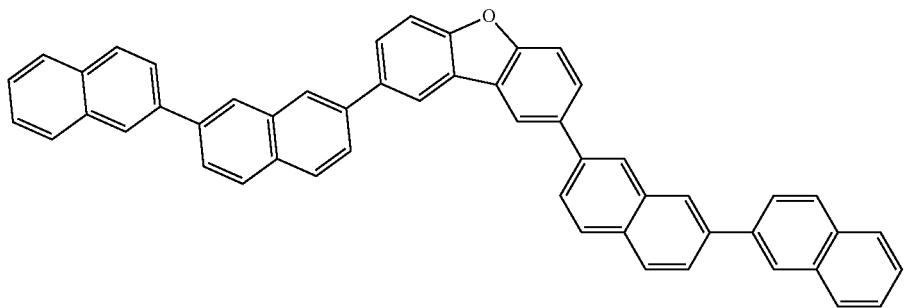
3-186

3-187
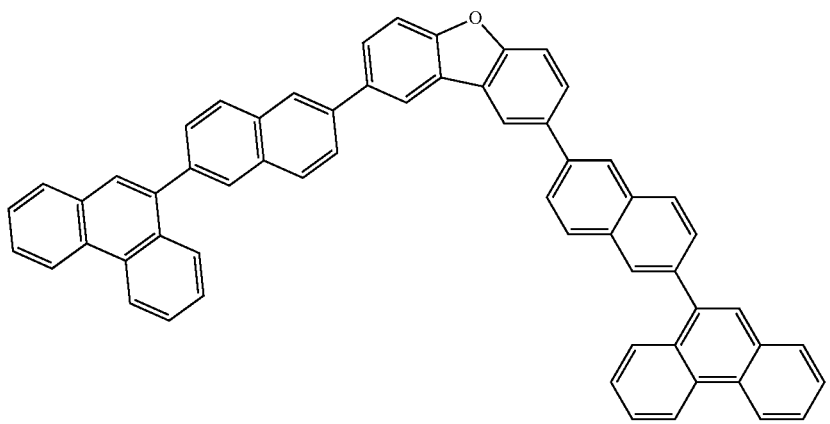
3-188
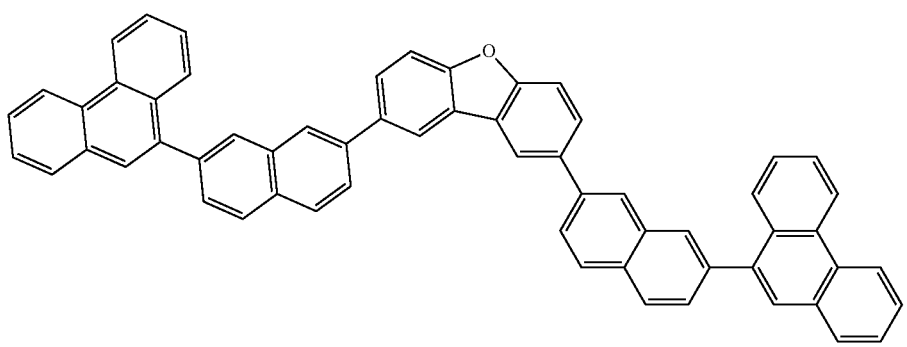
3-189
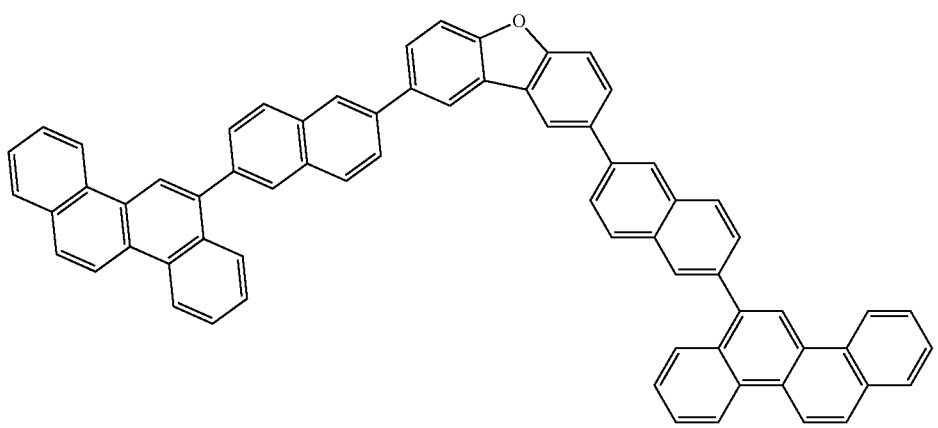
3-190
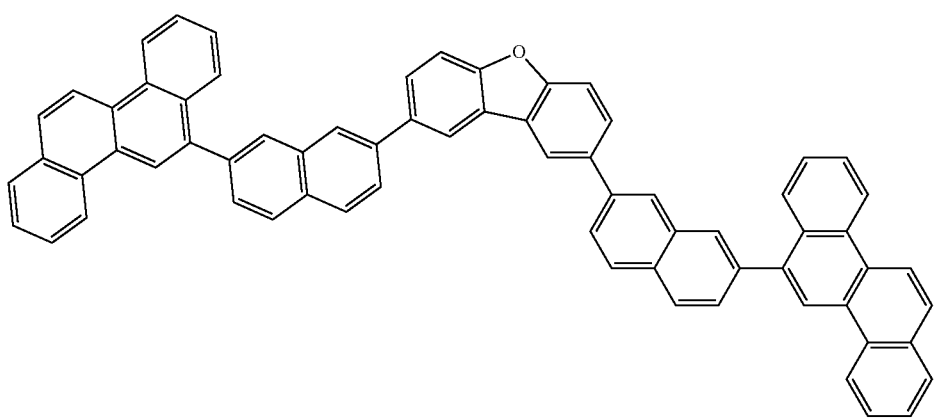

3-191
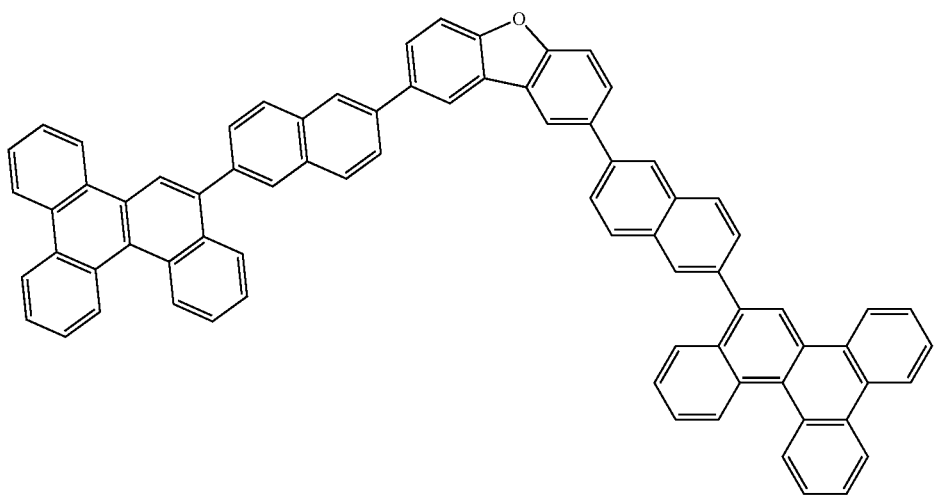
3-192
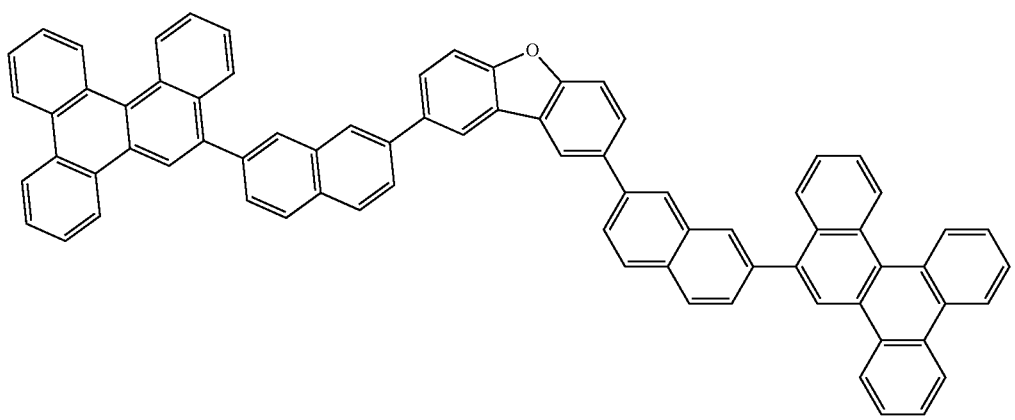
3-193
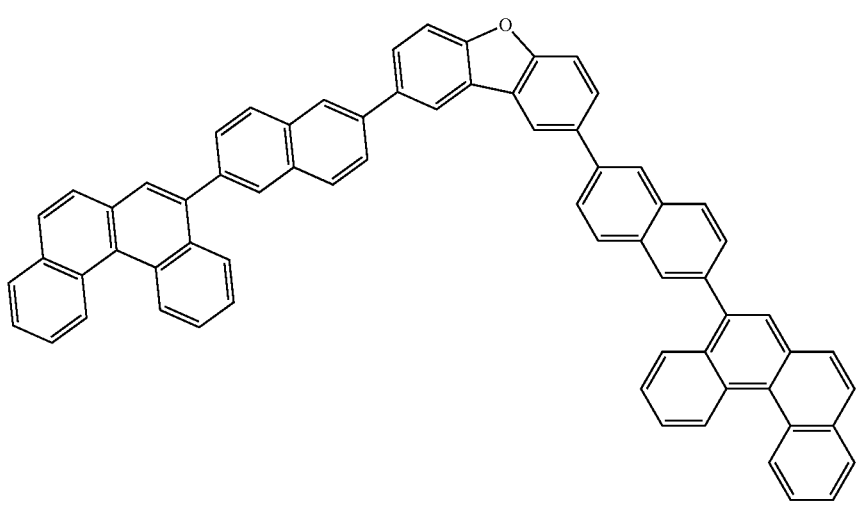

3-194
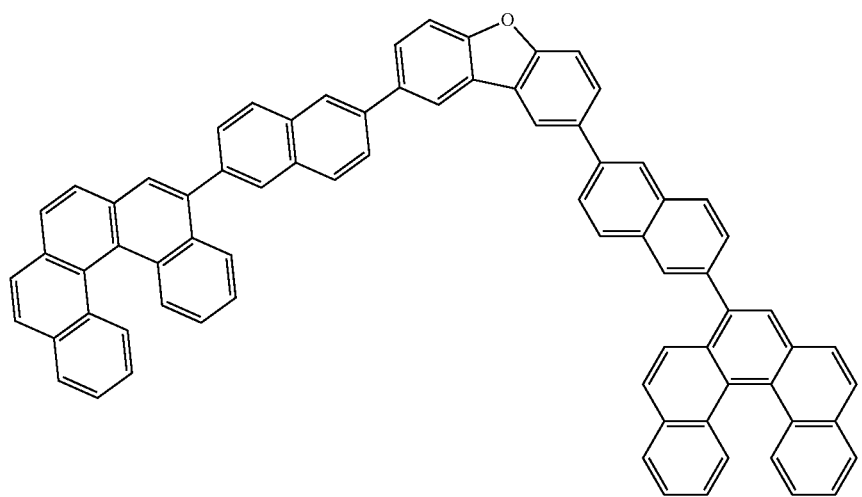
3-195
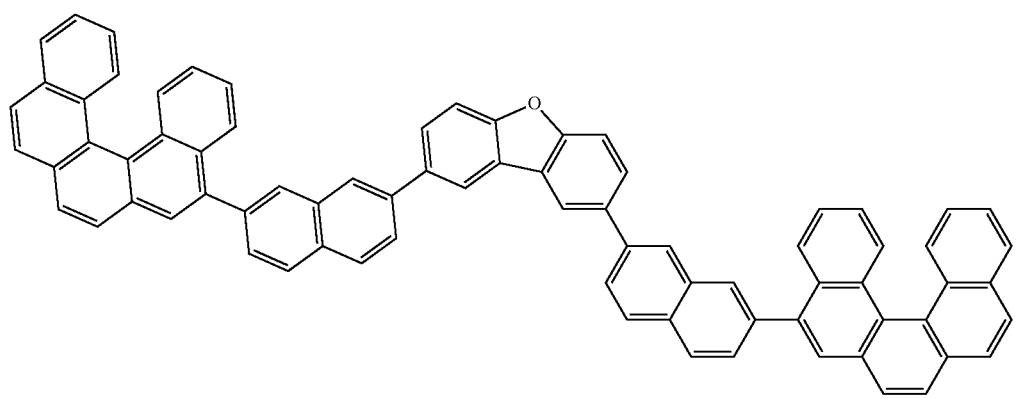
3-196

3-197
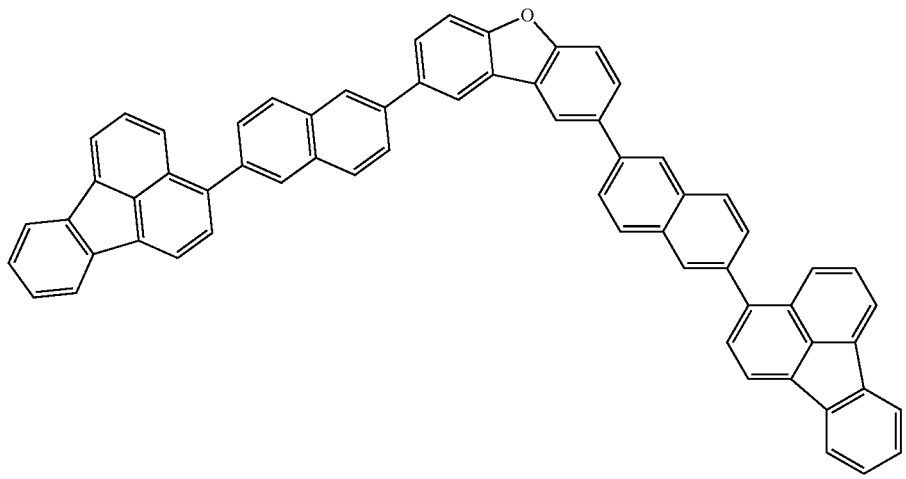
3-198
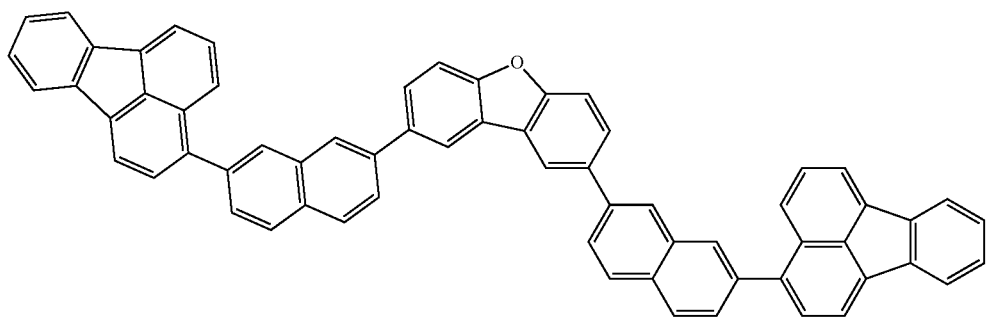
3-199
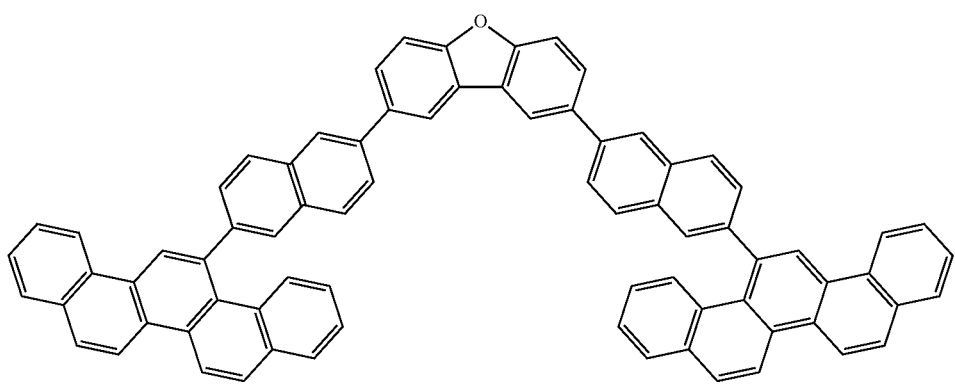
3-200
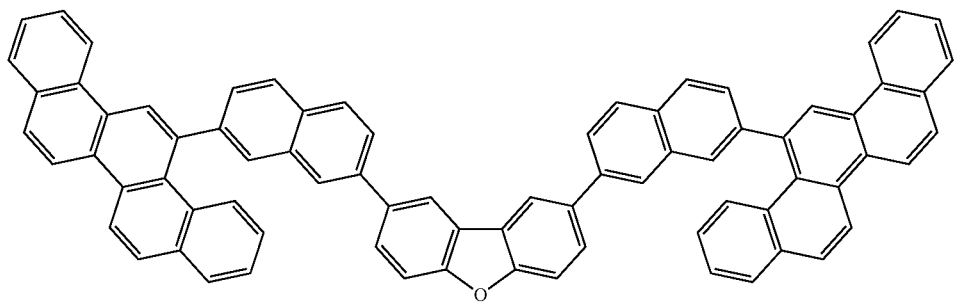

Examples of the material for organic electroluminescence device represented by formulae (B-1) to (B-4) are shown below.
2-46
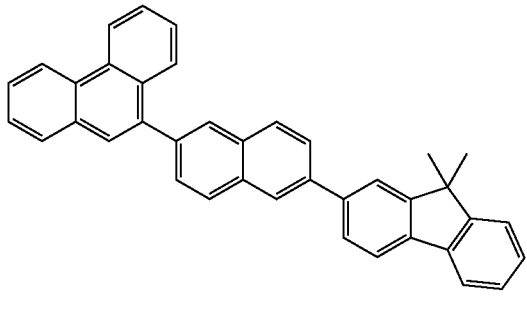
2-47
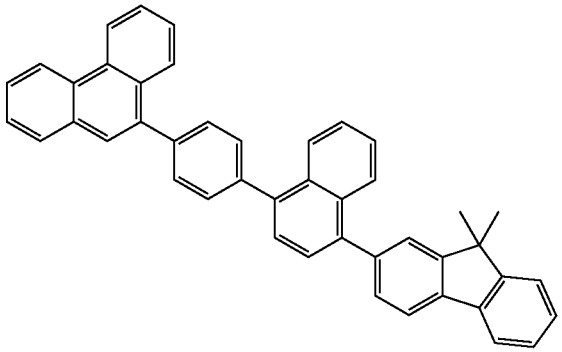
2-48
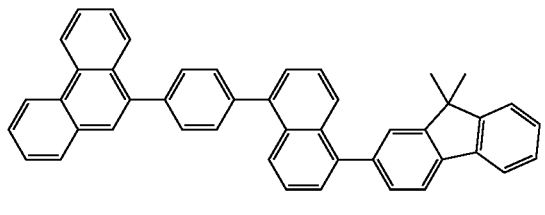
2-49
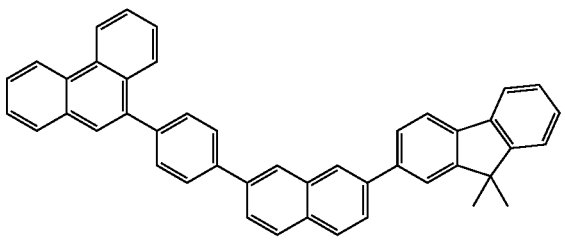
2-50
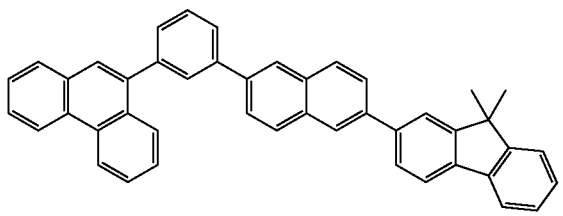
2-51
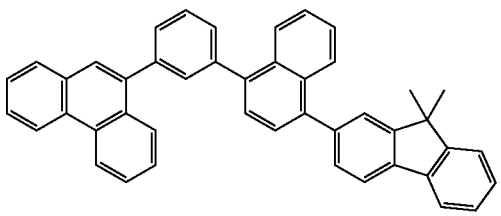
2-52
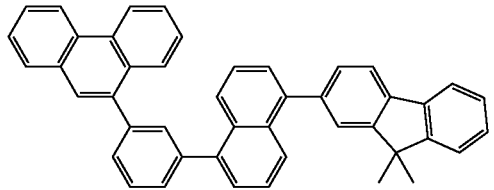
2-53
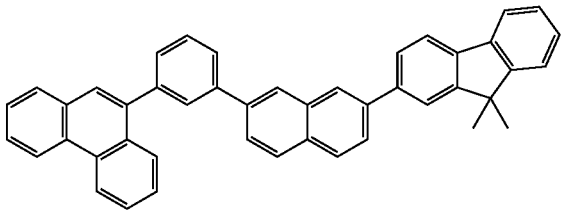
2-54
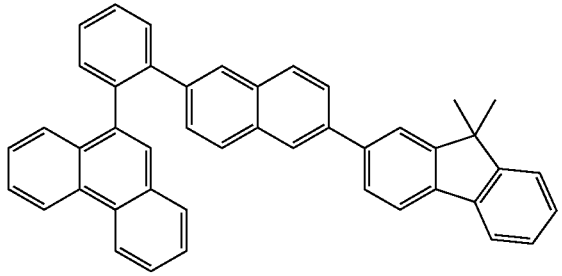
2-55
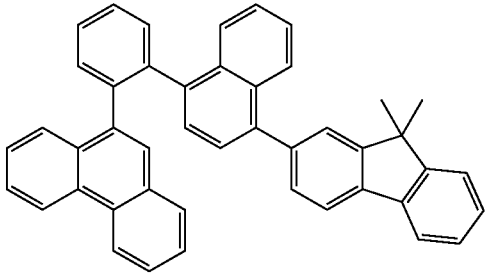

-continued
2-56
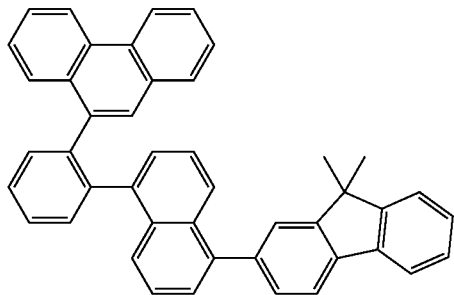
2-57
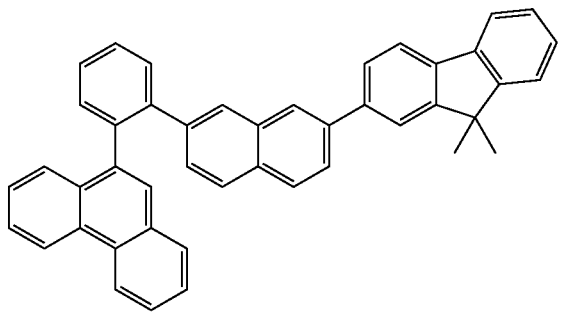
2-58
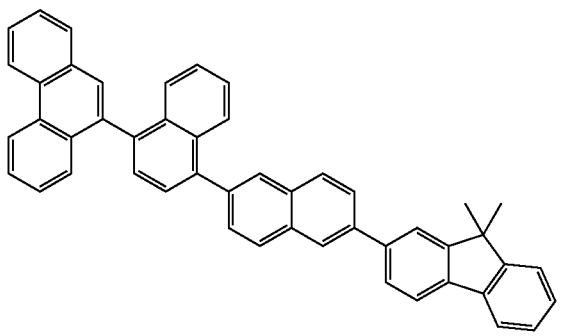
2-59
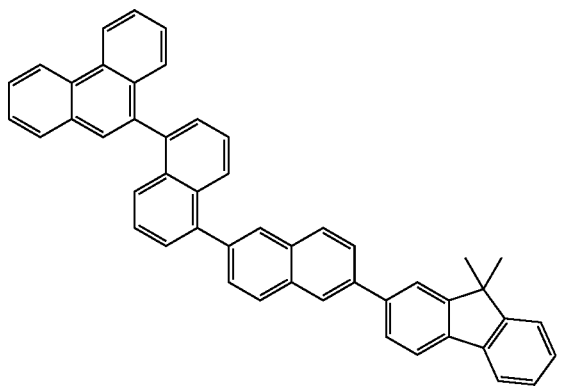
2-60
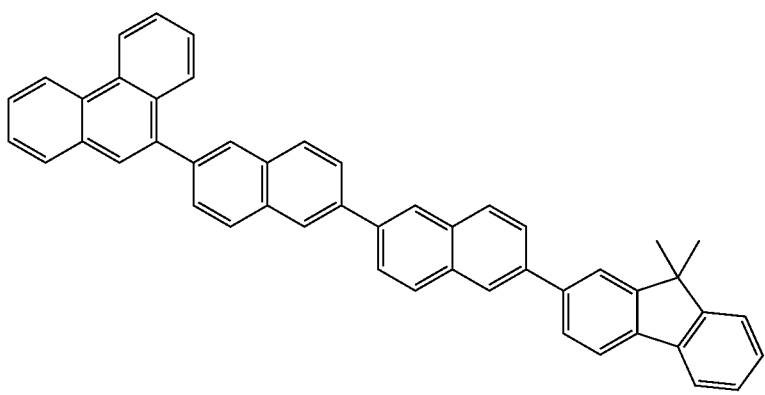
2-61
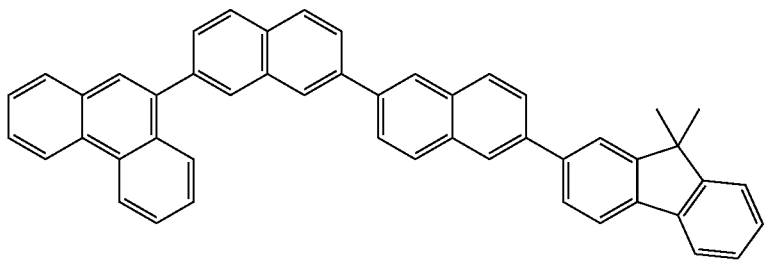

-continued
2-62
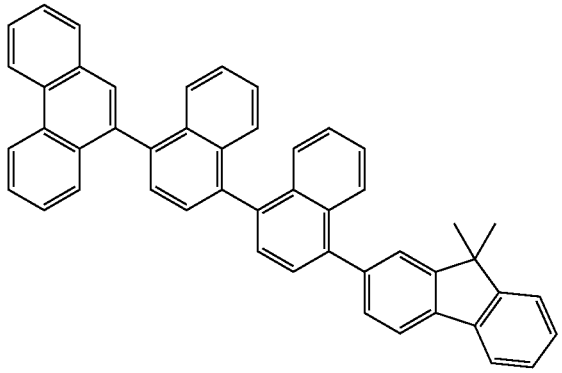
2-63
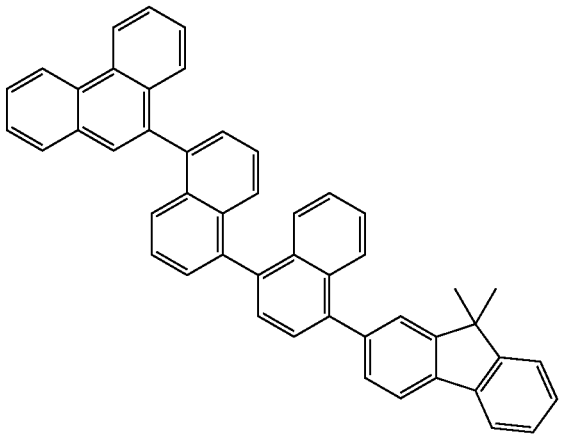
2-64
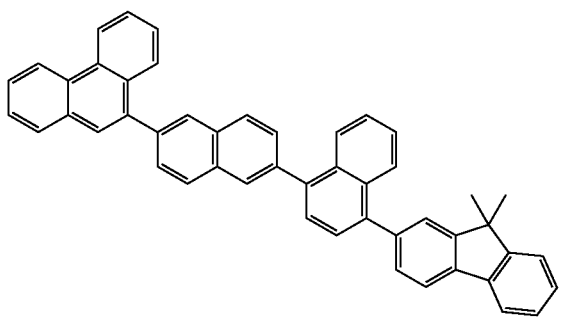
2-65
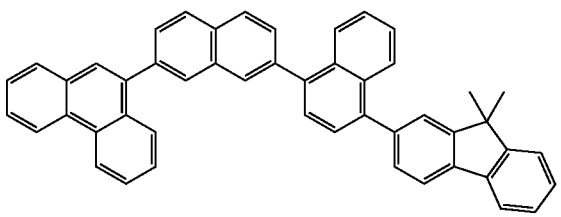
2-66
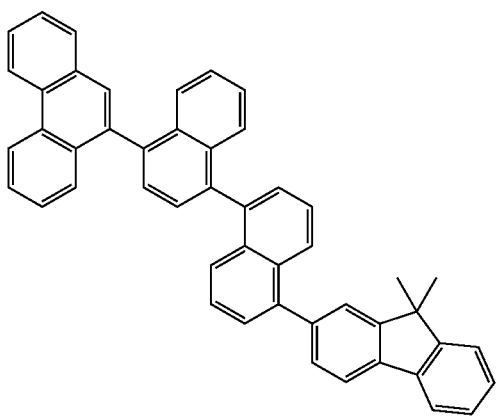
2-67
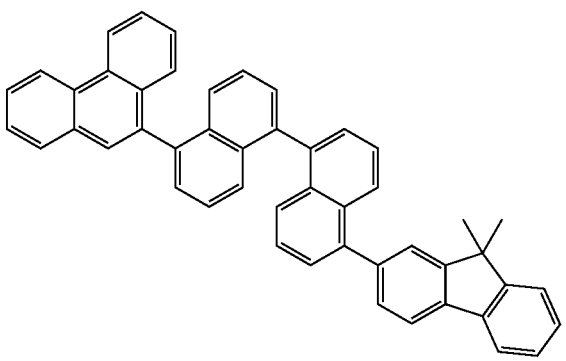
2-68
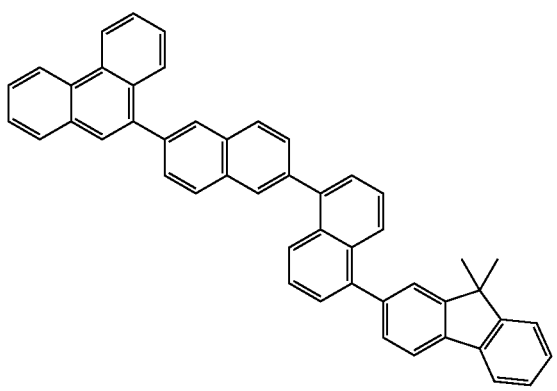
2-69

-continued
2-70
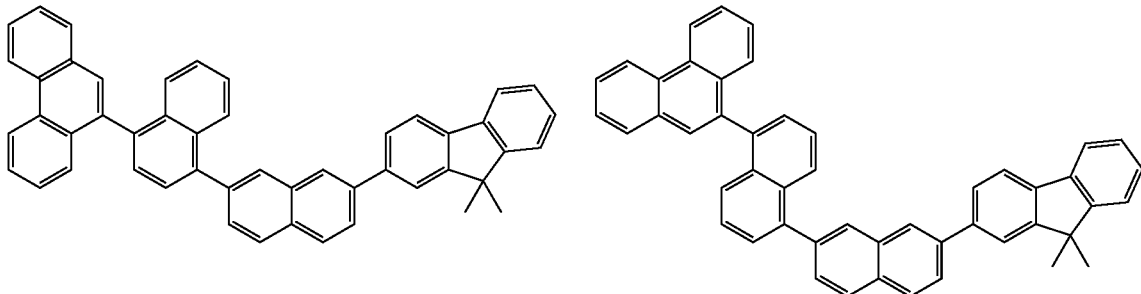
2-71
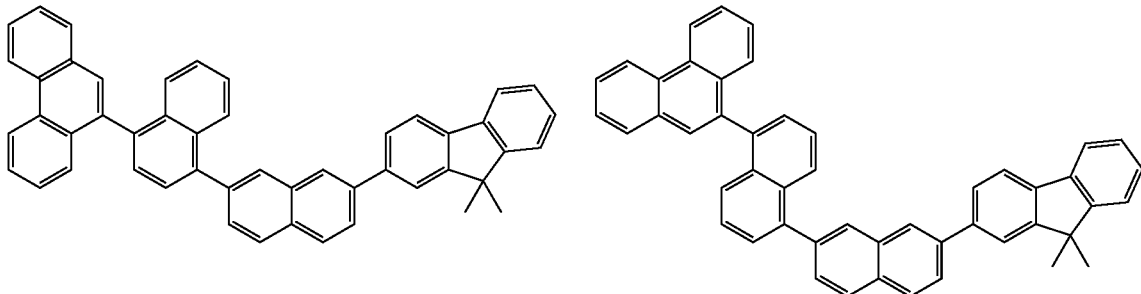
2-72
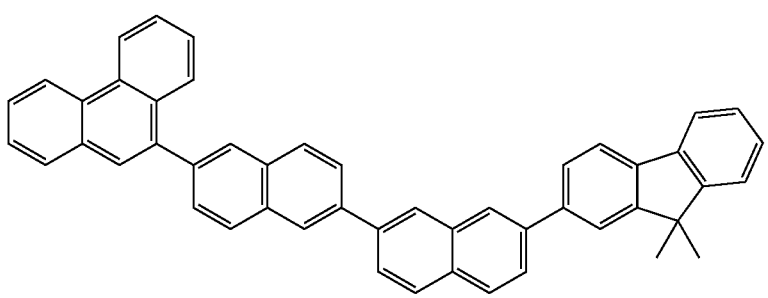
2-73
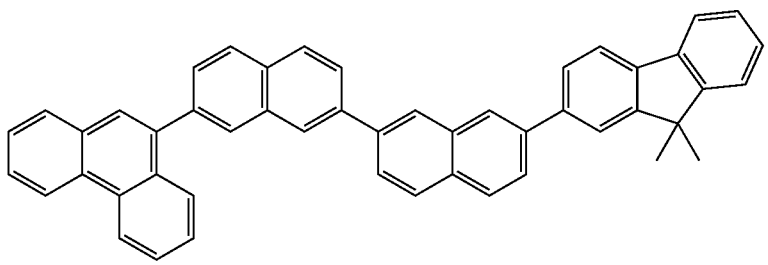
2-231
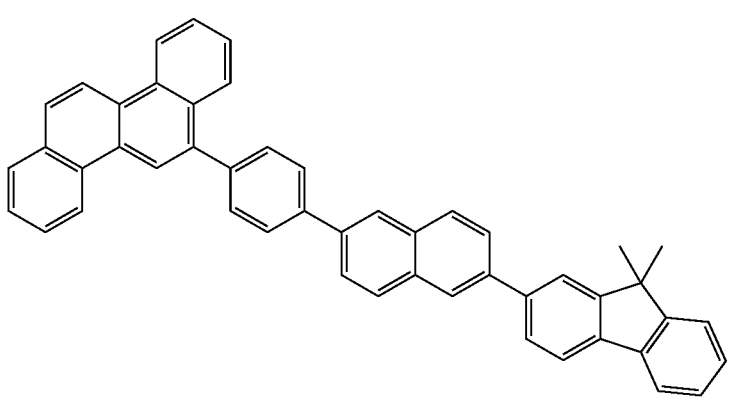

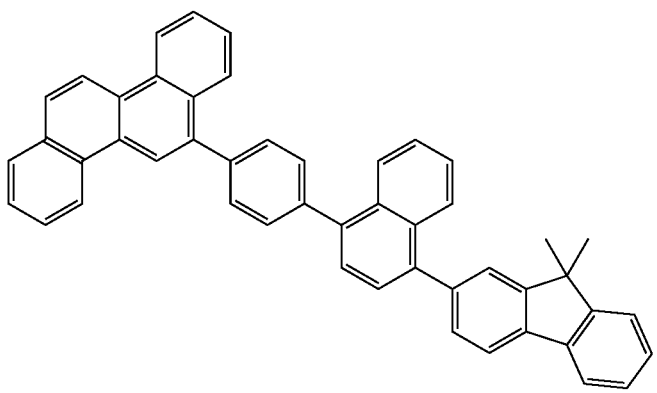
2-232
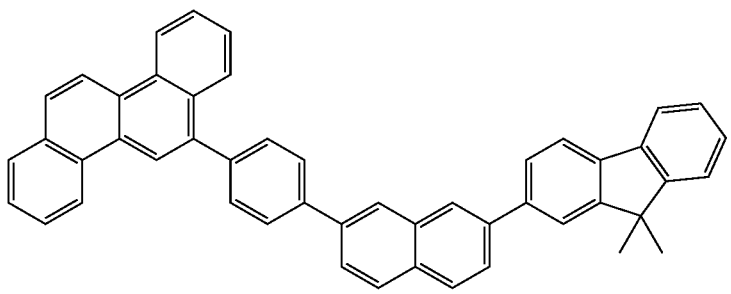
2-233
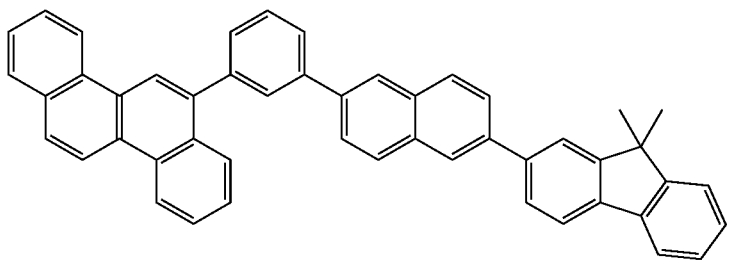
2-234
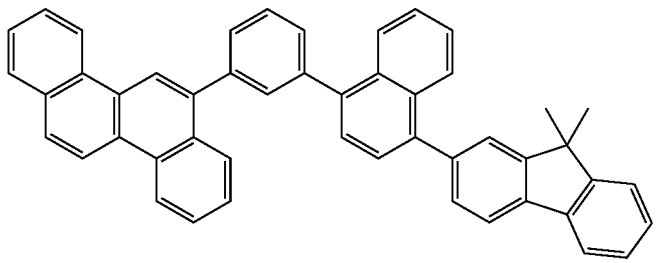
2-235
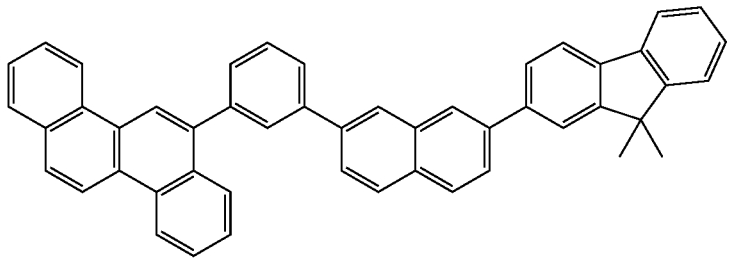
2-236

2-237
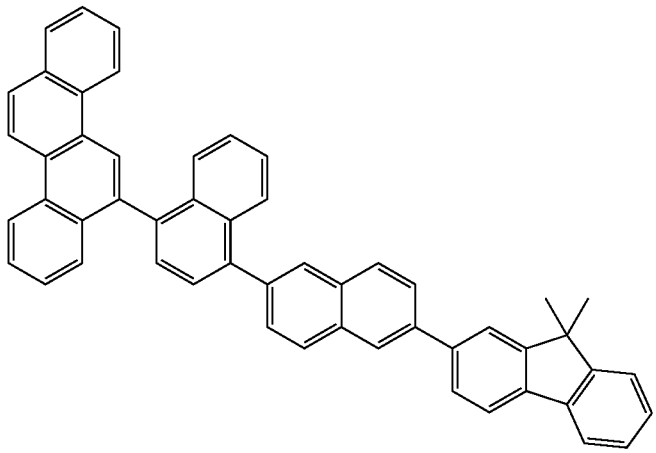
2-238
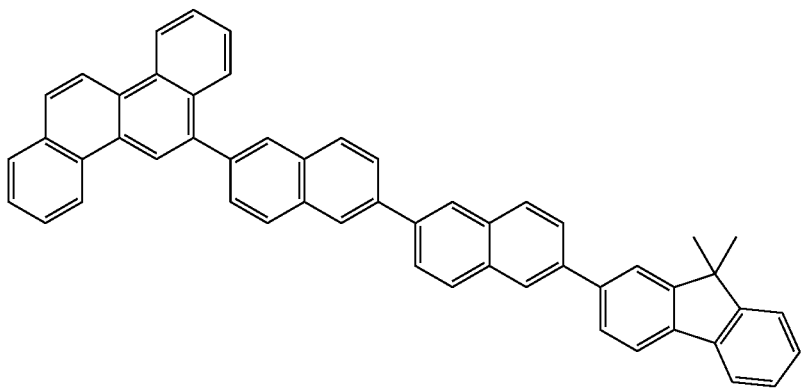
2-239
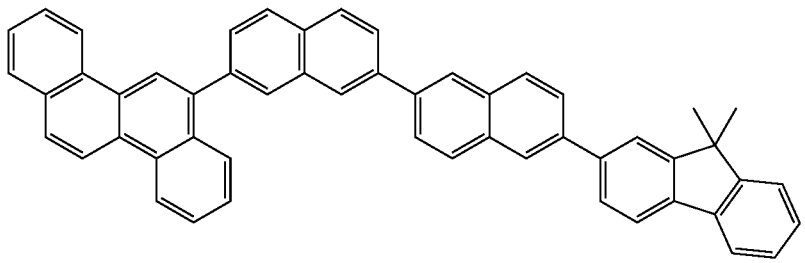
2-240
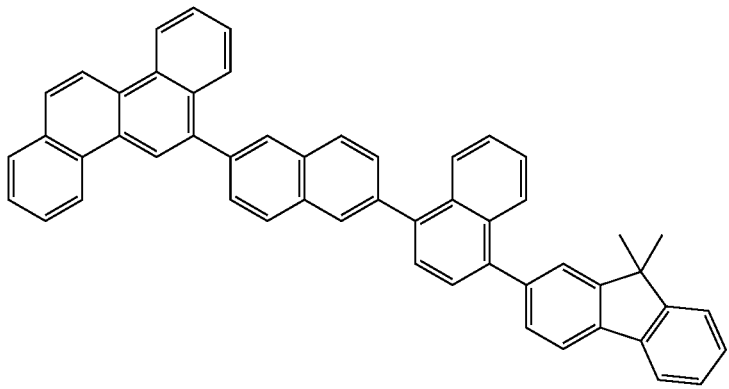

-continued
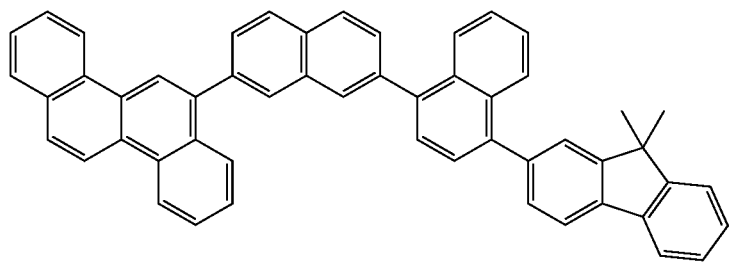
2-241
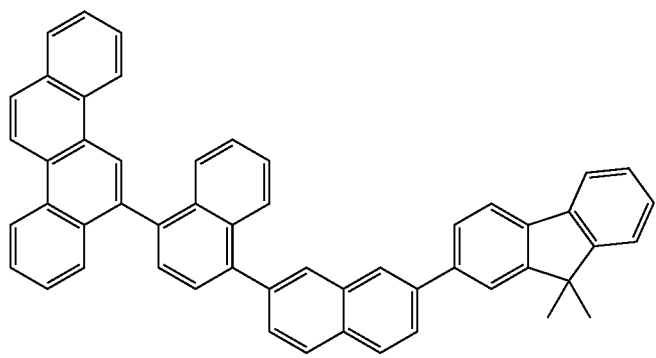
2-242
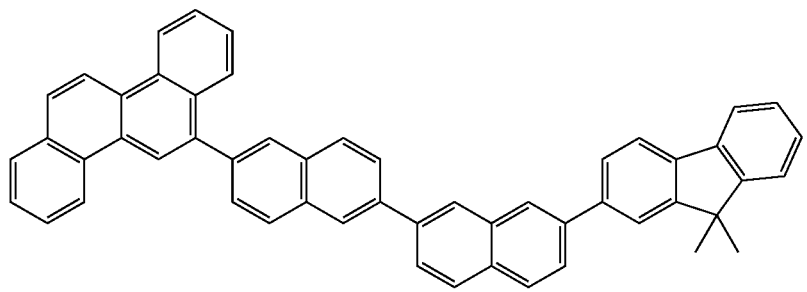
2-243
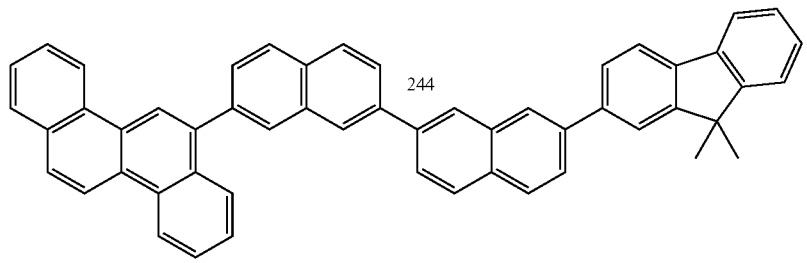
2-244
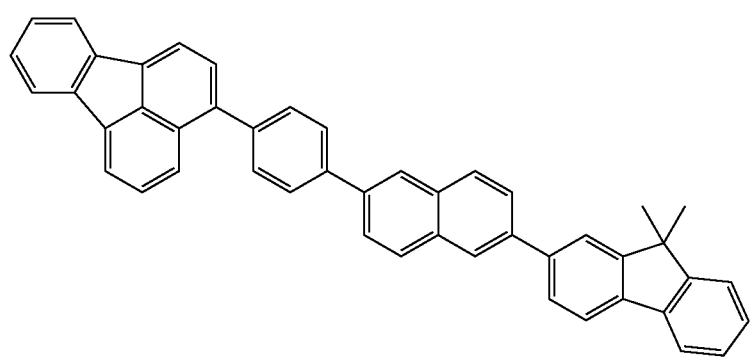
2-251

-continued
2-252
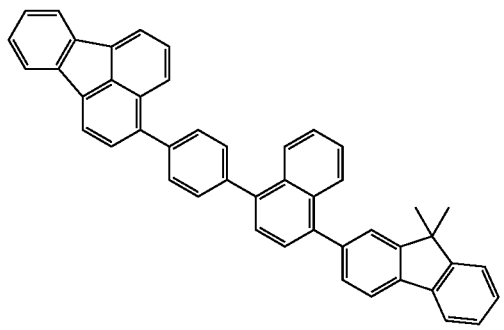
2-253
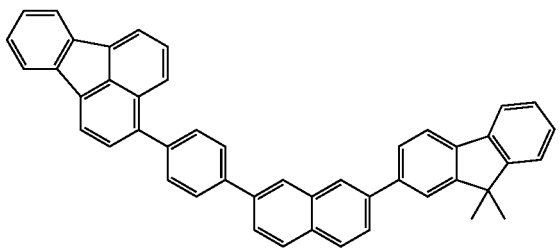
2-254
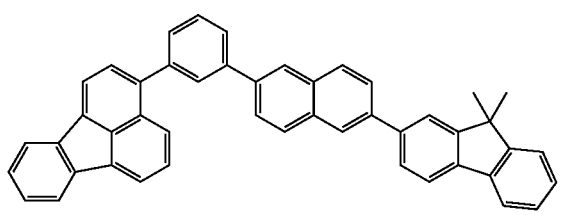
2-255
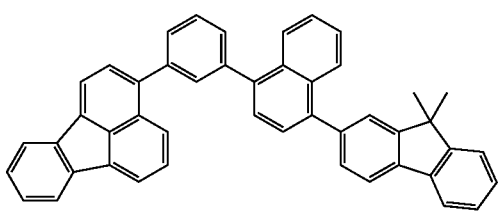
2-256
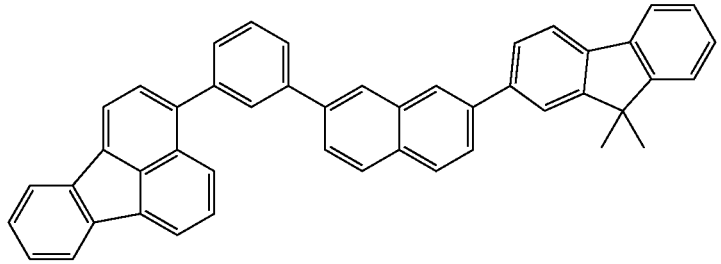
2-257
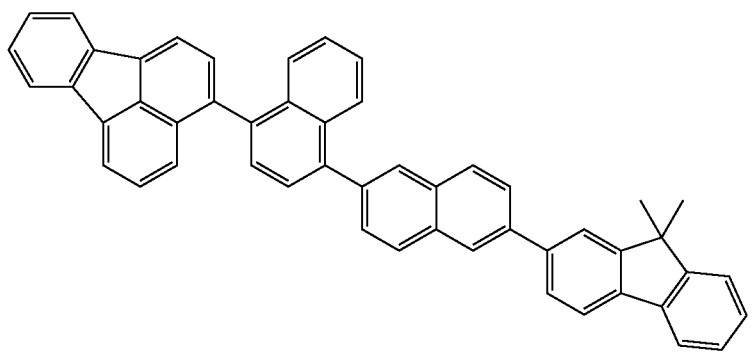
2-258
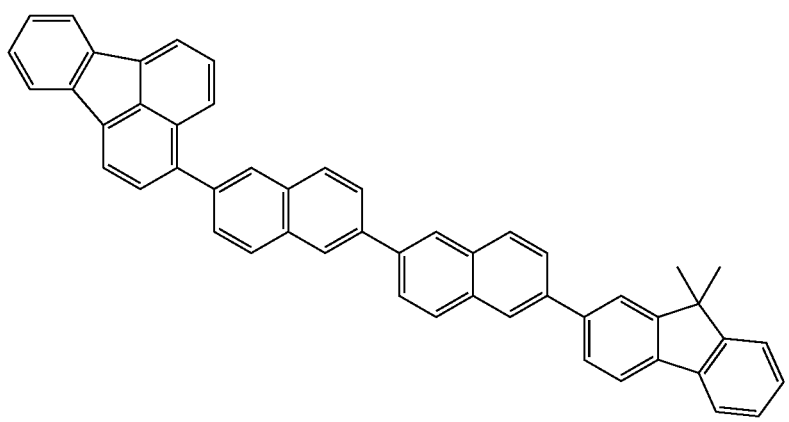

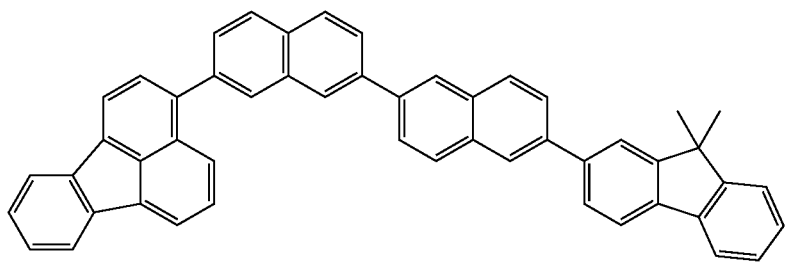
2-259
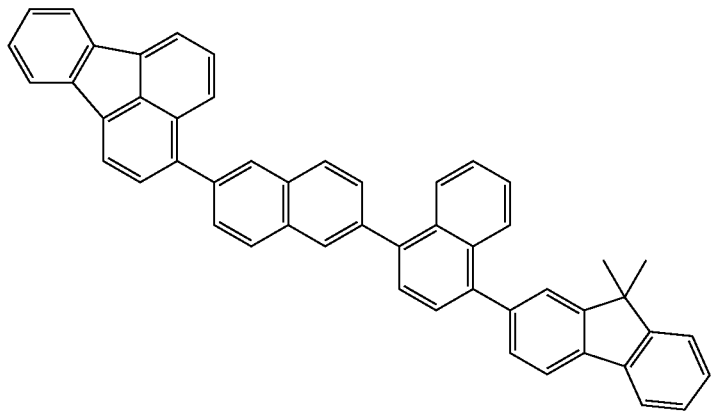
2-260
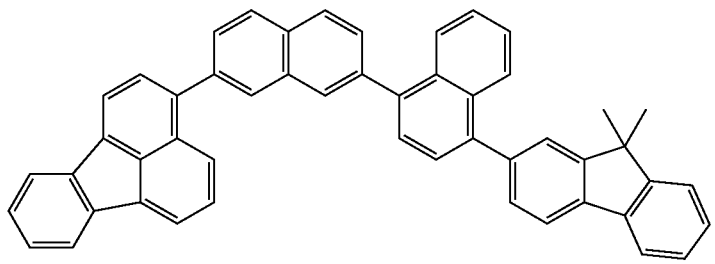
2-261
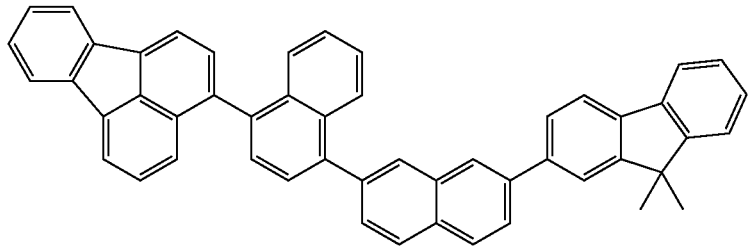
2-262
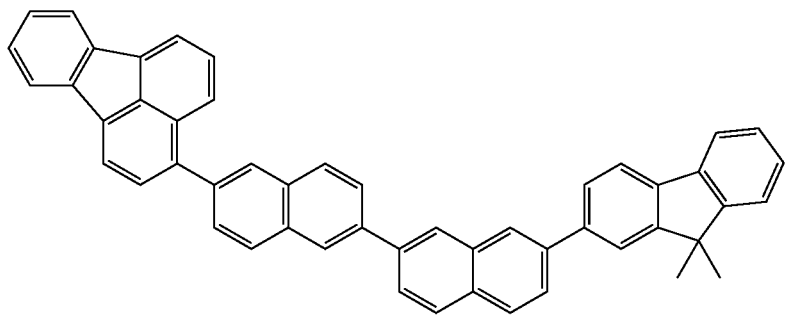
2-263

-continued
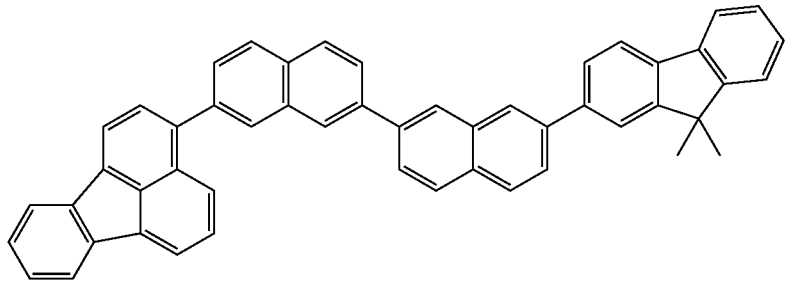
2-264
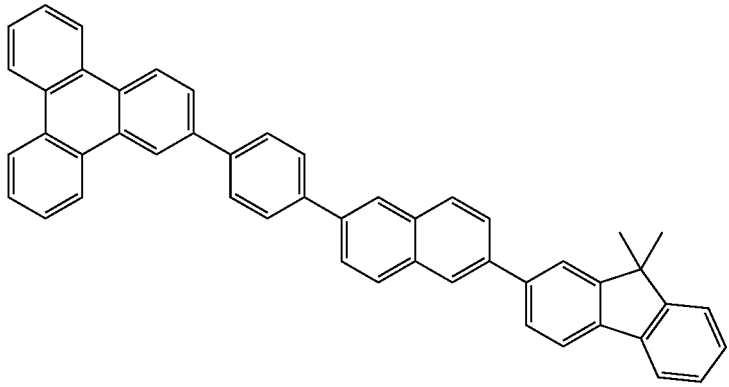
2-271
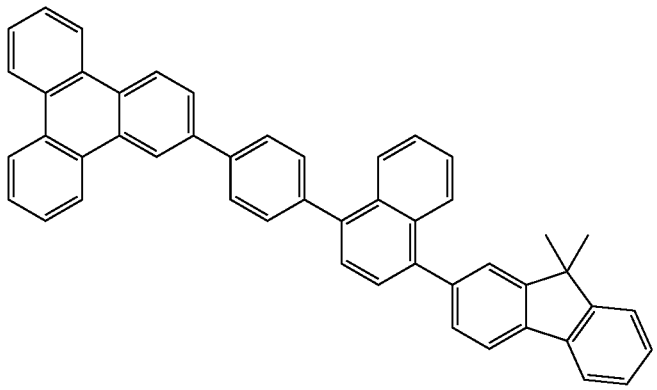
2-272
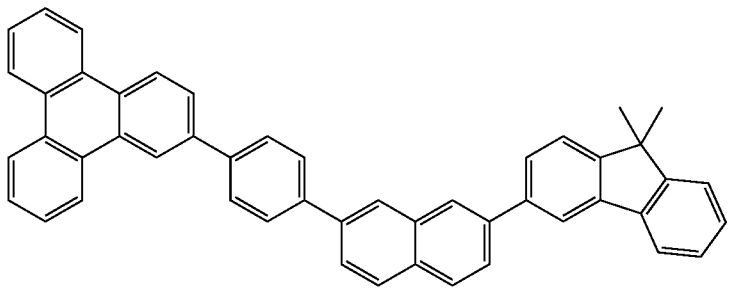
2-273
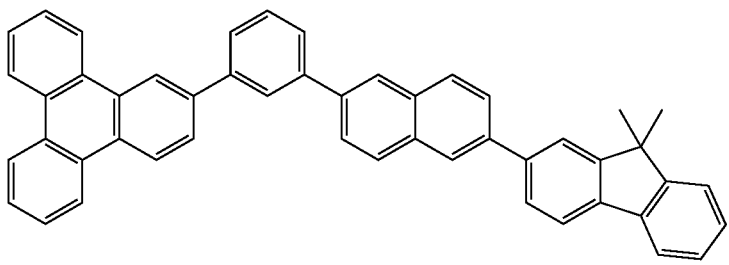
2-274

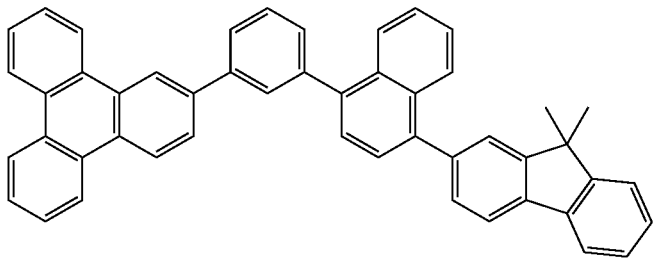
2-275
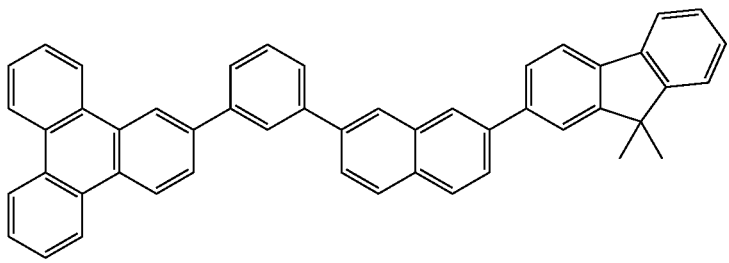
2-276
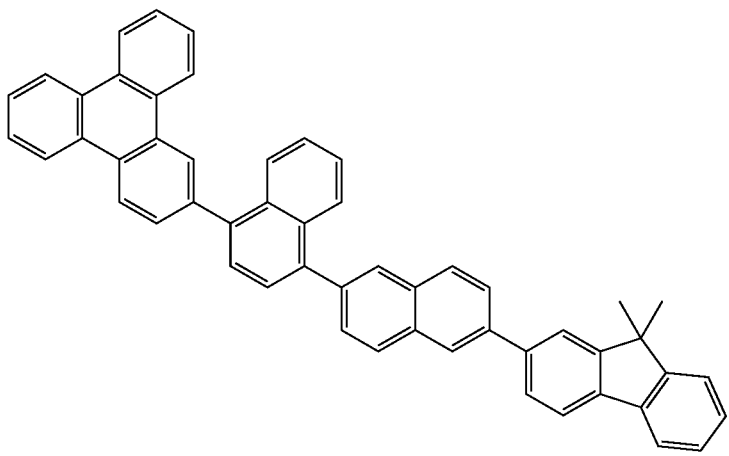
2-277
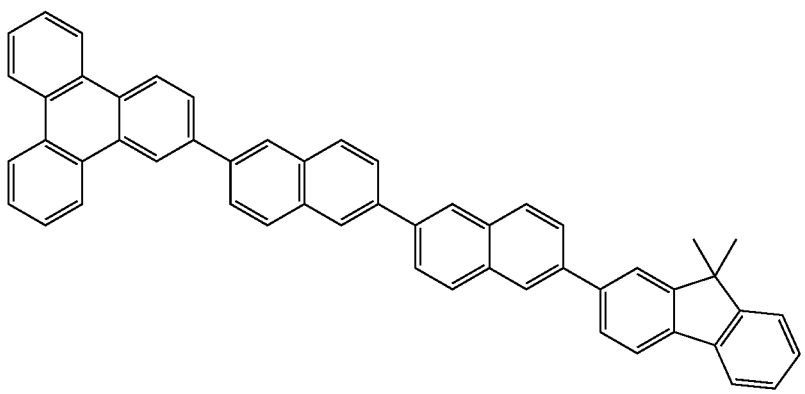
2-278
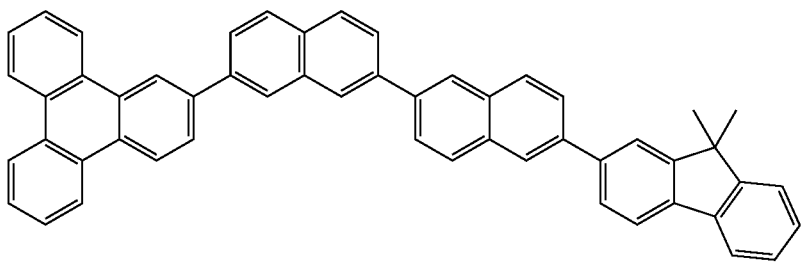
2-279

-continued
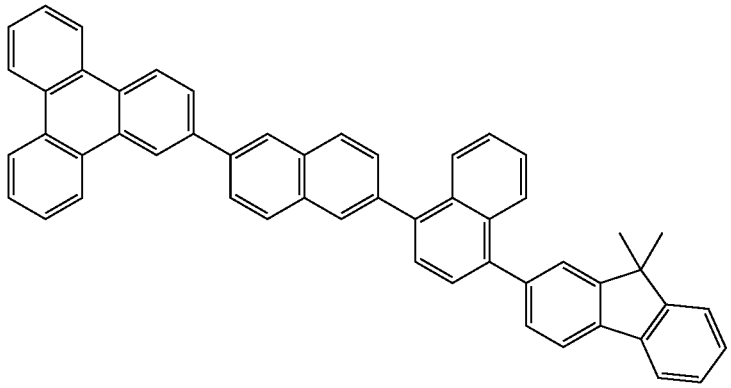
2-280
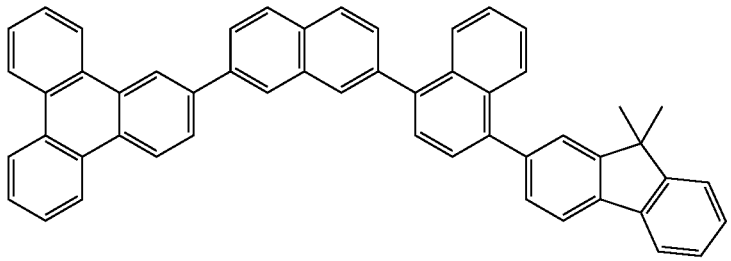
2-281
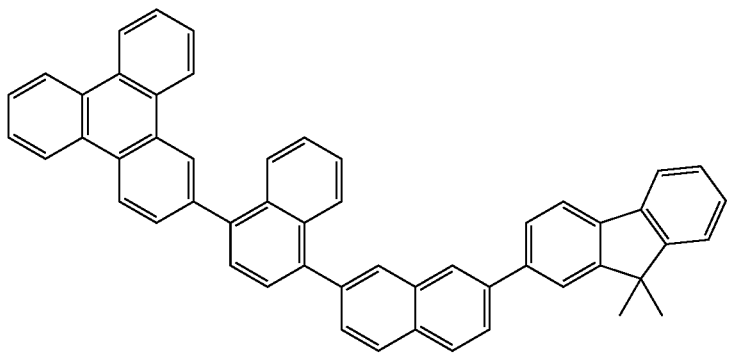
2-282
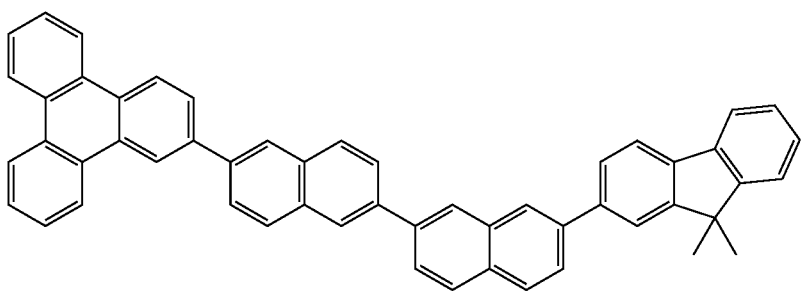
2-283
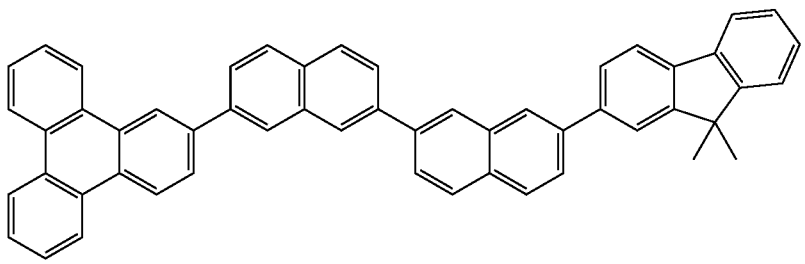
2-284

-continued
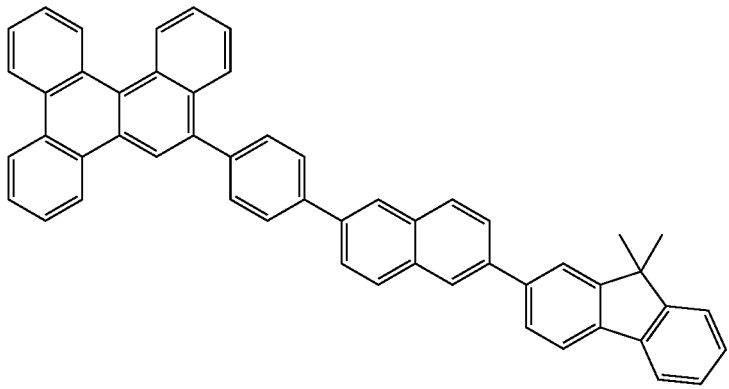
2-291
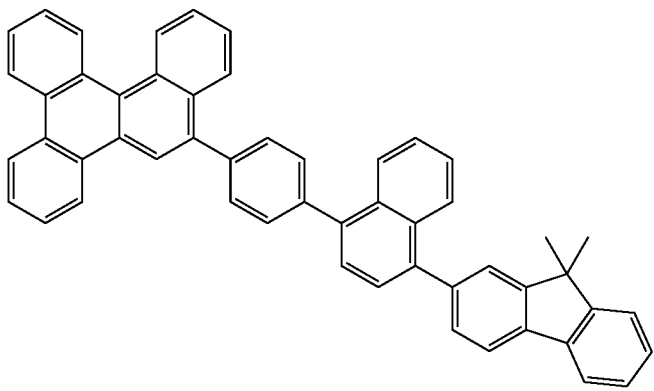
2-292
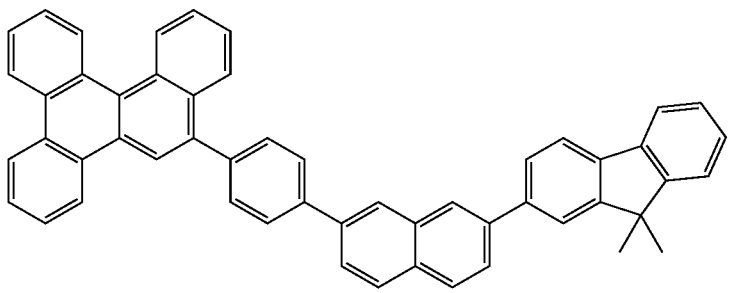
2-293
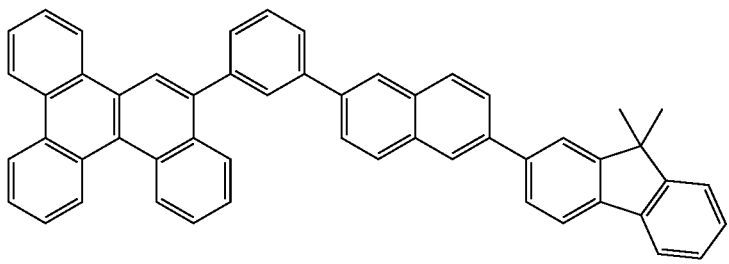
2-294
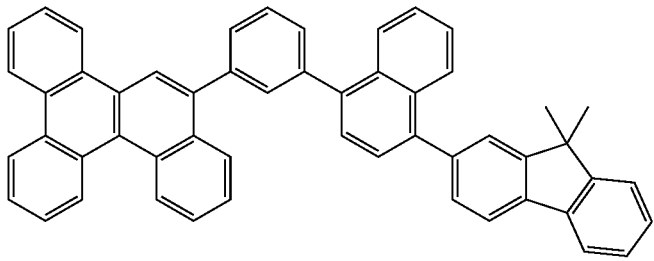
2-295

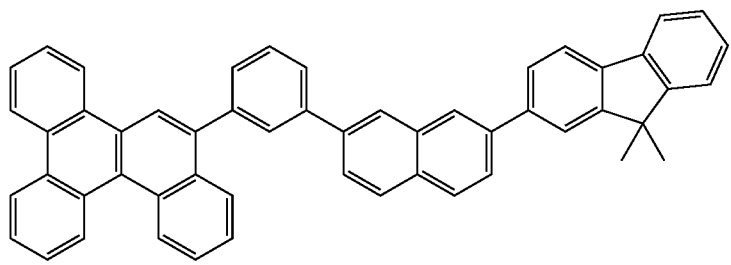
2-296
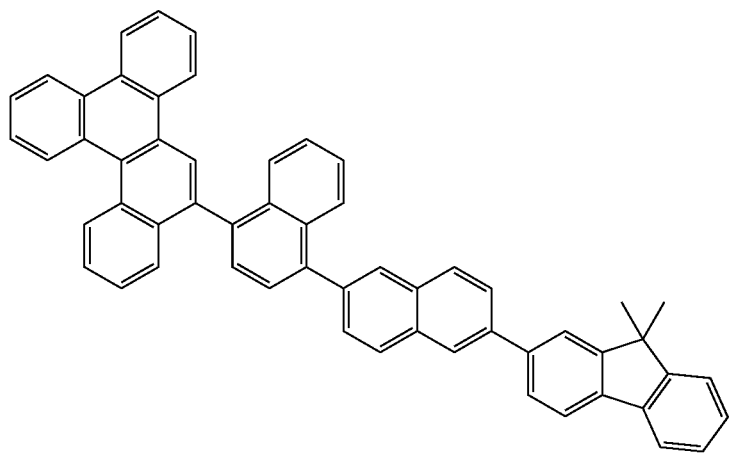
2-297
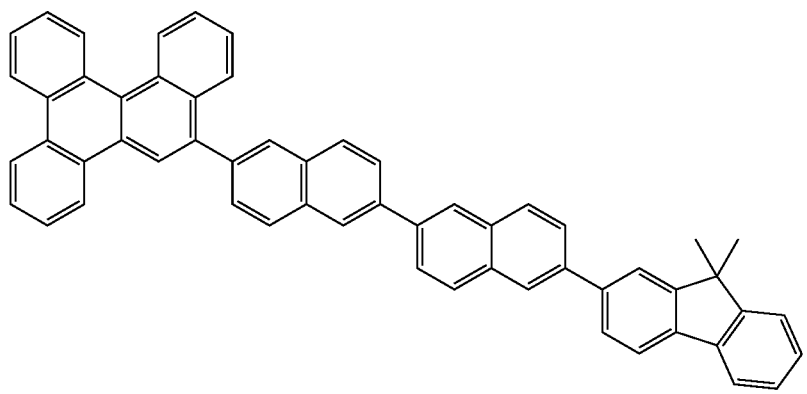
2-298
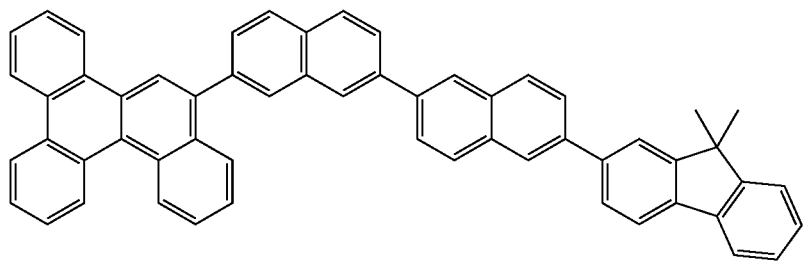
2-299

-continued
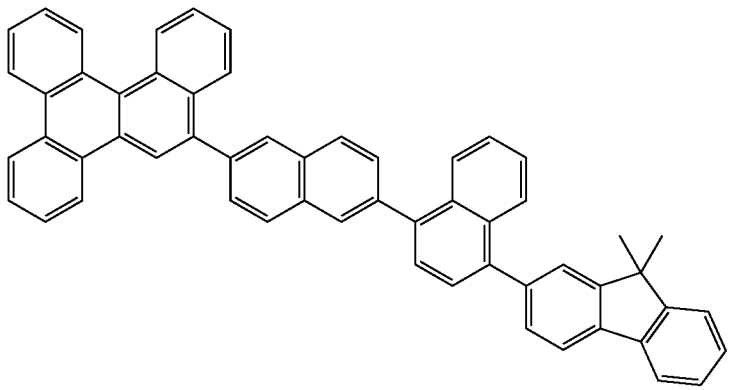
2-300
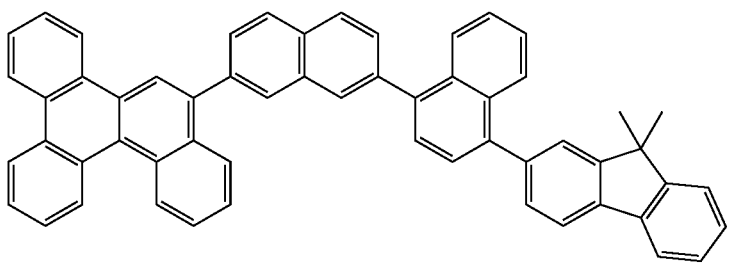
2-301
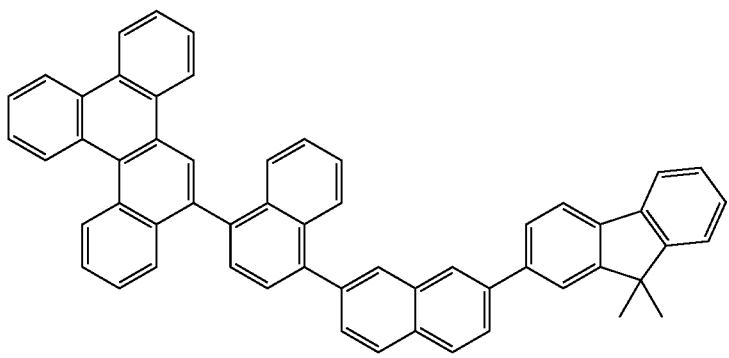
2-302
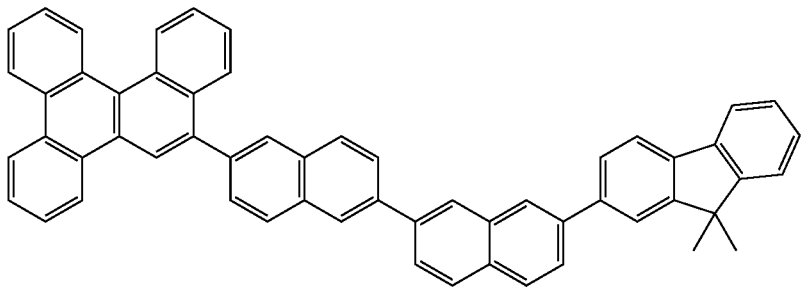
2-303
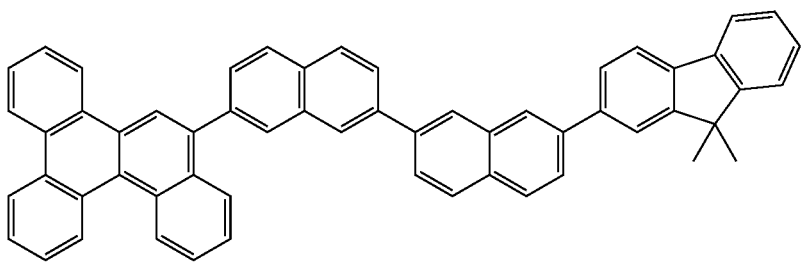
2-304

-continued
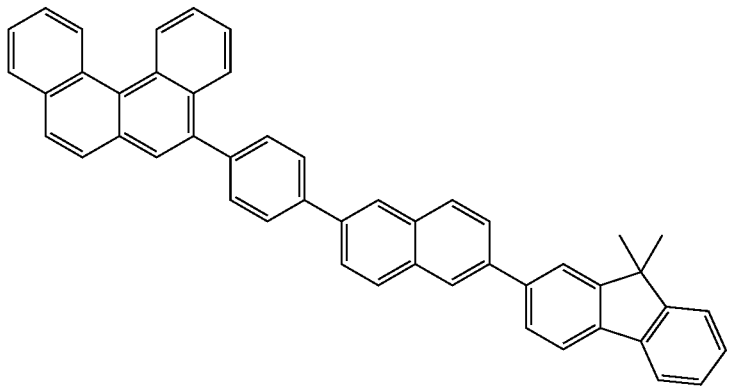
2-311
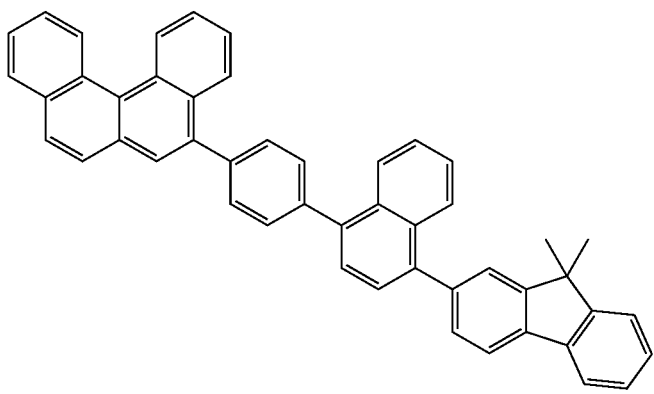
2-312
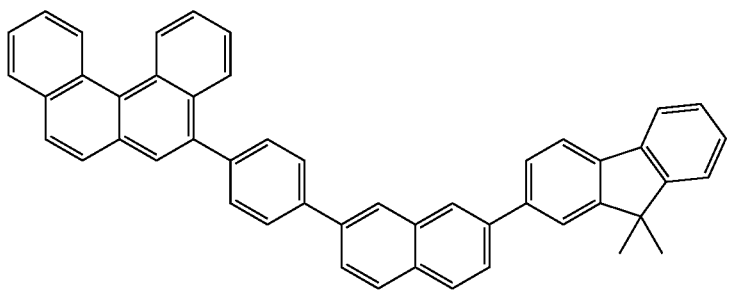
2-313
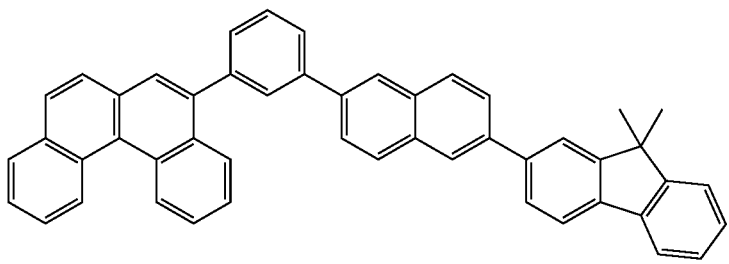
2-314
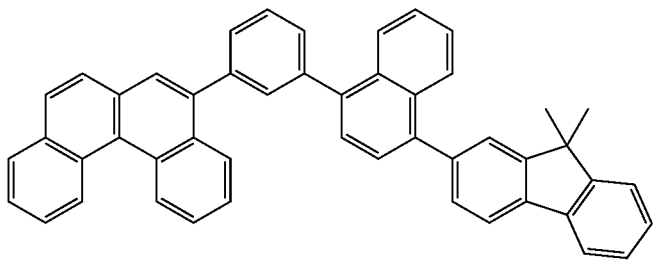
2-315

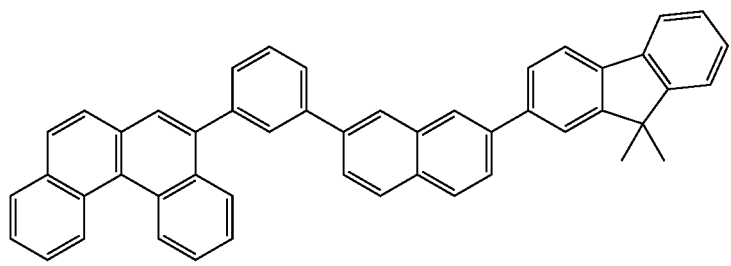
2-316
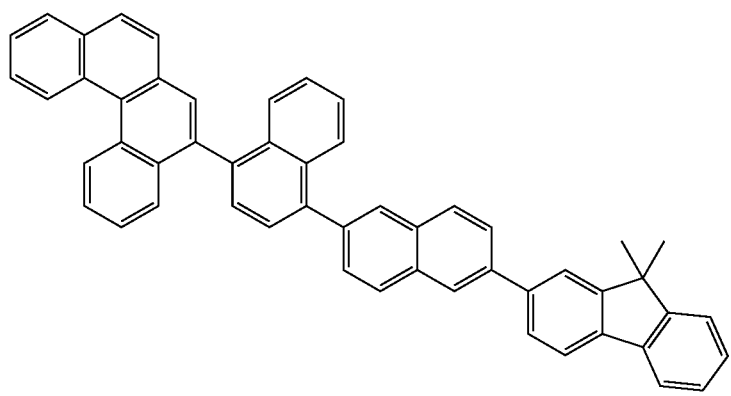
2-317
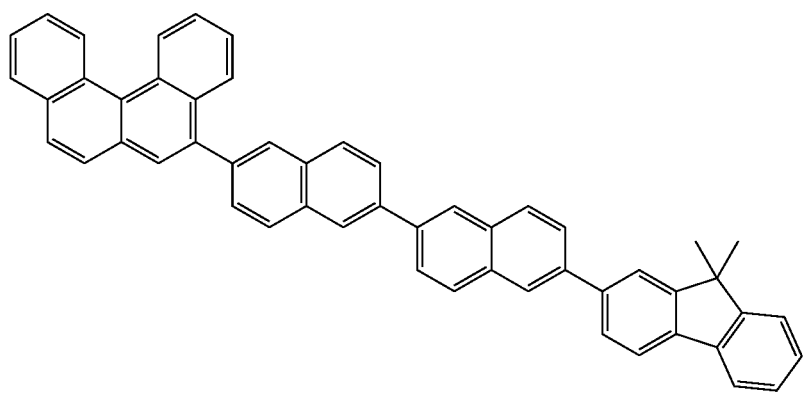
2-318
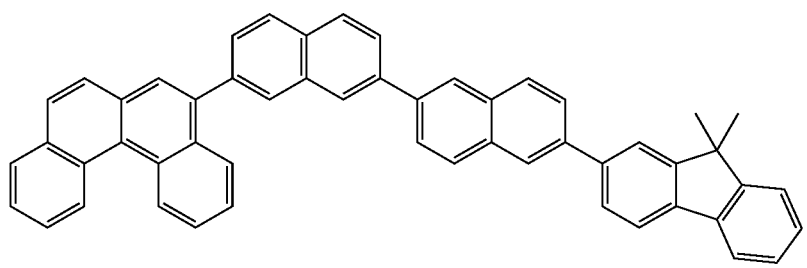
2-319

-continued
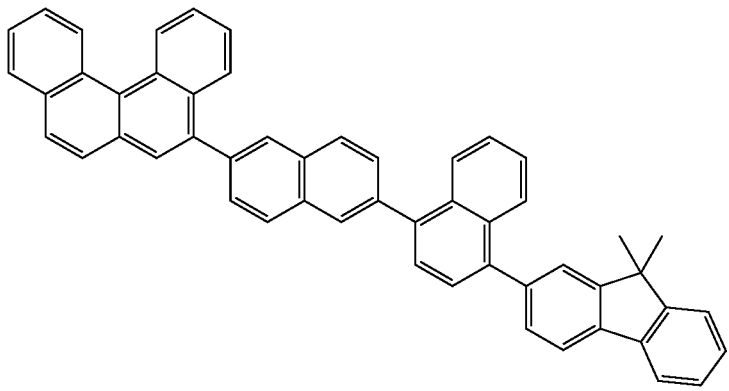
2-320
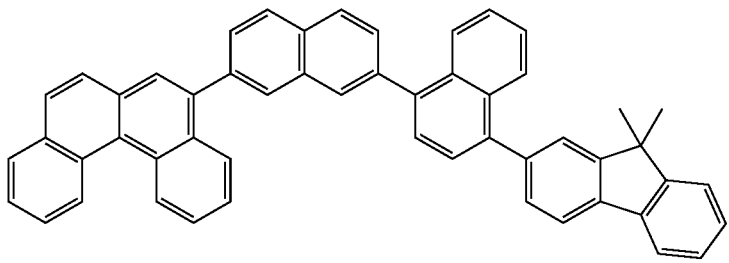
2-321
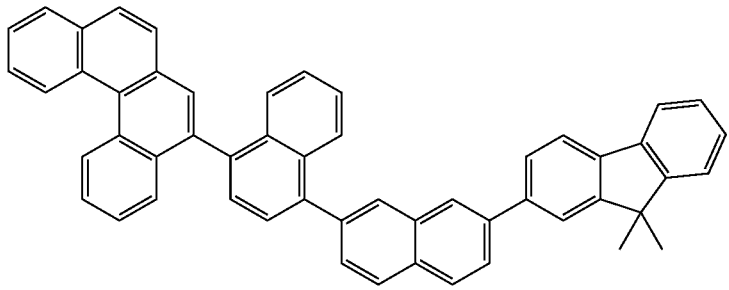
2-322
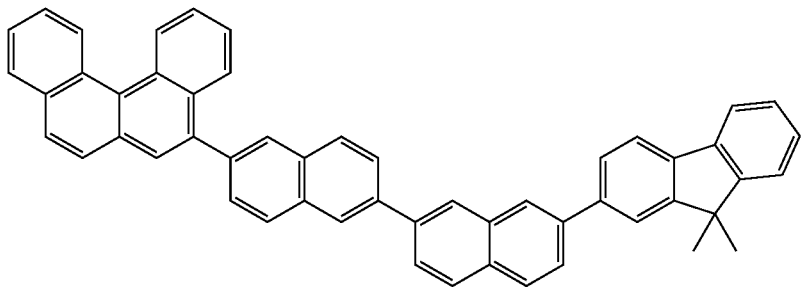
2-323
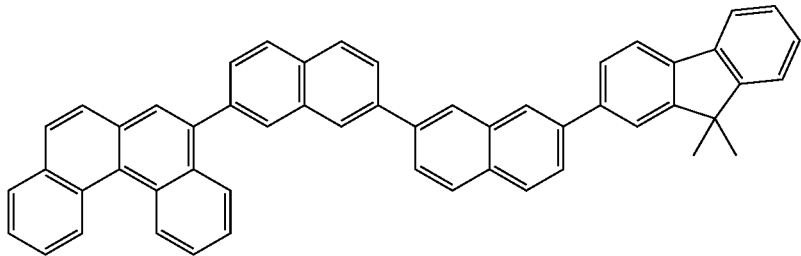
2-324

-continued
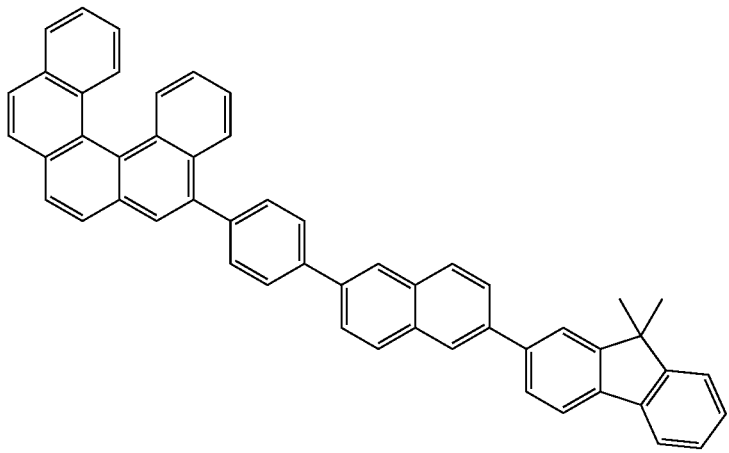
2-331
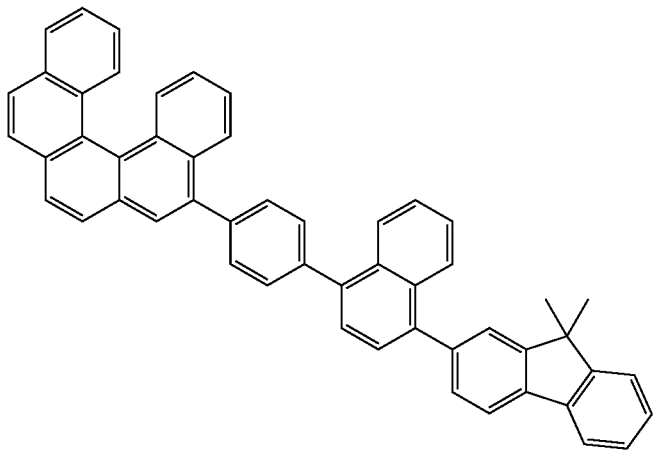
2-332
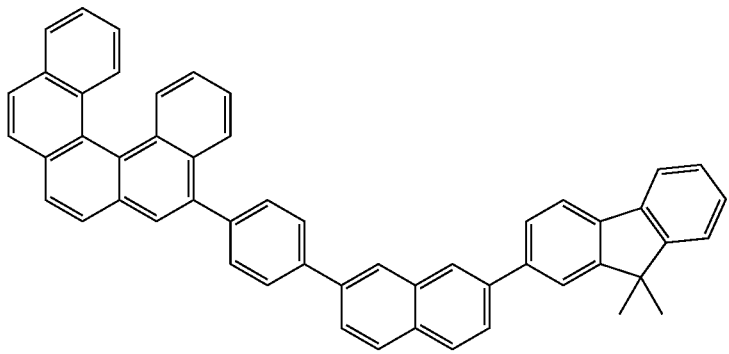
2-333
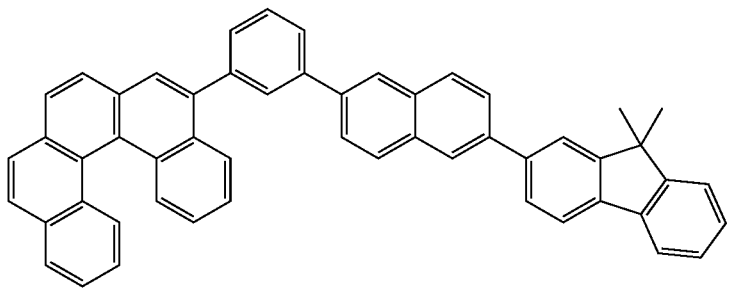
2-334

-continued
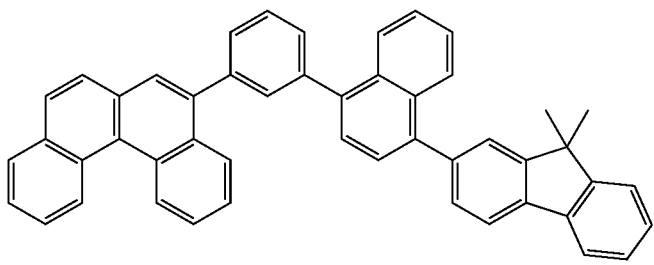
2-335
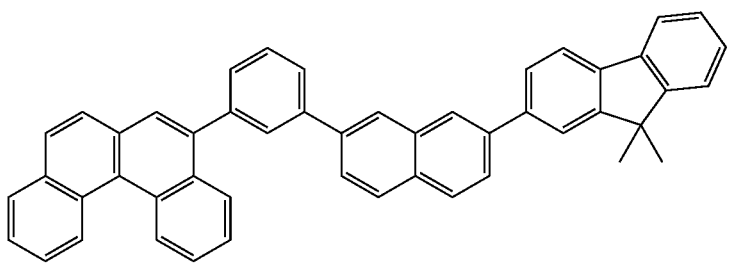
2-336
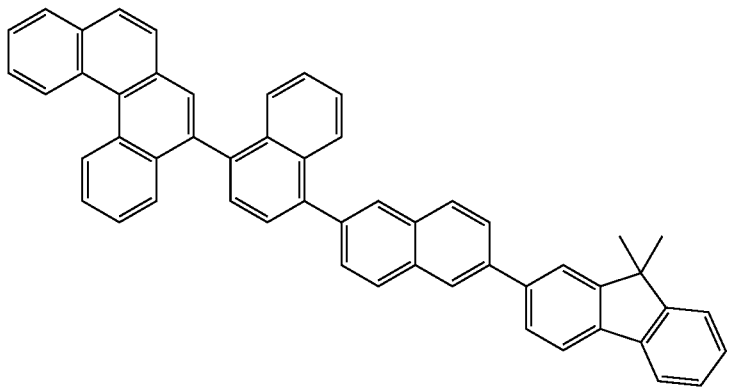
2-337
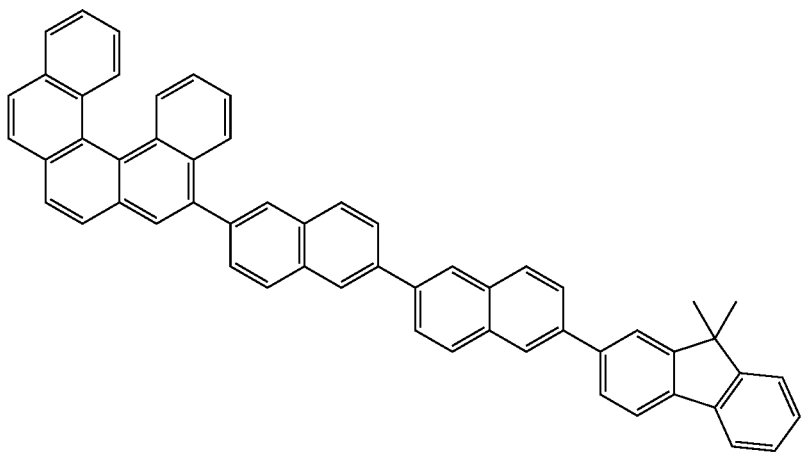
2-338

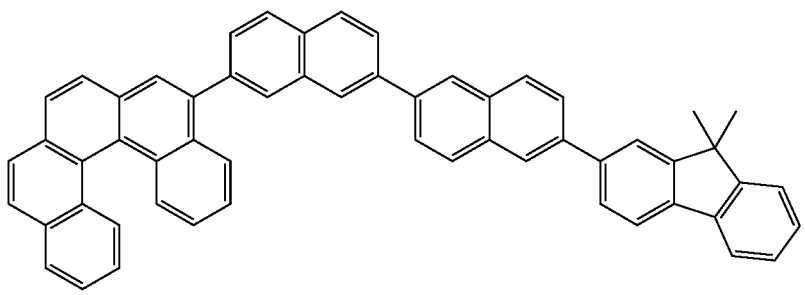
2-339
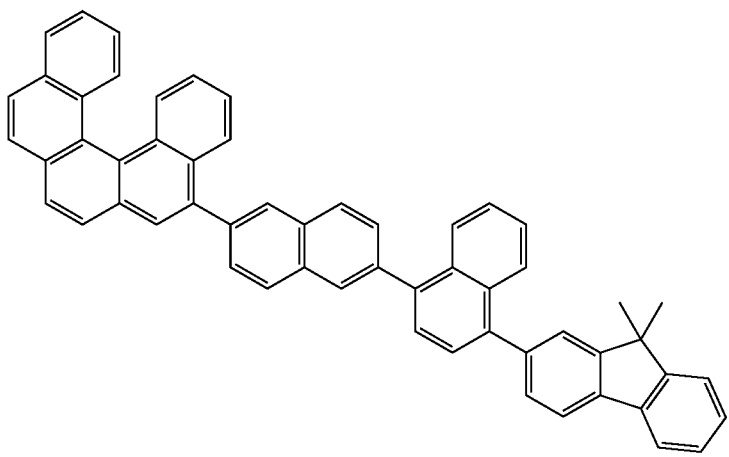
2-340
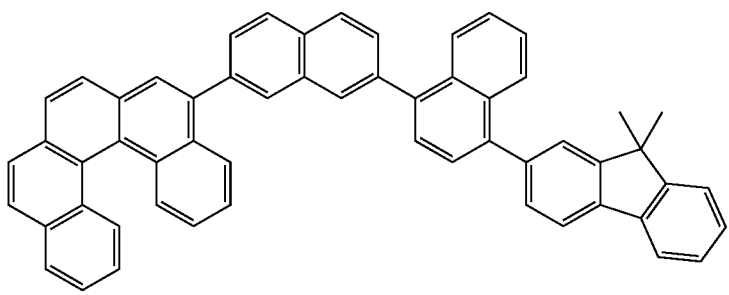
2-341
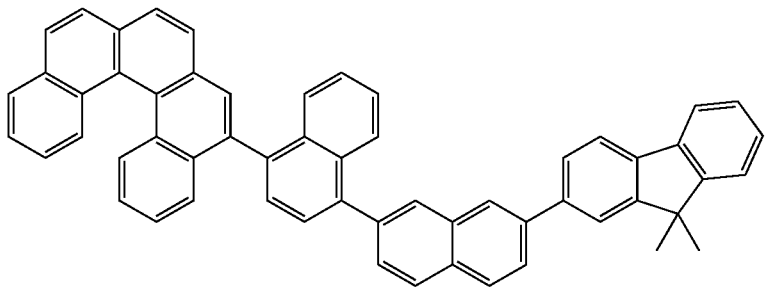
2-342

-continued
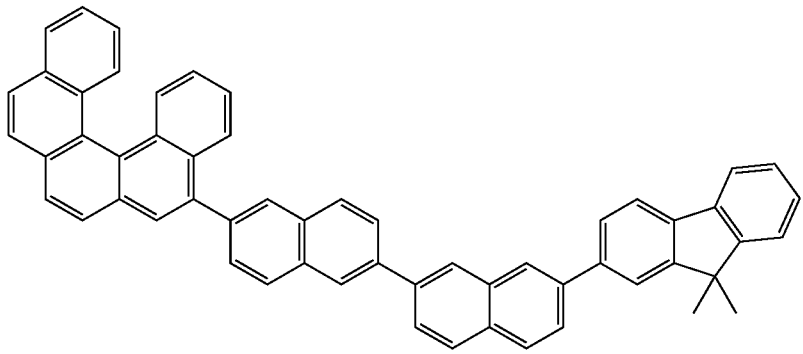
2-343
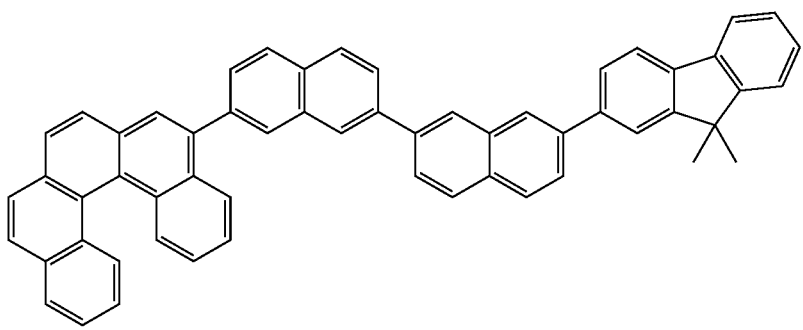
2-344
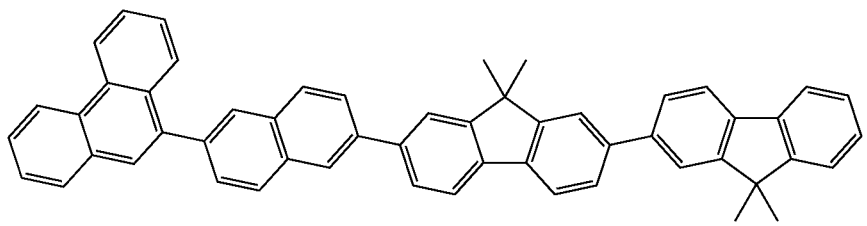
2-355
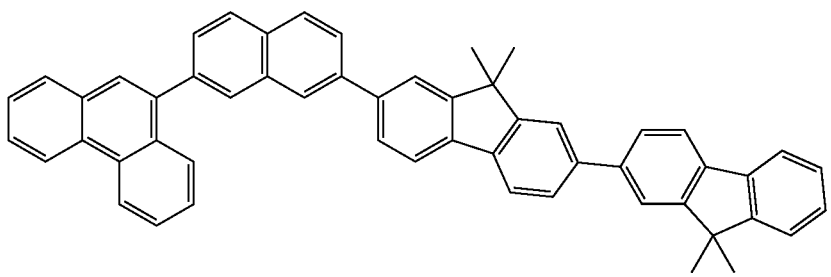
2-356
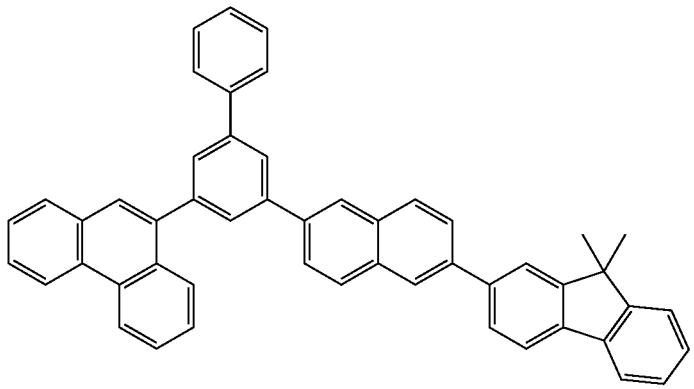
2-373

-continued
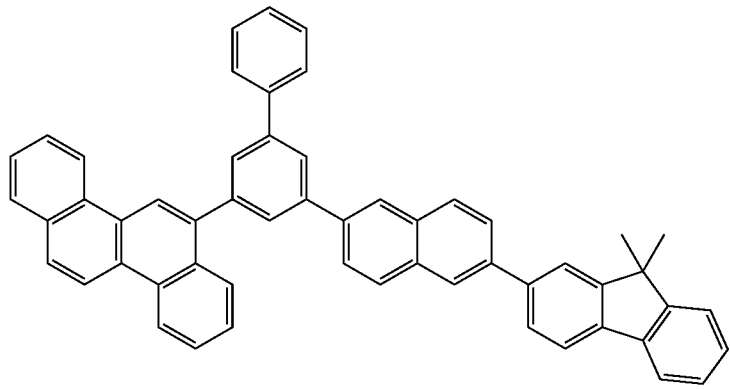
2-376
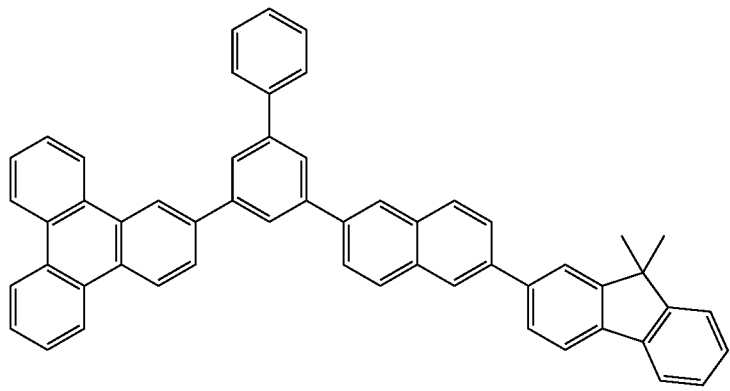
2-378
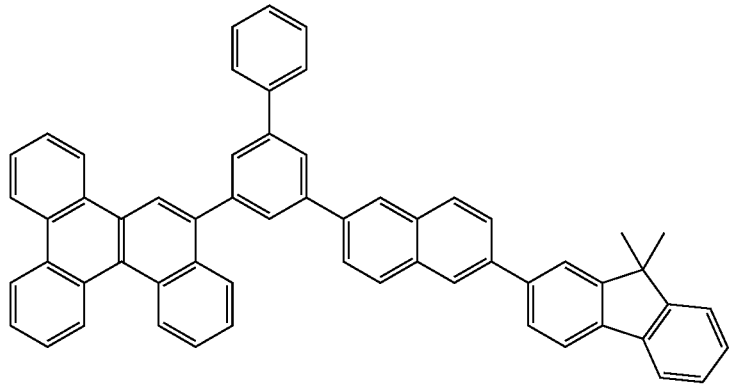
2-380
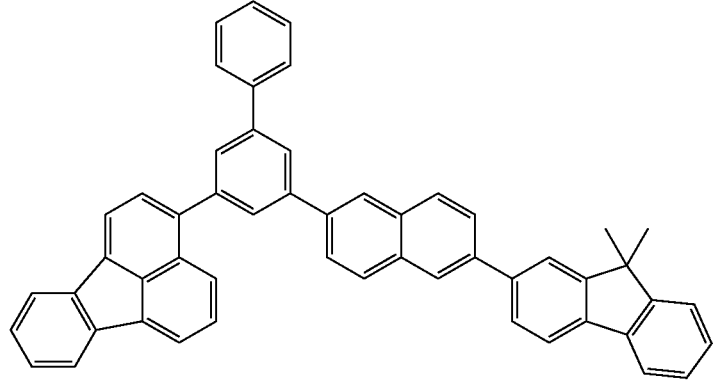
2-382

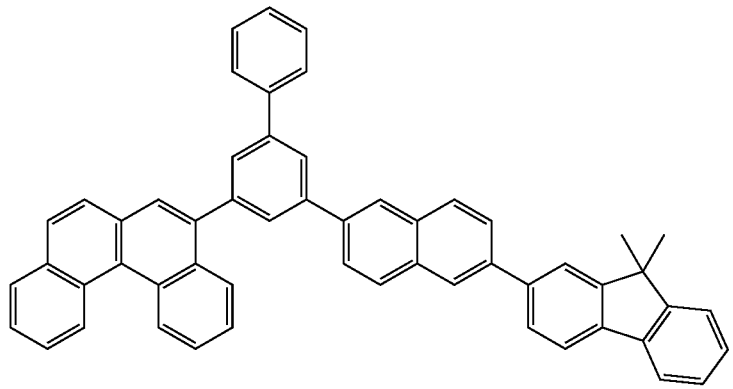
2-384
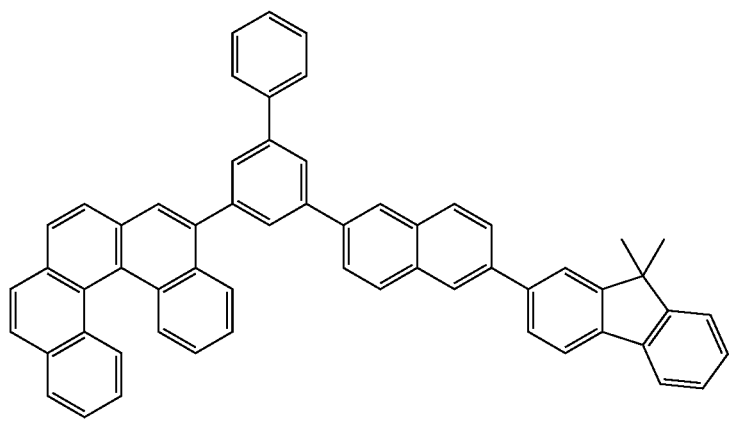
2-386
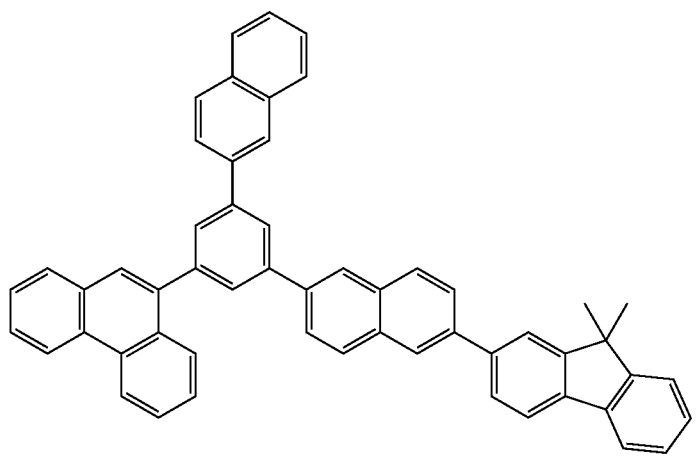
2-389

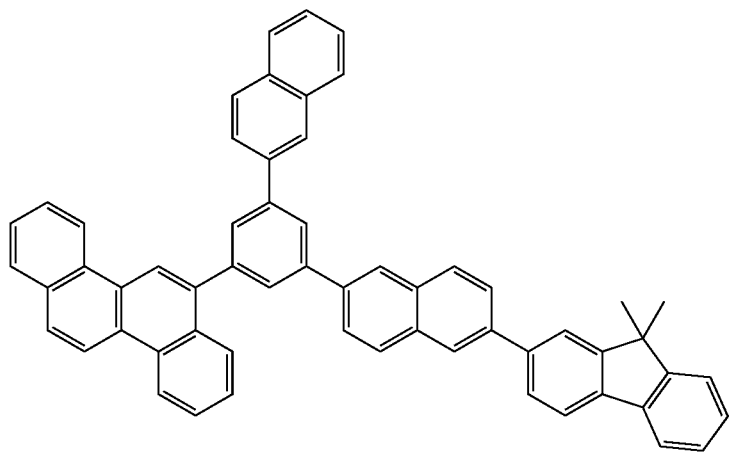
2-392
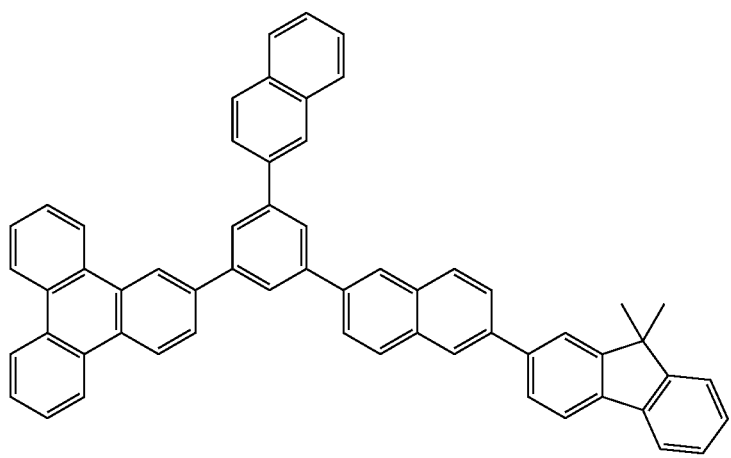
2-394
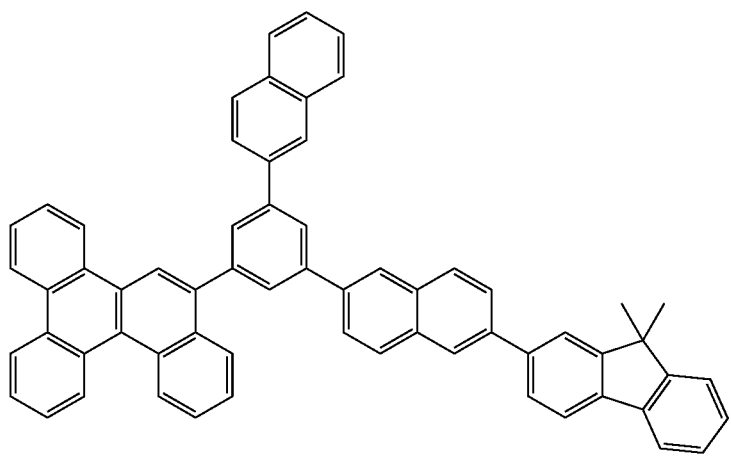
2-396

2-398
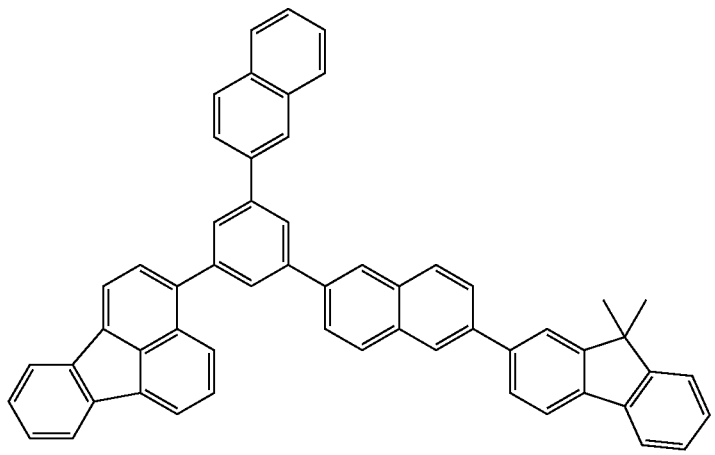
2-400
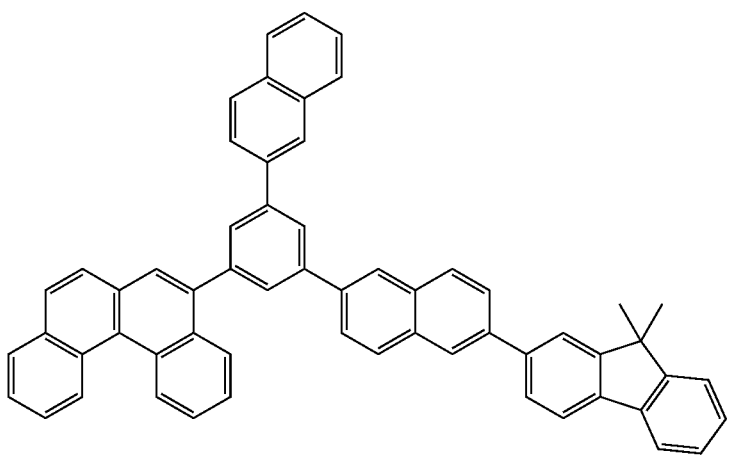
2-402
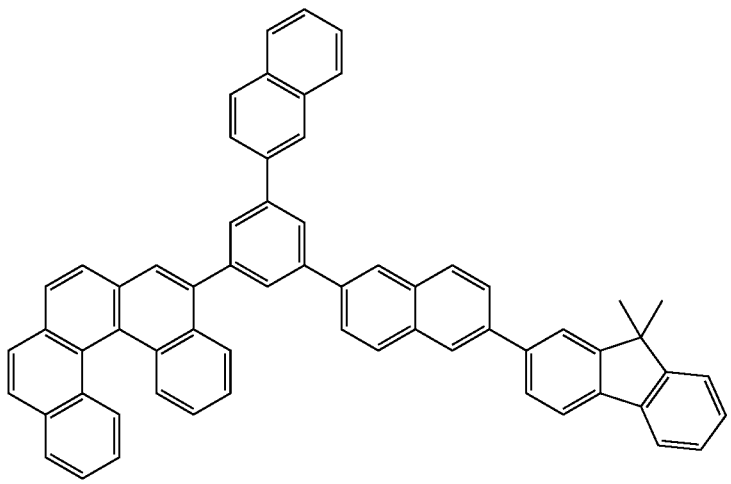

-continued
4-1
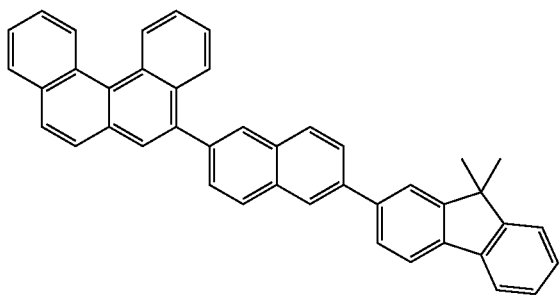
4-2
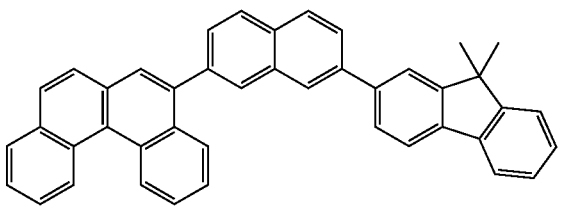
4-3
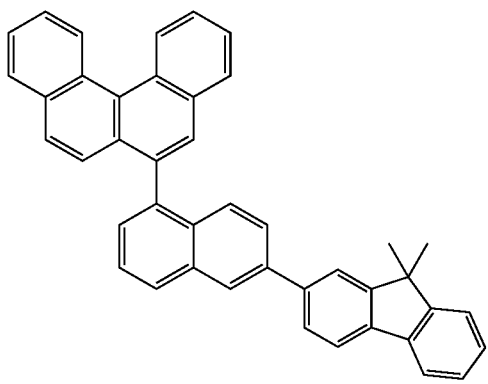
4-4
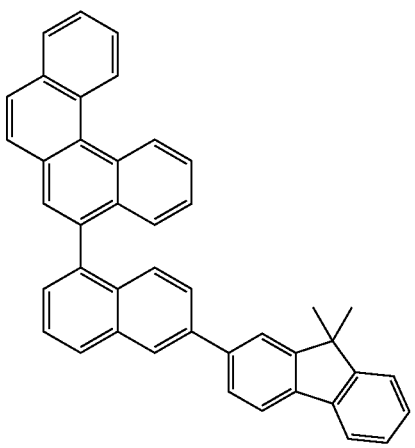
4-5
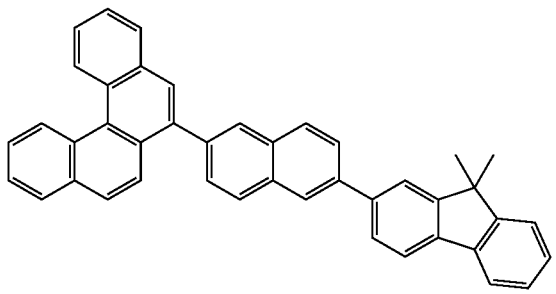
4-6
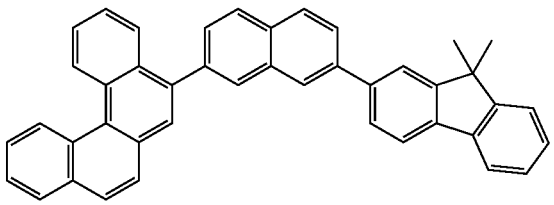
4-7
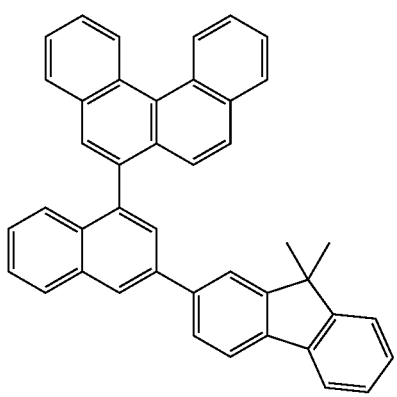
4-8
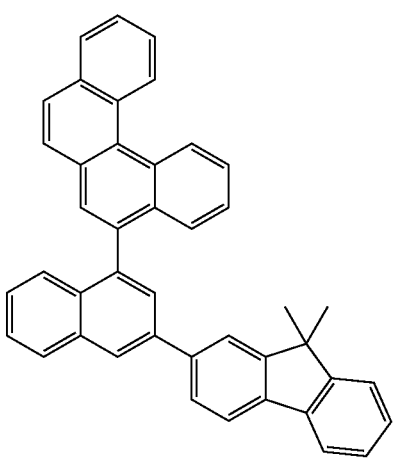

-continued
4-9
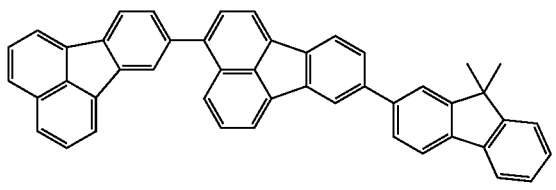
4-10
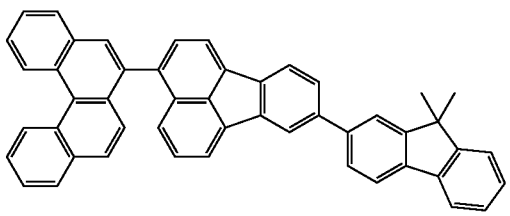
4-11
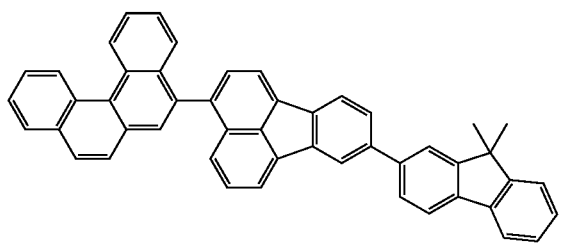
4-12
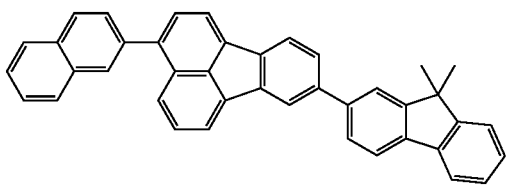
4-13
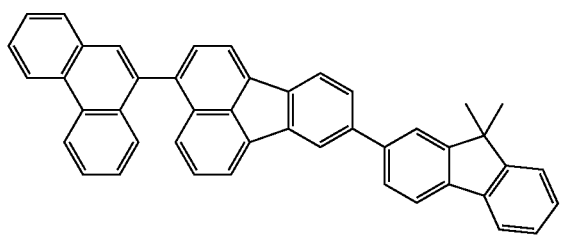
4-14
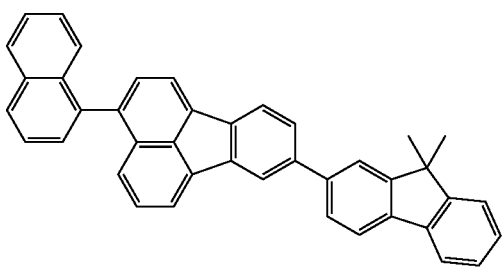
4-15
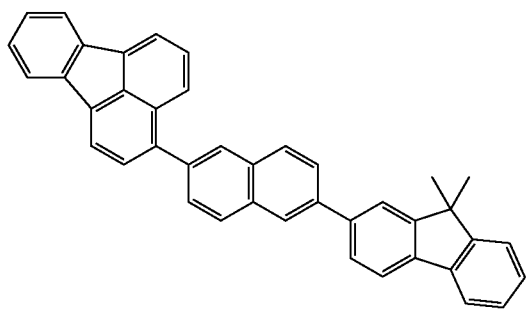
4-16
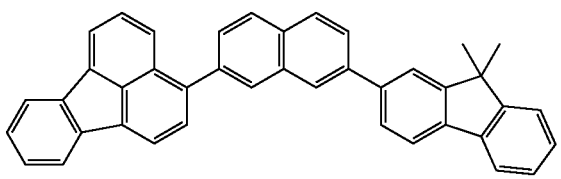
4-17
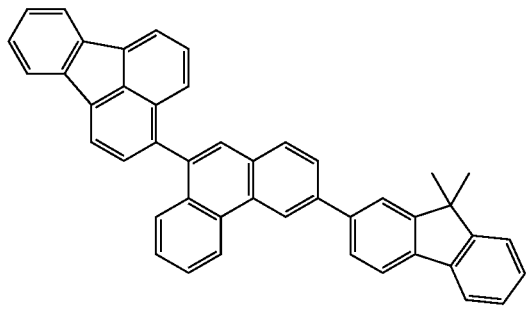
4-18
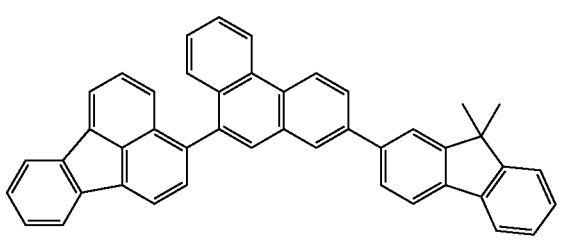

-continued
4-19
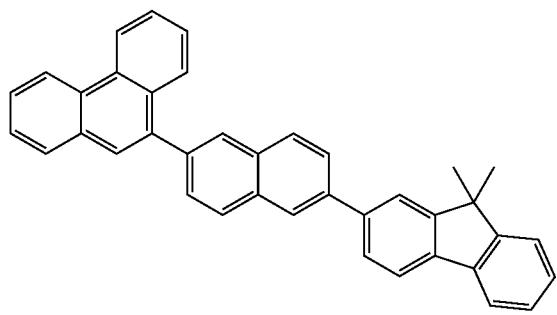
4-20
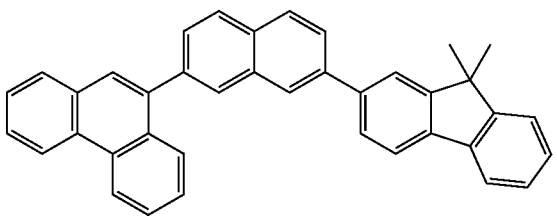
4-21
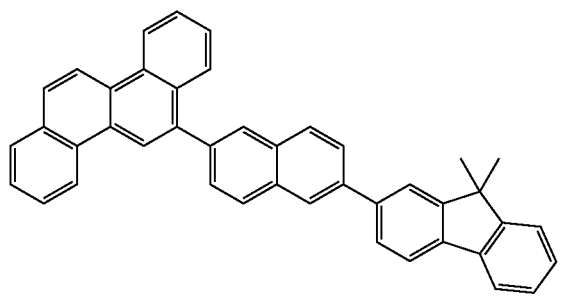
4-22
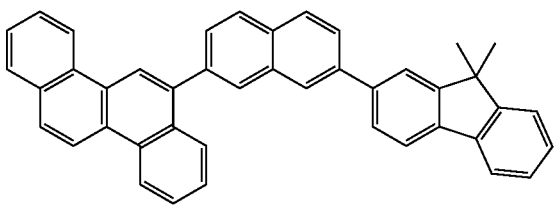
4-23
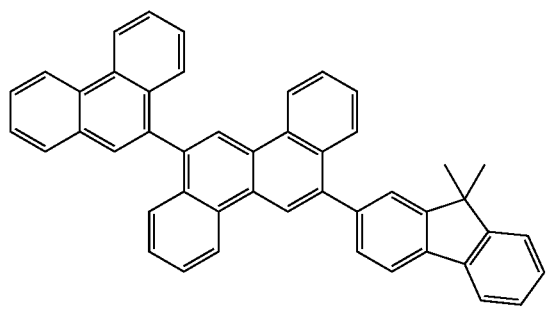
4-24
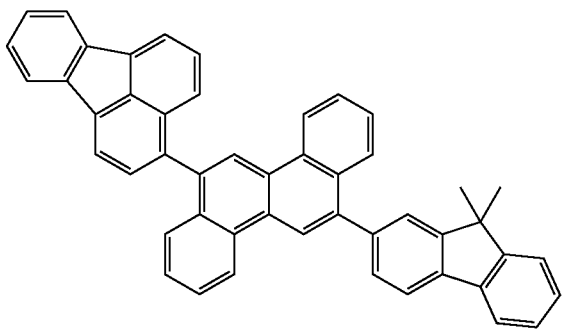
4-25
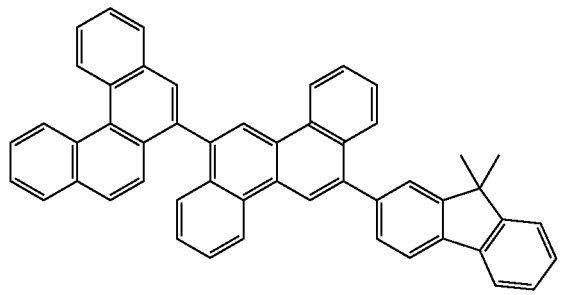
4-26
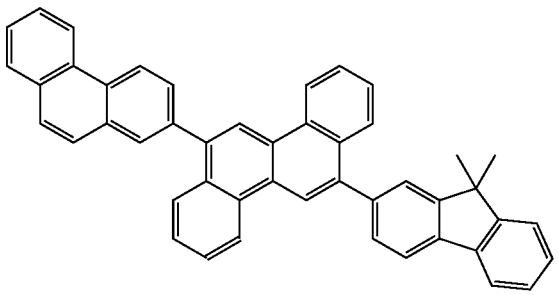

-continued
4-27
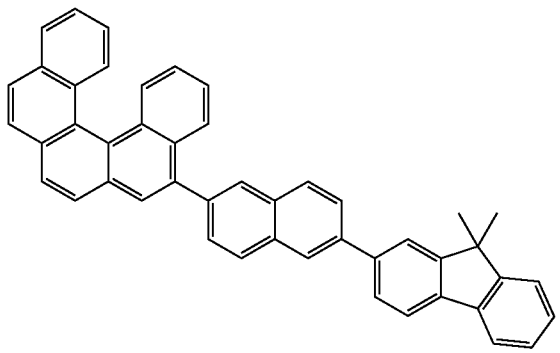
4-28
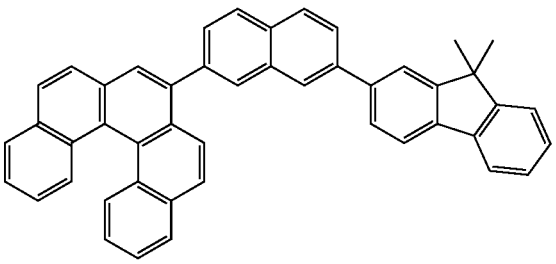
4-29
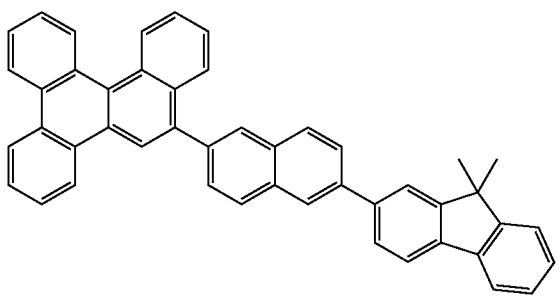
4-30
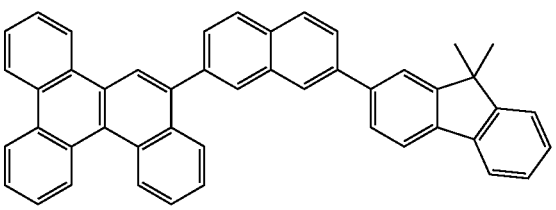
4-31
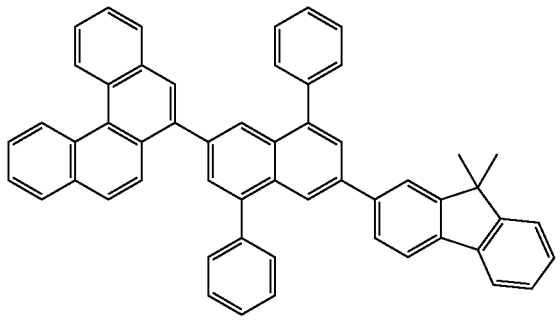
4-32
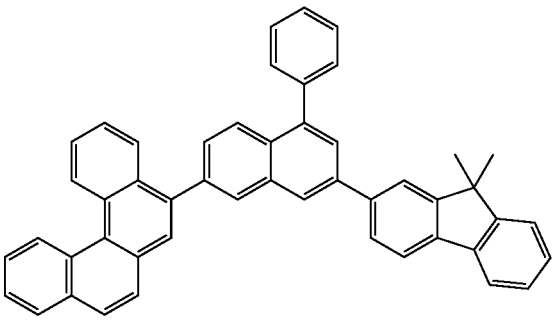
4-33
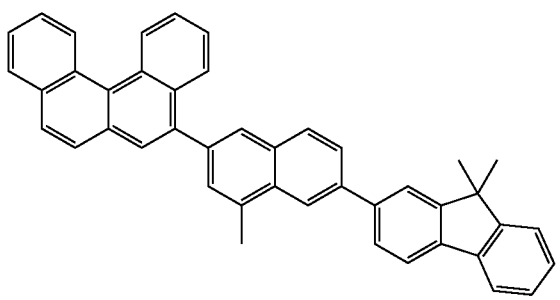
4-34
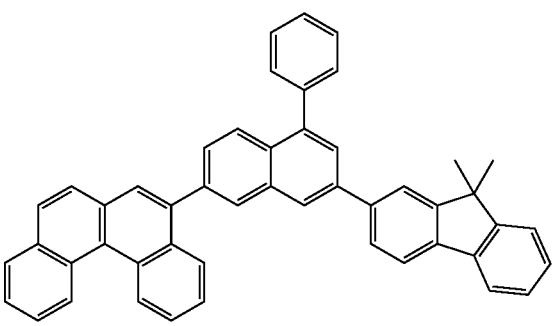
4-35
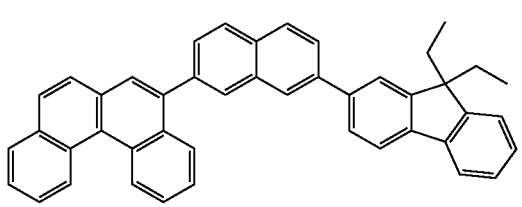
4-36
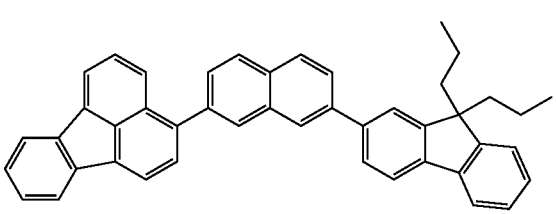

4-37
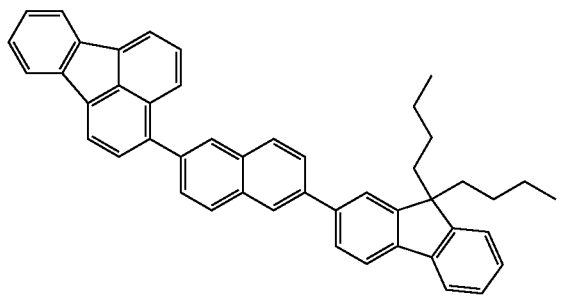
4-38
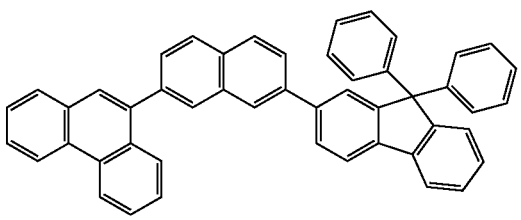
Examples of the material for organic electroluminescence device represented by formulae (C-1) to (C-6) are shown below.
2-1
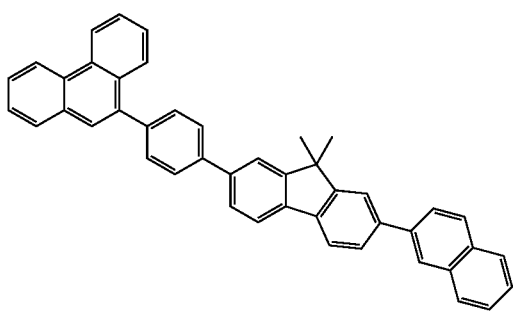
2-2
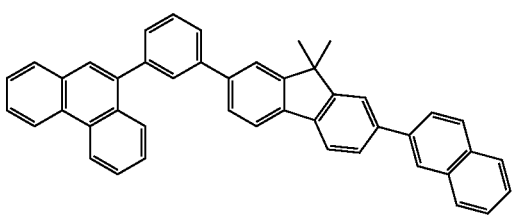
2-3
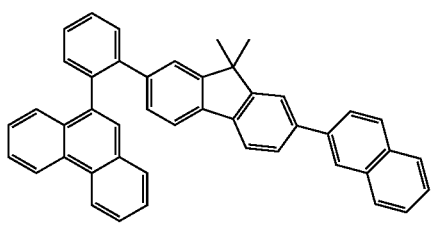
2-4
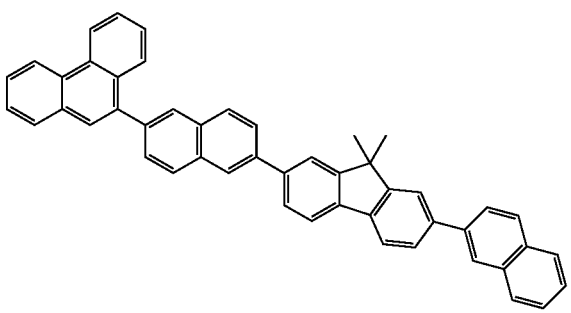
2-5
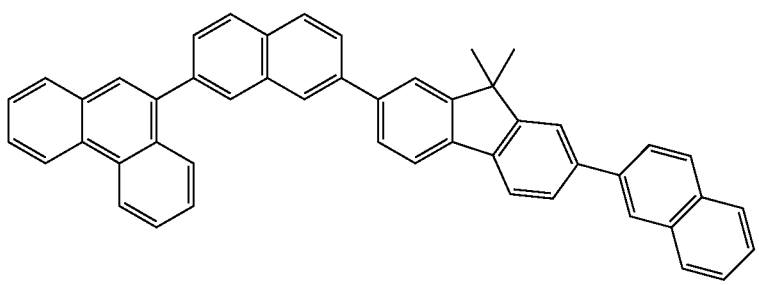

2-6
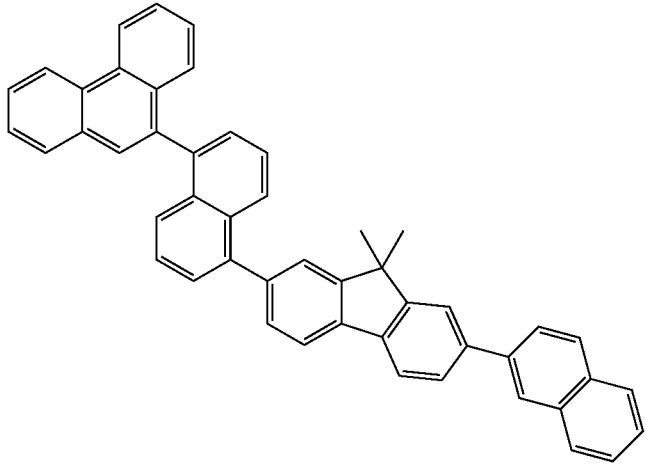
2-7
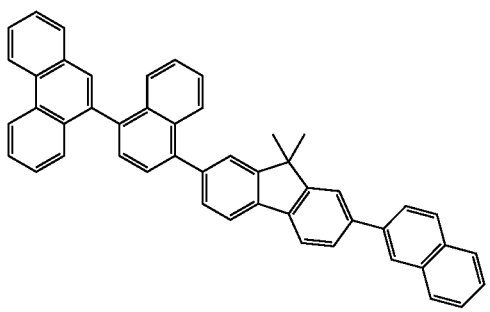
2-8
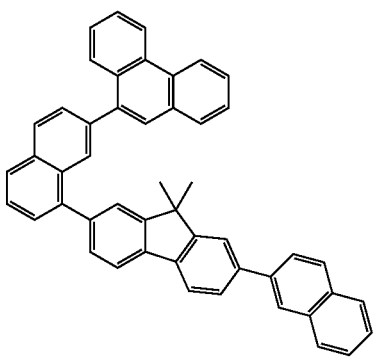
2-9
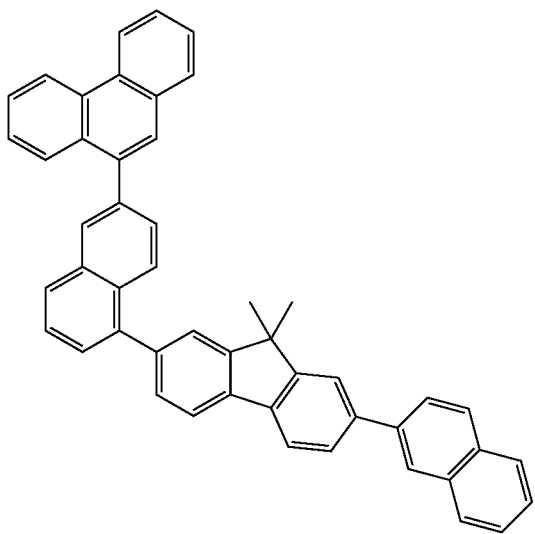

2-10
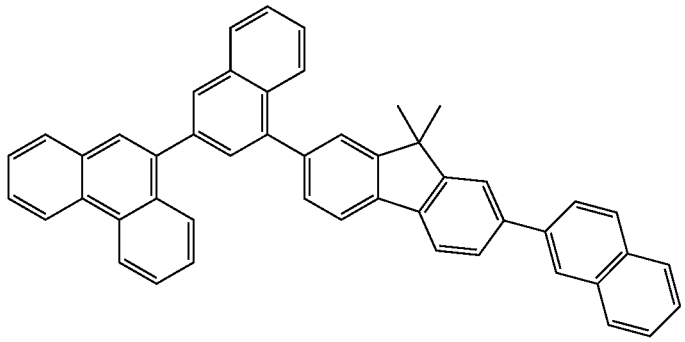
2-11
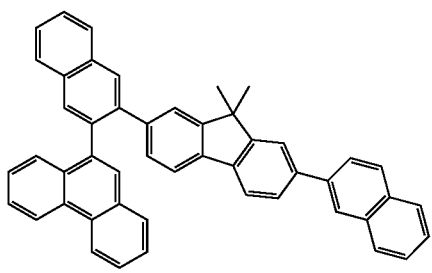
2-12
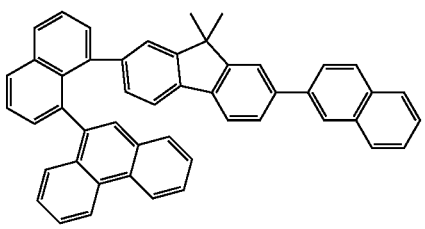
2-13
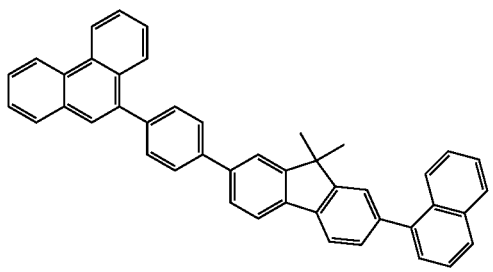
2-14
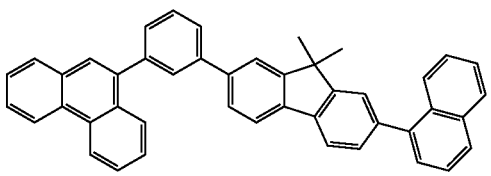
2-15
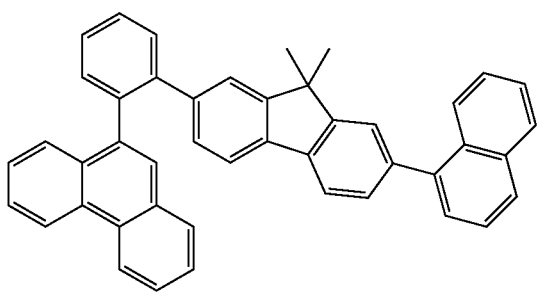
2-16
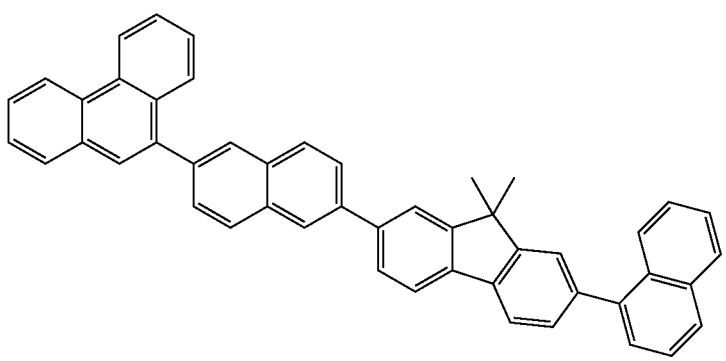

-continued
2-17
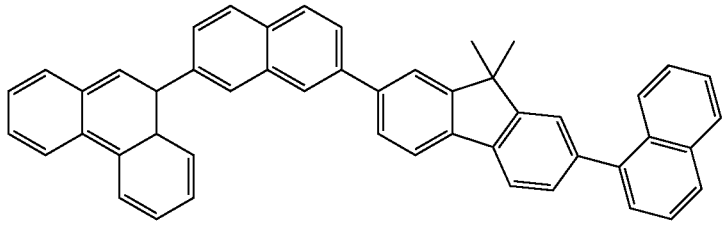
2-18
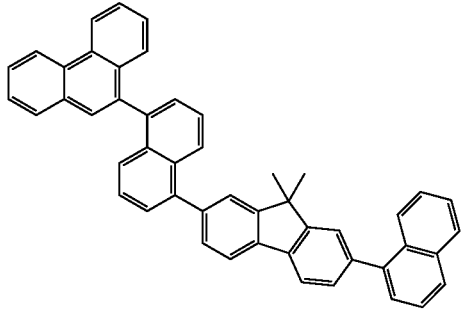
2-19
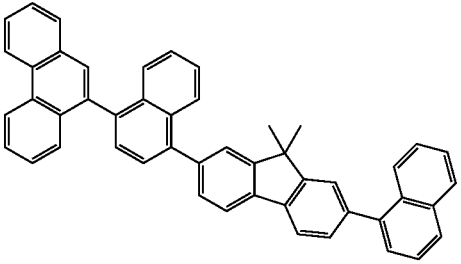
2-20
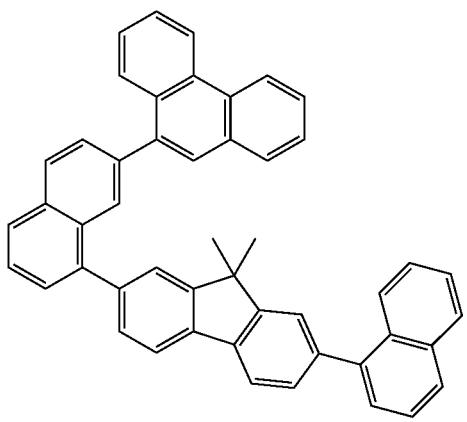
2-21
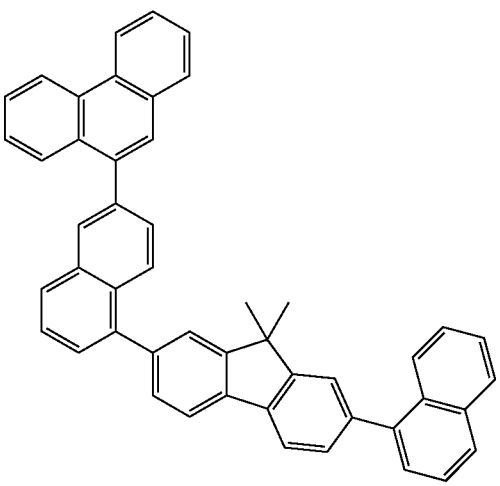
2-22
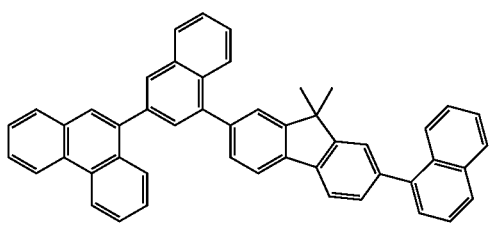
2-23
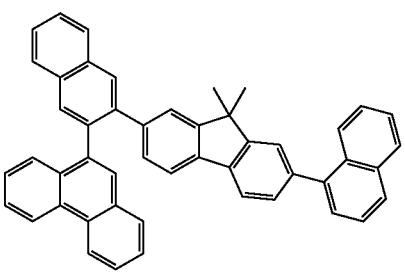
2-24
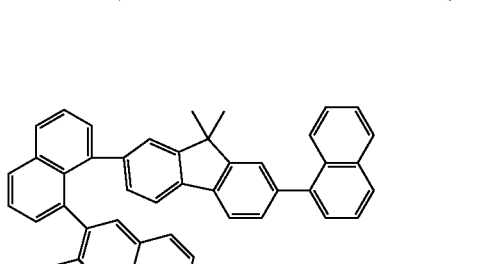
2-25
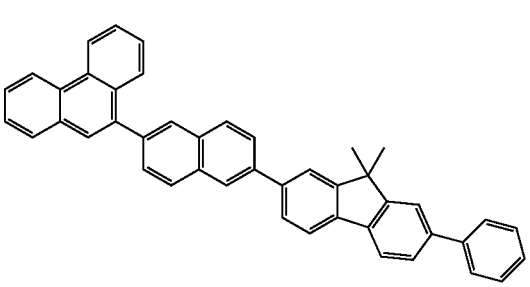

-continued
2-26
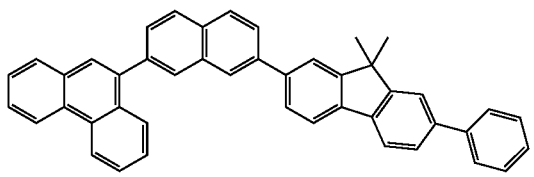
2-27
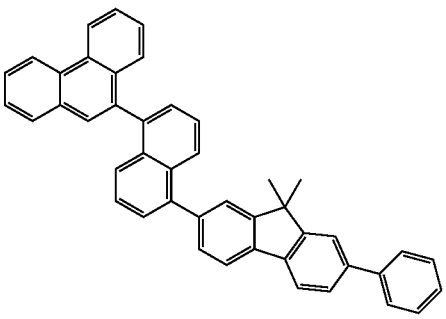
2-28
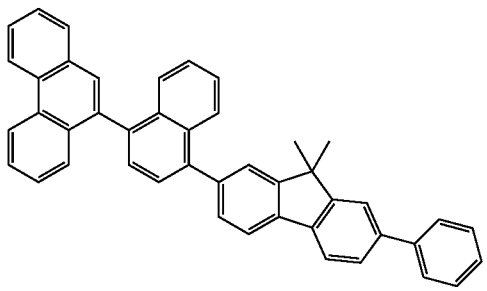
2-29
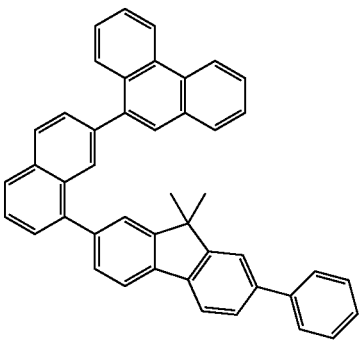
2-30
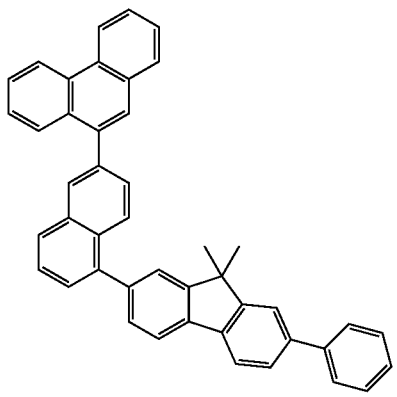
2-31
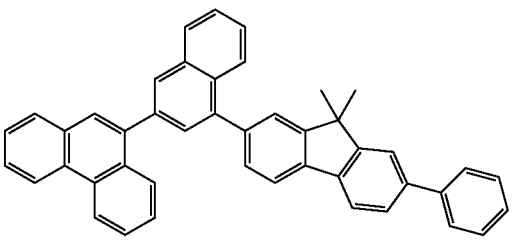
2-32
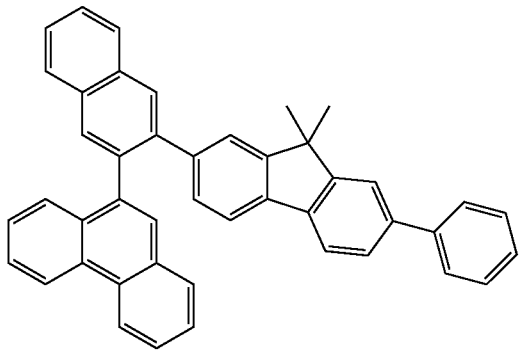
2-33
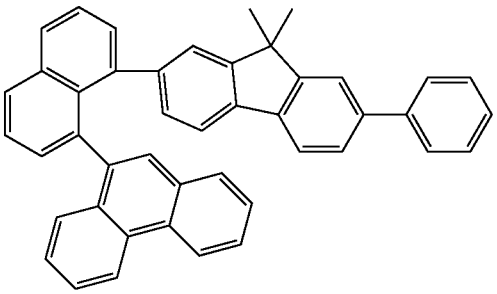

-continued
2-34
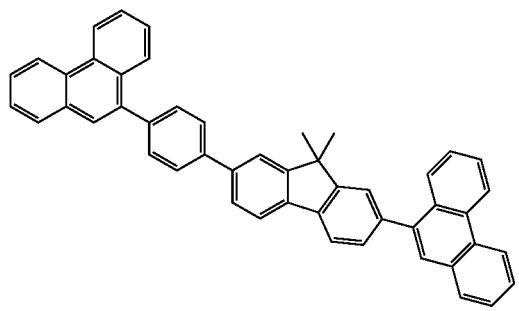
2-35
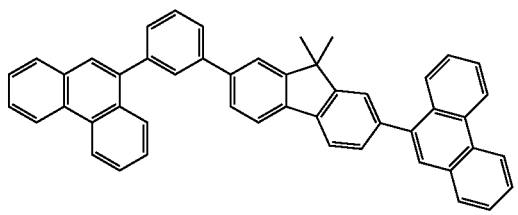
2-36
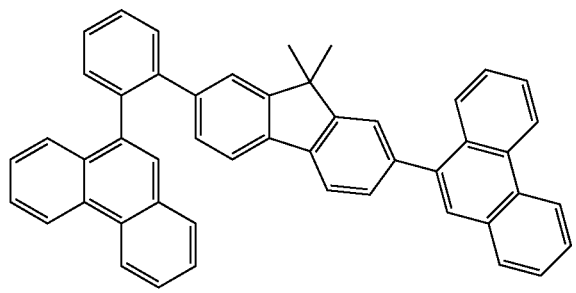
2-37
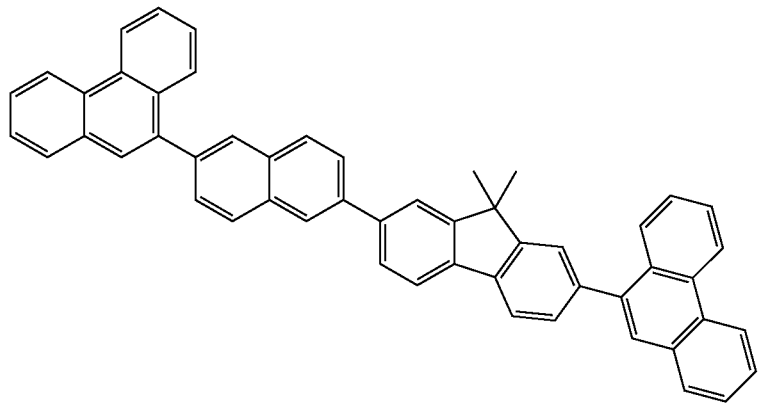
2-38
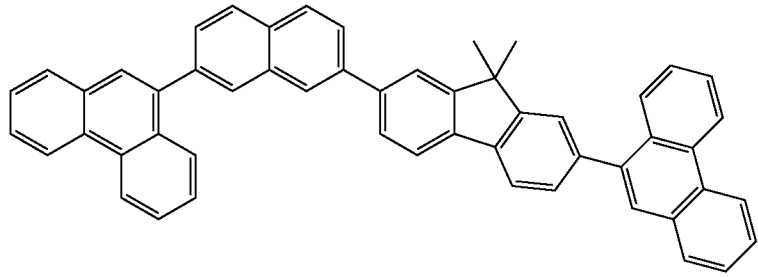

-continued
2-39
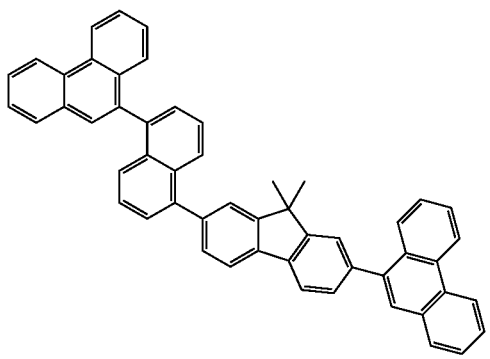
2-40
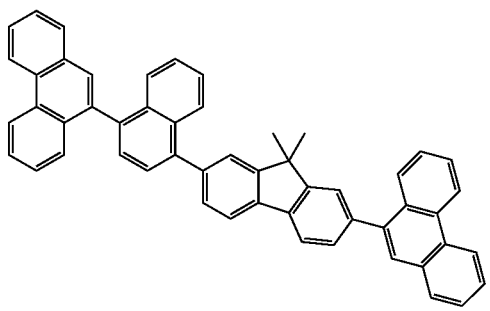
2-41
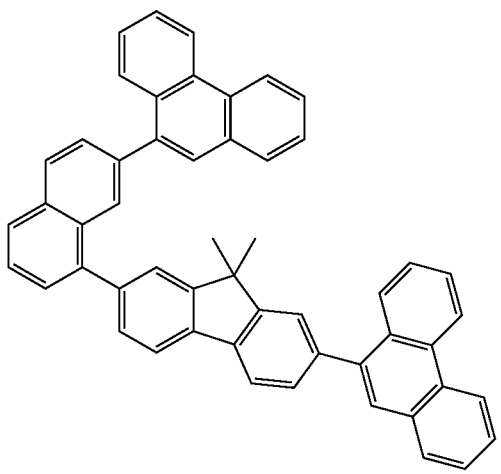
2-42
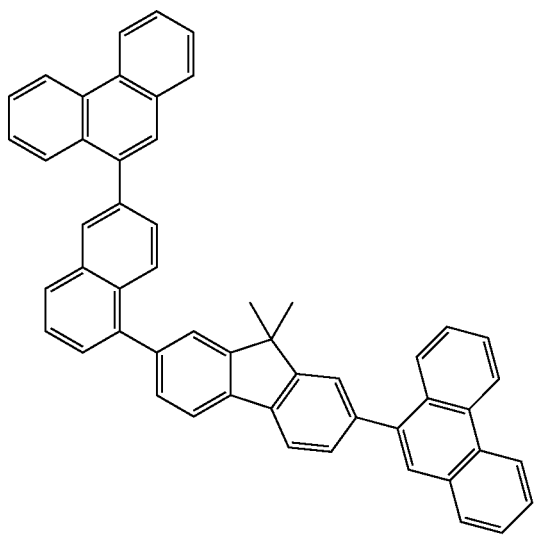
2-43
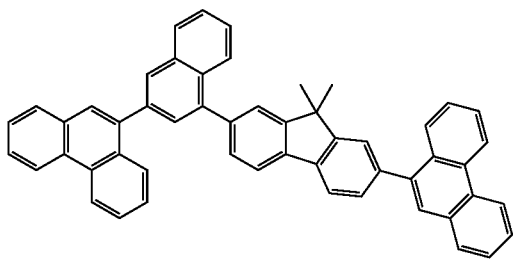
2-44
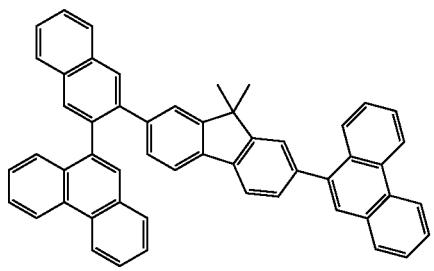
2-45
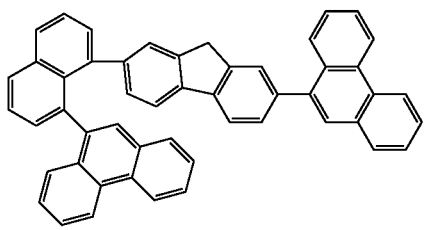
2-74
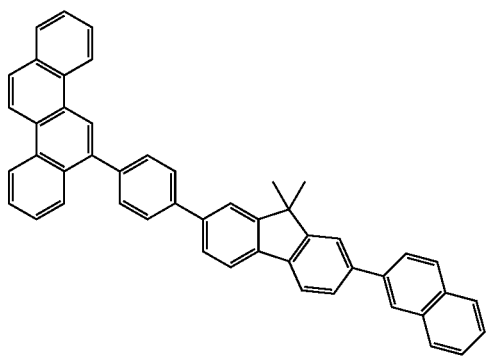

-continued
2-75
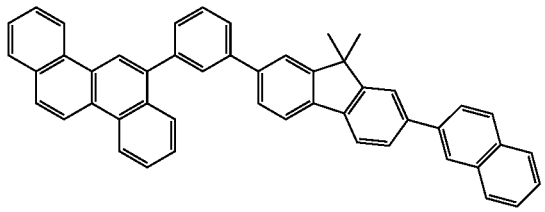
2-76
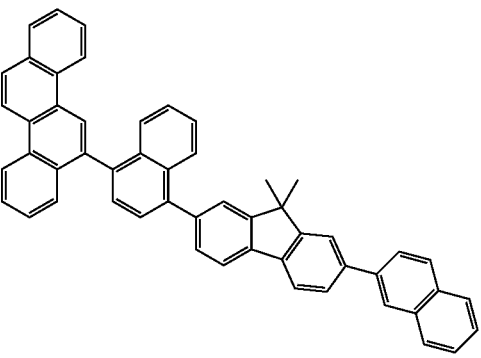
2-77
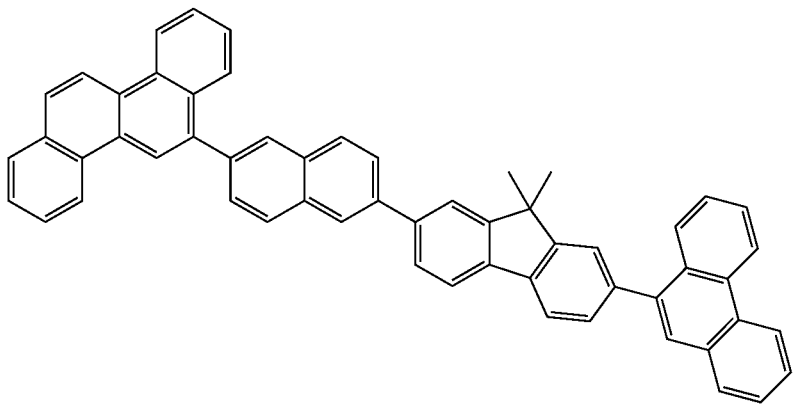
2-78
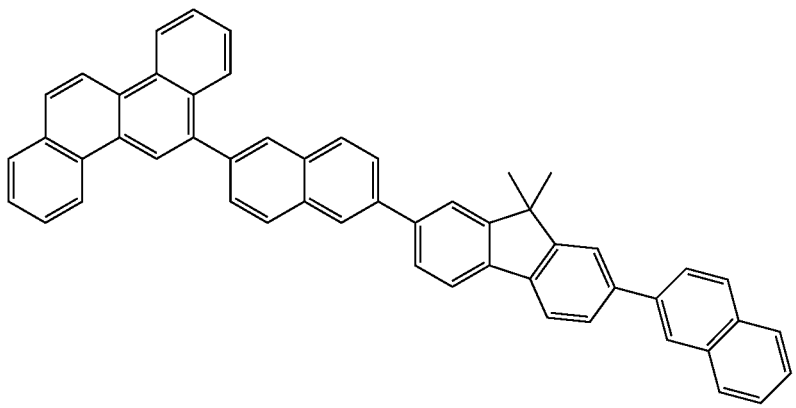
2-79
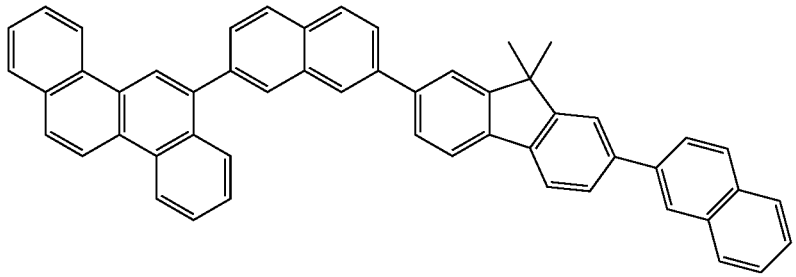

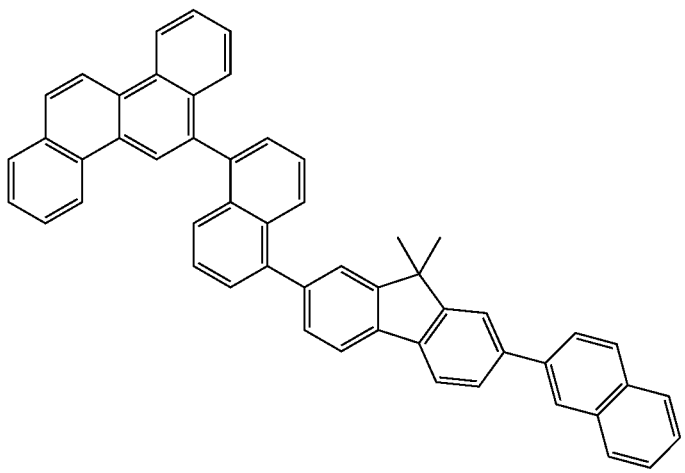
2-80
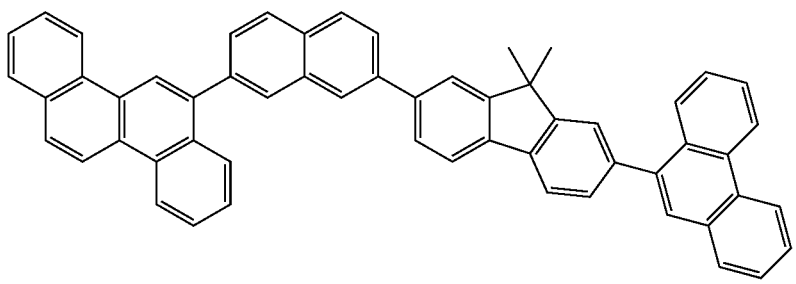
2-81
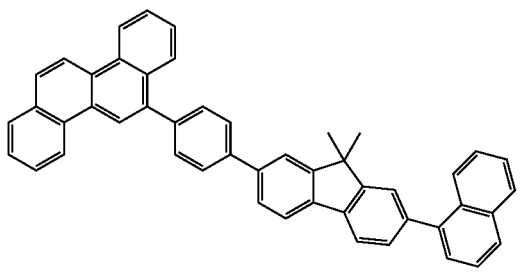
2-82
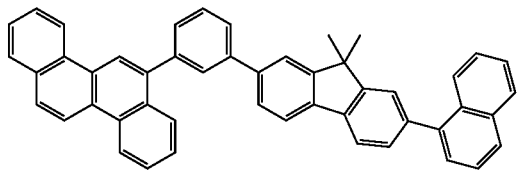
2-83
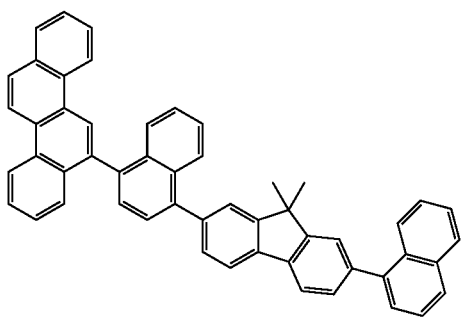
2-84
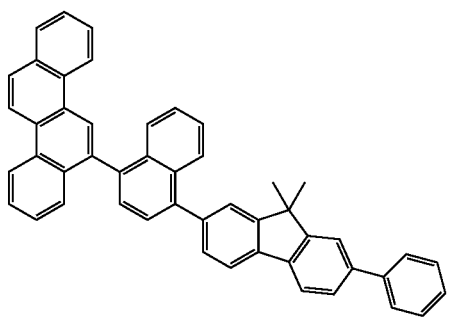
2-85

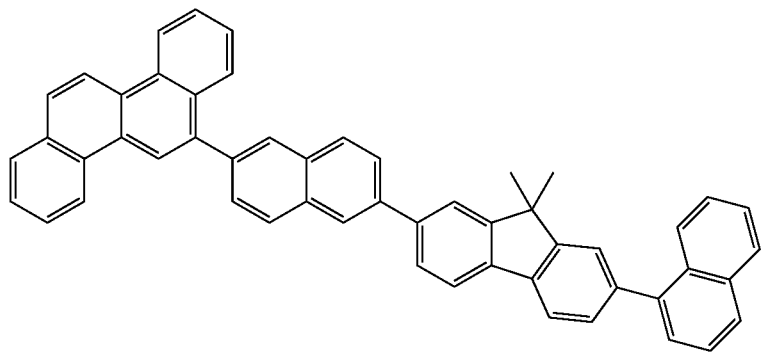
2-86
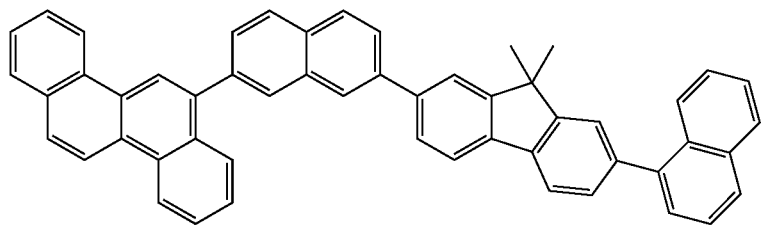
2-87
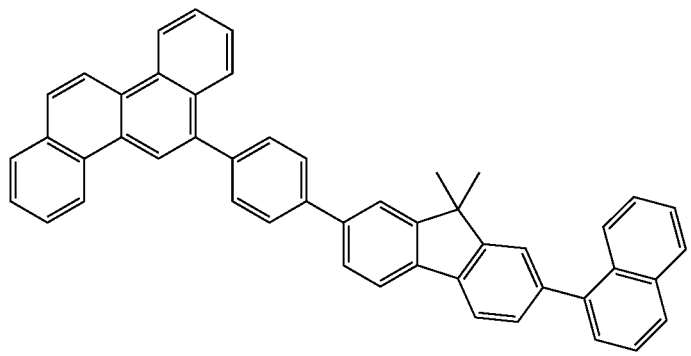
2-88
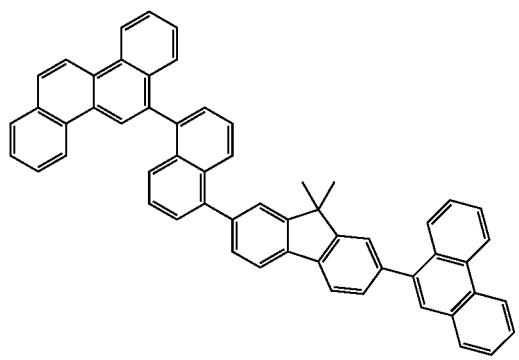
2-89
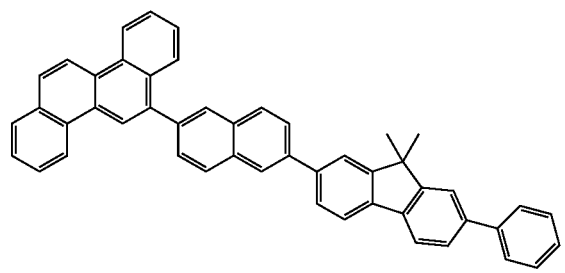
2-90

-continued
2-91
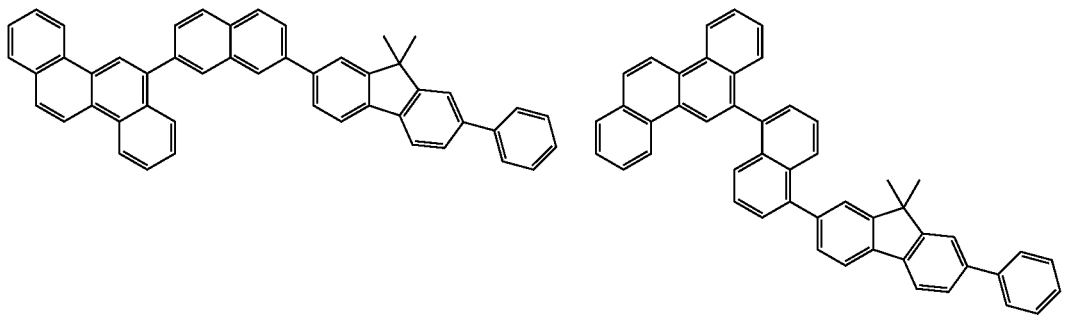
2-92
2-93
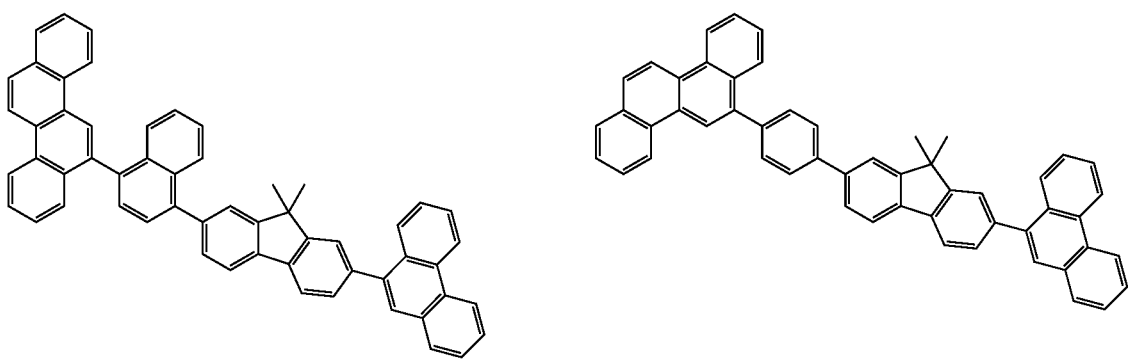
2-94
2-95
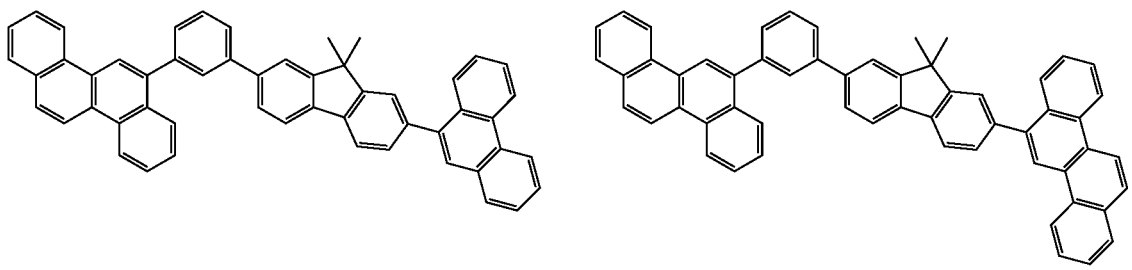
2-96
2-97
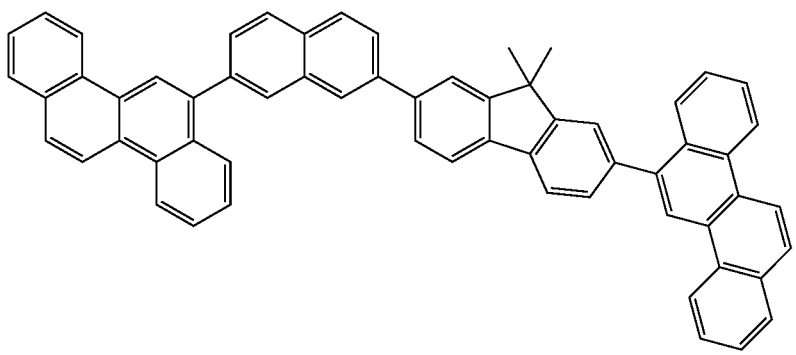
2-98
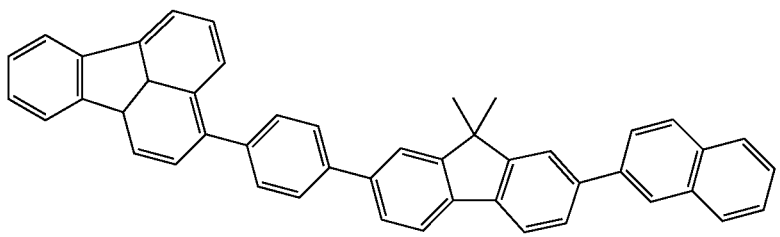

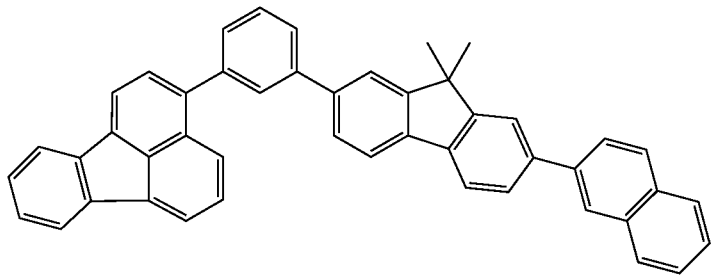
2-99
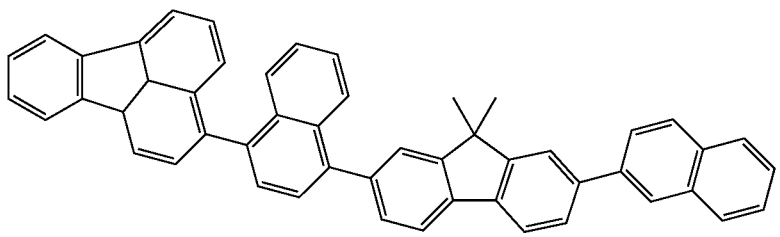
2-100
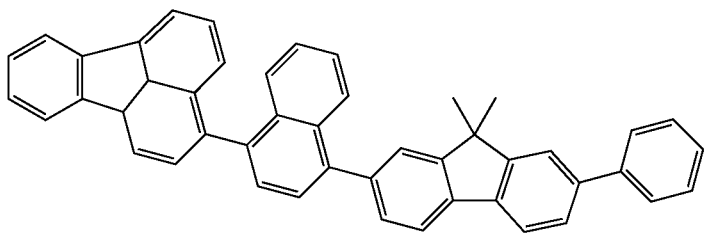
2-101
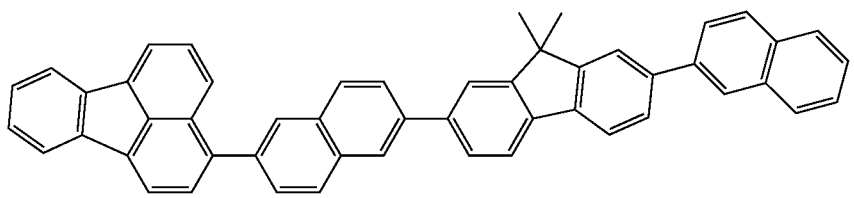
2-102
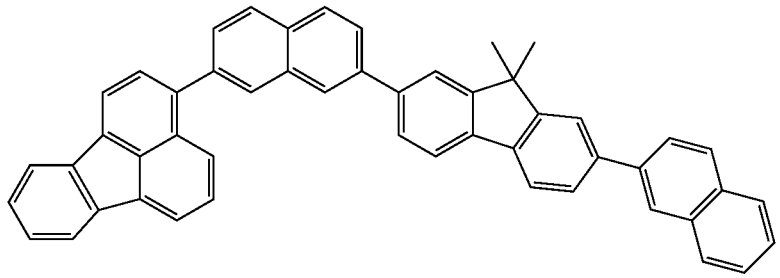
2-103
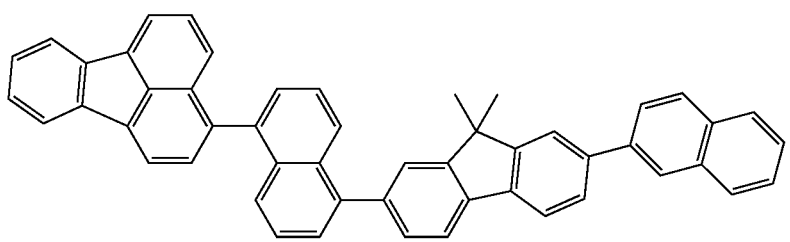
2-104

2-105
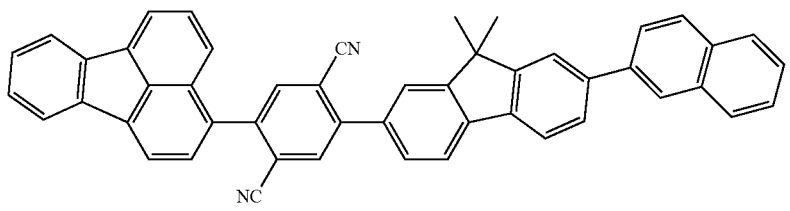
2-106
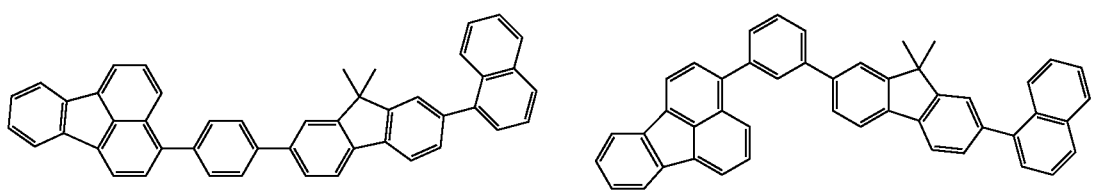
2-107
2-108
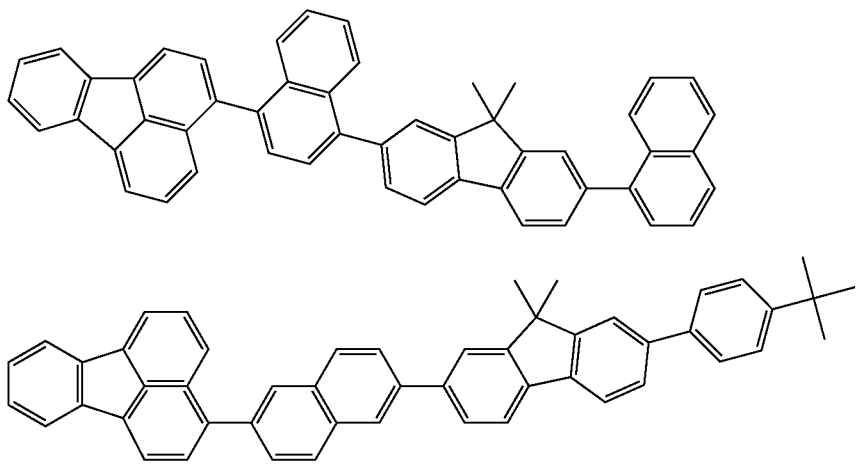
2-109
2-110
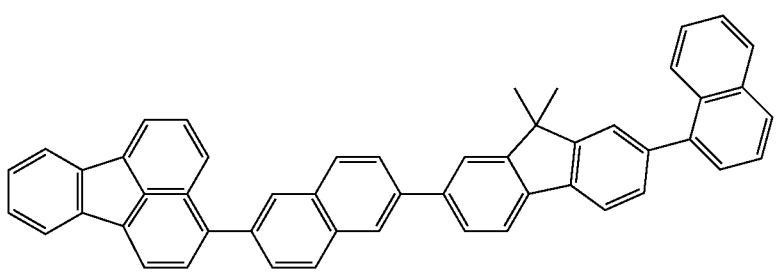
2-111
2-112
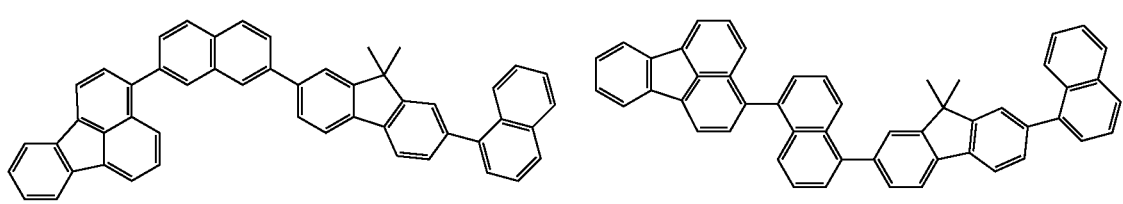
2-113
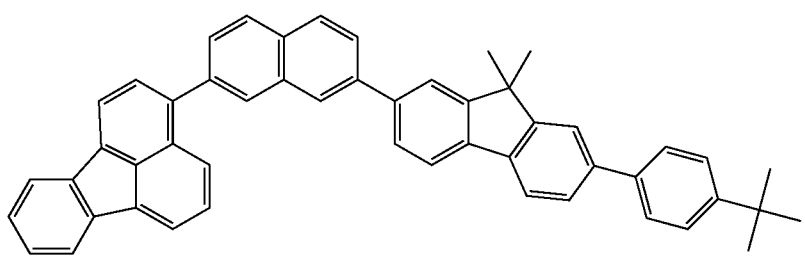

-continued
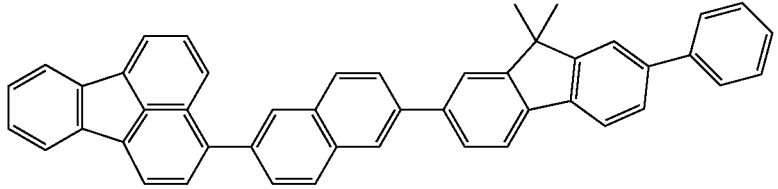
2-114
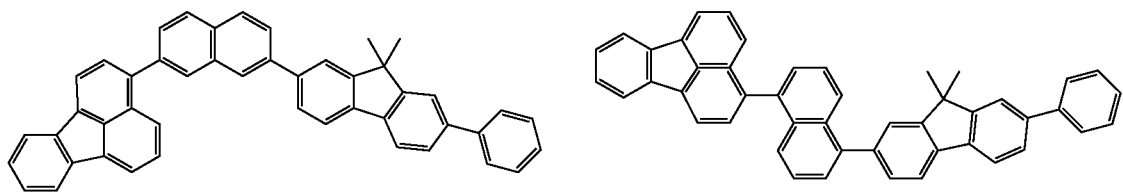
2-115
2-116
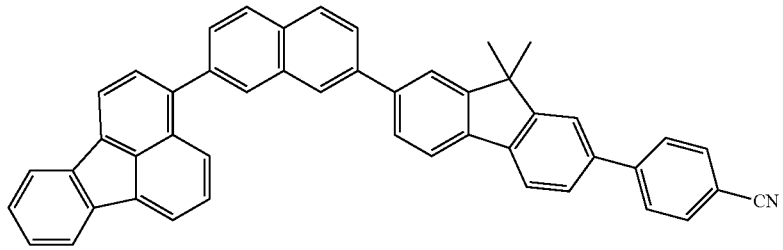
2-117
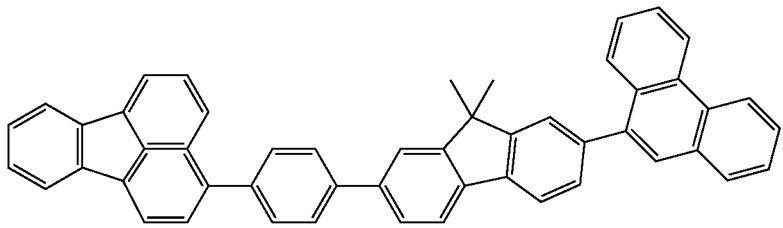
2-118
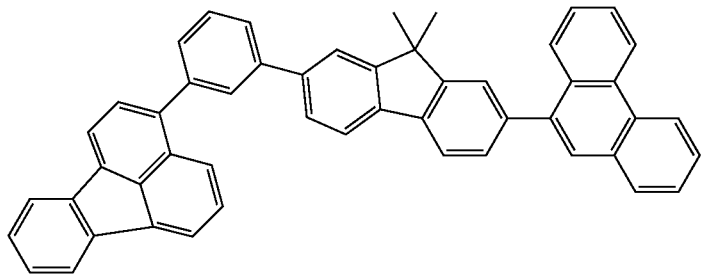
2-119
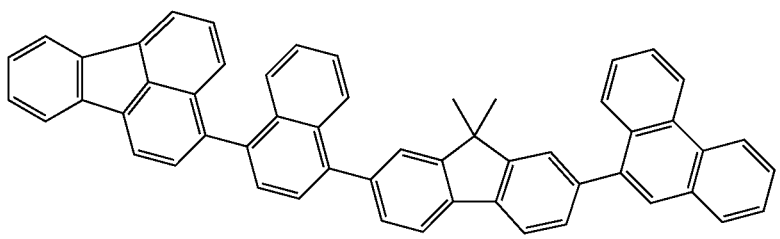
2-120

-continued
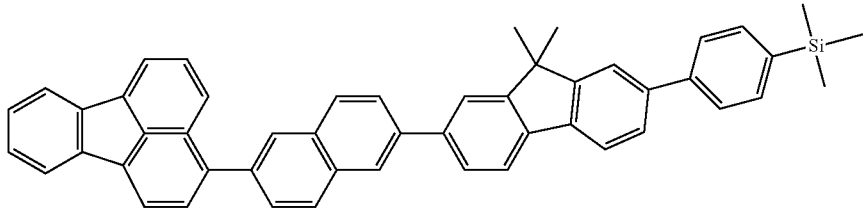
2-121
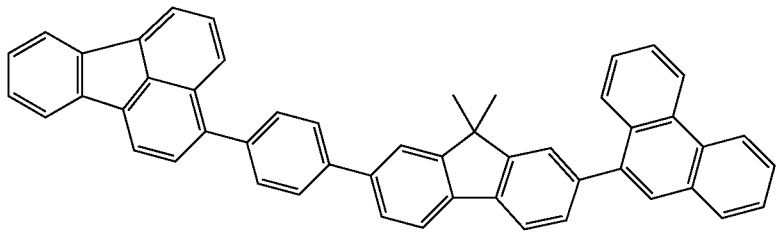
2-122
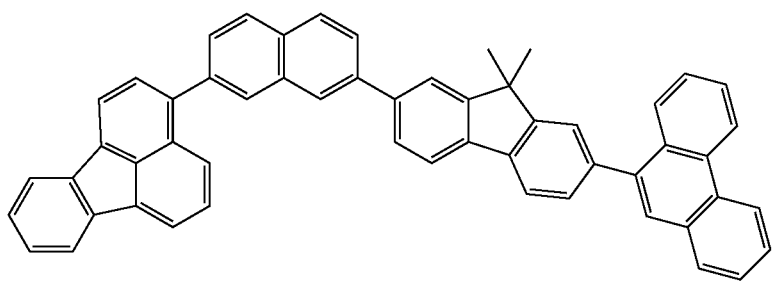
2-123
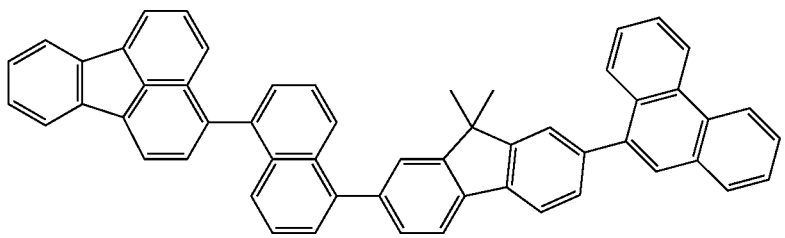
2-124
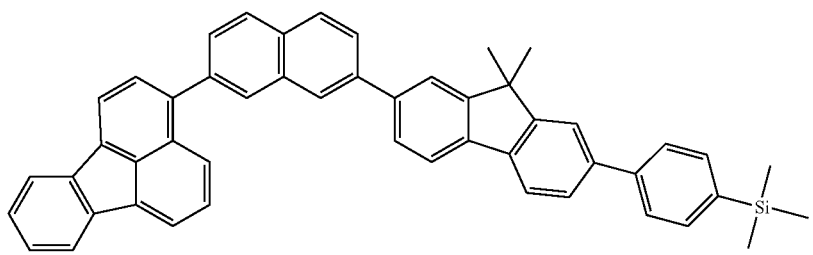
2-125
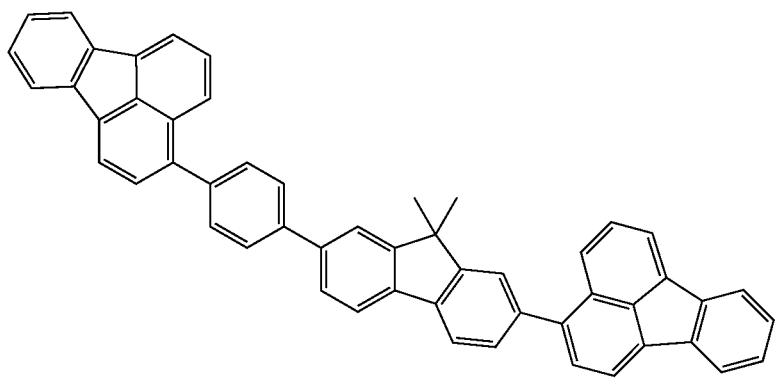
2-126

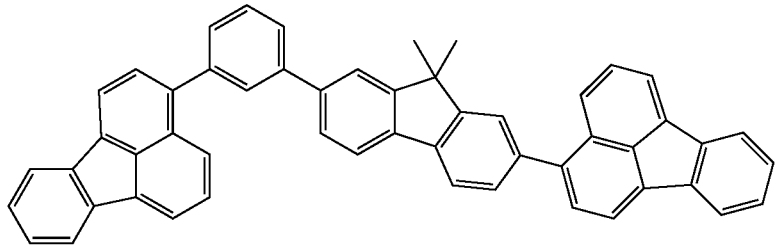
2-127
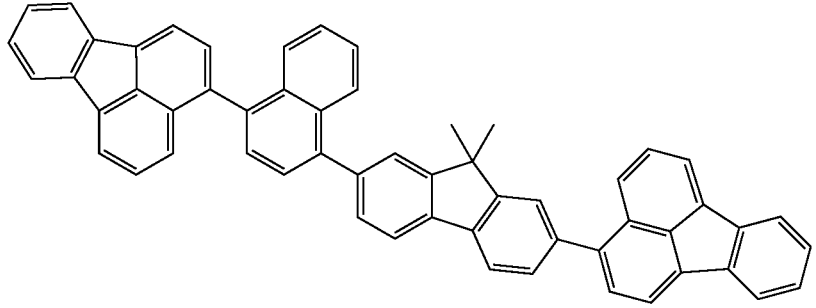
2-128
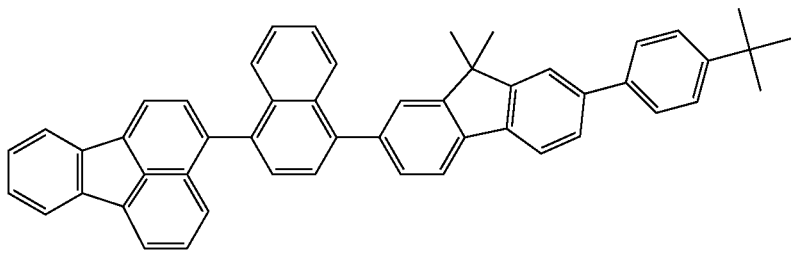
2-129
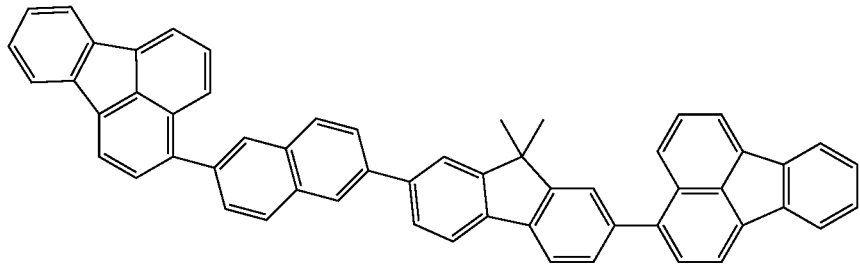
2-130
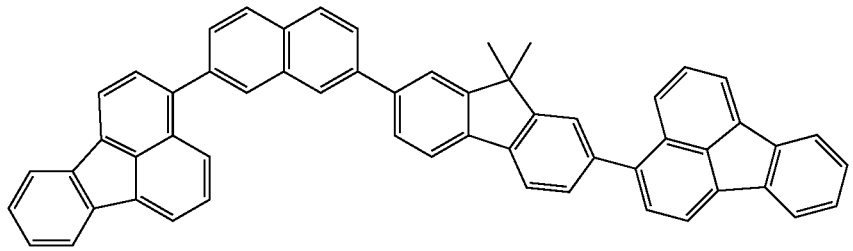
2-131
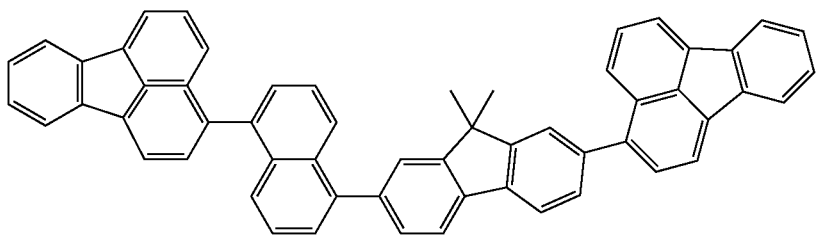
2-132

-continued
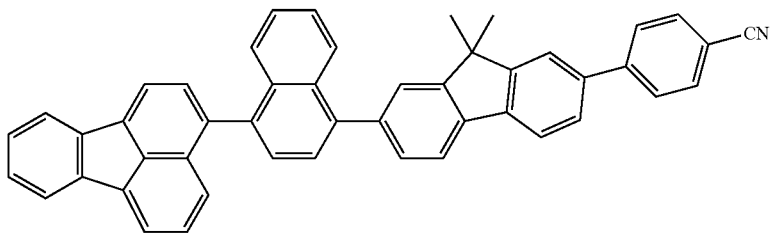
2-133
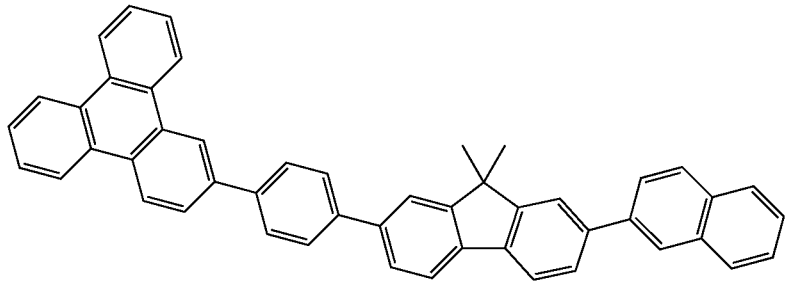
2-134
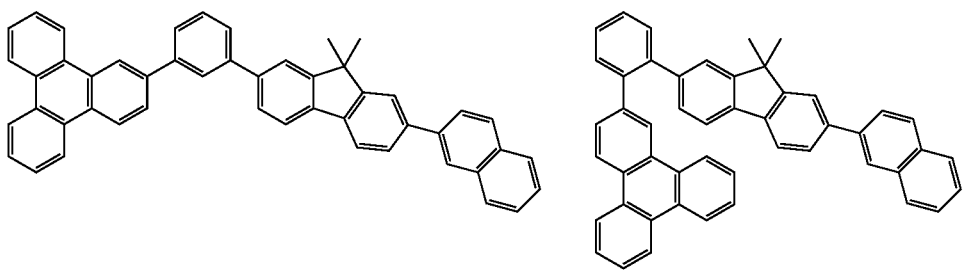
2-135　　　　　2-136
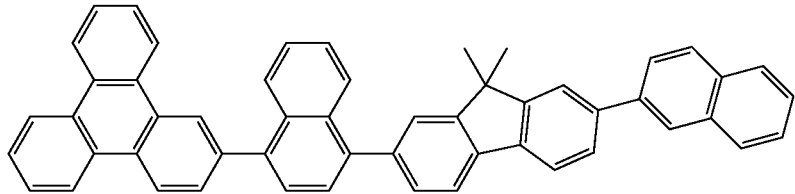
2-137
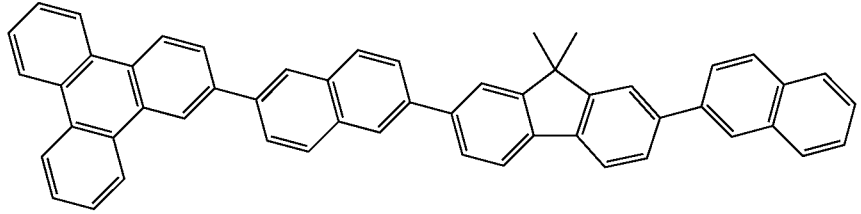
2-138
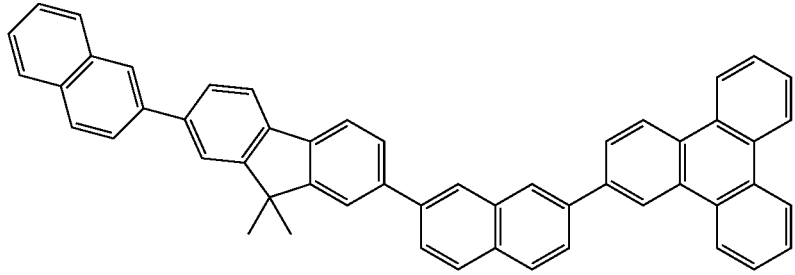
2-139

-continued
2-140
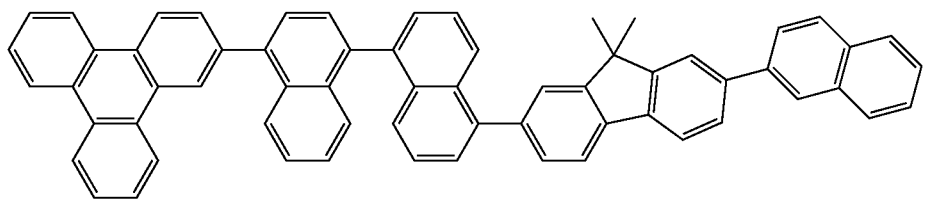
2-141
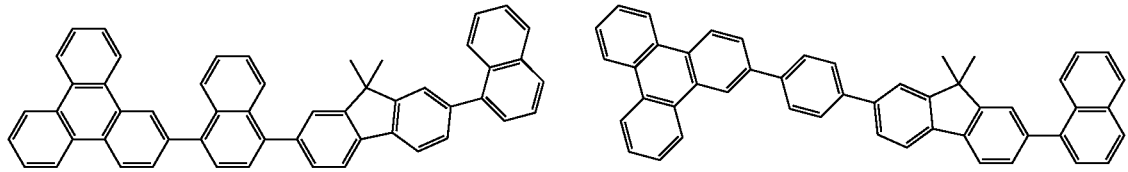
2-142
2-143
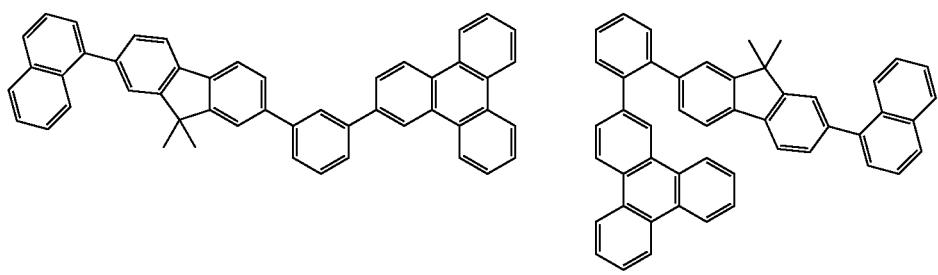
2-144
2-145
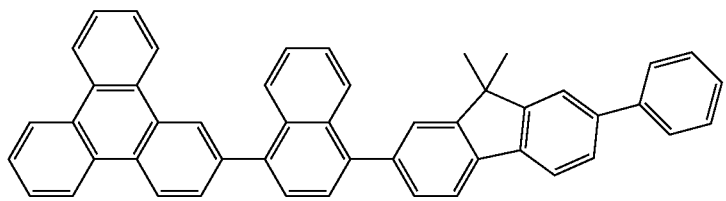
2-146
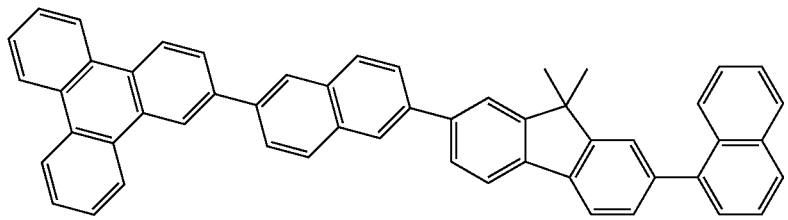
2-147
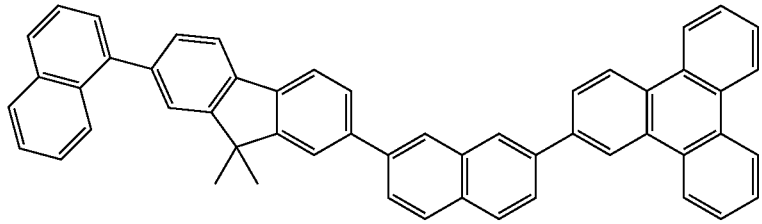
2-148
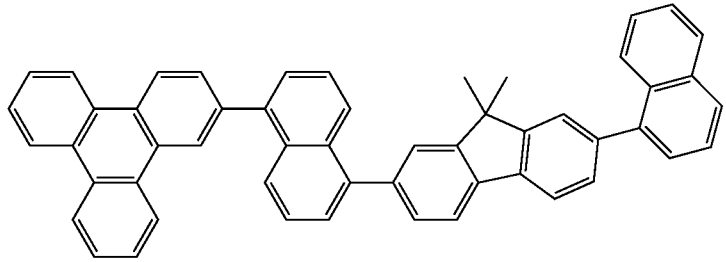

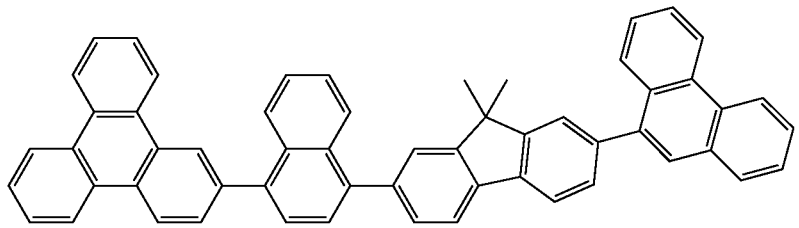
2-149
2-150
2-151
2-152
2-153
2-154

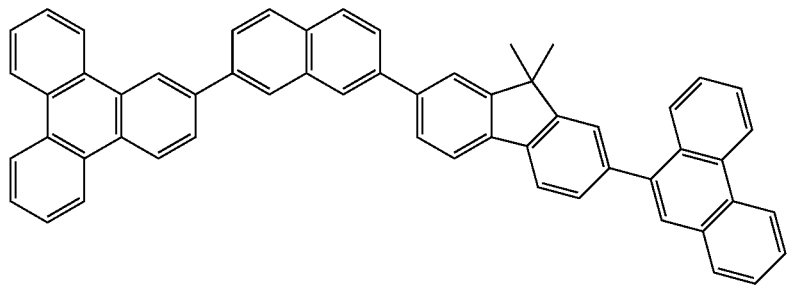
2-155
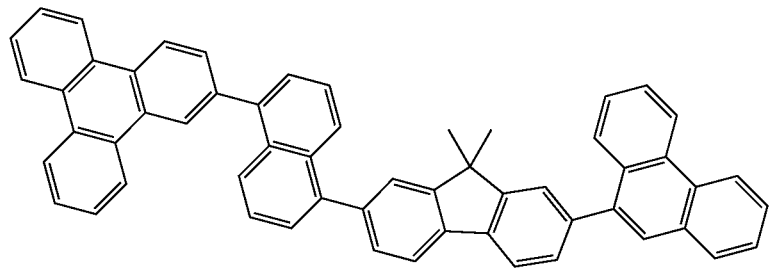
2-156
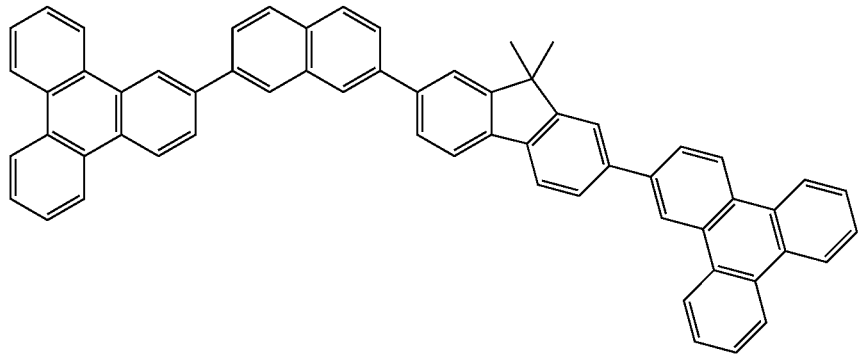
2-157
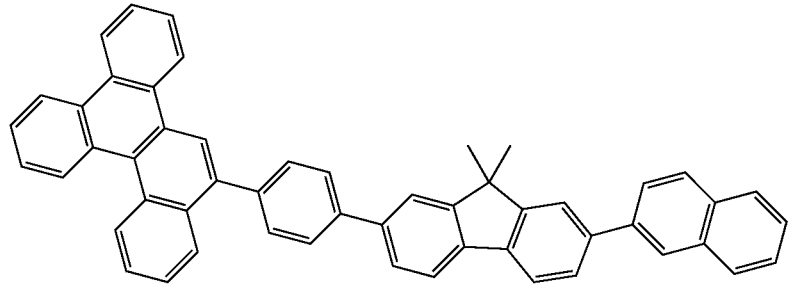
2-158
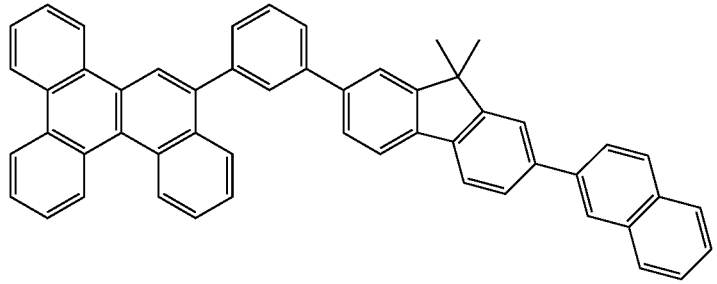
2-159

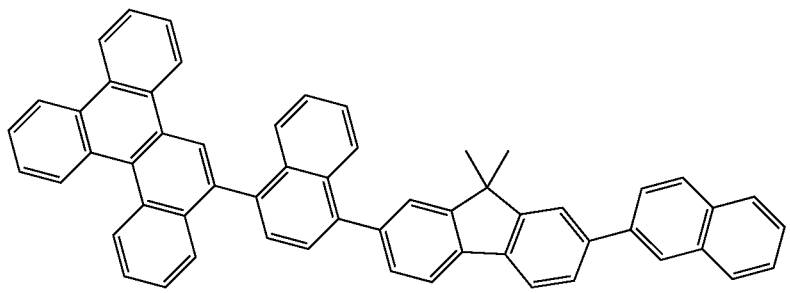
2-160
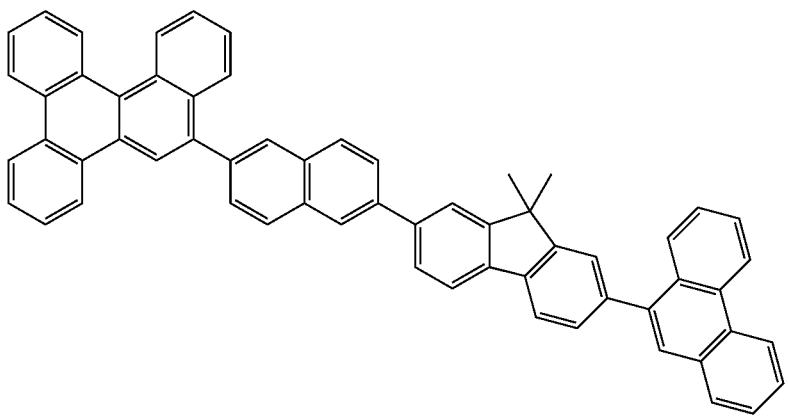
2-161
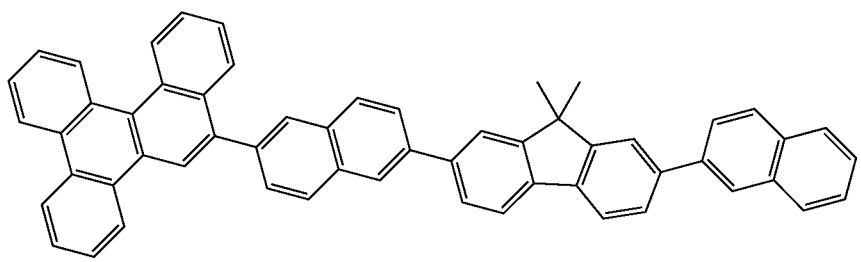
2-162
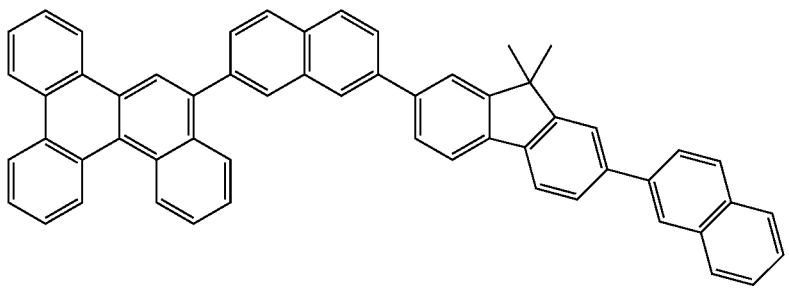
2-163
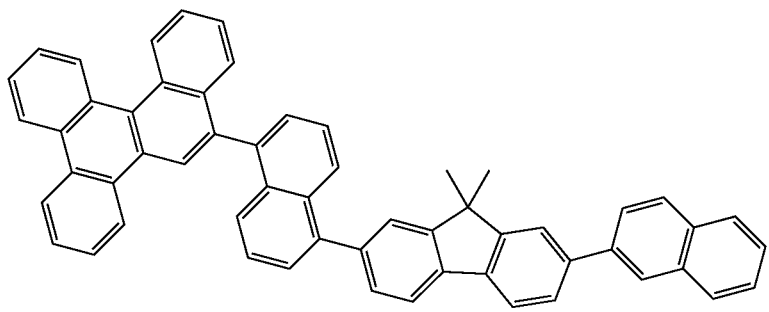
2-164

-continued
2-165
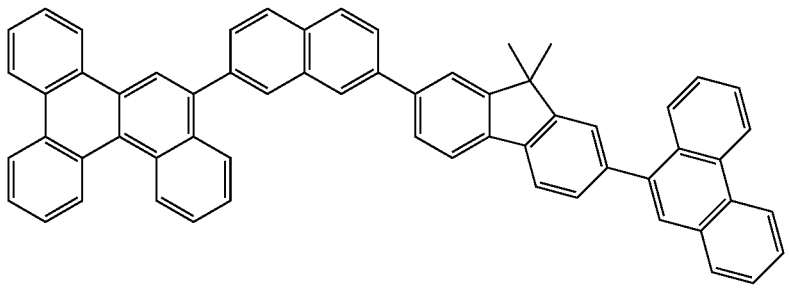
2-166
2-167
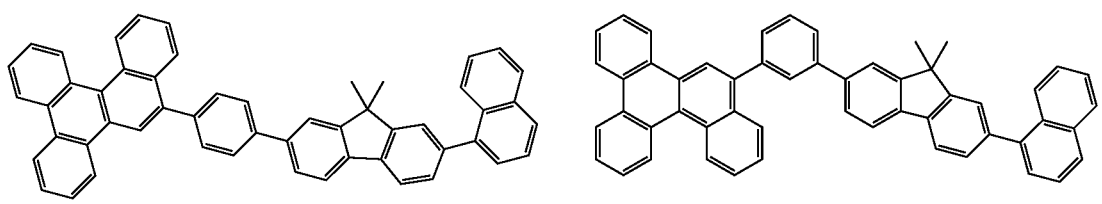
2-168
2-169
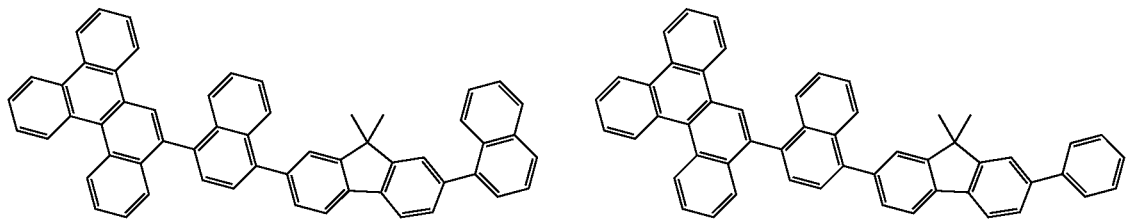
2-170
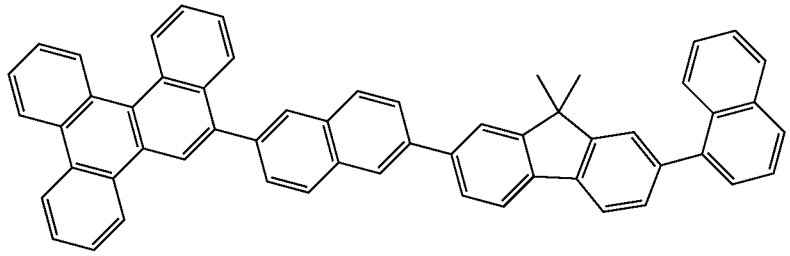
2-171
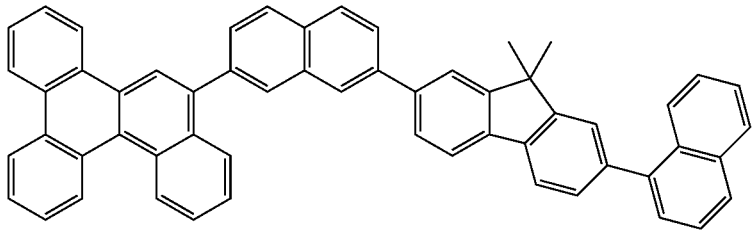
2-172
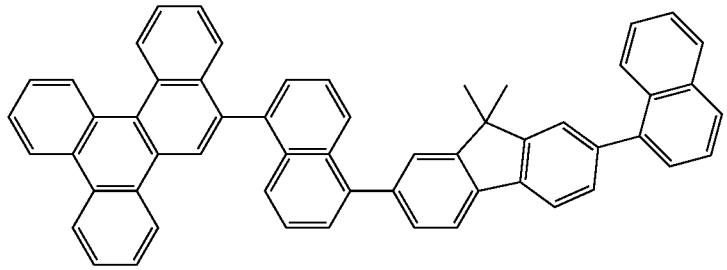

-continued
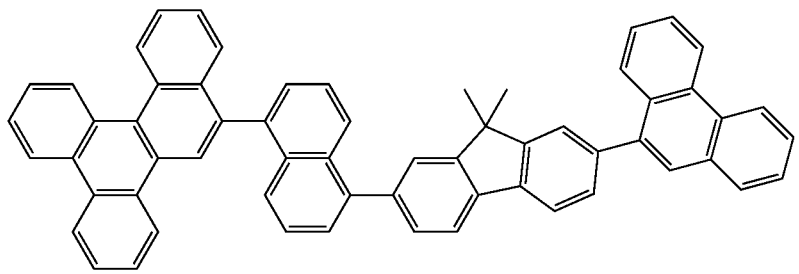
2-173
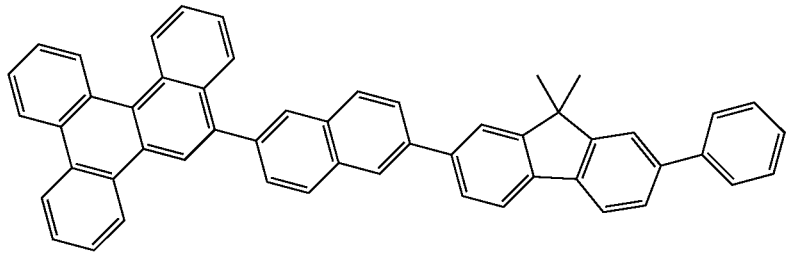
2-174
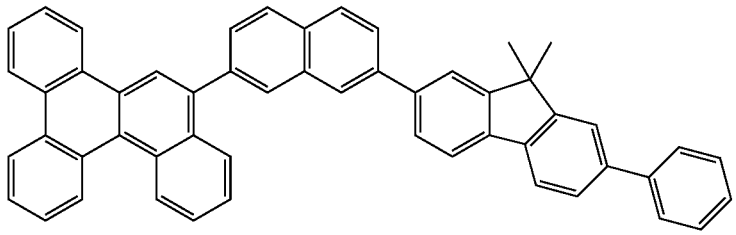
2-175
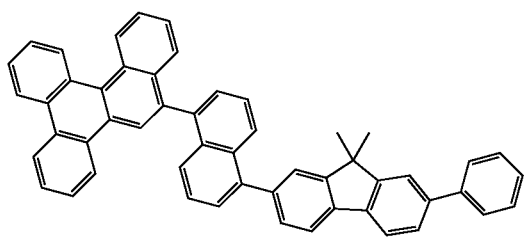
2-176
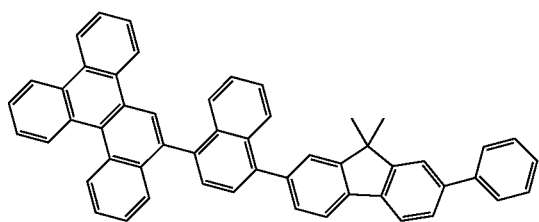
2-177
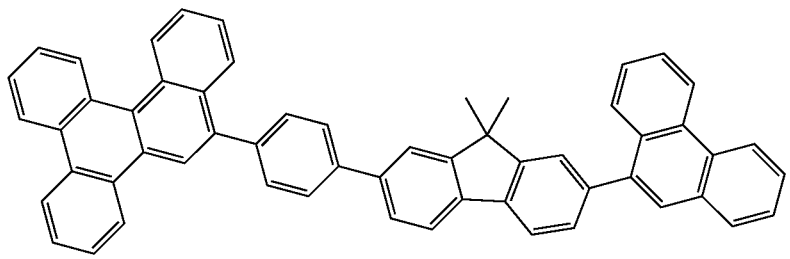
2-178
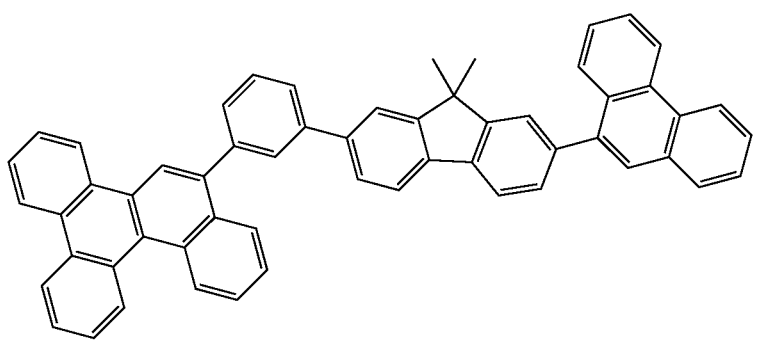
2-179

-continued
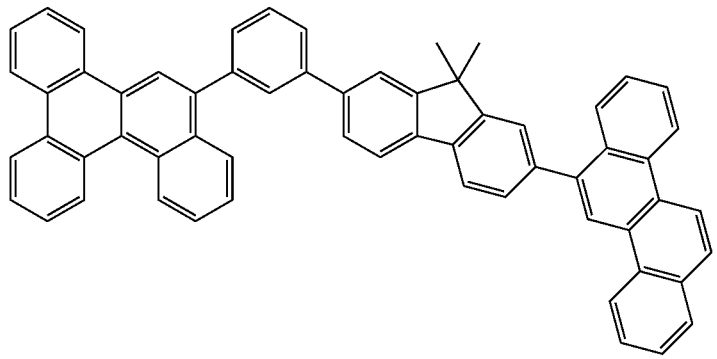
2-180
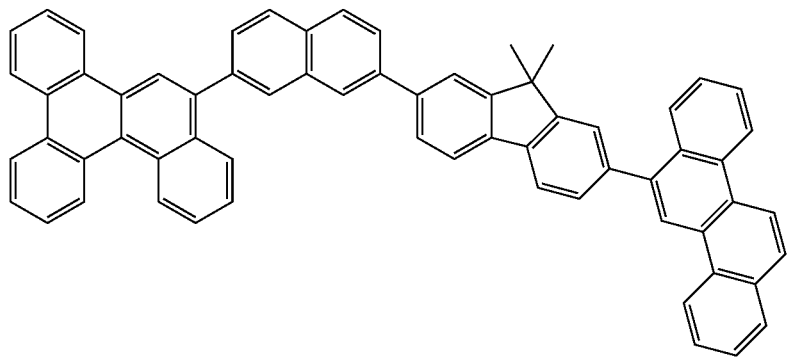
2-181
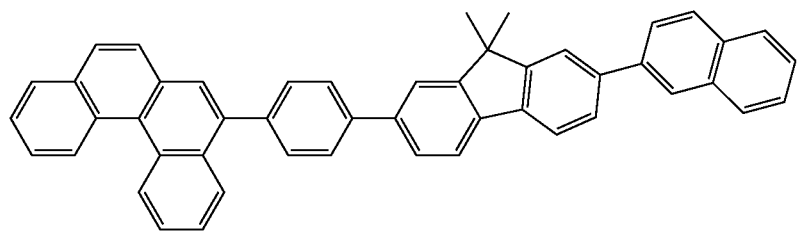
2-183
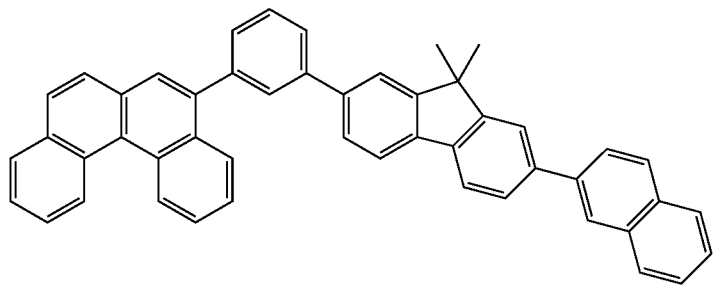
2-184
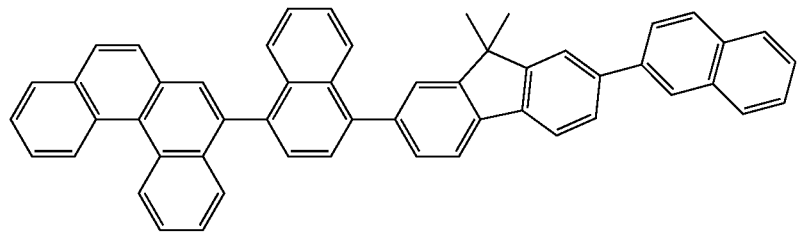
2-185

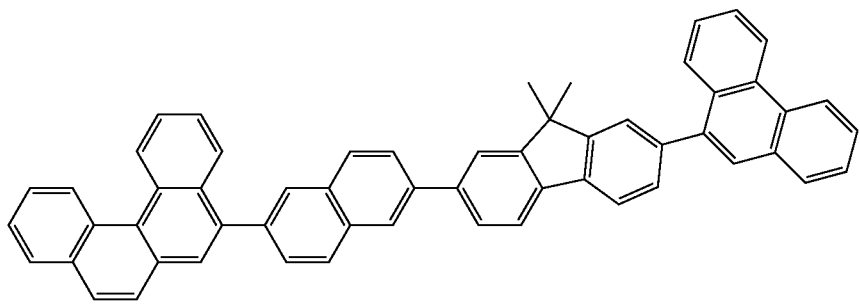
2-186
2-187
2-188
2-189
2-190

-continued
2-191
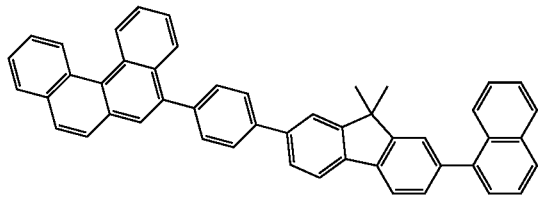
2-192
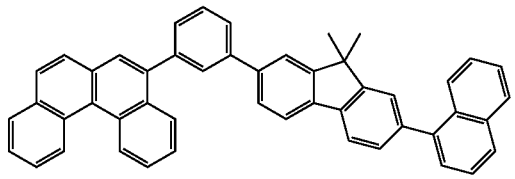
2-193
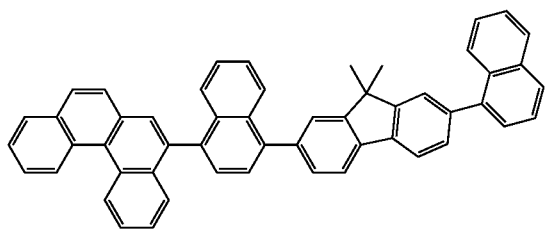
2-194
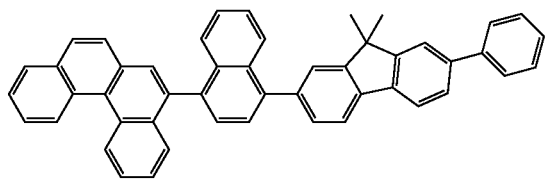
2-195
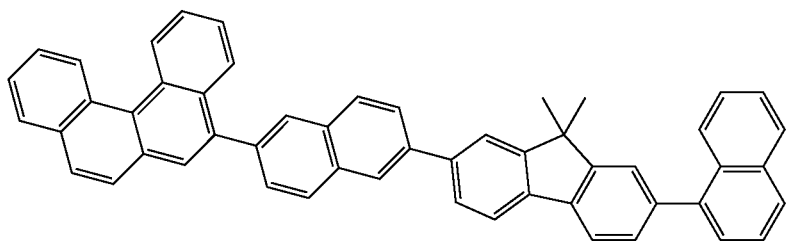
2-196
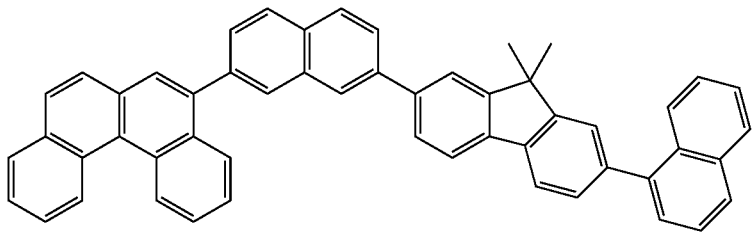
2-197
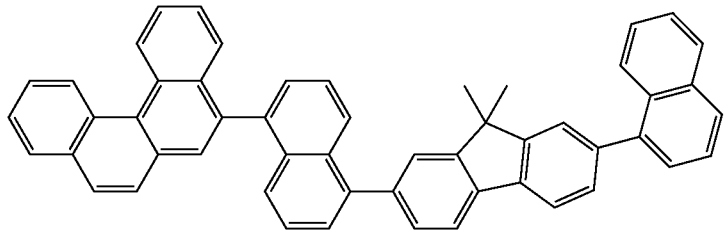
2-198
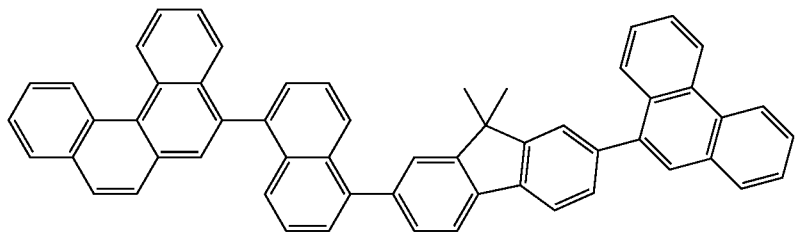

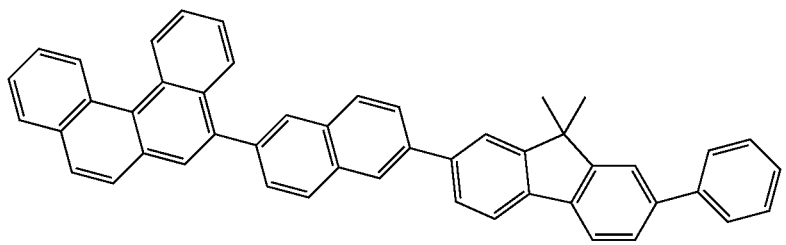
2-199
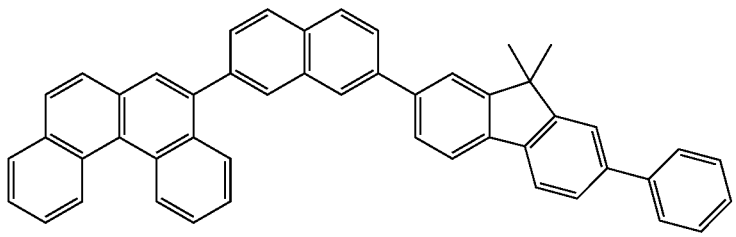
2-200
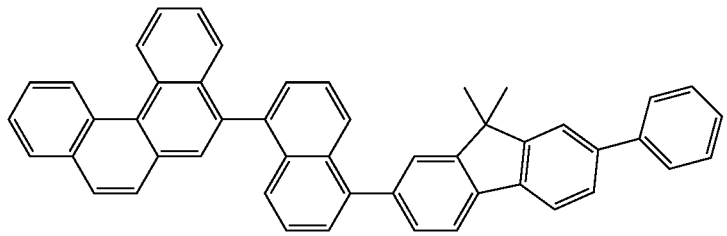
2-201
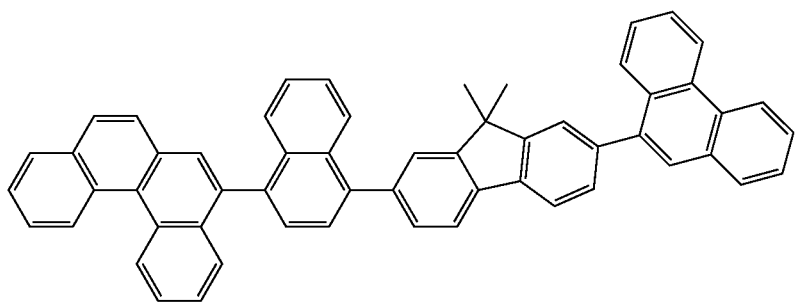
2-202
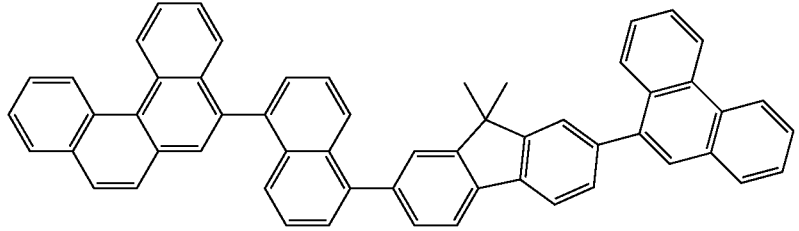
2-203
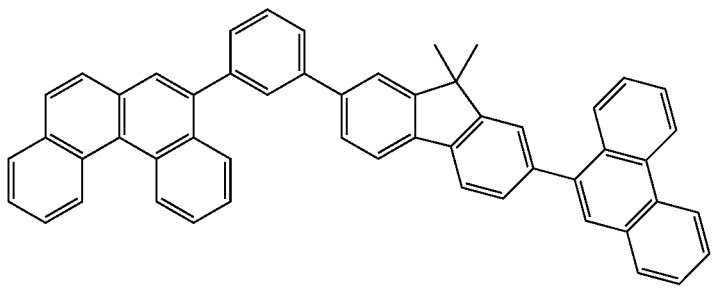
2-204

-continued
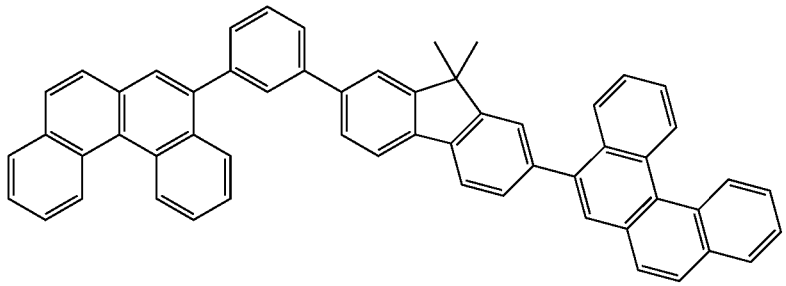
2-205
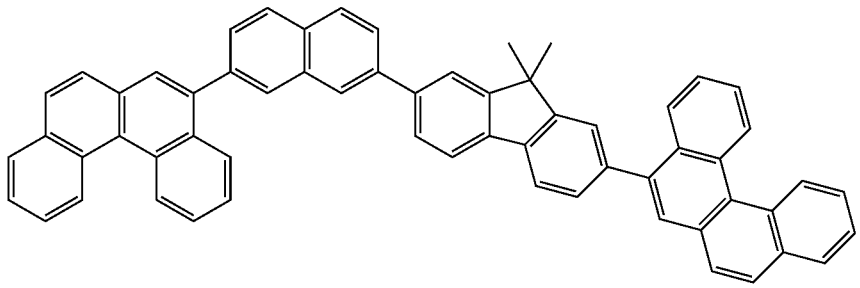
2-206
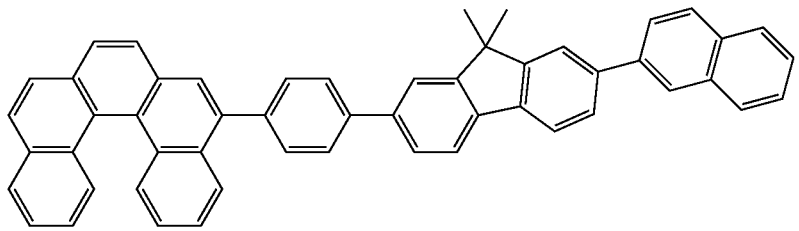
2-207
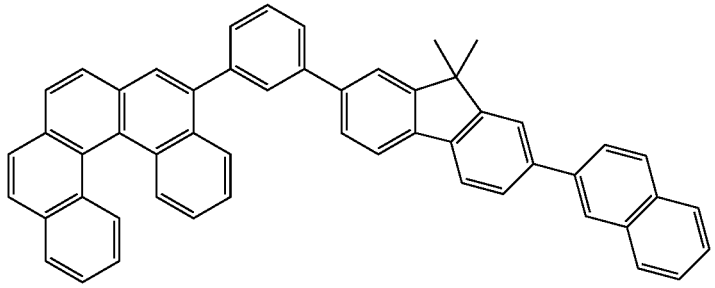
2-208
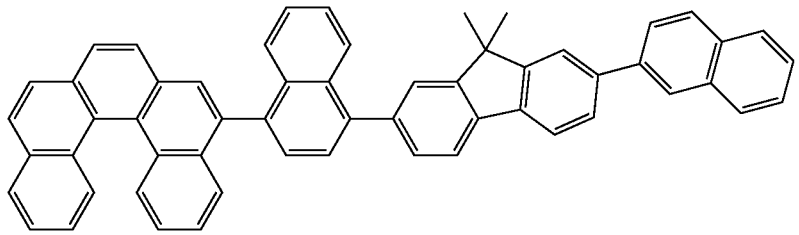
2-209

-continued
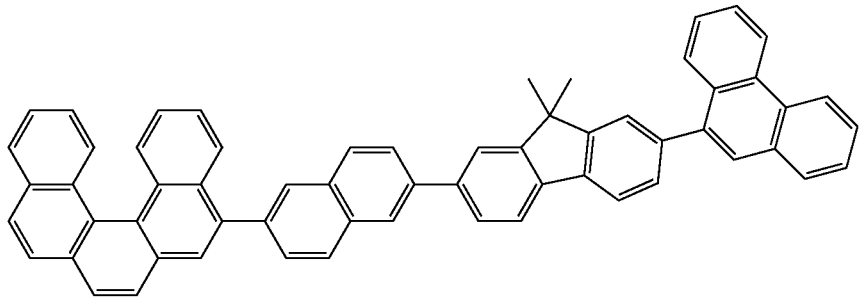
2-210
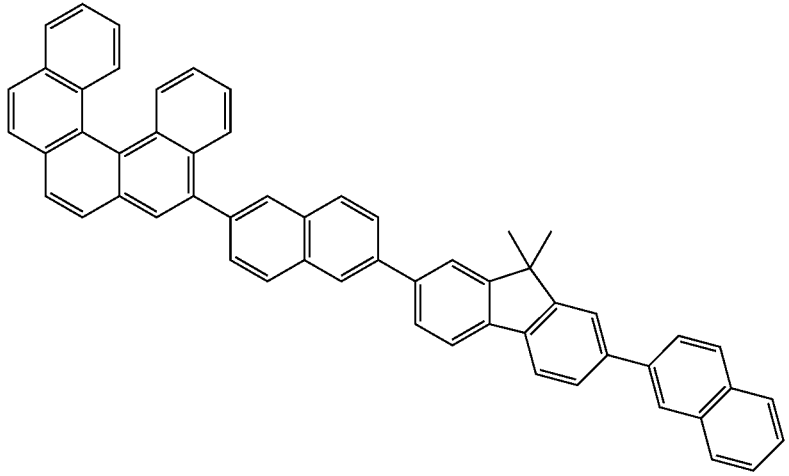
2-211
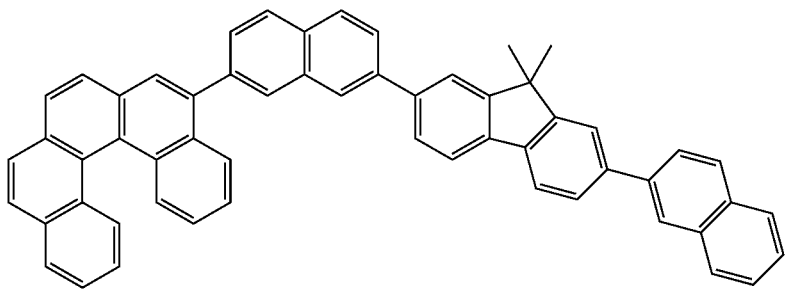
2-212
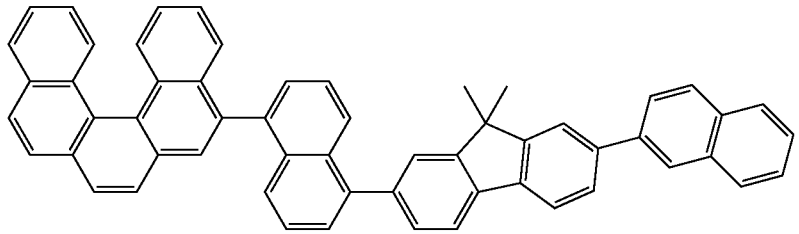
2-213
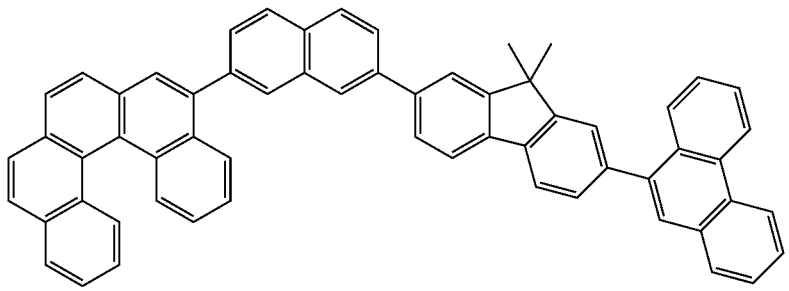
2-214

2-215
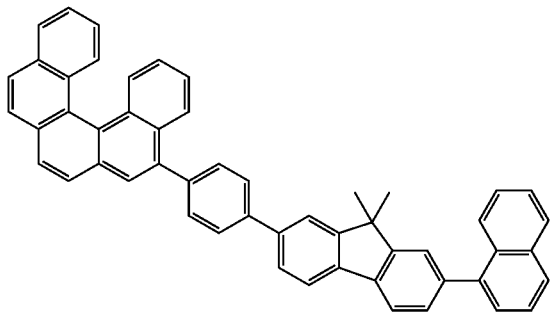
2-216
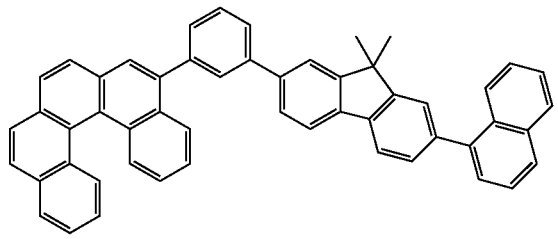
2-217
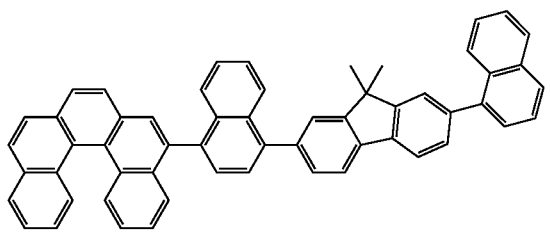
2-218
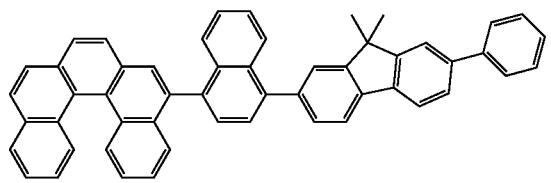
2-219
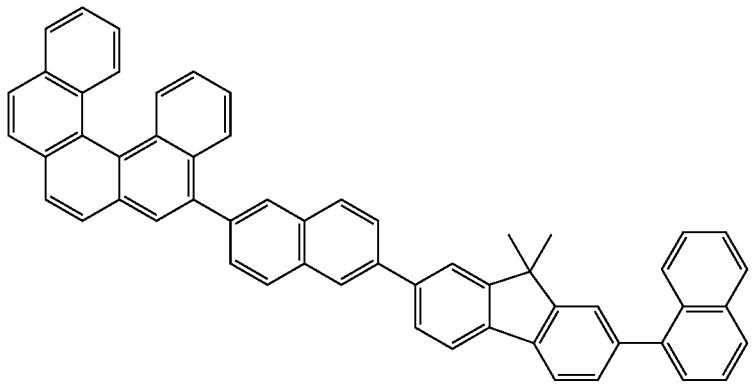
2-220
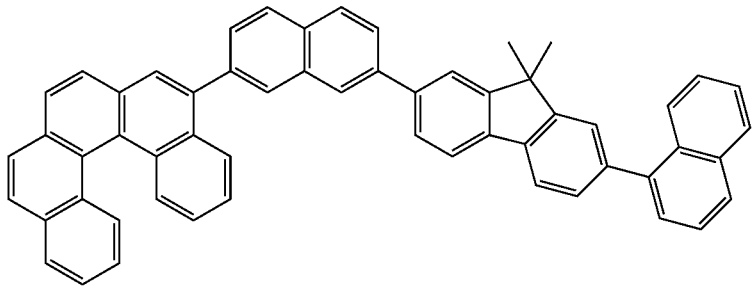
2-221
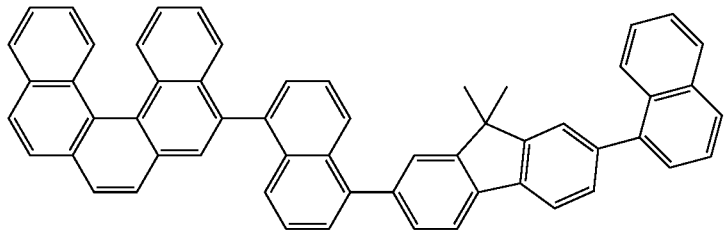

-continued
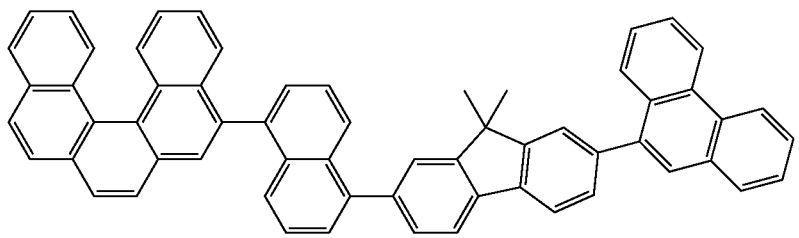
2-222
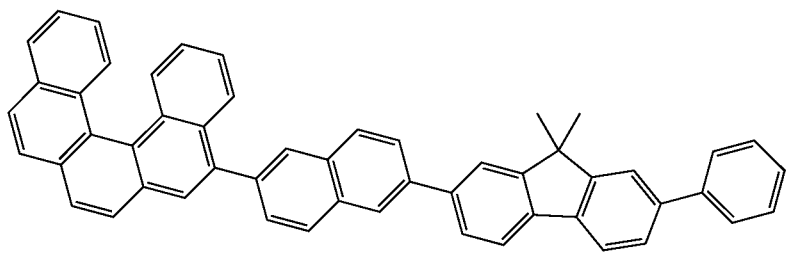
2-223
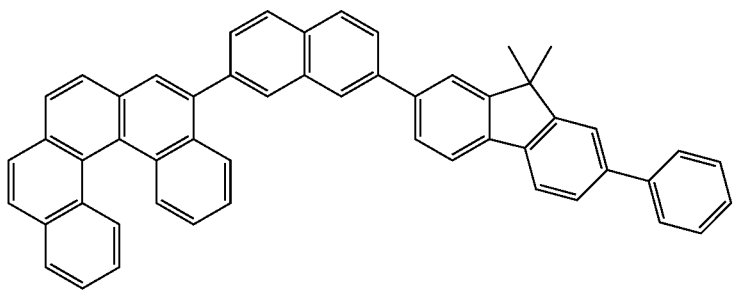
2-224
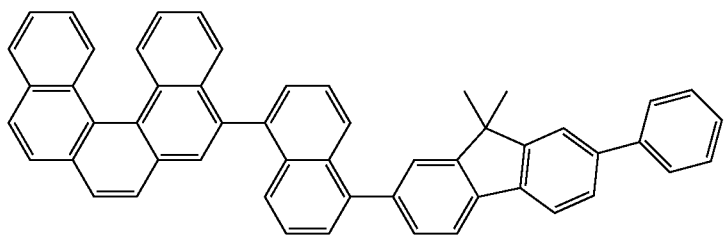
2-225
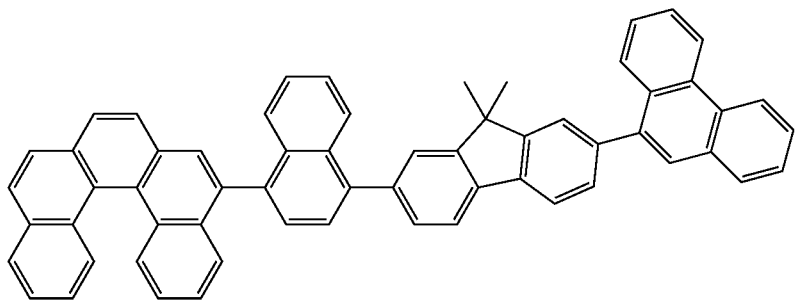
2-226
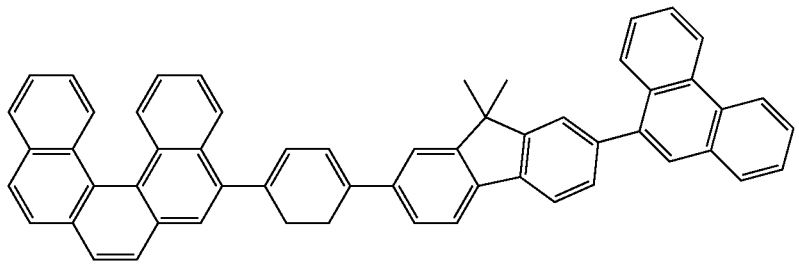
2-227

-continued
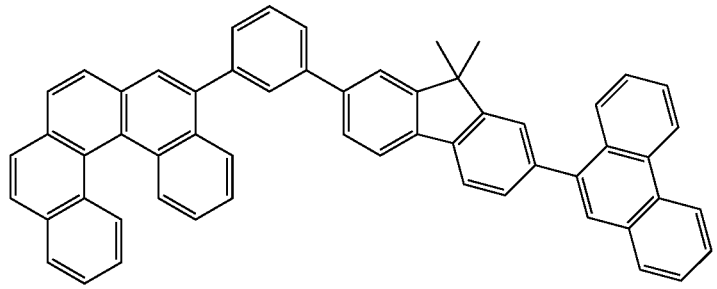
2-228
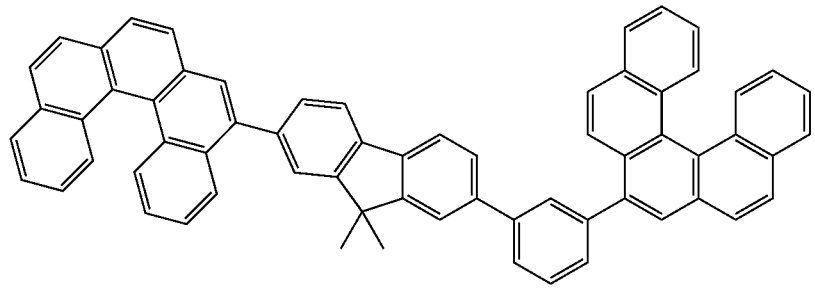
2-229
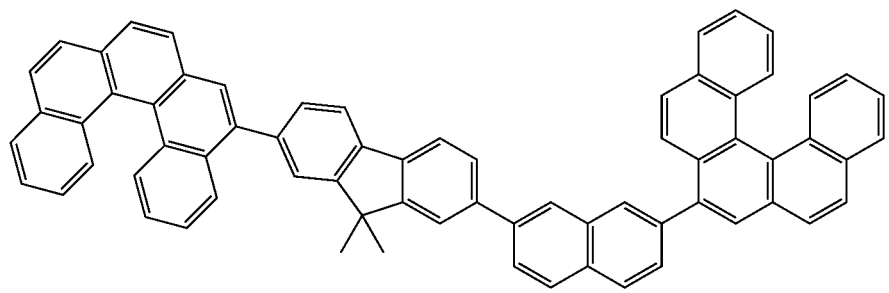
2-230
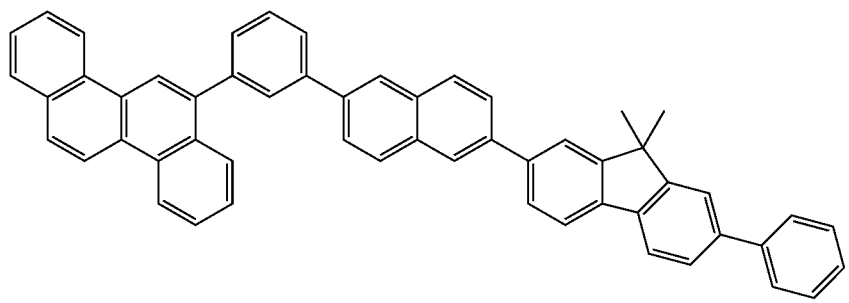
2-247
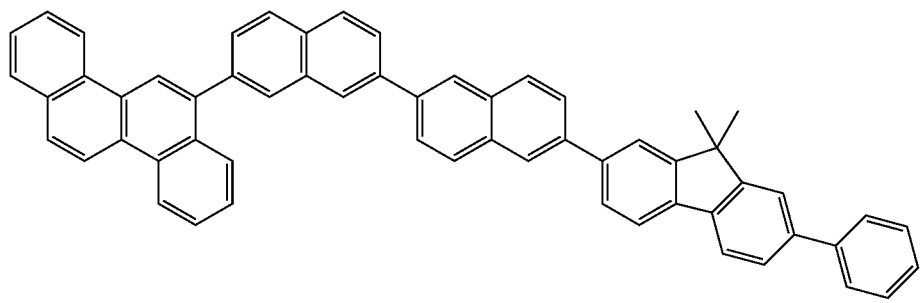
2-248

-continued
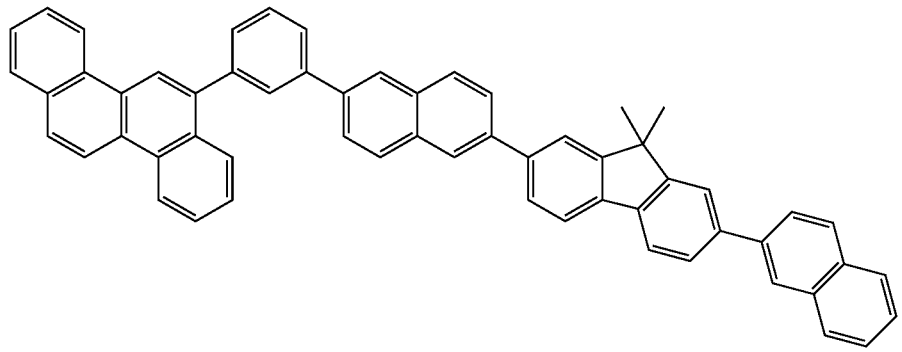
2-249
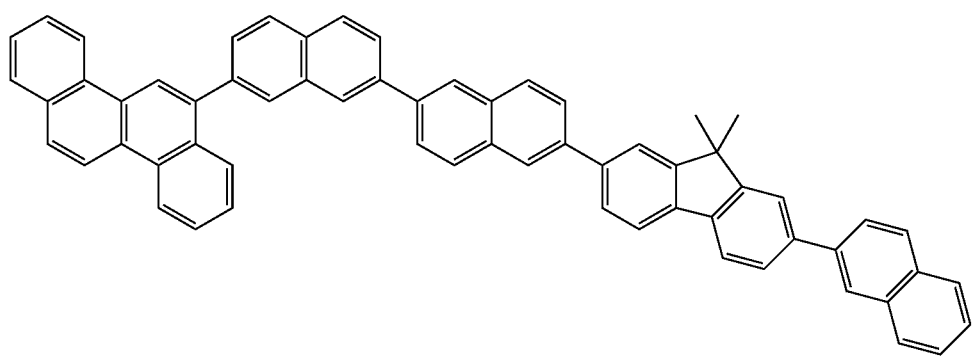
2-250
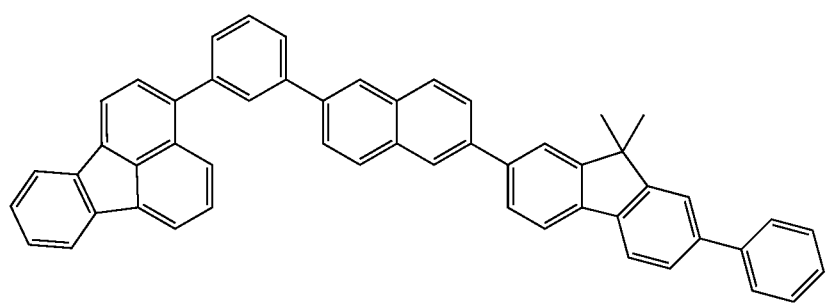
2-267
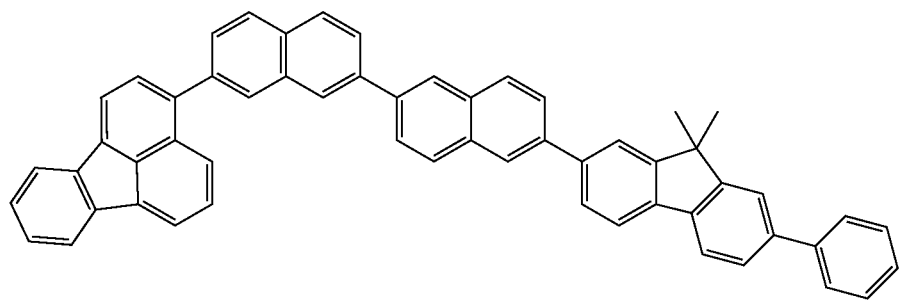
2-268

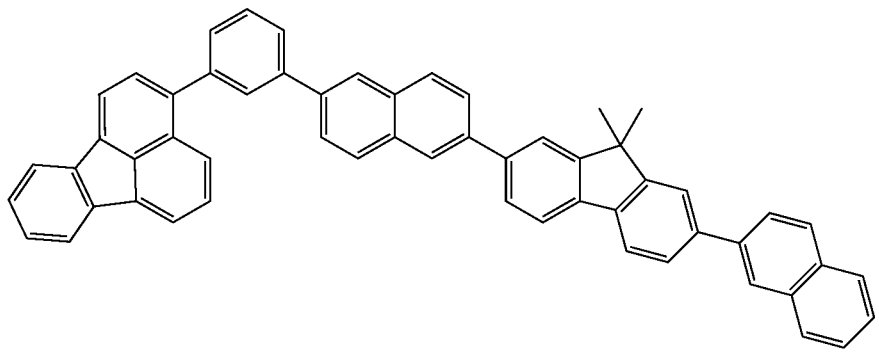
2-269
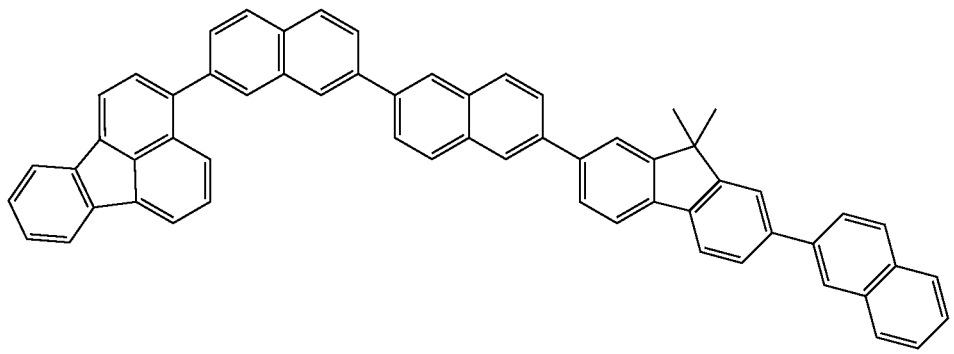
2-270
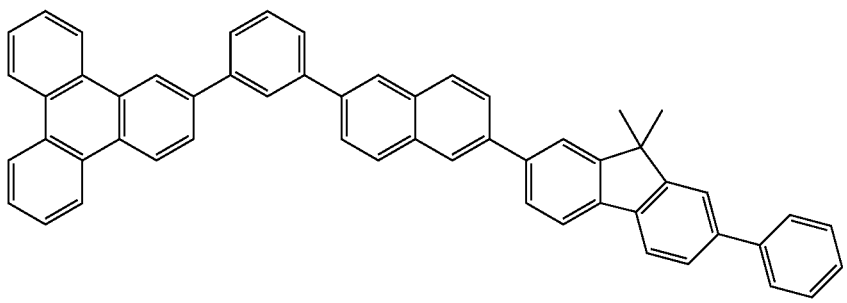
2-287
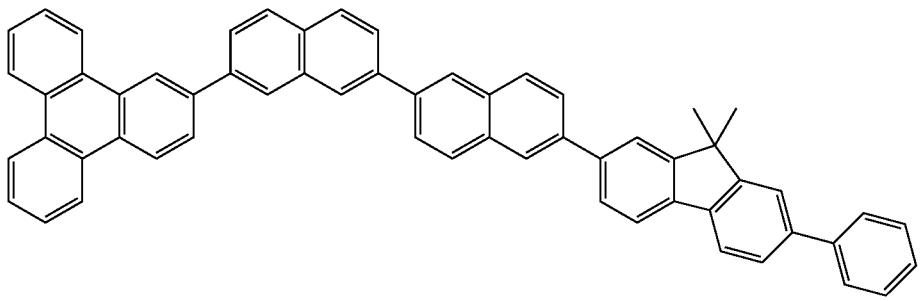
2-288

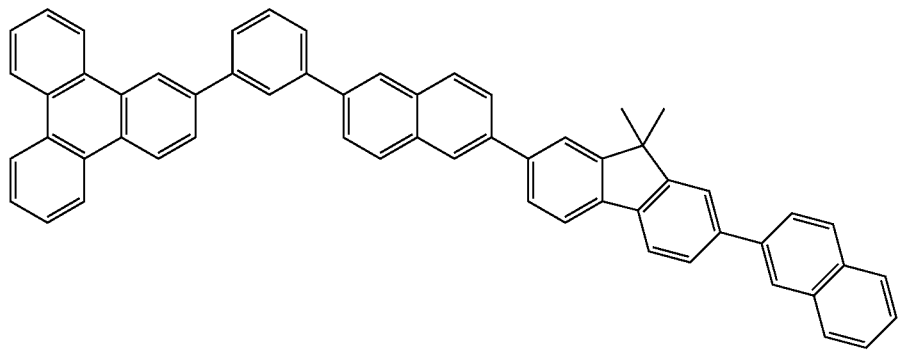
2-289
2-290
2-307
2-308

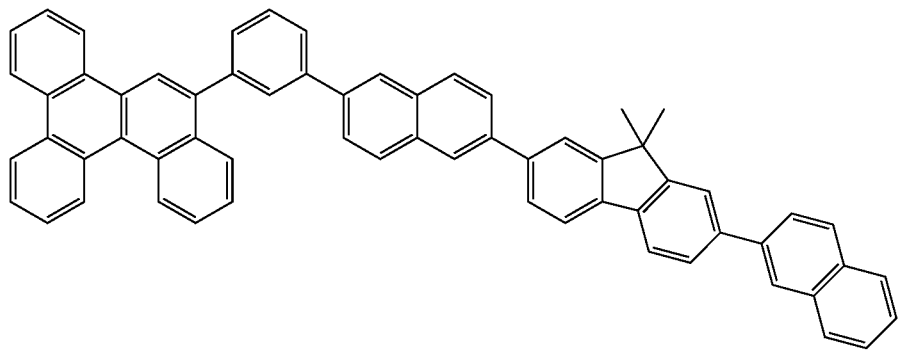
2-309
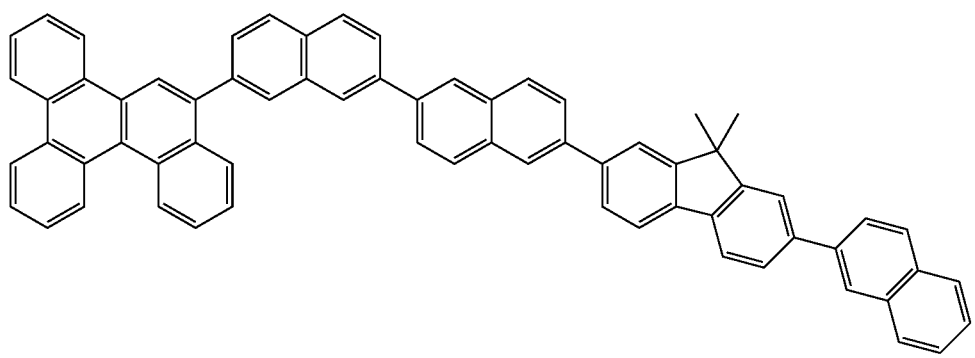
2-310
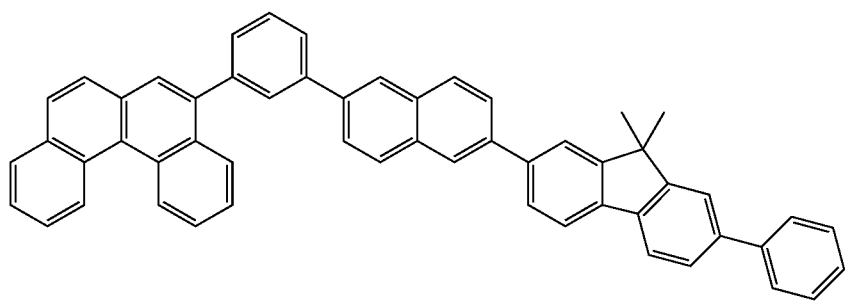
2-327
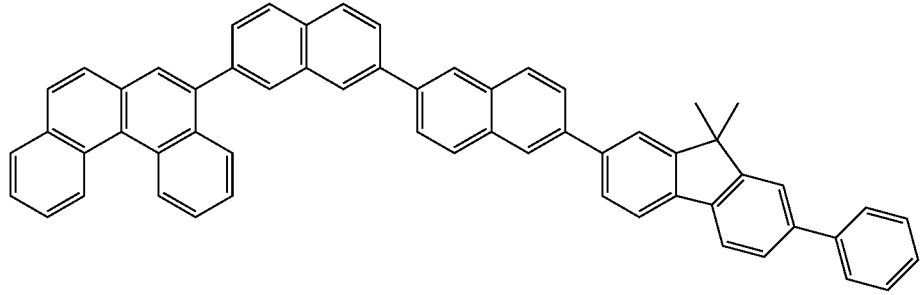
2-328

-continued
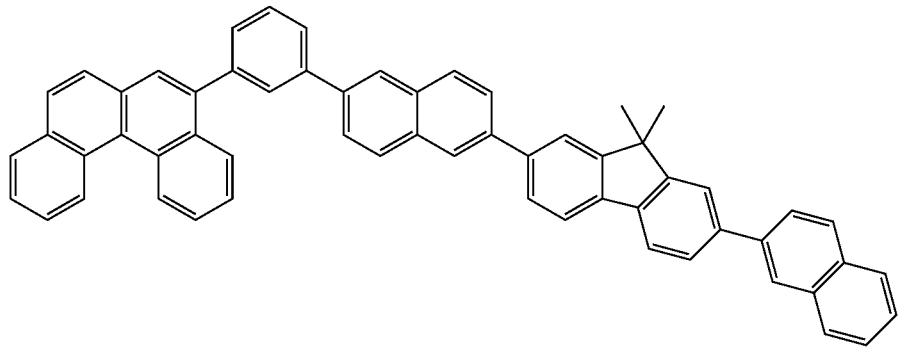
2-329
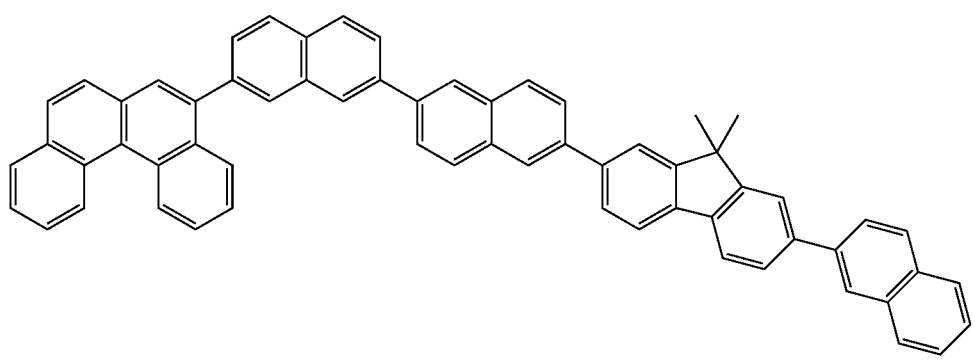
2-330
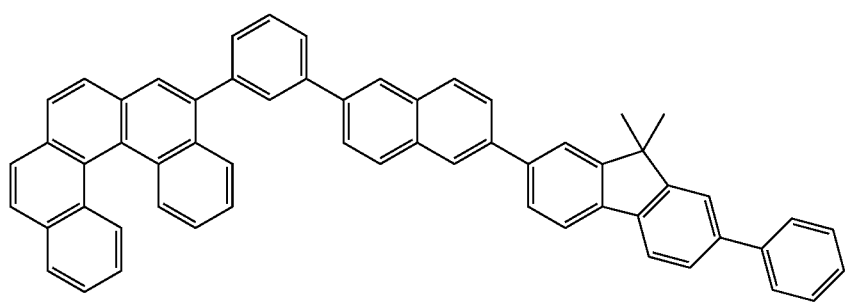
2-347
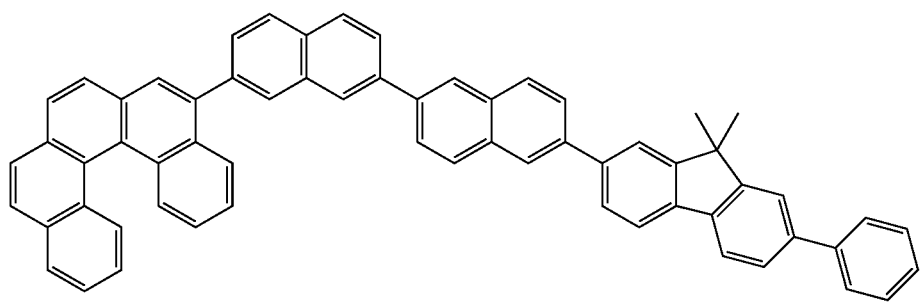
2-348

-continued
2-349
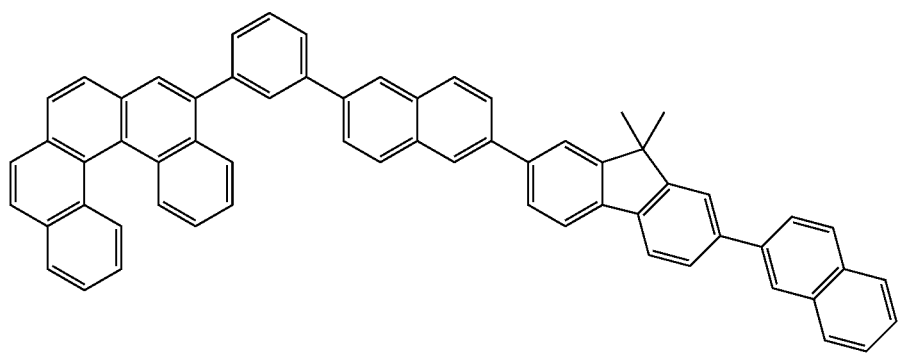
2-350
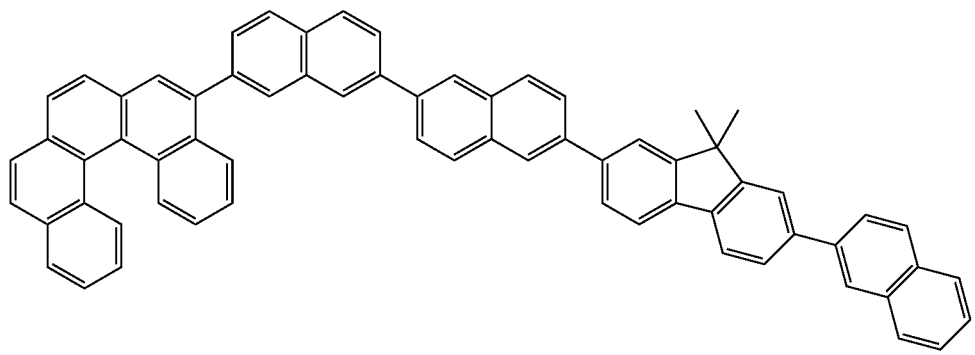
2-351
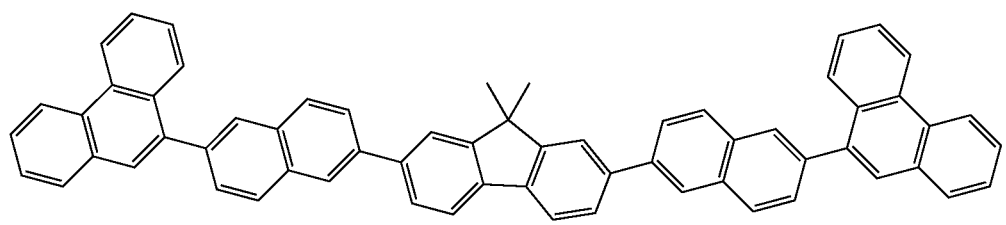
2-352
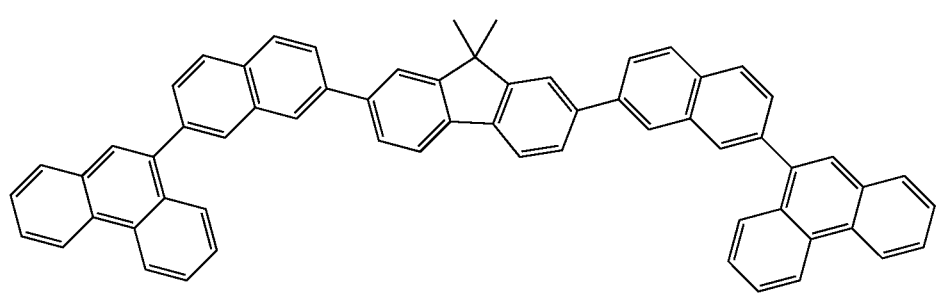
2-353
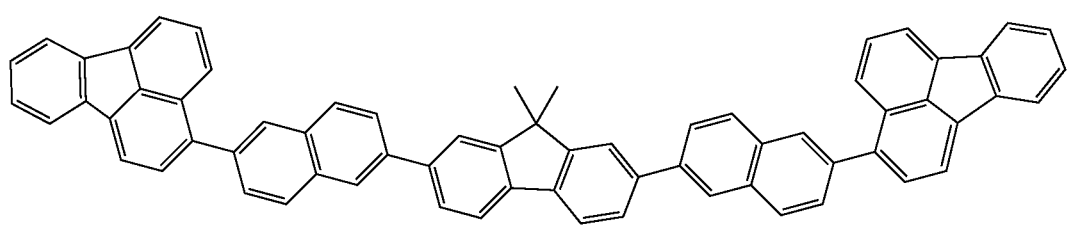

-continued
2-354
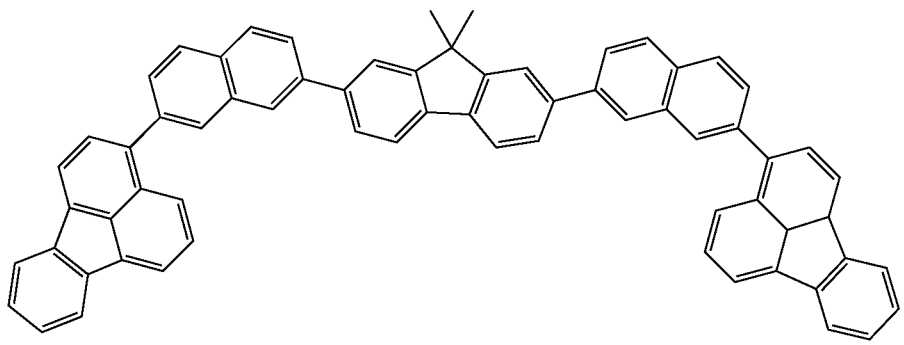
2-359
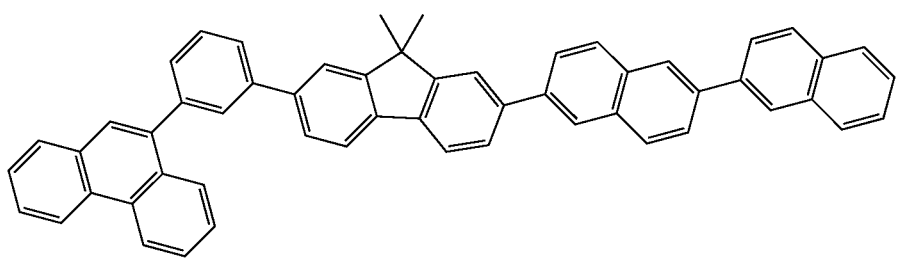
2-360
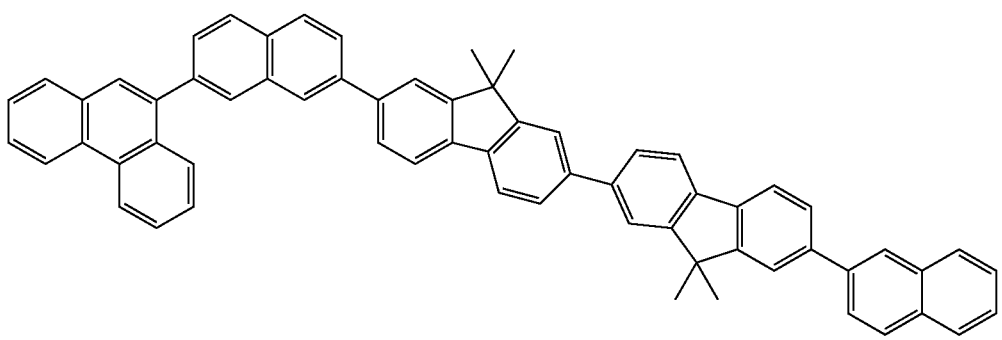
2-361
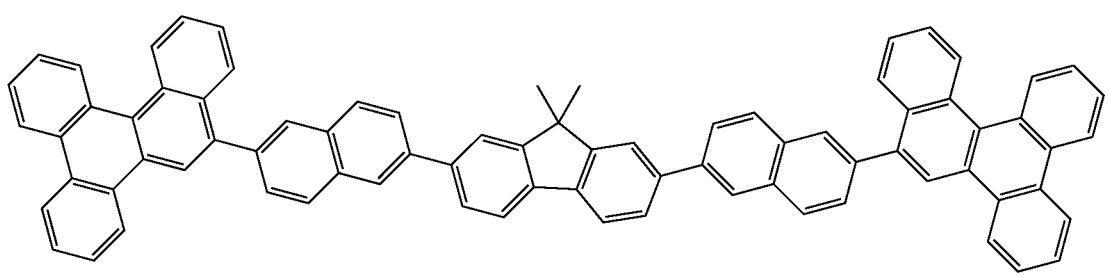
2-362
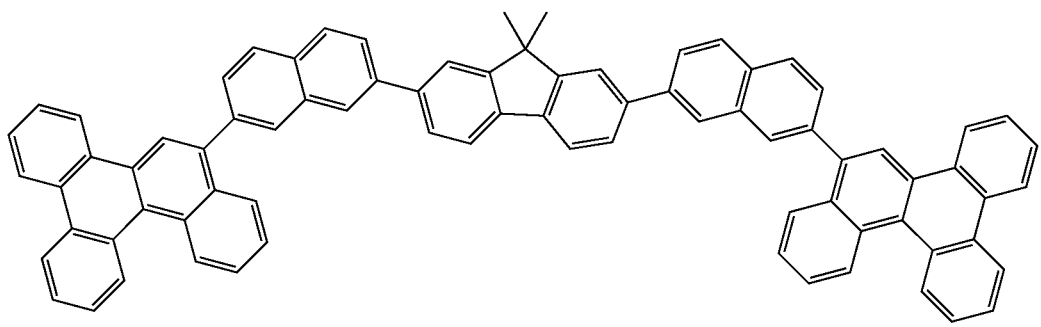

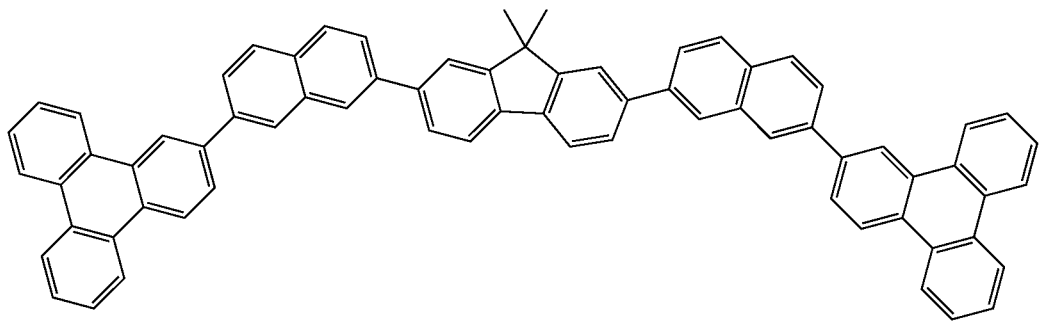
2-365
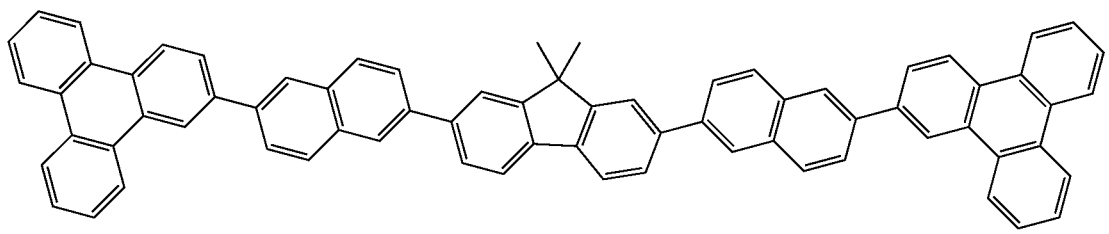
2-366
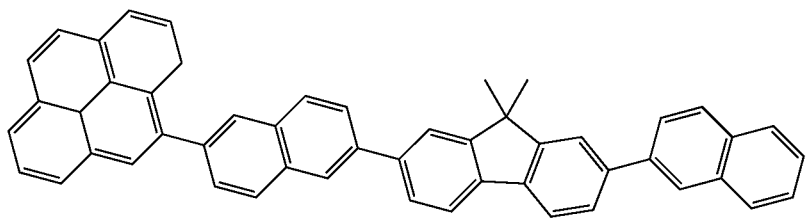
2-367
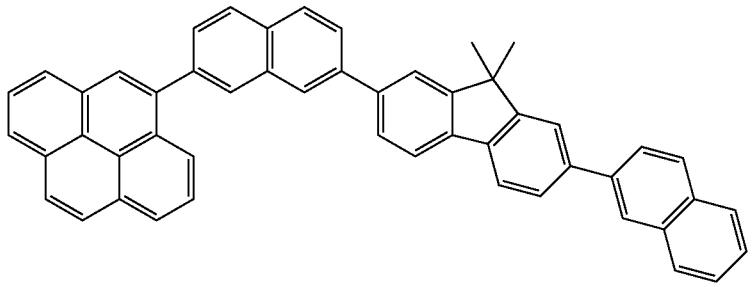
2-368
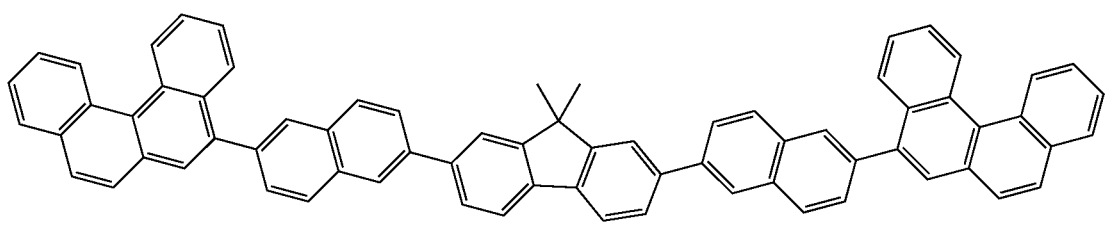
2-369

-continued
2-370
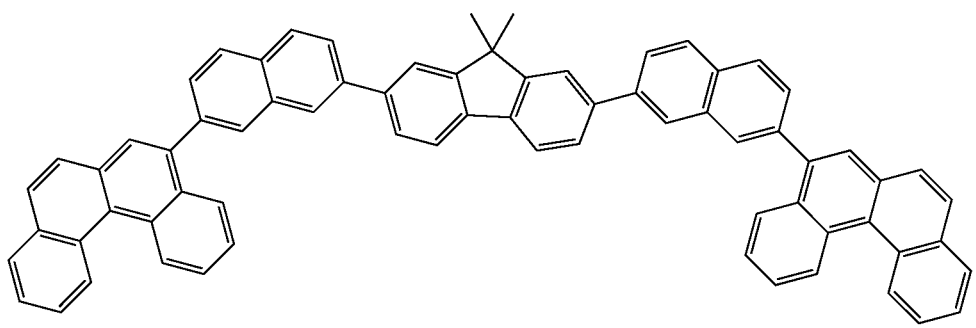
2-371
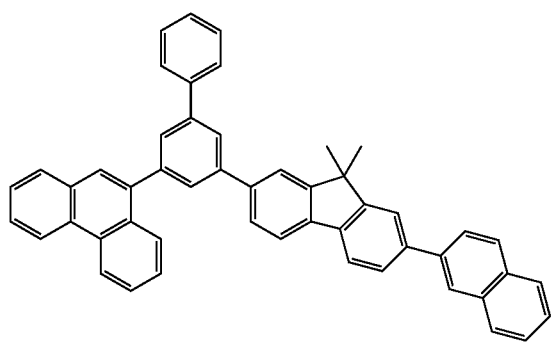
2-372
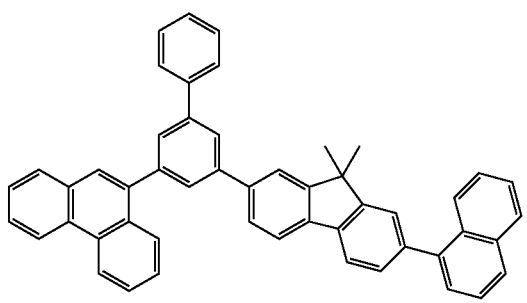
2-374
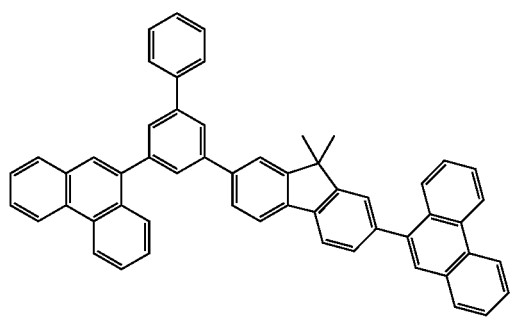
2-375
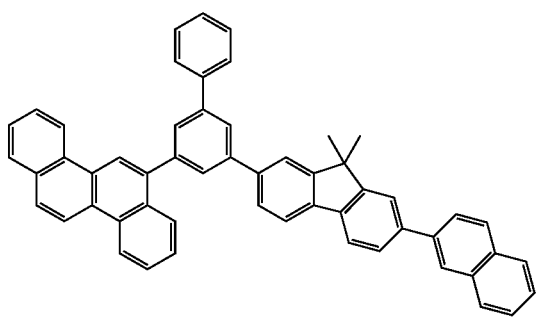
2-377
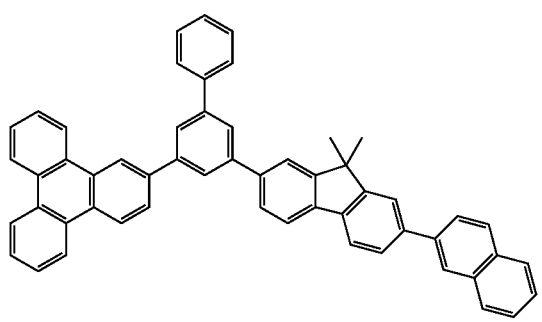
2-379
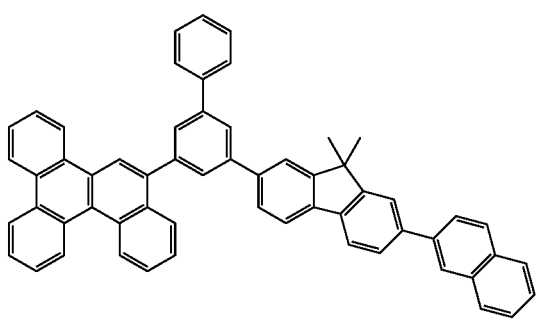

-continued
2-381
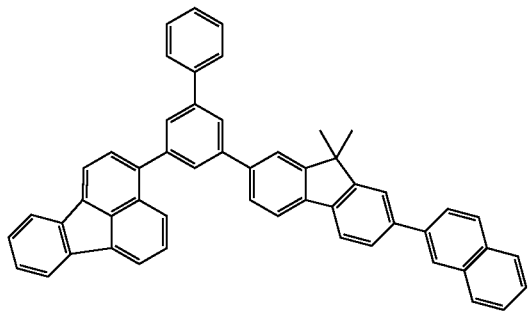
2-383
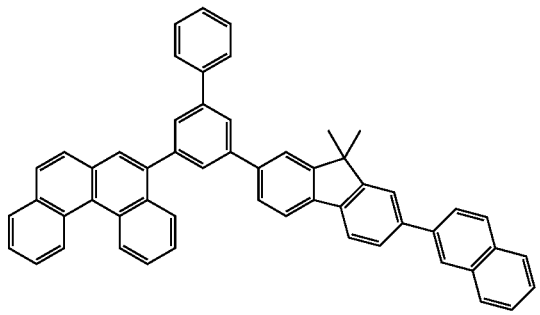
2-385
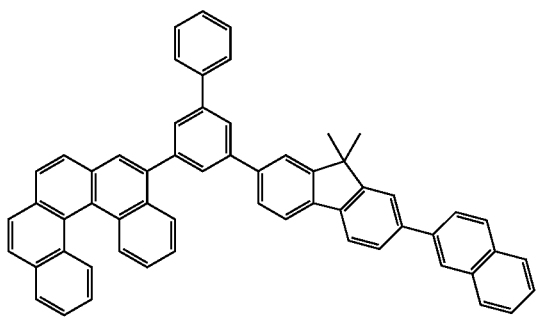
2-387
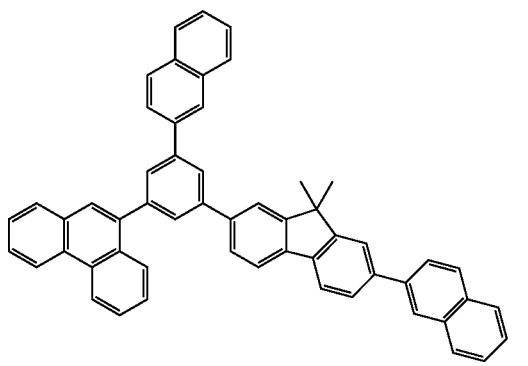
2-388
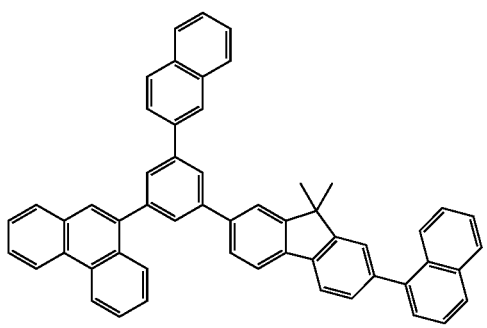
2-390
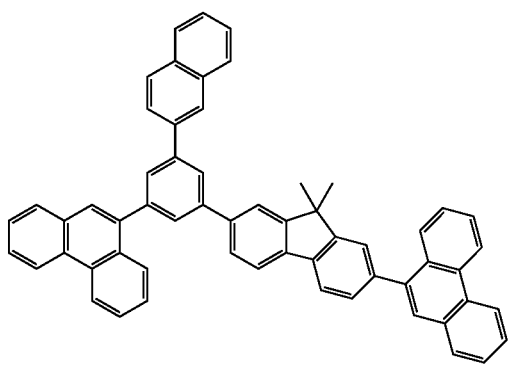
2-391
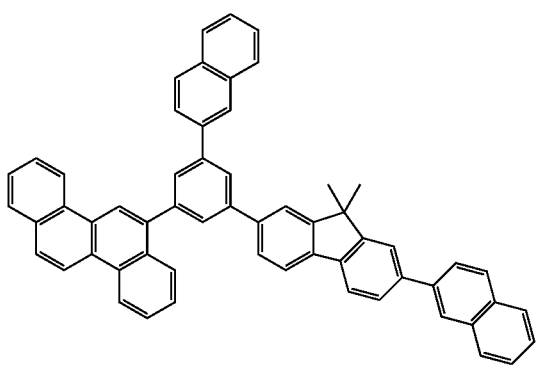
2-393
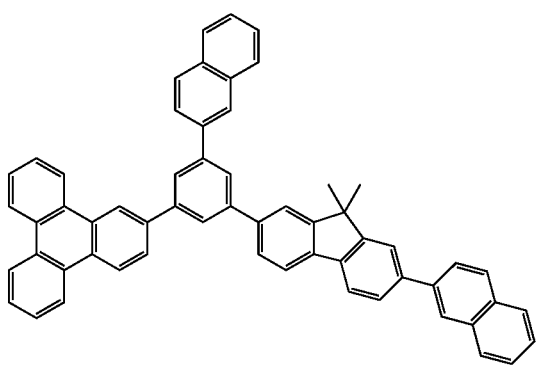

-continued
2-395
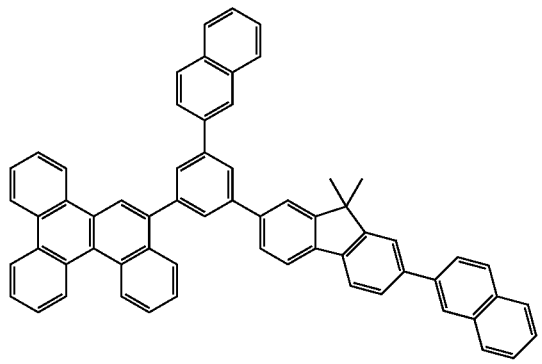
2-397
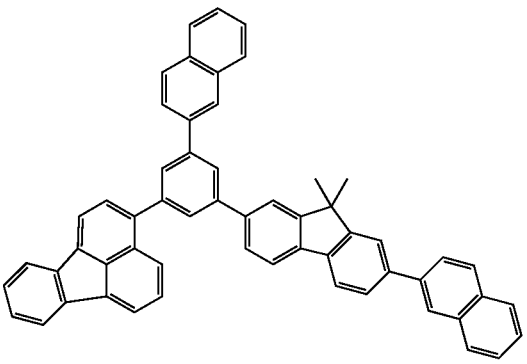
2-399
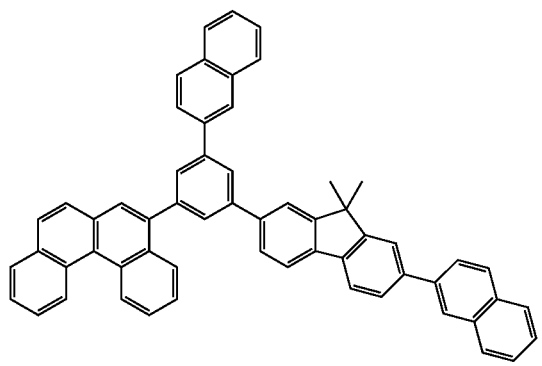
2-401
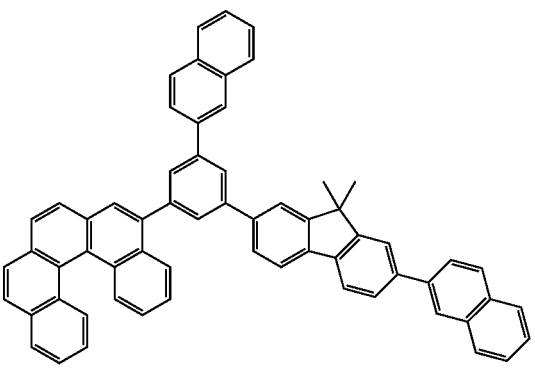
2-500
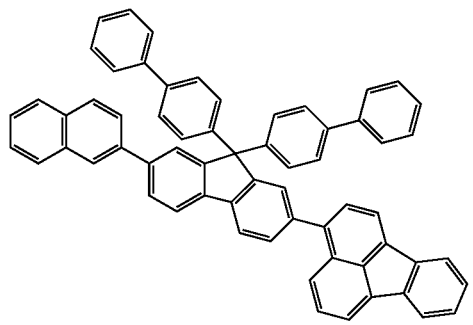
2-501
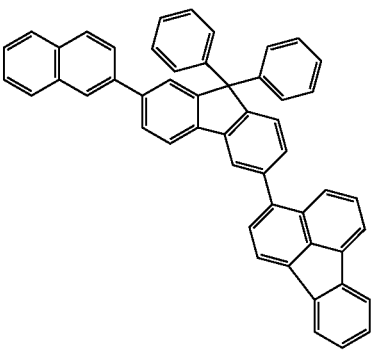
2-502
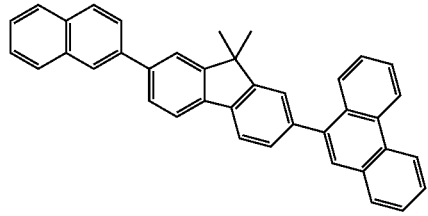
2-503
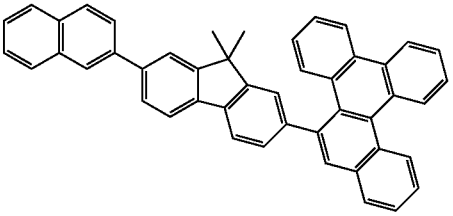
2-504
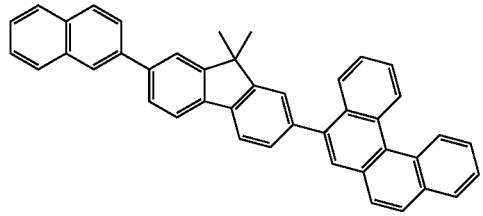
2-505
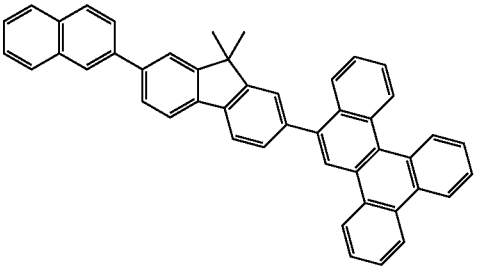

-continued
2-506
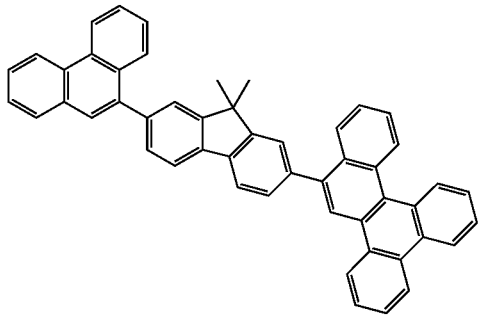
2-507
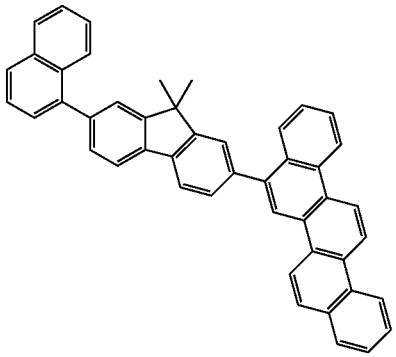
2-508
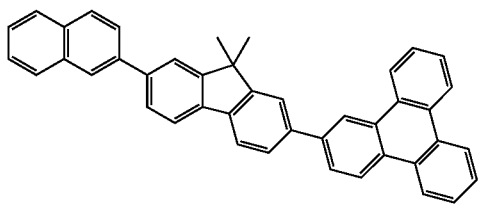
2-509
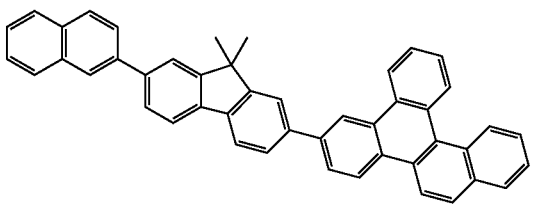
2-510
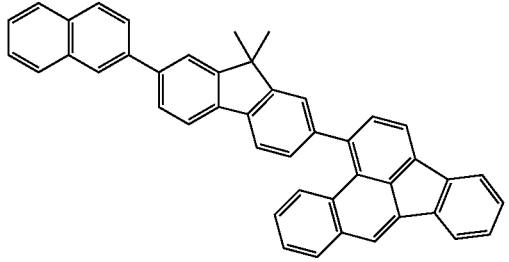
2-511
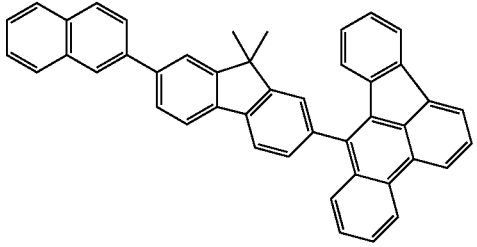
2-512
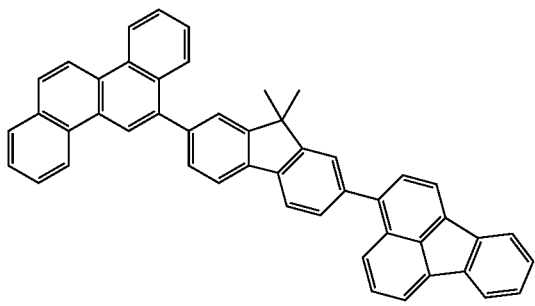
2-513
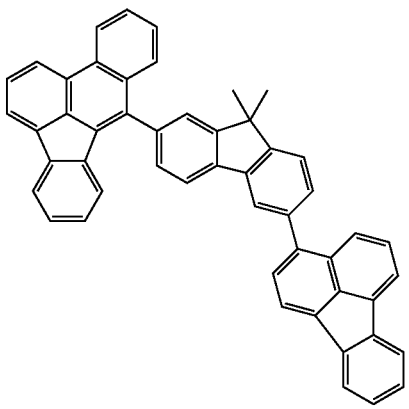
2-514
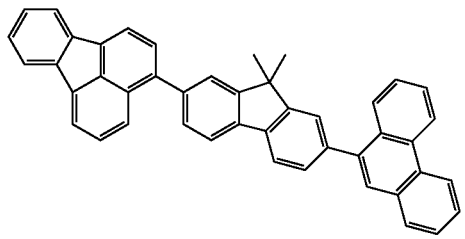
2-515
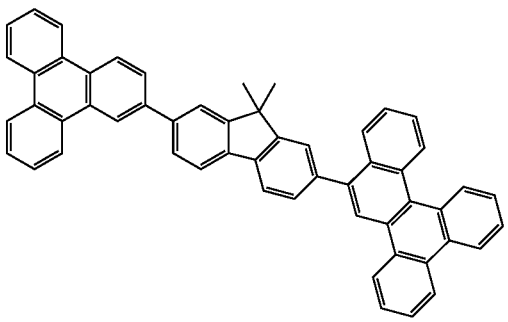

-continued
2-516
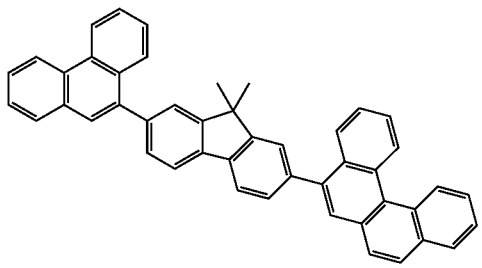
2-517
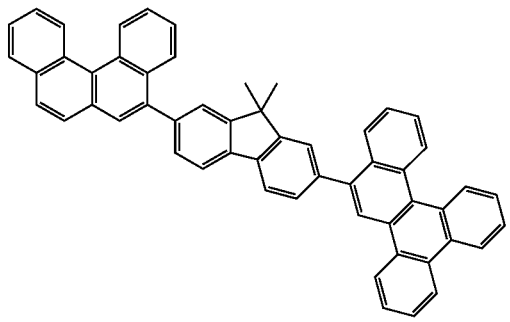
2-518
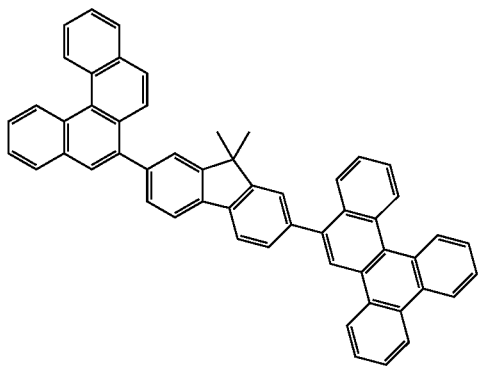
2-519
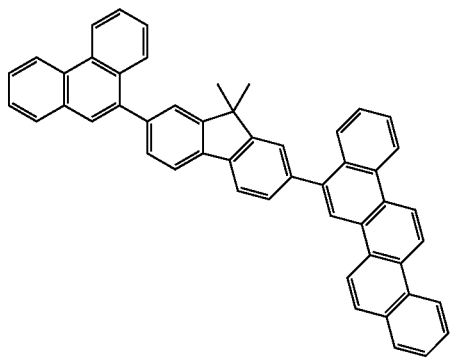
2-520
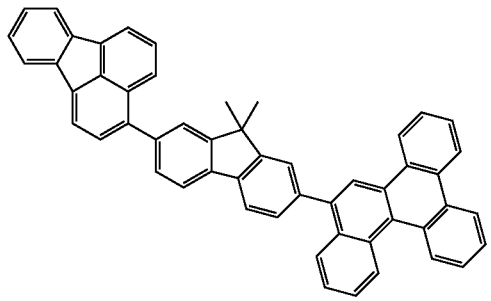
2-521
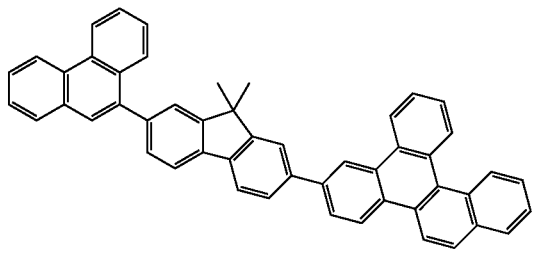
2-522
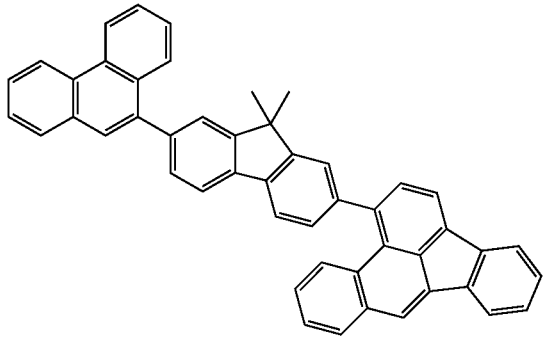
2-523
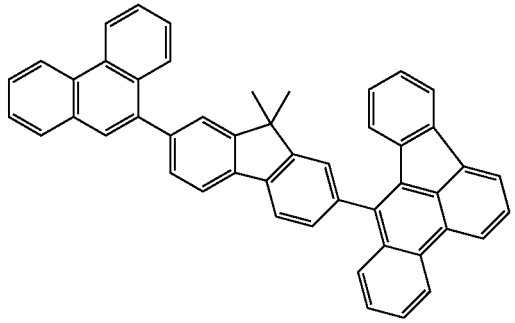

-continued
2-524
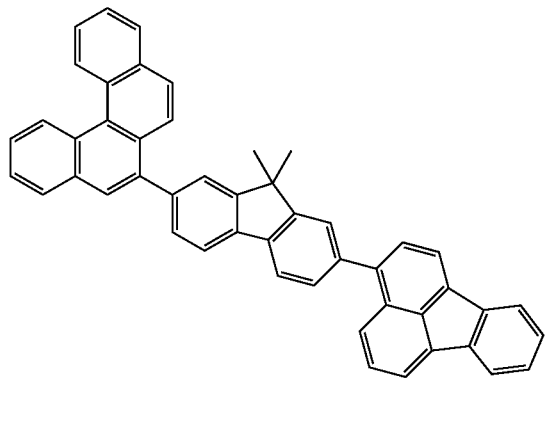
2-525
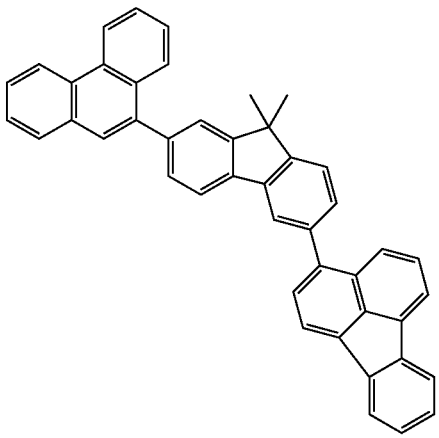
2-526
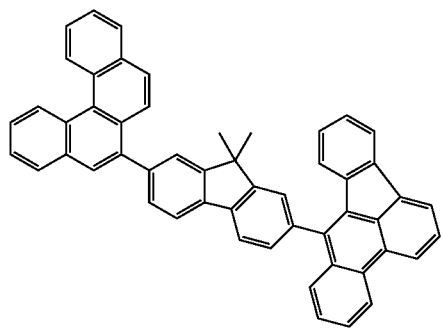
2-527
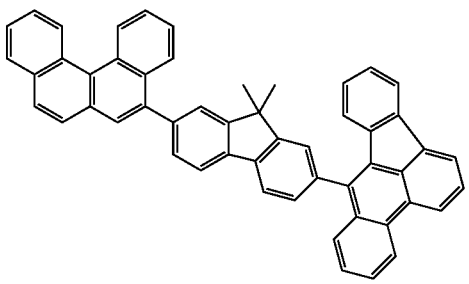
2-528
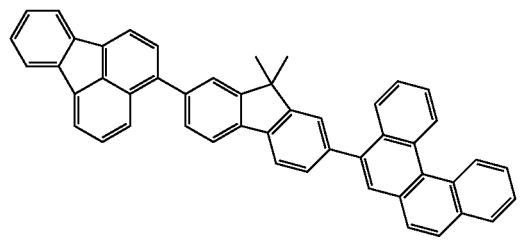
2-529
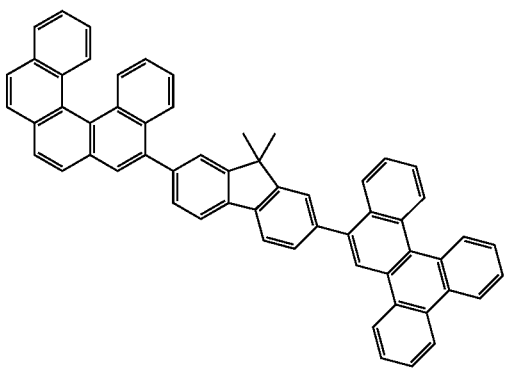
2-530
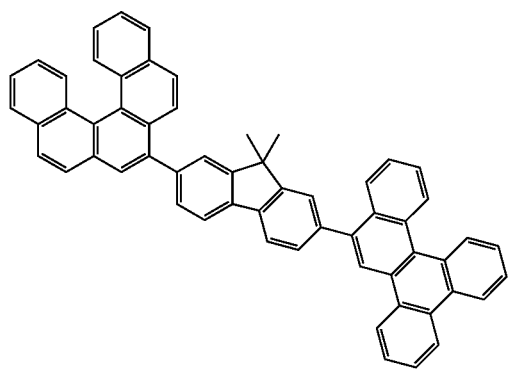
2-531
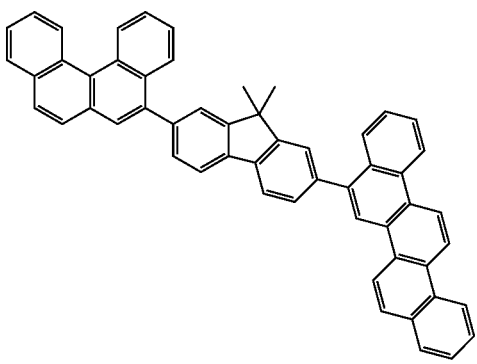

2-532
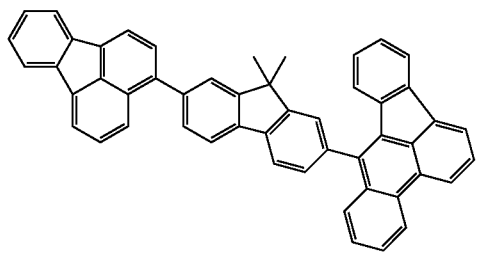
2-533
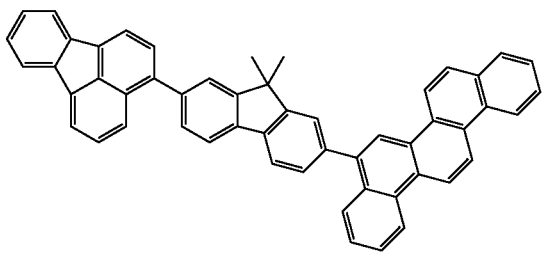
2-534
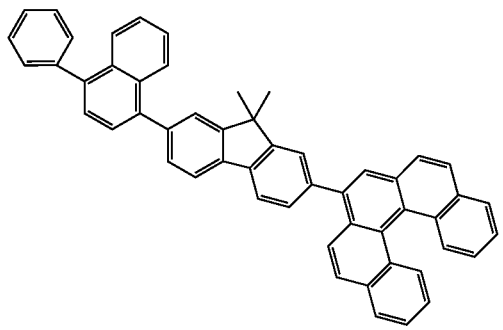
2-535
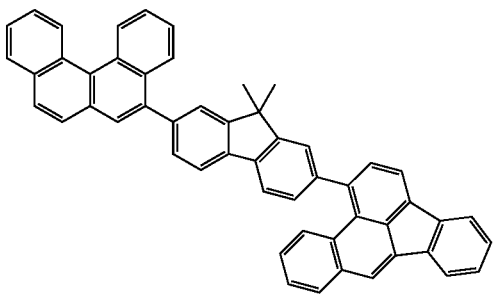
In addition to the compounds represented by formulae (A-1) to (A-5), (B-1 to (B-4), and (C-1) to (C-6), the following compounds are also usable as the material for organic electroluminescence device.
2-357
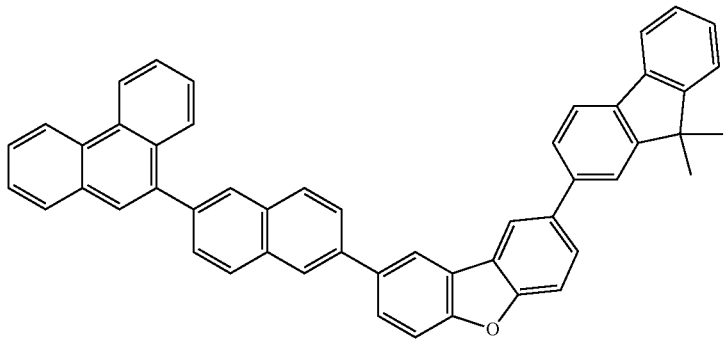
2-358
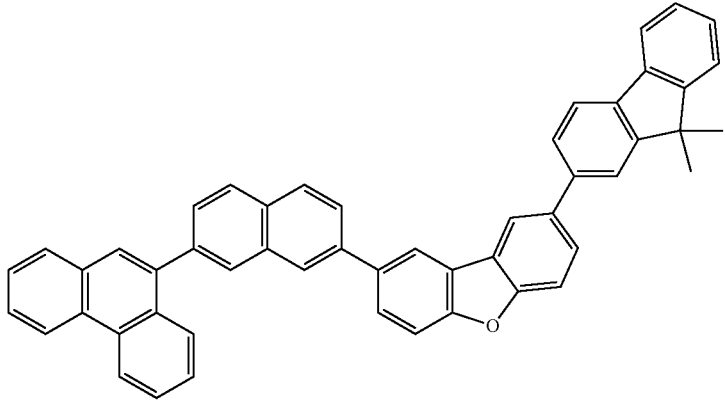

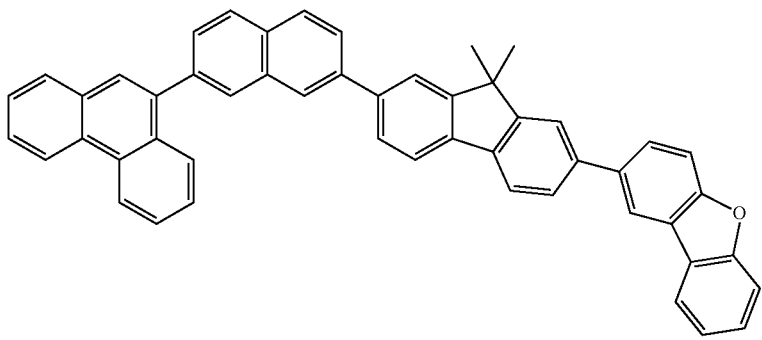
2-363
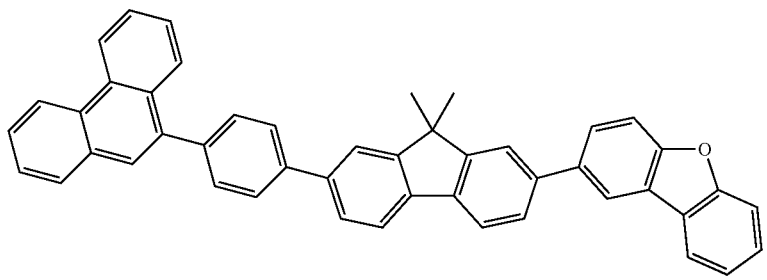
2-364
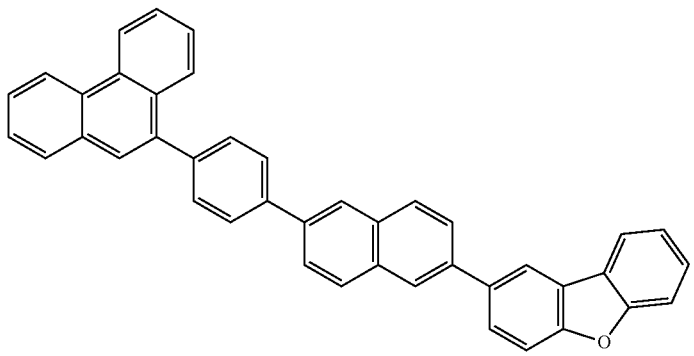
3-105
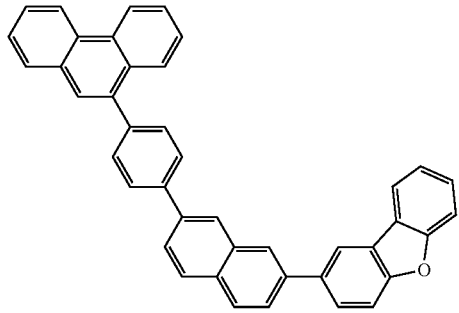
3-106
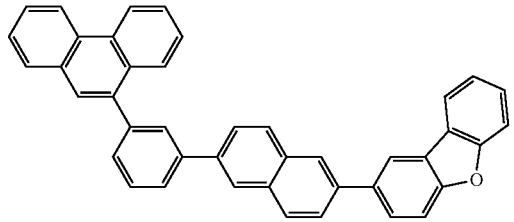
3-107
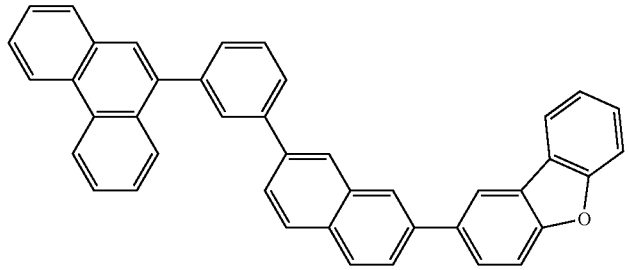
3-108

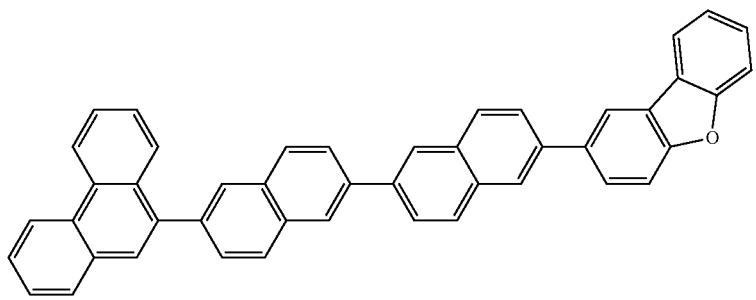
3-113
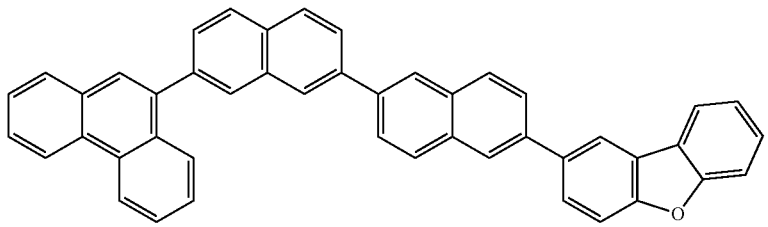
3-117
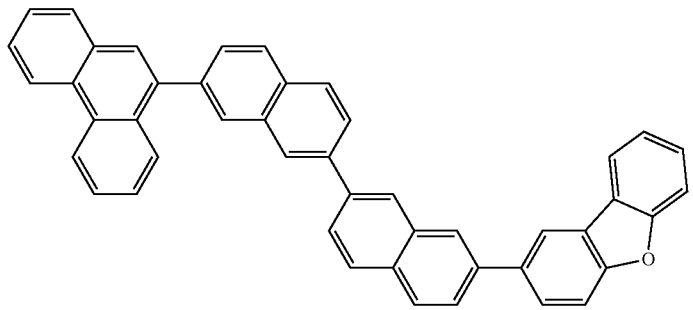
3-118
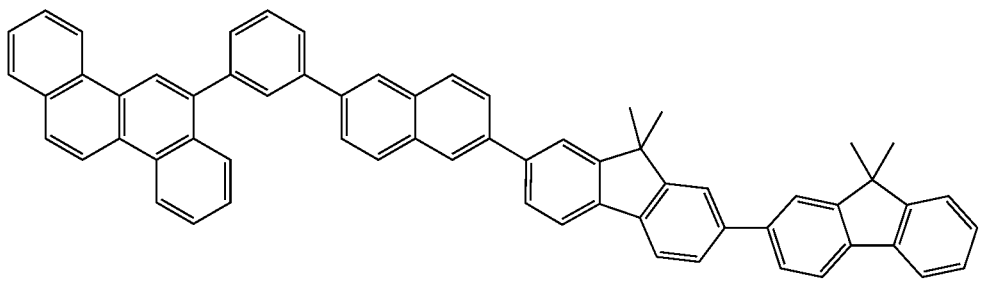
2-245
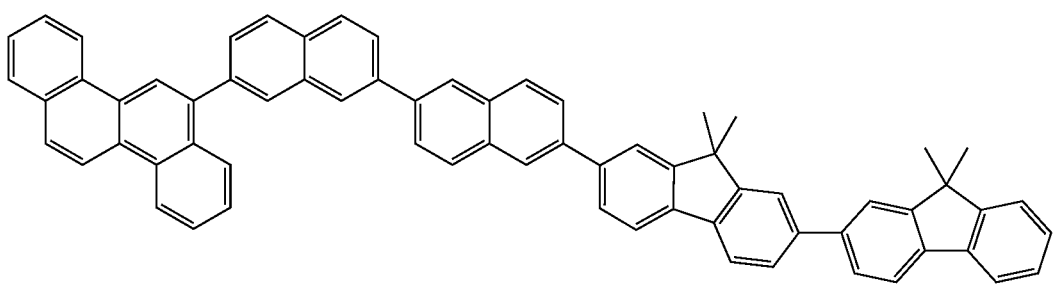
2-246

-continued
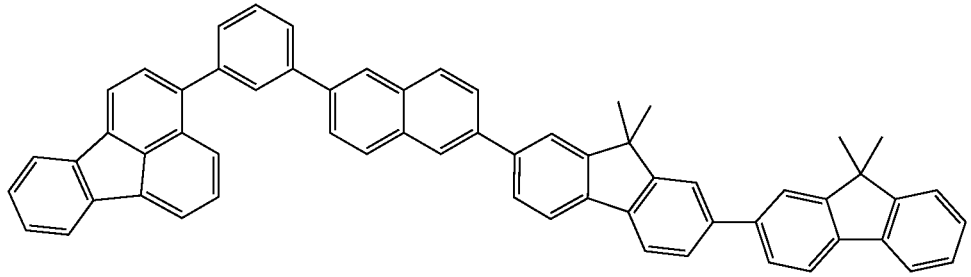
2-265
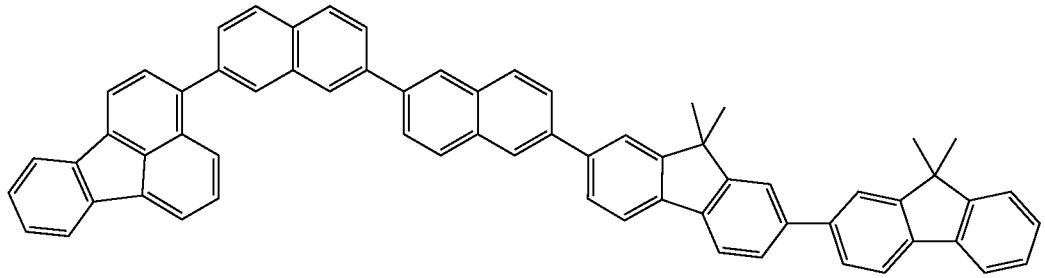
2-266
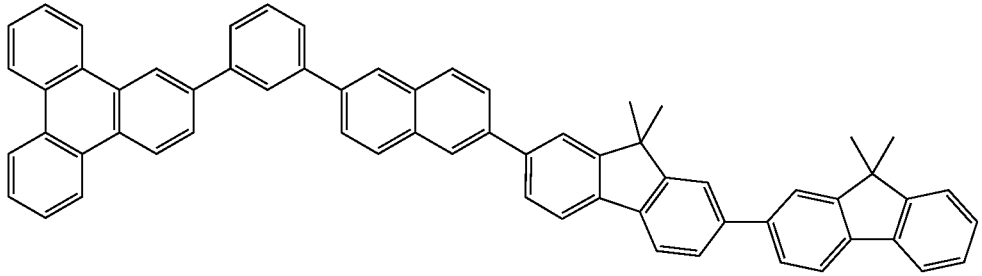
2-285
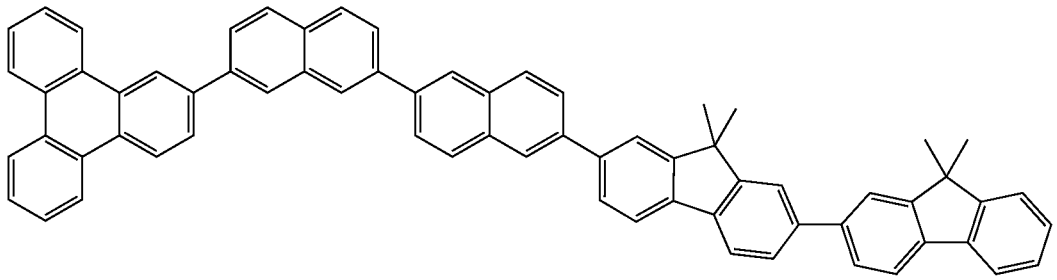
2-286
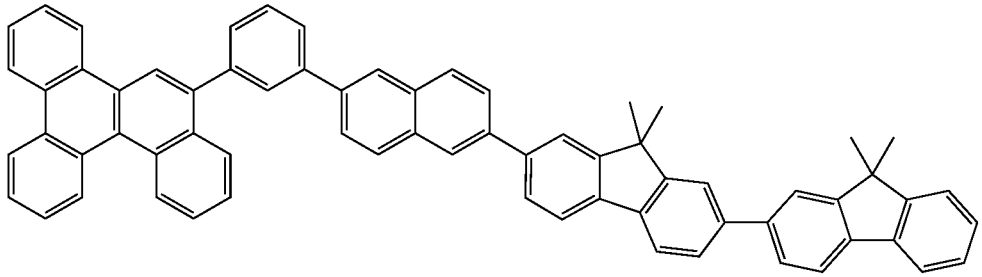
2-305

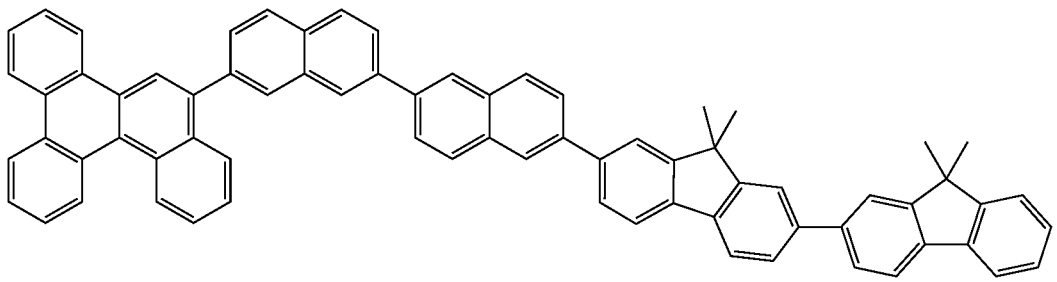

2-306

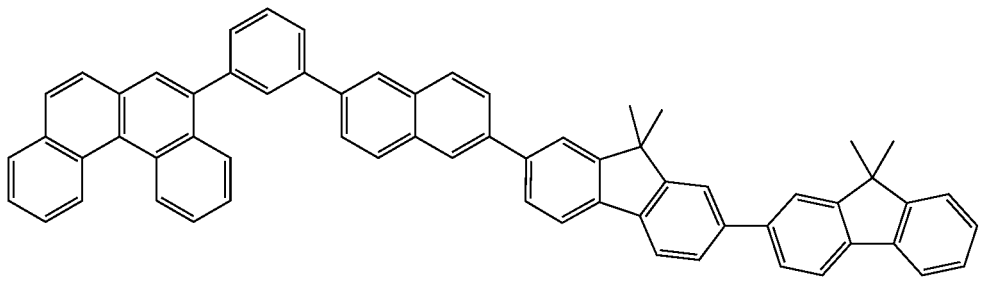

2-325

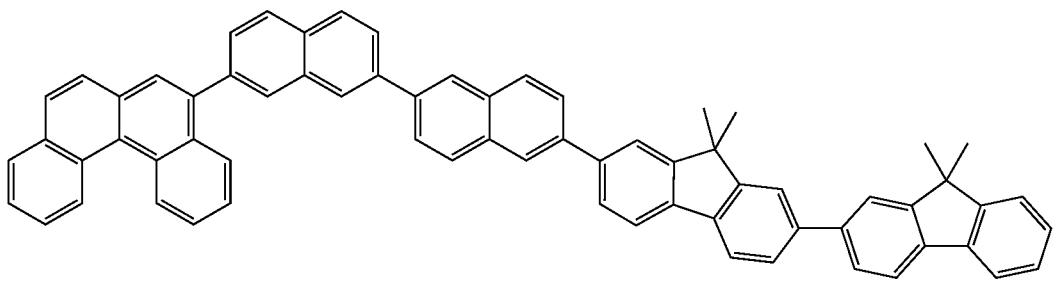

2-326

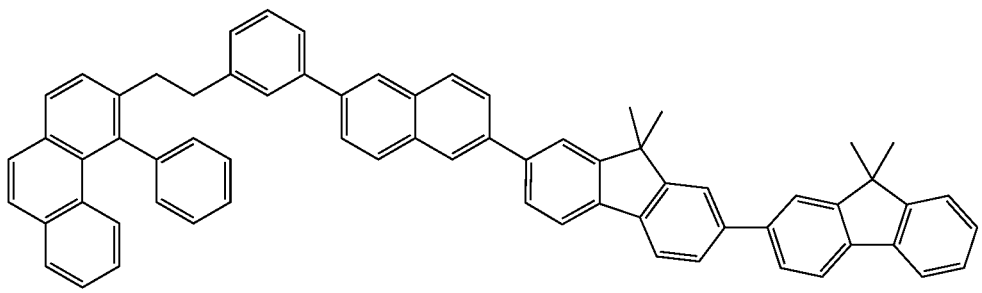

2-345

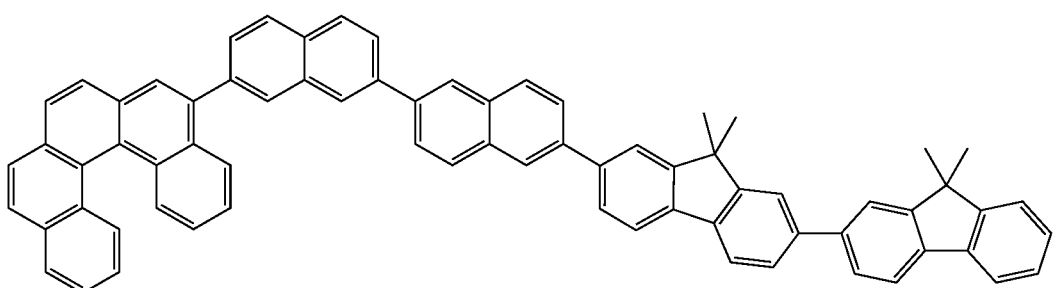

2-346

The phosphorescent emitting material used in the invention preferably comprises a metal complex which comprises a metal atom selected from Ir, Pt, Os, Au, Cu, Re, and Ru and a ligand. A ligand having an ortho metal bond is particularly preferred.

In view of obtaining a high phosphorescent quantum efficiency and further improving the external quantum efficiency of electroluminescence device, a compound comprising a metal selected from iridium (Ir), osmium (Os), and platinum (Pt) is preferred, with a metal complex, such as iridium complex, osmium complex, and platinum, being more preferred, iridium complex and platinum complex being still more preferred, and an ortho metallated iridium complex being most preferred.

Examples of the metal complex are shown below.
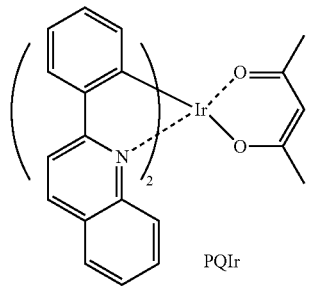
PQIr
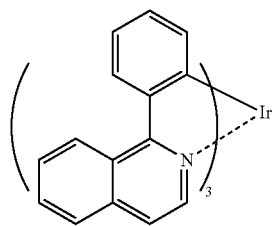
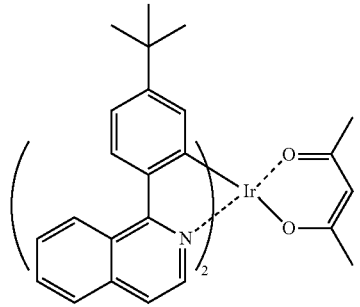
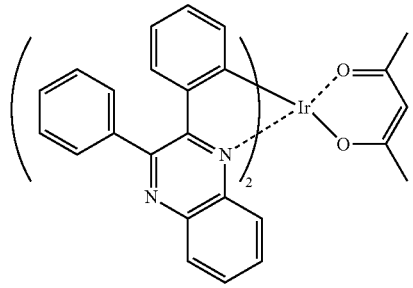
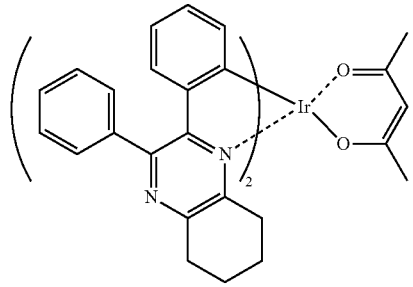
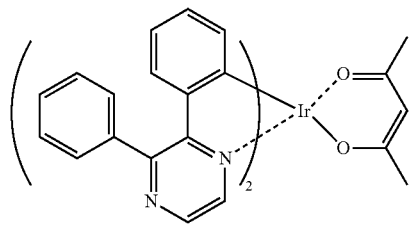
-continued
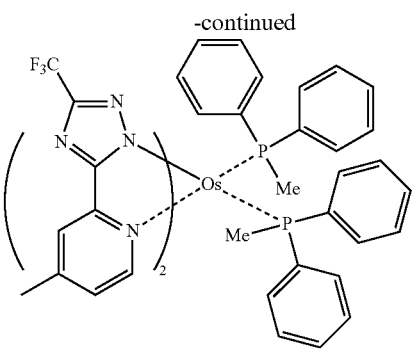
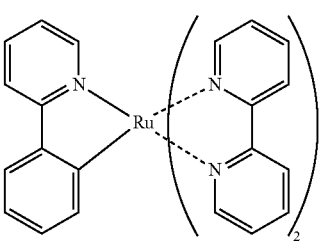
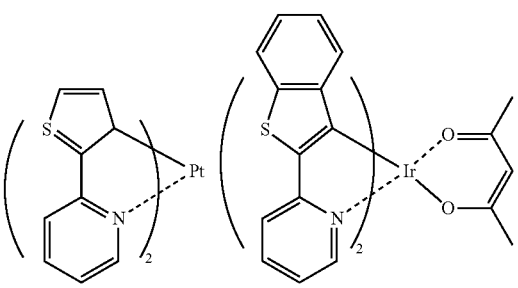
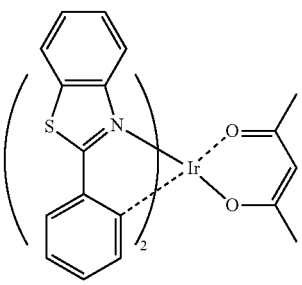
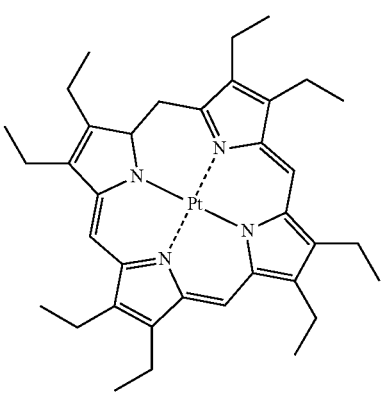

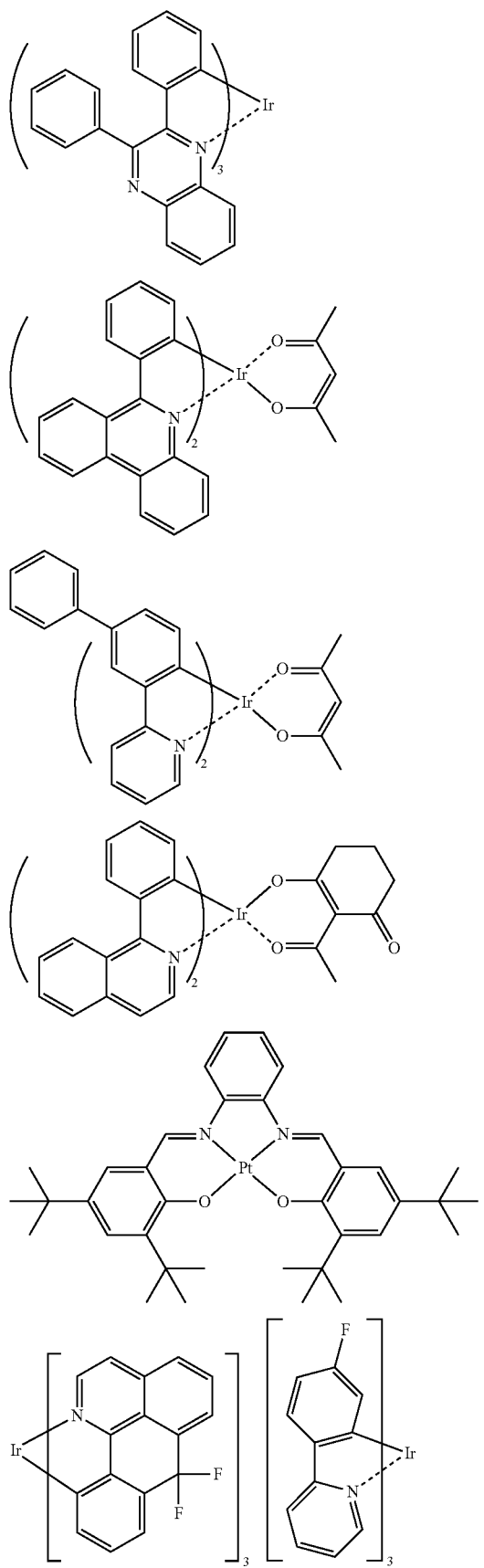
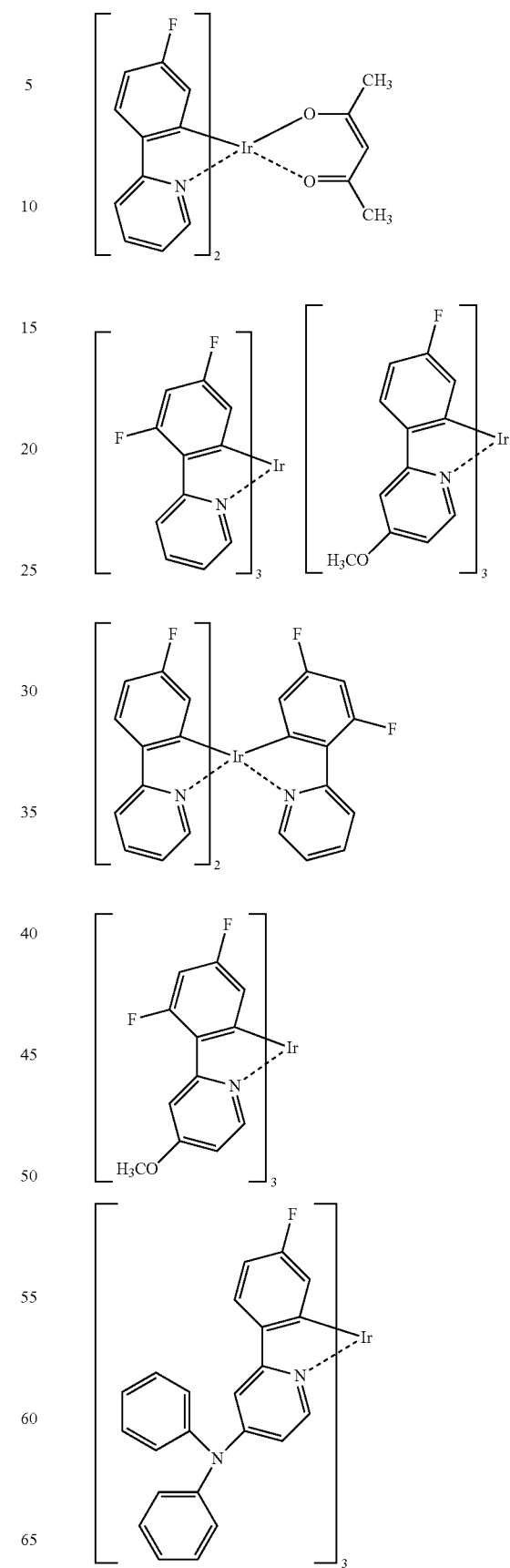

455
-continued
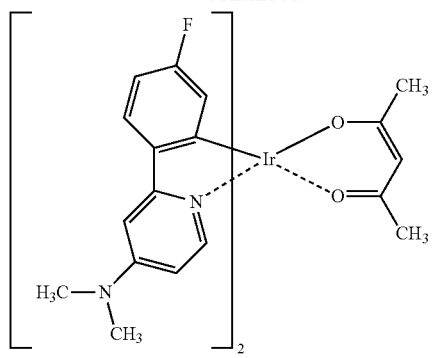
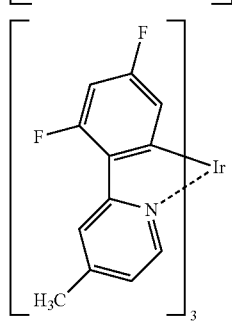
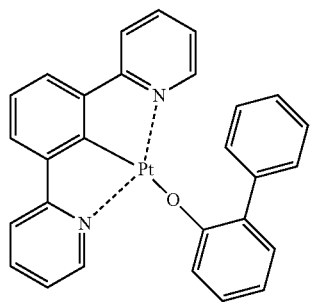
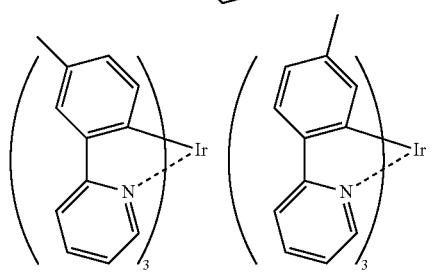
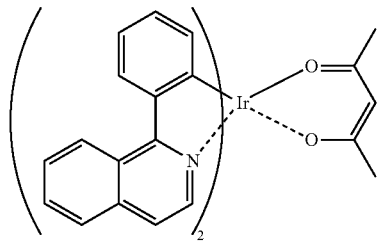
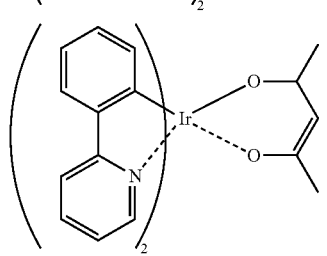
456
-continued
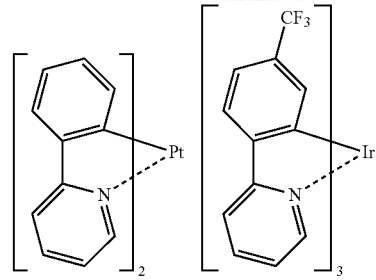
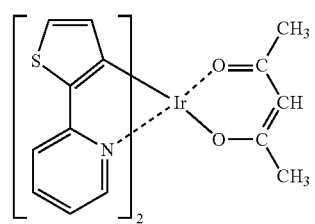
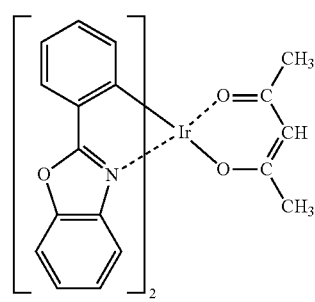
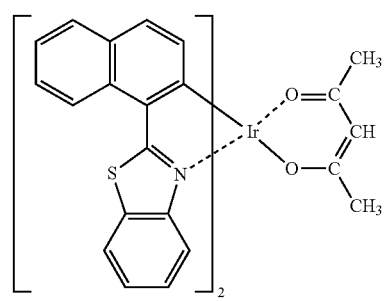
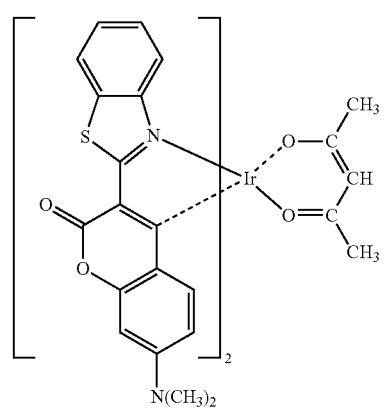

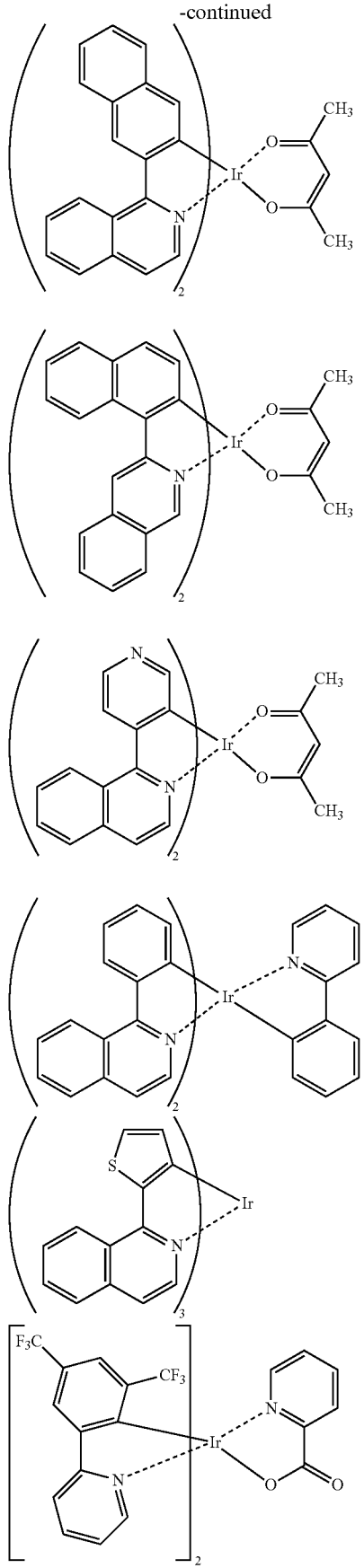
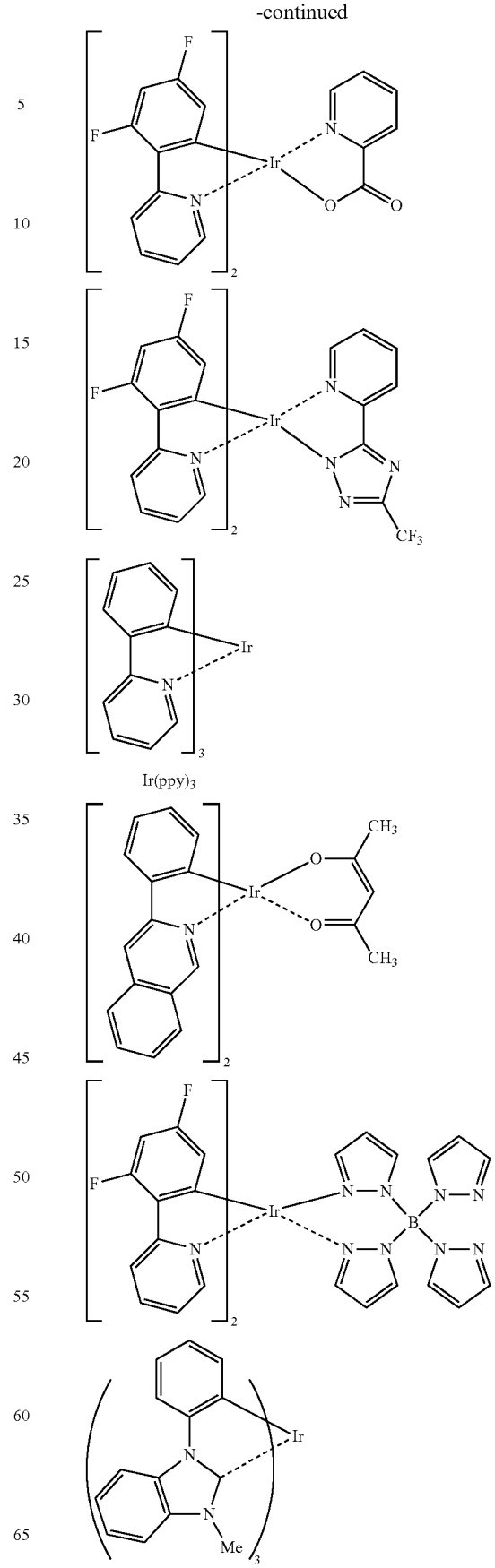

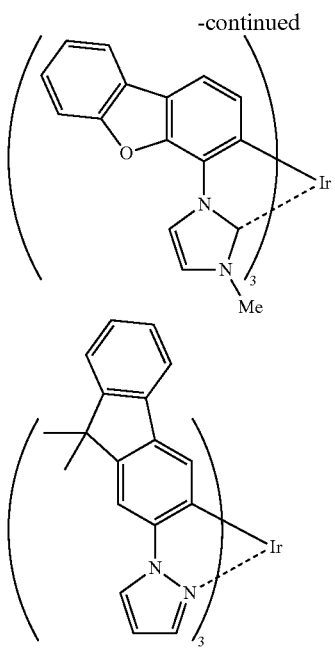

In the present invention, at least one of the phosphorescent emitting materials in the light emitting layer has emission maximum in a range preferably 500 nm or more and 720 nm or less.

A highly efficient organic EL device is obtained by forming the light emitting layer comprising the specific host material of the invention which is doped with the phosphorescent emitting material (phosphorescent dopant) showing such emission wavelength.

In a preferred embodiment of the invention, the organic EL device may have a hole transporting layer (hole injecting layer), and the hole transporting layer (hole injecting layer) contains the material for organic EL device of the invention. In another preferred embodiment, the organic EL device may have at least one of an electron transporting layer and a hole blocking layer, and at least one of the electron transporting layer and the hole blocking layer contains the material for organic EL device of the invention.

It is also preferred for the organic EL device of the invention to contain a reduction-causing dopant in the interfacial region between the cathode and the organic thin film layer.

With such a construction, the organic EL device has an improved luminance and an elongated lifetime.

Examples of the reduction-causing dopant include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include Ca (work function: 2.9 eV), Sr (work function: 2.0 to 2.5 eV), and Ba (work function: 2.52 eV), with those having a work function of 2.9 eV or less being particularly preferred.

Examples of the rare earth metal include Sc, Y, Ce, Tb, and Yb, with those having a work function of 2.9 eV or less being particularly preferred.

Since the preferred metals mentioned above has a particularly high reductivity, an organic electroluminescence device having an improved luminance and an elongated lifetime ban be obtained by its addition to the electron injecting region in a relatively small amount.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred.

Examples of the alkaline earth metal compound include BaO, SrO, CaO, and mixture thereof, such as $Ba_xSr_{1-x}O$ ($0<x<1$) and $Ba_xCa_{1-x}O$ ($0<x<1$), with BaO, SrO, and CaO being preferred.

Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligang is preferably, but limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The reduction-causing dopant is formed in the interfacial region preferably into a form of layer or island. The reduction-causing dopant is added preferably by co-depositing the reduction-causing dopant and the organic material for forming the interfacial region, such as a light emitting material and an electron injecting material, by a resistance heating deposition method, thereby dispersing the reduction-causing dopant into the organic material. The disperse concentration expressed by the molar ratio of the organic material and the reduction-causing dopant is 100:1 to 1:100 and preferably 5:1 to 1:5.

When the reduction-causing dopant is formed into a form of layer, a light emitting material or an electron injecting material is made into a layer which serves as an organic layer in the interface, and then, the reduction-causing dopant alone is deposited by a resistance heating deposition method into a layer having a thickness preferably 0.1 to 15 nm.

When the reduction-causing dopant is formed into a form of island, a light emitting material or an electron injecting material is made into a form of island which serves as an organic layer in the interface, and then, the reduction-causing dopant alone is deposited by a resistance heating deposition method into a form of island having a thickness preferably 0.05 to 1 nm.

The molar ratio of the main component and the reduction-causing dopant in the organic electroluminescence device of the invention is preferably 5:1 to 1:5 and more preferably 2:1 to 1:2.

In the organic EL device of the invention, an electron injecting layer is preferably disposed between the light emitting layer and the cathode, and the electron injecting layer preferably contains a nitrogen-containing ring derivative as a main component. The electron injecting layer may work as an electron transporting layer.

The term "main component" referred to herein means that 50% by mass or more of the electron injecting layer is the nitrogen-containing ring derivative.

The electron injecting layer or the electron transporting layer is a layer for facilitating the injection of electrons into the light emitting layer and has large electron mobility. The electron injecting layer is formed to adjust the energy level, for example, by reducing the abrupt change in energy level.

An aromatic heterocyclic compound having one or more heteroatoms in its molecule is preferably used as the electron injecting material for the electron injecting layer, with a nitrogen-containing ring derivative being particularly preferred. The nitrogen-containing ring derivative is preferably an aromatic ring compound having a nitrogen-containing 6- or 5-membered ring or a condensed aromatic ring compound having a nitrogen-containing 6- or 5-membered ring.

The nitrogen-containing ring derivative is preferably, for example, a chelate metal complex having a nitrogen-containing ring represented by formula (A):

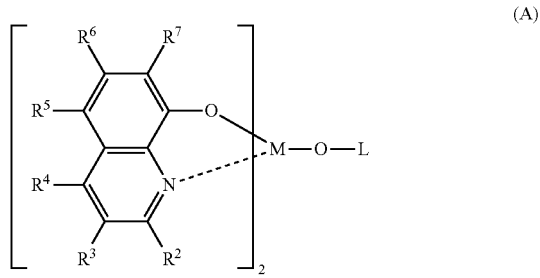

$R^2$ to $R^7$ are each independently hydrogen atom (inclusive of heavy hydrogen atom), a halogen atom, hydroxyl group, amino group, a hydrocarbon group having 1 to 40 carbon atoms, an alkoxy group, an aryloxy group, an alkoxycarbonyl group, or a heterocyclic group, each being optionally substituted.

The halogen atom may include fluorine, chlorine, bromine, and iodine. The substituted amino group may include an alkylamino group, an arylamino group, and an aralkylamino group.

The hydrocarbon group having 1 to 40 carbon atoms may include an alkyl group, an alkenyl group, a cycloalkyl group, an aryl group, and an aralkyl group, each being substituted or unsubstituted.

Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxyt-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodot-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group.

Of the above, preferred are methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, and 1-heptyloctyl group.

Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl1-butenyl group, with styryl group, 2,2-diphenylvinyl group, and 1,2-diphenylvinyl group being preferred.

Examples of the cycloalkyl group include cyclopentyl group, cyclohexyl group, cyclooctyl group, and 3,5-tetramethylcyclohexyl group, with cyclohexyl group, cyclooctyl group, and 3,5-tetramethylcyclohexyl group being preferred.

The alkoxy group is represented by —OY, wherein Y is an alkyl group. Examples and preferred examples thereof are the same as those described above.

Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Of the above, preferred are phenyl group, biphenyl-2-yl group, biphenyl-3-yl group, biphenyl-4-yl group, m-terphenyl-4-yl group, m-terphenyl-3-yl group, m-terphenyl-2-yl group, p-tolyl group, 3,4-xylyl group, and m-quaterphenyl-2-yl group.

Examples of the condensed aryl group include 1-naphthyl group, 2-naphthyl group.

The heterocyclic group may be monocyclic or condensed and has preferably 1 to 20 ring carbon atoms, more pre 1 to 12 ring carbon atoms, and more preferably 1 to 10 ring carbon atoms. The heterocyclic group is preferably an aromatic heterocyclic group having at least one heteroatom selected from nitrogen atom, oxygen atom, sulfur atom, and selenium atom. Examples of the heterocyclic group include the residues derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, tetrazaindene, carbazole, and azepine, with the residues of furan, thiophene, pyridine, pyrazine, pyrimidine, pyridazine, triazine, quinoline, phthalazine, naphthyridine, quinoxaline, and quinazoline being preferred, the residues derived from furan, thiophene, pyridine, and quinoline being more preferred, and quinolinyl group being still more preferred.

Examples of the aralkyl group include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group.

Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The aryloxy group is represented by —OY' wherein Y' is phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, or 4"-t-butyl-p-terphenyl-4-yl group.

The aryloxy group includes a heteroaryloxy group represented by —OZ', wherein Z' is 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The alkoxycarbonyl group is represented by —COOY', wherein Y' is an alkyl group and examples thereof are selected from those described above. The alkylamino group and the aralkylamino group are represented by —NQ$^1$Q$^2$, wherein Q$^1$ and Q$^2$ are each independently an alkyl group or an aralkyl group, examples and preferred examples being the same as those described above. One of Q$^1$ and Q$^2$ may be hydrogen atom (inclusive of heavy hydrogen atom).

The arylamino group represented by —NAr$^1$Ar$^2$, wherein Ar$^1$ and Ar$^2$ are each independently a non-condensed aryl group or a condensed aryl group, examples thereof being the same as those described above. One of Ar$^1$ and Ar$^2$ may be hydrogen atom (inclusive of heavy hydrogen atom).

M is aluminum (Al), gallium (Ga), or indium (In), with In being preferred.

L in formula (A) is a group represented by formula (A') or (A"):

(A')

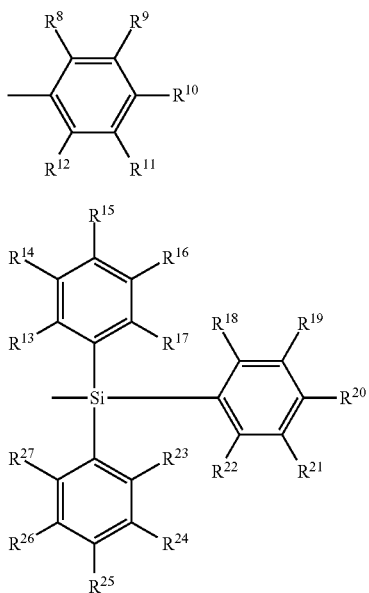

(A")

In the above formulae, $R^8$ to $R^{12}$ are each independently hydrogen atom (inclusive of heavy hydrogen atom) or a substituted or unsubstituted hydrocarbon group having 1 to 40 carbon atoms. The adjacent two groups may form a ring structure. $R^{13}$ to $R^{27}$ are each independently hydrogen atom (inclusive of heavy hydrogen atom) or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$.

Examples of the divalent group formed by the adjacent groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

Specific examples of the chelate metal complex having a nitrogen-containing ring represented by formula (A) are shown below, although not limited thereto.

(A-1)

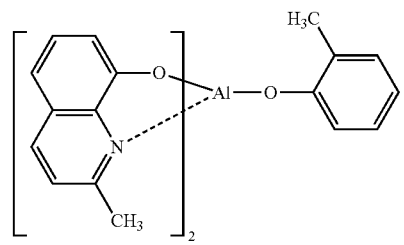

(A-2)

(A-3)

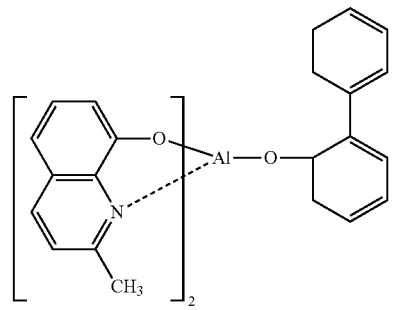

(A-4)

(A-5)

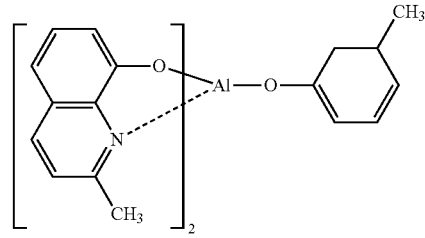

(A-6)

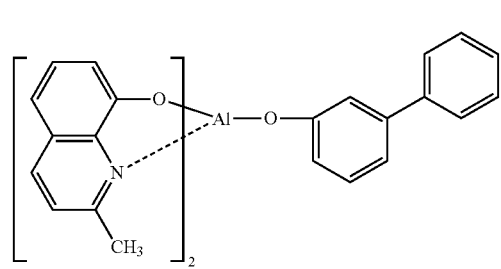

(A-7)

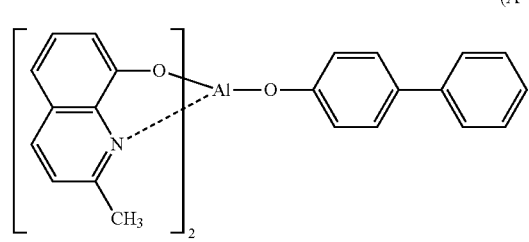

(A-8)

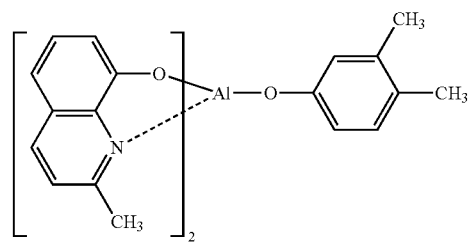

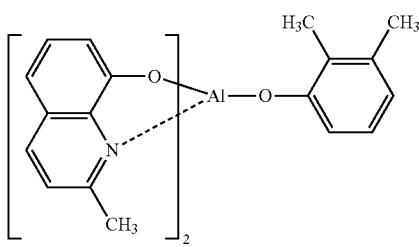 (A-9)
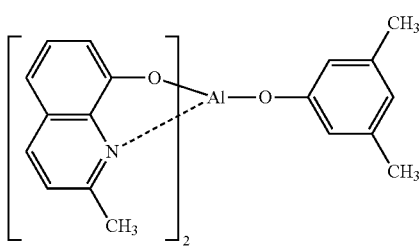 (A-10)
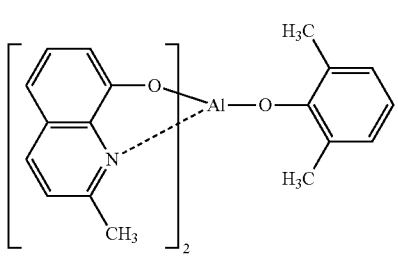 (A-11)
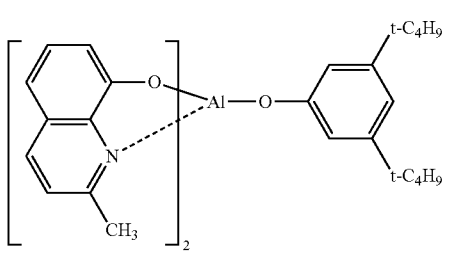 (A-12)
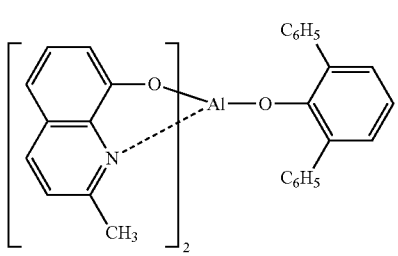 (A-13)
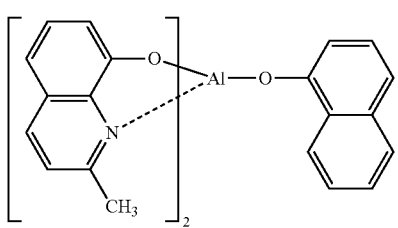 (A-14)
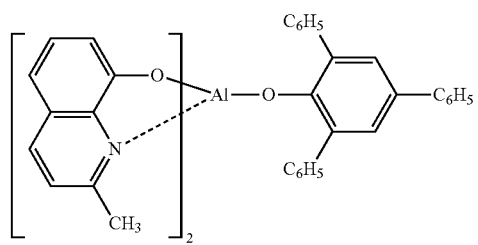 (A-15)
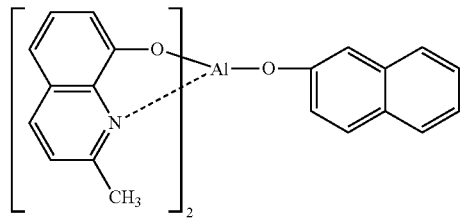 (A-16)
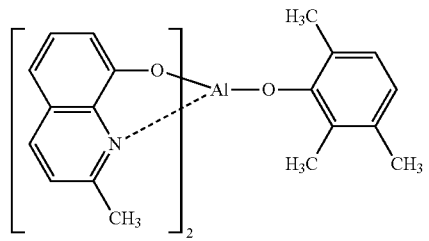 (A-17)
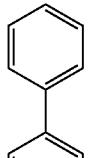 (A-18)
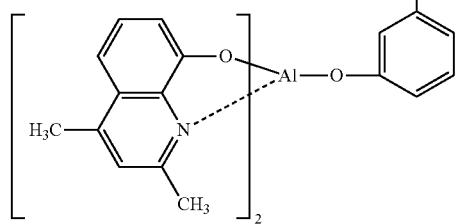
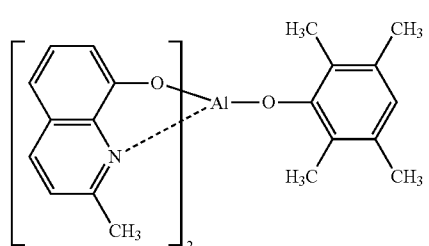 (A-19)
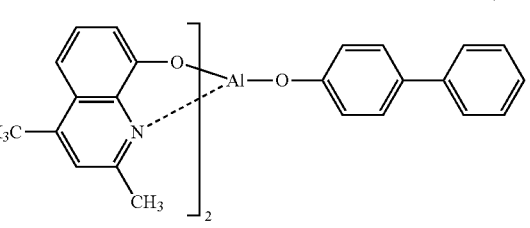 (A-20)

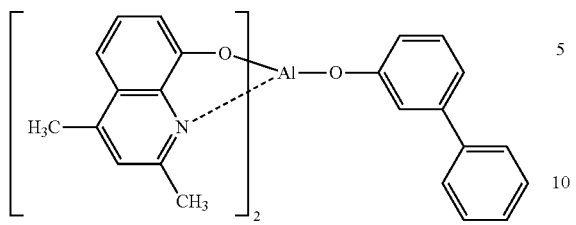 (A-21)
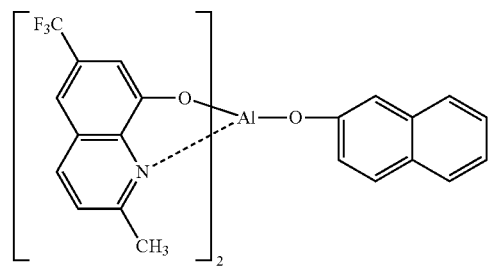 (A-27)
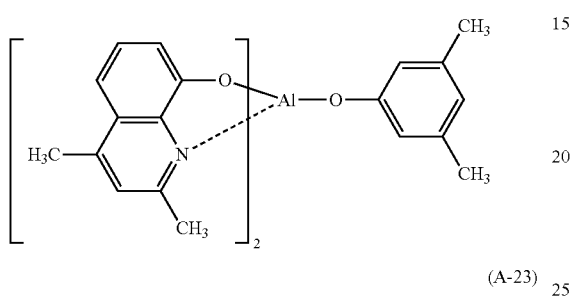 (A-22)
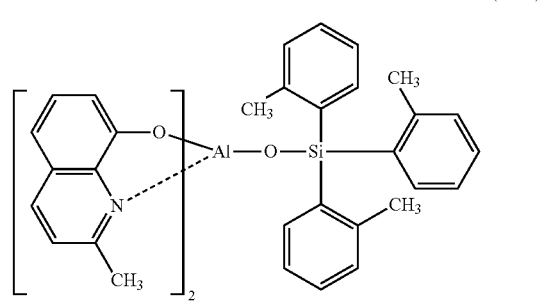 (A-28)
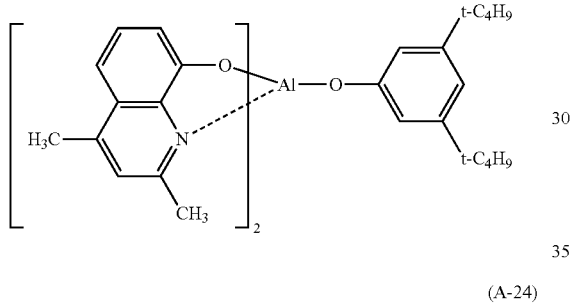 (A-23)
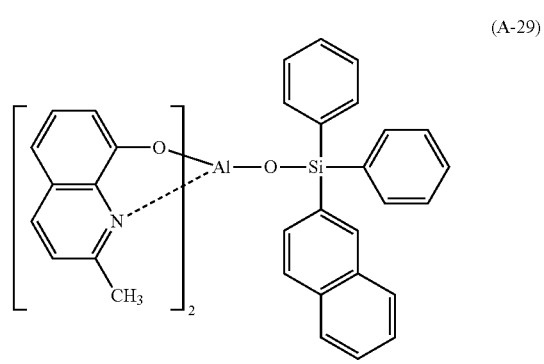 (A-29)
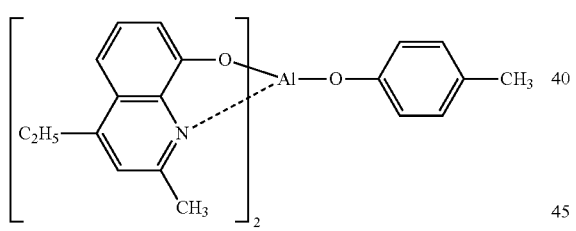 (A-24)
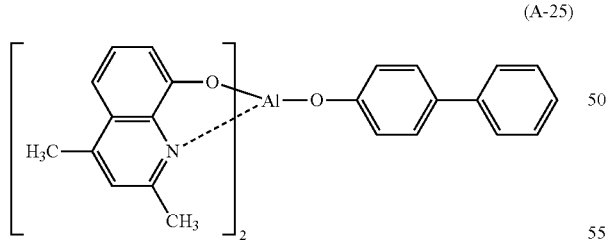 (A-25)
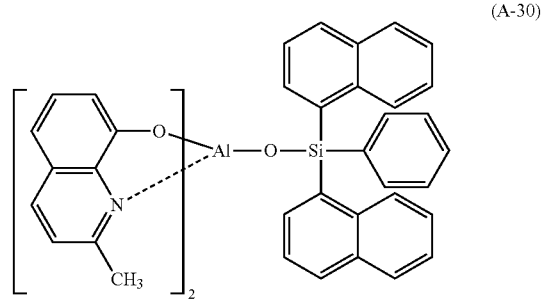 (A-30)
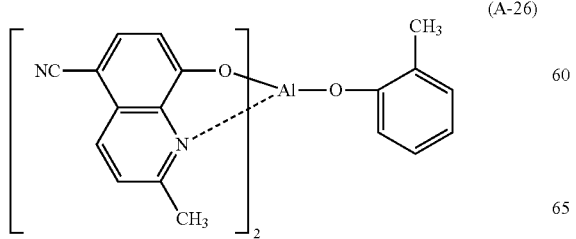 (A-26)
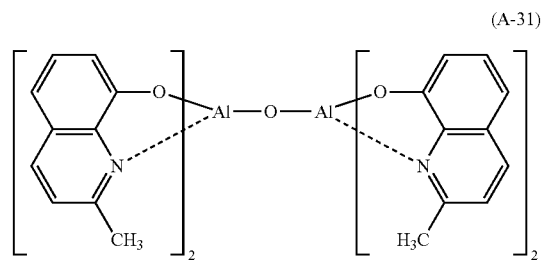 (A-31)

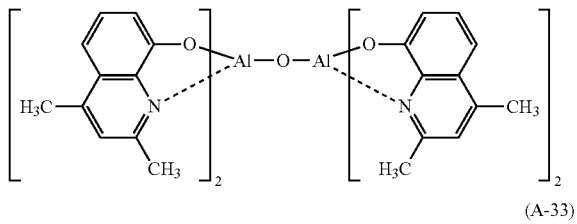
(A-32)

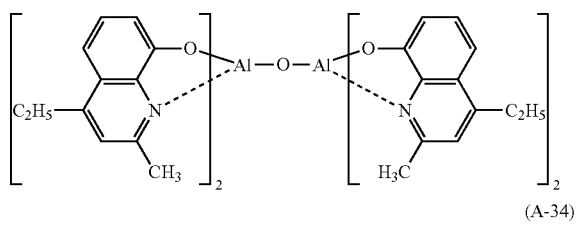
(A-33)

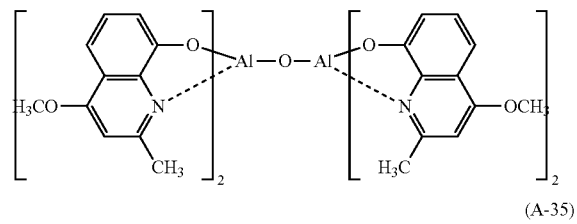
(A-34)

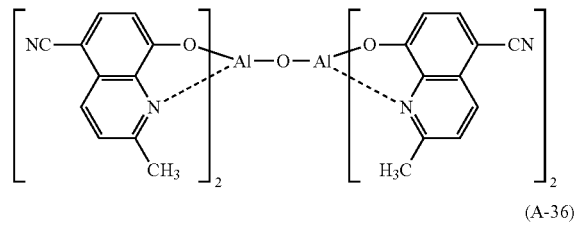
(A-35)

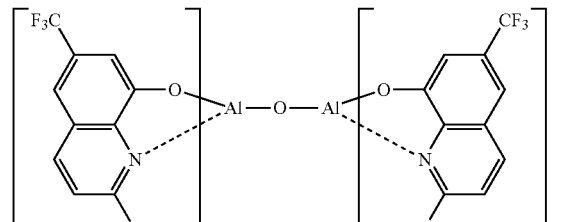
(A-36)

In the present invention, the electron injecting layer and the electron transporting layer preferably contain a nitrogen-containing heterocyclic derivative.

The electron injecting layer or the electron transporting layer is a layer for facilitating the injection of electrons into the light emitting layer and have large electron mobility. The electron injecting layer is formed to adjust the energy level, for example, by reducing the abrupt change in energy level. The material for the electron injecting layer or the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below.

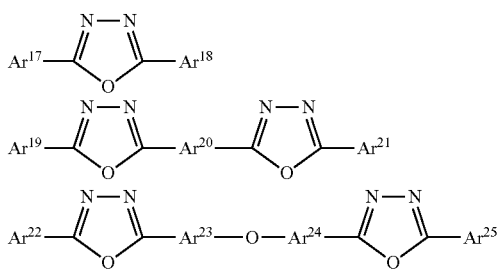

In the above formulae, each of $Ar^{17}$, $Ar^{18}$, $Ar^{19}$, $Ar^{20}$, $Ar^{21}$, $Ar^{22}$, and $Ar^{25}$ is a substituted or unsubstituted aryl group, and $Ar^{17}$ and $Ar^{18}$, $Ar^{19}$ and $Ar^{21}$, and $Ar^{22}$ and $Ar^{25}$ may be the same or different. Each of $Ar^{20}$, $Ar^{23}$, and $Ar^{24}$ is a substituted or unsubstituted arylene group, and $Ar^{23}$ and $Ar^{24}$ may be the same or different.

Examples of the arylene group include phenylene group, naphthylene group, biphenylene group, anthracenylene group, perylenylene group, and pyrenylene group. Examples of the substituent include an alkyl group having 1 to 10 carbon atoms, an alkoxy group having 1 to 10 carbon atoms, and cyano group. Electron transporting compounds which have a good thin film-forming property are preferably used. Examples of the electron transporting compound are shown below.

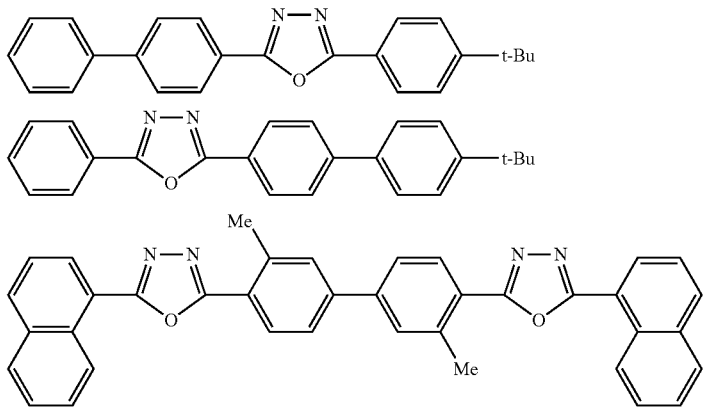

-continued

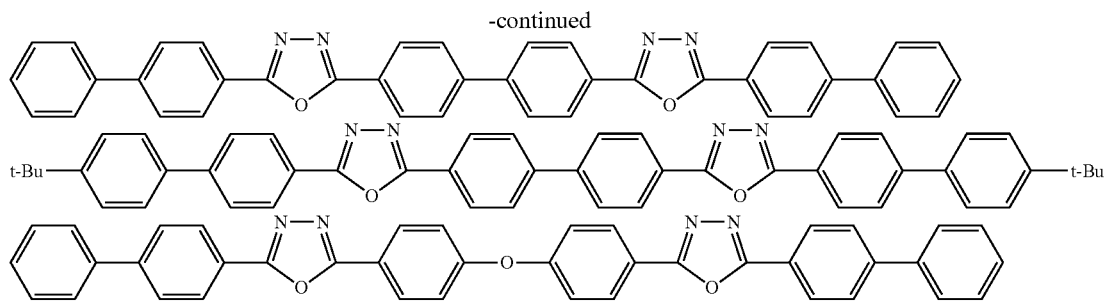

Examples of the nitrogen-containing heterocyclic derivative include a nitrogen-containing heterocyclic derivative having the following formulae but exclusive of metal complex, for example, a nitrogen-containing having a 5- or 6-membered ring having the skeleton represented by formula (A) or having the structure represented by formula (B).

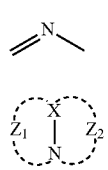

(A)

(B)

In formula (B), X is carbon atom or nitrogen atom. Z1 and Z2 are each independently a group of atoms for completing the nitrogen-containing heterering.

(C)

A nitrogen-containing aromatic polycyclic compound having a 5- or 6-membered ring is preferred. If two or more nitrogen atoms are included, the nitrogen-containing aromatic polycyclic compound preferably has a skeleton of a combination of (A) and (B) or a combination of (A) and (C).

The nitrogen-containing group of the nitrogen-containing organic compound is selected from the nitrogen-containing heterocyclic groups shown below.

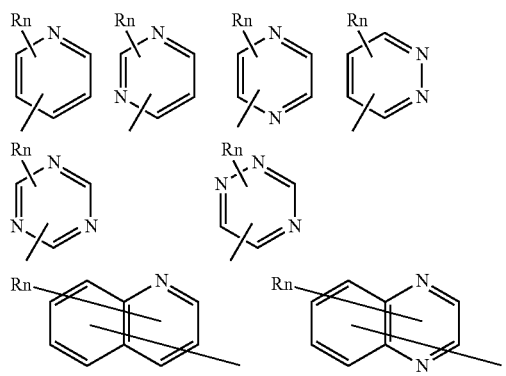

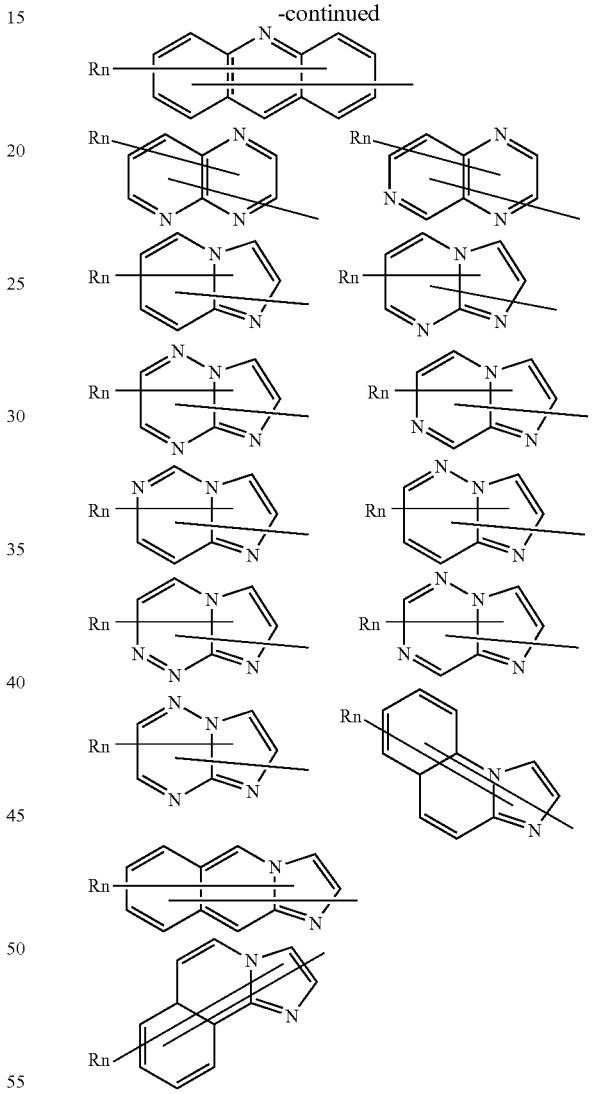

In the above formulae, R is an aryl group having 6 to 40 carbon atoms, a heteroaryl group having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

HAr-L$^1$-Ar$^1$—Ar$^2$

In the above formula, HAr is a substitute or unsubstituted nitrogen-containing heteroring having 3 to 40 carbon atoms; $L^1$ is a single bond, a substituted or unsubstituted arylene group having 6 to 40 carbon atoms, or a substituted or unsubstituted heteroarylene group having 3 to 40 carbon atoms; $Ar^1$ is a substitute or unsubstituted divalent aromatic hydrocarbon group having 6 to 40 carbon atoms; and $Ar^2$ is a substitute or unsubstituted aryl group having 6 to 40 carbon atoms or a substituted or unsubstituted heteroaryl group having 3 to 40 carbon atoms.

HAr is selected, for example, from the following group:

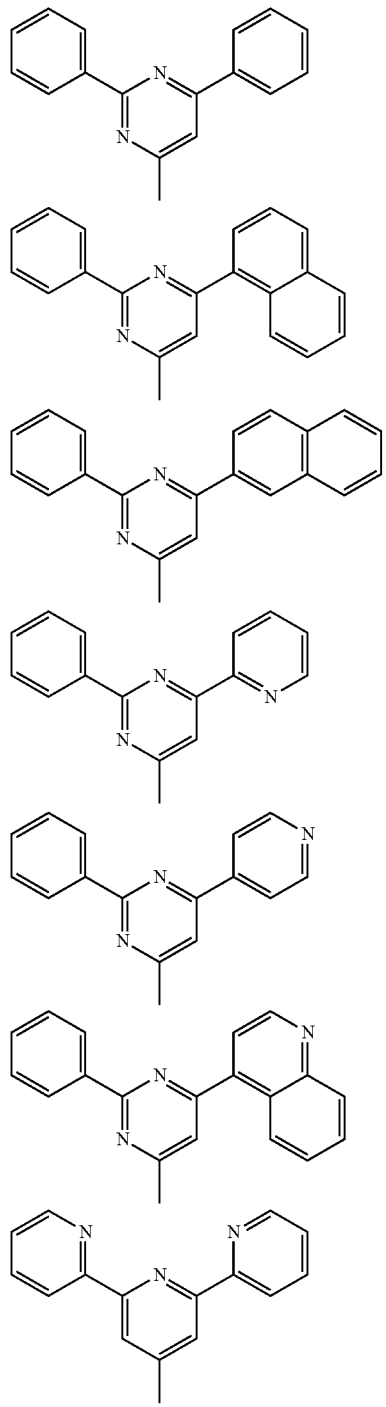

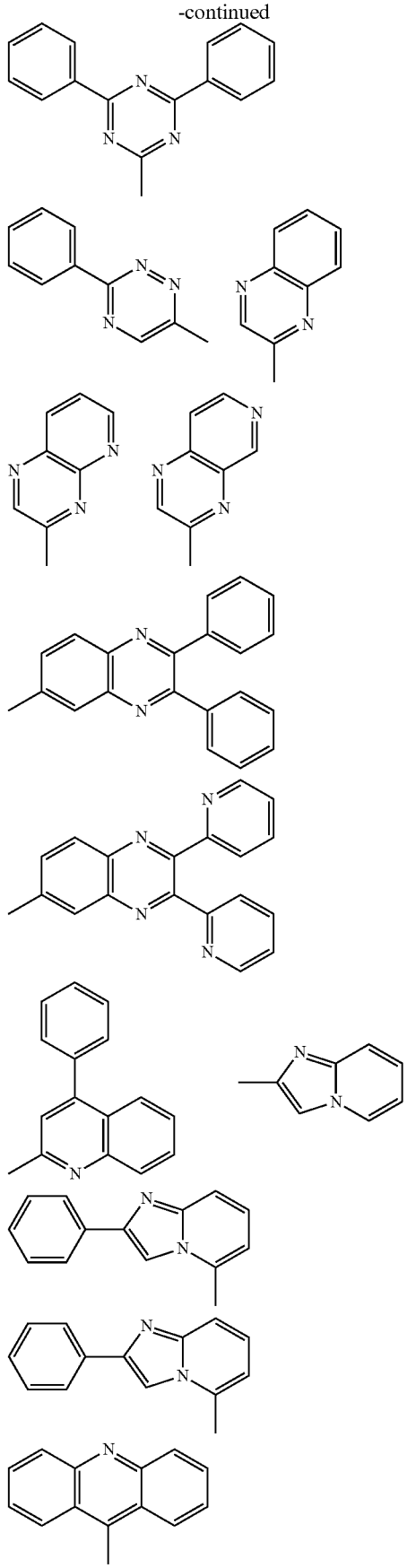

-continued

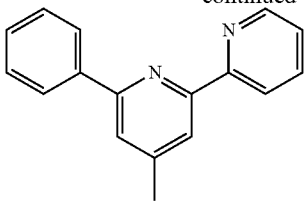

L¹ is selected, for example, from the following group:

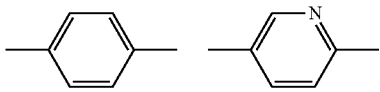

Ar² is selected, for example, from the following group:

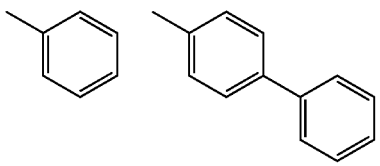

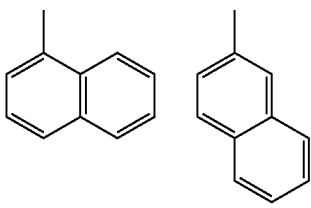

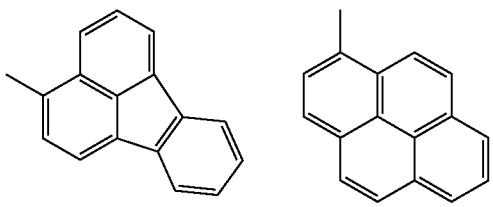

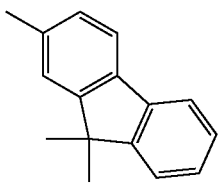

Ar¹ is selected, for example, from the following arylanthranyl groups:

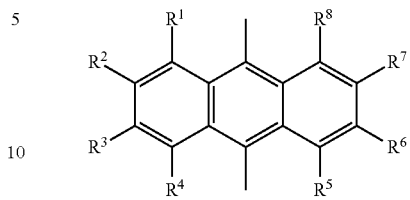

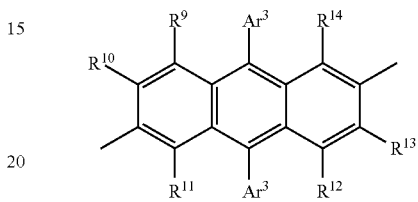

In the above formulae, $R^1$ to $R^{14}$ are each independently hydrogen atom (inclusive of heavy hydrogen atom), a halogen atom, an alkyl group having 1 to 20 carbon atoms, an alkoxy group having 1 to 20 carbon atoms, an aryloxy group having 6 to 40 carbon atoms, a substituted or unsubstituted aryl group having 6 to 40 carbon atoms, or a heteroaryl group having 3 to 40 carbon atoms; and $Ar^3$ is a substituted or unsubstituted aryl group having 6 to 40 carbon atoms or a substituted or unsubstituted heteroaryl group having 3 to 40 carbon atoms.

A nitrogen-containing heterocyclic derivative having $Ar^1$ wherein $R^1$ to $R^8$ are all hydrogen atoms (inclusive of heavy hydrogen atom) is preferred.

In addition, the following compound (JP 9-3448A) is preferred.

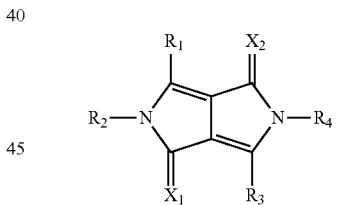

In the above formula, $R_1$ to $R_4$ are each independently hydrogen atom (inclusive of heavy hydrogen atom), a substituted or unsubstituted aliphatic group, a substituted or unsubstituted alicyclic group, a substituted or unsubstituted carbocyclic aromatic group, or a substituted or unsubstituted heterocyclic group; and $X_1$ and $X_2$ are each independently oxygen atom, sulfur atom, or dicyanomethylene group.

Further, the following compound (JP 2000-173774A) is also preferred.

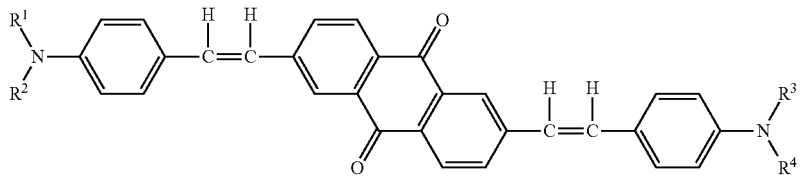

In the above formula, $R^1$, $R^2$, $R^3$, and $R^4$ may be the same or different and each represents an aryl group represented by the following formula:

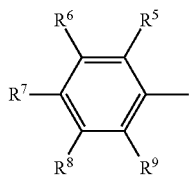

wherein $R^5$, $R^6$, $R^7$, $R^8$, and $R^9$ may be the same or different and each represent hydrogen atom (inclusive of heavy hydrogen atom) or at least one thereof is a saturated or unsaturated alkoxy group, an alkyl group, amino group, or an alkylamino group.

Further, a high molecular compound having the nitrogen-containing heterocyclic group or the nitrogen-containing heterocyclic derivative is also usable.

It is preferred for the electron transporting layer to contain any one of the nitrogen-containing heterocyclic derivatives represented by the following formulae (201) to (203):

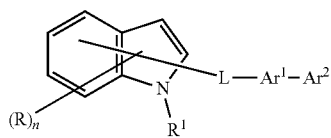 (201)

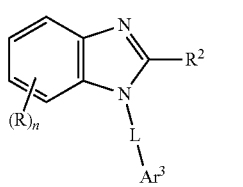 (202)

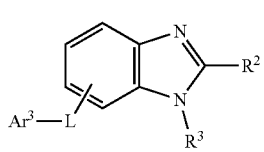 (203)

wherein R is hydrogen atom (inclusive of heavy hydrogen atom), a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; n is an integer of 0 to 4; $R^1$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms; $R^2$ and $R^3$ are each independently hydrogen atom (inclusive of heavy hydrogen atom), a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; L is a substituted or unsubstituted arylene group having 6 to 60 carbon atoms, a substituted or unsubstituted pyridinylene group, a substituted or unsubstituted quinolinylene group, or a substituted or unsubstituted fluorenylene group; $Ar^1$ is a substituted or unsubstituted arylene group having 6 to 60 carbon atoms, a substituted or unsubstituted pyridinylene group, or a substituted or unsubstituted quinolinylene group; and $Ar^2$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms.

$Ar^3$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by $—Ar^1—Ar^2$ wherein $Ar^1$ and $Ar^2$ are as defined above.

In formulae (201) to (203), R is hydrogen atom (inclusive of heavy hydrogen atom), a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of the aryl group having 6 to 60 carbon atoms, preferably 6 to 40 carbon atoms, and more preferably 6 to 20 carbon atoms include phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl)phenyl group, fluoranthenyl group, fluorenyl group, a monovalent residue of spirobifluorene, perfluorophenyl group, perfluoronaphthyl group, perfluoroanthryl group, perfluorobiphenyl group, a monovalent residue of 9-phenylanthracene, a monovalent residue of 9-(1'-naphthyl)anthracene, a monovalent residue of 9-(2'-naphthyl)anthracene, a monovalent residue of 6-phenylchrysene, and a monovalent residue of 9-[4-(diphenylamino)phenyl]anthracene, with phenyl group, naphthyl group, biphenyl group, terphenyl group, 9-(10-phenyl)anthryl group, 9-[10-(1'-naphthyl)]anthryl group, and 9-[10-(2'-naphthyl)]anthryl group being preferred.

Examples of the alkyl group having 1 to 20 carbon atoms, preferably 1 to 6 carbon atoms include methyl group, ethyl group, propyl group, butyl group, pentyl group, hexyl group, and a haloalkyl group, such as trifluoromethyl group. The alkyl group having 3 or more carbon atoms may be linear, cyclic or branched.

Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Examples of the substituent represented by R include a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, and a substituted or unsubstituted heteroaryl group having 3 to 40 carbon atoms.

Examples of the halogen atom include fluorine, chlorine, bromine, and iodine.

Examples of the alkyl group having 1 to 20 carbon atoms, the alkoxy group having 1 to 20 carbon atoms, and the aryl group having 6 to 40 carbon atoms are the same as those described above.

Examples of the aryloxy group having 6 to 40 carbon atoms include phenoxy group and biphenyloxy group.

Examples of the heteroaryl group having 3 to 40 carbon atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, and triazolyl group.

n is an integer of 0 to 4, preferably 0 to 2.

In formula (201), $R^1$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms.

Examples, preferred examples, and preferred carbon numbers of the above groups are the same as those described with respect to R.

In formulae (202) and (203), $R^2$ and $R^3$ are each independently hydrogen atom (inclusive of heavy hydrogen atom), a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of each group, preferred carbon numbers, and examples of substituent are the same as those described with respect to R.

In formulae (201) to (203), L is a substituted or unsubstituted arylene group having 6 to 60 carbon atoms, a substituted or unsubstituted pyridinylene group, a substituted or unsubstituted quinolinylene group, or a substituted or unsubstituted fluorenylene group.

Preferably the arylene group has 6 to 40 carbon atoms and more preferably 6 to 20 carbon atoms. Examples thereof include divalent groups formed by removing one hydrogen atom (inclusive of heavy hydrogen atom) from the aryl groups described with respect to R. Examples of the substituent of each group represented by L are the same as those described with respect to R.

L is preferably selected from the following group:

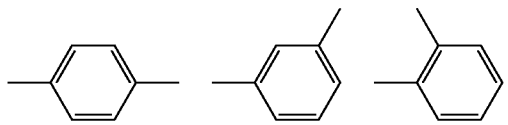

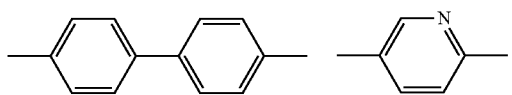

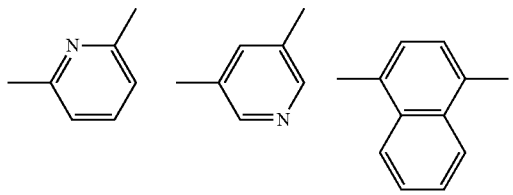

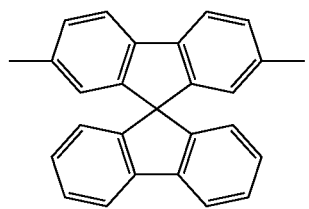

In formula (201), $Ar^1$ is a substituted or unsubstituted arylene group having 6 to 60 carbon atoms, a substituted or unsubstituted pyridinylene group, or a substituted or unsubstituted quinolinylene group. Examples of the substituent of each group represented by $Ar^1$ and $Ar^3$ are the same as those described with respect to R.

$Ar^1$ is preferably any one of condensed groups represented by the following formulae (101) to (110):

(101)

(102)

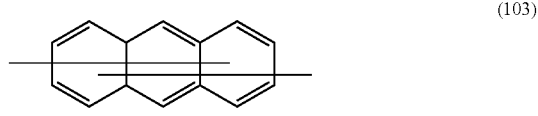

(103)

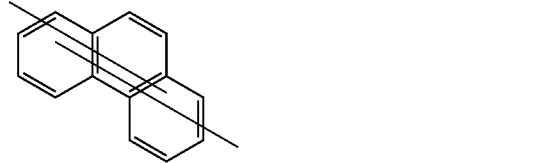

(104)

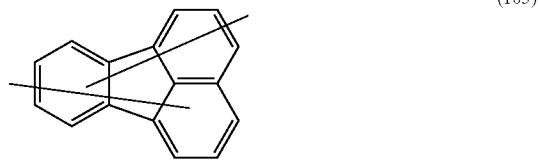

(105)

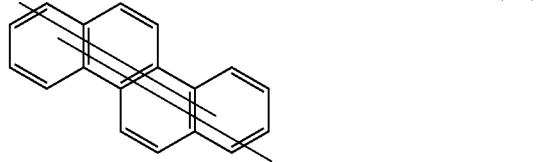

(106)

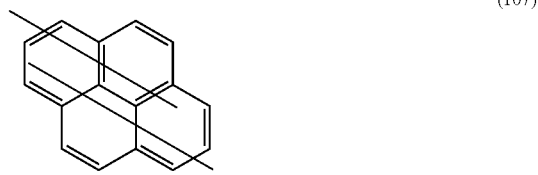

(107)

(108)

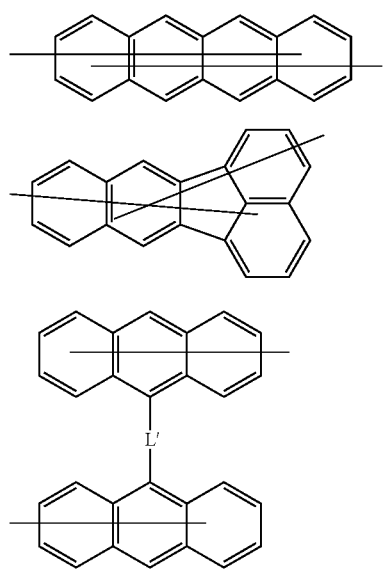

(109)

(110)

In formulae (101) to (110), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

In formula (110), L' is a single bond or a group selected from the following group:

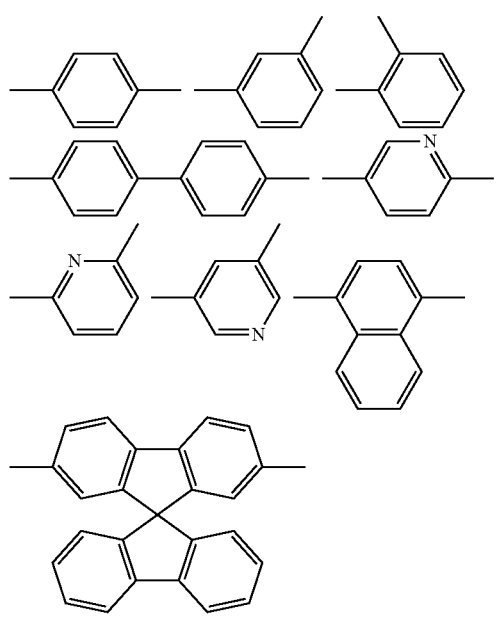

Formula (103) represented by $Ar^1$ is preferably the condensed ring group represented by the following formulae (111) to (125):

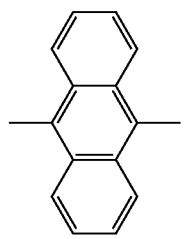
(111)

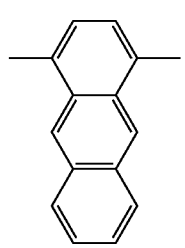
(112)

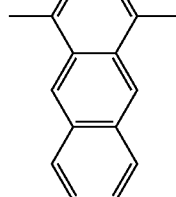

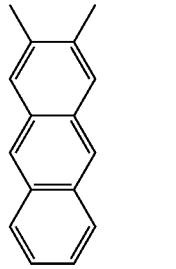
(113)

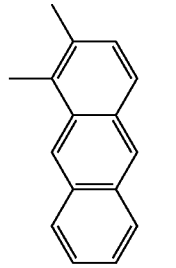
(114)

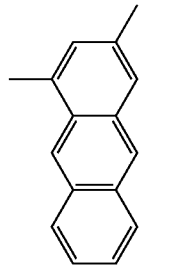
(115)

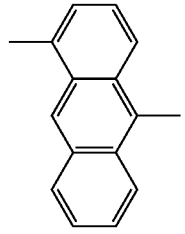
(116)

(117) 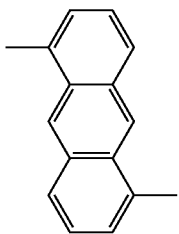

(118) 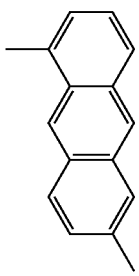

(119) 

(120) 

(121) 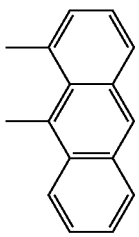

(122) 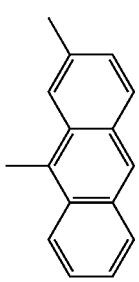

(123) 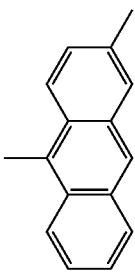

(124) 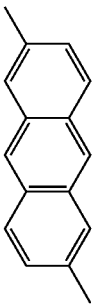

(125) 

In formulae (111) to (125), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

In formula (201), $Ar^2$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of each group, preferred carbon numbers, and examples of substituent are the same as those described with respect to R.

In formulae (202) and (203), $Ar^3$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^1$—$Ar^2$ wherein $Ar^1$ and $Ar^2$ are as defined above.

Examples of each group, preferred carbon numbers, and examples of substituent are the same as those described with respect to R.

Ar³ is preferably any one of condensed ring groups represented by the following formulae (126) to (135):

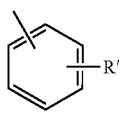
(126)

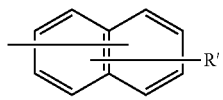
(127)

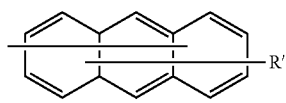
(128)

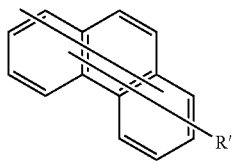
(129)

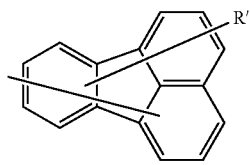
(130)

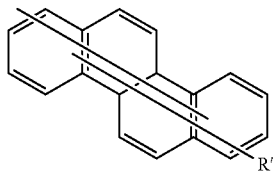
(131)

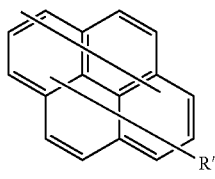
(132)

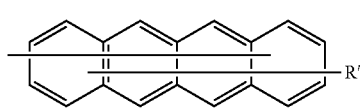
(133)

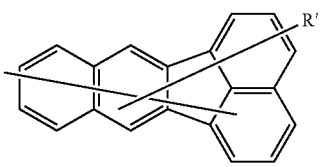
(134)

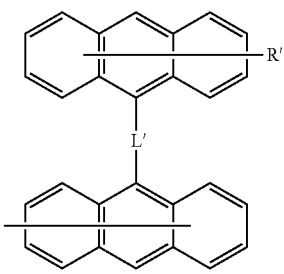
(135)

In formulae (126) to (135), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

In formula (135), L' is as defined above.

In formulae (126) to (135), R' is hydrogen atom (inclusive of heavy hydrogen atom), a substituted or unsubstituted alkyl group having 1 to 20 carbon atoms, a substituted or unsubstituted aryl group having 6 to 40 carbon atoms, or a substituted or unsubstituted heteroaryl group having 3 to 40 carbon atoms. Examples thereof are the same as those described above.

Formula (128) represented by Ar³ is preferably the condensed ring group represented by the following formulae (136) to (158):

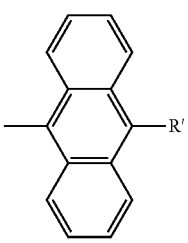
(136)

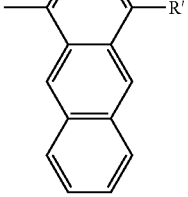
(137)

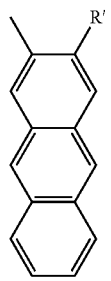
(137)
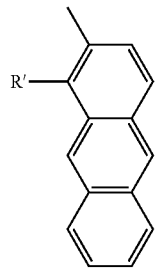
(138)
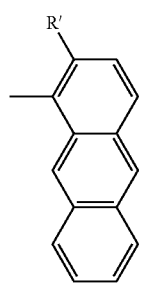
(139)
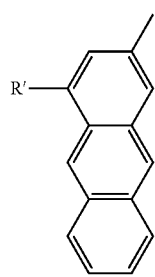
(140)
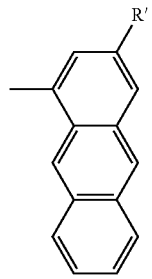
(141)
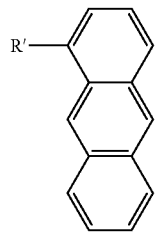
(142)
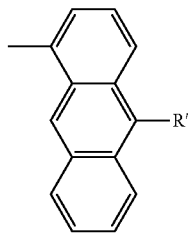
(143)
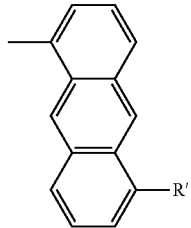
(144)
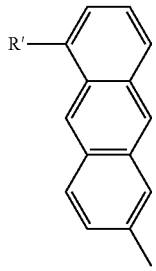
(145)
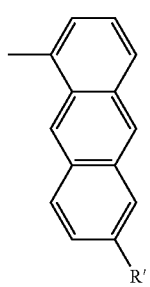
(146)
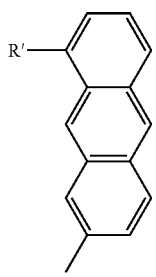
(147)
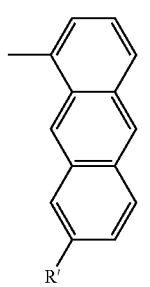
(148)

(150)
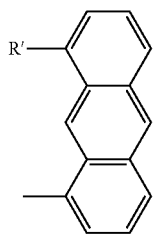

(151)
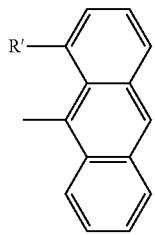

(152)
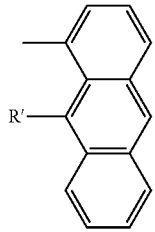

(153)
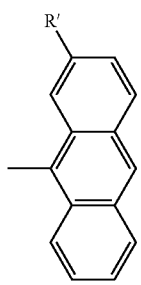

(154)
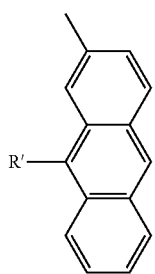

(155)
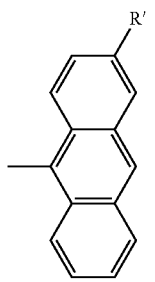

(156)
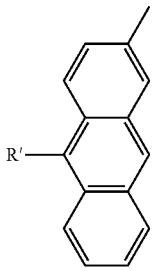

(157)
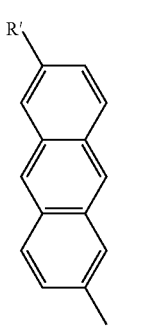

(158)
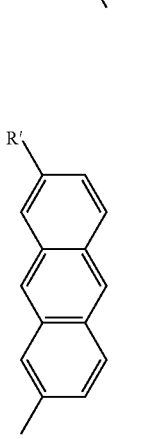

In formulae (136) to (158), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

Each of $Ar^2$ and $Ar^3$ is preferably selected from the following group:

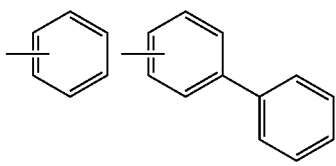

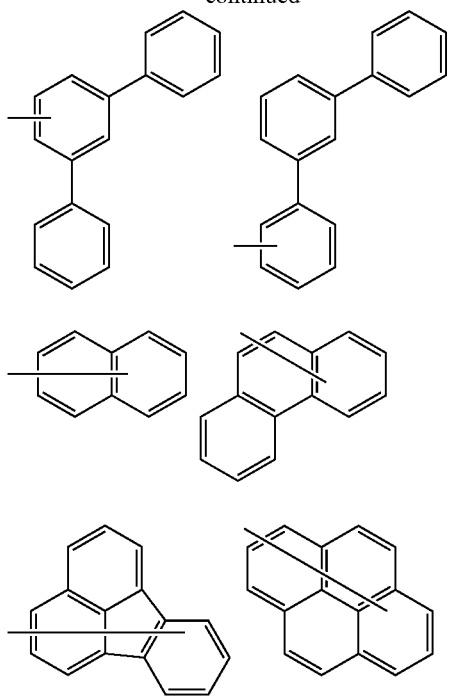
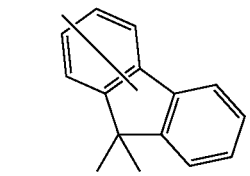
Examples of the nitrogen-containing heterocyclic derivative represented by formulae (201) to (203) are shown below. The nitrogen-containing heterocyclic derivative is, however, not limited to the following exemplary compounds.
In the following tables, HAr is the following structure in formulae (201) to (203).
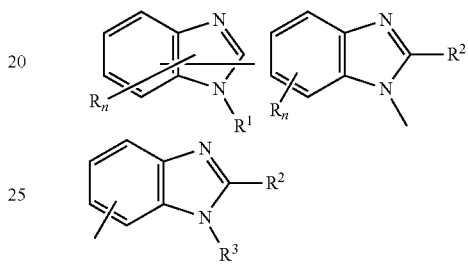

-continued
| HAr | L | Ar¹ | Ar² |
|---|---|---|---|
| 4 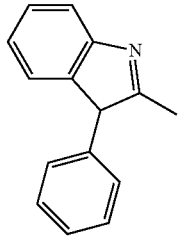 | 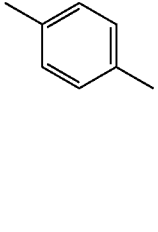 | 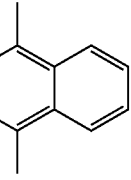 | 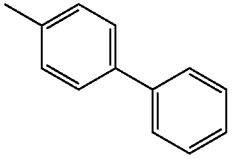 |
| 5 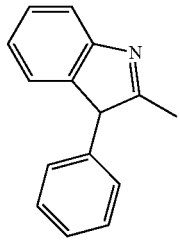 | 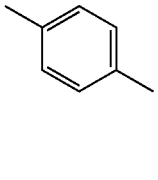 | 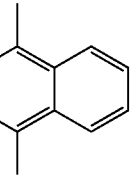 | 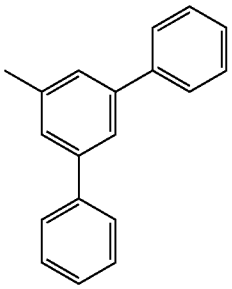 |
| 6 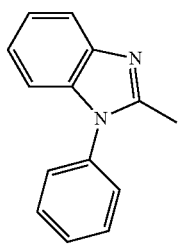 | 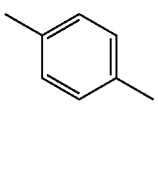 | 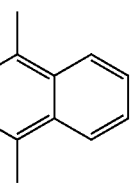 | 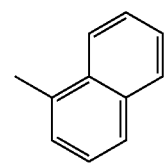 |
| 7 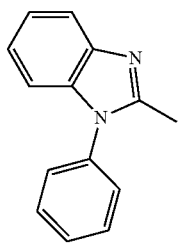 | 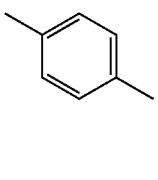 | 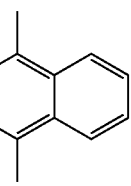 | 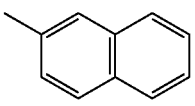 |
| 8 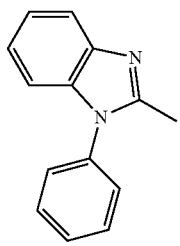 | 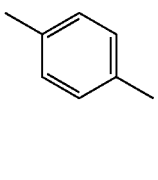 | 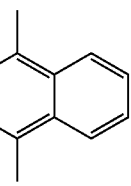 | 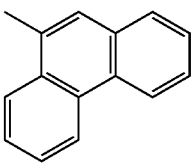 |
| 9 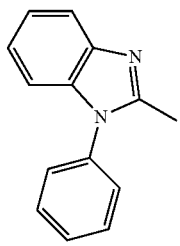 | 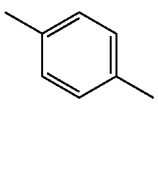 | 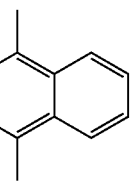 | 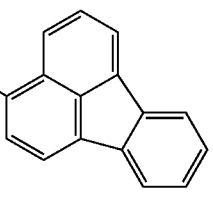 |

-continued
| HAr | L | Ar¹ | Ar² |
|---|---|---|---|
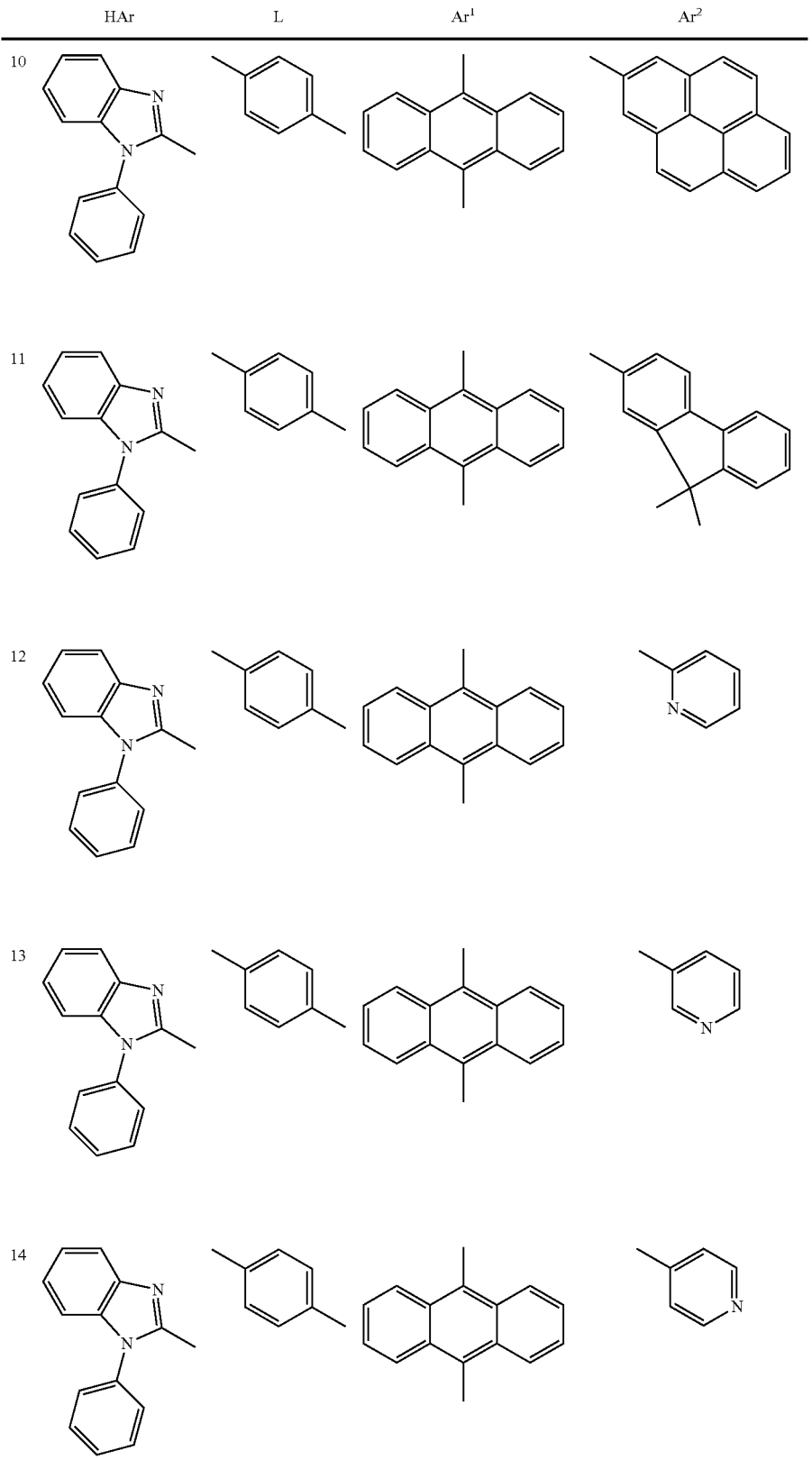

| | HAr | L | Ar¹ | Ar² |
|---|---|---|---|---|
| HAr—L—Ar¹—Ar² | | | | |
| 2-1 | | | | |
| 2 | | | | |
| 3 | | | | |
| 4 | | | | |
| 5 | | | | |
| 6 | | | | |

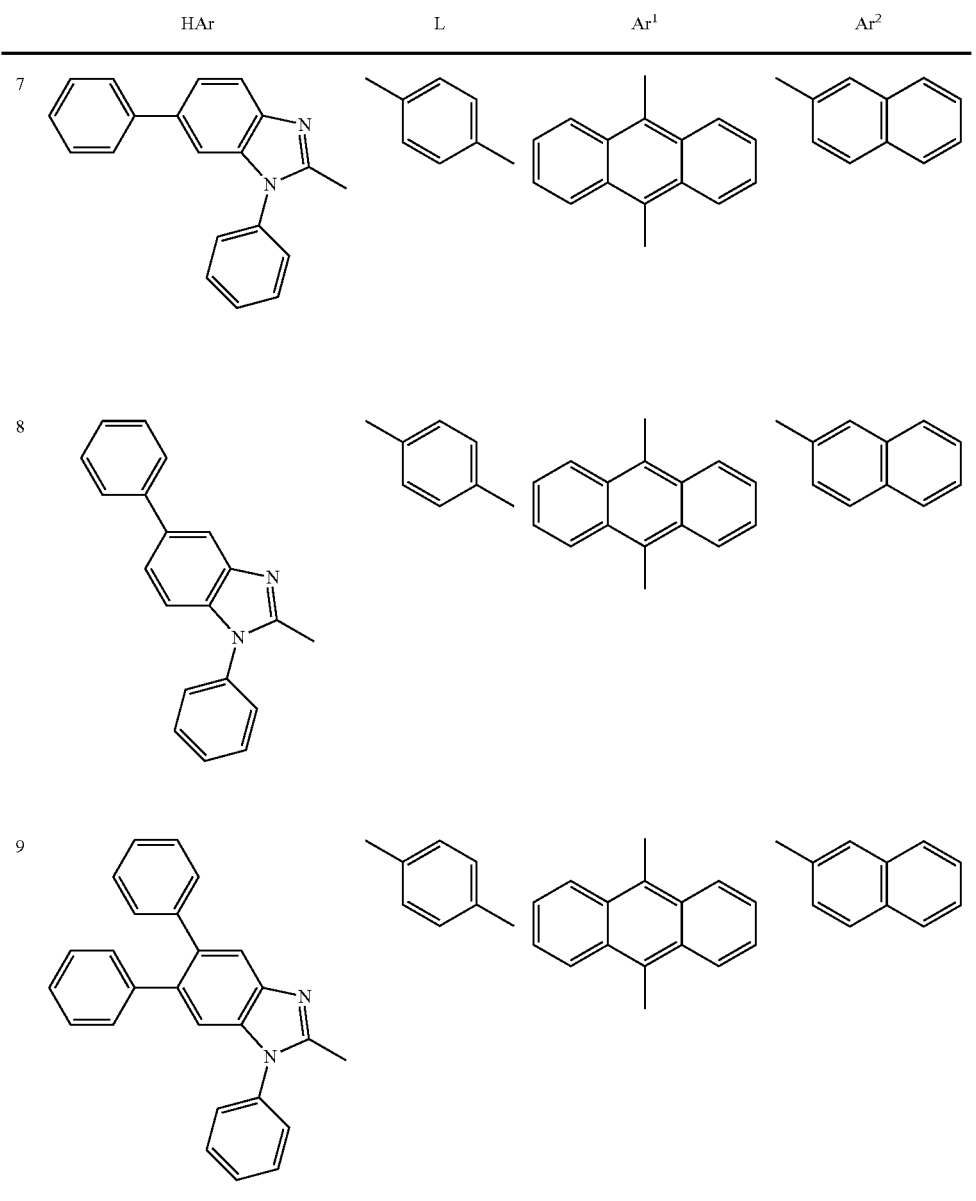
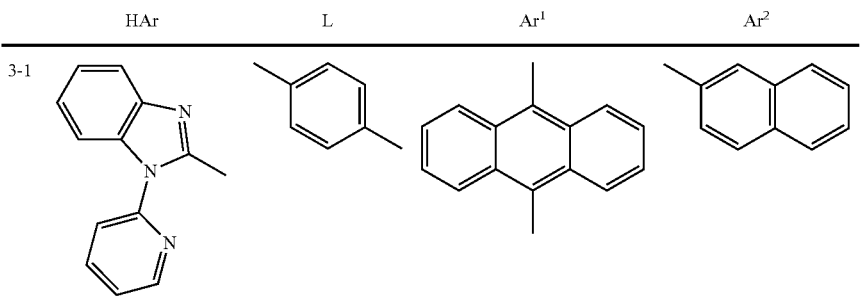

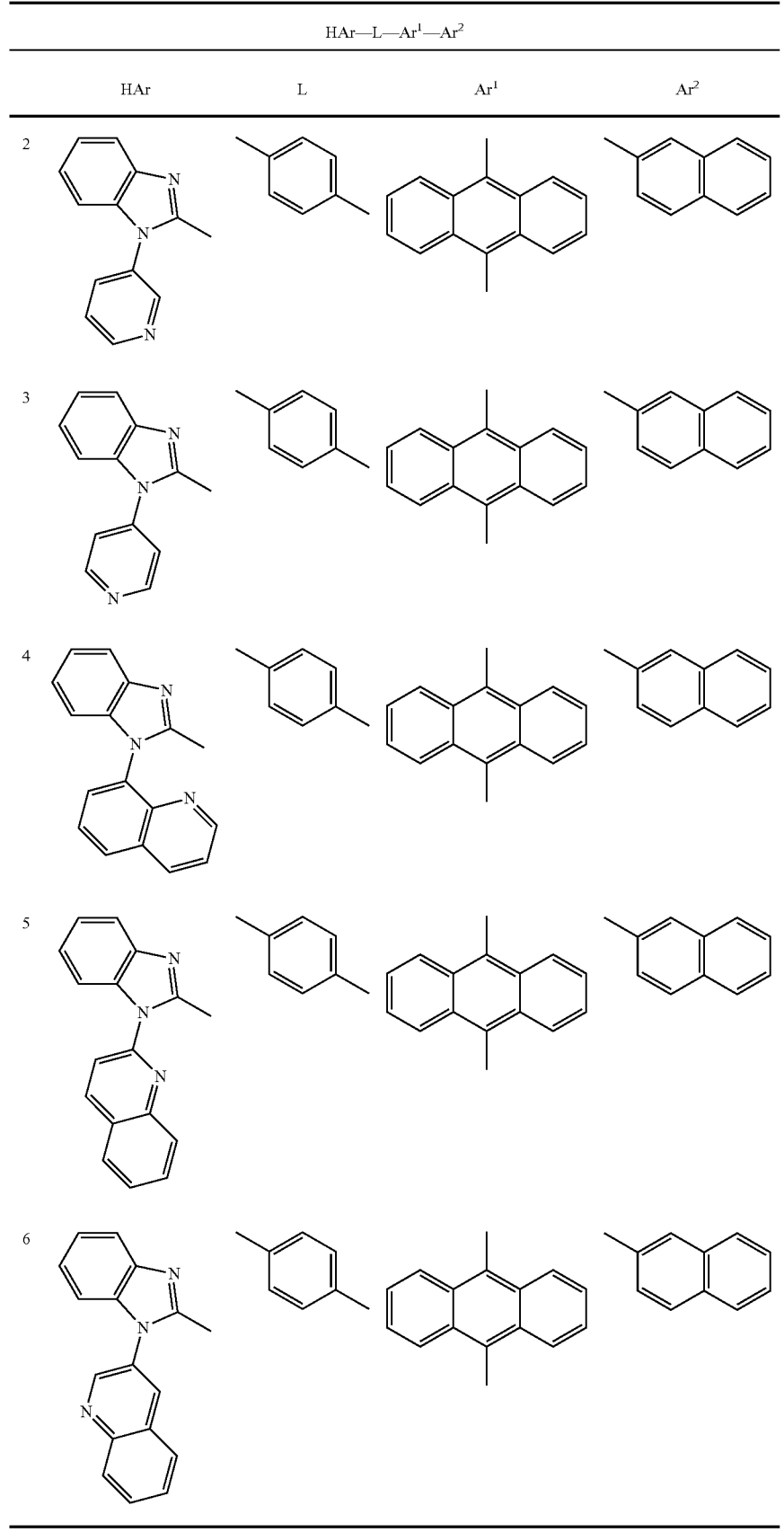

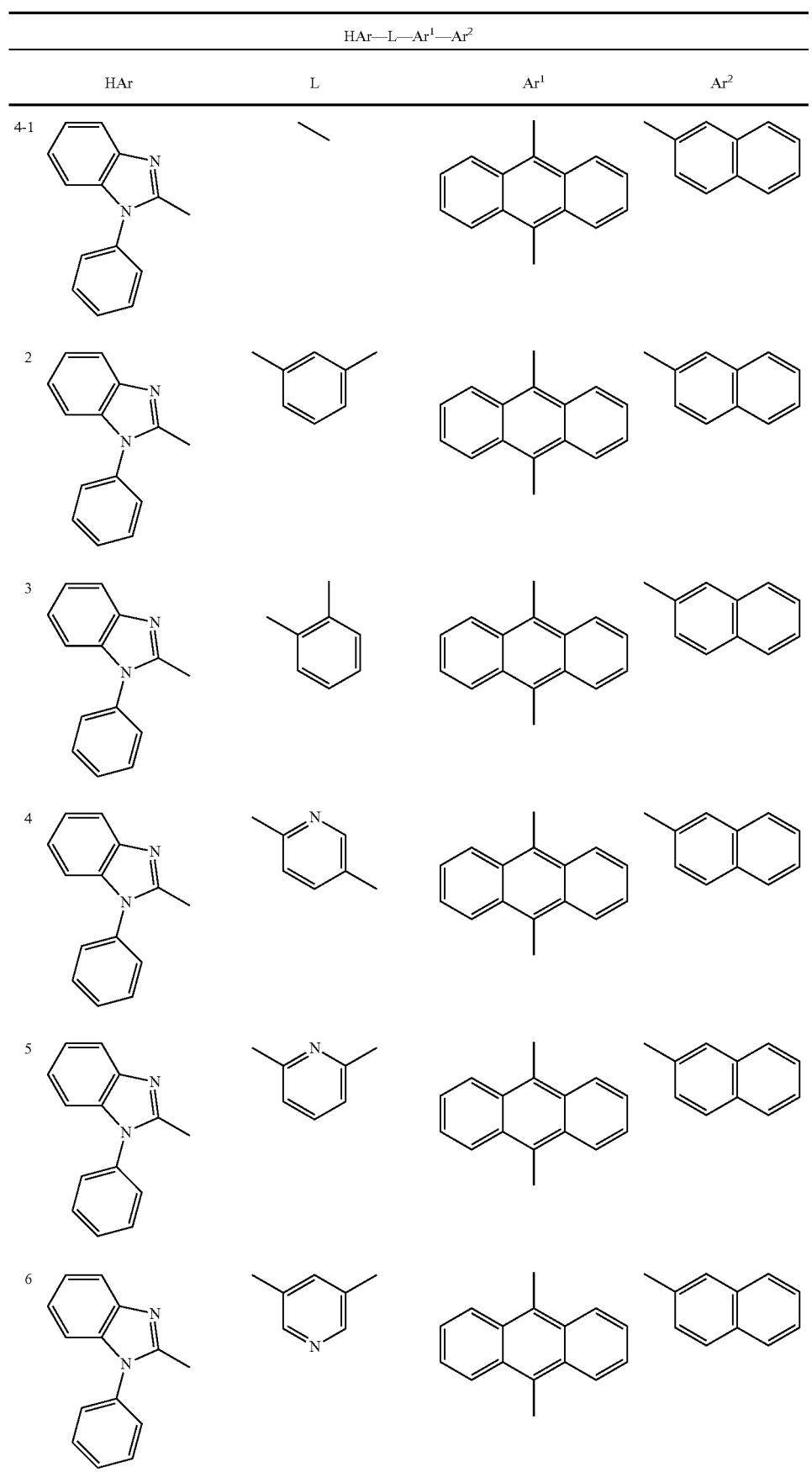

-continued

| | HAr—L—Ar¹—Ar² | | | |
|---|---|---|---|---|
| | HAr | L | Ar¹ | Ar² |
| 7 | | | | |
| 8 | | | | |
| 9 | | | | |
| 10 | | | | |
| 11 | | | | |
| 12 | | | | |

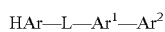
| | HAr—L—Ar¹—Ar² | | | |
|---|---|---|---|---|
| | HAr | L | Ar¹ | Ar² |

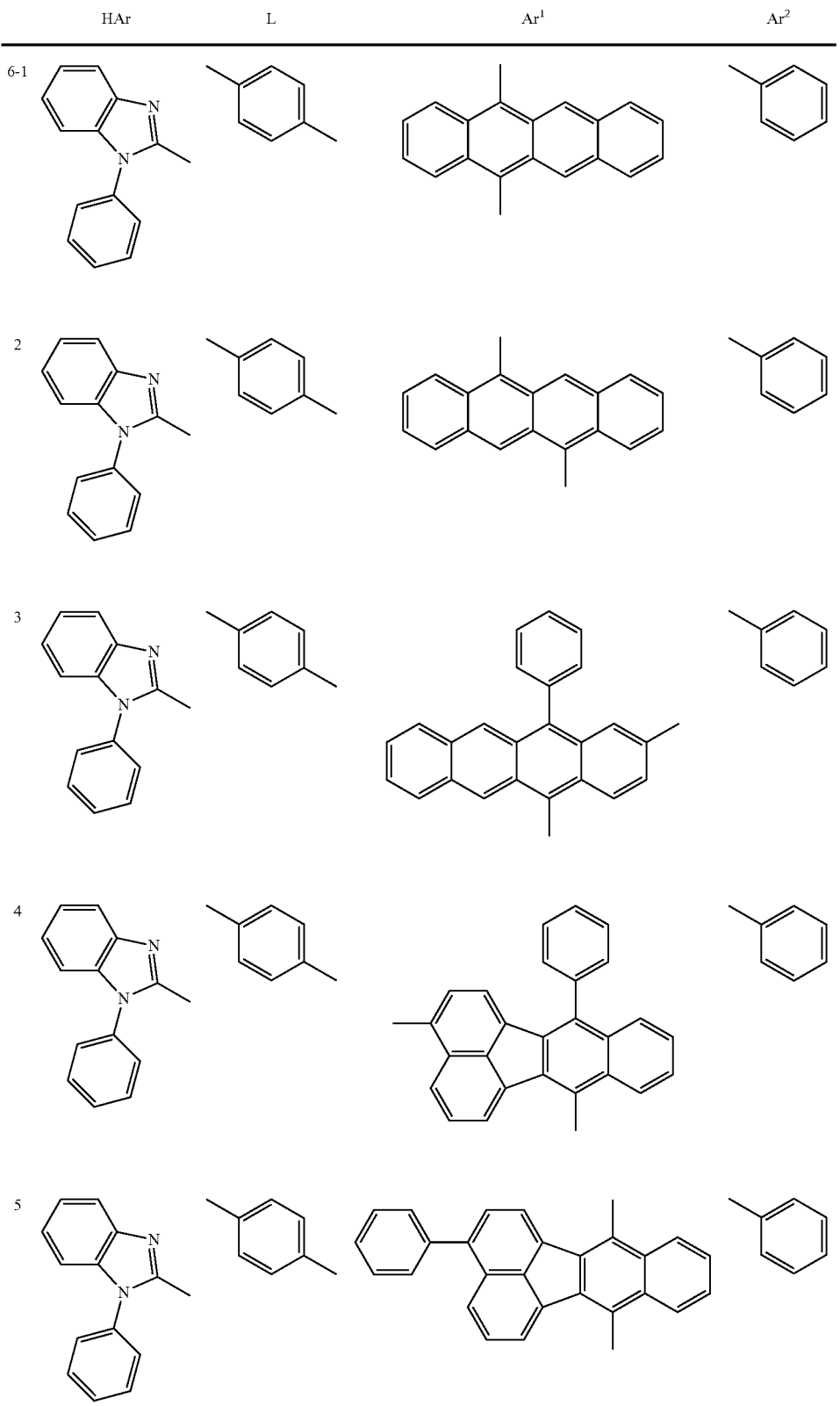

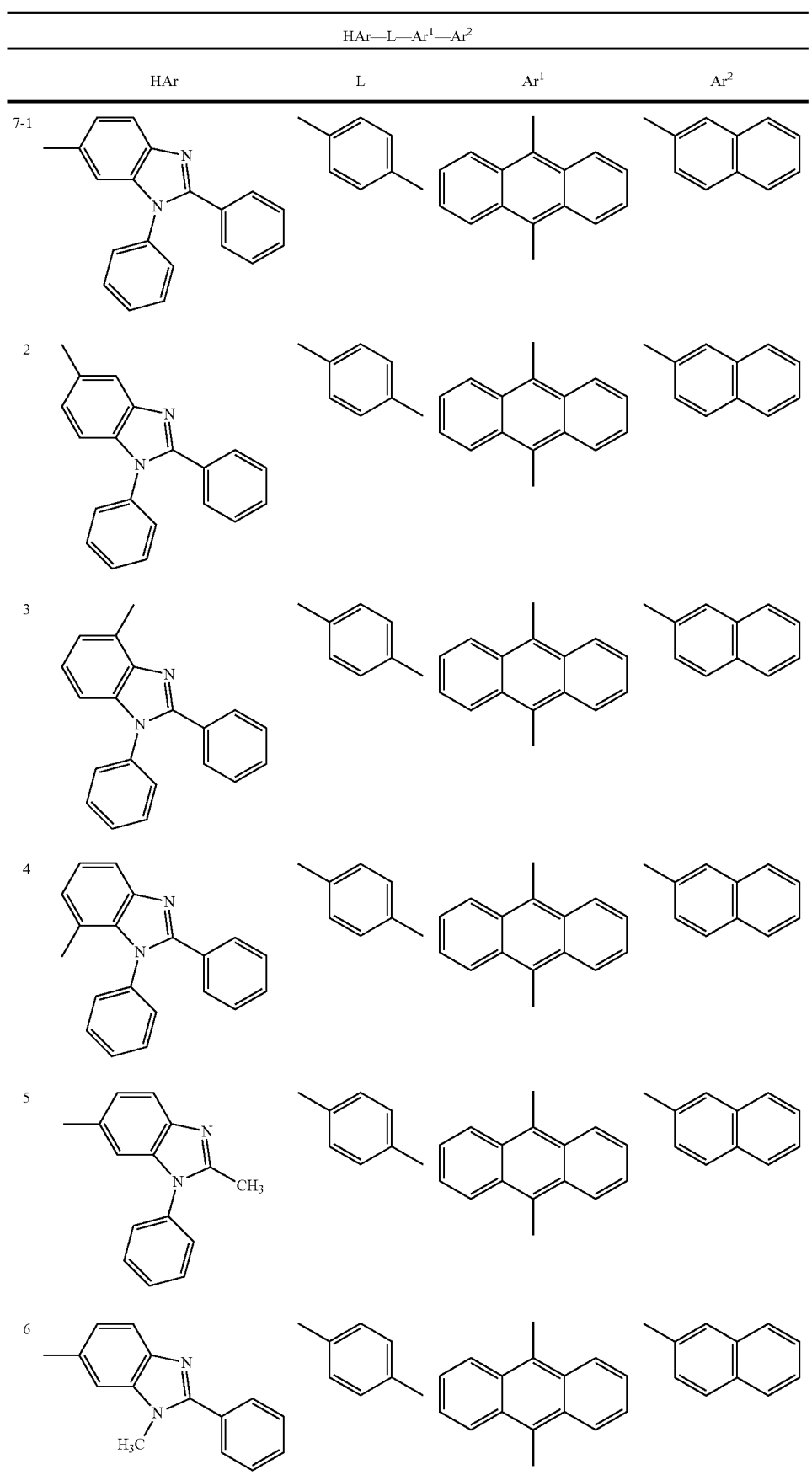

-continued
| | HAr—L—Ar¹—Ar² | | | |
|---|---|---|---|---|
| | HAr | L | Ar¹ | Ar² |
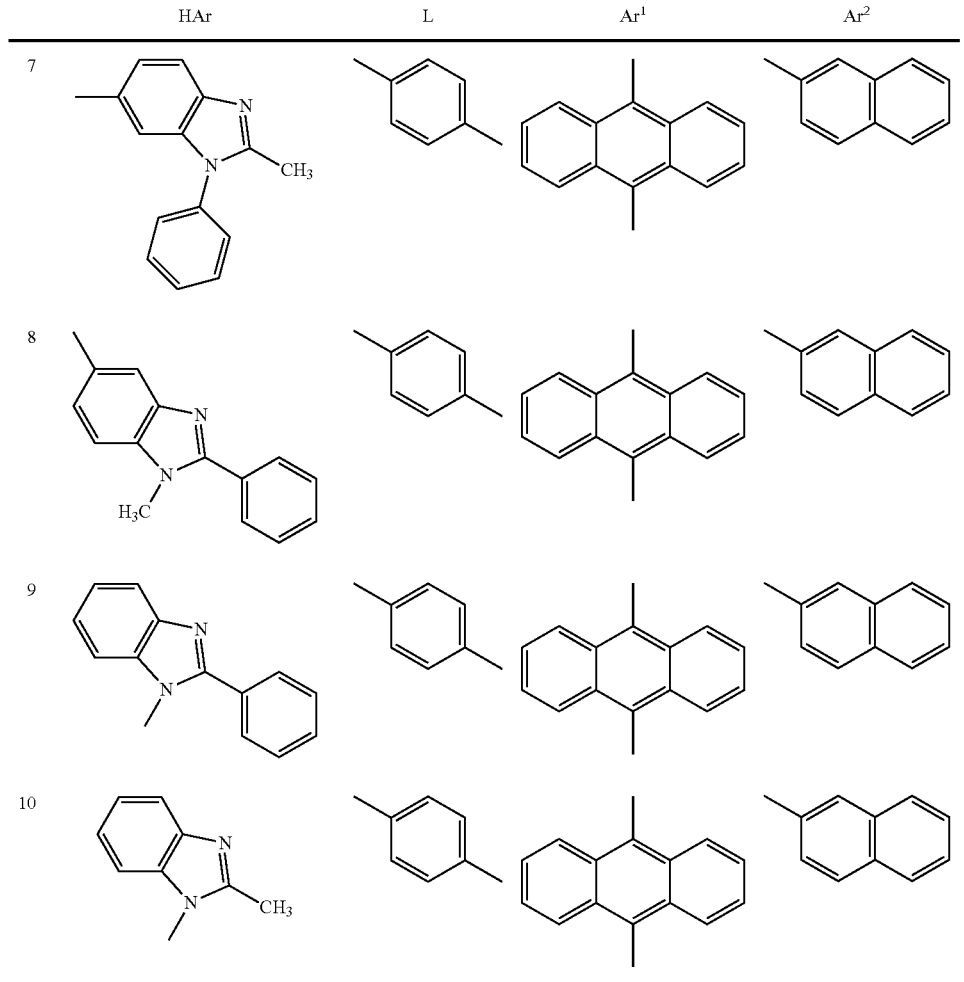
| | HAr—L—Ar¹—Ar² | | | |
|---|---|---|---|---|
| | HAr | L | Ar¹ | Ar² |
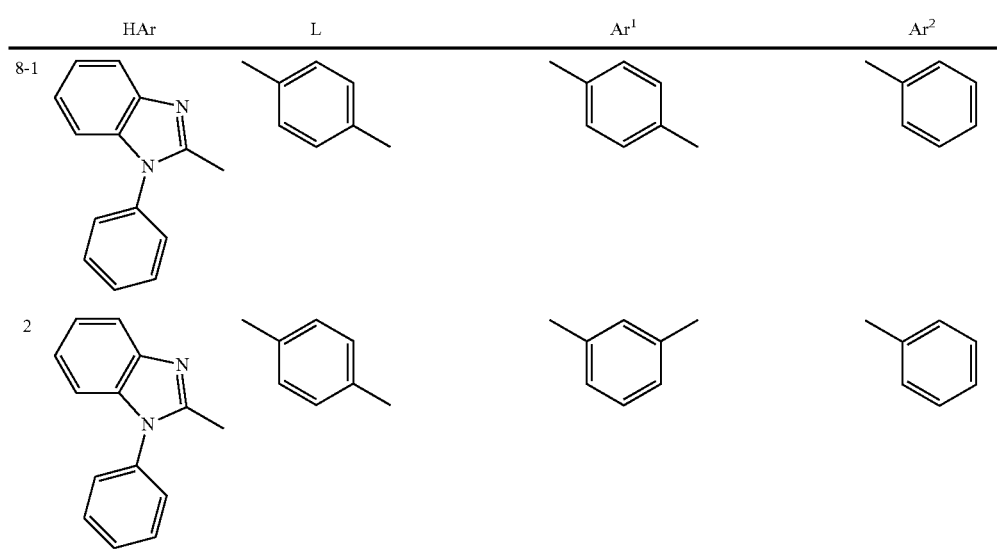

-continued

| | HAr | L | Ar¹ | Ar² |
|---|---|---|---|---|
| 3 | 1-phenyl-2-methyl-benzimidazole | 1,4-phenylene | 1,4-naphthylene | phenyl |
| 4 | 1-phenyl-2-methyl-benzimidazole | 1,4-phenylene | 2,6-naphthylene | phenyl |
| 5 | 1-phenyl-2-methyl-benzimidazole | 1,4-phenylene | phenanthrenyl | phenyl |
| 6 | 1-phenyl-2-methyl-benzimidazole | 1,4-phenylene | phenanthrenyl | phenyl |
| 7 | 1-phenyl-2-methyl-benzimidazole | 1,4-phenylene | phenanthrenyl | H |
| 8 | 1-phenyl-2-methyl-benzimidazole | 1,4-phenylene | chrysenyl | phenyl |

-continued
| | HAr—L—Ar¹—Ar² | | | |
|---|---|---|---|---|
| | HAr | L | Ar¹ | Ar² |
| 9 | 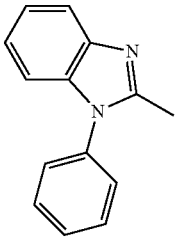 | 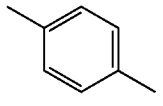 | 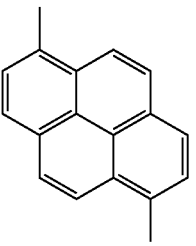 | 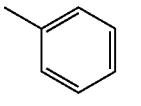 |
| 10 | 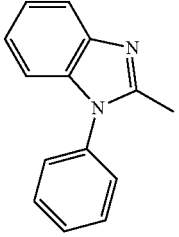 | 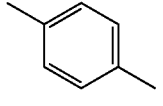 | 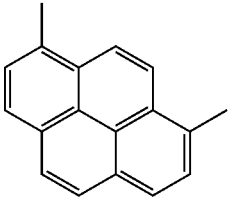 | 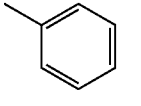 |
| 11 | 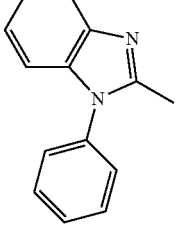 | 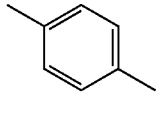 | 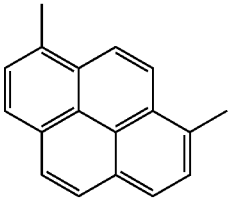 | —H |
| 12 |  | 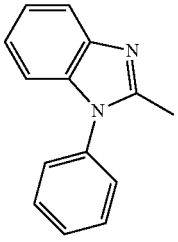 | 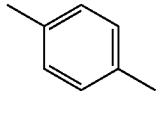 | 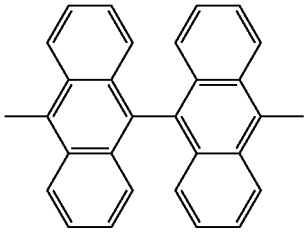 |
| 13 | 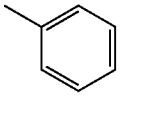 | 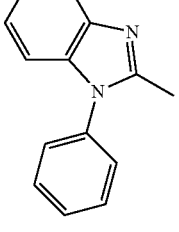 | 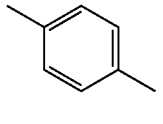 | 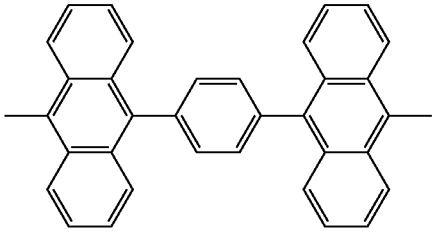 |

| | HAr | L | Ar¹ | Ar² |
|---|---|---|---|---|
| 9-1 | 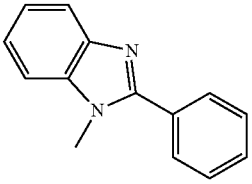 | 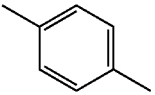 | 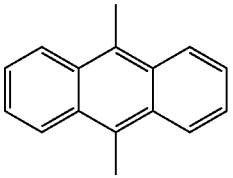 | 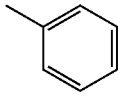 |
| 2 | 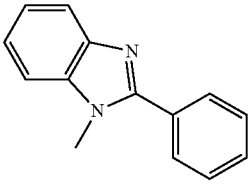 | 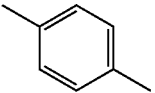 | 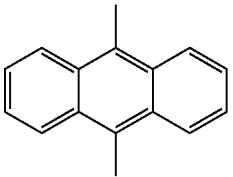 | 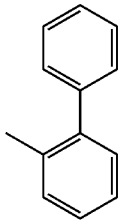 |
| 3 | 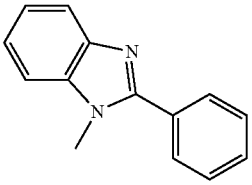 | 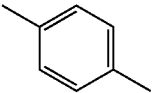 | 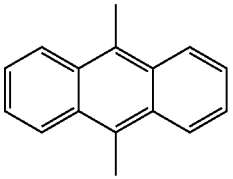 | 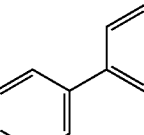 |
| 4 | 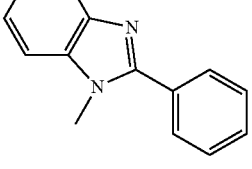 | 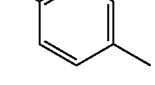 | 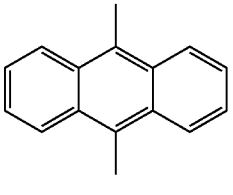 | 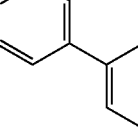 |
| 5 | 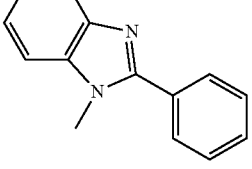 | 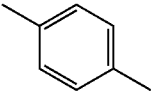 | 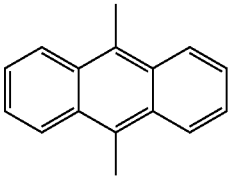 | 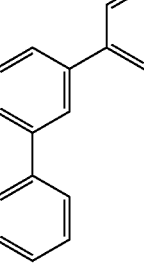 |
| 6 | 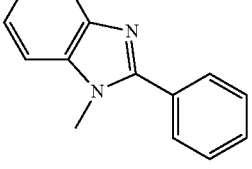 | 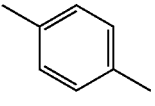 | 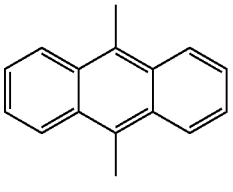 | 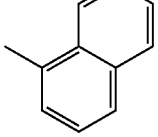 |
| 7 | 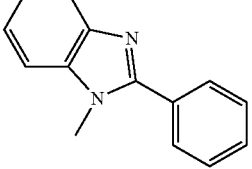 | 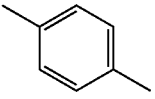 | 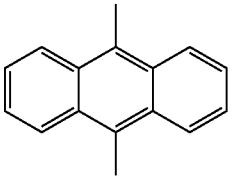 | 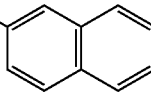 |

-continued

| | HAr | L | Ar¹ | Ar² |
|---|---|---|---|---|
| 8 | | | | |
| 9 | | | | |
| 10 | | | | |
| 11 | | | | |
| 12 | | | | |
| 13 | | | | |
| 14 | | | | |

| | HAr | L | Ar¹ | Ar² |
|---|---|---|---|---|
| 10-1 | 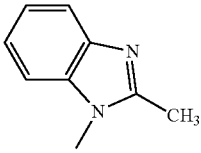 | 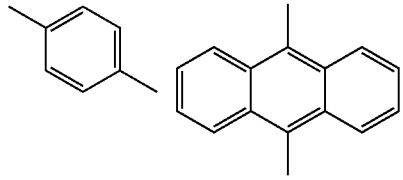 | 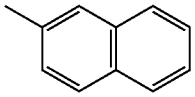 | 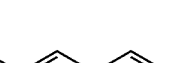 |
| 2 | 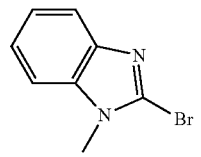 | 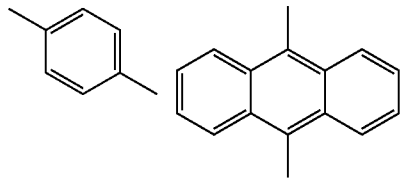 | 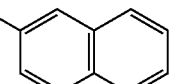 | 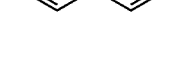 |
| 3 | 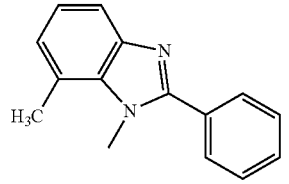 | 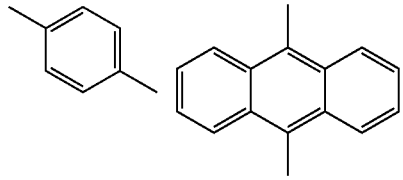 | 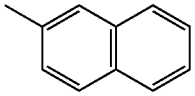 |  |
| 4 | 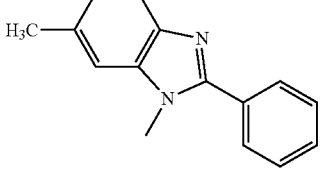 | 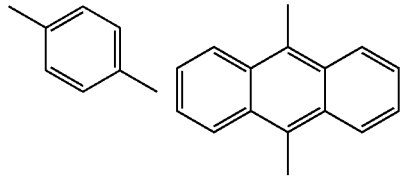 | 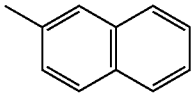 |  |
| 5 | 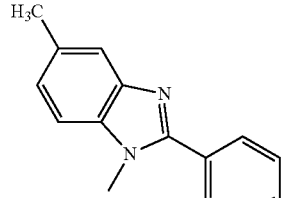 | 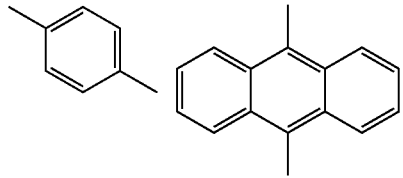 | 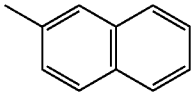 |  |
| 6 | 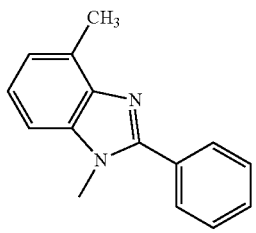 | 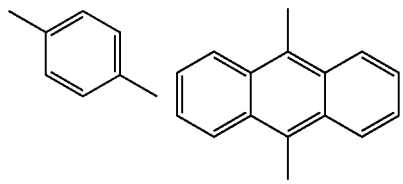 | 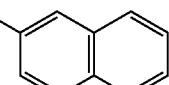 | 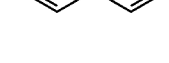 |
| 7 | 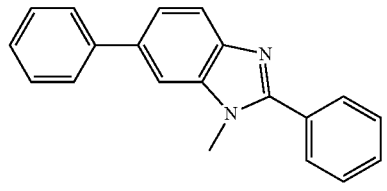 | 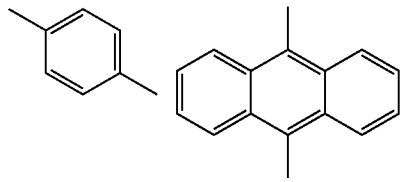 | 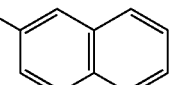 | 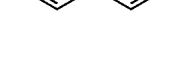 |

-continued
| | HAr | L | Ar¹ | Ar² |
|---|---|---|---|---|
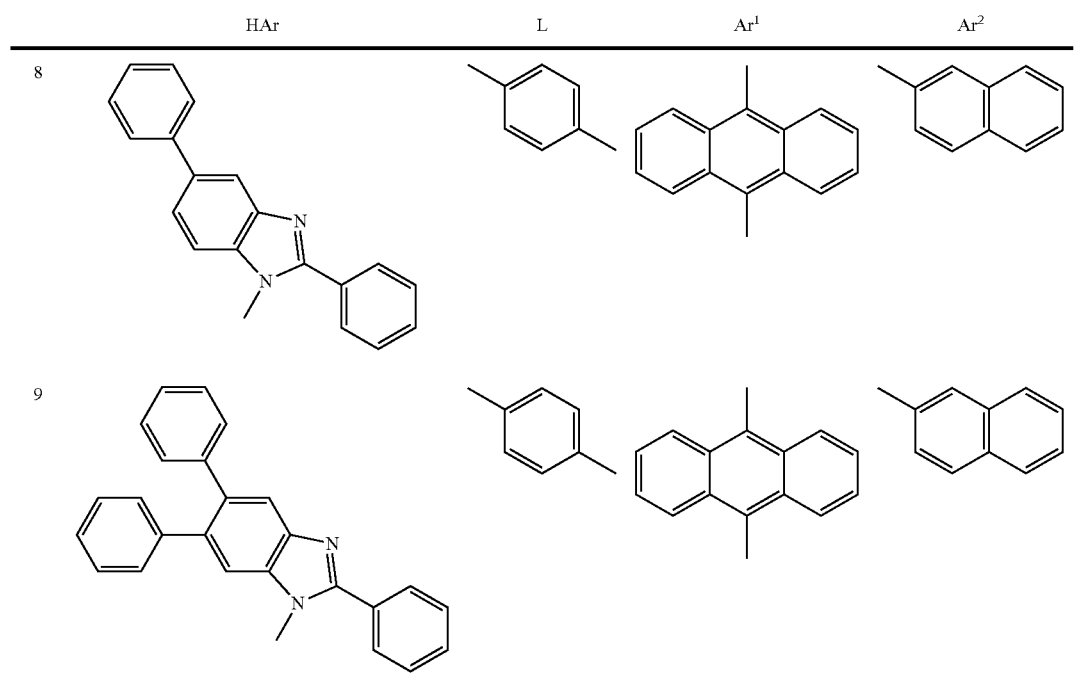
| | HAr | L | Ar¹ | Ar² |
|---|---|---|---|---|
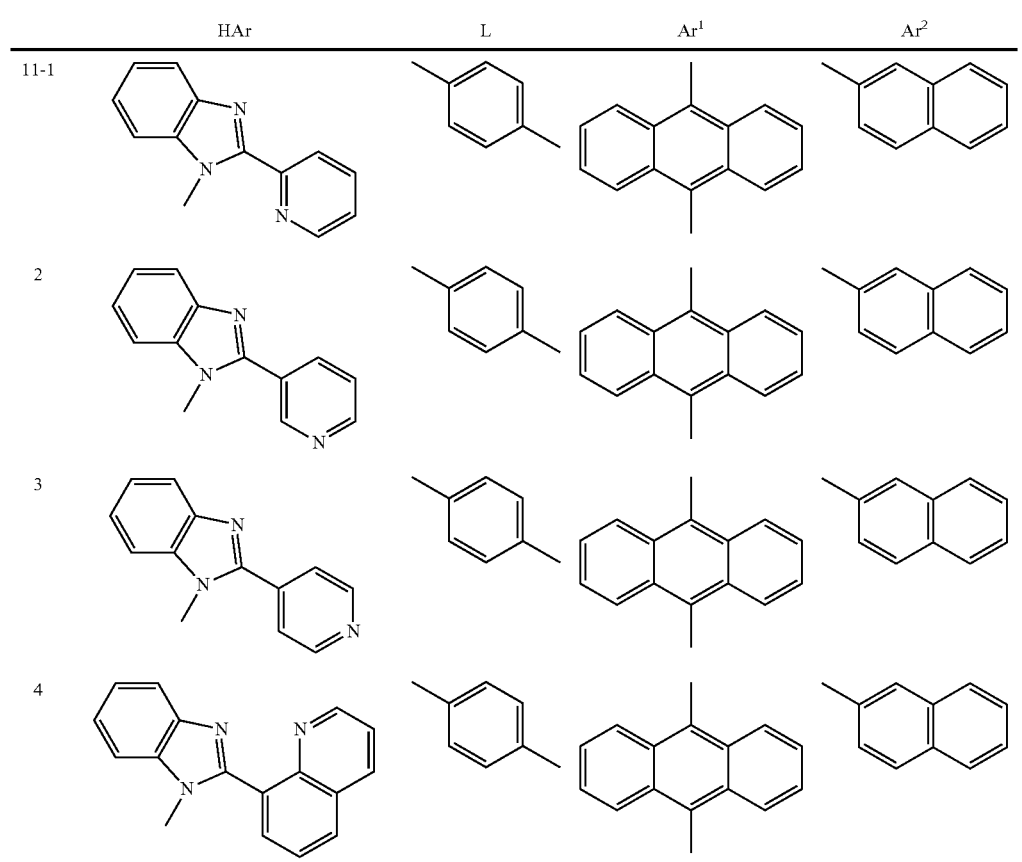

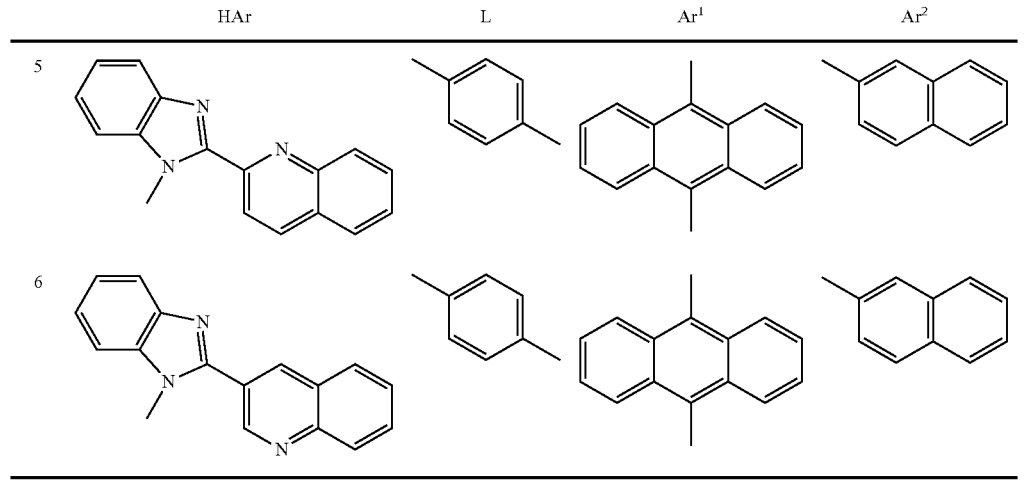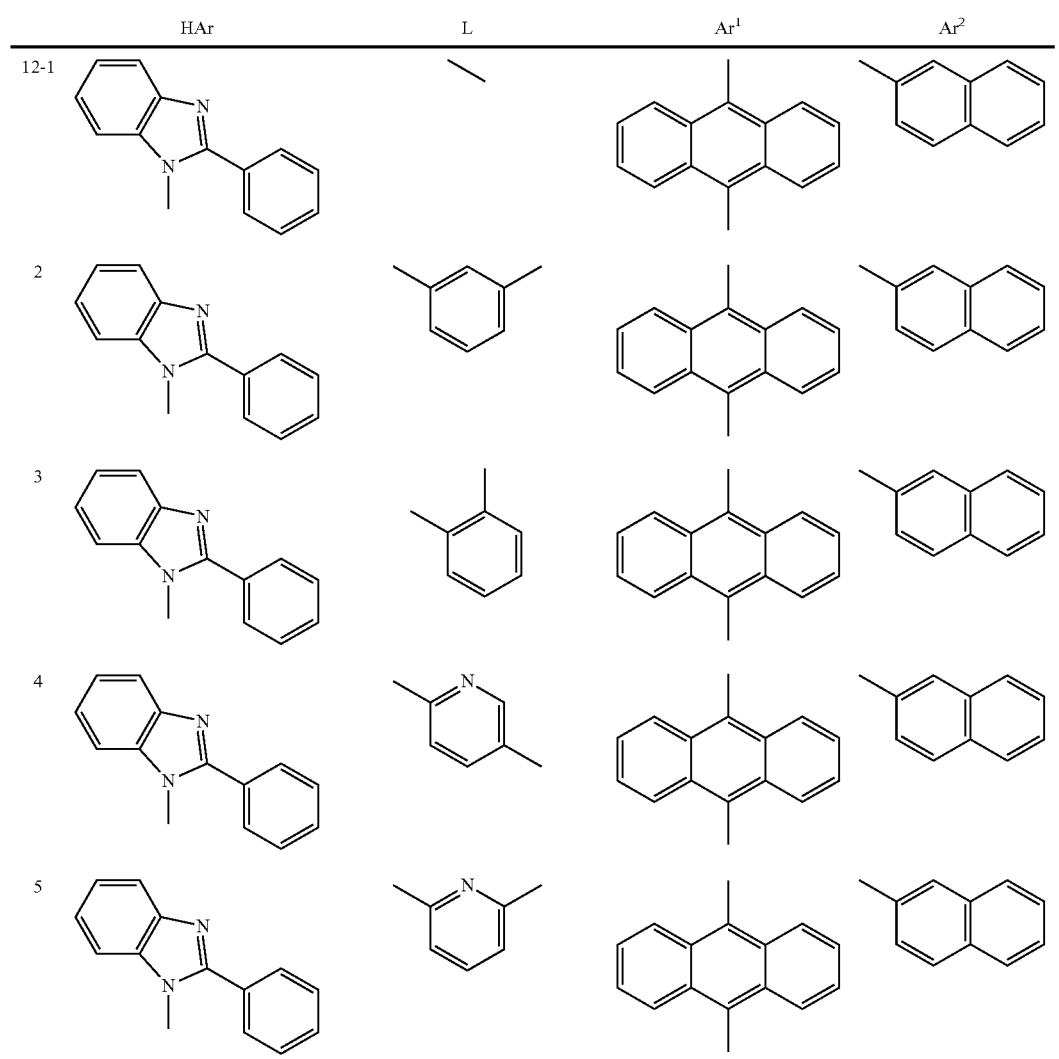

-continued
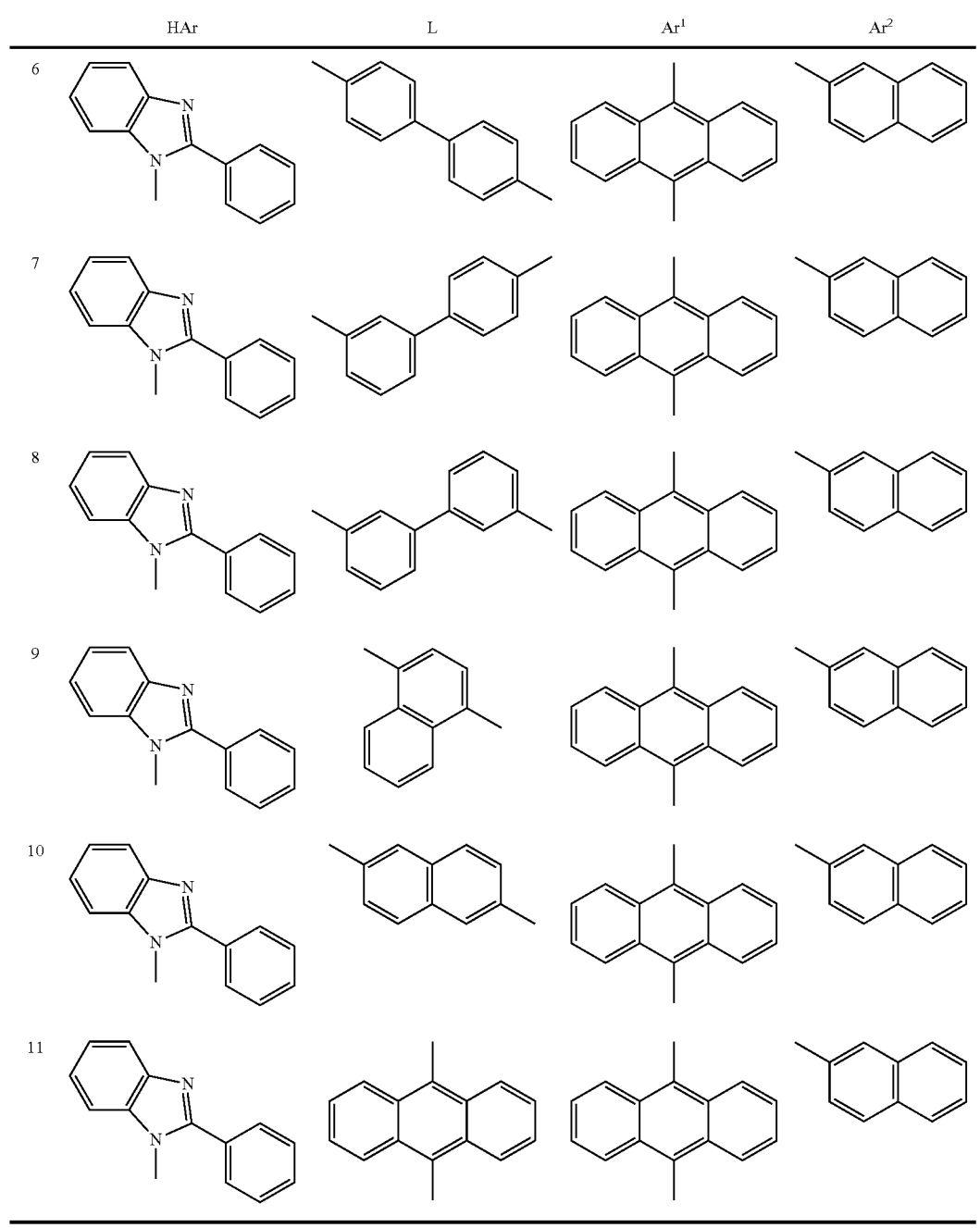
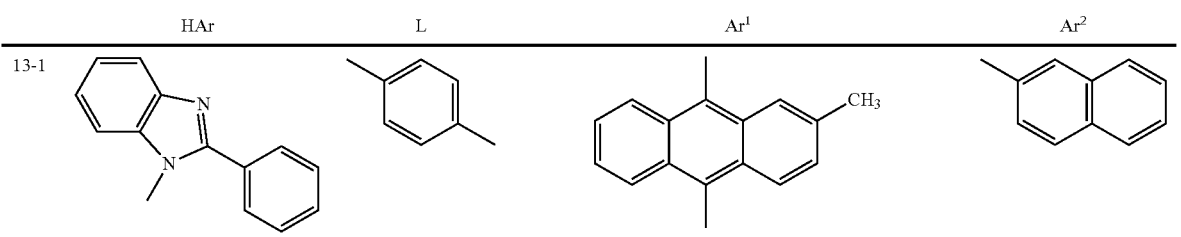

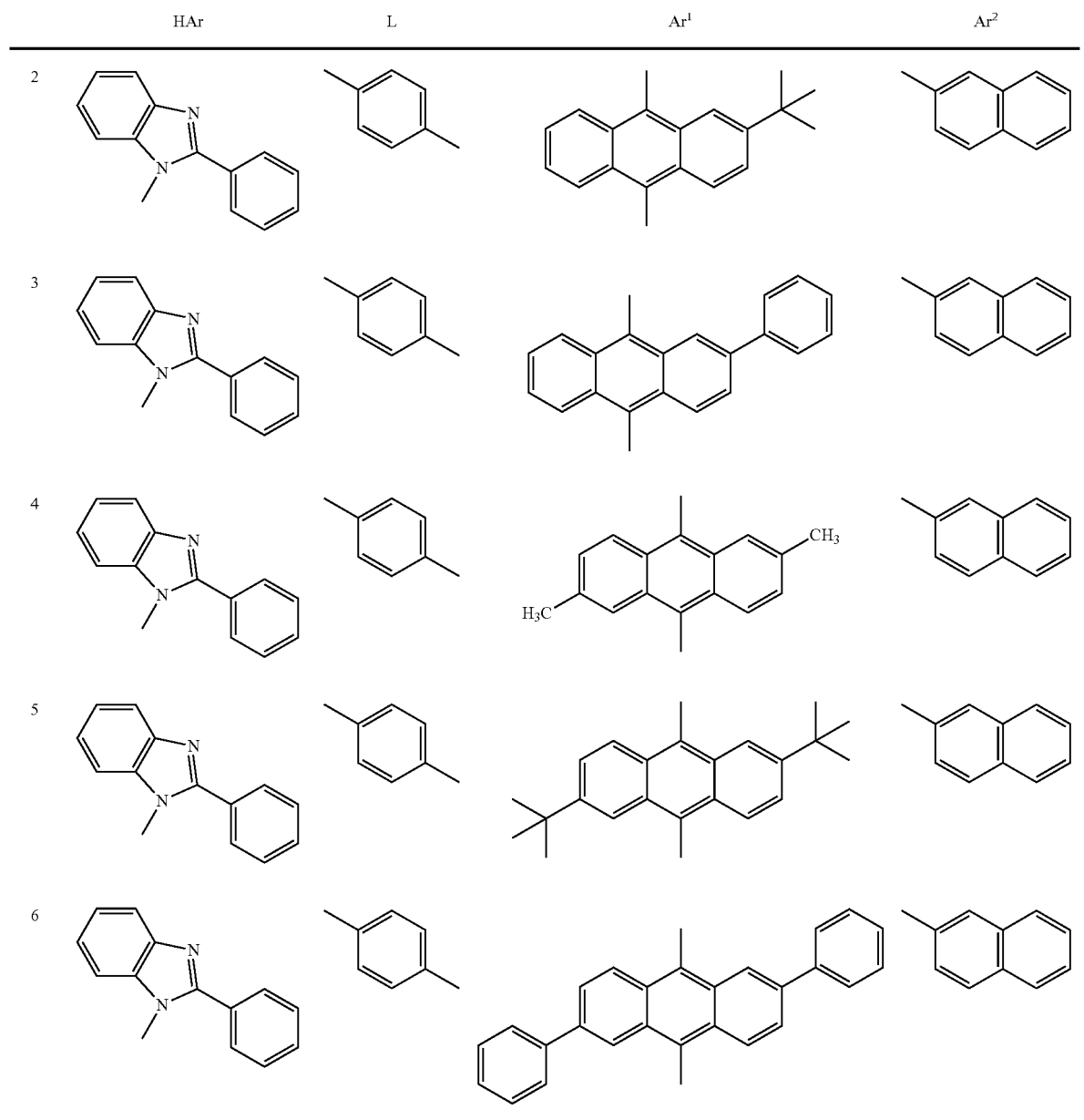
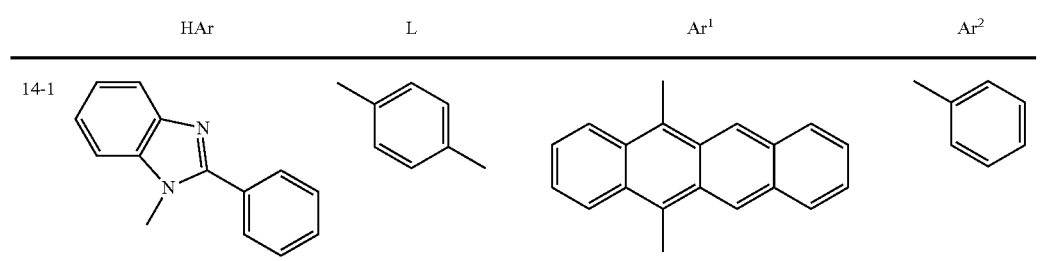

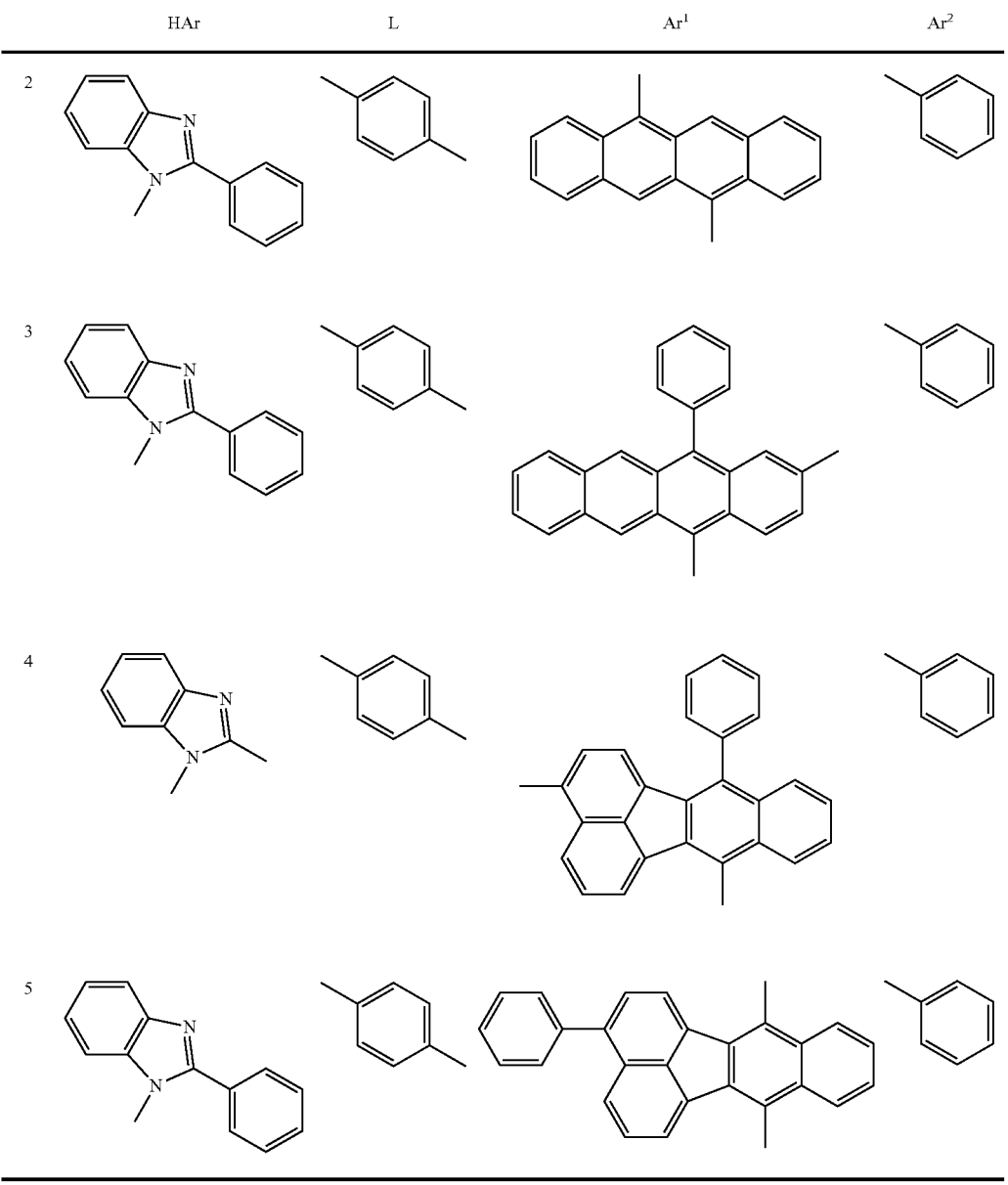
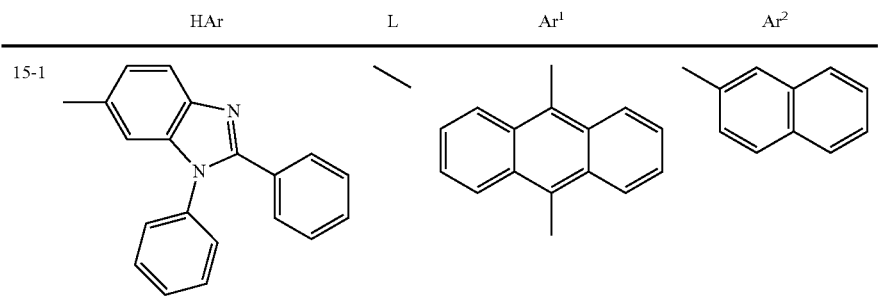

-continued

| | HAr | L | Ar¹ | Ar² |
|---|---|---|---|---|
| 2 | | — | | |
| 3 | | — | | |
| 4 | | — | | |
| 5 | | — | | |
| 6 | | — | | |
| 7 | | — | | |

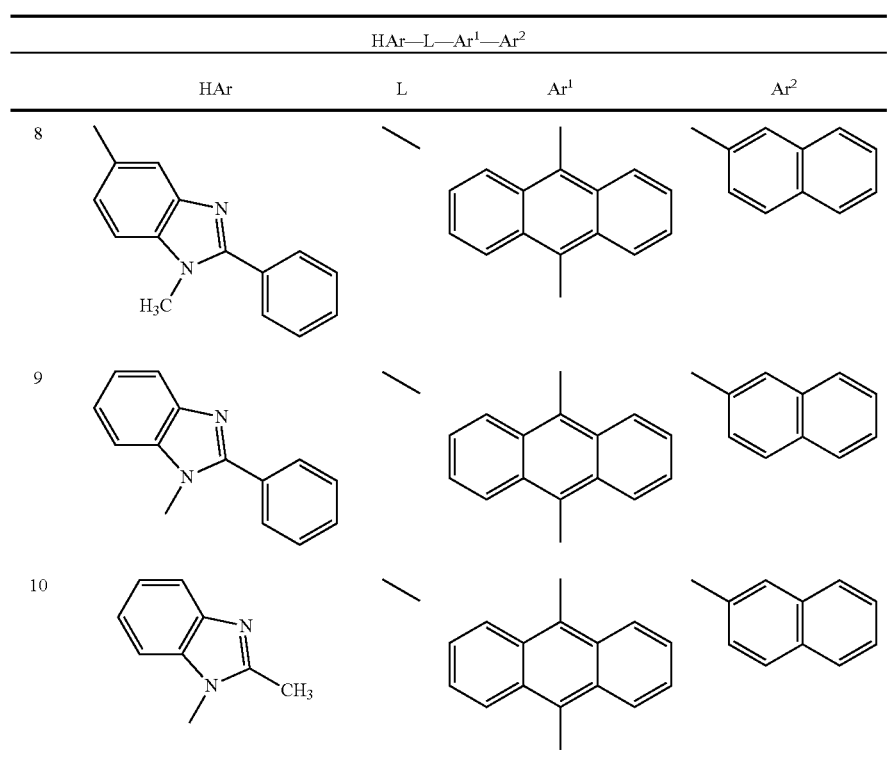
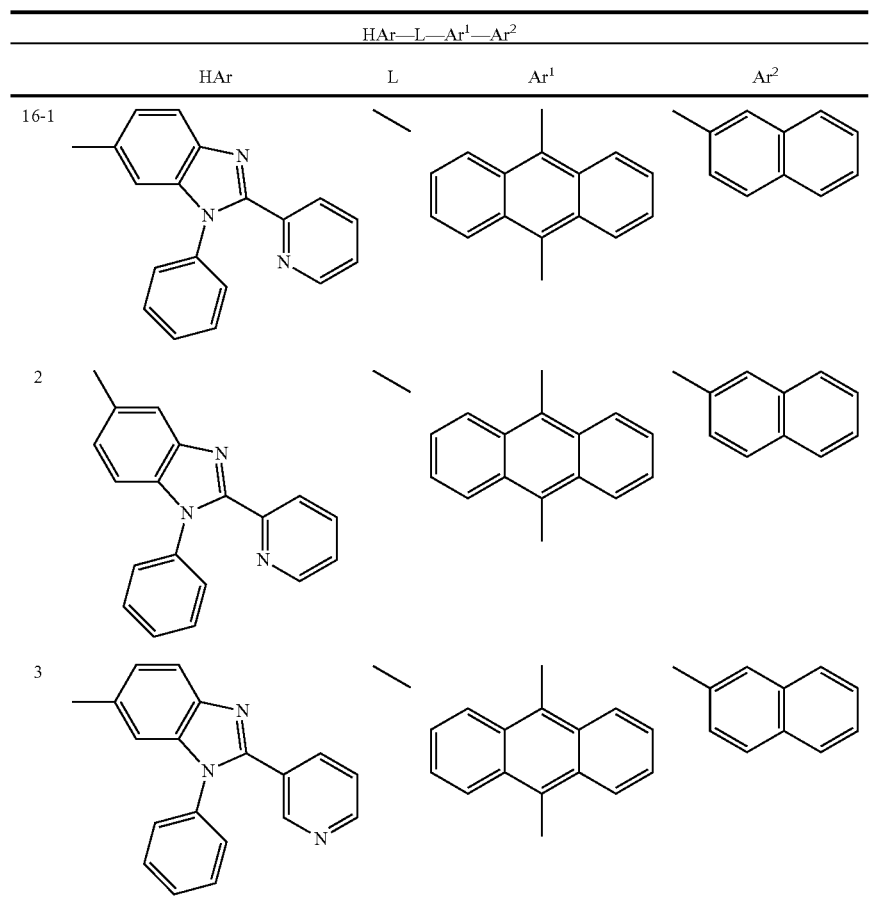

-continued
| HAr | L | Ar¹ | Ar² |
|---|---|---|---|
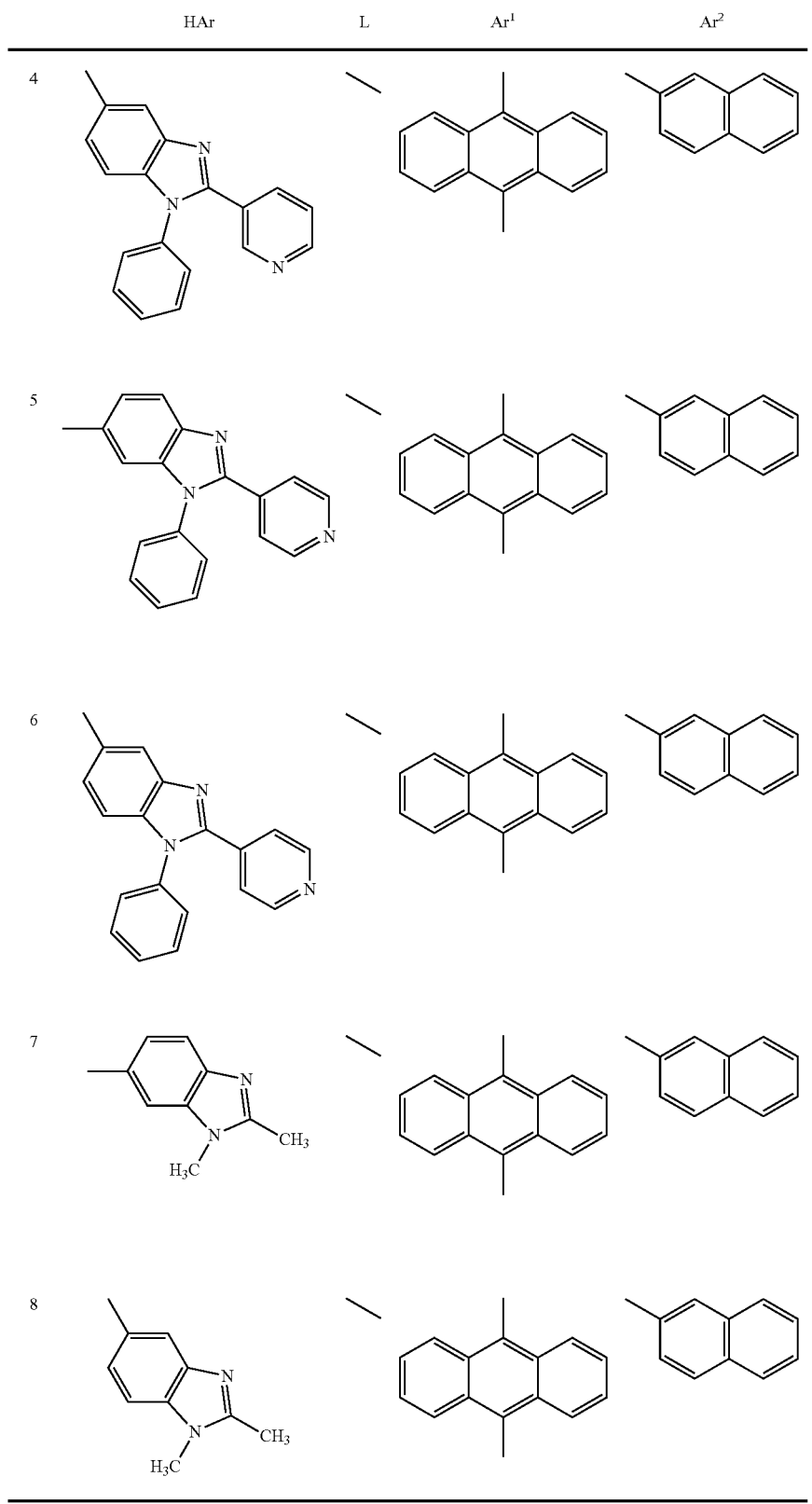

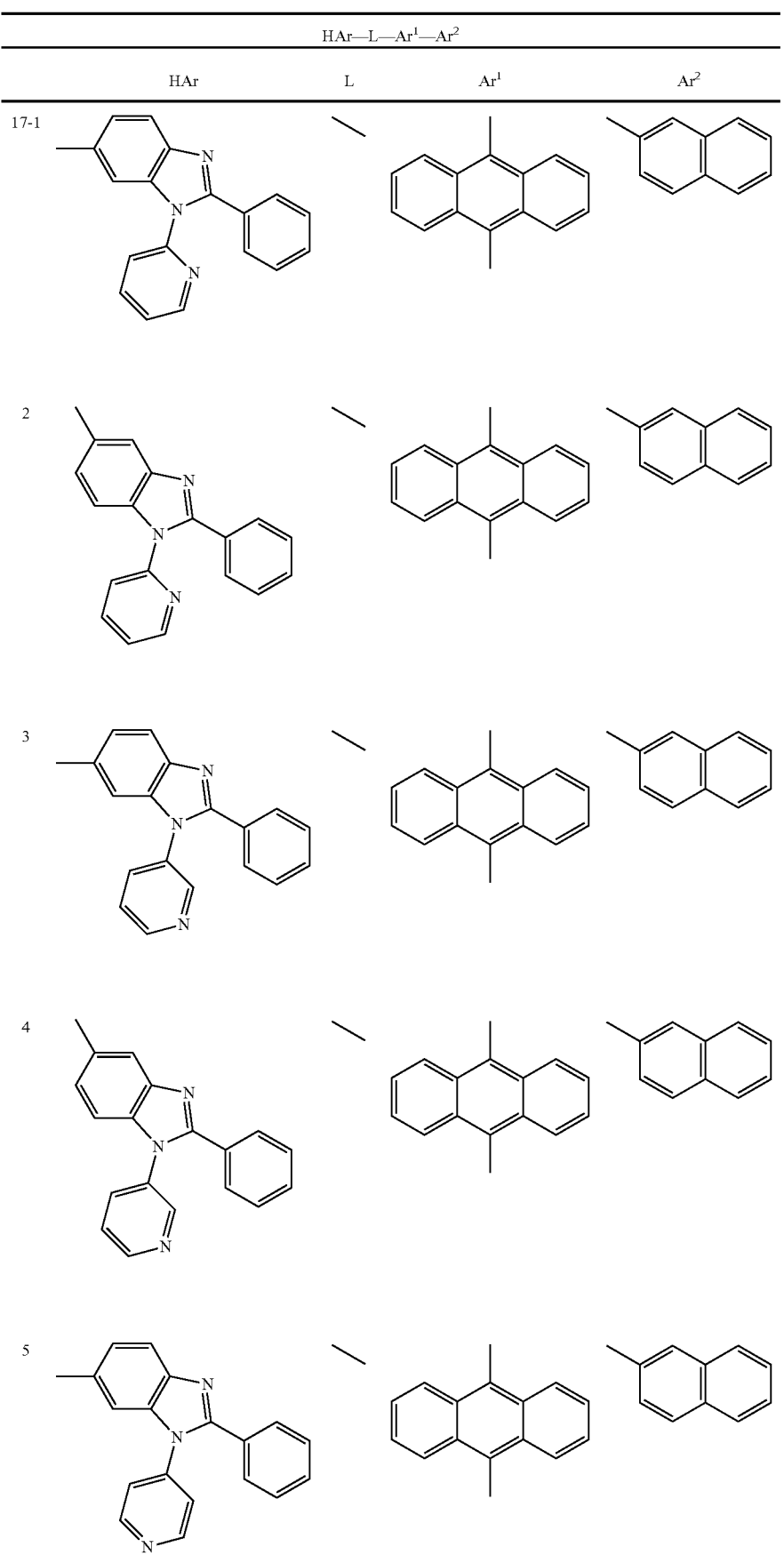

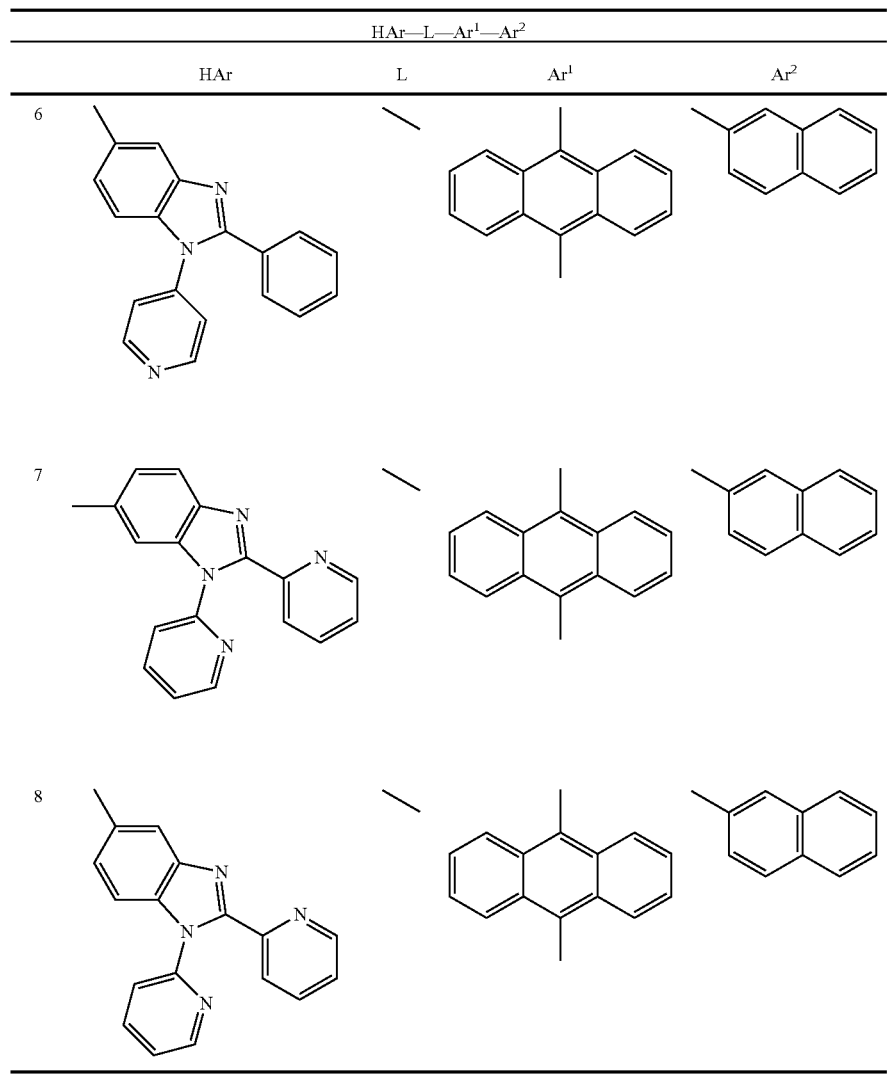

Of the above exemplary compounds, particularly preferred are the compounds (1-1), (1-5), (1-7), (2-1), (3-1), (4-2), (4-6), (7-2), (7-7), (7-8), (7-9), (9-1), and (9-7).

The thickness of the electron injecting layer and the electron transporting layer is preferably, but not particularly limited to, 1 to 100 nm.

It is preferred that the electron injecting layer is constituted by an inorganic compound, such as an insulating material and a semiconductor, in addition to the nitrogen-containing ring derivative. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhance. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe.

Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the reduction-causing dopant mentioned above.

The hole injecting layer or the hole transporting layer (inclusive of a hole injecting/transporting layer) is preferably formed from an aromatic amine compound, for example, an aromatic amine derivative represented by the following formula (I):

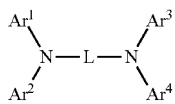

In formula (I), each of $Ar^1$ to $Ar^4$ is a substituted or unsubstituted aryl group having 6 to 50 ring carbon atoms, a substituted or unsubstituted heteroaryl group having 5 to 50 ring atoms, or a group formed by bonding the preceding aryl group and heteroaryl group to each other.

Examples of the substituted or unsubstituted aryl group having 6 to 50 ring carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, and fluorenyl group.

Examples of the substituted or unsubstituted heteroaryl group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group, with phenyl group, naphthyl group, biphenyl group, anthranyl group, phenanthryl group, pyrenyl group, chrysenyl group, fluoranthenyl group, and fluorenyl group being preferred.

L is a linking group, for example, a substituted or unsubstituted arylene group having 6 to 50 ring carbon atoms, a substituted or unsubstituted heteroarylene group having 5 to 50 ring atoms, or a divalent group derived from two or more arylene groups or heteroarylene groups by bonding these groups vis a single bond, an ether bond, a thioether bond, an alkylene group having 1 to 20 carbon atoms, an alkenylene group having 2 to 20 carbon atoms, or amino group. Examples of the arylene group having 6 to 50 ring carbon atoms include 1,4-phenylene group, 1,2-phenylene group, 1,3-phenylene group, 1,4-naphthylene group, 2,6-naphthylene group, 1,5-naphthylene group, 9,10-anthracenylene group, 9,10-phenanthrenylene group, 3,6-phenanthrenylene group, 1,6-pyrenylene group, 2,7-pyrenylene group, 6,12-chrysenylene group, 4,4'-biphenylene group, 3,3'-biphenylene group, 2,2'-biphenylene group, and 2,7-fluorenylene group. Examples of the heteroarylene group having 5 to 50 ring atoms include 2,5-thiophenylene group, 2,5-silolylene group, and 2,5-oxadiazolylene group. Of the above groups, preferred are 1,4-phenylene group, 1,2-phenylene group, 1,3-phenylene group, 1,4-naphthylene group, 9,10-anthracenylene group, 6,12-chrysenylene group, 4,4'-biphenylene group, 3,3'-biphenylene group, 2,2'-biphenylene group, and 2,7-fluorenylene group.

If L is a linking group having two or more arylene groups or heteroarylene groups, adjacent arylene groups or adjacent heteroarylene group may bond to each other via a divalent group to form a ring. Examples of the divalent group for completing such ring include tetramethylene group, pentamethylene group, hexamethylene group, diphenylmethane-2,2'-diyl group, diphenylethane-3,3'-diyl group, and diphenylpropane-4,4'-diyl group.

Examples of the substituent of $Ar^1$ to $Ar^4$ and L include a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted heteroaryloxy group having 5 to 50 ring atoms, a substituted or unsubstituted arylthio group having 6 to 50 ring carbon atoms, a substituted or unsubstituted heteroarylthio group having 5 to 50 ring atoms, a substituted or unsubstituted alkoxycarbonyl group having 2 to 50 carbon atoms, an amino group substituted by a substituted or unsubstituted aryl group having 6 to 50 ring carbon atoms or a substituted or unsubstituted heteroaryl group having 5 to 50 ring atoms, halogen atom, cyano group, nitro group, and hydroxyl group.

Examples of the substituted or unsubstituted aryl group having 6 to 50 ring carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, and fluorenyl group.

Examples of the substituted or unsubstituted heteroaryl group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the substituted or unsubstituted alkyl group having 1 to 50 carbon atoms include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted cycloalkyl group having 3 to 50 ring carbon atoms include cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

The substituted or unsubstituted alkoxy group having 1 to 50 carbon atoms is represented by —OY. Examples of Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxybutyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodotbutyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted aralkyl group having 7 to 50 carbon atoms include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

The substituted or unsubstituted aryloxy group having 6 to 50 ring carbon atoms is represented by —OY'. Examples of Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4''-t-butyl-p-terphenyl-4-yl group.

The substituted or unsubstituted heteroaryloxy group having 5 to 50 ring atoms is represented by —OZ'. Examples of Z' include 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted arylthio group having 6 to 50 ring carbon atoms is represented by —SY". Examples of Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

The substituted or unsubstituted heteroarylthio group having 5 to 50 ring atoms is represented by —SZ". Examples of Z" include 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted alkoxycarbonyl group having 2 to 50 carbon atoms is represented by —COOZ. Examples of Z include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxyt-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodot-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

The amino group substituted by a substituted or unsubstituted aryl group having 6 to 50 ring carbon atoms or a substituted or unsubstituted heteroaryl group having 5 to 50 ring atoms is represented by —NPQ. Examples of P and Q include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the compound represented by formula (I) are shown below, although not limited thereto.

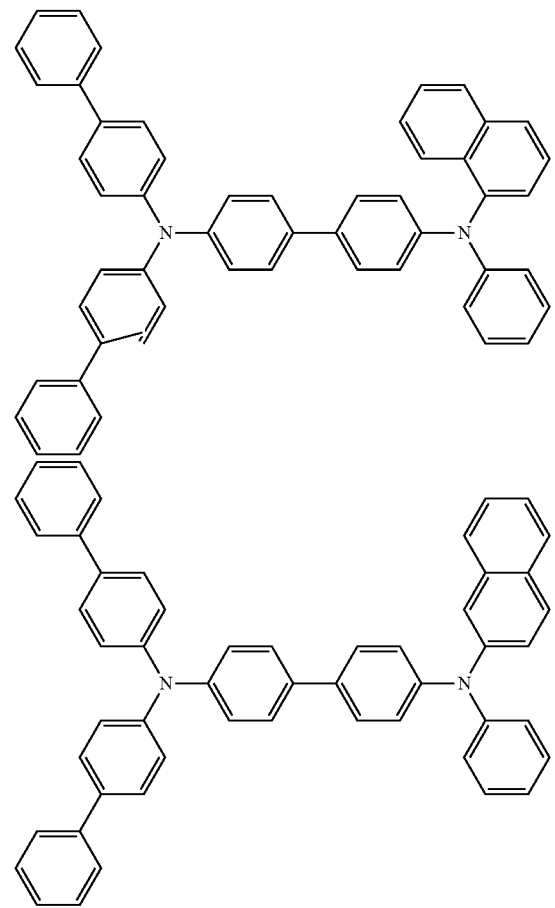

557
-continued
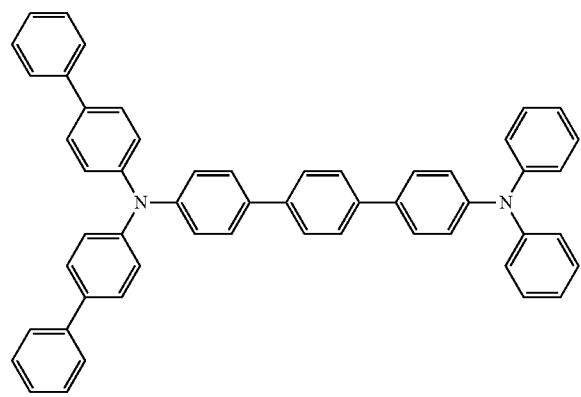
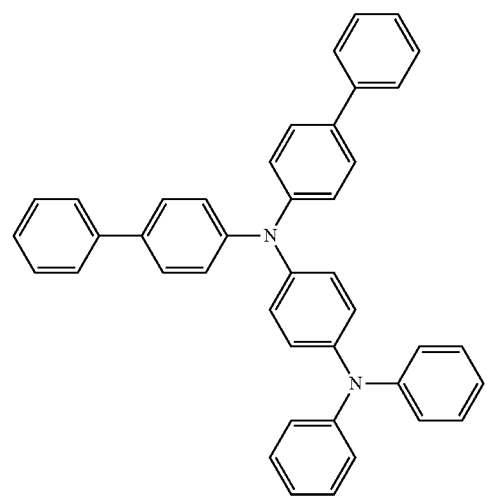
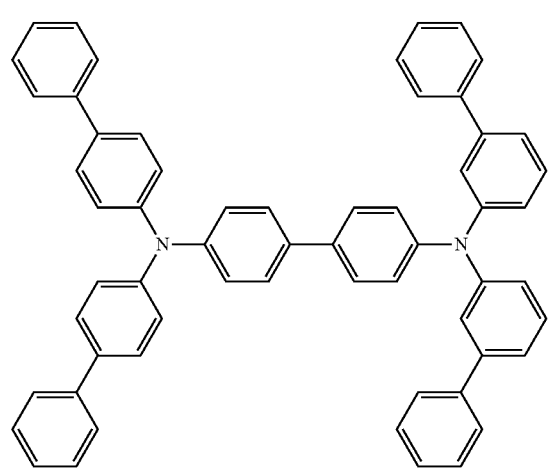
558
-continued
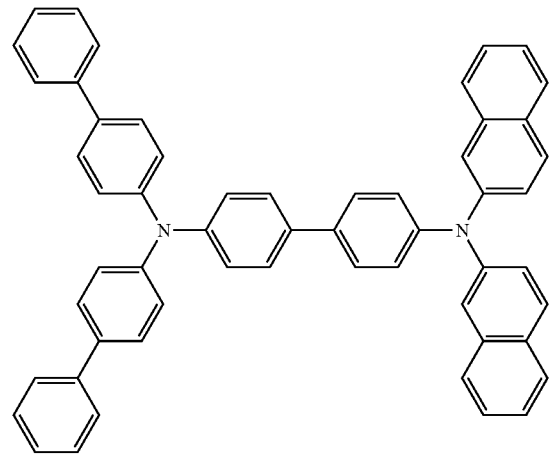
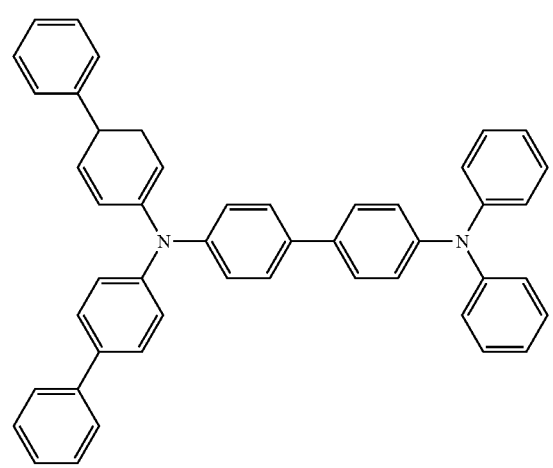
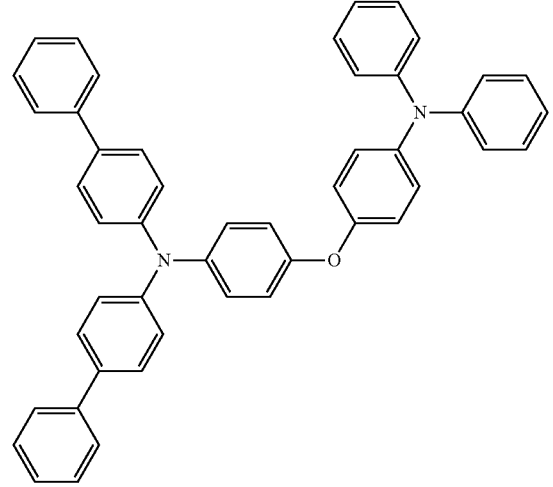

559
-continued
560
-continued
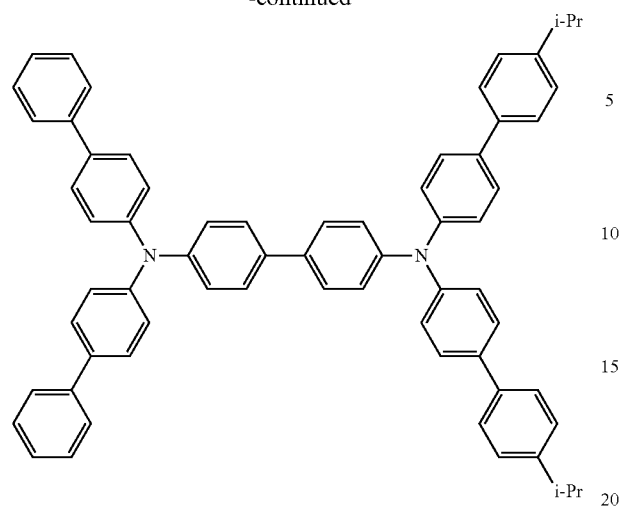
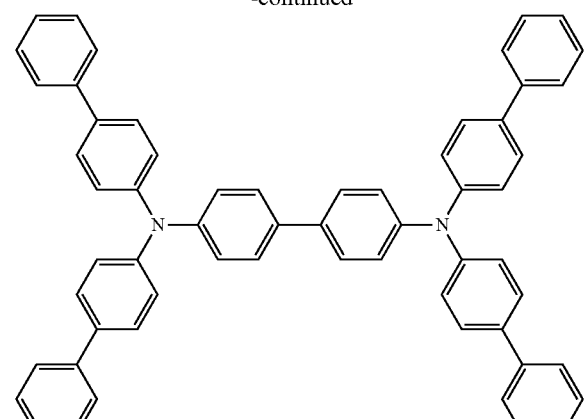
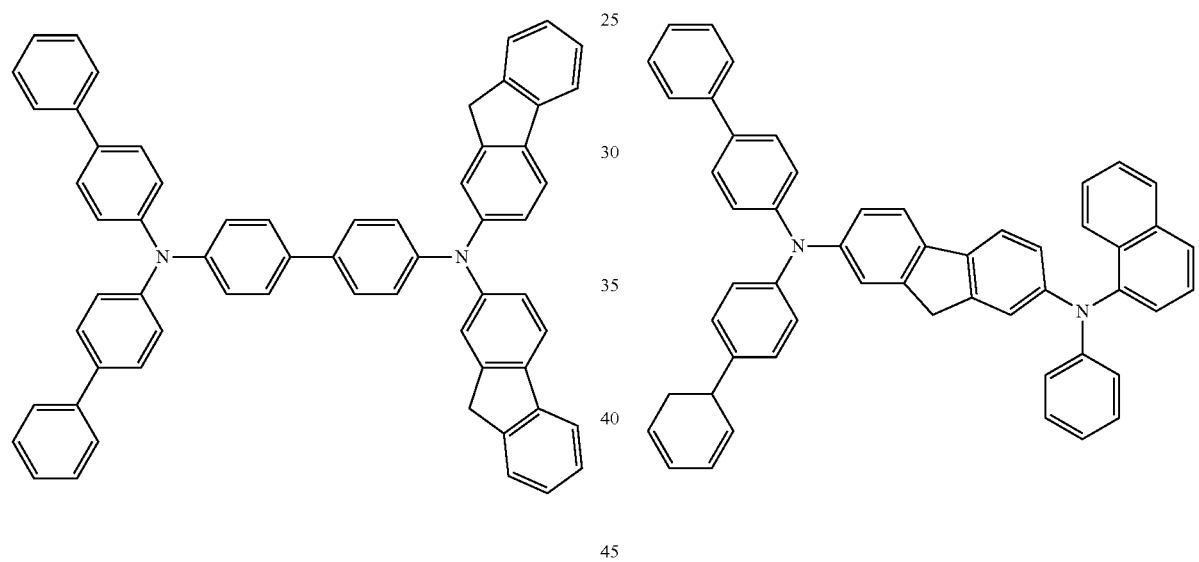
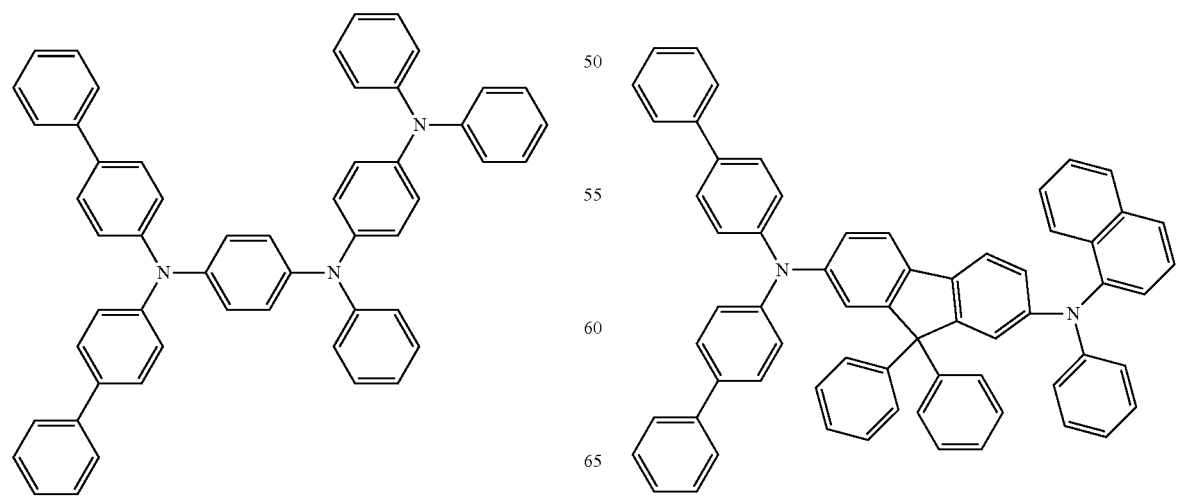

561
-continued
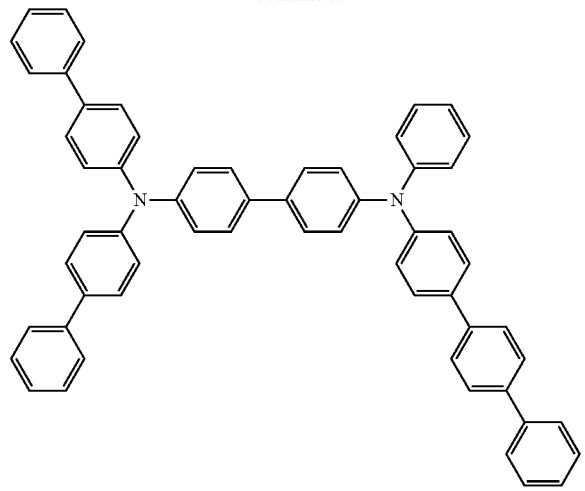
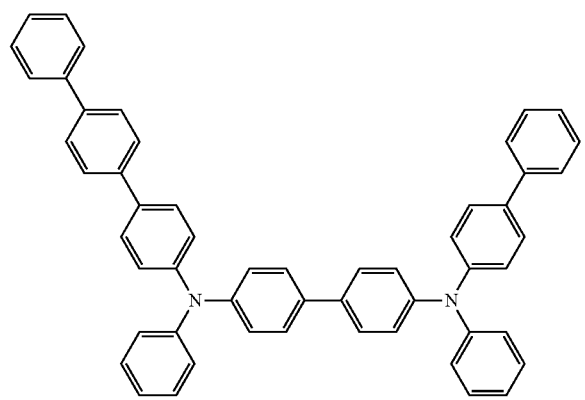
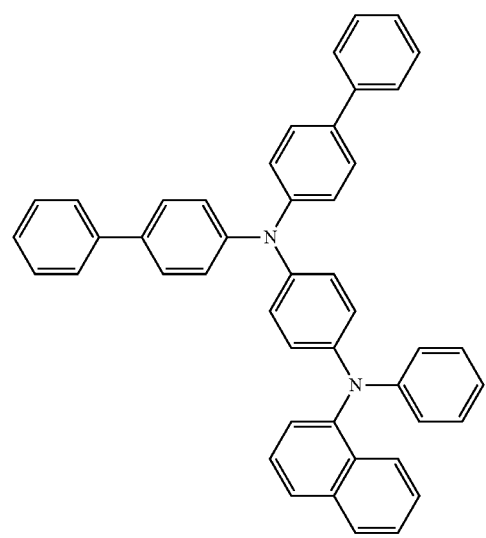
562
-continued
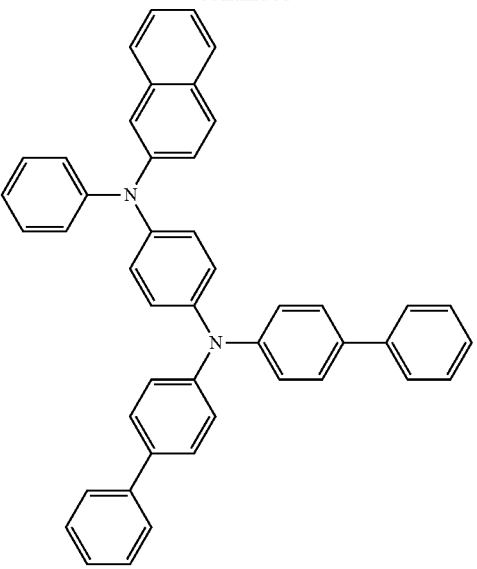
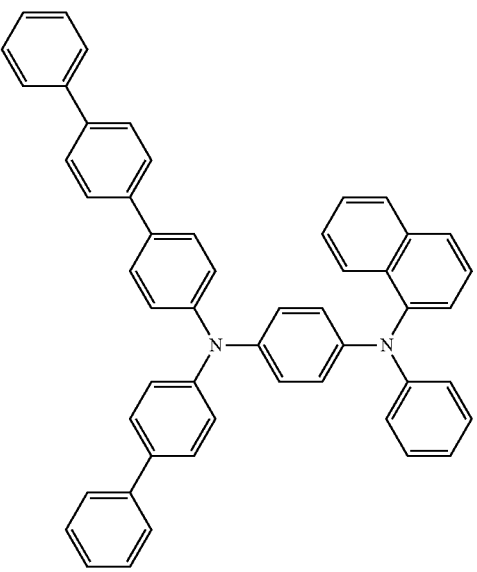
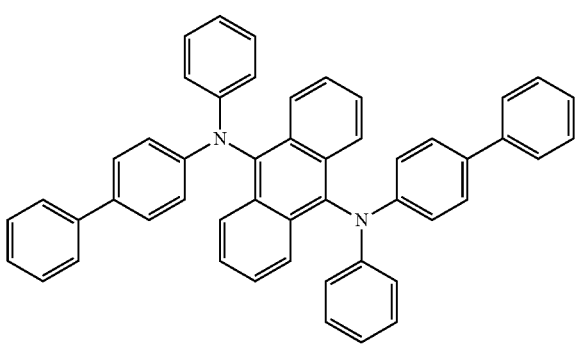

563
-continued
564
-continued
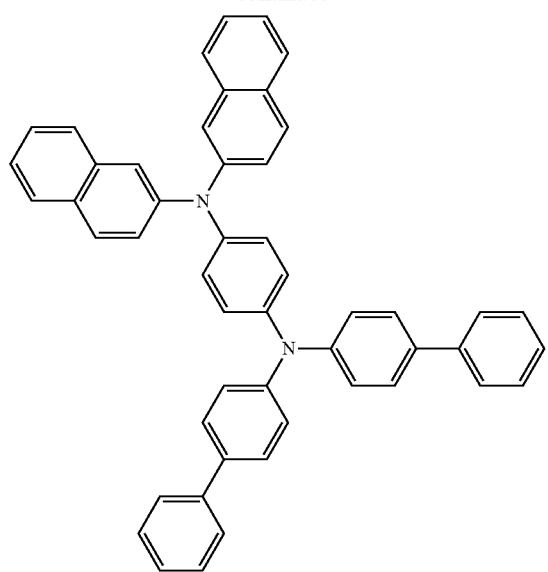
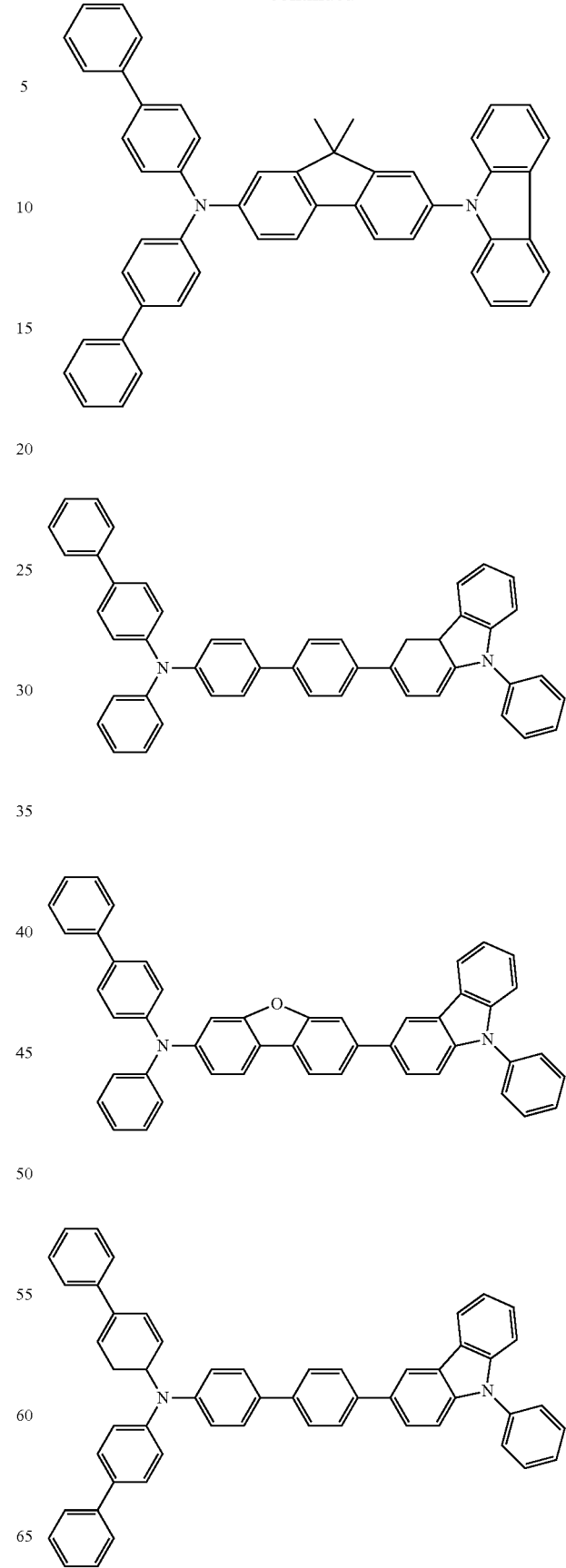

565
-continued

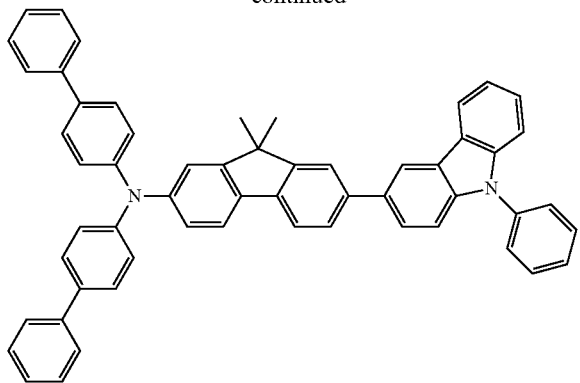

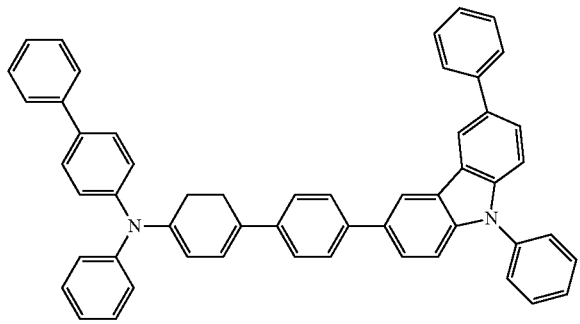

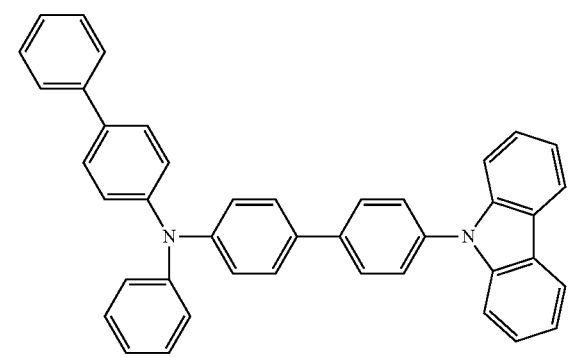

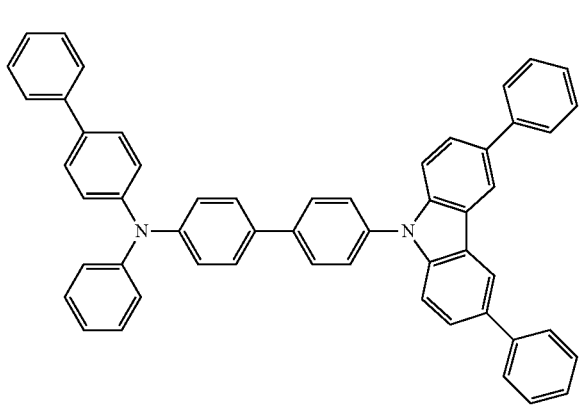

566
-continued

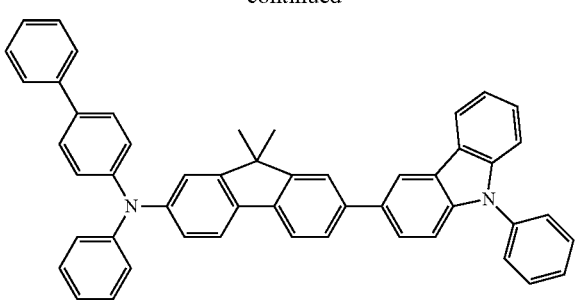

An aromatic amine represented by the following formula (II) is also preferably used to form the hole injecting layer or the hole transporting layer.

$$Ar^2-N\begin{matrix}Ar^1\\Ar^3\end{matrix} \qquad (II)$$

In formula (II), $Ar^1$ to $Ar^3$ are the same as defined in $Ar^1$ to $Ar^4$ of formula (I). Examples of the compound represented by formula (II) are shown below, although not limited thereto.

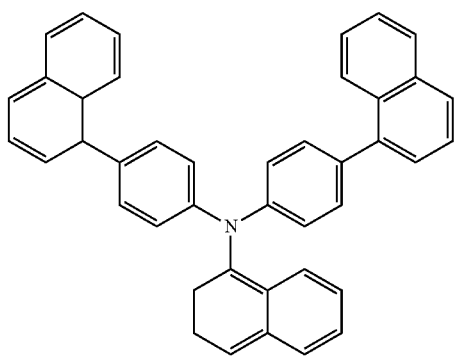

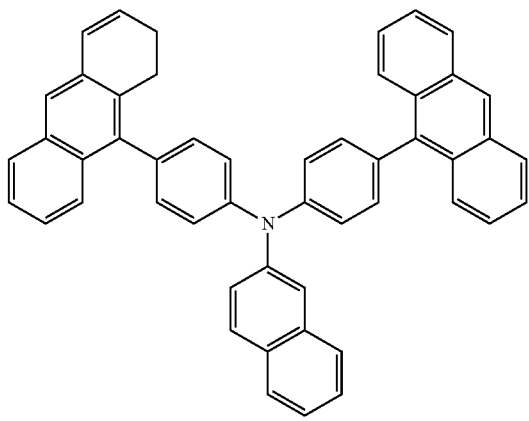

567
-continued
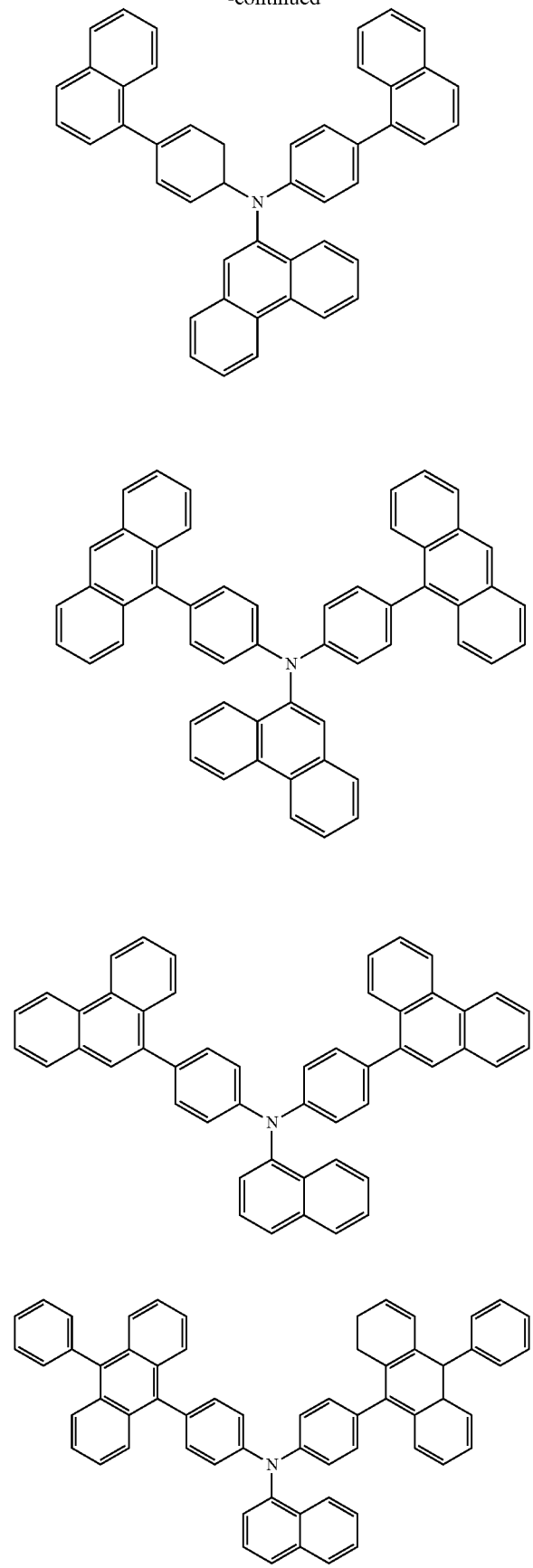
568
-continued
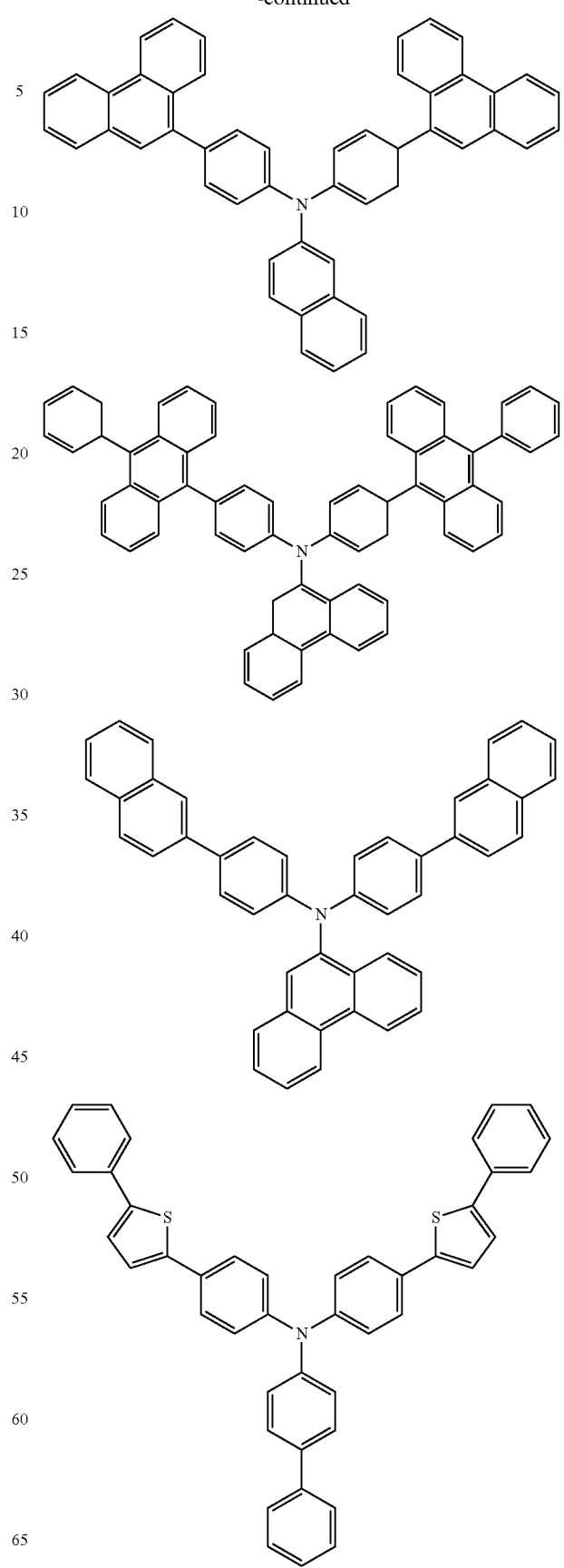

569
-continued
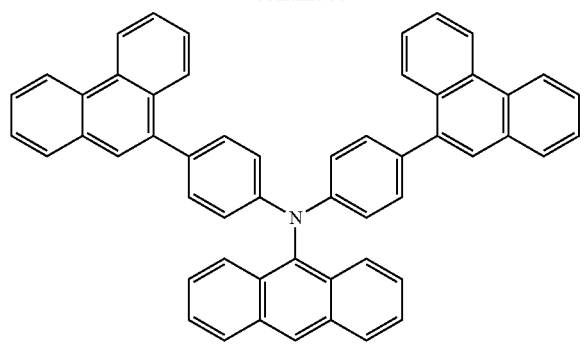
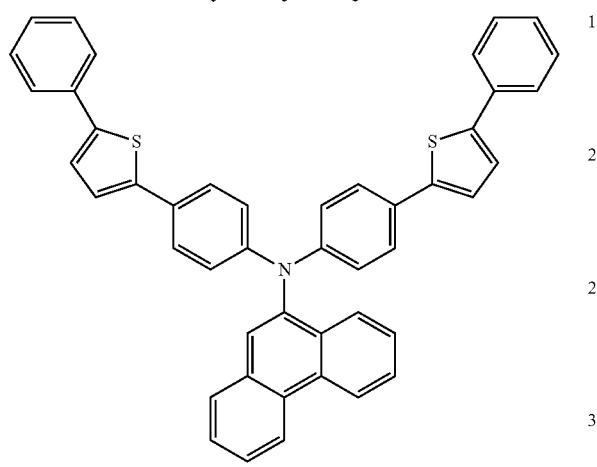
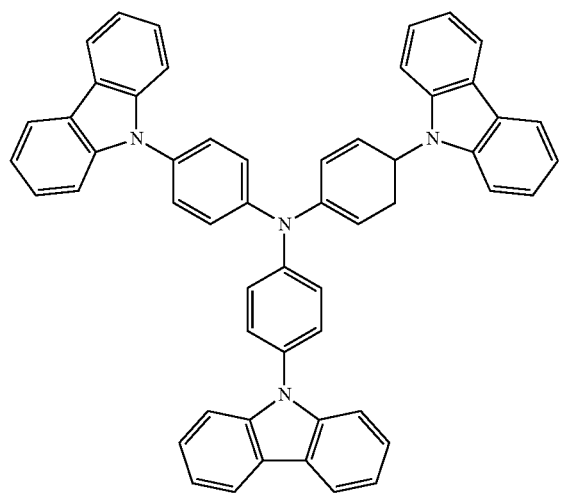
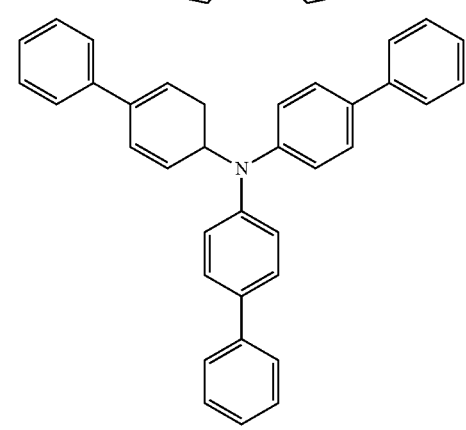
570
-continued
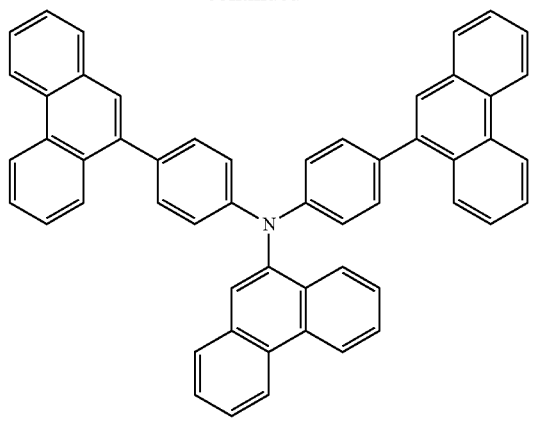
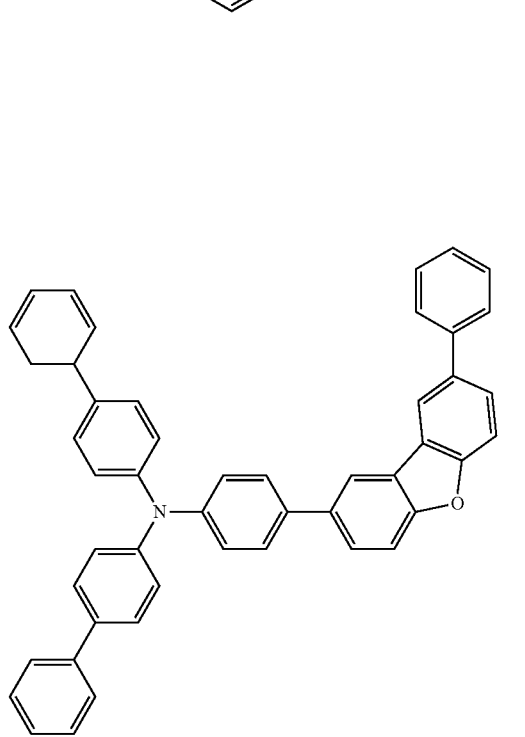
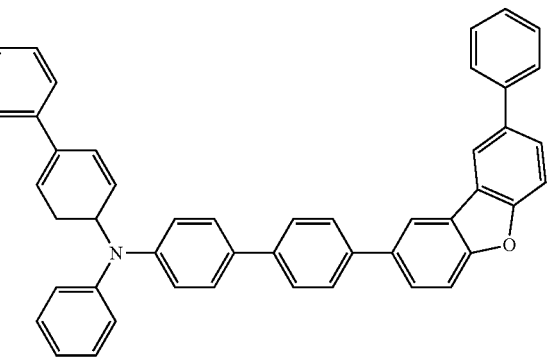

-continued

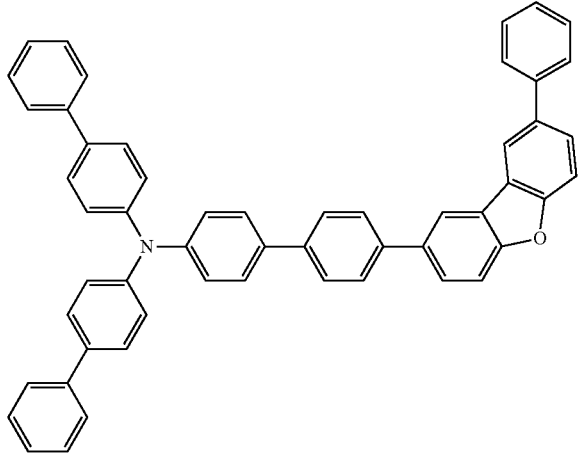

The present invention is not limited to the embodiments described above, and variations and modifications can be effected within the spirit and scope of the invention.

For example, the following modification is a preferred embodiment of the invention.

It is also preferred that the light emitting layer of the invention contains a charge injecting aid.

When the light emitting layer is formed by using a host material having a wide energy gap, the difference between the ionization potential (Ip) of the host material and Ip of the hole injecting/transporting layer, etc., this being likely to make the injection of holes into the light emitting layer difficult to increase the driving voltage for obtaining sufficient luminance.

In this case, by incorporating a hole injecting/transporting charge injecting aid into the light emitting layer, the injection of holes into the light emitting layer is facilitated and the driving voltage is reduced.

For example, a hole injecting/transporting material generally known is usable as the charge injecting aid.

Examples thereof include triazole derivatives (U.S. Pat. No. 3,112,197), oxadiazole derivatives (U.S. Pat. No. 3,189, 447), imidazole derivatives (JP 37-16096B), polyarylalkane derivatives (U.S. Pat. No. 3,615,402, U.S. Pat. No. 3,820,989, U.S. Pat. No. 3,542,544, JP 45-555B, JP 51-10983B, JP 51-93224A, JP 55-17105A, JP 56-4148A, JP 55-108667A, JP 55-156953A, JP 56-36656A), pyrazoline derivatives and pyrazolone derivatives (U.S. Pat. No. 3,180,729, U.S. Pat. No. 4,278,746, JP 55-88064A, JP 55-88065A, JP 49-105537A, JP 55-51086A, JP 56-80051A, JP 56-88141A, JP 57-45545A, JP 54-112637A, JP 55-74546A), phenylene-diamine derivatives (U.S. Pat. No. 3,615,404, JP 51-10105B, JP 46-3712B, JP 47-25336B, JP 54-53435A, JP 54-110536A, JP 54-119925A), arylamine derivatives (U.S. Pat. No. 3,567, 450, U.S. Pat. No. 3,180,703, U.S. Pat. No. 3,240,597, U.S. Pat. No. 3,658,520, U.S. Pat. No. 4,232,103, U.S. Pat. No. 4,175,961, U.S. Pat. No. 4,012,376, JP 49-35702B, JP 39-27577B, JP 55-144250A, JP 56-119132A, JP 56-22437A, DE 1,110,518), amino-substituted chalcone derivatives (U.S. Pat. No. 3,526,501), oxazole derivatives (U.S. Pat. No. 3,257, 203), styrylanthracene derivative (JP 56-46234A), fluorenone derivatives (JP 54-110837A), hydrazone derivatives (U.S. Pat. No. 3,717,462, JP 54-59143A, JP 55-52063A, JP 55-52064A, JP 55-46760A, JP 55-85495A, JP 57-11350A, JP 57-148749A, JP 2-311591A), stilbene derivatives (JP 61-210363A, JP 61-228451A, JP 61-14642A, JP 61-72255A, JP 62-47646A, JP 62-36674A, JP 62-10652A, JP 62-30255A, JP 60-93455A, JP 60-94462A, JP 60-174749A, JP 60-175052A), silazane derivatives (U.S. Pat. No. 4,950, 950), polysilanes (JP 2-204996A), aniline-based copolymer (JP 2-282263A), and electroconductive high molecular weight oligomer (particularly, thiophene oligomer) disclosed in JP 1-211399A.

In addition to the hole injecting material mentioned above, porphyrin compounds (JP 63-295695A), and aromatic tertiary amines and styryl amine compounds (U.S. Pat. No. 4,127,412, JP 53-27033A, JP 54-58445A, JP 54-149634A, JP 54-64299A, JP 55-79450A, JP 55-144250A, JP 56-119132A, JP 61-295558A, JP 61-98353A, JP 63-295695A) are usable, with the aromatic tertiary amines being particularly preferred.

A compound having two condensed aromatic rings in its molecule described in U.S. Pat. No. 5,061,569, for example, 4,4'-bis(N-(1-naphthyl)-N-phenylamino)biphenyl (NPD), and 4,4',4''-tris(N-(3-methylphenyl)-N-phenylamino)triphenylamine (MTDATA) in which three triphenylamine units are linked to each other in starburst configuration are also usable.

Further, hexaazatriphenylene derivatives described in JP 3614405, JP 3571977, or U.S. Pat. No. 4,780,536 are preferably used as the hole injecting material.

An organic compound, such as p-type Si and p-type SiC, is also usable as the hole injecting material.

The method of forming each layer of the organic EL device of the invention is not particularly limited, and each layer can be formed by a known method, such as a vacuum vapor deposition method and a spin coating method. The organic thin film layer in the organic EL device of the invention may be formed by a known method, for example, by a vacuum vapor deposition method, a molecular beam evaporation method (MBE method), and a coating method, such as a dipping method, a spin coating method, a casting method, a bar coating method and a roll coating method, each using a solvent solution.

The film thickness of each organic layer in the organic EL device of the invention is not particularly limited. Since detects, such as pinholes, are likely to be caused if the film thickness is excessively small and high applied voltage is required to reduce the efficiency if the film thickness is excessively large, the film thickness is preferably from several nanometers to 1 μm.

The compound of the invention can be synthesized by Suzuki-Miyaura cross-coupling reaction or others, for example, by the following reaction scheme, in which formulae (1) to (4) are abbreviated as $Ar^1—Ar^2-[\ ]_m-Ar^3$.

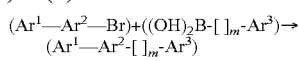

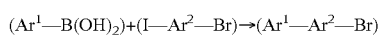

EXAMPLES

The production of the materials of the invention will be described with reference to synthetic examples, but it should be noted that the present invention is not limited thereto.

Synthetic Reference Example 1-1

Synthesis of 2-bromo-9,9-dimethyl-7-(naphthalene-2-yl)-9H-fluorene

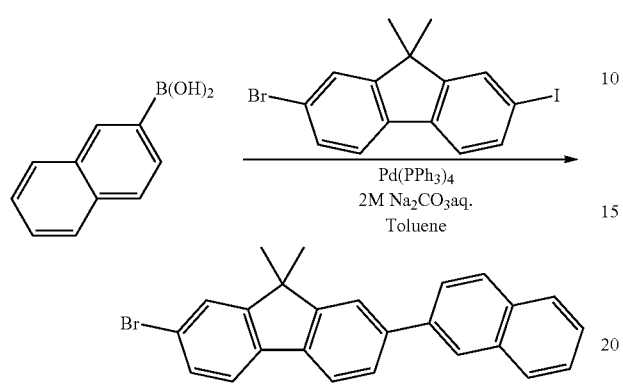

In argon atmosphere, a mixture of 13.91 g (80.9 mmol) of 2-naphthaleneboronic acid, 30.0 g (80.9 mmol) of 2-bromo-7-iodo-9,9-dimethylfluorene, 4.67 g (4.0 mmol) of tetrakis(triphenylphosphine)palladium (0), 200 ml of toluene, 200 ml of dimethoxyethane, and 122.36 g of a 2 M sodium carbonate aqueous solution was refluxed under stirring for 8 h and left standing overnight. After adding water, the mixture was stirred at room temperature for one hour. After filtration and extraction with toluene, the organic phase was washed with water and then with a saturated saline solution. After drying over sodium sulfate, the toluene was distilled off under reduced pressure. The residue was purified by silica gel chromatography to obtain 21.3 g (yield: 76.1%) of 2-bromo-9,9-dimethyl-7-(naphthalene-2-yl)-9H-fluorene.

Synthetic Reference Example 1-2

Synthesis of 9,9-dimethyl-7-(naphthalene-2-yl)-9H-fluorene-2-ylboronic acid

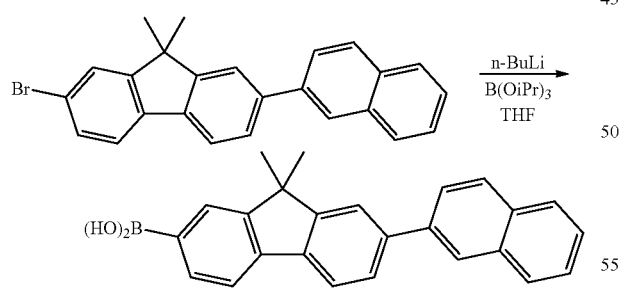

In argon atmosphere, a liquid mixture of 6.00 g (15.0 mmol) of 2-bromo-9,9-dimethyl-7-(naphthalene-2-yl)-9H-fluorene and 150 ml of dry THF was cooled to −60° C., and 11.6 ml (18.0 mmol) of a 1.55 M hexane solution of n-butyl-lithium was added dropwise under stirring. Then, the reaction mixture was stirred at −70° C. for 2 h. The reaction solution was cooled again to −70° C., and 8.48 g (45.1 mol) of triisopropyl borate was added dropwise. The reaction mixture was heated up to room temperature, stirred for one hour, and left standing overnight. The reaction mixture was cooled on ice bath, added with a 6 N hydrochloric acid, and stirred at room temperature for one hour. The reaction mixture was added with dichloromethane and allowed to stand for separation into liquid phases. The organic phase was washed with water and dried over sodium sulfate. The solvent was distilled off under reduced pressure, and the residue was purified by silica gel chromatography to obtain 3.50 g (yield: 64%) of 9,9-dimethyl-7-(naphthalene-2-yl)-9H-fluorene-2-ylboronic acid.

Synthetic Reference Example 2-1

Synthesis of 2-(6-bromonaphthalene-2-yl)-9,9-dimethyl-9H-fluorene

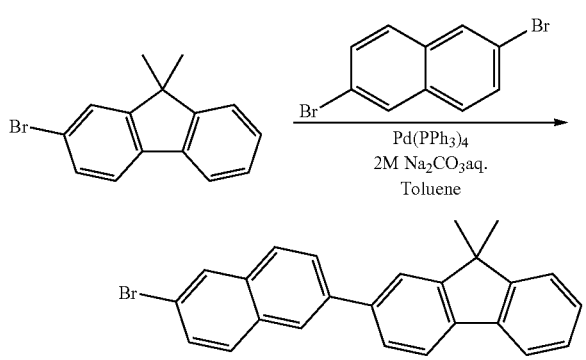

In argon atmosphere, a mixture of 16.65 g (69.9 mmol) of 9,9-dimethyl-9H-fluorene-2-ylboronic acid, 20.0 g (69.9 mmol) of 2,6-dibromonaphthalene, 4.04 g (3.50 mmol) of tetrakis(triphenylphosphine)palladium (0), 200 ml of toluene, 200 ml of dimethoxyethane, and 106 g of a 2 M sodium carbonate aqueous solution was stirred at 85° C. for 8 h and left standing overnight. After adding water, the mixture was stirred at room temperature for one hour. After filtration and extraction with toluene, the organic phase was washed with water and then with a saturated saline solution. After drying over sodium sulfate, the toluene was distilled off under reduced pressure. The obtained brown oily substance was purified by silica gel chromatography to obtain 11.84 g (yield: 42.4%) of 2-(6-bromonaphthalene-2-yl)-9,9-dimethyl-9H-fluorene.

Synthetic Reference Example 2-2

Synthesis of 6-(9,9-dimethyl-9H-fluorene-2-yl)naphthalene-2-ylboronic acid

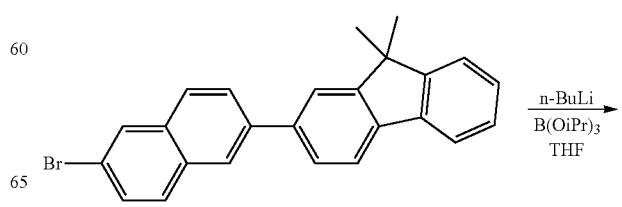

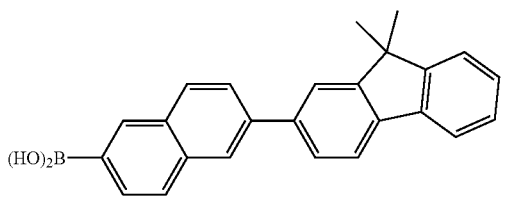

In argon atmosphere, a liquid mixture of 12.00 g (30.1 mmol) of 2-(6-bromonaphthalene-2-yl)-9,9-dimethyl-9H-fluorene and 120 ml of dry THF was cooled to −70° C., and 23.3 ml (36.0 mmol) of a 1.55 M hexane solution of n-butyl-lithium was added dropwise while stirring. Then, the reaction mixture was stirred at −70° C. for 2 h. The reaction solution was cooled again to −70° C., and 17.0 g (90.2 mol) of triisopropyl borate was added dropwise. The reaction mixture was heated up to room temperature, stirred for one hour, and left standing overnight. The reaction mixture was cooled on an ice bath, added with a 6 N hydrochloric acid, and stirred at room temperature for one hour. The reaction mixture was added with dichloromethane and allowed to stand for separation of liquid phases. The organic phase was washed with water and dried over sodium sulfate. The solvent was distilled off under reduced pressure, and the residue was purified by silica gel chromatography to obtain 6.25 g (yield: 57%) of 6-(9,9-dimethyl-9H-fluorene-2-yl)naphthalene-2-ylboronic acid.

Synthetic Reference Example 3-1

Synthesis of 9-(3-bromophenyl)phenanthrene

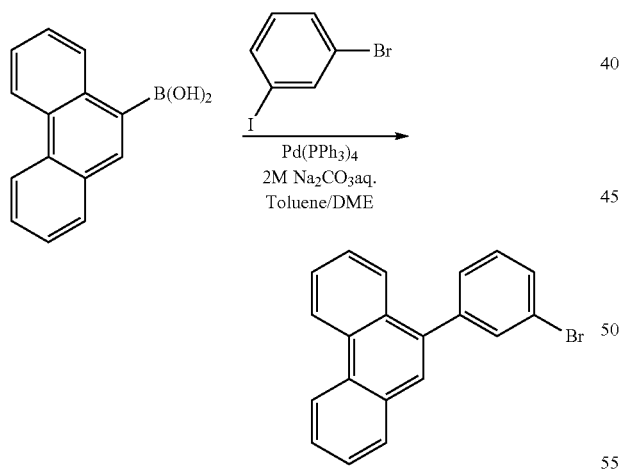

In argon atmosphere, a mixture of 31.4 g (141 mmol) of 9-phenanthreneboronic acid, 40.0 g (141 mmol) of 3-bromoiodobenzene, 3.30 g (2.83 mmol) of tetrakis(triphenylphosphine)palladium (0), 200 ml of toluene, 50 ml of dimethoxyethane and 212 ml of a 2 M sodium carbonate aqueous solution, and the mixture was refluxed under stirring for 4 h. After the reaction, the reaction mixture was added with toluene and washed with water. The organic phase was dried over sodium sulfate, and then toluene was removed by distillation under reduced pressure. The residue was purified by silica gel chromatography to obtain 34.7 g (yield: 74%) of 9-(3-bromophenyl)phenanthrene.

Synthetic Reference Example 3-2

Synthesis of 3-(9-phenanthrenyl)phenylboronic acid

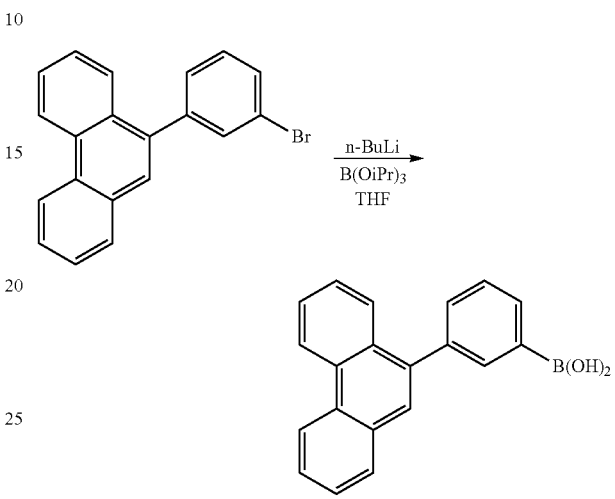

In argon atmosphere, a liquid mixture of 15.45 g (46.4 mmol) of 9-(3-bromophenyl)phenanthrene and 150 ml of dry THF was cooled to −60° C., and 35.9 ml (55.6 mmol) of a 1.55 M hexane solution of n-butyllithium was added dropwise under stirring. Then, the reaction mixture was stirred at −60° C. for 2 h. The reaction solution was cooled again to −60° C., and 26.2 g (139 mol) of triisopropyl borate was added dropwise. The reaction mixture was heated up to room temperature, stirred for one hour, and left standing overnight. The solvent was removed by distillation under reduced pressure to concentrate the reaction mixture. The concentrated reaction mixture was cooled to 0° C., added with hydrochloric acid, and stirred at room temperature for one hour. After the reaction, dichloromethane was added to the reaction mixture, and the aqueous phase was removed. The organic phase was dried over sodium sulfate, and then the solvent was removed by distillation under reduced pressure. The residue was purified by silica gel chromatography to obtain 13.4 g (yield: 67%) of 3-(9-phenanthrenyl)phenylboronic acid.

Synthetic Reference Example 4-1

Synthesis of 9-(4-bromophenyl)phenanthrene

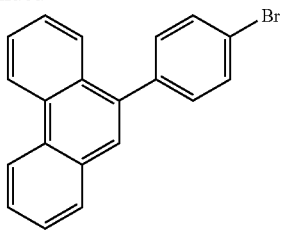

In argon atmosphere, a mixture of 39.25 g (177 mmol) of 9-phenanthreneboronic acid, 50.0 g (177 mmol) of 4-bromoiodobenzene, 4.10 g (3.54 mmol) of tetrakis(triphenylphosphine)palladium (0), 400 ml of toluene, and 265 ml of a 2 M sodium carbonate aqueous solution was refluxed under stirring for 24 h. After the reaction, the reaction mixture was filtered and the aqueous phase was removed. The organic phase was washed with water and dried over magnesium sulfate, and then the toluene was removed by distillation under reduced pressure. The residue was purified by silica gel chromatography to obtain 42.6 g (yield: 72%) of 9-(4-bromophenyl)phenanthrene.

Synthetic Reference Example 4-2

Synthesis of 4-(9-phenanthrenyl)phenylboronic acid

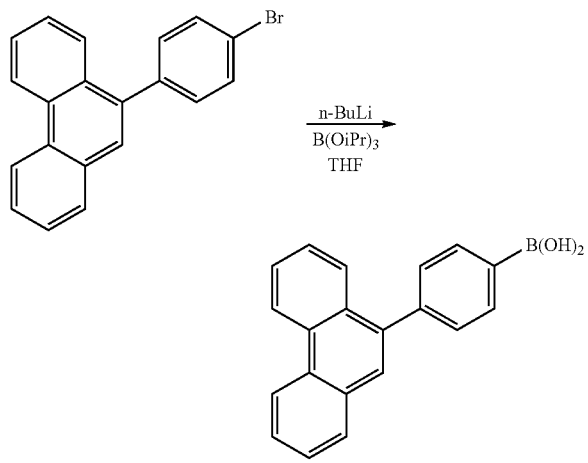

In argon atmosphere, a liquid mixture of 21.3 (63.9 mmol) of 9-(4-bromophenyl)phenanthrene and 200 ml of dry THF was cooled to −60° C. under argon atmosphere, and 49.2 ml (76.7 mmol) of a 1.55 M hexane solution of n-butyllithium was added dropwise under stirring. Further, the reaction mixture was stirred at −60° C. for 2 h. The reaction solution was cooled again to −60° C., and 36.1 g (192 mol) of triisopropyl borate was added dropwise. The reaction mixture was heated up to room temperature and stirred for 17 h. The reaction mixture was cooled to 0° C., added with hydrochloric acid, and stirred at room temperature for one hour. After the reaction, toluene was added to the reaction mixture and the aqueous phase was removed. The organic phase was dried over magnesium sulfate, and then the solvent was removed by distillation under reduced pressure. The residue was recrystallized from toluene and then from hexane to obtain 13.8 g (yield: 72%) of 4-(9-phenanthrenyl)phenylboronic acid.

Synthetic Reference Example 5-1

Synthesis of 6-bromo-2-(9-phenanthrenyl)naphthalene

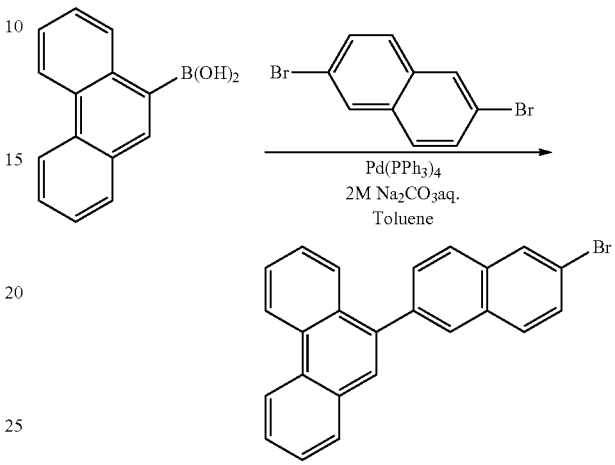

In argon atmosphere, a mixture of 15.53 g (69.6 mmol) of 9-phenanthreneboronic acid, 20.00 g (69.9 mmol) of 2,6-dibromonaphthalene, 1.62 g (1.40 mmol) of tetrakis(triphenylphosphine)palladium (0), 150 ml of dimethoxyethane, 150 ml of toluene, and 106 g of a 2 M sodium carbonate aqueous solution was stirred at a bath temperature of 85° C. for 7 h. The reaction mixture was added with water and extracted with toluene. After washing with water, the organic phase was dried over magnesium sulfate. Then the toluene was removed by distillation under reduced pressure. The residue was purified by silica gel chromatography to obtain 11.6 g (yield: 43%) of 6-bromo-2-(9-phenanthrenyl)naphthalene.

Synthetic Reference Example 5-2

Synthesis of 2-(9-phenanthrenyl)naphthalene-6-boronic acid

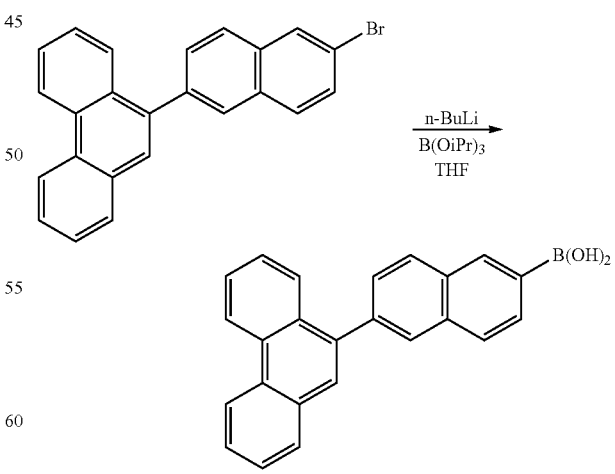

In argon atmosphere, a liquid mixture of 9.80 (25.6 mmol) of 6-bromo-2-(9-phenanthrenyl)naphthalene, 100 ml of dry toluene, and 100 ml of dry diethyl ether was cooled to −10° C. and 19.7 ml (30.7 mmol) of a 1.56 M hexane solution of n-butyllithium was added dropwise under stirring. Further, the reaction mixture was stirred at −10° C. for 4 h. The reaction solution was cooled to −60° C., and 14.4 g (76.7 mmol) of triisopropyl borate was added dropwise. The reaction mixture was heated and stirred at room temperature for 16 h. The reaction mixture was added with hydrochloric acid and stirred at room temperature overnight. After the reaction, the reaction mixture was separated into liquid phases, and the organic phase was washed with water. The solvent was removed by distillation under reduced pressure until the mixture was turned to slurry. After adding hexane to the residue, the solid matter was collected by filtration and recrystallized from THF and then from hexane to obtain 5.20 g (yield: 58%) of 2-(9-phenanthrenyl)naphthalene-6-boronic acid.

Synthetic Reference Example 6-1

Synthesis of
7-bromo-2-(9-phenanthrenyl)naphthalene

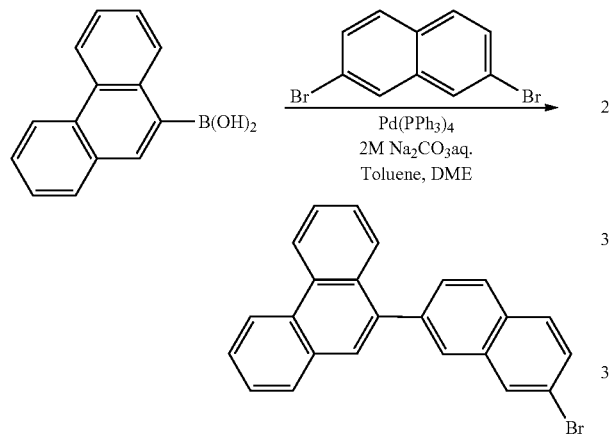

In argon atmosphere, a mixture of 18.64 g (83.9 mmol) of 9-phenanthreneboronic acid, 30.00 g (104.9 mmol) of 2,7-dibromonaphthalene, 4.85 g (4.2 mmol) of tetrakis(triphenylphosphine)palladium (0), 200 ml of dimethoxyethane, 200 ml of toluene, and 106 ml of a 2 M sodium carbonate was stirred at a bath temperature of 85° C. for 7 h. The reaction mixture was added with water and extracted with toluene. After washing with water, the organic phase was dried over magnesium sulfate. Then, the toluene was removed by distillation under reduced pressure, and the residue was purified by silica gel chromatography to obtain 12.46 g (yield: 31.0%) of 7-bromo-2-(9-phenanthrenyl)naphthalene.

Synthetic Reference Example 6-2

Synthesis of
2-(9-phenanthrenyl)naphthalene-7-boronic acid

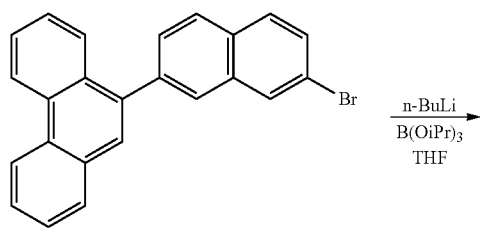

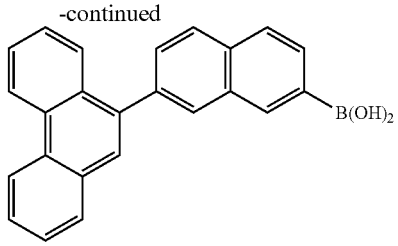

In argon atmosphere, a liquid mixture of 12.27 (32.01 mmol) of 7-bromo-2-(9-phenanthrenyl)naphthalene and 130 ml of dry THF was cooled to −70° C., and 24.8 ml (38.4 mmol) of a 1.56 M hexane solution of n-butyllithium was added dropwise under stirring. Further, the reaction mixture was stirred at −70° C. for 4 h. The reaction mixture was added dropwise with 18.06 g (96.04 mmol) of triisopropyl borate while maintaining the temperature at −60° C. or lower and then stirred for one hour. The reaction mixture was heated, stirred at room temperature for 3 h, and then allowed to stand overnight. The reaction mixture was added with 100 ml of a 6 N hydrochloric acid while maintaining the temperature at 20° C. or lower by cooling on an ice bath. The reaction mixture was stirred at room temperature for 30 min, added with dichloromethane, and then allowed to separate into liquid phases. The organic phase was washed with water and dried over anhydrous sodium sulfate. The solvent was removed by distillation to obtain 9.50 g (yield: 85%) of 2-(9-phenanthrenyl)naphthalene-7-boronic acid.

Synthetic Reference Example 7-1

Synthesis of
4-bromo-2-(9-phenanthrenyl)naphthalene

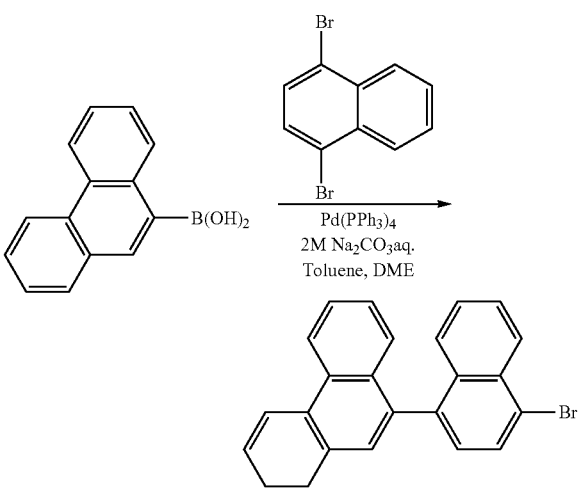

In argon atmosphere, a mixture of 19.41 g (87.4 mmol) of 9-phenanthreneboronic acid, 25.00 g (87.4 mmol) of 1,4-dibromonaphthalene, 2.02 g (1.70 mmol) of tetrakis(triphenylphosphine)palladium (0), 50 ml of dimethoxyethane, 200 ml of toluene, and 132 g of a 2 M sodium carbonate aqueous solution was stirred at a bath temperature of 85° C. for 6 h. The reaction mixture was added with water and extracted with toluene. After washing with water, the organic phase was dried over magnesium sulfate. The solvent was removed by distillation under reduced pressure, and the residue was purified by silica gel chromatography to obtain 16.02 g (yield: 55.0%) of 4-bromo-2-(9-phenanthrenyl)naphthalene.

Synthetic Reference Example 7-2

Synthesis of 2-(9-phenanthrenyl)naphthalene-4-boronic acid

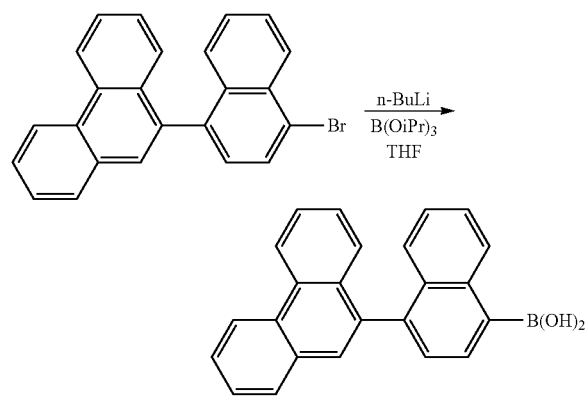

In argon atmosphere, a liquid mixture of 16.00 (41.74 mmol) of 4-bromo-2-(9-phenanthrenyl)naphthalene and 160 ml of dry THF was cooled to −70° C., and 32.2 ml (38.4 mmol) of a 1.56 M hexane solution of n-butyllithium was added dropwise under stirring. Further, the reaction mixture was stirred at −70° C. for 3 h. After adding 18.06 g (96.04 mmol) of triisopropyl borate while maintaining the temperature at −60° C. or lower, the mixture was stirred for one hour. The reaction mixture was heated, stirred at room temperature for 3 h, and left standing overnight. The reaction mixture was added with 50 ml of a concentrated hydrochloric acid while maintaining the temperature at 20° C. or lower by cooling on an ice bath and then stirred at room temperature for one hour. The reaction mixture was added with dichloromethane and allowed to separate into liquid phases. The organic phase was washed with water and dried over anhydrous sodium sulfate, and the solvent was removed by distillation. After recrystallizing from toluene, 5.40 g (yield: 37%) of 2-(9-phenanthrenyl)naphthalene-4-boronic acid was obtained.

Synthetic Reference Example 8-1

Synthesis of 5-(3-bromophenyl)benzo[c]phenanthrene

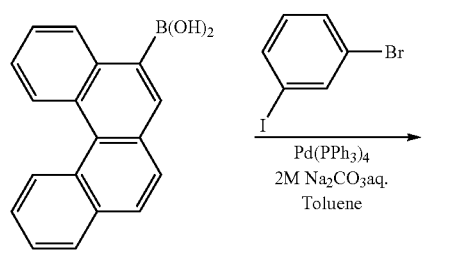

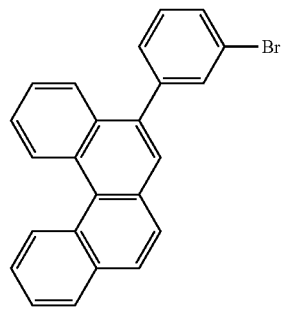

In argon atmosphere, a mixture of 6.32 g (22.3 mmol) of 5-benzo[c]phenanthreneboronic acid, 5.07 g (18.6 mmol) of 3-bromoiodobenzene, 1.29 g (1.12 mmol) of tetrakis(triphenylphosphine)palladium (0), 80 ml of toluene, 80 ml of dimethoxyethane, and 33.8 g of a 2 M sodium carbonate aqueous solution was refluxed for 8 h under stirring. After the reaction, the reaction mixture was added with water and extracted with toluene. The organic phase was washed with water and dried over sodium sulfate, and then the toluene was removed by distillation under reduced pressure. The residue was purified by silica gel chromatography to obtain 4.53 g (yield: 56.8%) of 5-(3-bromophenyl)benzo[c]phenanthrene.

Synthetic Reference Example 9-1

Synthesis of 3-(3-bromophenyl)-fluoranthene

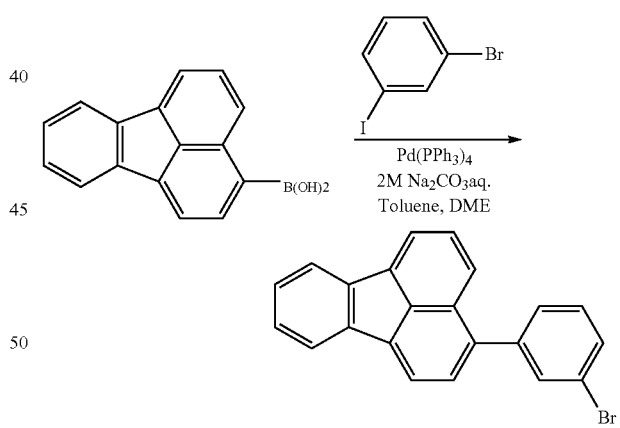

In argon atmosphere, a mixture of 18.18 g (81.3 mmol) of 3-fluorantheneboronic acid, 22.99 g (81.3 mmol) of 3-bromoiodobenzene, 4.70 g (4.10 mmol) of tetrakis(triphenylphosphine)palladium (0), 80 ml of toluene, 80 ml of dimethoxyethane, and 123 g of a 2 M sodium carbonate aqueous solution was refluxed for 8 h under stirring. After the reaction, the reaction mixture was added with water and stirred at room temperature for one hour. After adding methanol, the solid matter was collected by filtration and purified by silica gel chromatography to obtain 20.43 g (yield: 70.4%) of 3-(3-bromophenyl)fluoranthene.

Synthetic Reference Example 10-1

Synthesis of 6-(3-bromophenyl)chrysene

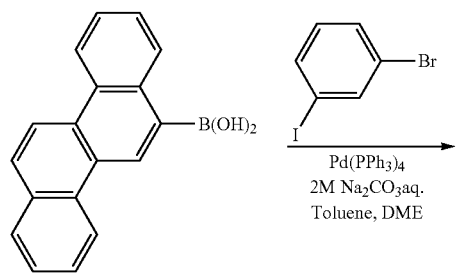

In argon atmosphere, a mixture of 5.00 g (18.37 mmol) of 6-chryseneboronic acid, 5.20 g (18.37 mmol) of 3-bromoiodobenzene, 1.06 g (0.92 mmol) of tetrakis(triphenylphosphine)palladium (0), 30 ml of toluene, 30 ml of dimethoxyethane, and 27.6 g of a 2 M sodium carbonate aqueous solution was refluxed for 8 h under stirring and left standing overnight. The reaction mixture was added with water and stirred at room temperature for one hour. After adding methanol, the solid matter was collected by filtration and purified by silica gel chromatography to obtain 2.00 g (yield: 28.4%) of 6-(3-bromophenyl)chrysene.

Synthetic Reference Example 11-1

Synthesis of 10-(3-bromophenyl)benzo[g]chrysene

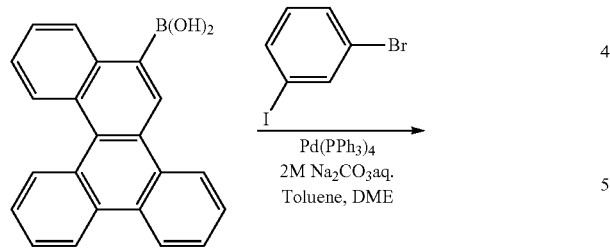

In argon atmosphere, a mixture of 5.00 g (15.52 mmol) of 10-benzo[g]chryseneboronic acid, 4.39 g (15.52 mmol) of 3-bromoiodobenzene, 0.90 g (0.78 mmol) of tetrakis(triphenylphosphine)palladium (0), 30 ml of toluene, 30 ml of dimethoxyethane, and 23.28 g of a 2 M sodium carbonate aqueous solution was refluxed for 8 h under stirring and left standing overnight. The reaction mixture was added with water and stirred at room temperature for one hour. After adding methanol, the solid matter was collected by filtration and purified by silica gel chromatography to obtain 2.30 g (yield: 34.2%) of 10-(3-bromophenyl)benzo[g]chrysene.

Synthetic Reference Example 12-1

Synthesis of 2-bromo-8-(naphthalene-2-yl)dibenzofuran

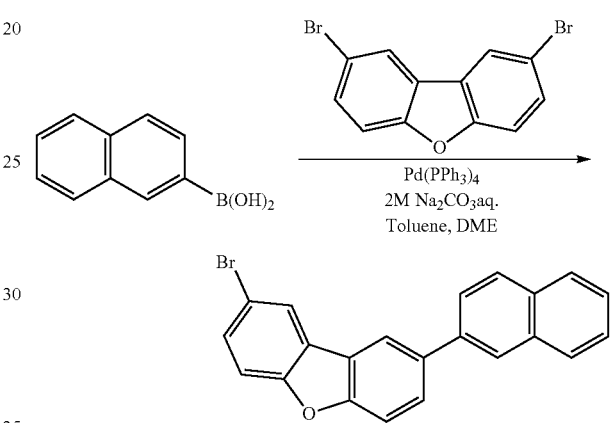

In argon atmosphere, a mixture of 13.19 g (76.7 mmol) of 2-naphthaleneboronic acid, 25.00 g (76.7 mmol) of 2,8-dibromobenzofuran, 4.43 g (3.80 mmol) of tetrakis(triphenylphosphine)palladium (0), 300 ml of dimethoxyethane, and 116 g of a 2 M sodium carbonate aqueous solution was stirred at a bath temperature of 85° C. for 7 h. The reaction mixture was added with water and extracted with toluene. After washing with water, the organic phase was dried over magnesium sulfate. Then, the solvent was removed by distillation under reduced pressure, and the residue was purified by silica gel chromatography to obtain 13.50 g (yield: 44%) of 2-bromo-8-(naphthalene-2-yl)dibenzofuran.

Synthetic Reference Example 12-2

Synthesis of 8-(naphthalene-2-yl)dibenzofuran-2-ylboronic acid

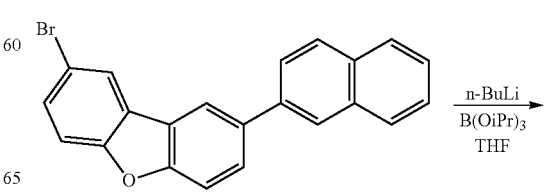

-continued

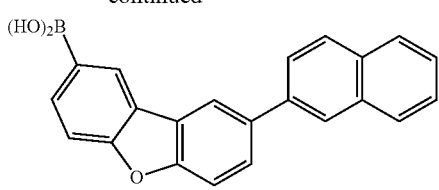

In argon atmosphere, a liquid mixture of 7.47 g (20.0 mmol) of 2-bromo-8-(naphthalene-2-yl)dibenzofuran and 75 ml of dry THF was cooled to −60° C. and 15.5 ml (24.0 mmol) of a 1.55 M hexane solution of n-butyllithium was added dropwise under stirring. Further, the reaction mixture was stirred at −70° C. for 2 h. The reaction solution was cooled again to −70° C., and 11.29 g (60.0 mol) of triisopropyl borate was added dropwise. The reaction mixture was heated up to room temperature, stirred for one hour, and left standing overnight. The reaction mixture was cooled on an ice bath, added with a 6 N hydrochloric acid, and stirred at room temperature for one hour. After adding dichloromethane, the reaction mixture was allowed to separate into liquid phases, and the organic phase was washed with water and dried over sodium sulfate. The solvent was removed by distillation under reduced pressure, and the residue was purified by silica gel chromatography to obtain 3.65 g (yield: 54%) of 8-(naphthalene-2-yl)dibenzofuran-2-ylboronic acid.

Synthetic Reference Example 13-1

Synthesis of 2-bromo-8-(naphthalene-2-yl)dibenzofuran

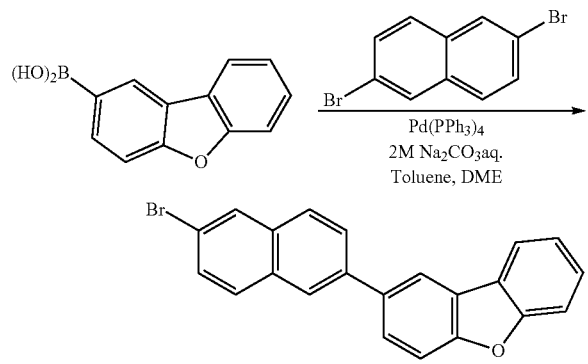

In argon atmosphere, a mixture of 18.53 g (87.4 mmol) of 2-dibenzofuranboronic acid, 25.00 g (87.4 mmol) of 2,6-dibromonaphthalene, 5.05 g (4.40 mmol) of tetrakis(triphenylphosphine)palladium (0), 300 ml of dimethoxyethane, and 132 g of a 2 M sodium carbonate aqueous solution was stirred at a bath temperature of 85° C. for 7 h. The reaction mixture was added with water and extracted with toluene. After washing with water, the organic phase was dried over magnesium sulfate. Then, the solvent was removed by distillation under reduced pressure, and the residue was purified by silica gel chromatography to obtain 13.20 g (yield: 38%) of 2-(6-bromonaphthalene-2-yl)dibenzofuran.

Synthetic Reference Example 13-2

Synthesis of 6-(dibenzofuran-2-yl)naphthalene-2-ylboronic acid

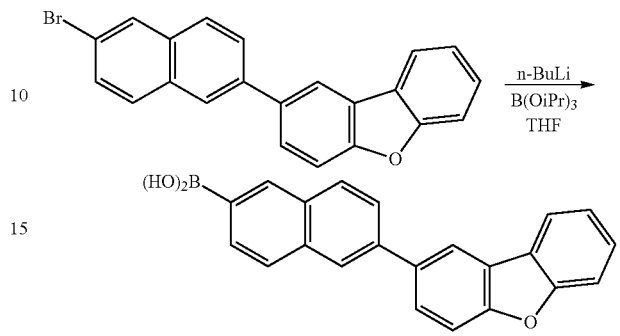

In argon atmosphere, a liquid mixture of 7.47 g (20.0 mmol) of 2-(6-bromonaphthalene-2-yl)dibenzofuran and 75 ml of dry THF was cooled to −60° C., and 15.5 ml (24.0 mmol) of a 1.55 M hexane solution of n-butyllithium was added dropwise under stirring. Further, the reaction mixture was stirred at −70° C. for 2 h. The reaction solution was cooled again to −70° C., and 11.29 g (60.0 mol) of triisopropyl borate was added dropwise. The reaction mixture was heated up to room temperature, stirred for one hour, and left standing overnight. The reaction mixture was cooled on an ice bath, added with a 6 N hydrochloric acid, and stirred at room temperature for one hour. After adding dichloromethane, the reaction mixture was allowed to separate into liquid phases, and the organic phase was washed with water and dried over sodium sulfate. The solvent was removed by distillation under reduced pressure, and the residue was purified by silica gel chromatography to obtain 4.20 g (yield: 62%) of 6-(dibenzofuran-2-yl)naphthalene-2-ylboronic acid.

Synthetic Reference Example 14-1

Synthesis of 2-(7-bromonaphthalene-2-O-9,9-dimethyl-9H-fluorene

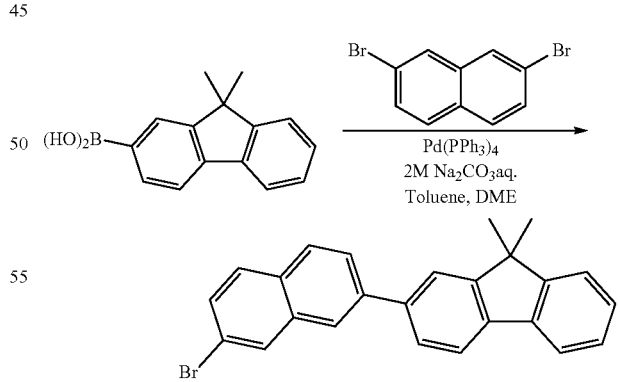

In argon atmosphere, a mixture of 16.65 g (69.9 mmol) of 9,9-dimethyl-9H-fluorene-2-ylboronic acid, 20.00 g (69.9 mmol) of 2,7-dibromonaphthalene, 4.04 g (3.50 mmol) of tetrakis(triphenylphosphine)palladium (0), 200 ml of toluene, 200 ml of dimethoxyethane, and 106 g of a 2 M sodium carbonate aqueous solution was stirred at 85° C. for 9 h and left standing overnight. The reaction mixture was added with water and stirred at room temperature for one hour. After filtration, the filtrate was extracted with toluene. The organic phase was washed with water and then with a saturated saline solution and dried over sodium sulfate, and then the toluene was removed by distillation under reduced pressure. The obtained brown oily substance was purified by silica gel chromatography to obtain 13.4 g (yield: 48%) of 2-(7-bromonaphthalene-2-yl)-9,9-dimethyl-9H-fluorene.

Invention A

Synthetic Example A-1

Synthesis of Compound 2-2

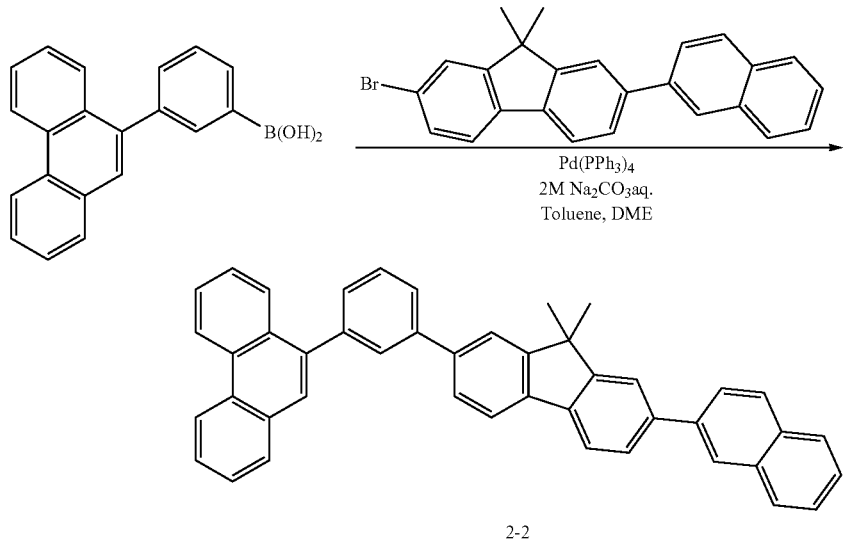

2-2

In argon atmosphere, a mixture of 3.30 g (8.26 mmol) of 2-boromo-9,9-dimethyl-7-(naphthalene-2-yl)-9H-fluorene, 2.46 g (8.26 mmol) of 3-(phenanthrene-9-yl)phenylboronic acid, 0.38 g (0.33 mmol) of tetrakis(triphenylphosphine)palladium (0), 90 ml of toluene, 30 ml of dimethoxyethane, and 12.5 g of a 2 M sodium carbonate aqueous solution was stirred at 85° C. for 8 h. The reaction mixture was left cooled down to room temperature, added with water, stirred for one hour, and left standing overnight. Then, the reaction mixture was added with water and stirred at room temperature for one hour. After filtration, the filtrate was extracted with toluene. The organic phase was washed with water and then with a saturated saline solution and dried over sodium sulfate, and then toluene was removed by distillation under reduced pressure. The obtained oily substance was purified by silica gel chromatography to obtain 3.40 g (yield: 72%) of compound 2-2.

Mass spectrum analysis showed m/e=572 to the molecular weight of 572.25.

Synthetic Example A-2

Synthesis of Compound 2-1

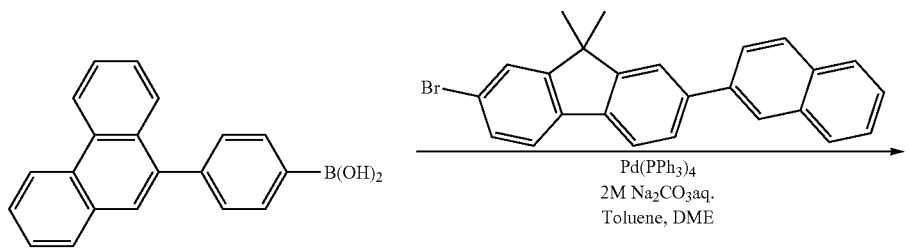

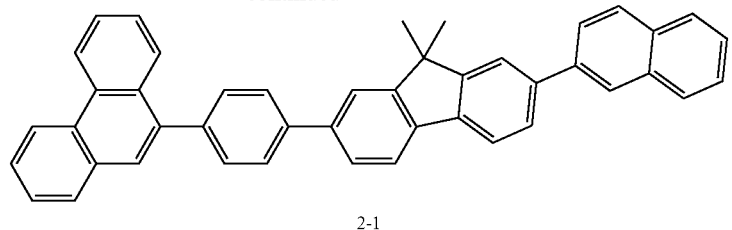

2-1

Compound 2-1 was synthesized in the same manner as in the synthesis of compound 2-2 except for using 4-(phenanthrene-9-yl)phenylboronic acid in place of 3-(phenanthrene-9-yl)phenylboronic acid.

Mass spectrum analysis showed m/e=572 to the molecular weight of 572.25.

Synthetic Example A-3

Synthesis of Compound 2-4

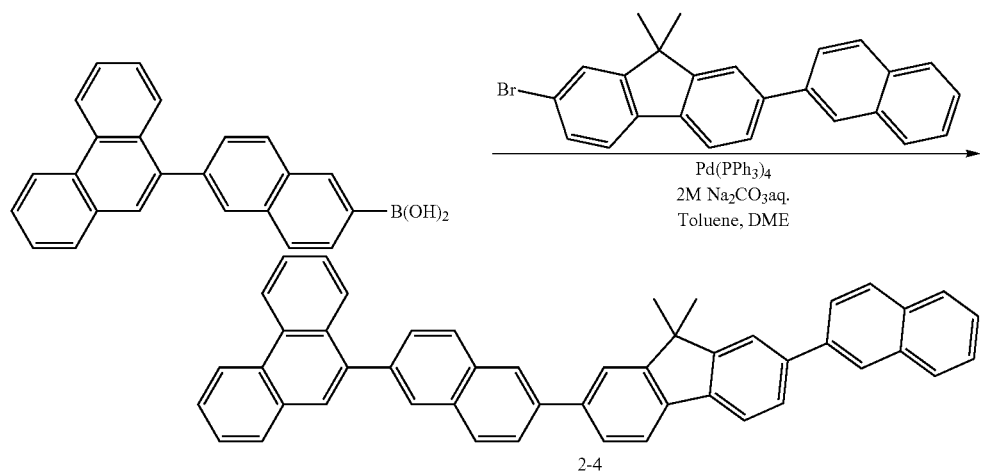

2-4

Compound 2-4 was synthesized in the same manner as in the synthesis of compound 2-2 except for using 6-(phenanthrene-9-yl)naphthalene-2-ylboronic acid in place of 3-(phenanthrene-9-yl)phenylboronic acid.

Mass spectrum analysis showed m/e=622 to the molecular weight of 622.27.

Synthetic Example A-4

Synthesis of Compound 2-5

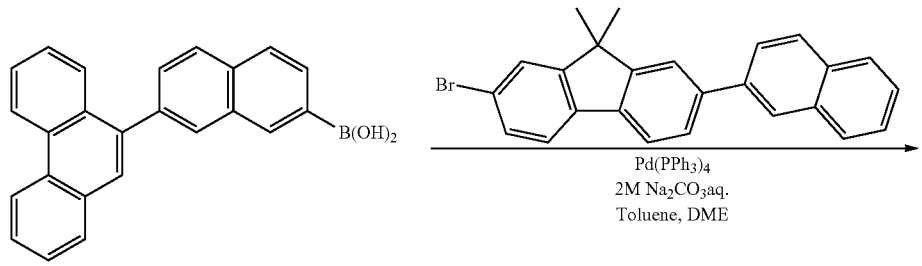

-continued

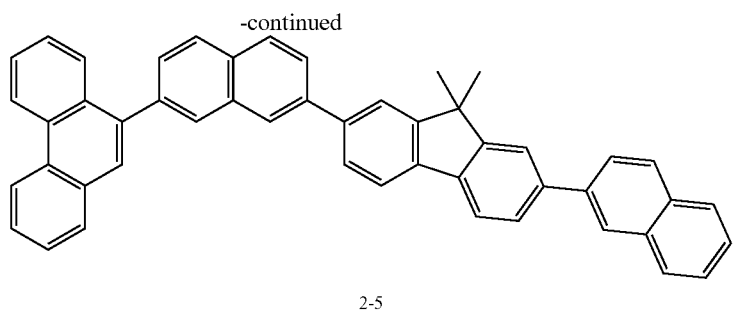

2-5

Compound 2-5 was synthesized in the same manner as in the synthesis of compound 2-2 except for using 7-(phenanthrene-9-yl)naphthalene-2-ylboronic acid in place of 3-(phenanthrene-9-yl)phenylboronic acid.

Mass spectrum analysis showed m/e=622 to the molecular weight of 622.27.

Synthetic Example A-5

Synthesis of Compound 2-7

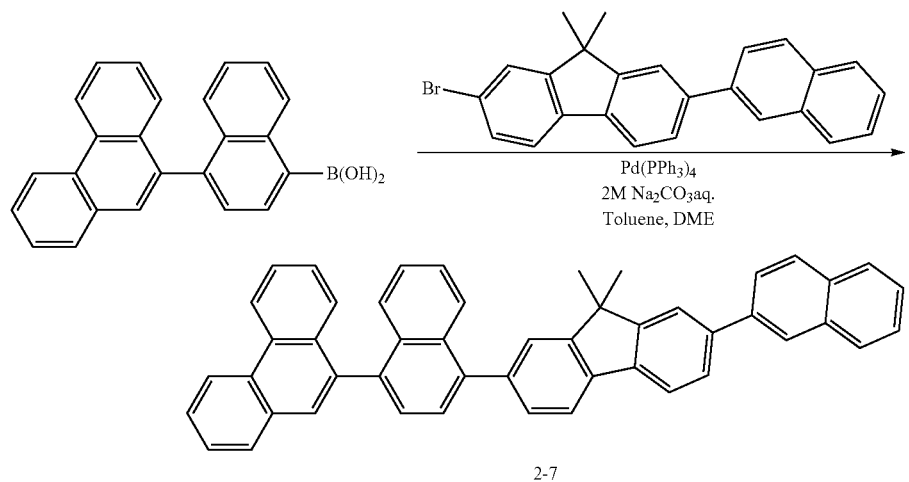

2-7

Compound 2-7 was synthesized in the same manner as in the synthesis of compound 2-2 except for using 4-(phenanthrene-9-yl)naphthalene-1-ylboronic acid in place of 3-(phenanthrene-9-yl)phenylboronic acid.

Mass spectrum analysis showed m/e=622 to the molecular weight of 622.27.

Synthetic Example A-6

Synthesis of Compound 2-184

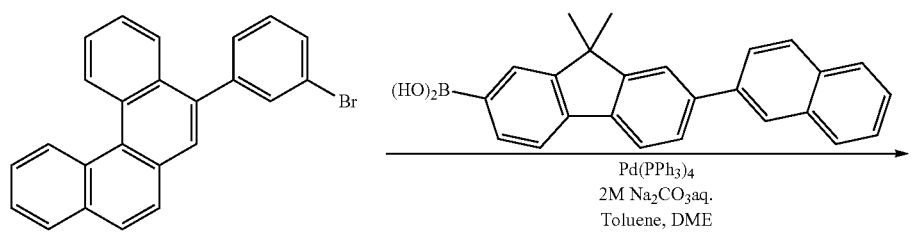

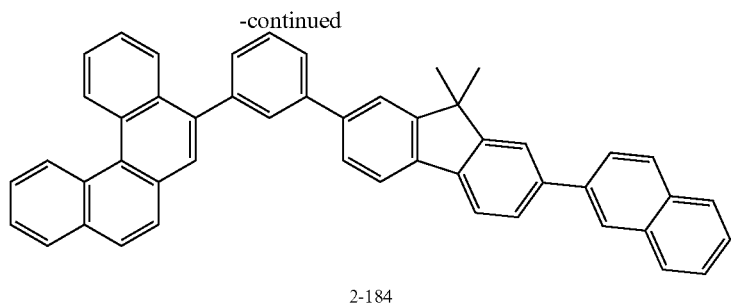

2-184

Compound 2-184 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 5-(3-bromophenyl)benzo[c]phenanthrene in place of 2-boromo-9,9-dimethyl-7-(naphthalene-2-yl)-9H-fluorene.

Mass spectrum analysis showed m/e=622 to the molecular weight of 622.27.

Synthetic Example A-7

Synthesis of Compound 2-75

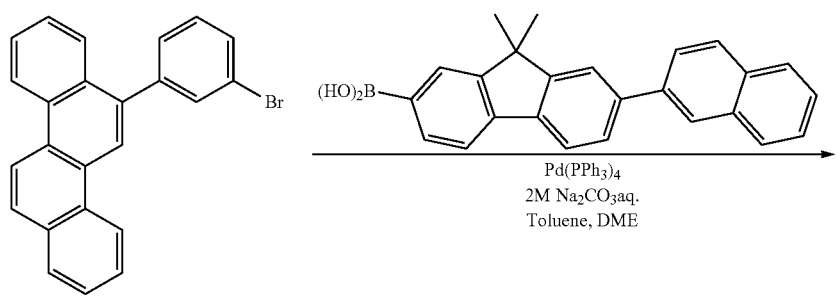

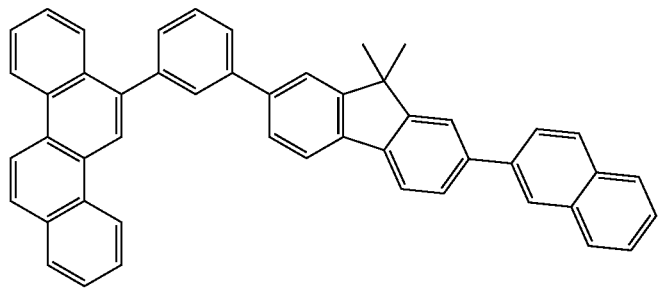

2-75

Compound 2-75 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 6-(3-bromophenyl)chrysene in place of 2-boromo-9,9-dimethyl-7-(naphthalene-2-yl)-9H-fluorene.

Mass spectrum analysis showed m/e=622 to the molecular weight of 622.27.

Synthetic Example A-8

Synthesis of Compound 2-159

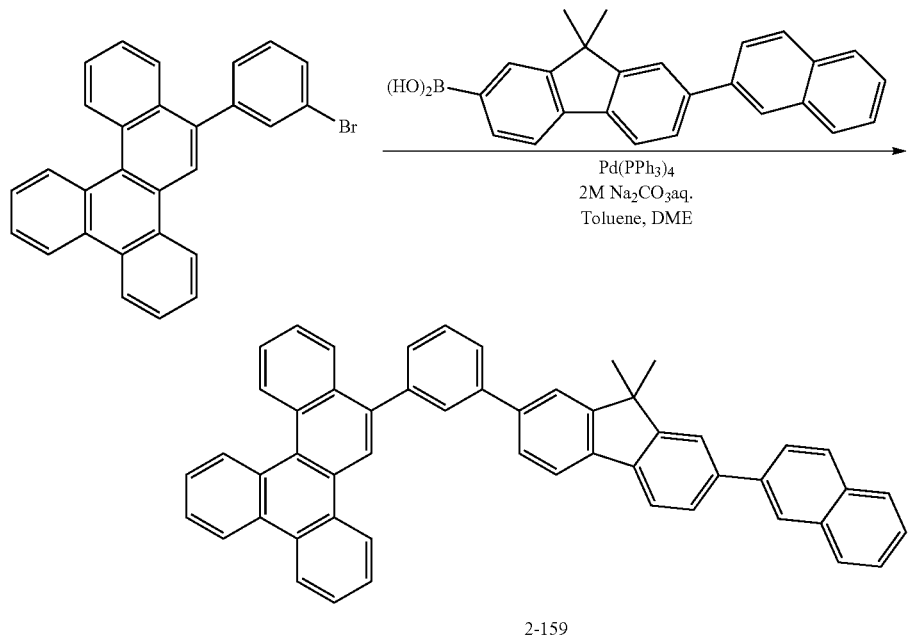

2-159

Compound 2-159 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 10-(3-bromophenyl)benzo[g]chrysene in place of 2-boromo-9,9-dimethyl-7-(naphthalene-2-yl)-9H-fluorene.

Mass spectrum analysis showed m/e=672 to the molecular weight of 672.28.

Synthetic Example A-9

Synthesis of Compound 2-99

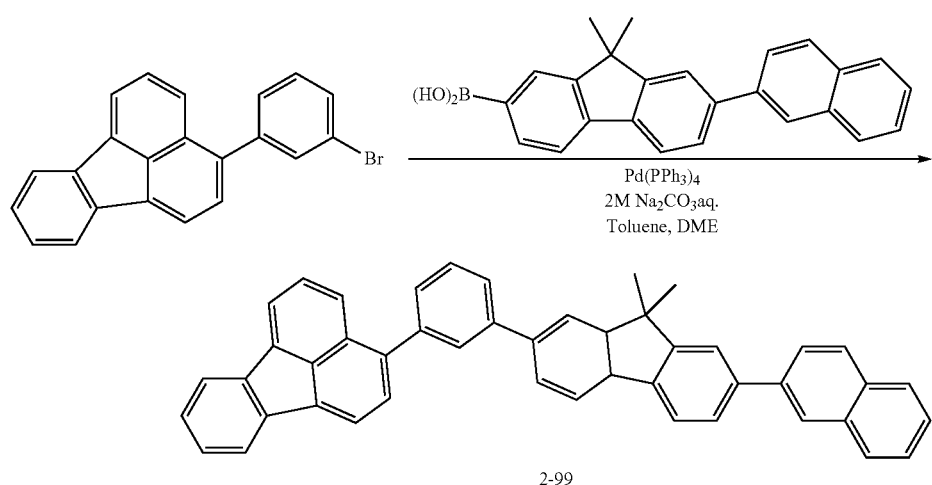

2-99

Compound 2-99 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 3-(3-bromophenyl)fluoranthene in place of 2-boromo-9,9-dimethyl-7-(naphthalene-2-yl)-9H-fluorene.

Mass spectrum analysis showed m/e=596 to the molecular weight of 596.25.

Synthetic Example A-10

Synthesis of Compound 3-97

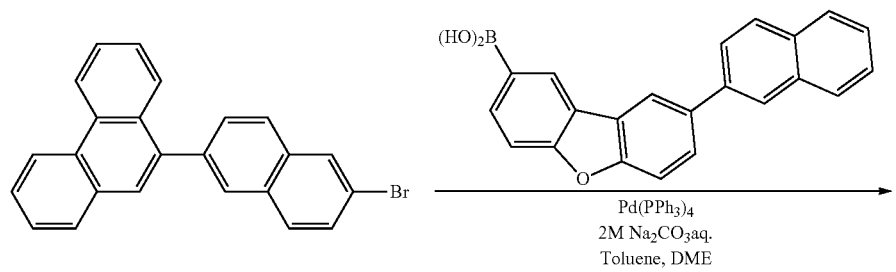

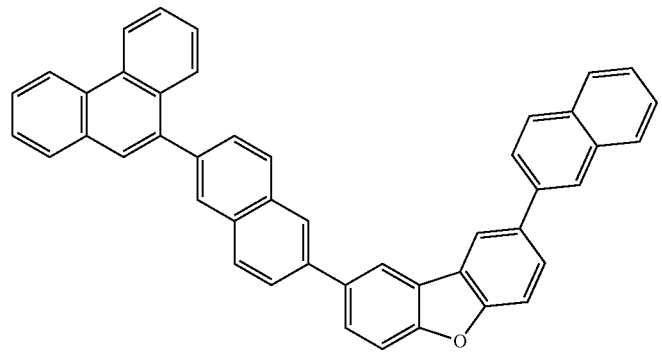

3-97

Compound 3-97 was synthesized in the same manner as in the synthesis of compound 2-2 except for using 8-(naphthalene-2-yl)dibenzofluorene-2-ylboronic acid in place of 3-(phenanthrene-9-yl)phenylboronic acid and using 6-bromo-2-(9-phenanthrenyl)naphthalene in place of 2-boromo-9,9-dimethyl-7-(naphthalene-2-yl)-9H-fluorene.

Mass spectrum analysis showed m/e=596 to the molecular weight of 596.21.

In the synthetic examples described above, the mass spectrum analysis was carried out by FD-MS (field desorption mass analysis). The apparatus and measuring conditions used for measurement of FD-MS (field desorption mass analysis) are shown below.

Apparatus: JSM-700 (manufactured by JEOL Ltd.)
Conditions: accelerating voltage: 8 kV
  scanning range: m/z=50 to 3000
  emitter: carbon
  emitter current: 0 mA→2 mA/min→40 mA (held for 10 min)

Next, the present invention will be explained in further details with reference to examples. However, it should be noted that the present invention is not limited to the following examples.

The structures of the compounds used in the examples and the comparative examples other than the compounds obtained in the synthetic examples are shown below.

599
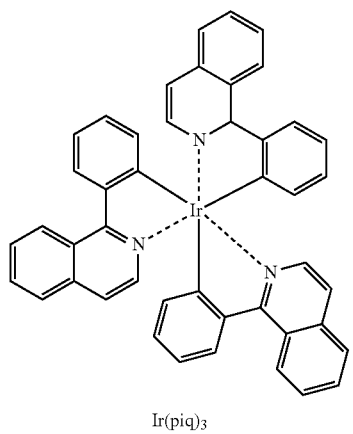
Ir(piq)₃
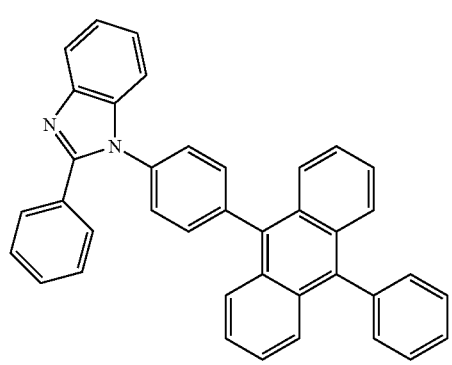
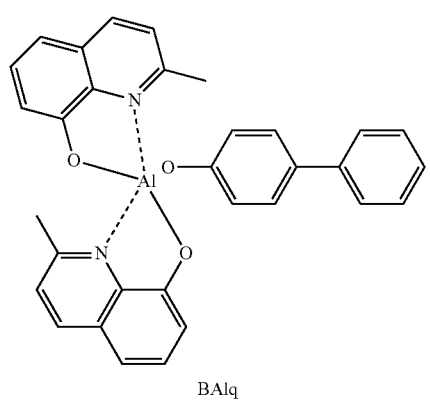
BAlq
600
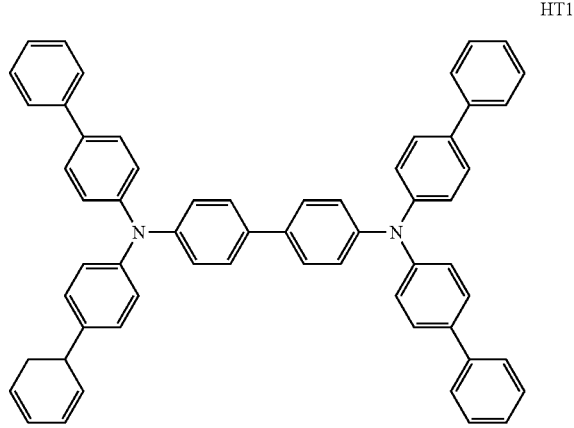
HT1
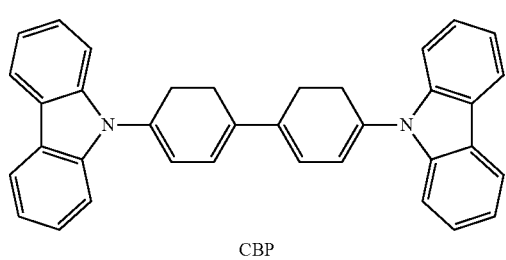
ET1
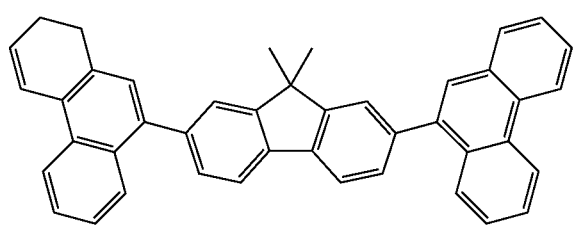
CBP
A-A
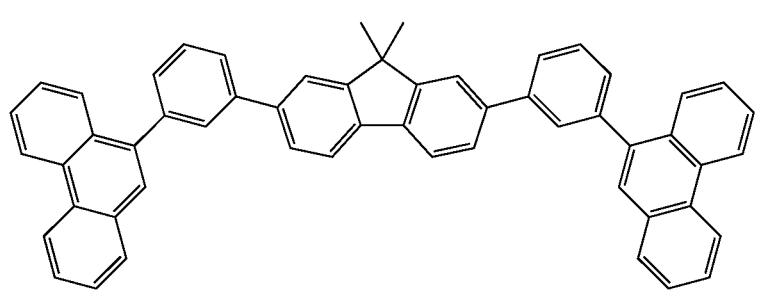
A-B -continued
A-C
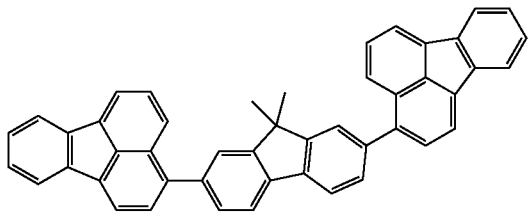
A-D
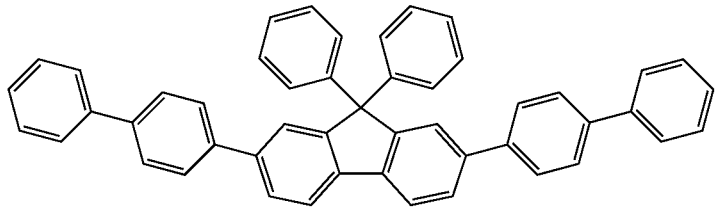
A-E
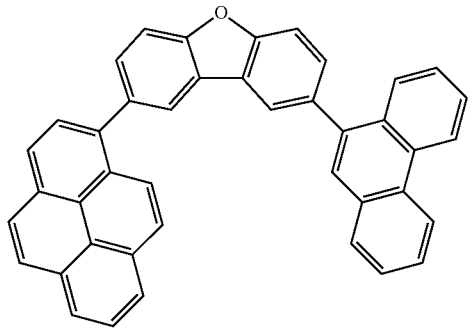
A-F
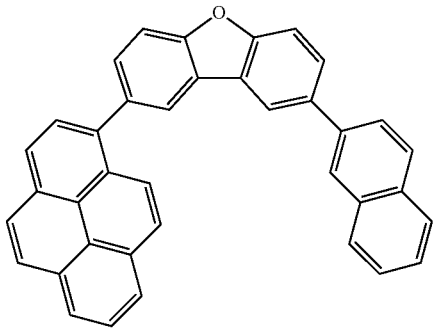
A-G
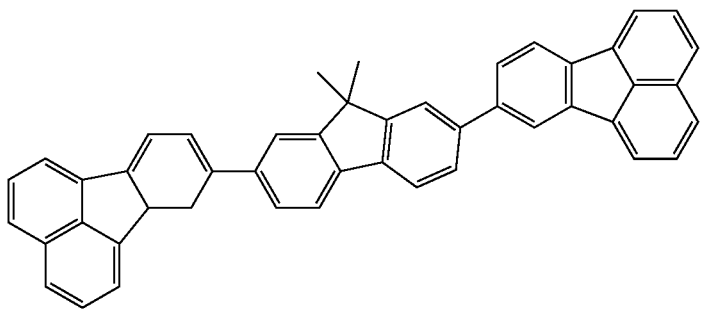
Complex A
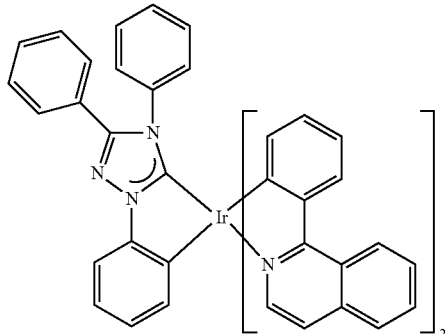
Complex B
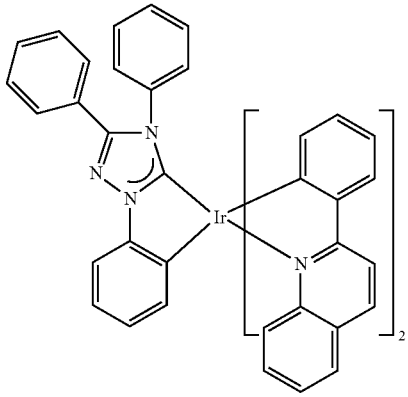

Example A-1

Preparation of Organic EL Device

A glass substrate of 25 mm×75 mm×0.7 mm thickness provided with an ITO transparent electrode (manufactured by Asahi Glass Co., Ltd.) was ultrasonically washed in isopropyl alcohol for 5 min and then to UV-ozone washed for 30 min. The washed glass substrate was mounted in a substrate holder of a vacuum vapor deposition apparatus, and a film of HT1 of 50 nm thick was formed so as to cover the transparent electrode. The film of HT1 works as a hole injecting transporting layer. After forming the hole injecting transporting layer, a film of 40 nm thick was successively formed by co-depositing the novel host compound 2-2 and Ir(piq)$_3$ as a phosphorescent dopant in an amount of 10% by mass under resistance heating. The film thus formed works as a light emitting layer (phosphorescent emitting layer). After forming the light emitting layer, a film of ET1 of 40 nm thick was formed. The film thus formed works as an electron transporting layer. Thereafter, an electron injecting electrode (cathode) of 0.5 nm thick was formed from LiF at a film forming speed of 1 Å/min. A metal cathode of 150 nm thick was formed on the LiF layer by vapor-depositing metal Al, to produce an organic EL device.

Examples A-2 to A-10 and Comparative Examples A-1 to A-9

Each organic EL device was produced in the same manner as in Example A-1 except for using the host compound shown in Table 1 in place of the novel host compound 2-2 used in Example A-1.

Example A-11

An organic EL device was produced in the same manner as in Example A-6 except for changing the dopant (complex) to Complex A.

Example A-12

An organic EL device was produced in the same manner as in Example A-11 except for changing Complex A to Complex B.

Comparative Example A-10

An organic EL device was produced in the same manner as in Example A-11 except for changing the host compound 2-148 to CBP.

Comparative Example A-11

An organic EL device was produced in the same manner as in Example A-12 except for changing the host compound 2-148 to BAlq.

Evaluation Of Emission Performance Of Organic EL Devices

The organic EL devices produced in Examples A-1 to A-12 and Comparative Examples A-1 to A-11 were allowed to emit light by DC driving to measure the voltage, current efficiency and half lifetime of luminance (initial luminance: 5000 cd/m$^2$) at a current density of 10 mA/cm$^2$. Results of the evaluation are shown in Table 1.

TABLE 1

| | Dopant | Host | Voltage (V) | Current efficiency (cd/A) | Half lifetime of luminance at room temperature (hour) |
|---|---|---|---|---|---|
| Examples | | | | | |
| A-1 | Ir(piq)$_3$ | 2-2 | 4.7 | 8.2 | 4,800 |
| A-2 | Ir(piq)$_3$ | 2-1 | 4.7 | 8.2 | 4,500 |
| A-3 | Ir(piq)$_3$ | 2-4 | 4.6 | 8.1 | 4,000 |
| A-4 | Ir(piq)$_3$ | 2-5 | 4.5 | 7.8 | 3,800 |
| A-5 | Ir(piq)$_3$ | 2-7 | 4.4 | 8.0 | 3,400 |
| A-6 | Ir(piq)$_3$ | 2-184 | 4.6 | 8.0 | 4,000 |
| A-7 | Ir(piq)$_3$ | 2-75 | 4.4 | 7.8 | 3,800 |
| A-8 | Ir(piq)$_3$ | 2-159 | 4.3 | 8.0 | 3,700 |
| A-9 | Ir(piq)$_3$ | 2-99 | 4.8 | 7.6 | 4,200 |
| A-10 | Ir(piq)$_3$ | 3-97 | 4.1 | 7.5 | 3,500 |
| Comparative Examples | | | | | |
| A-1 | Ir(piq)$_3$ | CBP | 5.4 | 6.3 | 500 |
| A-2 | Ir(piq)$_3$ | BAlq | 5.3 | 7.0 | 1,000 |
| A-3 | Ir(piq)$_3$ | compound A-A | 4.8 | 7.0 | 450 |
| A-4 | Ir(piq)$_3$ | compound A-B | 5.2 | 7.1 | 1,200 |
| A-5 | Ir(piq)$_3$ | compound A-C | 4.8 | 7.2 | 200 |
| A-6 | Ir(piq)$_3$ | compound A-D | 5.2 | 7.1 | 380 |
| A-7 | Ir(piq)$_3$ | compound A-E | 5.4 | 3.8 | 40 |
| A-8 | Ir(piq)$_3$ | compound A-F | 5.5 | 3.8 | 20 |
| A-9 | Ir(piq)$_3$ | compound A-G | 5.1 | 6.5 | 310 |
| Examples | | | | | |
| A-11 | complex A | 2-184 | 4.5 | 8.2 | 3,100 |
| A-12 | complex B | 2-184 | 4.7 | 7.8 | 2,800 |
| Comparative Examples | | | | | |
| A-10 | complex A | CBP | 5.8 | 4.2 | 800 |
| A-11 | complex B | BAlq | 5.1 | 5.0 | 1,300 |

The results of Table 1 show that the organic EL devices of Examples A-1 to A-10 employing the host materials of the invention have high current efficiency and extremely long lifetime. On the other hand, the organic EL devices of Comparative Examples A-1 and A-2 require high voltage and have short lifetime. The organic EL devices of Comparative Examples A-3 and A-5 are driven at the same voltage as in the examples, but have extremely short lifetime. The organic EL devices of Comparative Examples A-4, A-6, and A-9 require high voltage and have short lifetime. The organic EL devices of Comparative Examples A-7 and A-8 require high voltage and have extremely low efficiency and extremely short lifetime. As compared with the organic EL devices of Comparative Examples A-10 and A-11, the organic EL devices of Examples A-11 and A-12 are driven at low voltage and have high efficiency and long lifetime.

The characteristic features of combinations in the present invention are that:

the triplet energy gap of the host materials and the triplet energy gap of the dopants are suited to improve the current efficiency;

a naphthalene ring is bonded to the fluorene ring residue at a position capable of extending the conjugated system, thereby reducing the driving voltage; and since the host material is not substituted with a nitrogen-containing ring and a nitrogen atom, the light emitting material is highly resistant to holes and electrons, allowing the lifetime to be extended more than those of the combinations ever known.

Invention B

Synthetic Example B-1

Synthesis of Compound 2-50

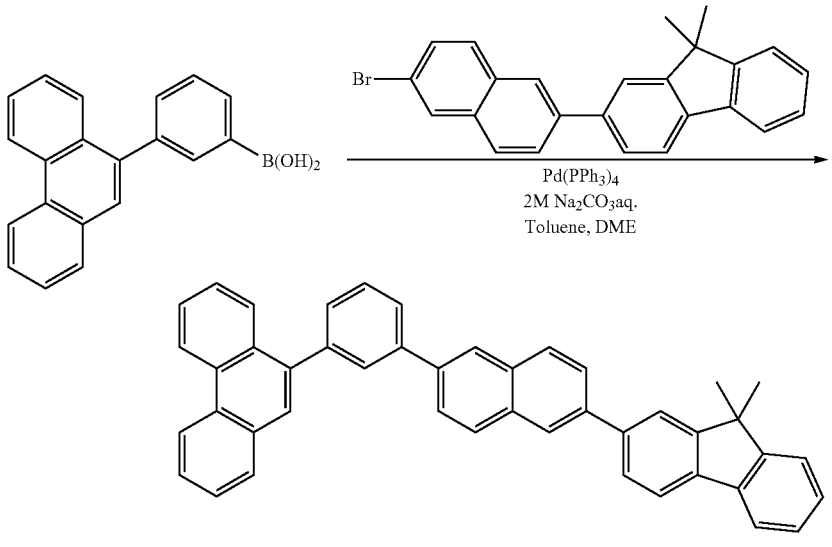

2-50

In argon atmosphere, a mixture of 3.30 g (8.26 mmol) of 2-(6-boromonaphthalene-2-yl)-9,9-dimethyl-9H-fluorene, 2.46 g (8.26 mmol) of 3-(phenanthrene-9-yl)phenylboronic acid, 0.38 g (0.33 mmol) of tetrakis(triphenylphosphine)palladium (0), 90 ml of toluene, 30 ml of dimethoxyethane, and 12.5 g of a 2 M sodium carbonate aqueous solution was stirred at 85° C. for 8 h. The reaction mixture was allowed to cool down to room temperature, added with water, and stirred for one hour. After filtration, the filtrate was extracted with toluene. The organic phase was washed with water and then with a saturated saline solution and dried over sodium sulfate, and then the toluene was removed by distillation under reduced pressure. The residue was recrystallized from toluene and then hexane to obtain 3.86 g (yield: 82%) of compound 2-50.

Mass spectrum analysis showed m/e=572 to the molecular weight of 572.25.

Synthetic Example B-2
Synthesis of Compound 2-46

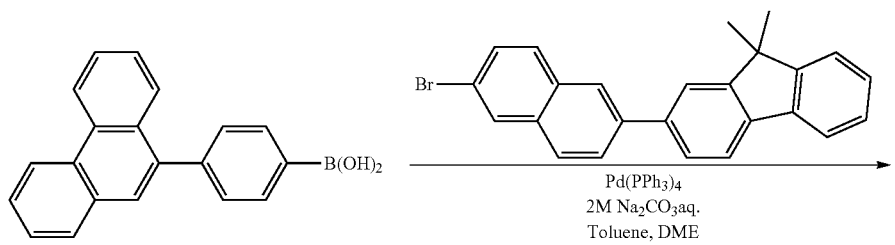

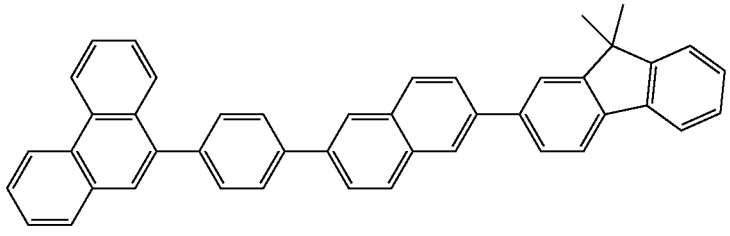

2-46

Compound 2-46 was synthesized in the same manner as in the synthesis of compound 2-50 except for using 4-(phenanthrene-9-yl)phenylboronic acid in place of 3-(phenanthrene-9-yl)phenylboronic acid.

Mass spectrum analysis showed m/e=572 to the molecular weight of 572.25.

Synthetic Example B-3

Synthesis of Compound 2-60

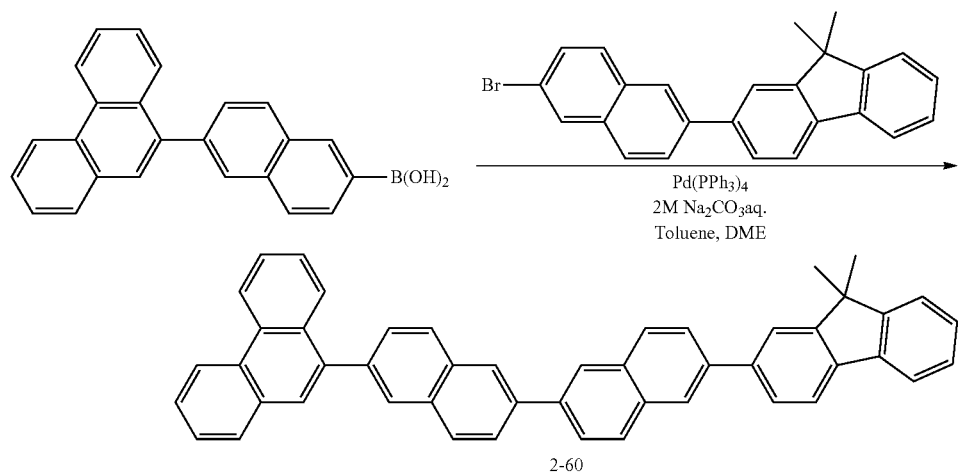

2-60

Compound 2-60 was synthesized in the same manner as in the synthesis of compound 2-50 except for using 6-(phenanthrene-9-yl)naphthalene-2-ylboronic acid in place of 3-(phenanthrene-9-yl)phenylboronic acid.

Mass spectrum analysis showed m/e=622 to the molecular weight of 622.27.

Synthetic Example B-4

Synthesis of Compound 2-61

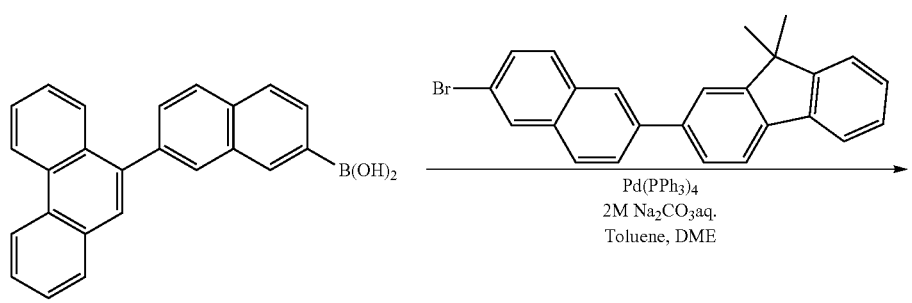

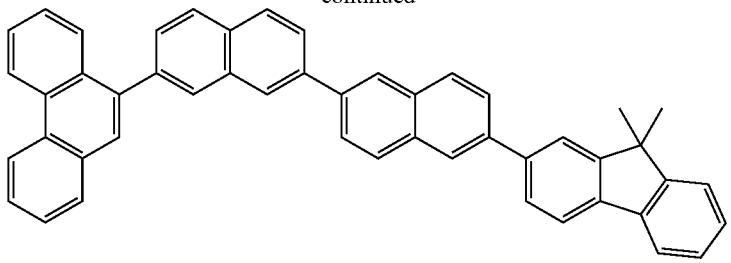

2-61

Compound 2-61 was synthesized in the same manner as in the synthesis of compound 2-50 except for using 7-(phenanthrene-9-yl)naphthalene-2-ylboronic acid in place of 3-(phenanthrene-9-yl)phenylboronic acid.

Mass spectrum analysis showed m/e=622 to the molecular weight of 622.27.

Synthetic Example B-5

Synthesis of Compound 2-58

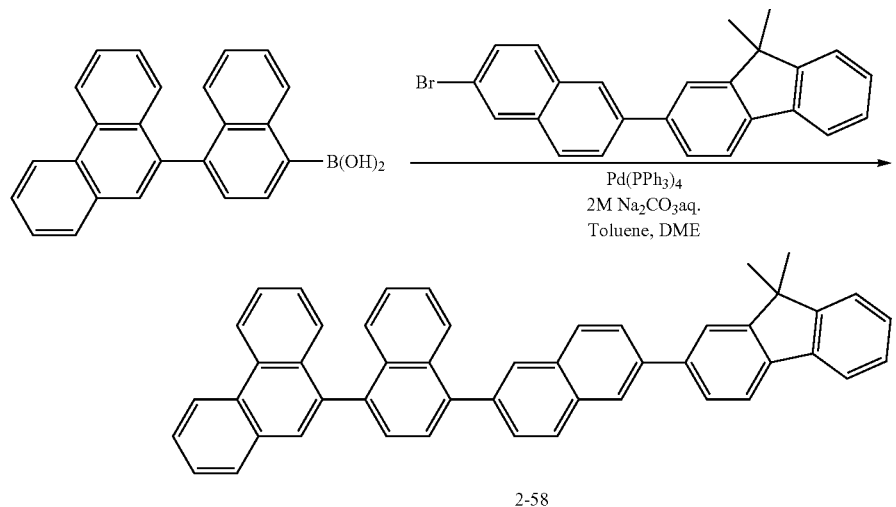

2-58

Compound 2-58 was synthesized in the same manner as in the synthesis of compound 2-50 except for using 4-(phenanthrene-9-yl)naphthalene-1-ylboronic acid in place of 3-(phenanthrene-9-yl)phenylboronic acid.

Mass spectrum analysis showed m/e=622 to the molecular weight of 622.27.

Synthetic Example B-6

Synthesis of Compound 2-314

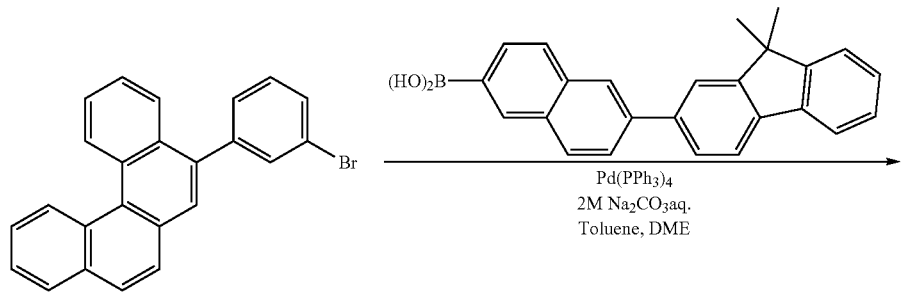

-continued

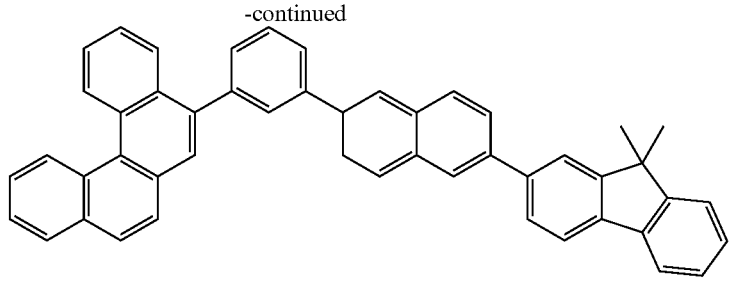

2-314

Compound 2-314 was synthesized in the same manner as in the synthesis of compound 2-50 except for using 6-(9,9-dimethyl-9H-fluorene-2-yl)naphthalene-2-ylboronic acid in place of 3-(phenanthrene-9-yl)phenylboronic acid and using 5-(3-bromophenyl)benzo[c]phenanthrene in place of 2-boromo-9,9-dimethyl-7-(naphthalene-2-yl)-9H-fluorene.

Mass spectrum analysis showed m/e=622 to the molecular weight of 622.27.

Synthetic Example B-7

Synthesis of Compound 2-234

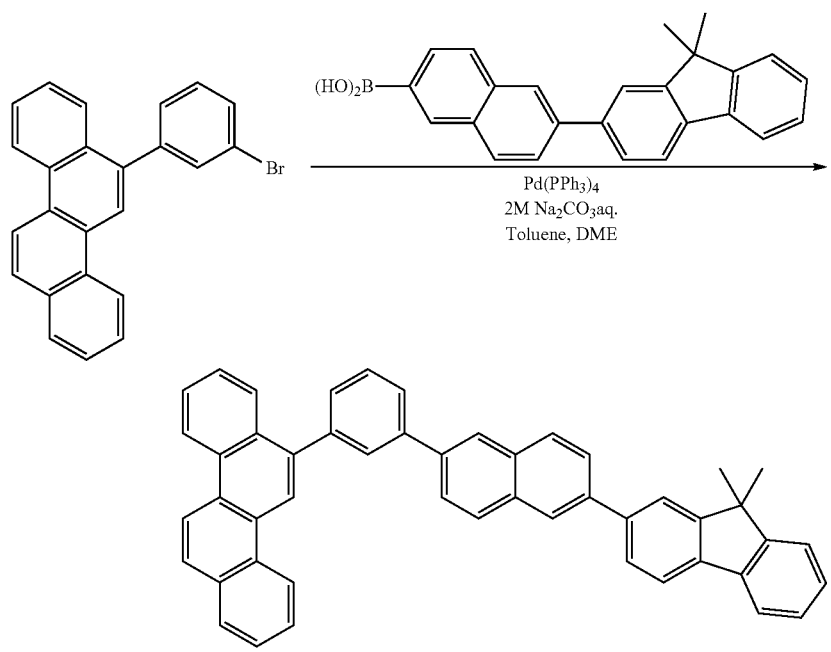

2-234

Compound 2-234 was synthesized in the same manner as in the synthesis of compound 2-50 except for using 6-(9,9-dimethyl-9H-fluorene-2-yl)naphthalene-2-ylboronic acid in place of 3-(phenanthrene-9-yl)phenylboronic acid and using 6-(3-bromophenyl)chrysene in place of 2-boromo-9,9-dimethyl-7-(naphthalene-2-yl)-9H-fluorene.

Mass spectrum analysis showed m/e=622 to the molecular weight of 622.27.

Synthetic Example B-8

Synthesis of Compound 2-294

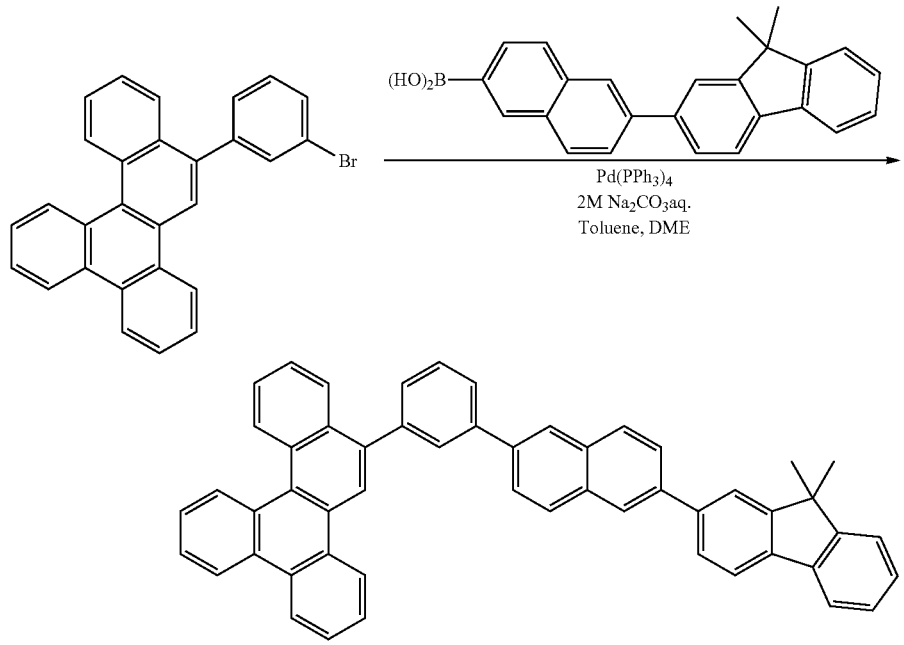

2-294

Compound 2-294 was synthesized in the same manner as in the synthesis of compound 2-2 except for using 6-(9,9-dimethyl-9H-fluorene-2-yl)naphthalene-2-ylboronic acid in place of 3-(phenanthrene-9-yl)phenylboronic acid and using 10-(3-bromophenyl)benzo[g]chrysene in place of 2-boromo-9,9-dimethyl-7-(naphthalene-2-yl)-9H-fluorene.

Mass spectrum analysis showed m/e=672 to the molecular weight of 672.28.

Synthetic Example B-9

Synthesis of Compound 2-254

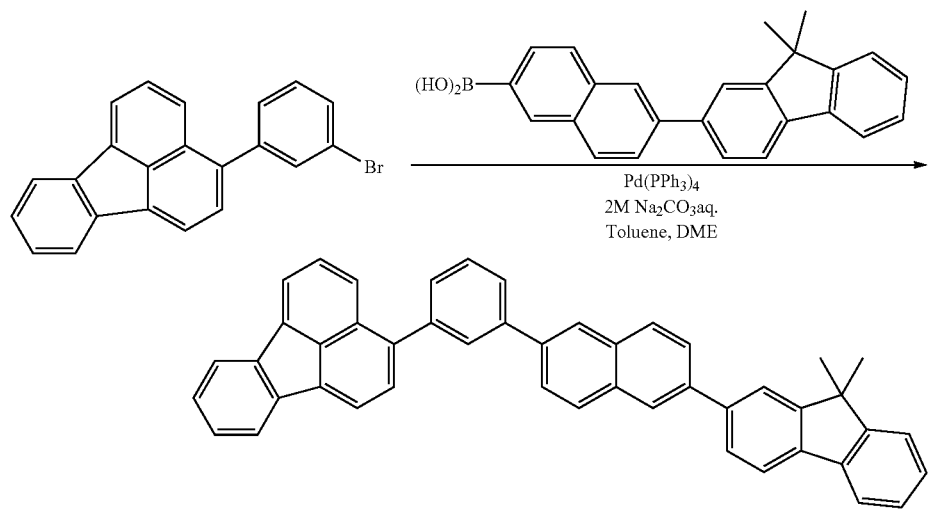

2-254

Compound 2-254 was synthesized in the same manner as in the synthesis of compound 2-2 except for using 6-(9,9-dimethyl-9H-fluorene-2-yl)naphthalene-2-ylboronic acid in place of 3-(phenanthrene-9-yl)phenylboronic acid and using 3-(3-bromophenyl)fluoranthene in place of 2-boromo-9,9-dimethyl-7-(naphthalene-2-yl)-9H-fluorene.

Mass spectrum analysis showed m/e=596 to the molecular weight of 596.25.

Synthetic Example B-10

Synthesis of Compound 4-16

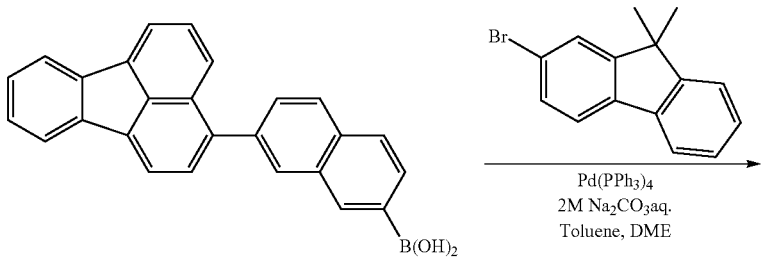

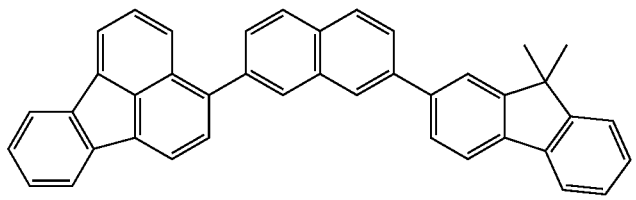

4-16

In argon atmosphere, a mixture of 2.26 g (8.26 mmol) of 2-boromo-9,9-dimethyl-9H-fluorene, 3.07 g (8.26 mmol) of 7-(fluoranthene-3-yl)naphthalene-2-ylboronic acid, 0.38 g (0.33 mmol) of tetrakis(triphenylphosphine)palladium (0), 90 ml of toluene, 30 ml of dimethoxyethane, and 12.5 g of a 2 M sodium carbonate aqueous solution was stirred at 85° C. for 10 h. The reaction mixture was allowed to cool down to room temperature, added with water, and stirred for one hour. After filtration, the filtrate was extracted with toluene. The organic phase was washed with water and then with a saturated saline solution and dried over sodium sulfate, and then the toluene was removed by distillation under reduced pressure. The residue was recrystallized from toluene and then hexane to obtain 2.42 g (yield: 56%) of compound 2-16.

Mass spectrum analysis showed m/e=520 to the molecular weight of 520.66.

Synthetic Example B-11

Synthesis of Compound 4-1

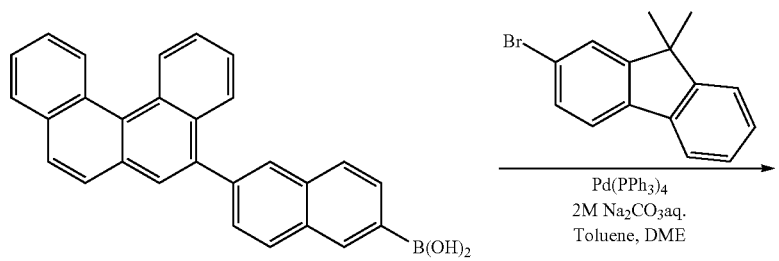

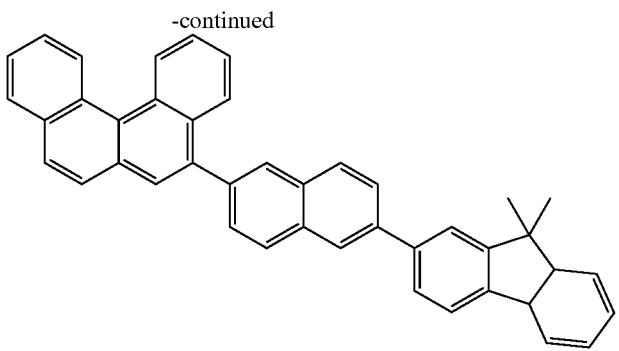

4-1

In the same manner using the compounds in the same molar amounts and the same purification as in the synthesis of compound 4-16 except for using 6-(benzo[c]phenanthrene-5-yl)naphthalene-2-ylboronic acid in place of 7-(fluoranthene-3-yl)naphthalene-2-ylboronic acid, 3.24 g (yield: 71%) of compound 4-1 was obtained.

Mass spectrum analysis showed m/e=546 to the molecular weight of 546.70.

Synthetic Example B-12

Synthesis of Compound 4-15

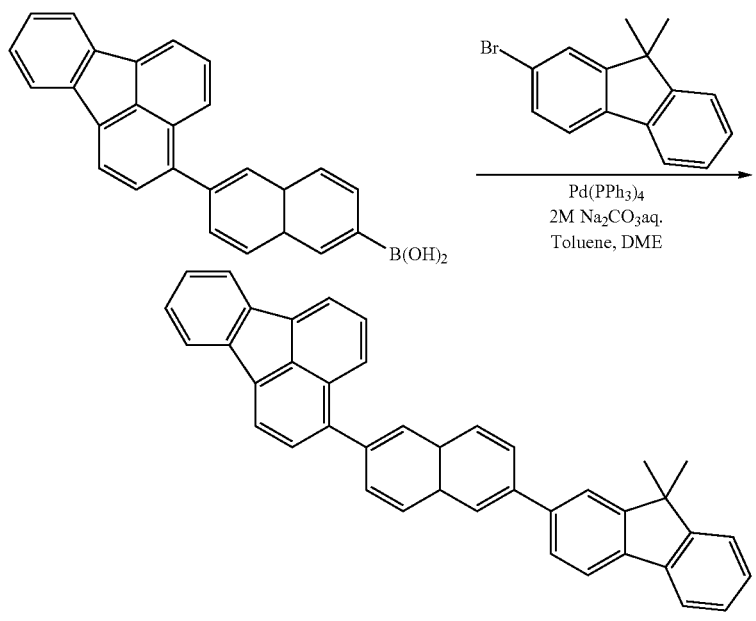

4-15

In the same manner using the compounds in the same molar amounts and the same purification as in the synthesis of compound 4-16 except for using 6-(fluoranthene-3-yl)naphthalene-2-ylboronic acid in place of 7-(fluoranthene-3-yl)naphthalene-2-ylboronic acid, 2.88 g (yield: 67%) of compound 4-15 was obtained.

Mass spectrum analysis showed m/e=520 to the molecular weight of 520.66.

In the synthetic examples described above, the mass spectrum analysis was carried out by FD-MS (field desorption mass analysis). An apparatus and measuring conditions used for measurement of FD-MS (field desorption mass analysis) are shown below.

Apparatus: JSM-700 (manufactured by JEOL Ltd.)

Conditions: accelerating voltage: 8 kV
  scanning range: m/z=50 to 3000
  emitter: carbon
  emitter current: 0 mA→2 mA/min→40 mA (held for 10 min)

Synthetic Example B-13

Synthesis of Compound 4-30

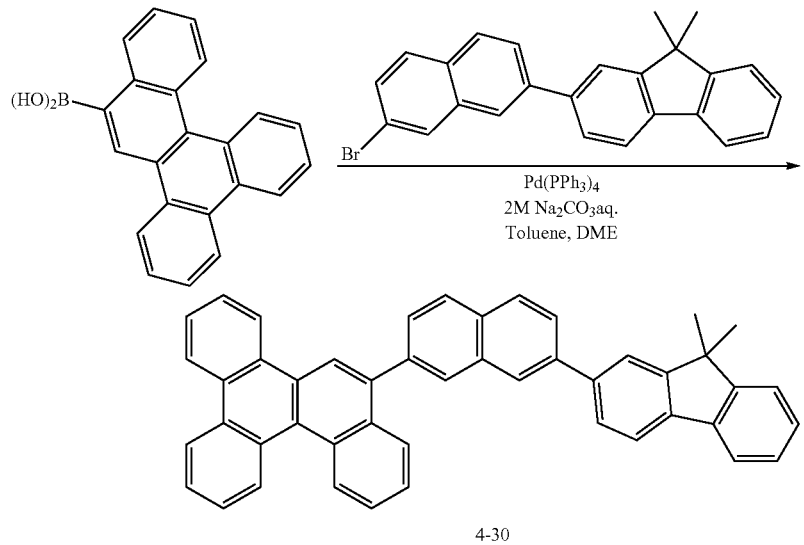

4-30

In argon atmosphere, a mixture of 3.6 g (9.0 mmol) of 2-(7-boromonaphthalene-2-yl)-9,9-dimethyl-9H-fluorene, 2.9 g (9.0 mmol) of 10-benzo[g]chryseneboronic acid, 526 mg (0.45 mmol) of tetrakis(triphenylphosphine)palladium (0), 40 ml of toluene, 40 ml of dimethoxyethane, and 13.5 g of a 2 M sodium carbonate aqueous solution was refluxed under stirring for 8 h. After the reaction, the reaction mixture was added with water and extracted with toluene. The organic phase was washed with water and dried over sodium sulfate, and then the toluene was removed by distillation under reduced pressure. The residue was purified by silica gel chromatography and recrystallized, to obtain 2.2 g (yield: 40%) of compound 4-30.

Synthetic Example B-14

Synthesis of Compound 4-6

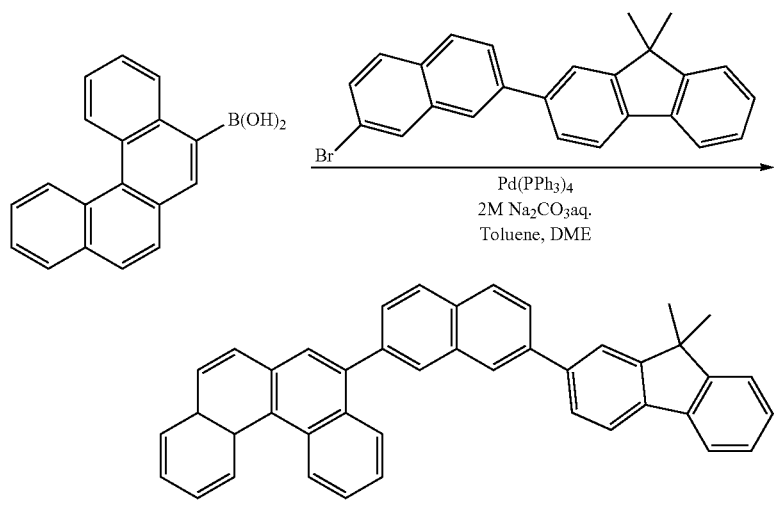

4-6

In argon atmosphere, a mixture of 3.6 g (9.0 mmol) of 2-(7-boromonaphthalene-2-yl)-9,9-dimethyl-9H-fluorene, 2.55 g (9.0 mmol) of 5-benzo[g]phenanthreneboronic acid, 526 mg (0.45 mmol) of tetrakis(triphenylphosphine)palladium (0), 40 ml of toluene, 40 ml of dimethoxyethane and 13.5 g of a 2 M sodium carbonate aqueous solution, and the mixture was stirred under refluxing by heating for 8 h. After finishing the reaction, water was added to the reaction mixture. The liquid was extracted with toluene, and the extract was washed with water. The organic phase was dried on sodium sulfate, and then toluene was removed by distillation under reduced pressure. The residue was purified by silica gel chromatography and recrystallized, and then 2.8 g (yield: 57%) of the compound 4-6 was obtained.

Next, the present invention will be explained in further details with reference to examples, but the present invention is not limited to the following examples.

The structures of compounds used in the examples and the comparative examples other than the compounds obtained in the synthetic examples are shown below.

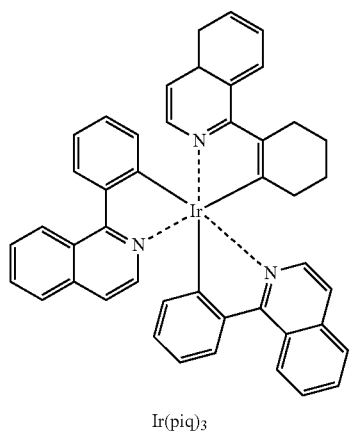

Ir(piq)₃

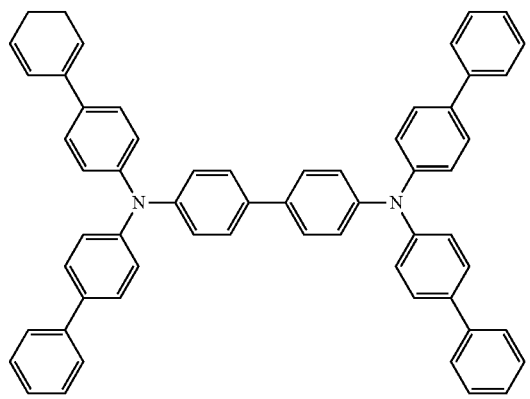

HT1

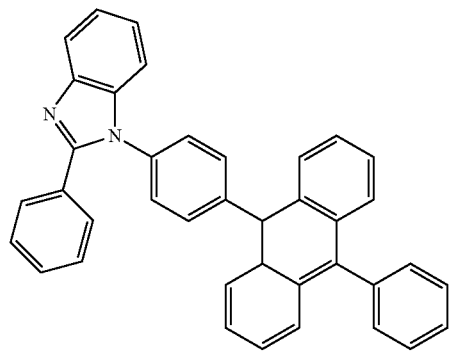

ET1

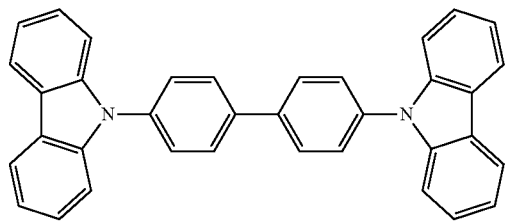

CBP

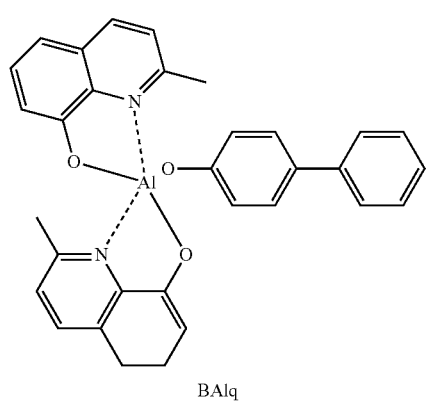

BAlq

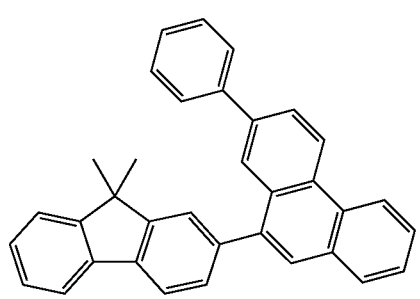

B-A

-continued
B-B
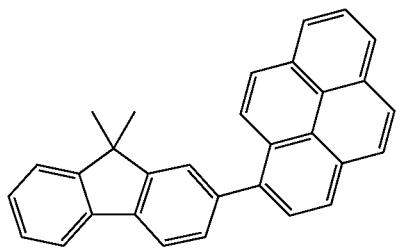
B-C
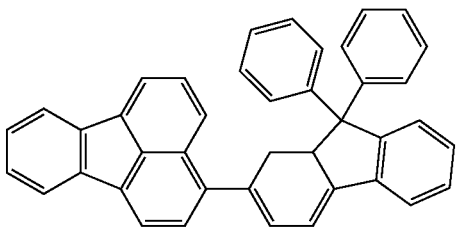
B-D
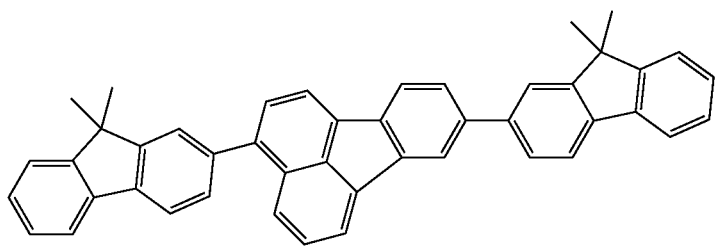
B-E
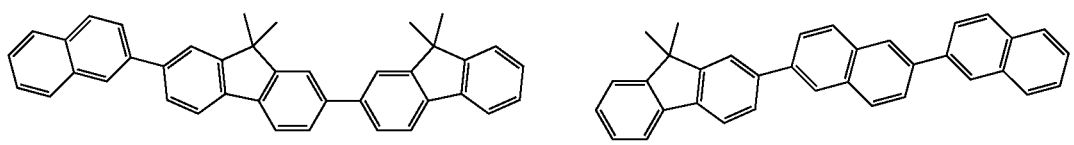
B-F
B-G
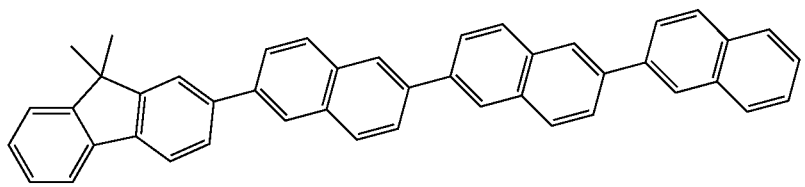
B-H
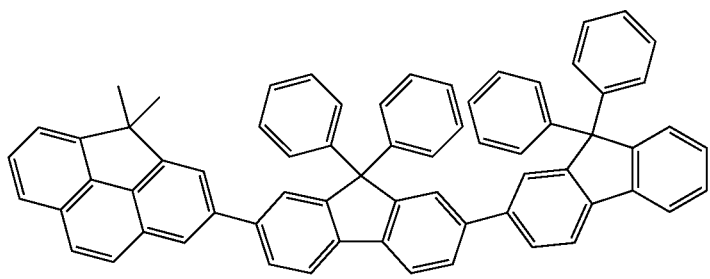
Complex A
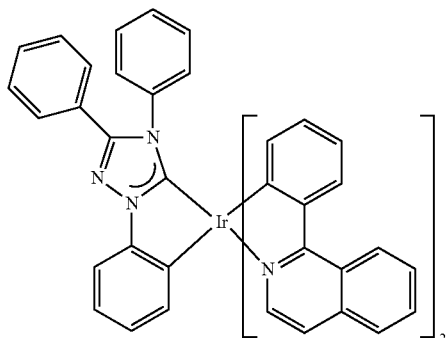
Complex B
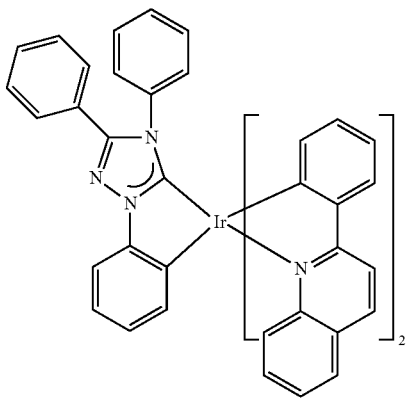

Example B-1

Preparation of Organic EL Device

A glass substrate of 25 mm×75 mm×0.7 mm thickness provided with an ITO transparent electrode (manufactured by Asahi Glass Co., Ltd.) was ultrasonically washed in isopropyl alcohol for 5 min and then to UV-ozone washed for 30 min. The washed glass substrate was mounted in a substrate holder of a vacuum vapor deposition apparatus, and a film of HT1 of 50 nm thick was formed so as to cover the transparent electrode. The film of HT1 works as a hole injecting transporting layer. After forming the hole injecting transporting layer, a film of 40 nm thick was successively formed by co-depositing the novel host compound 2-2 and Ir(piq)$_3$ as a phosphorescent dopant in an amount of 10% by mass under resistance heating. The film thus formed works as a light emitting layer (phosphorescent emitting layer). After forming the light emitting layer, a film of ET1 of 40 nm thick was formed. The film thus formed works as an electron transporting layer. Thereafter, an electron injecting electrode (cathode) of 0.5 nm thick was formed from LiF at a film forming speed of 1 Å/min. A metal cathode of 150 nm thick was formed on the LiF layer by vapor-depositing metal Al, to produce an organic EL device.

Examples B-2 to B-14 and Comparative Examples B-1 to B-10

Each organic EL device was produced in the same manner as in Example B-1 except for using the host compound shown in Table 2 in place of the novel host compound 2-2 used in Example B-1.

Example B-15

An organic EL device was produced in the same manner as in Example B-13 except for changing the dopant (complex) to Complex A.

Example B-16

An organic EL device was produced in the same manner as in Example B-13 except for changing Complex A to Complex B.

Comparative Example B-11

An organic EL device was produced in the same manner as in Example B-15 except for changing the host compound 4-30 to CBP.

Comparative Example B-12

An organic EL device was produced in the same manner as in Example B-16 except for changing the host compound 4-30 to BAlq.

Evaluation of Emission Performance of Organic EL Devices

The organic EL devices produced in Examples B-1 to B-16 and Comparative Examples B-1 to B-12 were allowed to emit light by DC driving to measure the voltage, current efficiency and half lifetime of luminance (initial luminance: 5000 cd/m$^2$) at a current density of 10 mA/cm$^2$. Results of the evaluation are shown in Table 2.

TABLE 2

| | Dopant | Host | Voltage (V) | Current efficiency (cd/A) | Half lifetime of luminance at room temperature (hour) |
|---|---|---|---|---|---|
| Examples | | | | | |
| B-1 | Ir(piq)$_3$ | 2-50 | 4.8 | 8.0 | 4,700 |
| B-2 | Ir(piq)$_3$ | 2-46 | 4.8 | 7.6 | 4,200 |
| B-3 | Ir(piq)$_3$ | 2-60 | 4.3 | 7.4 | 3,400 |
| B-4 | Ir(piq)$_3$ | 2-61 | 4.5 | 8.1 | 4,100 |
| B-5 | Ir(piq)$_3$ | 2-58 | 4.4 | 7.4 | 3,700 |
| B-6 | Ir(piq)$_3$ | 2-314 | 4.7 | 8.2 | 4,500 |
| B-7 | Ir(piq)$_3$ | 2-234 | 4.3 | 7.5 | 3,400 |
| B-8 | Ir(piq)$_3$ | 2-294 | 4.3 | 7.5 | 4,000 |
| B-9 | Ir(piq)$_3$ | 2-254 | 4.3 | 8.3 | 4,700 |
| B-10 | Ir(piq)$_3$ | 4-16 | 4.4 | 8.3 | 4,200 |
| B-11 | Ir(piq)$_3$ | 4-1 | 4.3 | 8.6 | 4,800 |
| B-12 | Ir(piq)$_3$ | 4-15 | 4.3 | 7.7 | 3,900 |
| B-13 | Ir(piq)$_3$ | 4-30 | 4.4 | 7.9 | 3,900 |
| B-14 | Ir(piq)$_3$ | 4-6 | 4.4 | 8.1 | 4,300 |
| Comparative Examples | | | | | |
| B-1 | Ir(piq)$_3$ | CBP | 5.4 | 6.3 | 500 |
| B-2 | Ir(piq)$_3$ | BAlq | 5.3 | 7.0 | 1,000 |
| B-3 | Ir(piq)$_3$ | compound B-A | 5.0 | 7.0 | 1,200 |
| B-4 | Ir(piq)$_3$ | compound B-B | 5.4 | 1.3 | Impossible to measure |
| B-5 | Ir(piq)$_3$ | compound B-C | 5.1 | 7.2 | 1,900 |
| B-6 | Ir(piq)$_3$ | compound B-D | 4.8 | 6.8 | 1,400 |
| B-7 | Ir(piq)$_3$ | compound B-E | 4.8 | 4.9 | 400 |
| B-8 | Ir(piq)$_3$ | compound B-F | 4.6 | 7.0 | 170 |
| B-9 | Ir(piq)$_3$ | compound B-G | 4.6 | 7.2 | 280 |
| B-10 | Ir(piq)$_3$ | compound B-H | 4.9 | 4.1 | 250 |
| Examples | | | | | |
| B-15 | complex A | 4-30 | 4.3 | 7.4 | 2,700 |
| B-16 | complex B | 4-30 | 4.4 | 7.6 | 2,900 |
| Comparative Examples | | | | | |
| B-11 | complex A | CBP | 5.8 | 4.2 | 800 |
| B-12 | complex B | BAlq | 5.1 | 5.0 | 1,300 |

The results of Table 2 show that the organic EL devices of Examples B-1 to B-14 employing the host materials of the invention have high current efficiency and extremely long lifetime. On the other hand, the organic EL devices of Comparative Examples B-1 and B-3 require high voltage and have short lifetime. The organic EL device of Comparative Example B-4 has poor current efficiency and extremely short lifetime. The organic EL device of Comparative Example B-5 requires high voltage and have short lifetime. The organic EL device of Comparative Example B-6 is driven at lower voltage, but has short lifetime as compared with those of the examples. The organic EL device of Comparative Example B-7 has poor efficiency and extremely short lifetime. The organic EL devices of Comparative Examples B-8 to B-10 have extremely short lifetime. As compared with the organic EL devices of Comparative Examples B-11 and B-12, the organic EL devices of Examples B-15 and B-16 are driven at low voltage and have high efficiency and long lifetime.

The characteristic features of combinations in the present invention are that:

the triplet energy gap of the host materials and the triplet energy gap of the dopants are well suited to improve the current efficiency;

a specific condensed polycyclic hydrocarbon residue is bonded to the fluorene ring residue, thereby reducing the driving voltage; and since the host material is not substituted with a nitrogen-containing ring and a nitrogen atom, the light emitting material is highly resistant to holes and electrons, allowing the lifetime to be extended more than those of the combinations ever known.

Invention C

Synthetic Example C-1

Synthesis of Compound 2-2

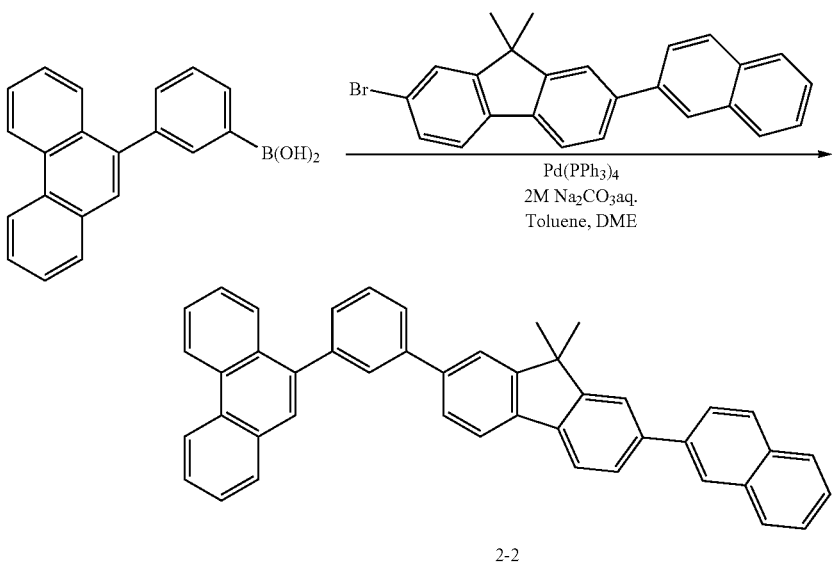

In argon atmosphere, a mixture of 3.30 g (8.26 mmol) of 2-boromo-9,9-dimethyl-7-(naphthalene-2-yl)-9H-fluorene, 2.46 g (8.26 mmol) of 3-(phenanthrene-9-yl)phenylboronic acid, 0.38 g (0.33 mmol) of tetrakis(triphenylphosphine)palladium (0), 90 ml of toluene, 30 ml of dimethoxyethane, and 12.5 g of a 2 M sodium carbonate aqueous solution was stirred at 85° C. for 8 h. The reaction mixture was allowed cool down to room temperature, added with water, stirred for one hour, and left standing overnight. Then, the reaction mixture was added with water and stirred at room temperature for one hour. After filtration, the filtrate was extracted with toluene. The organic phase was washed with water and then with a saturated saline solution and dried over sodium sulfate, and then the toluene was removed by distillation under reduced pressure. The obtained oily substance was purified by silica gel chromatography to obtain 3.40 g (yield: 72%) of compound 2-2.

Mass spectrum analysis showed m/e=572 to the molecular weight of 572.25.

Synthetic Example C-2

Synthesis of Compound 2-1

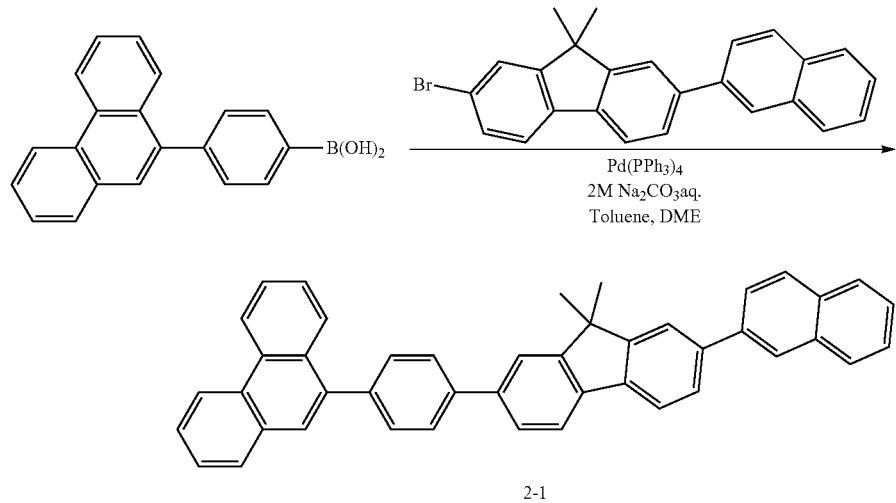

2-1

Compound 2-1 was synthesized in the same manner as in the synthesis of compound 2-2 except for using 4-(phenan-threne-9-yl)phenylboronic acid in place of 3-(phenanthrene-9-yl)phenylboronic acid.

Mass spectrum analysis showed m/e=572 to the molecular weight of 572.25.

Synthetic Example C-3

Synthesis of Compound 2-4

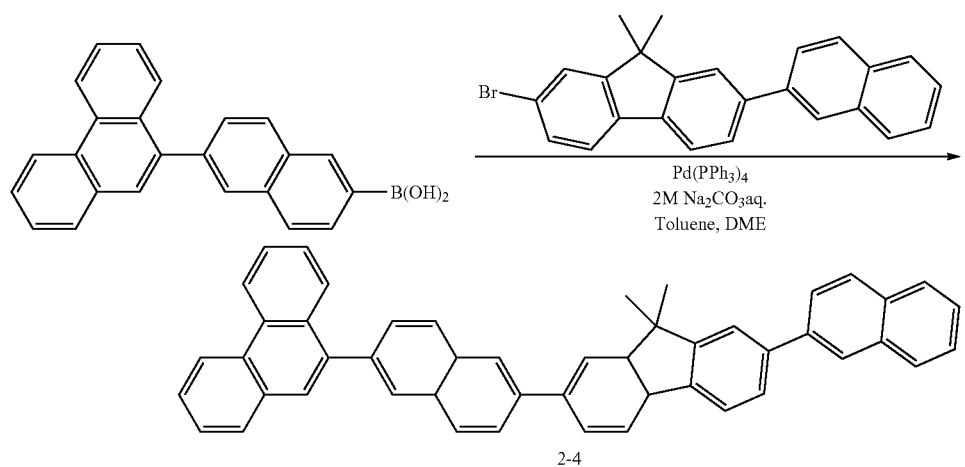

2-4

Compound 2-4 was synthesized in the same manner as in the synthesis of compound 2-2 except for using 6-(phenan-threne-9-yl)naphthalene-2-ylboronic acid in place of 3-(phenanthrene-9-yl)phenylboronic acid.

Mass spectrum analysis showed m/e=622 to the molecular weight of 622.27.

Synthetic Example C-4

Synthesis of Compound 2-5

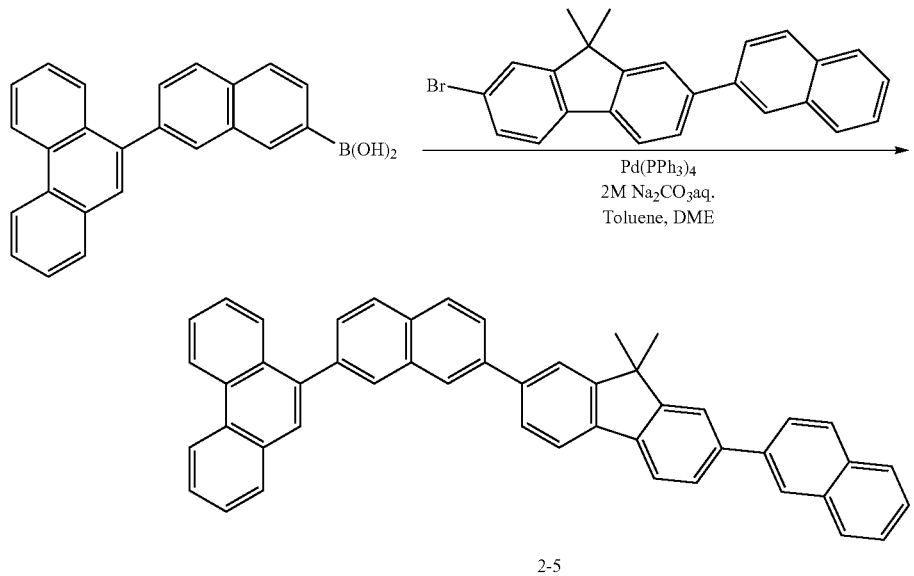

2-5

Compound 2-5 was synthesized in the same manner as in the synthesis of compound 2-2 except for using 7-(phenanthrene-9-yl)naphthalene-2-ylboronic acid in place of 3-(phenanthrene-9-yl)phenylboronic acid.

Mass spectrum analysis showed m/e=622 to the molecular weight of 622.27.

Synthetic Example C-5

Synthesis of Compound 2-7

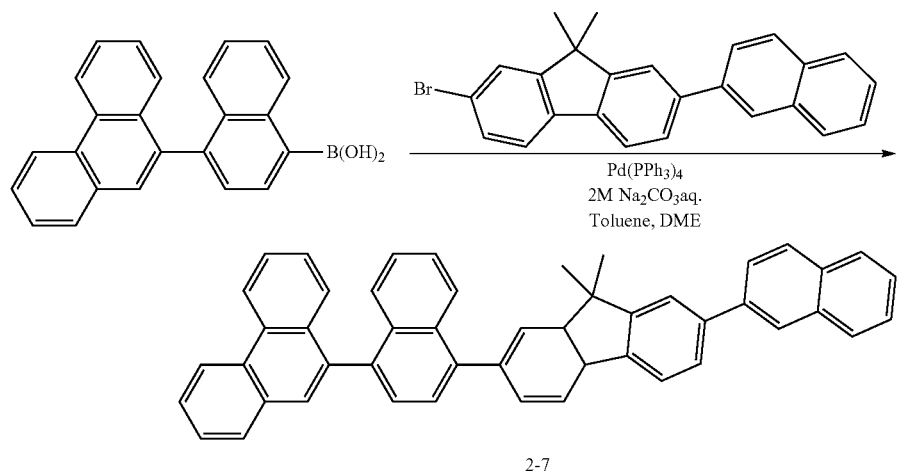

2-7

Compound 2-7 was synthesized in the same manner as in the synthesis of compound 2-2 except for using 4-(phenanthrene-9-yl)naphthalene-1-ylboronic acid in place of 3-(phenanthrene-9-yl)phenylboronic acid.

Mass spectrum analysis showed m/e=622 to the molecular weight of 622.27.

Synthetic Example C-6

Synthesis of Compound 2-184

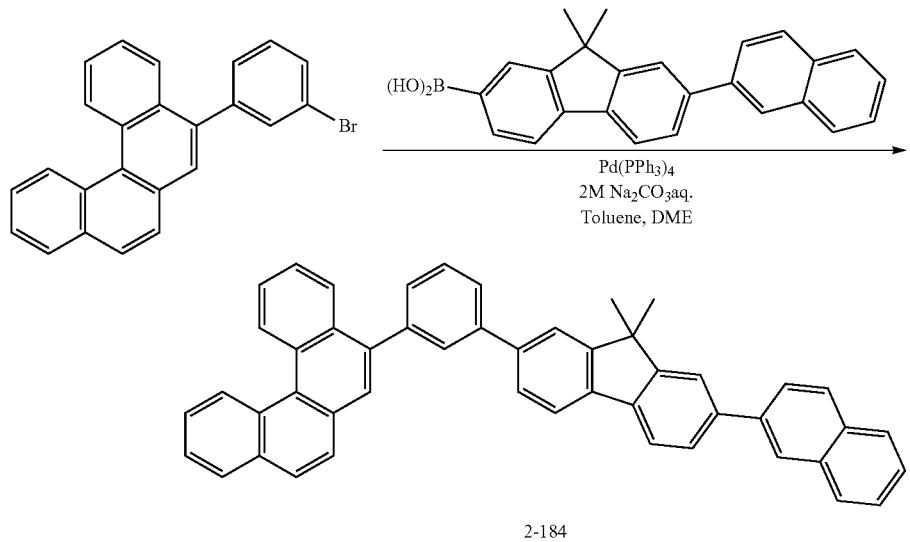

2-184

Compound 2-184 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 5-(3-bromophenyl)benzo[c]phenanthrene in place of 2-boromo-9,9-dimethyl-7-(naphthalene-2-yl)-9H-fluorene.

Mass spectrum analysis showed m/e=622 to the molecular weight of 622.27.

Synthetic Example C-7

Synthesis of Compound 2-75

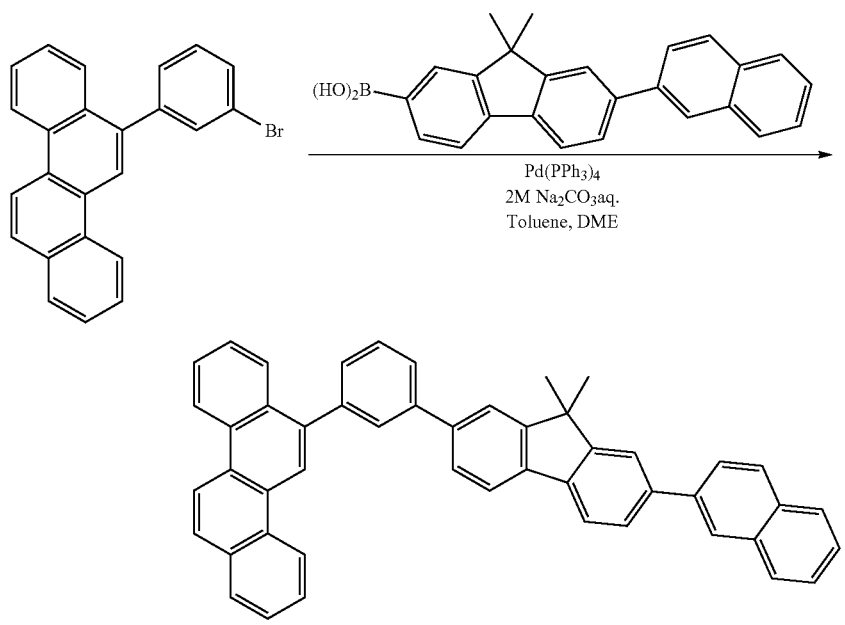

2-75

Compound 2-75 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 6-(3-bromophenyl)chrysene in place of 2-boromo-9,9-dimethyl-7-(naphthalene-2-yl)-9H-fluorene.

Mass spectrum analysis showed m/e=622 to the molecular weight of 622.27.

Synthetic Example C-8

Synthesis of Compound 2-159

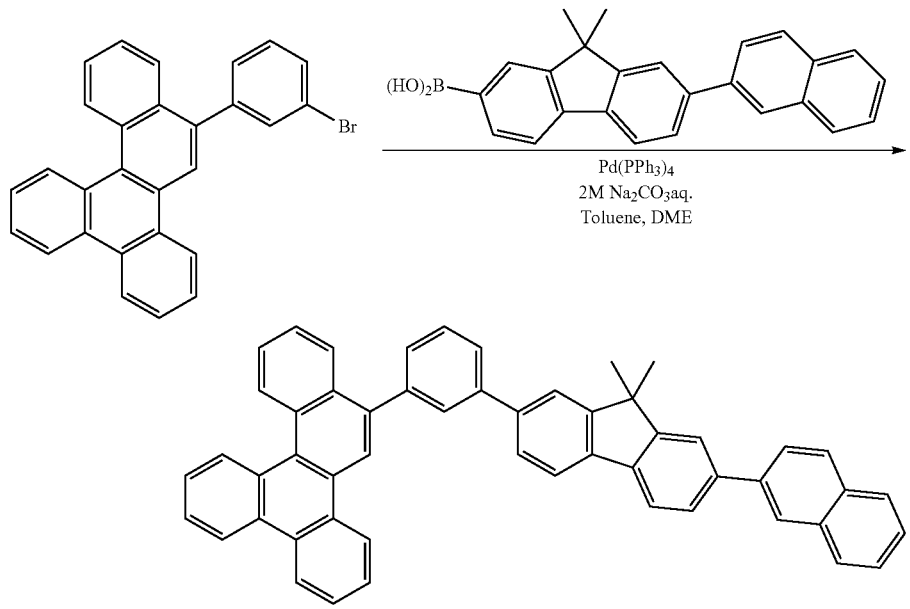

2-159

Compound 2-159 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 10-(3-bromophenyl)benzo[g]chrysene in place of 2-boromo-9,9-dimethyl-7-(naphthalene-2-yl)-9H-fluorene.

Mass spectrum analysis showed m/e=672 to the molecular weight of 672.28.

Synthetic Example C-9

Synthesis of Compound 2-99

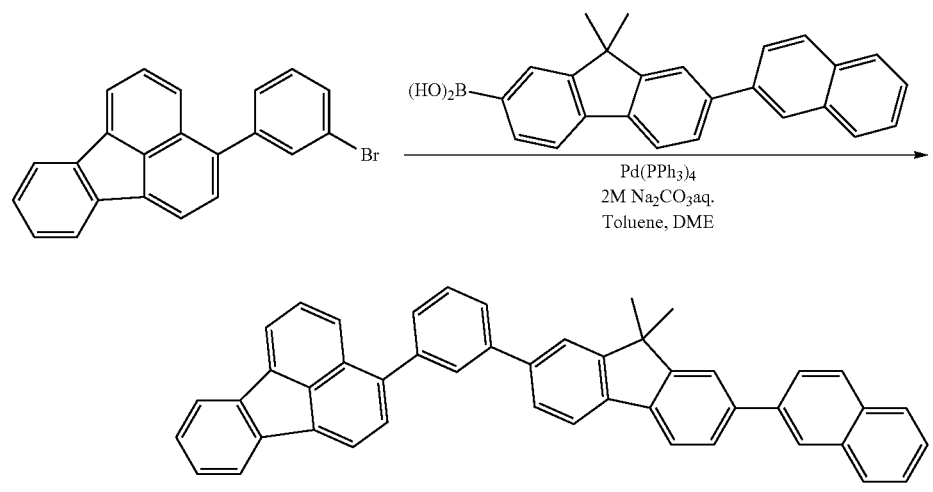

2-99

Compound 2-99 was synthesized in the same manner as in the synthesis of compound 2-2 except for using 9,9-dimethyl-7-(naphthalene-2-yl)-9H-fluorene-2-ylboronic acid in place of 3-(phenanthrene-9-yl)phenylboronic acid and using 3-(3-bromophenyl)-fluoranthene in place of 2-boromo-9,9-dimethyl-7-(naphthalene-2-yl)-9H-fluorene.

Mass spectrum analysis showed m/e=596 to the molecular weight of 596.25.

Synthetic Example C-10

Synthesis of Compound 2-504

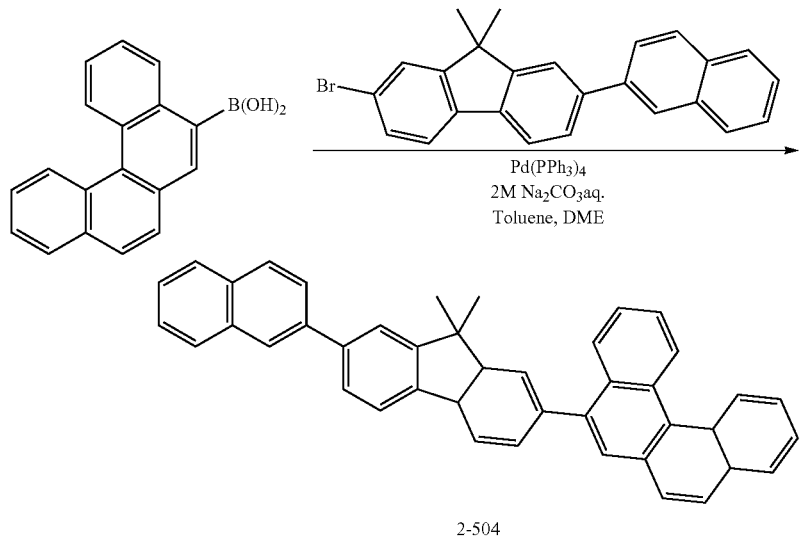

2-504

In argon atmosphere, a mixture of 3.30 g (8.26 mmol) of 2-boromo-9,9-dimethyl-7-(naphthalene-2-yl)-9H-fluorene, 2.25 g (8.26 mmol) of 5-benzo[g]phenanthreneboronic acid, 0.38 g (0.33 mmol) of tetrakis(triphenylphosphine)palladium (0), 90 ml of toluene, 30 ml of dimethoxyethane, and 12.5 g of a 2 M sodium carbonate aqueous solution was stirred at 85° C. for 9 h. The reaction mixture was allowed to cool down to room temperature, added with water, stirred for one hour, and left standing overnight. The reaction mixture was further added with water and stirred at room temperature for one hour. After filtration, the filtrate was extracted with toluene. The organic phase was washed with water and then with a saturated saline solution and dried over sodium sulfate, and then the toluene was removed by distillation under reduced pressure. The obtained oily substance was purified by silica gel chromatography to obtain 3.11 g (yield: 69%) of compound 2-504.

Mass spectrum analysis showed m/e=546 to the molecular weight of 546.7.

Synthetic Example C-11

Synthesis of Compound 2-517

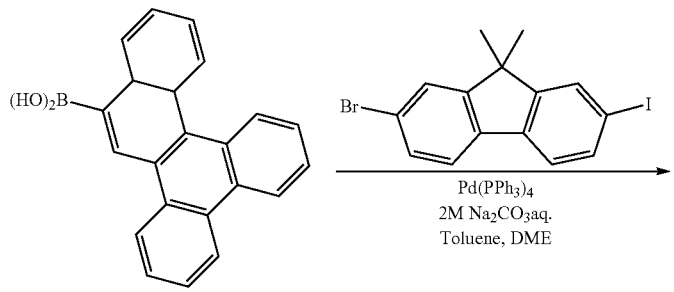

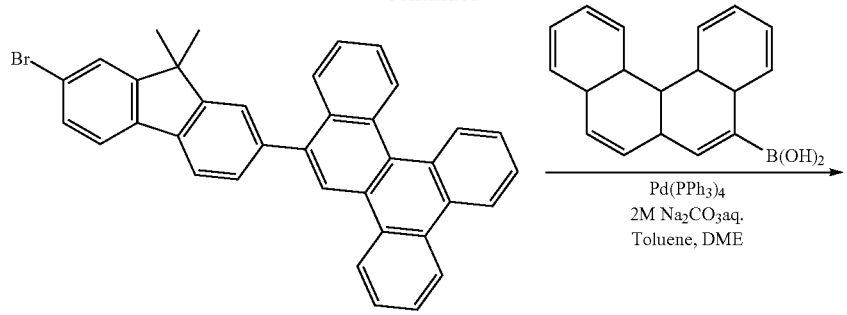

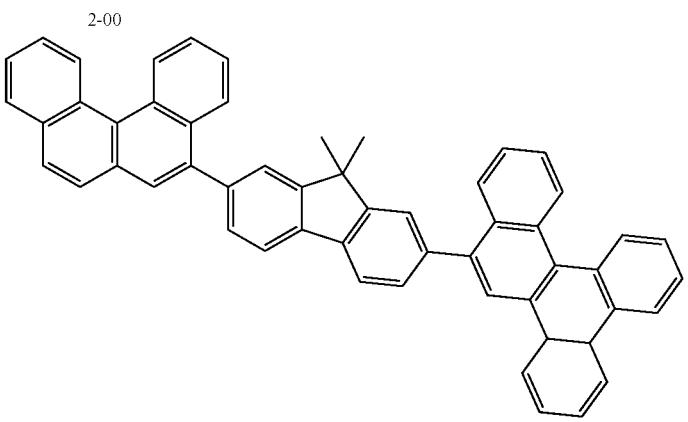

2-517

In argon atmosphere, a mixture of 5.00 g (15.52 mmol) of 10-benzo[g]chryseneboronic acid, 5.76 g (15.52 mmol) of 2-boromo-7-iodo-9,9-dimethylfluorene, 0.90 g (0.768 mmol) of tetrakis(triphenylphosphine)palladium (0), 40 ml of toluene, 40 ml of dimethoxyethane, and 23.5 g of a 2 M sodium carbonate aqueous solution was refluxed under stirring for 10 h and left standing overnight. The reaction mixture was added with water and stirred at room temperature for one hour. After filtration, the filtrate was extracted with toluene. The organic phase was washed with water and then with a saturated saline solution and dried over sodium sulfate, and then the toluene was removed by distillation under reduced pressure. The residue was purified by silica gel chromatography to obtain 6.23 g (yield: 73%) of intermediate 2-00.

Then, in argon atmosphere, a mixture of 3.0 g (5.46 mmol) of the intermediate 2-00, 1.49 g (5.46 mmol) of 5-benzo[c]phenanthreneboronic acid, 0.25 g (0.22 mmol) of tetrakis(triphenylphosphine)palladium (0), 50 ml of toluene, 20 ml of dimethoxyethane, and 8.3 g of a 2 M sodium carbonate aqueous solution was stirred at 85° C. for 9 h. The reaction mixture was allowed to cool down to room temperature, added with water, stirred for one hour, and left standing overnight. The reaction mixture was further added with water and stirred at room temperature for one hour. After filtration, the filtrate was extracted with toluene. The organic phase was washed with water and then a saturated saline solution and dried over sodium sulfate, and then the toluene was removed by distillation under reduced pressure. The obtained oily substance was purified by silica gel chromatography to obtain 2.02 g (yield: 53%) of compound 2-517.

Mass spectrum analysis showed m/e=696 to the molecular weight of 696.87.

Synthetic Example C-12

Synthesis of Compound 2-520

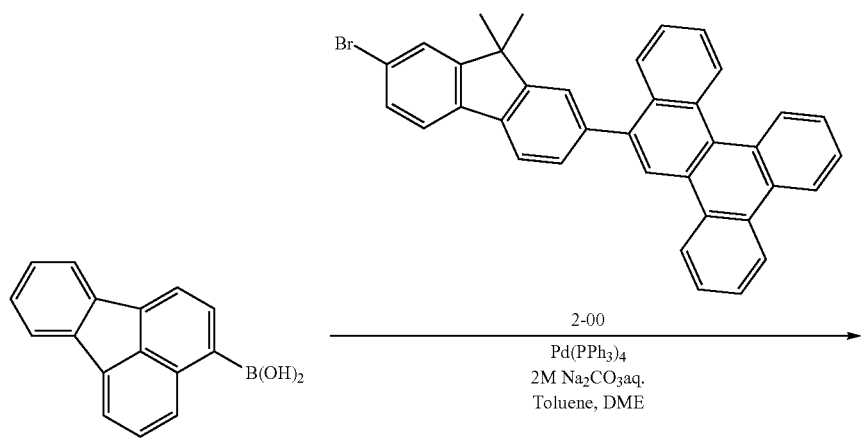

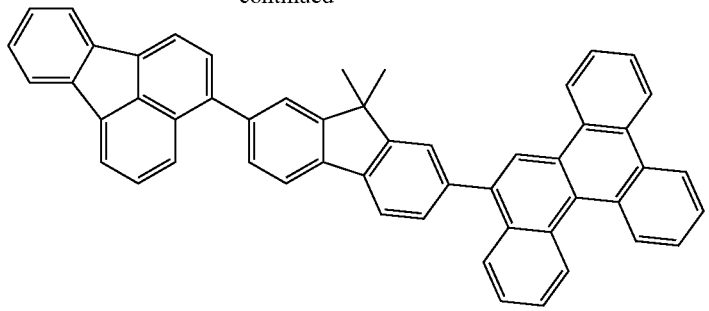

2-520

In argon atmosphere, a mixture of 3.0 g (5.46 mmol) of the intermediate 2-00, 1.34 g (5.46 mmol) of 3-fluoranthenylboronic acid, 0.25 g (0.22 mmol) of tetrakis(triphenylphosphine)palladium (0), 50 ml of toluene, 20 ml of dimethoxyethane, and 8.3 g of a 2 M sodium carbonate aqueous solution was stirred at 85° C. for 9 h. The reaction mixture was allowed to cool down to room temperature, added with water, stirred for one hour, and left standing overnight. The reaction mixture was further added with water and stirred at room temperature for one hour. After filtration, the filtrate was extracted with toluene. The organic phase was washed with water and then with a saturated saline solution and dried on sodium sulfate, and then the toluene was removed by distillation under reduced pressure. The obtained oily substance was purified by silica gel chromatography to obtain 1.83 g (yield: 50%) of compound 2-520.

Mass spectrum analysis showed m/e=670 to the molecular weight of 670.84.

Synthetic Example C-13

Synthesis of Compound 2-528

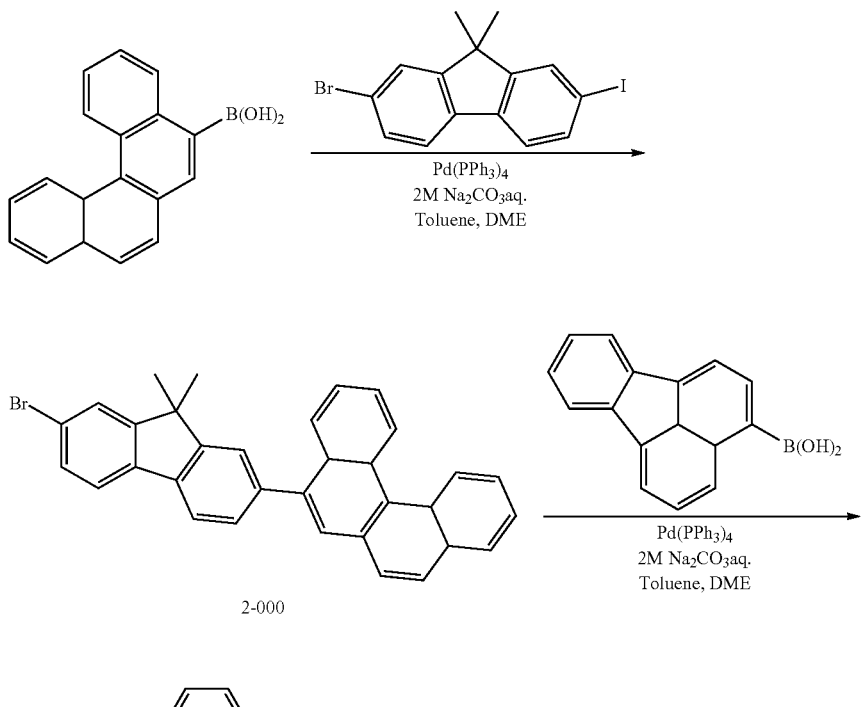

2-000

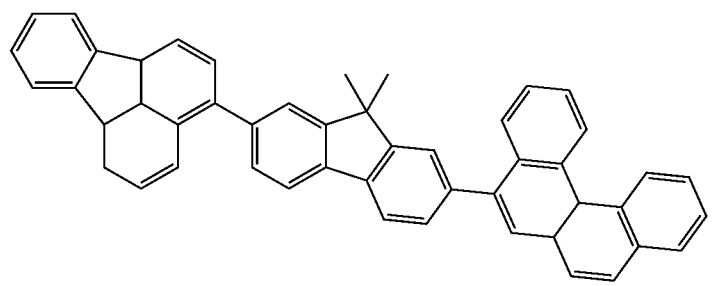

2-528

In argon atmosphere, a mixture of 2.11 g (7.76 mmol) of 5-benzo[c]phenanthreneboronic acid, 2.88 g (7.76 mmol) of 2-boromo-7-iodo-9,9-dimethylfluorene, 0.45 g (0.39 mmol) of tetrakis(triphenylphosphine)palladium (0), 20 ml of toluene, 20 ml of dimethoxyethane, and 12.0 g of a 2 M sodium carbonate aqueous solution was refluxed under stirring for 10 h and left standing overnight. The reaction mixture was added with water and stirred at room temperature for one hour. After filtration, the filtrate was extracted with toluene. The organic phase was washed with water and then with a saturated saline solution and dried over sodium sulfate, and then the toluene was removed by distillation under reduced pressure. The residue was purified by silica gel chromatography to obtain 2.65 g (yield: 68%) of intermediate 2-000.

Then, in argon atmosphere, a mixture of 2.50 g (5.00 mmol) of the intermediate 2-000, 1.36 g (5.00 mmol) of 5-benzo[g]phenanthreneboronic acid, 0.23 g (0.20 mmol) of tetrakis(triphenylphosphine)palladium (0), 50 ml of toluene, 20 ml of dimethoxyethane, and 8.0 g of a 2 M sodium carbonate aqueous solution was stirred at 85° C. for 10 h. The reaction mixture was allowed to cool down to room temperature, added with water, stirred for one hour, and left standing overnight. The reaction mixture was further added with water and stirred at room temperature for one hour. After filtration, the filtrate was extracted with toluene. The organic phase was washed with water and then with a saturated saline solution and dried over sodium sulfate, and then the toluene was removed by distillation under reduced pressure. The obtained oily substance was purified by silica gel chromatography to obtain 2.11 g (yield: 68%) of compound 2-528.

Mass spectrum analysis showed m/e=620 to the molecular weight of 620.78.

In the synthetic examples described above, the mass spectrum analysis was carried out by FD-MS (field desorption mass analysis). An apparatus and measuring conditions used for measurement of FD-MS (field desorption mass analysis) are shown below.

Apparatus: JSM-700 (manufactured by JEOL Ltd.)
Conditions: accelerating voltage: 8 kV
  scanning range: m/z=50 to 3000
  emitter: carbon
  emitter current: 0 mA→2 mA/min→40 mA (held for 10 min)

Next, the present invention will be explained in further details with reference to examples, but the present invention is not limited to the following examples.

The structures of compounds used in the examples and the comparative examples other than the compounds obtained in the synthetic examples are shown below.

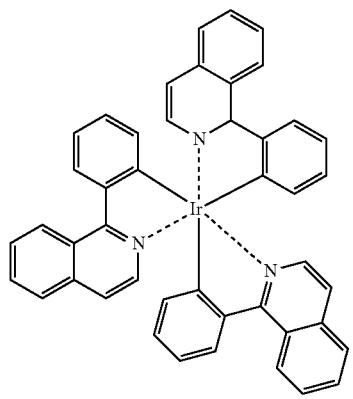

Ir(piq)$_3$

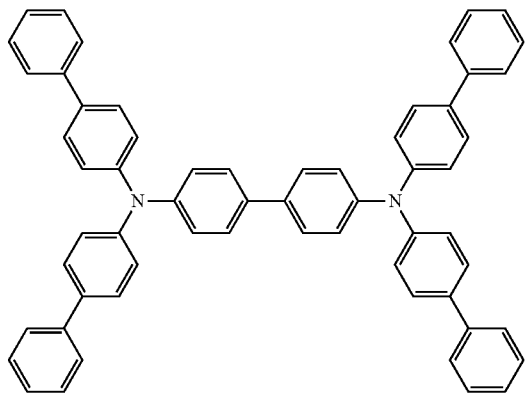

HT1

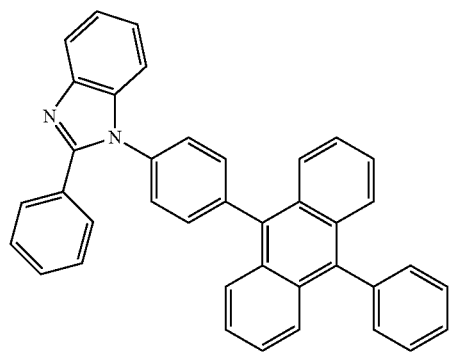

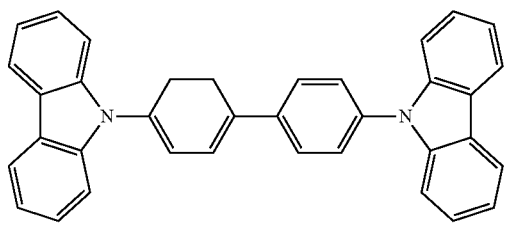

ET1

CBP

-continued
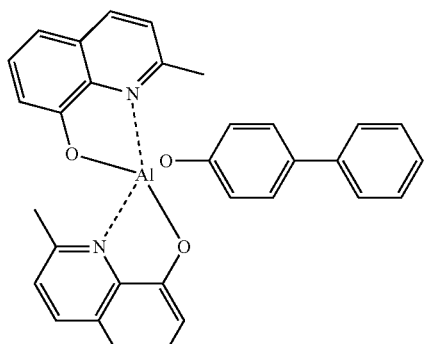
BAlq
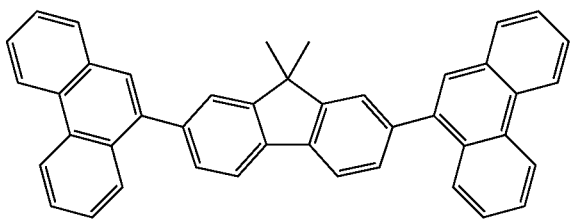
C-A
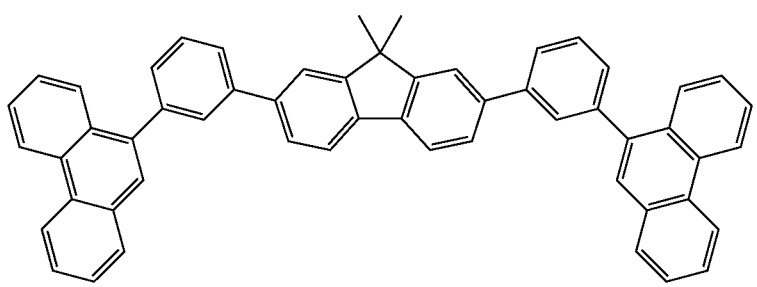
C-B
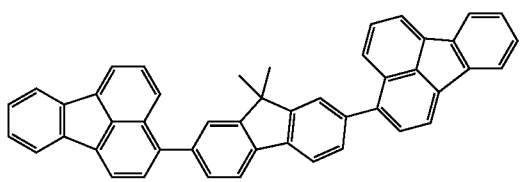
C-C
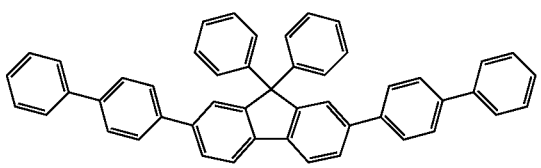
C-D
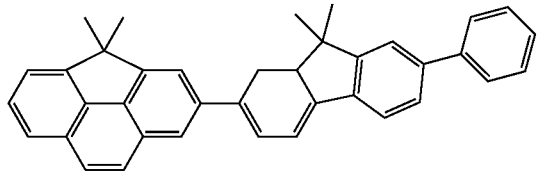
C-E
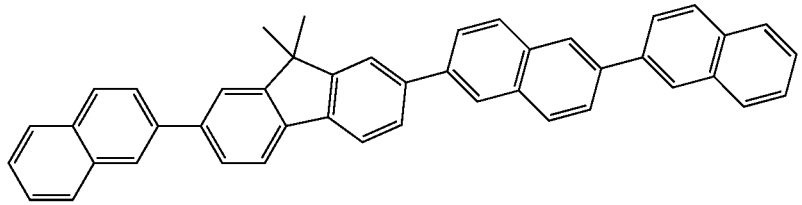
C-F
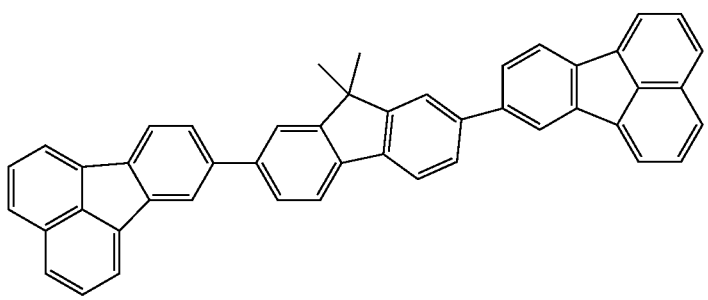
C-G

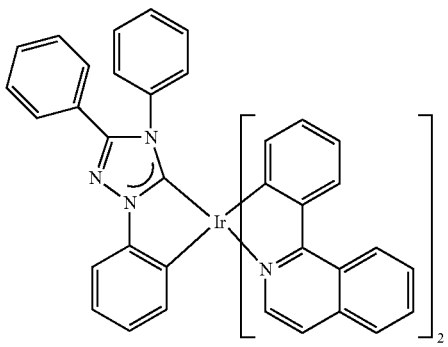

Complex A

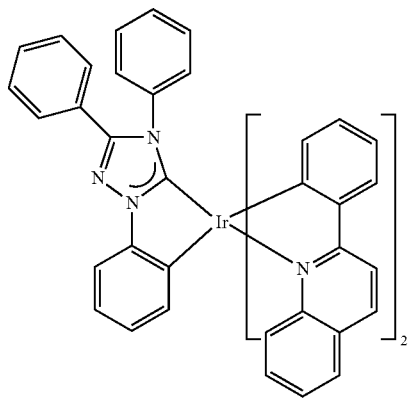

Complex B

Example C-1

Preparation of Organic EL Device

A glass substrate of 25 mm×75 mm×0.7 mm thickness provided with an ITO transparent electrode (manufactured by Asahi Glass Co., Ltd.) was ultrasonically washed in isopropyl alcohol for 5 min and then to UV-ozone washed for 30 min. The washed glass substrate was mounted in a substrate holder of a vacuum vapor deposition apparatus, and a film of HT1 of 50 nm thick was formed so as to cover the transparent electrode. The film of HT1 works as a hole injecting transporting layer. After forming the hole injecting transporting layer, a film of 40 nm thick was successively formed by co-depositing the novel host compound 2-2 and Ir(piq)$_3$ as a phosphorescent dopant in an amount of 10% by mass under resistance heating. The film thus formed works as a light emitting layer (phosphorescent emitting layer). After forming the light emitting layer, a film of ET1 of 40 nm thick was formed. The film thus formed works as an electron transporting layer. Thereafter, an electron injecting electrode (cathode) of 0.5 nm thick was formed from LiF at a film forming speed of 1 Å/min. A metal cathode of 150 nm thick was formed on the LiF layer by vapor-depositing metal Al, to produce an organic EL device.

Examples C-2 to C-13 and Comparative Examples C-1 to C-9

Each organic EL device was produced in the same manner as in Example C-1 except for using the host compound shown in Table 3 in place of the novel host compound 2-2 used in Example 1.

Example C-14

An organic EL device was produced in the same manner as in Example C-8 except for changing the dopant (complex) to Complex A.

Example C-15

An organic EL device was produced in the same manner as in Example C-14 except for changing Complex A to Complex B.

Comparative Example C-10

An organic EL device was produced in the same manner as in Example C-14 except for changing the host compound 2-159 to CBP.

Comparative Example C-11

An organic EL device was produced in the same manner as in Example C-15 except for changing the host compound 2-159 to BAlq.

Evaluation of Emission Performance of Organic EL Devices

The organic EL devices produced in Examples C-1 to C-15 and Comparative Examples C-1 to C-11 were allowed to emit light by DC driving to measure the voltage, current efficiency and half lifetime of luminance (initial luminance: 5000 cd/m$^2$) at a current density of 10 mA/cm$^2$. Results of the evaluation are shown in Table 2.

TABLE 3

| | Dopant | Host | Voltage (V) | Current efficiency (cd/A) | Half lifetime of luminance at room temperature (hour) |
|---|---|---|---|---|---|
| Examples | | | | | |
| C-1 | Ir(piq)$_3$ | 2-2 | 4.7 | 8.2 | 4,800 |
| C-2 | Ir(piq)$_3$ | 2-1 | 4.7 | 8.2 | 4,500 |
| C-3 | Ir(piq)$_3$ | 2-4 | 4.6 | 8.1 | 4,000 |
| C-4 | Ir(piq)$_3$ | 2-5 | 4.5 | 7.8 | 3,800 |
| C-5 | Ir(piq)$_3$ | 2-7 | 4.4 | 8.0 | 3,400 |
| C-6 | Ir(piq)$_3$ | 2-184 | 4.6 | 8.0 | 4,000 |
| C-7 | Ir(piq)$_3$ | 2-75 | 4.4 | 7.8 | 3,800 |
| C-8 | Ir(piq)$_3$ | 2-159 | 4.3 | 8.0 | 3,700 |
| C-9 | Ir(piq)$_3$ | 2-99 | 4.8 | 7.6 | 4,200 |

TABLE 3-continued

| | Dopant | Host | Voltage (V) | Current efficiency (cd/A) | Half lifetime of luminance at room temperature (hour) |
|---|---|---|---|---|---|
| C-10 | Ir(piq)$_3$ | 2-504 | 4.5 | 7.9 | 3,300 |
| C-11 | Ir(piq)$_3$ | 2-517 | 4.4 | 8.5 | 3,800 |
| C-12 | Ir(piq)$_3$ | 2-520 | 4.3 | 8.3 | 4,000 |
| C-13 | Ir(piq)$_3$ | 2-528 | 4.3 | 8.3 | 4,100 |
| Comparative Examples | | | | | |
| C-1 | Ir(piq)$_3$ | CBP | 5.4 | 6.3 | 500 |
| C-2 | Ir(piq)$_3$ | BAlq | 5.3 | 7.0 | 1,000 |
| C-3 | Ir(piq)$_3$ | compound C-A | 4.8 | 7.0 | 450 |
| C-4 | Ir(piq)$_3$ | compound C-B | 5.2 | 7.1 | 1,200 |
| C-5 | Ir(piq)$_3$ | compound C-C | 4.8 | 7.2 | 200 |
| C-6 | Ir(piq)$_3$ | compound C-D | 5.2 | 7.1 | 380 |
| C-7 | Ir(piq)$_3$ | compound C-E | 5.1 | 5.9 | 800 |
| C-8 | Ir(piq)$_3$ | compound C-F | 4.8 | 7.4 | 170 |
| C-9 | Ir(piq)$_3$ | compound C-G | 5.1 | 6.5 | 310 |
| Examples | | | | | |
| C-14 | complex A | 2-159 | 4.4 | 7.7 | 2,500 |
| C-15 | complex B | 2-159 | 4.4 | 7.5 | 2,900 |
| Comparative Examples | | | | | |
| C-10 | complex A | CBP | 5.8 | 4.2 | 800 |
| C-11 | complex B | BAlq | 5.1 | 5.0 | 1,300 |

The results of Table 3 show that the organic EL devices of Examples C-1 to C-13 employing the host materials of the invention have high current efficiency and extremely long lifetime. On the other hand, the organic EL devices of Comparative Examples C-1 and C-2 require high voltage and have short lifetime. The organic EL devices of Comparative Examples C-3, C-5 and C-8 are driven at the same voltage as in the examples, but have extremely short lifetime. The organic EL devices of Comparative Examples C-4 and C-7 require high voltage and have short lifetime. The organic EL devices of Comparative Examples C-6 and C-9 require high voltage and have extremely short lifetime. As compared with the organic EL devices of Comparative Examples C-10 and C-11, the organic EL devices of Examples C-14 and C-15 are driven at low voltage and have high efficiency and long lifetime.

The characteristic features of combinations in the present invention are that:

the triplet energy gap of the host materials and the triplet energy gap of the dopants are well suited to improve the current efficiency;

a specific condensed polycyclic hydrocarbon residue is bonded to the divalent fluorene ring residue, thereby reducing the driving voltage; and since the host material is not substituted with a nitrogen-containing ring and a nitrogen atom, the light emitting material is highly resistant to holes and electrons, allowing the lifetime to be extended more than those of the combinations ever known.

INDUSTRIAL APPLICABILITY

The present invention provides a phosphorescent organic EL device having high efficiency and long lifetime and a material for realizing a phosphorescent organic EL device having high efficiency and long lifetime.

What is claimed is:
1. A material represented by any one of the following formulae:

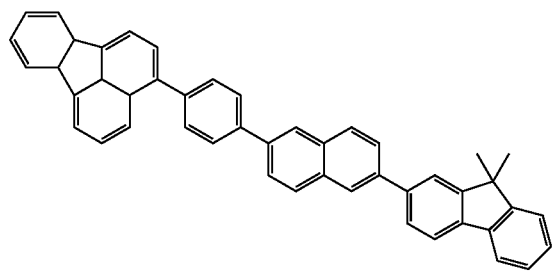

2-251

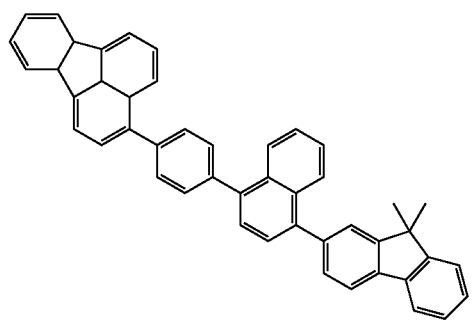

2-252

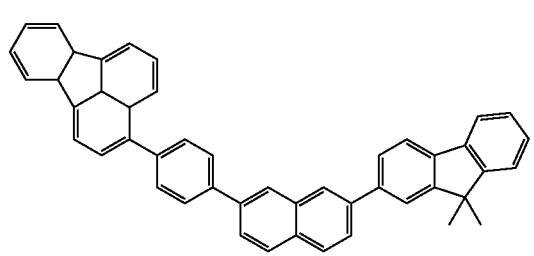

2-253

-continued

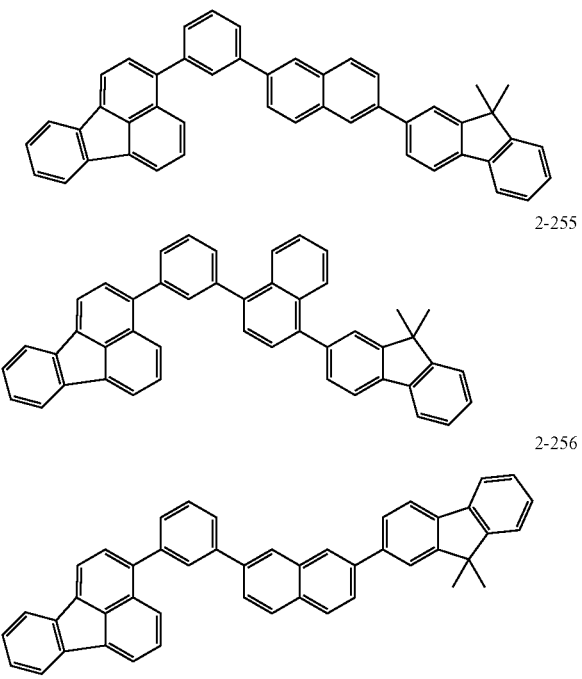

wherein the material is suitable for an organic electroluminescence device.

2. The material according to claim 1, wherein the material is represented by the following formula:

2-254

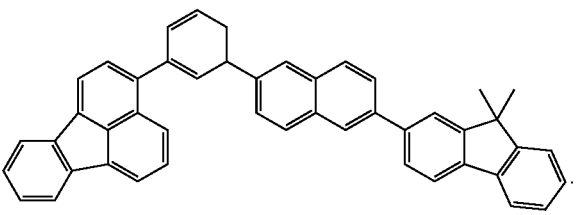

3. An organic electroluminescence device, comprising an organic thin film layer between a cathode and an anode, the organic thin film layer comprising one or more layers, wherein the organic thin film layer comprises one or more light emitting layers, and
wherein at least one of the layers of the organic thin film layer comprises a phosphorescent material and a first material comprising the material of claim 1.

4. The device of claim 3, wherein at least one of the light emitting layers comprises the phosphorescent material and the first material.

5. The device of claim 3, wherein the phosphorescent material comprises a metal complex, and the metal complex comprises:
a ligand; and
a metal atom selected from the group consisting of Ir, Pt, Os, Au, Cu, Re, and Ru.

6. The device of claim 5, wherein the ligand is orthometalated by the metal atom which forms the metal complex.

7. The device of claim 3, wherein an exited triplet energy of the first material is 2.0 eV or more and 2.8 eV or less.

8. The device of claim 3, wherein a wavelength of a maximum emission of at least one of the phosphorescent materials is 520 nm or more and 720 nm or less.

9. The device of claim 3, wherein the organic thin film layer comprises an electron transporting layer which is disposed between the cathode and the light emitting layer, and
wherein the electron transporting layer comprises the first material.

10. The device of claim 3, wherein the organic thin film layer comprises an electron transporting layer or an electron injecting layer each of which is disposed between the cathode and the light emitting layer, and
wherein the electron transporting layer or the electron injecting layer comprises an aromatic ring compound having a nitrogen-containing six- or five-membered ring or a condensed aromatic ring compound comprising a nitrogen-containing six- or five-membered ring.

11. The device of claim 3, wherein the organic thin film layer comprises an electron transporting layer or an electron injecting layer each of which is disposed between the cathode and the light emitting layer, and
wherein the electron transporting layer or the electron injecting layer comprises the first material.

12. The device of claim 3, wherein a reduction-causing dopant is added to an interfacial area between the cathode and the organic thin film layer.

* * * * *